United States Patent
Daemen et al.

(10) Patent No.: US 11,676,731 B2
(45) Date of Patent: *Jun. 13, 2023

(54) DIAGNOSTIC AND THERAPEUTIC METHODS FOR THE TREATMENT OF BREAST CANCER

(71) Applicant: Genentech, Inc., South San Francisco, CA (US)

(72) Inventors: Anneleen Daemen, South San Francisco, CA (US); Ciara Metcalfe, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/359,186

(22) Filed: Jun. 25, 2021

(65) Prior Publication Data

US 2022/0044819 A1 Feb. 10, 2022

Related U.S. Application Data

(63) Continuation of application No. 16/542,817, filed on Aug. 16, 2019, now Pat. No. 11,081,236.

(Continued)

(51) Int. Cl.
*G16H 50/30* (2018.01)
*G16H 50/20* (2018.01)
(Continued)

(52) U.S. Cl.
CPC ....... *G16H 50/30* (2018.01); *G01N 33/57415* (2013.01); *G16H 50/20* (2018.01); *G16H 80/00* (2018.01)

(58) Field of Classification Search
USPC .......................................................... 700/91
See application file for complete search history.

(56) References Cited

U.S. PATENT DOCUMENTS

| 7,612,114 B2 | 11/2009 | Hamaoka et al. |
| 8,399,520 B2 | 3/2013 | Hamaoka et al. |

(Continued)

FOREIGN PATENT DOCUMENTS

| WO | 2009108215 A1 | 9/2009 |
| WO | 2015038682 A1 | 3/2015 |

(Continued)

OTHER PUBLICATIONS

International Search Report and Written Opinion for PCT Application No. PCT/US2019/046814, dated Feb. 12, 2020, 17 pages.

(Continued)

*Primary Examiner* — Pierre E Elisca
(74) *Attorney, Agent, or Firm* — Mintz, Levin, Cohn, Ferris, Glovsky and Popeo, P.C.

(57) ABSTRACT

Provided herein, inter alia, are predictive diagnostic, pharmacodynamic, and therapeutic methods for the treatment of breast cancer. In embodiments, the methods and compositions are based, at least in part, on the discovery that the estradiol (E2)-induced score or estrogen receptor (ER) pathway activity score determined from a sample (e.g., a tissue sample, e.g., a tumor tissue sample, e.g., a FFPE, a FF, an archival, a fresh, or a frozen tumor tissue sample) from an individual can be used in methods of determining whether the individual having breast cancer is likely to respond to a treatment including an endocrine therapy, selecting a therapy for an individual having breast cancer; treating an individual having breast cancer; and monitoring therapeutic efficacy of an endocrine therapy, as well as related kits.

22 Claims, 27 Drawing Sheets

Specification includes a Sequence Listing.

Related U.S. Application Data

(60) Provisional application No. 62/719,545, filed on Aug. 17, 2018.

(51) Int. Cl.
*G16H 80/00* (2018.01)
*G01N 33/574* (2006.01)

(56) References Cited

U.S. PATENT DOCUMENTS

| | | | |
|---|---|---|---|
| 8,703,810 | B2 | 4/2014 | Kahraman et al. |
| 9,475,791 | B2 | 10/2016 | Thatcher et al. |
| 9,499,538 | B2 | 11/2016 | Smith et al. |
| 9,586,952 | B2 | 3/2017 | Smith et al. |
| 11,081,236 | B2 | 8/2021 | Daemen et al. |
| 2004/0091423 | A1* | 5/2004 | Hung ............ A61K 31/352 424/9.1 |
| 2015/0045406 | A1* | 2/2015 | Gudkov ........... A61K 31/403 435/7.92 |
| 2015/0284357 | A1 | 10/2015 | Thatcher et al. |
| 2015/0347672 | A1 | 12/2015 | Van Ooijen et al. |
| 2016/0117439 | A1* | 4/2016 | Van Ooijen ......... G16B 20/00 514/249 |
| 2017/0129855 | A1 | 5/2017 | Liang et al. |
| 2020/0082944 | A1 | 3/2020 | Daemen et al. |

FOREIGN PATENT DOCUMENTS

| | | |
|---|---|---|
| WO | 2017136688 A1 | 8/2017 |
| WO | 2017140669 A1 | 8/2017 |
| WO | 2017162206 A1 | 9/2017 |
| WO | 2017216279 A1 | 12/2017 |
| WO | 2017216280 A1 | 12/2017 |
| WO | 2018019793 A1 | 2/2018 |
| WO | 2018077260 A1 | 5/2018 |
| WO | 2018077630 A1 | 5/2018 |
| WO | 2018081168 A2 | 5/2018 |
| WO | 2018091153 A1 | 5/2018 |
| WO | 2018081168 A3 | 6/2018 |
| WO | 2018129387 A1 | 7/2018 |
| WO | 2020037203 A2 | 2/2020 |
| WO | 2020037203 A3 | 3/2020 |

OTHER PUBLICATIONS

Daemen et al. (Jan. 30, 2018) "HER2 is not a Cancer Subtype but Rather a Pancancer Event and is Highly Enriched in AR-driven Breast Tumors", Breast Cancer Research, 20(1):8 pages.
Huber et al. (Feb. 2015) "Orchestrating High-throughput Genomic Analysis with Bioconductor", Nature Methods, 12(2):115-121.
Inda et al. (Nov. 14, 2019) "Estrogen Receptor Pathway Activity Score to Predict Clinical Response or Resistance to Neoadjuvant Endocrine Therapy in Primary Breast Cancer", Molecular Cancer Therapeutics, 19(2):680-689.
Klijn et al. (e-published Dec. 8, 2014, Mar. 2015) "A Comprehensive Transcriptional Portrait of Human Cancer Cell Lines", Nature Biotechnology, 33(3):306-312.
Ma et al. (Jun. 2004) "A Two-Gene Expression Ratio Predicts Clinical Outcome in Breast Cancer Patients Treated with Tamoxifen", Cancer Cell, 5(6):607-616.
Wang et al. (Nov. 1, 2007) "The Prognostic Biomarkers HOXB13, IL17BR, and CHDH are Regulated by Estrogen in Breast Cancer", Clinical Cancer Research, 13(21):6327-6334.
Wu et al. (Feb. 10, 2010) "Fast and SNP-Tolerant Detection of Complex Variants and Splicing in Short Reads", Bioinformatics, 26(7):873-881.

* cited by examiner

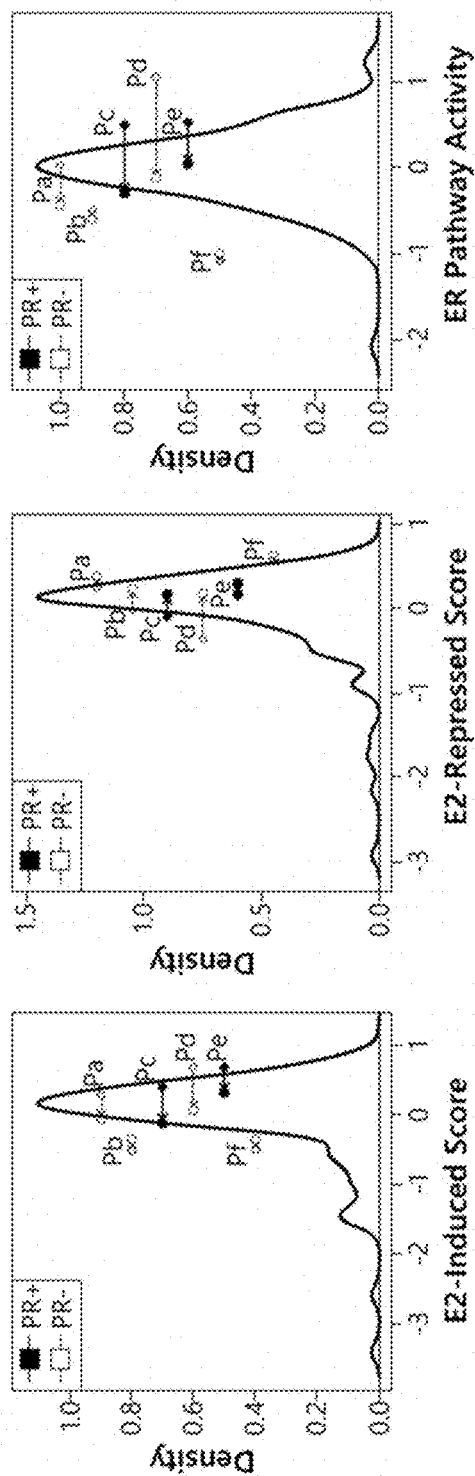

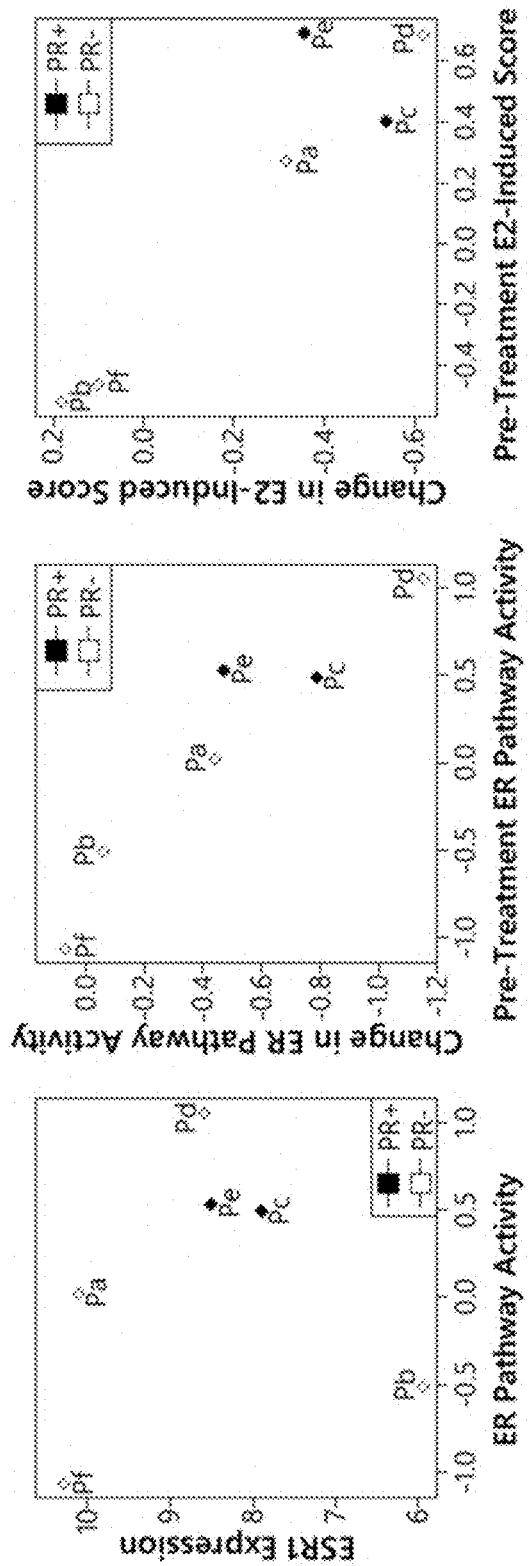

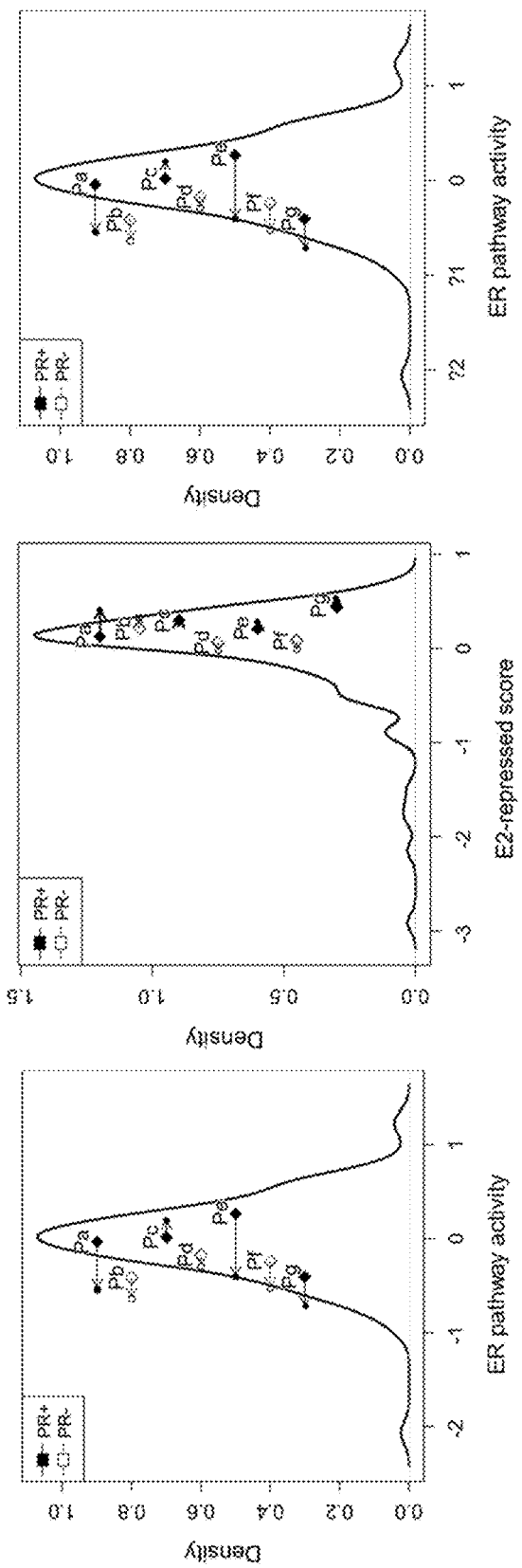

| E2-Induced | E2-repressed |
|---|---|
| AGR3 | BAMBI |
| AMZ1 | BCAS1 |
| AREG | CCNG2 |
| C5AR2 | DDIT4 |
| CELSR2 | EGLN3 |
| CT62 | FAM171B |
| FKBP4 | GRM4 |
| FMN1 | IL1R1 |
| GREB1 | LIPH |
| IGFBP4 | NBEA |
| NOS1AP | PNPLA7 |
| NXPH3 | PSCA |
| OLFM1 | SEMA3E |
| PGR | SSPO |
| PPM1J | STON1 |
| RAPGEFL1 | TGFB3 |
| RBM24 | TP53INP1 |
| RERG | TP53INP2 |
| RET | |
| SGK3 | |
| SLC9A3R1 | |
| TFF1 | |
| ZNF703 | |

FIG. 4J

| E2-Induced | E2-Repressed |
|---|---|
| AMZ1 | BCAS1 |
| AREG | CCNG2 |
| CSAR2 | IL1R1 |
| CELSR2 | NBEA |
| FKBP4 | PNPLA7 |
| FMN1 | SEMA3E |
| GREB1 | STON1 |
| OLFM1 | TP53INP1 |
| RBM24 | |
| SLC9A3R1 | |
| TFF1 | |

FIG. 4K

| E2-Induced | E2-Repressed |
|---|---|
| AMZ1 | BCAS1 |
| CSAR2 | CCNG2 |
| CELSR2 | IL1R1 |
| FKBP4 | PNPLA7 |
| GREB1 | SEMA3E |
| OLFM1 | STON1 |
| SLC9A3R1 | |
| TFF1 | |

FIG. 4L

SEQUENCE LISTING

```
<160> NUMBER OF SEQ ID NOS: 90

<210> SEQ ID NO 1
<211> LENGTH: 767
<212> TYPE: DNA
<213> ORGANISM: Homo sapiens

<400> SEQUENCE: 1
agaaacatcc agaatacatt tccaacaaga gcactggcca agtcagcttc ttctgagaga      60
gtctctagaa gacatgatgc tacactcagc tttgggtctc tgcctcttac tcgtcacagt     120
ttcttccaac cttgccattg caataaaaaa ggaaagagg cctcctcaga cactctcaag     180
aggatgggga gatgacatca cttgggtaca aacttatgaa gaaggtctct tttatgctca     240
aaaaagtaag aagccattaa tggttattca tcacctggag gattgtcaat actctcaagc     300
actaaagaaa gtatttgccc aaaatgaaga aatacaagaa atggctcaga ataagttcat     360
catgctaaac cttatgcatg aaaccactga taagaattta tcacctgatg ggcaatatgt     420
gcctagaatc atgtttgtag acccttcttt aacagttaga gctgacatag ctggaagata     480
ctctaacaga ttgtacacat atgagcctcg ggatttaccc ctattgatag aaaacatgaa     540
gaaagcatta agacttattc agtcagagct ataagagatg atggaaaaaa gccttcactt     600
caaagaagtc aaatttcatg aagaaaacct ctggcacatt gacaaatact aaatgtgcaa     660
gtatatagat tttgtaatat tactatttag tttttttaat gtgtttgcaa tagtcttatt     720
aaaataaatg tttttaaat ctgagactga aaaaaaaaa aaaaaaa                    767

<210> SEQ ID NO 2
<211> LENGTH: 166
<212> TYPE: PRT
<213> ORGANISM: Homo sapiens

<400> SEQUENCE: 2

Met Met Leu His Ser Ala Leu Gly Leu Cys Leu Leu Val Thr Val
1               5                   10                  15

Ser Ser Asn Leu Ala Ile Ala Ile Lys Lys Glu Lys Arg Pro Pro Gln
                20                  25                  30

Thr Leu Ser Arg Gly Trp Gly Asp Asp Ile Thr Trp Val Gln Thr Tyr
```

```
                35                  40                  45
Glu Glu Gly Leu Phe Tyr Ala Gln Lys Ser Lys Lys Pro Leu Met Val
             50                  55                  60

Ile His His Leu Glu Asp Cys Gln Tyr Ser Gln Ala Leu Lys Lys Val
65                  70                  75                  80

Phe Ala Gln Asn Glu Glu Ile Gln Glu Met Ala Gln Asn Lys Phe Ile
                 85                  90                  95

Met Leu Asn Leu Met His Glu Thr Thr Asp Lys Asn Leu Ser Pro Asp
            100                 105                 110

Gly Gln Tyr Val Pro Arg Ile Met Phe Val Asp Pro Ser Leu Thr Val
            115                 120                 125

Arg Ala Asp Ile Ala Gly Arg Tyr Ser Asn Arg Leu Tyr Thr Tyr Glu
            130                 135                 140

Pro Arg Asp Leu Pro Leu Leu Ile Glu Asn Met Lys Lys Ala Leu Arg
145                 150                 155                 160

Leu Ile Gln Ser Glu Leu
                165

<210> SEQ ID NO 3
<211> LENGTH: 5531
<212> TYPE: DNA
<213> ORGANISM: Homo sapiens

<400> SEQUENCE: 3
gattggtgct gtgacctgcg gcagcacagc cgcctgcgtt gagcgcccac ggtgggctgg      60
actttgcact aggtgctgac aggaccggca gaggtggcca ctgccctcgt ccccagcctg     120
cactcctggg cgaaggctga cgctgaacag ggtgctgtgg gcccagaagc gcccatgcct     180
gagagcgtcc aggaccaggc agagctgggc cttaagggcc cttggaccag tgtctgtctg     240
cagggagccc ccggtagcca ctcggatcag cccgagggaa gattctggac gagaccgtgg     300
ccgtcccccg ggtggcccat ggacagcagc aggggctccc aggagtggcc aggccctgcc     360
cgcccaccat gctgcagtgt agacccgcac aggagttcag cttcgggccc cgggccttga     420
aggacgctct ggtctccact gacgcagccc tgcagcagct gtatgtgtcc gccttctccc     480
ctgccgagcg gctcttcctg gccgaggcct acaacccgca gaggacgctc ttctgcaccc     540
tgctcatccg cacgggcttc gactggctcc tgagccgacc cgaggctccc gaggacttcc     600
agaccttcca cgcctccctg cagcaccgga gccccgcct ggctcggaag cacatctacc     660
tacagccgat agacctgagc gaggagccgg tgggaagctc cctgctgcac cagctgtgca     720
gctgcacaga ggccttcttc ctgggcctgc gcgtcaagtg cctgccgtcg gtggcagccg     780
cgtccatccg ctgctcctcg cggcccagcc gggactctga caggctccag ctccacacag     840
acggcatcct gtccttcttg aagaacaaca agccagggga cgcgctgtgt gtgctgggcc     900
tcacactgtc tgacctgtac ccccatgagg cctggagctt cacctttcagc aagttccttc     960 cagggcacga agtgggcgtc tgcagcttcg cccggttctc aggggaattc ccgaagtcgg    1020
ggcccagcgc ccctgatctg gccctggtag aggcagcagc agacggcccc gaggccccc     1080 tgcaggacag gggctgggcc ctgtgcttca gtgccctggg gatggttcag tgctgcaagg    1140
tcacgtgcca cgagctctgc caccttctgg gcctggggaa ctgccgctgg ctccgctgcc    1200
tcatgcaggg tgcgctcagc ctggacgagg ccctgcggcg ccccctggac ctctgtccca    1260
tctgcctgag gaagctgcag catgtcctgg gtttcaggct catcgagagg taccagagac    1320
tctacacctg gactcaggcg gtggtgggga cgtggcccag ccaggaggcg ggggagccgt    1380
```

```
cagtgtggga ggacaccccg cctgccagcg ccgactcggg catgtgctgt gagagtgact    1440
cggagcccgg caccagtgtg tcggagcccc tcacccctga tgccgggagt cacaccttcg    1500
cctcggggcc agaggaaggg ctgagctacc tggcagcctc agaggctccg ctgccacctg    1560
ggggccctgc ggaggccatc aaggagcatg aacggtggct ggccatgtgc atccaggccc    1620
tgcagcggga agtggcagag gaggacctgg tgcaggtgga cagagccgtg gacgccctcg    1680
accgctggga gatgttcacg ggccagctcc cggccaccag gcaggaccca cccagcagca    1740
gggacagcgt ggggctgcgc aaggtgctgg gggacaagtt ctcctccctg aggaggaagc    1800
tgagtgcccg aaaactcgcc agagcagagt cggccccccg tccctgggat ggggaagaga    1860
gttagtacag caggggctgc cctacgtctc cttccctaag gatgctggcc agcactgtcc    1920
agtagctgag gccactactg acctgccagg gataaagagg aagggtctgc ctgggtggtg    1980
gctcaggcct gtcatcccat cactttgaga ggccaggagt ttgagaccag actgggcaac    2040
atggtgagac tctgcctcta caaagaaaa attaaaaaat tagctggatg aagtggttca    2100
tgcctgtgtt cccagctatt caggaggctg aggtgggagg attgcttgag cctaggaggt    2160
cgaggctgca gtgggatgtg atcataccac tgtactgcag tctgggccac acagaaagac    2220
tgtctccaga aaaaaaaag ttctttggag aagccacaga ccacctgtct tcaggcgcct    2280
ccttcaactc ctgagtccca gccagccgct cccaggggcc tgcacacatg gagaggcctc    2340
cctgatcctg ggtgcttctc gtggagtaca agccggactg tgctgaggtt gggacagagc    2400
cccctcccct gcagaggcag aaggaagcag cgtgcgtcct gtctccttcc aggctgtggg    2460
cctgcccttc agttatttat agctggagct ggagaggctg gctcagatga ggagtgaccc    2520 cggggcaca caggctccac actgccaccc agcttccaag gctgagtctc ctccctaacg    2580
gggaagtgac ggggttttgt ctctatcatc tcaggcgtca accacatgca cacacacact    2640
gtcacgttct gtggcgctaa cagcatcctg atcctgacgg acttcaccgg ggctctccag    2700
gcatctcttc tgacaaacac tgcaggaggt gagggtgtct gacgtgcact gagggcagag    2760 gccccttat tcctgaggcg gctacagctc accgtgggga agatcaactg tggtgatgtt    2820
tttgggacag tttcttggca aaggtggccg cgctgtcagt accaagtagc tggaggtggt    2880
gatcagatga tctgtctttc cttttttttt cggtctagtt ctgtcagttg ctgagagagg    2940
ggtattattg ccatgctggg cgtttgatc tgtctccctt tagttttgcc ggattttgct    3000
tcctgcactt tgaagctcct ttacgtccct gcacatttga ttgttgtgtc ttcctgagga    3060 attgacccctt ttattgtcac acgtaccccc tcagcctgtg gtggagggtc tctgggagag    3120
agacttccgg ttctgacagc ggaatccctt cggagtgacg agggcggggt cacagctcgc    3180
gcaccctcat ctggagagag gcaagaacag ggcagcttgg accttttgtg ggtggtggc    3240 tcacacggtt atggagggct tctaagaaaa acaaaataca aaactaaaac tagaagggct    3300
atgcaggtga ggtgggctga ggcttccttg tgaatctgac attggtggag ccgactgaa    3360 ggctcccggt cctggtccca ctccgtgttg acttcagaga agcaaagatg cagctcagaa    3420
gtagcattag gatcttcgtc ccgttctctt ttgcgtagct tcaaaaaggc gtaacagtga    3480
cctgggaggg gagatgaaga gctaggcctt tcagaaagtg accaatggaa ggtgccggca    3540
gagcaccctg cagtaacaga aggtgaaagc cggagcctgg tggctgttgc tgcaaacaac    3600
cacccaaaac ttagtggctt aaaatcacca cagtctagct catgaatctg taacttgggc    3660
agagctcggt ggagacggtt tgcccctgtg gctcgactgg agtgttcgtt cacacggctg    3720
```

```
ccaagtggaa tttggctggg aatctcaggc cttggttcct gcccacgtga gactctccat    3780
ggaggagggg catcttctta ggaaggcagc tgccataccg tgaggaaacc cgacaaacag    3840
ggcagccaga gccagacagc aggctcctgg tcccagtccc ggaaaatgca aagggacaag    3900
tatgtgttga tttcagagaa gctcagatgt agcattagga ccttcatcca taccttctc    3960
ttttgcatgg cttctaaagg gcatgacagt gacctgggag gtaactgtgc cagaataaag    4020
aggggagacg aaaaaaagag ggtcactttc agaaagggac ctgggcttcc tcacaatatg    4080
gcggttgccc tcctaaggtg gacatcggga gggtcagatg gaagctctgt ggcctttcct    4140
aactcggcct cacgtcacag agcgtcacct ttcctgcact ccacggcggc agtgacaagg    4200
accccacccc aggttcacgg ggaggggacg tggcaggaa  tgtgagacaa cacaatattg    4260
ctgtggccat tcatgaacag tcagtcagcc ccactcggcg ttcactgtgg ggatttggct    4320
ggtgcacctg cgaggtggcc tgacctgttt tccgatttcc ttcatcttct gcaaaaggtt    4380
aaccgctgga gtgatgcgag attaaacaga ggtgataaaa atagaatgcc tggctcatgc    4440
tgagggtggg agcccactgg ggttatgacc aaagcctcgg cgctctctgt acccgtgtcc    4500
tttgaccctc agctgtgatg tgtgtcccaa aaaagcgttt tgaagtggga aggagcaaac    4560
cactaaaaaa aactccttt  atccgcagcg tttaccaact tgcagatgtc agtgaaattt    4620
tttaagacag ctgttagaag gactgttttg aaatgcaact tgaggaaga  gaaattggtt    4680
tccctcctct cccccgtgtt agccccaggt tctgtctgtg ctgtggtgaa gagtgacttg    4740
ggacagtcac caggaaagac gcaaggcaga ggagagagaa tgagggctgc cttctcgagg    4800
aaggtcacag ctcacgaatc tttctaaact taagtgctgc agaagttgaa ctgagattaa    4860
atttagagat gatggtttcc aagacacaca gggccacggt tctttcagtt tttaaacacg    4920
tgcaaagtcc actgaattgc tttctcgtct catctgtcag aagcccctgc attcacaagg    4980
atgggtcttc cagcttgacg atgacctctc ttcggagagc ctcacccatc ttggtaagcc    5040
aagtcagcgg ggcctcatgg agctaaaaat agtttcaggt catgacagat gttatctgta    5100
ttgctgtgtg tgcgatgagt ctggggaagc taacacatgc cttctgaagt ggctagaata    5160
cacactccca cgtcacagcc atgctatgat gaagggggtga gaagcagtgt ccctctgag    5220
gcaaatctct cttcaggcag ccccgcagtc ctcttccgaa atctcattct tttccctctc    5280
ttcctcccca aaagcccaa  actcattgtc agagtgggga gagggagaa  gcagcatcct    5340
gactcctgtc catggtgtga accctgaggg cacgggacag tgagtggagc tctgccacca    5400
cccgttttcca gagcatgggt gaggaggggag ggatgccgac ctgttaatat ttgcttcaga    5460
cctttccccg atgaacgaaa tctccaaaag ccttaaacat aaaatggctt agtcaaaaaa    5520
aaaaaaaaaa a                                                         5531
```

<210> SEQ ID NO 4
<211> LENGTH: 498
<212> TYPE: PRT
<213> ORGANISM: Homo sapiens

<400> SEQUENCE: 4

```
Met Leu Gln Cys Arg Pro Ala Gln Glu Phe Ser Phe Gly Pro Arg Ala
1               5                   10                  15

Leu Lys Asp Ala Leu Val Ser Thr Asp Ala Ala Leu Gln Gln Leu Tyr
                20                  25                  30

Val Ser Ala Phe Ser Pro Ala Glu Arg Leu Phe Leu Ala Glu Ala Tyr
            35                  40                  45
```

```
Asn Pro Gln Arg Thr Leu Phe Cys Thr Leu Leu Ile Arg Thr Gly Phe
     50                  55                  60

Asp Trp Leu Leu Ser Arg Pro Glu Ala Pro Glu Asp Phe Gln Thr Phe
 65                  70                  75                  80

His Ala Ser Leu Gln His Arg Lys Pro Arg Leu Ala Arg Lys His Ile
                 85                  90                  95

Tyr Leu Gln Pro Ile Asp Leu Ser Glu Glu Pro Val Gly Ser Ser Leu
                100                 105                 110

Leu His Gln Leu Cys Ser Cys Thr Glu Ala Phe Phe Leu Gly Leu Arg
             115                 120                 125

Val Lys Cys Leu Pro Ser Val Ala Ala Ala Ser Ile Arg Cys Ser Ser
130                 135                 140

Arg Pro Ser Arg Asp Ser Asp Arg Leu Gln Leu His Thr Asp Gly Ile
145                 150                 155                 160

Leu Ser Phe Leu Lys Asn Asn Lys Pro Gly Asp Ala Leu Cys Val Leu
                165                 170                 175

Gly Leu Thr Leu Ser Asp Leu Tyr Pro His Glu Ala Trp Ser Phe Thr
             180                 185                 190

Phe Ser Lys Phe Leu Pro Gly His Glu Val Gly Val Cys Ser Phe Ala
         195                 200                 205

Arg Phe Ser Gly Glu Phe Pro Lys Ser Gly Pro Ser Ala Pro Asp Leu
210                 215                 220

Ala Leu Val Glu Ala Ala Ala Asp Gly Pro Glu Ala Pro Leu Gln Asp
225                 230                 235                 240

Arg Gly Trp Ala Leu Cys Phe Ser Ala Leu Gly Met Val Gln Cys Cys
                245                 250                 255

Lys Val Thr Cys His Glu Leu Cys His Leu Leu Gly Leu Gly Asn Cys
             260                 265                 270

Arg Trp Leu Arg Cys Leu Met Gln Gly Ala Leu Ser Leu Asp Glu Ala
         275                 280                 285

Leu Arg Arg Pro Leu Asp Leu Cys Pro Ile Cys Leu Arg Lys Leu Gln
290                 295                 300

His Val Leu Gly Phe Arg Leu Ile Glu Arg Tyr Gln Arg Leu Tyr Thr
305                 310                 315                 320

Trp Thr Gln Ala Val Val Gly Thr Trp Pro Ser Gln Glu Ala Gly Glu
                325                 330                 335

Pro Ser Val Trp Glu Asp Thr Pro Pro Ala Ser Ala Asp Ser Gly Met
             340                 345                 350

Cys Cys Glu Ser Asp Ser Glu Pro Gly Thr Ser Val Ser Glu Pro Leu
         355                 360                 365

Thr Pro Asp Ala Gly Ser His Thr Phe Ala Ser Gly Pro Glu Glu Gly
370                 375                 380

Leu Ser Tyr Leu Ala Ala Ser Glu Ala Pro Leu Pro Pro Gly Gly Pro
385                 390                 395                 400

Ala Glu Ala Ile Lys Glu His Glu Arg Trp Leu Ala Met Cys Ile Gln
                405                 410                 415

Ala Leu Gln Arg Glu Val Ala Glu Glu Asp Leu Val Gln Val Asp Arg
             420                 425                 430

Ala Val Asp Ala Leu Asp Arg Trp Glu Met Phe Thr Gly Gln Leu Pro
         435                 440                 445

Ala Thr Arg Gln Asp Pro Pro Ser Ser Arg Asp Ser Val Gly Leu Arg
450                 455                 460

Lys Val Leu Gly Asp Lys Phe Ser Ser Leu Arg Arg Lys Leu Ser Ala
```

```
                465                 470                 475                 480
Arg Lys Leu Ala Arg Ala Glu Ser Ala Pro Arg Pro Trp Asp Gly Glu
                    485                 490                 495

Glu Ser

<210> SEQ ID NO 5
<211> LENGTH: 1290
<212> TYPE: DNA
<213> ORGANISM: Homo sapiens

<400> SEQUENCE: 5
ggctgagcct ataaagcggc aggtgcgcgc cgccctacag acgttcgcac acctgggtgc      60
cagcgcccca gaggtcccgg gacagcccga ggcgccgcgc ccgccgcccc gagctcccca     120
agccttcgag agcggcgcac actcccggtc tccactcgct cttccaacac ccgctcgttt     180
tggcggcagc tcgtgtccca gagaccgagt tgccccagag accgagacgc cgccgctgcg     240
aaggaccaat gagagcccca ctgctaccgc cggcgccggt ggtgctgtcg ctcttgatac     300
tcggctcagg ccattatgct gctggattgg acctcaatga cacctactct gggaagcgtg     360
aaccattttc tggggaccac agtgctgatg gatttgaggt tacctcaaga agtgagatgt     420
cttcagggag tgagatttcc cctgtgagtg aaatgccttc tagtagtgaa ccgtcctcgg     480
gagccgacta tgactactca gaagagtatg ataacgaacc acaaatacct ggctatattg     540
tcgatgattc agtcagagtt gaacaggtag ttaagccccc ccaaaacaag acggaaagtg     600
aaaatacttc agataaaccc aaaagaaaga aaaagggagg caaaaatgga aaaaatagaa     660
gaaacagaaa gaagaaaaat ccatgtaatg cagaatttca aaatttctgc attcacggag     720
aatgcaaata tatagagcac ctggaagcag taacatgcaa atgtcagcaa gaatatttcg     780
gtgaacggtg tggggaaaag tccatgaaaa ctcacagcat gattgacagt agtttatcaa     840
aaattgcatt agcagccata gctgccttta tgtctgctgt gatcctcaca gctgttgctg     900
ttattacagt ccagcttaga agacaatacg tcaggaaata tgaaggagaa gctgaggaac     960
gaaagaaact tcgacaagag aatggaaatg tacatgctat agcataactg aagataaaat    1020
tacaggatat cacattggag tcactgccaa gtcatagcca taaatgatga gtcggtcctc    1080
tttccagtgg atcataagac aatggaccct ttttgttatg atggttttaa actttcaatt    1140 gtcactttt atgctatttc tgtatataaa ggtgcacgaa ggtaaaaagt atttttcaa     1200 gttgtaaata atttatttaa tatttaatgg aagtgtattt attttacagc tcattaaact    1260
tttttaacca aacagaaaaa aaaaaaaaaa                                      1290

<210> SEQ ID NO 6
<211> LENGTH: 252
<212> TYPE: PRT
<213> ORGANISM: Homo sapiens

<400> SEQUENCE: 6

Met Arg Ala Pro Leu Leu Pro Pro Ala Pro Val Val Leu Ser Leu Leu
1               5                   10                  15

Ile Leu Gly Ser Gly His Tyr Ala Ala Gly Leu Asp Leu Asn Asp Thr
            20                  25                  30

Tyr Ser Gly Lys Arg Glu Pro Phe Ser Gly Asp His Ser Ala Asp Gly
        35                  40                  45

Phe Glu Val Thr Ser Arg Ser Glu Met Ser Ser Gly Ser Glu Ile Ser
    50                  55                  60
```

```
Pro Val Ser Glu Met Pro Ser Ser Ser Glu Pro Ser Ser Gly Ala Asp
 65                  70                  75                  80

Tyr Asp Tyr Ser Glu Glu Tyr Asp Asn Glu Pro Gln Ile Pro Gly Tyr
                 85                  90                  95

Ile Val Asp Asp Ser Val Arg Val Glu Gln Val Val Lys Pro Pro Gln
            100                 105                 110

Asn Lys Thr Glu Ser Glu Asn Thr Ser Asp Lys Pro Lys Arg Lys Lys
        115                 120                 125

Lys Gly Gly Lys Asn Gly Lys Asn Arg Arg Asn Arg Lys Lys Lys Asn
130                 135                 140

Pro Cys Asn Ala Glu Phe Gln Asn Phe Cys Ile His Gly Glu Cys Lys
145                 150                 155                 160

Tyr Ile Glu His Leu Glu Ala Val Thr Cys Lys Cys Gln Gln Glu Tyr
                165                 170                 175

Phe Gly Glu Arg Cys Gly Glu Lys Ser Met Lys Thr His Ser Met Ile
            180                 185                 190

Asp Ser Ser Leu Ser Lys Ile Ala Leu Ala Ala Ile Ala Ala Phe Met
        195                 200                 205

Ser Ala Val Ile Leu Thr Ala Val Ala Val Ile Thr Val Gln Leu Arg
210                 215                 220

Arg Gln Tyr Val Arg Lys Tyr Glu Gly Glu Ala Glu Glu Arg Lys Lys
225                 230                 235                 240

Leu Arg Gln Glu Asn Gly Asn Val His Ala Ile Ala
                245                 250
```

<210> SEQ ID NO 7
<211> LENGTH: 1434
<212> TYPE: DNA
<213> ORGANISM: Homo sapiens

<400> SEQUENCE: 7

| | | | | | |
|---|---|---|---|---|---|
| tataaagatt | cactgggact | ggtgaggtgg | cagtgctcag | cagcatccga | caggagccct | 60 |
| ggcaaacagg | acggatttcc | aggactctac | cagctgccag | acacggcagg | gagagacccc | 120 |
| agacctcctg | gtcctggct | gtgggcccgg | attgggctcc | caagtggcgt | ttgactcacg | 180 |
| tggggacact | cttggaagag | acgacaccag | gagcctgaat | ggggaacgat | tctgtcagct | 240 |
| acgagtatgg | ggattacagc | gacctctcgg | accgccctgt | ggactgcctg | gatgcgcct | 300 |
| gcctggccat | cgaccgctg | cgcgtggccc | cgctcccact | gtatgccgcc | atcttcctgg | 360 |
| tgggggtgcc | gggcaatgcc | atggtggcct | gggtggctgg | gaaggtggcc | cgccggaggg | 420 |
| tgggtgccac | ctggttgctc | cacctggccg | tgcggattt | gctgtgctgt | ttgtctctgc | 480 |
| ccatcctggc | agtgcccatt | gcccgtggag | gccactggcc | gtatggtgca | gtgggctgtc | 540 |
| gggcgctgcc | ctccatcatc | ctgctgacca | tgtatgccag | cgtcctgctc | ctggcagctc | 600 |
| tcagtgccga | cctctgcttc | ctggctctcg | ggcctgcctg | gtggtctacg | gttcagcggg | 660 |
| cgtgcgggt | gcaggtggcc | tgtggggcag | cctggacact | ggccttgctg | ctcaccgtgc | 720 |
| cctccgccat | ctaccgccgg | ctgcaccagg | agcacttccc | agcccggctg | cagtgtgtgg | 780 |
| tggactacgg | cggctcctcc | agcaccgaga | atgcggtgac | tgccatccgg | tttcttttg | 840 |
| gcttcctggg | gcccctggtg | gccgtggcca | gctgccacag | tgccctcctg | tgctgggcag | 900 |
| cccgacgctg | ccggccgctg | ggcacagcca | ttgtggtggg | gttttttgtc | tgctgggcac | 960 |
| cctaccacct | gctgggctg | gtgctcactg | tggcggcccc | gaactccgca | ctcctggcca | 1020 |
| gggcctgcg | ggctgaaccc | ctcatcgtgg | gccttgccct | cgctcacagc | tgcctcaatc | 1080 |

-continued

```
ccatgctctt cctgtatttt gggagggctc aactccgccg gtcactgcca gctgcctgtc   1140
actgggccct gagggagtcc cagggccagg acgaaagtgt ggacagcaag aaatccacca   1200
gccatgacct ggtctcggag atggaggtgt aggctggaga cattgtgg gtgtgtatct     1260 tcttatctca tttcacaaga ctggcttcag gcatagctgg atccaggagc tcaatgatgt   1320
cttcatttta ttccttcctt cattcaacag atatccatca tgcacttgct atgtgcaagg   1380 ccttttagg cactagagat atagcagtga ccaaaacaga cacaaatcct gccc           1434
```

<210> SEQ ID NO 8
<211> LENGTH: 337
<212> TYPE: PRT
<213> ORGANISM: Homo sapiens

<400> SEQUENCE: 8

```
Met Gly Asn Asp Ser Val Ser Tyr Glu Tyr Gly Asp Tyr Ser Asp Leu
1               5                   10                  15

Ser Asp Arg Pro Val Asp Cys Leu Asp Gly Ala Cys Leu Ala Ile Asp
            20                  25                  30

Pro Leu Arg Val Ala Pro Leu Pro Leu Tyr Ala Ala Ile Phe Leu Val
        35                  40                  45

Gly Val Pro Gly Asn Ala Met Val Ala Trp Val Ala Gly Lys Val Ala
    50                  55                  60

Arg Arg Arg Val Gly Ala Thr Trp Leu Leu His Leu Ala Val Ala Asp
65                  70                  75                  80

Leu Leu Cys Cys Leu Ser Leu Pro Ile Leu Ala Val Pro Ile Ala Arg
                85                  90                  95

Gly Gly His Trp Pro Tyr Gly Ala Val Gly Cys Arg Ala Leu Pro Ser
            100                 105                 110

Ile Ile Leu Leu Thr Met Tyr Ala Ser Val Leu Leu Leu Ala Ala Leu
        115                 120                 125

Ser Ala Asp Leu Cys Phe Leu Ala Leu Gly Pro Ala Trp Trp Ser Thr
    130                 135                 140

Val Gln Arg Ala Cys Gly Val Gln Val Ala Cys Gly Ala Ala Trp Thr
145                 150                 155                 160

Leu Ala Leu Leu Leu Thr Val Pro Ser Ala Ile Tyr Arg Arg Leu His
                165                 170                 175

Gln Glu His Phe Pro Ala Arg Leu Gln Cys Val Val Asp Tyr Gly Gly
            180                 185                 190

Ser Ser Ser Thr Glu Asn Ala Val Thr Ala Ile Arg Phe Leu Phe Gly
        195                 200                 205

Phe Leu Gly Pro Leu Val Ala Val Ala Ser Cys His Ser Ala Leu Leu
    210                 215                 220

Cys Trp Ala Ala Arg Arg Cys Arg Pro Leu Gly Thr Ala Ile Val Val
225                 230                 235                 240

Gly Phe Phe Val Cys Trp Ala Pro Tyr His Leu Leu Gly Leu Val Leu
                245                 250                 255

Thr Val Ala Ala Pro Asn Ser Ala Leu Leu Ala Arg Ala Leu Arg Ala
            260                 265                 270

Glu Pro Leu Ile Val Gly Leu Ala Leu Ala His Ser Cys Leu Asn Pro
        275                 280                 285

Met Leu Phe Leu Tyr Phe Gly Arg Ala Gln Leu Arg Arg Ser Leu Pro
    290                 295                 300

Ala Ala Cys His Trp Ala Leu Arg Glu Ser Gln Gly Gln Asp Glu Ser
```

| | 305 | | | 310 | | | 315 | | | 320 | |
|---|---|---|---|---|---|---|---|---|---|---|---|
Val Asp Ser Lys Lys Ser Thr Ser His Asp Leu Val Ser Glu Met Glu
            325                 330                 335

Val

<210> SEQ ID NO 9
<211> LENGTH: 10540
<212> TYPE: DNA
<213> ORGANISM: Homo sapiens

<400> SEQUENCE: 9

| | | | | | |
|---|---|---|---|---|---|
| aggagccgga | ggaggagccg | ccgccgccgt | tgacccggcc | gccggccggg | agctgggaga | 60 |
| gatgcggagc | ccggccaccg | gcgtccccct | cccaacgccg | ccgccgccgc | tgctgctgct | 120 |
| gttgctgctg | ctgctgccgc | cgccactatt | gggagaccaa | gtggggccct | gtcgttcctt | 180 |
| ggggtccagg | ggacgaggct | cttcggggc | ctgcgccccc | atgggctggc | tctgtccatc | 240 |
| ctcagcgtcg | aacctctggc | tctacaccag | ccgctgcagg | gatgcgggca | ctgagctgac | 300 |
| tggccacctg | gtaccccacc | acgatggcct | gagggtttgg | tgtccagaat | ccgaggccca | 360 |
| tattcccta | ccaccagctc | ctgaaggctg | ccctggagc | tgtcgcctcc | tgggcattgg | 420 |
| aggccacctt | tccccacagg | gcaagctcac | actgcccgag | gagcacccgt | gcttaaaggc | 480 |
| tccacggctc | agatgccagt | cctgcaagct | ggcacaggcc | cccggctca | gggcagggga | 540 |
| aaggtcacca | gaagagtccc | tgggtgggcg | tcggaaaagg | aatgtaaata | cagccccca | 600 |
| gttccagccc | cccagctacc | aggccacagt | gccgagaac | cagccagcag | gcacccctgt | 660 |
| tgcatccctg | agggccatcg | acccggacga | gggtgaggca | ggtcgactgg | agtacaccat | 720 |
| ggatgccctc | tttgatagcc | gctccaacca | gttcttctcc | ctggacccag | tcactggtgc | 780 |
| agtaaccaca | gccgaggagc | tggatcgtga | gaccaagagc | acccacgtct | tcagggtcac | 840 |
| ggcgcaggac | cacggcatgc | cccgacgaag | tgccctggct | acactcacca | tcttggttac | 900 |
| tgacaccaat | gaccatgacc | ctgtgttcga | gcagcaggag | tacaaggaga | gcctcaggga | 960 |
| gaacctggag | gttggctatg | aggtgctcac | tgtcagggcc | acggatggtg | atgcccctcc | 1020 |
| caatgccaat | attctgtacc | gcctgctgga | ggggtctggg | ggcagcccct | ctgaagtctt | 1080 |
| tgagatcgac | cctcgctctg | gggtgatccg | aacccgtggc | cctgtggatc | gggaagaggt | 1140 |
| ggaatcctac | cagctgacgg | tagaggcaag | tgaccagggt | cgggacccgg | gtcctcggag | 1200 |
| taccacagcc | gctgtttcc | tttctgtgga | ggatgacaat | gataatgccc | cccagtttag | 1260 |
| tgagaagcgc | tatgtggtcc | aggtgaggga | ggatgtgact | ccaggggccc | cagtactccg | 1320 |
| agtcacagcc | tcggatcgag | acaaggggag | caatgccgtg | gtgcactata | gcatcatgag | 1380 |
| tggcaatgct | cggggacagt | tttatctgga | tgcccagact | ggagctctgg | atgtggtgag | 1440 |
| ccctcttgac | tatgagacga | ccaaggagta | caccctacgg | gtgcgagcac | aggatggtgg | 1500 |
| ccgtccccca | ctctctaatg | tctctggctt | ggtgacagta | caggtcctgg | atatcaacga | 1560 |
| caatgcccc | atcttcgtca | gcaccccttt | ccaggctact | gtcctggaga | gtgtcccctt | 1620 |
| aggctacctg | gttctccatg | tccaggctat | cgacgctgat | gctggtgaca | atgcccgcct | 1680 |
| ggaataccgc | cttgctgggg | tgggacatga | cttcccttc | accatcaaca | atggcacagg | 1740 |
| ctggatctct | gtggctgctg | aactggaccg | ggaggaagtt | gatttctaca | gctttgggt | 1800 |
| agaagctcga | gaccatggca | ctccagcact | cactgcctcg | gccagtgtca | gcgtgactgt | 1860 |
| cctggatgtc | aacgacaaca | atccaacctt | tacccaacca | gagtacacag | tgcggctcaa | 1920 |

```
tgaggatgca gctgtgggca ccagcgtggt gacggtgtca gctgtggacc gtgatgctca    1980
tagtgtcatc acctaccaga tcaccagtgg caatactcga aaccgcttct ccatcaccag    2040
ccaaagtggt ggtgggctgg tatcccttgc cctgccactg gactacaaac ttgagcggca    2100
gtatgtgttg gctgttaccg cctccgatgg cactcggcag gacacggcac agattgtggt    2160
gaatgtcacc gacgccaaca cccatcgtcc tgtctttcag agctcccact atacagtgaa    2220
tgttaatgag gaccggccgg caggcaccac ggtggtgctg atcagcgcca cggatgagga    2280
cacaggtgag aatgcccgca tcacctactt catggaggac agcatcccc  agttccgcat    2340
cgatgcagac acgggggctg tcaccaccca ggctgagctg gactatgaag ccaagtgtc    2400
ttacaccctg gccattactg ctcgggacaa tggcattccc cagaagtccg acaccaccta    2460
cctggagatc ctggtgaacg acgtgaatga caatgcccct cagttcctgc gagactccta    2520
ccagggcagt gtctatgagg atgtgccacc cttcactagc gtcctgcaga tctcagccac    2580
tgatcgtgat tctggactta atggcagggt cttctacacc ttccaaggag gcgacgatgg    2640
agacggtgac tttattgttg agtccacgtc aggcatcgtg cgaacgctac ggaggctgga    2700
tcgagagaac gtggcccagt atgtcttgcg ggcatatgca gtggacaagg ggatgccccc    2760
agcccgcaca cctatggaag tgacagtcac tgtgttggat gtgaatgaca atccccctgt    2820
ctttgagcag gatgagtttg atgtgtttgt ggaagagaac agcccccattg gctagccgt    2880
ggcccgggtc acagccactg accccgatga aggcaccaat gcccagatta tgtaccagat    2940
tgtggagggc aacatccctg aggtctttca gctggacatc ttctccgggg agctgacagc    3000
cctggtagac ttagactacg aggaccggcc tgagtacgtc ctggtcatcc aggccacgtc    3060
agctcctctg gtgagccggg ctacagtcca cgtccgcctc cttgaccgca atgacaaccc    3120
accagtgctg ggcaactttg agatccttt  caacaactat gtcaccaatc gctcaagcag    3180
cttccctggg ggtgccattg gccgagtacc tgcccatgac cctgatatct cagatagtct    3240
gacttacagc tttgagcggg gaaatgaact cagcctggtc ctgctcaatg cctccacggg    3300
tgagctgaag ctaagccgcg cactggacaa caaccggcct ctggaggcca tcatgagcgt    3360
gctggtgtca gacggcgtac acagcgtgac cgcccagtgc gcgctgcgtg tgaccatcat    3420
caccgatgag atgctcaccc acagcatcac gctgcgcctg gaggacatgt cacccgagcg    3480
cttcctgtca ccactgctag gcctcttcat ccaggcggtg gccgccacgc tggccacgcc    3540
accggaccac gtggtggtct tcaacgtaca gcgggacacc gacgccccg  ggggccacat    3600
cctcaacgtg agcctgtcgg tgggccagcc gccaggcc   ggggcgggc cgcccttcct    3660
gccctctgag gacctgcagg agcgcctata cctcaaccgc agcctgctga cggccatctc    3720
ggcacagcgc gtgctgccct cgacgacaa  catctgcctg cgggagccct gcagagaacta    3780
catgcgctgc gtgtcggtgc tgcgcttcga ctcctccgcg cccttcatcg cctcctcctc    3840
cgtgctcttc cggcccatcc acccgtcgg  agggctgcgc tgccgctgcc cgcccggctt    3900
cacgggtgac tactgcgaga ccgaggtgga cctctgctac tcgcggccct gtggccccca    3960
cgggcgctgc cgcagccgcg agggcggcta cacctgcctc tgtcgtgatg gctacacggg    4020
tgagcactgt gaggtgagtg ctcgctcagg ccgttgcacc ccgggtgtct gcaagaatgg    4080
gggcacctgt gtcaacctgc tggtgggcgg tttcaagtgc gattgcccat ctggagactt    4140
cgagaagccc tactgccagg tgaccacgcg cagcttcccc gcccactcct tcatcacctt    4200
tcgcggcctc cgccagcgtt tccacttcac cctggccctc tcgtttgcca caaggagcg    4260
cgacggggttg ctgttgtaca atgggcgttt caatgagaag catgactttg tggccctcga    4320
```

```
ggtgatccag gagcaggtcc agctcacctt ctctgcaggg gagtcaacca ccacggtgtc    4380
cccattcgtg cccggaggag tcagtgatgg ccagtggcat acggtgcagc tgaaatacta    4440
caataagcca ctgttgggtc agacagggct cccacagggc ccatcagagc agaaggtggc    4500
tgtggtgacc gtggatggct gtgacacagg agtggccttg cgcttcggat ctgtcctggg    4560
caactactcc tgtgctgccc agggcaccca gggtggcagc aagaagtctc tggatctgac    4620
gggccccctg ctactaggcg gggtgcctga cctgcccgag agcttccagt ccgaatgcg    4680 gcagttcgtg ggctgcatgc ggaacctgca ggtggacagc cggcacatag acatggctga    4740
cttcattgcc aacaatggca ccgtgcctgg ctgccctgcc aagaagaacg tgtgtgacag    4800
caacacttgc cacaatgggg gcacttgcgt gaaccagtgg gacgcgttca gctgcgagtg    4860
cccccctggg tttgggggca agagctgcgc ccaggaaatg gccaatccac agcacttcct    4920
gggcagcagc ctggtggcct ggcatggcct ctcgctgccc atctcccaac cctggtacct    4980
cagcctcatg ttccgcacgc gccaggccga cggtgtcctg ctgcaggcca tcaccagggg    5040
gcgcagcacc atcaccctac agctacgaga gggccacgtg atgctgagcg tggagggcac    5100
agggcttcag gcctcctctc tccgtctgga gccaggccgg gccaatgacg gtgactggca    5160
ccatgcacag ctggcactgg gagccagcgg ggggcccggc catgccattc tgtccttcga    5220
ttatgggcag cagagagcag agggcaacct gggcccccgg ctgcatggtc tgcacctgag    5280
caacataaca gtgggcggaa tacctgggcc agccggcggt gtggcccgtg gctttcgggg    5340
ctgtttgcag ggtgtgcggg tgagcgatac gccggagggg gttaacagcc tggatcccag    5400
ccatggggag agcatcaacg tggagcaagg ctgtagcctg cctgacccct tgtgactcaaa    5460 cccgtgtcct gctaacagct attgcagcaa cgactgggac agctattcct gcagctgtga    5520
tccaggttac tatggtgaca actgtactaa tgtgtgtgac ctgaacccgt gtgagcacca    5580
gtctgtgtgt acccgcaagc ccagtgcccc ccatggctat acctgcgagt gtccccccaaa    5640 ttaccttggg ccatactgtg agaccaggat tgaccagcct tgtccccgtg gctggtgggg    5700
acatcccaca tgtggcccat gcaactgtga tgtcagcaaa ggctttgacc cagactgcaa    5760
caagacaagc ggcgagtgcc actgcaagga gaaccactac cggcccccag gcagccccac    5820
ctgcctcttg tgtgactgct accccacagg ctccttgtcc agagtctgtg accctgagga    5880
tggccagtgt ccatgcaagc caggtgtcat cgggcgtcag tgtgaccgct gtgacaaccc    5940
ttttgctgag gtcaccacca atggctgtga agtgaattat gacagctgcc cacgagcgat    6000
tgaggctggg atctggtggc cccgtacccg cttcgggctg cctgctgctg ctccctgtcc    6060
caaaggctcc tttgggactg ctgtgcgcca ctgtgatgag cacaggggggt ggctccccc    6120 aaacctcttc aactgcacgt ccatcacctt ctcagaactg aagggcttcg ctgagcggct    6180
acagcggaat gagtcaggcc tagactcagg gcgctcccag cagctagccc tgctcctgcg    6240
caacgccacg cagcacacag ctggctactt cggcagcgac gtcaaggtgg cctaccagct    6300
ggccacgcgg ctgctggccc acgagagcac ccagcggggc tttgggctgt ctgccacaca    6360
ggacgtgcac ttcactgaga atctgctgcg ggtgggcagc gccctcctgg acacagccaa    6420
caagcggcac tgggagctga tccagcagac agagggtggc accgcctggc tgctccagca    6480
ctatgaggcc tacgccagtg ccctggccca gaacatgcgg cacacctacc taagccccctt    6540 caccatcgtc acgcccaaca ttgtcatctc cgtagtgcgc ttggacaaag gaactttgc    6600 tggggccaag ctgcccccgct acgaggccct gcgtggggag cagccccccgg accttgagac    6660
```

```
aacagtcatt ctgcctgagt ctgtcttcag agagacgccc cccgtggtca ggcccgcagg    6720
ccccggagag gcccaggagc cagaggagct ggcacggcga cagcgacggc acccggagct    6780
gagccagggt gaggctgtgg ccagcgtcat catctaccgc accctggccg ggctactgcc    6840
tcataactat gaccctgaca agcgcagctt gagagtcccc aaacgcccga tcatcaacac    6900
acccgtggtg agcatcagcg tccatgatga tgaggagctt ctgccccggg ccctggacaa    6960
acccgtcacg gtgcagttcc gcctgctgga gacagaggag cggaccaagc ccatctgtgt    7020
cttctggaac cattcaatcc tggtcagtgg cacaggtggc tggtcggcca gaggctgtga    7080
agtcgtcttc cgcaatgaga gccacgtcag ctgccagtgc aaccacatga cgagcttcgc    7140
tgtgctcatg gacgtttctc ggcgggagaa tggggagatc ctgccactga agacactgac    7200
atacgtggct ctaggtgtca ccttggctgc ccttctgctc accttcttct tcctcactct    7260
cttgcgtatc ctgcgctcca accaacacgg catccgacgt aacctgacag ctgccctggg    7320
cctggctcag ctggtcttcc tcctgggaat caaccaggct gacctccctt ttgcctgcac    7380
agtcattgcc atcctgctgc acttcctgta cctctgcacc ttttcctggg ctctgctgga    7440
ggccttgcac ctgtaccggg cactcactga ggtgcgcgat gtcaacaccg gccccatgcg    7500
cttctactac atgctgggct ggggcgtgcc tgccttcatc acagggctag ccgtgggcct    7560
ggaccccgag ggctacggga accctgactt ctgctggctc tccatctatg acacgctcat    7620
ctggagtttt gctggcccgg tggcctttgc cgtctcgatg agtgtcttcc tgtacatcct    7680
ggcggcccgg gcctcctgtg ctgcccagcg gcagggcttt gagaagaaag gtcctgtctc    7740
gggcctgcag ccctccttcg ccgtcctcct gctgctgagc gccacgtggc tgctggcact    7800
gctctctgtc aacagcgaca ccctcctctt ccactacctc tttgctacct gcaattgcat    7860
ccagggcccc ttcatcttcc tctcctatgt ggtgcttagc aaggaggtcc ggaaagcact    7920
caagcttgcc tgcagccgca agcccagccc tgaccctgct ctgaccacca agtccaccct    7980
gacctcgtcc tacaactgcc ccagccccta cgcagatggg cggctgtacc agccctacgg    8040
agactcggcc ggctctctgc acagcaccag tcgctcgggc aagagtcagc ccagctacat    8100
ccccttcttg ctgaggagg agtccgcact gaaccctggc caaggccccc ctggcctggg    8160
ggatccaggc agcctgttcc tggaaggtca agaccagcag catgatcctg acacggactc    8220
cgacagtgac ctgtccttag aagacgacca gagtggctcc tatgcctcta cccactcatc    8280
agacagtgag gaggaagaag aggaggagga agaggaggcc gccttccctg agagcagggg    8340
ctgggatagc ctgctggggc ctggagcaga gagactgccc ctgcacagta ctcccaagga    8400 tggggggccca gggcctggca aggccccctg gccaggagac tttgggacca cagcaaaaga    8460
gagtagtggc aacggggccc ctgaggagcg gctgcgggag aatggagatg ccctgtctcg    8520
agaggggtcc ctaggccccc ttccaggctc ttctgcccag cctcacaaag gcatccttaa    8580
gaagaagtgt ctgcccacca tcagcgagaa gagcagcctc ctgcggctcc ccctggagca    8640
atgcacaggg tcttcccggg gctcctccgc tagtgagggc agccggggag ccccccctcc    8700
ccgcccaccg ccccggcaga gcctccagga gcagctgaac ggggtcatgc ccatcgccat    8760
gagcatcaag gcaggcacgg tggatgagga ctcgtcaggc tccgaatttc tcttcttaa     8820 cttcctgcat taaccctggg ccgtggttcc tacgcccgag gctcccttcc cttccccagc    8880
cgcactcatg ccctgctcct gtcttgtgct ttatcctgcc ccgctcccca tcgcctgccc    8940
gcagcagcga cgaaacgtcc atctgaggag cctgggcctt gccgggaggg gtactcaccc    9000 caccctaaggc catctagtgc caactccccc cccaccattc ccctcactgc actttggacc    9060
```

```
cctggggcca acatctccaa gacaaagttt ttcagaaaag aggaaaaaaa gaatttaaaa    9120
aaggatctcc actcttcatg acttcaggga ttcatttttt ttatacgctg gaaattgact    9180
cccctttccc ttcccaaaga ggataggacc tcccaggatg cttcccagcc tctcctcagt    9240
ttcccatctg ctgtgcctct gggaggagag ggactcctgg ggggcctgcc cctcatacgc    9300
catcaccaaa aggaaaggac aaagccacac gcagccaggg cttcacaccc ttcaggctgc    9360
acccgggcag gcctcagaac ggtgaggggc cagggcaaag ggtgtgcctc gtcctgcccg    9420
cactgcctct cccaggaact ggaaaagccc tgtccggtga gggggcagaa ggactcagcg    9480
cccctggacc cccaaatgct gcatgaacac attttcaggg gagcctgtgc ccccaggcgg    9540
gggtcgggca gccccagccc ctctccttt cctggactct ggccgtgcgc ggcagcccag    9600
gtgtttgctc agttgctgac ccaaaagtgc ttcattttc gtgcccgccc cgcgcccgg    9660
gcaggccagt catgtgttaa gttgcgcttc tttgctgtga tgtgggtggg ggaggaagag    9720
taaacacagt gctggctcgg ctgccctgag ggtgctcaat caagcacagg tttcaagtct    9780
gggttctggt gtccactcac ccaccccacc ccccaaaatc agacaaatgc tactttgtct    9840
aacctgctgt ggcctctgag acatgttcta tttttaaccc cttcttggaa ttggctctct    9900
tcttcaaagg accaggtcct gttcctcttt ctccccgact ccaccccagc tccctgtgaa    9960
gagagagtta atatatttgt tttatttatt tgcttttgt gttgggatgg ttcgtgtcc    10020
agtcccgggg gtctgatatg gccatcacag gctgggtgtt cccagcagcc ctggcttggg    10080
ggcttgacgc cctccccctt gccccaggcc atcatctccc cacctctcct ccctctcct    10140
cagttttgcc gactgctttt catctgagtc accatttact ccaagcatgt attccagact    10200
tgtcactgac tttccttctg gagcaggtgg ctagaaaaag aggctgtggg caggaaagaa    10260
aggctcctgt ttctcatttg tgaggccagc ctctggcttt tctgccgtgg attctccccc    10320
gtcttctccc ctcagcaatt cctgcaaagg gttaaaaatt taactggttt ttactactga    10380
tgacttgatt taaaaaaat acaaagatgc tggatgctaa cttggtacta accatcagat    10440
tgtacagttt ggttgttgct gtaaataggg tagcgttttg ttgttgttgt tttttcatgc    10500
cccatactac tgaataaact agttctgtgc gggtacagca                         10540
```

<210> SEQ ID NO 10
<211> LENGTH: 2923
<212> TYPE: PRT
<213> ORGANISM: Homo sapiens

<400> SEQUENCE: 10

Met Arg Ser Pro Ala Thr Gly Val Pro Leu Pro Thr Pro Pro Pro Pro
1               5                   10                  15

Leu Leu Leu Leu Leu Leu Leu Leu Pro Pro Pro Leu Leu Gly Asp
            20                  25                  30

Gln Val Gly Pro Cys Arg Ser Leu Gly Ser Arg Gly Arg Gly Ser Ser
        35                  40                  45

Gly Ala Cys Ala Pro Met Gly Trp Leu Cys Pro Ser Ser Ala Ser Asn
    50                  55                  60

Leu Trp Leu Tyr Thr Ser Arg Cys Arg Asp Ala Gly Thr Glu Leu Thr
65                  70                  75                  80

Gly His Leu Val Pro His His Asp Gly Leu Arg Val Trp Cys Pro Glu
                85                  90                  95

Ser Glu Ala His Ile Pro Leu Pro Pro Ala Pro Glu Gly Cys Pro Trp
            100                 105                 110

```
Ser Cys Arg Leu Leu Gly Ile Gly Gly His Leu Ser Pro Gln Gly Lys
            115                 120                 125

Leu Thr Leu Pro Glu Glu His Pro Cys Leu Lys Ala Pro Arg Leu Arg
        130                 135                 140

Cys Gln Ser Cys Lys Leu Ala Gln Ala Pro Gly Leu Arg Ala Gly Glu
145                 150                 155                 160

Arg Ser Pro Glu Glu Ser Leu Gly Gly Arg Arg Lys Arg Asn Val Asn
                165                 170                 175

Thr Ala Pro Gln Phe Gln Pro Pro Ser Tyr Gln Ala Thr Val Pro Glu
            180                 185                 190

Asn Gln Pro Ala Gly Thr Pro Val Ala Ser Leu Arg Ala Ile Asp Pro
        195                 200                 205

Asp Glu Gly Glu Ala Gly Arg Leu Glu Tyr Thr Met Asp Ala Leu Phe
210                 215                 220

Asp Ser Arg Ser Asn Gln Phe Phe Ser Leu Asp Pro Val Thr Gly Ala
225                 230                 235                 240

Val Thr Thr Ala Glu Glu Leu Asp Arg Glu Thr Lys Ser Thr His Val
                245                 250                 255

Phe Arg Val Thr Ala Gln Asp His Gly Met Pro Arg Arg Ser Ala Leu
            260                 265                 270

Ala Thr Leu Thr Ile Leu Val Thr Asp Thr Asn Asp His Asp Pro Val
        275                 280                 285

Phe Glu Gln Gln Glu Tyr Lys Glu Ser Leu Arg Glu Asn Leu Glu Val
290                 295                 300

Gly Tyr Glu Val Leu Thr Val Arg Ala Thr Asp Gly Asp Ala Pro Pro
305                 310                 315                 320

Asn Ala Asn Ile Leu Tyr Arg Leu Leu Glu Gly Ser Gly Gly Ser Pro
                325                 330                 335

Ser Glu Val Phe Glu Ile Asp Pro Arg Ser Gly Val Ile Arg Thr Arg
            340                 345                 350

Gly Pro Val Asp Arg Glu Glu Val Glu Ser Tyr Gln Leu Thr Val Glu
        355                 360                 365

Ala Ser Asp Gln Gly Arg Asp Pro Gly Pro Arg Ser Thr Thr Ala Ala
370                 375                 380

Val Phe Leu Ser Val Glu Asp Asp Asn Asp Asn Ala Pro Gln Phe Ser
385                 390                 395                 400

Glu Lys Arg Tyr Val Val Gln Val Arg Glu Asp Val Thr Pro Gly Ala
                405                 410                 415

Pro Val Leu Arg Val Thr Ala Ser Asp Arg Asp Lys Gly Ser Asn Ala
            420                 425                 430

Val Val His Tyr Ser Ile Met Ser Gly Asn Ala Arg Gly Gln Phe Tyr
        435                 440                 445

Leu Asp Ala Gln Thr Gly Ala Leu Asp Val Val Ser Pro Leu Asp Tyr
450                 455                 460

Glu Thr Thr Lys Glu Tyr Thr Leu Arg Val Arg Ala Gln Asp Gly Gly
465                 470                 475                 480

Arg Pro Pro Leu Ser Asn Val Ser Gly Leu Val Thr Val Gln Val Leu
                485                 490                 495

Asp Ile Asn Asp Asn Ala Pro Ile Phe Val Ser Thr Pro Phe Gln Ala
            500                 505                 510

Thr Val Leu Glu Ser Val Pro Leu Gly Tyr Leu Val Leu His Val Gln
        515                 520                 525
```

-continued

```
Ala Ile Asp Ala Asp Ala Gly Asp Asn Ala Arg Leu Glu Tyr Arg Leu
    530                 535                 540

Ala Gly Val Gly His Asp Phe Pro Phe Thr Ile Asn Asn Gly Thr Gly
545                 550                 555                 560

Trp Ile Ser Val Ala Ala Glu Leu Asp Arg Glu Glu Val Asp Phe Tyr
                565                 570                 575

Ser Phe Gly Val Glu Ala Arg Asp His Gly Thr Pro Ala Leu Thr Ala
            580                 585                 590

Ser Ala Ser Val Ser Val Thr Val Leu Asp Val Asn Asp Asn Pro
        595                 600                 605

Thr Phe Thr Gln Pro Glu Tyr Thr Val Arg Leu Asn Glu Asp Ala Ala
    610                 615                 620

Val Gly Thr Ser Val Val Thr Val Ser Ala Val Asp Arg Asp Ala His
625                 630                 635                 640

Ser Val Ile Thr Tyr Gln Ile Thr Ser Gly Asn Thr Arg Asn Arg Phe
                645                 650                 655

Ser Ile Thr Ser Gln Ser Gly Gly Leu Val Ser Leu Ala Leu Pro
            660                 665                 670

Leu Asp Tyr Lys Leu Glu Arg Gln Tyr Val Leu Ala Val Thr Ala Ser
        675                 680                 685

Asp Gly Thr Arg Gln Asp Thr Ala Gln Ile Val Val Asn Val Thr Asp
    690                 695                 700

Ala Asn Thr His Arg Pro Val Phe Gln Ser Ser His Tyr Thr Val Asn
705                 710                 715                 720

Val Asn Glu Asp Arg Pro Ala Gly Thr Thr Val Val Leu Ile Ser Ala
                725                 730                 735

Thr Asp Glu Asp Thr Gly Glu Asn Ala Arg Ile Thr Tyr Phe Met Glu
            740                 745                 750

Asp Ser Ile Pro Gln Phe Arg Ile Asp Ala Asp Thr Gly Ala Val Thr
        755                 760                 765

Thr Gln Ala Glu Leu Asp Tyr Glu Asp Gln Val Ser Tyr Thr Leu Ala
    770                 775                 780

Ile Thr Ala Arg Asp Asn Gly Ile Pro Gln Lys Ser Asp Thr Thr Tyr
785                 790                 795                 800

Leu Glu Ile Leu Val Asn Asp Val Asn Asp Asn Ala Pro Gln Phe Leu
                805                 810                 815

Arg Asp Ser Tyr Gln Gly Ser Val Tyr Glu Asp Val Pro Pro Phe Thr
            820                 825                 830

Ser Val Leu Gln Ile Ser Ala Thr Asp Arg Asp Ser Gly Leu Asn Gly
        835                 840                 845

Arg Val Phe Tyr Thr Phe Gln Gly Gly Asp Asp Gly Asp Gly Asp Phe
    850                 855                 860

Ile Val Glu Ser Thr Ser Gly Ile Val Arg Thr Leu Arg Arg Leu Asp
865                 870                 875                 880

Arg Glu Asn Val Ala Gln Tyr Val Leu Arg Ala Tyr Ala Val Asp Lys
                885                 890                 895

Gly Met Pro Pro Ala Arg Thr Pro Met Glu Val Thr Val Thr Val Leu
            900                 905                 910

Asp Val Asn Asp Asn Pro Pro Val Phe Glu Gln Asp Glu Phe Asp Val
        915                 920                 925

Phe Val Glu Glu Asn Ser Pro Ile Gly Leu Ala Val Ala Arg Val Thr
    930                 935                 940

Ala Thr Asp Pro Asp Glu Gly Thr Asn Ala Gln Ile Met Tyr Gln Ile
```

```
                945                 950                 955                 960
         Val Glu Gly Asn Ile Pro Glu Val Phe Gln Leu Asp Ile Phe Ser Gly
                         965                 970                 975
         Glu Leu Thr Ala Leu Val Asp Leu Asp Tyr Glu Asp Arg Pro Glu Tyr
                         980                 985                 990
         Val Leu Val Ile Gln Ala Thr Ser Ala Pro Leu Val Ser Arg Ala Thr
                         995                 1000                1005
         Val His Val Arg Leu Leu Asp Arg Asn Asp Asn Pro Pro Val Leu
                 1010                1015                1020
         Gly Asn Phe Glu Ile Leu Phe Asn Asn Tyr Val Thr Asn Arg Ser
                 1025                1030                1035
         Ser Ser Phe Pro Gly Gly Ala Ile Gly Arg Val Pro Ala His Asp
                 1040                1045                1050
         Pro Asp Ile Ser Asp Ser Leu Thr Tyr Ser Phe Glu Arg Gly Asn
                 1055                1060                1065
         Glu Leu Ser Leu Val Leu Leu Asn Ala Ser Thr Gly Glu Leu Lys
                 1070                1075                1080
         Leu Ser Arg Ala Leu Asp Asn Asn Arg Pro Leu Glu Ala Ile Met
                 1085                1090                1095
         Ser Val Leu Val Ser Asp Gly Val His Ser Val Thr Ala Gln Cys
                 1100                1105                1110
         Ala Leu Arg Val Thr Ile Ile Thr Asp Glu Met Leu Thr His Ser
                 1115                1120                1125
         Ile Thr Leu Arg Leu Glu Asp Met Ser Pro Glu Arg Phe Leu Ser
                 1130                1135                1140
         Pro Leu Leu Gly Leu Phe Ile Gln Ala Val Ala Ala Thr Leu Ala
                 1145                1150                1155
         Thr Pro Pro Asp His Val Val Val Phe Asn Val Gln Arg Asp Thr
                 1160                1165                1170
         Asp Ala Pro Gly Gly His Ile Leu Asn Val Ser Leu Ser Val Gly
                 1175                1180                1185
         Gln Pro Pro Gly Pro Gly Gly Pro Pro Phe Leu Pro Ser Glu
                 1190                1195                1200
         Asp Leu Gln Glu Arg Leu Tyr Leu Asn Arg Ser Leu Leu Thr Ala
                 1205                1210                1215
         Ile Ser Ala Gln Arg Val Leu Pro Phe Asp Asp Asn Ile Cys Leu
                 1220                1225                1230
         Arg Glu Pro Cys Glu Asn Tyr Met Arg Cys Val Ser Val Leu Arg
                 1235                1240                1245
         Phe Asp Ser Ser Ala Pro Phe Ile Ala Ser Ser Val Leu Phe
                 1250                1255                1260
         Arg Pro Ile His Pro Val Gly Gly Leu Arg Cys Arg Cys Pro Pro
                 1265                1270                1275
         Gly Phe Thr Gly Asp Tyr Cys Glu Thr Glu Val Asp Leu Cys Tyr
                 1280                1285                1290
         Ser Arg Pro Cys Gly Pro His Gly Arg Cys Arg Ser Arg Glu Gly
                 1295                1300                1305
         Gly Tyr Thr Cys Leu Cys Arg Asp Gly Tyr Thr Gly Glu His Cys
                 1310                1315                1320
         Glu Val Ser Ala Arg Ser Gly Arg Cys Thr Pro Gly Val Cys Lys
                 1325                1330                1335
         Asn Gly Gly Thr Cys Val Asn Leu Leu Val Gly Gly Phe Lys Cys
                 1340                1345                1350
```

```
Asp Cys Pro Ser Gly Asp Phe Glu Lys Pro Tyr Cys Gln Val Thr
    1355                1360                1365

Thr Arg Ser Phe Pro Ala His Ser Phe Ile Thr Phe Arg Gly Leu
    1370                1375                1380

Arg Gln Arg Phe His Phe Thr Leu Ala Leu Ser Phe Ala Thr Lys
    1385                1390                1395

Glu Arg Asp Gly Leu Leu Leu Tyr Asn Gly Arg Phe Asn Glu Lys
    1400                1405                1410

His Asp Phe Val Ala Leu Glu Val Ile Gln Glu Gln Val Gln Leu
    1415                1420                1425

Thr Phe Ser Ala Gly Glu Ser Thr Thr Thr Val Ser Pro Phe Val
    1430                1435                1440

Pro Gly Gly Val Ser Asp Gly Gln Trp His Thr Val Gln Leu Lys
    1445                1450                1455

Tyr Tyr Asn Lys Pro Leu Leu Gly Gln Thr Gly Leu Pro Gln Gly
    1460                1465                1470

Pro Ser Glu Gln Lys Val Ala Val Val Thr Val Asp Gly Cys Asp
    1475                1480                1485

Thr Gly Val Ala Leu Arg Phe Gly Ser Val Leu Gly Asn Tyr Ser
    1490                1495                1500

Cys Ala Ala Gln Gly Thr Gln Gly Gly Ser Lys Lys Ser Leu Asp
    1505                1510                1515

Leu Thr Gly Pro Leu Leu Leu Gly Gly Val Pro Asp Leu Pro Glu
    1520                1525                1530

Ser Phe Pro Val Arg Met Arg Gln Phe Val Gly Cys Met Arg Asn
    1535                1540                1545

Leu Gln Val Asp Ser Arg His Ile Asp Met Ala Asp Phe Ile Ala
    1550                1555                1560

Asn Asn Gly Thr Val Pro Gly Cys Pro Ala Lys Lys Asn Val Cys
    1565                1570                1575

Asp Ser Asn Thr Cys His Asn Gly Gly Thr Cys Val Asn Gln Trp
    1580                1585                1590

Asp Ala Phe Ser Cys Glu Cys Pro Leu Gly Phe Gly Gly Lys Ser
    1595                1600                1605

Cys Ala Gln Glu Met Ala Asn Pro Gln His Phe Leu Gly Ser Ser
    1610                1615                1620

Leu Val Ala Trp His Gly Leu Ser Leu Pro Ile Ser Gln Pro Trp
    1625                1630                1635

Tyr Leu Ser Leu Met Phe Arg Thr Arg Gln Ala Asp Gly Val Leu
    1640                1645                1650

Leu Gln Ala Ile Thr Arg Gly Arg Ser Thr Ile Thr Leu Gln Leu
    1655                1660                1665

Arg Glu Gly His Val Met Leu Ser Val Glu Gly Thr Gly Leu Gln
    1670                1675                1680

Ala Ser Ser Leu Arg Leu Glu Pro Gly Arg Ala Asn Asp Gly Asp
    1685                1690                1695

Trp His His Ala Gln Leu Ala Leu Gly Ala Ser Gly Gly Pro Gly
    1700                1705                1710

His Ala Ile Leu Ser Phe Asp Tyr Gly Gln Gln Arg Ala Glu Gly
    1715                1720                1725

Asn Leu Gly Pro Arg Leu His Gly Leu His Leu Ser Asn Ile Thr
    1730                1735                1740
```

```
Val Gly Gly Ile Pro Gly Pro Ala Gly Gly Val Ala Arg Gly Phe
1745             1750                 1755

Arg Gly Cys Leu Gln Gly Val Arg Val Ser Asp Thr Pro Glu Gly
1760             1765                 1770

Val Asn Ser Leu Asp Pro Ser His Gly Glu Ser Ile Asn Val Glu
1775             1780                 1785

Gln Gly Cys Ser Leu Pro Asp Pro Cys Asp Ser Asn Pro Cys Pro
1790             1795                 1800

Ala Asn Ser Tyr Cys Ser Asn Asp Trp Asp Ser Tyr Ser Cys Ser
1805             1810                 1815

Cys Asp Pro Gly Tyr Tyr Gly Asp Asn Cys Thr Asn Val Cys Asp
1820             1825                 1830

Leu Asn Pro Cys Glu His Gln Ser Val Cys Thr Arg Lys Pro Ser
1835             1840                 1845

Ala Pro His Gly Tyr Thr Cys Glu Cys Pro Pro Asn Tyr Leu Gly
1850             1855                 1860

Pro Tyr Cys Glu Thr Arg Ile Asp Gln Pro Cys Pro Arg Gly Trp
1865             1870                 1875

Trp Gly His Pro Thr Cys Gly Pro Cys Asn Cys Asp Val Ser Lys
1880             1885                 1890

Gly Phe Asp Pro Asp Cys Asn Lys Thr Ser Gly Glu Cys His Cys
1895             1900                 1905

Lys Glu Asn His Tyr Arg Pro Pro Gly Ser Pro Thr Cys Leu Leu
1910             1915                 1920

Cys Asp Cys Tyr Pro Thr Gly Ser Leu Ser Arg Val Cys Asp Pro
1925             1930                 1935

Glu Asp Gly Gln Cys Pro Cys Lys Pro Gly Val Ile Gly Arg Gln
1940             1945                 1950

Cys Asp Arg Cys Asp Asn Pro Phe Ala Glu Val Thr Thr Asn Gly
1955             1960                 1965

Cys Glu Val Asn Tyr Asp Ser Cys Pro Arg Ala Ile Glu Ala Gly
1970             1975                 1980

Ile Trp Trp Pro Arg Thr Arg Phe Gly Leu Pro Ala Ala Ala Pro
1985             1990                 1995

Cys Pro Lys Gly Ser Phe Gly Thr Ala Val Arg His Cys Asp Glu
2000             2005                 2010

His Arg Gly Trp Leu Pro Pro Asn Leu Phe Asn Cys Thr Ser Ile
2015             2020                 2025

Thr Phe Ser Glu Leu Lys Gly Phe Ala Glu Arg Leu Gln Arg Asn
2030             2035                 2040

Glu Ser Gly Leu Asp Ser Gly Arg Ser Gln Gln Leu Ala Leu Leu
2045             2050                 2055

Leu Arg Asn Ala Thr Gln His Thr Ala Gly Tyr Phe Gly Ser Asp
2060             2065                 2070

Val Lys Val Ala Tyr Gln Leu Ala Thr Arg Leu Leu Ala His Glu
2075             2080                 2085

Ser Thr Gln Arg Gly Phe Gly Leu Ser Ala Thr Gln Asp Val His
2090             2095                 2100

Phe Thr Glu Asn Leu Leu Arg Val Gly Ser Ala Leu Leu Asp Thr
2105             2110                 2115

Ala Asn Lys Arg His Trp Glu Leu Ile Gln Gln Thr Glu Gly Gly
2120             2125                 2130

Thr Ala Trp Leu Leu Gln His Tyr Glu Ala Tyr Ala Ser Ala Leu
```

-continued

```
            2135                2140                2145
Ala Gln Asn Met Arg His Thr Tyr Leu Ser Pro Phe Thr Ile Val
    2150                2155                2160
Thr Pro Asn Ile Val Ile Ser Val Val Arg Leu Asp Lys Gly Asn
    2165                2170                2175
Phe Ala Gly Ala Lys Leu Pro Arg Tyr Glu Ala Leu Arg Gly Glu
    2180                2185                2190
Gln Pro Pro Asp Leu Glu Thr Thr Val Ile Leu Pro Glu Ser Val
    2195                2200                2205
Phe Arg Glu Thr Pro Pro Val Val Arg Pro Ala Gly Pro Gly Glu
    2210                2215                2220
Ala Gln Glu Pro Glu Glu Leu Ala Arg Arg Gln Arg Arg His Pro
    2225                2230                2235
Glu Leu Ser Gln Gly Glu Ala Val Ala Ser Val Ile Ile Tyr Arg
    2240                2245                2250
Thr Leu Ala Gly Leu Leu Pro His Asn Tyr Asp Pro Asp Lys Arg
    2255                2260                2265
Ser Leu Arg Val Pro Lys Arg Pro Ile Ile Asn Thr Pro Val Val
    2270                2275                2280
Ser Ile Ser Val His Asp Asp Glu Glu Leu Leu Pro Arg Ala Leu
    2285                2290                2295
Asp Lys Pro Val Thr Val Gln Phe Arg Leu Leu Glu Thr Glu Glu
    2300                2305                2310
Arg Thr Lys Pro Ile Cys Val Phe Trp Asn His Ser Ile Leu Val
    2315                2320                2325
Ser Gly Thr Gly Gly Trp Ser Ala Arg Gly Cys Glu Val Val Phe
    2330                2335                2340
Arg Asn Glu Ser His Val Ser Cys Gln Cys Asn His Met Thr Ser
    2345                2350                2355
Phe Ala Val Leu Met Asp Val Ser Arg Arg Glu Asn Gly Glu Ile
    2360                2365                2370
Leu Pro Leu Lys Thr Leu Thr Tyr Val Ala Leu Gly Val Thr Leu
    2375                2380                2385
Ala Ala Leu Leu Leu Thr Phe Phe Leu Thr Leu Leu Arg Ile
    2390                2395                2400
Leu Arg Ser Asn Gln His Gly Ile Arg Arg Asn Leu Thr Ala Ala
    2405                2410                2415
Leu Gly Leu Ala Gln Leu Val Phe Leu Leu Gly Ile Asn Gln Ala
    2420                2425                2430
Asp Leu Pro Phe Ala Cys Thr Val Ile Ala Ile Leu Leu His Phe
    2435                2440                2445
Leu Tyr Leu Cys Thr Phe Ser Trp Ala Leu Leu Glu Ala Leu His
    2450                2455                2460
Leu Tyr Arg Ala Leu Thr Glu Val Arg Asp Val Asn Thr Gly Pro
    2465                2470                2475
Met Arg Phe Tyr Tyr Met Leu Gly Trp Gly Val Pro Ala Phe Ile
    2480                2485                2490
Thr Gly Leu Ala Val Gly Leu Asp Pro Glu Gly Tyr Gly Asn Pro
    2495                2500                2505
Asp Phe Cys Trp Leu Ser Ile Tyr Asp Thr Leu Ile Trp Ser Phe
    2510                2515                2520
Ala Gly Pro Val Ala Phe Ala Val Ser Met Ser Val Phe Leu Tyr
    2525                2530                2535
```

```
Ile Leu Ala Ala Arg Ala Ser Cys Ala Ala Gln Arg Gln Gly Phe
        2540                2545                2550

Glu Lys Lys Gly Pro Val Ser Gly Leu Gln Pro Ser Phe Ala Val
        2555                2560                2565

Leu Leu Leu Leu Ser Ala Thr Trp Leu Leu Ala Leu Leu Ser Val
        2570                2575                2580

Asn Ser Asp Thr Leu Leu Phe His Tyr Leu Phe Ala Thr Cys Asn
        2585                2590                2595

Cys Ile Gln Gly Pro Phe Ile Phe Leu Ser Tyr Val Val Leu Ser
        2600                2605                2610

Lys Glu Val Arg Lys Ala Leu Lys Leu Ala Cys Ser Arg Lys Pro
        2615                2620                2625

Ser Pro Asp Pro Ala Leu Thr Thr Lys Ser Thr Leu Thr Ser Ser
        2630                2635                2640

Tyr Asn Cys Pro Ser Pro Tyr Ala Asp Gly Arg Leu Tyr Gln Pro
        2645                2650                2655

Tyr Gly Asp Ser Ala Gly Ser Leu His Ser Thr Ser Arg Ser Gly
        2660                2665                2670

Lys Ser Gln Pro Ser Tyr Ile Pro Phe Leu Leu Arg Glu Glu Ser
        2675                2680                2685

Ala Leu Asn Pro Gly Gln Gly Pro Pro Gly Leu Gly Asp Pro Gly
        2690                2695                2700

Ser Leu Phe Leu Glu Gly Gln Asp Gln Gln His Asp Pro Asp Thr
        2705                2710                2715

Asp Ser Asp Ser Asp Leu Ser Leu Glu Asp Asp Gln Ser Gly Ser
        2720                2725                2730

Tyr Ala Ser Thr His Ser Ser Asp Ser Glu Glu Glu Glu Glu Glu
        2735                2740                2745

Glu Glu Glu Glu Ala Ala Phe Pro Gly Glu Gln Gly Trp Asp Ser
        2750                2755                2760

Leu Leu Gly Pro Gly Ala Glu Arg Leu Pro Leu His Ser Thr Pro
        2765                2770                2775

Lys Asp Gly Gly Pro Gly Pro Gly Lys Ala Pro Trp Pro Gly Asp
        2780                2785                2790

Phe Gly Thr Thr Ala Lys Glu Ser Ser Gly Asn Gly Ala Pro Glu
        2795                2800                2805

Glu Arg Leu Arg Glu Asn Gly Asp Ala Leu Ser Arg Glu Gly Ser
        2810                2815                2820

Leu Gly Pro Leu Pro Gly Ser Ser Ala Gln Pro His Lys Gly Ile
        2825                2830                2835

Leu Lys Lys Lys Cys Leu Pro Thr Ile Ser Glu Lys Ser Ser Leu
        2840                2845                2850

Leu Arg Leu Pro Leu Glu Gln Cys Thr Gly Ser Ser Arg Gly Ser
        2855                2860                2865

Ser Ala Ser Glu Gly Ser Arg Gly Gly Pro Pro Arg Pro Pro
        2870                2875                2880

Pro Arg Gln Ser Leu Gln Glu Gln Leu Asn Gly Val Met Pro Ile
        2885                2890                2895

Ala Met Ser Ile Lys Ala Gly Thr Val Asp Glu Asp Ser Ser Gly
        2900                2905                2910

Ser Glu Phe Leu Phe Phe Asn Phe Leu His
        2915                2920
```

<210> SEQ ID NO 11
<211> LENGTH: 2091
<212> TYPE: DNA
<213> ORGANISM: Homo sapiens

<400> SEQUENCE: 11

```
cgctgtgccc cgattccgcg tcgggctgcg cgggcggcca gcggttcagg cgcgcgcgga      60
gagctctggc tcagagtttg cgatccgaga gcgggatccg cgctccctcg gtccttcctc     120
cctcccctct tgcggcctcc cgctgtcatc tggagccgct cctgccgccc cctggcggcg     180
accgcgggaa gggccggccc ccatccgcac ccctgacccc ggaggtcaac aacgggatgg     240
tccctgggtc ccaggggaag agacatcacc cagtaggagg gagtacggtc tagacagagg     300
ccacgagggc gggaggggc gagagtggag agtggcccag ctggccaggg tcgtctaagt      360
gagaggaaaa gggagagggc ggttgagacc aggccctgaa ttccgcgttc atcttatcct     420
gaggtctgtg gggacctgtt gaaggactgg ggcaggggac ggacgcgggc atccttccat     480
ttggaacagc cattccggca gcatcaggat ggggcggagg caaagcgggg agtgggcgag     540
gcaagtggtg ctgtaaacct gtgcgagaag ggggcggtga ctctaagggc aggaaggagc     600
cctggtcaca cacacactcc cacgcaaggt attcagtgcc gagtgtggcc ttggtgctag     660
gattcaaaga ggaaaggaag aaaactttcc attctaaaag aaactccacg tgaggcgaag     720
aagatgaaat atagtcagaa aaccatacca gtaggtggta gttaagttga taaatgatgc     780
atacgacatc ctatagaaga ctgtcaccac cccacctcac tgatcagccc tctgcctaca     840
gccacaccca cagaacattc agccatttct cctgtggttc ccagcctgca gcacagcgtc     900
tgcacgtgga actctggaat gctgacctac agtctgagtt cctgtgccct gcctggggc      960
tgactctcta cttgacctgt aacccacaac tgggcaagag aaaattctgc agccacagct    1020
ctgaggacat gagcaaaatg gtttccagac ggaatgtcaa ggattcccat gaagtgtcag    1080
ggagtcttca ggccacactt caggttatct ccttctcttt ccctttctg cttcacactt     1140
gctctcatcc tctttctcac cccacatctg gtcagaggag ataggaaggt tcttgttacc    1200
tggtacaaga caacttttgg aatcccagat attcagatta tttccccttt tcctctttgc    1260
aaatgataat actcacagcc aagaggcatc acccggatcc gaggctgctt ctccttagga    1320
catgcagaca gaaggagaag gcggggctgg cagcctccag tccacagcct cccttcttc     1380
ttccggcgat gattaactag gcctagacaa tggagatcta cggcatacgc ccagggcctc    1440
ctcttctcaa gcatggctga tcagtcactt tcccgtctat ccttcattta ttgaagccaa    1500
ctatgaacga ctaaaggaag gatgagaaaa gtcacccaaa gtcaaggggg acagcgtggg    1560
agactgttct agacagaagg aaacaccttt gcaaagaccc tgaggaaggc aggggactct    1620
ccaggagcag aagggctgtg tggcttcaga gtccacaaaa gagagcagat acaggacact    1680
ggctagagca ggccctggag cccgctgctg tcctggaggc cttggggagg cccagtgttc    1740
ccagggtgga agaagtaggg gacagcttga cgtagtggct gttgatcagc tgatatggaa    1800
gtatgtcatt ttattaacaa ttgagaaagg agtgctgtgc aattccattc aatgccagtg    1860
atgcttatgg ccgtttttat gagttctgtc attttcaaat gagcaagagg aagcctctaa    1920
gggggtttaa gcagggactg acgtaatcag atctgtgttt ttccaaaggg agaggagaa     1980
aaagaacatt tcttattttt caaaaaaggt aatgcaaaag catcattcca caattctctt    2040
gtaatgaaaa aataaatgc aaacttaagc aaatccatca ttctgaaaga a              2091
```

```
<210> SEQ ID NO 12
<211> LENGTH: 136
<212> TYPE: PRT
<213> ORGANISM: Homo sapiens

<400> SEQUENCE: 12

Met Met His Thr Thr Ser Tyr Arg Arg Leu Ser Pro Pro His Leu Thr
1               5                   10                  15

Asp Gln Pro Ser Ala Tyr Ser His Thr His Arg Thr Phe Ser His Phe
                20                  25                  30

Ser Cys Gly Ser Gln Pro Ala Ala Gln Arg Leu His Val Glu Leu Trp
            35                  40                  45

Asn Ala Asp Leu Gln Ser Glu Phe Leu Cys Pro Cys Leu Gly Leu Thr
        50                  55                  60

Leu Tyr Leu Thr Cys Asn Pro Gln Leu Gly Lys Arg Lys Phe Cys Ser
65                  70                  75                  80

His Ser Ser Glu Asp Met Ser Lys Met Val Ser Arg Arg Asn Val Lys
                85                  90                  95

Asp Ser His Glu Val Ser Gly Ser Leu Gln Ala Thr Leu Gln Val Ile
                100                 105                 110

Ser Phe Phe Pro Phe Pro Leu Leu His Thr Cys Ser His Pro Leu Ser
            115                 120                 125

His Pro Thr Ser Gly Gln Arg Arg
        130                 135

<210> SEQ ID NO 13
<211> LENGTH: 3715
<212> TYPE: DNA
<213> ORGANISM: Homo sapiens

<400> SEQUENCE: 13 cctacccag  ctctcgcgcc  gcgtgcagag  gtgctcaagc  ctcctcgcgg  tccgcagtca     60
gtgccgccgc  gccggcctc  ccgcacgccc  cgcaggtagc  gccccgccc  gcggcccaga    120
gtgcgctcgc  gccggcacca  gctcccggat  aaacggcgcg  ccgcgcggag  atgacagccg    180
aggagatgaa  ggcgaccgag  agcggggcgc  agtcggcgcc  gctgcccatg  gagggagtgg    240
acatcagccc  caaacaggac  gaaggcgtgc  tgaaggtcat  caagagagag  ggcacaggta    300
cagagatgcc  catgattggg  gaccgagtct  tgtccacta  cactggctgg  ctattagatg    360
gcacaaagtt  tgactccagt  ctggatcgca  aggacaaatt  ctcctttgac  ctgggaaaag    420
gggaggtcat  caaggcttgg  gacattgcca  tagccaccat  gaaggtgggg  gaggtgtgcc    480
acatcacctg  caaaccagaa  tatgcctacg  gttcagcagg  cagtcctcca  aagattcccc    540
ccaatgccac  gcttgtattt  gaggtggagt  tgtttgagtt  taaggagaa   atctgacgg    600
aagaggaaga  tggcggaatc  attcgcagaa  tacagactcg  cggtgaaggc  tatgctaagc    660
ccaatgaggg  tgctatcgtg  gaggttcac  tggaagggta  ctacaaggac  aagctctttg    720
accagcggga  gctccgcttt  gagattggcg  aggggagaa   cctggatctg  ccttatggtc    780
tggagagggc  cattcagcgc  atggagaaag  agaacattc   catcgtgtac  ctcaagccca    840
gctatgcttt  tggcagtgtt  gggaaggaa   agttccaaat  cccaccaaat  gctgagctga    900
aatatgaatt  acacctcaag  agttttgaaa  aggccaagga  gtcttgggag  atgaattcag    960
aagagaagct  ggaacagagc  accatagtga  aagagcgggg  cactgtgtac  ttcaaggaag   1020
gtaaatacaa  gcaagcttta  ctacagtata  agaagatcgt  gtcttggctg  aatatgagt   1080
ctagttttc   caatgaggaa  gcacagaaag  cacaggccct  tcgactggcc  tctcacctca   1140
```

```
acctggccat gtgtcatctg aaactacagg ccttctctgc tgccattgaa agctgtaaca    1200
aggccctaga actggacagc aacaacgaga agggcctctt ccgccgggga gaggcccacc    1260
tggccgtgaa tgactttgaa ctggcacggg ctgatttcca gaaggtcctg cagctctacc    1320
ccaacaacaa agccgccaag cccagctggg ctgtgtgcca gcagcggatc cgaaggcagc    1380
ttgcccggga gaagaagctc tatgccaata tgtttgagag gctggctgag gaggagaaca    1440
aggccaaggc agaggcttcc tcaggagacc atcccactga cacagagatg aaggaggagc    1500
agaagagcaa cacggcaggg agccagtctc aggtggagac agaagcatag cccctctcca    1560
ccagccctac tcctgcggct gcctgccccc cagtctcccc actccaccct gttagttttg    1620
taaaaactga agaattttga gtgaattaga ccttattttt tctatctggt tggatggtgg    1680
ctttagggga aggggaaag gtgtaggctg ggggattgag gtggggaatc attttagctg    1740
gtgtcagccc ctcttccctt cctccattgc acatgaacat atgtccatcc atatatattc    1800
atcagaatgt taatttattt tgctccctct gttaggtcca ttttctaagg gtagaagagg    1860
caagtggtag ggatgaggtc tgataagaac ccagggtgga gagggagact cctgggcagc    1920
cgttttcctc atcctttccc tctcccagtc catttccaaa tgtggcctcc atgtgggtgc    1980
tagggacatg ggaaaaacca ctgctatgcc atttcttctc tctgttccct tcctcacccc    2040
cgacggtgtg gctgatgatg tcttctggtg tcatggtgac caccccctgt tccctgttct    2100
ggtatttccc ctgtcagttt cccctctcgg ccaggttgtg tcccaaaatc ccctcagcct    2160
cttctctgca cgttgctgaa ggtccaggct tgcctcaagt tccatgcttg agcaataaag    2220
tggaaacaat aaaacctggg tgtcagacaa ccctttctgt tcagccttgg agtggtgggt    2280
atgggtgggt acataatggg tagtagcaca atcaagggt cacccactta gttccagttg    2340
agcttaaata agtgagcatc tcatgtagat gccatagttg ggcaggaagc agccccacca    2400
tgcatggctt cctgagcact gcacaggctg ccgctgggat ttgtgtctat ggcttcgccc    2460
aaggttccca gcactccctc cctccagcaa cctggcagtt ttagtgcctc tggttttctt    2520
ccctgacact taggaagacg aaagtataaa gatctagaag actgggacac catgcatgtt    2580
cattttgaag ttggaattgg tcttctgcct acctctgatc tggcagaggt atctgcattt    2640
tggtttgtta acaaggtaaa actcctggtg tcactgacct cctcctgtca gataacttac    2700
atgattaagg ttaagagtaa agcagagtgt tcacgtccag cttccttctc agccttaaca    2760
ggaaaaggct tgtgcttttt ttctaactat gctttgaccc ttaactccta tggcatgatg    2820
gggccctggg agaagccagg cagcacaagc cagtcatgct gagctgcctc cagataatcc    2880
tggctccagg ccagagcccg tgtctgccct catccctctc tcctactgtg agctctccag    2940
tcctttccca acagcgatgt ggttgtctgc ttagccacat gcctgtatag ttccttccag    3000
aagaaatgta taatggtgga agatgtattt ctgtgtgaaa attttcacca agtcatacaa    3060
cacagctgat gctggagcca ggattaaaat tggggtgtac aagtctccca gtgtgagtat    3120
cccttgagcc caagacacca aggatgcaga gaactgtgac tgtgccactg cacgccagcc    3180
tgggcaagag agtgagacca tctctttttt aaaaaagtcc ctgtgtaact gctttcttac    3240
tgggcttacc tcacatcaca gccctgtgtt tgtggtttgt gtctgggtcc tcttggtatt    3300
tcaaaagtag tagattctta cgcctgcagc caacaataat cactaactca agcatttatg    3360
gagtaagcct agcactgtac tgacagcatc acatgagtga aactgaatcc ttgcaaccat    3420
cctacaaaga aggtataact ttaataaccc tatttacaga taagaaaacc aagactcaga    3480
```

-continued

```
agttaaatgg aaaggtgagg tctctgaact aatccagact ctcccatgag gttcctttgg    3540
caagtcctgg gcttctgtcc tcatctgcaa aatcgaaagc attcctgagg tttcttccag    3600
ctctgcatcc tgtaggattc caagaatgta aaactgcatg taaccgtgga acatctagag    3660
ataagtctta gtttatgtaa cattaaaact gtctagtgag gatgttttgt taaaa         3715
```

<210> SEQ ID NO 14
<211> LENGTH: 459
<212> TYPE: PRT
<213> ORGANISM: Homo sapiens

<400> SEQUENCE: 14

```
Met Thr Ala Glu Glu Met Lys Ala Thr Glu Ser Gly Ala Gln Ser Ala
1               5                   10                  15

Pro Leu Pro Met Glu Gly Val Asp Ile Ser Pro Lys Gln Asp Glu Gly
            20                  25                  30

Val Leu Lys Val Ile Lys Arg Glu Gly Thr Gly Thr Glu Met Pro Met
        35                  40                  45

Ile Gly Asp Arg Val Phe Val His Tyr Thr Gly Trp Leu Leu Asp Gly
    50                  55                  60

Thr Lys Phe Asp Ser Ser Leu Asp Arg Lys Asp Lys Phe Ser Phe Asp
65                  70                  75                  80

Leu Gly Lys Gly Glu Val Ile Lys Ala Trp Asp Ile Ala Ile Ala Thr
                85                  90                  95

Met Lys Val Gly Glu Val Cys His Ile Thr Cys Lys Pro Glu Tyr Ala
            100                 105                 110

Tyr Gly Ser Ala Gly Ser Pro Pro Lys Ile Pro Pro Asn Ala Thr Leu
        115                 120                 125

Val Phe Glu Val Glu Leu Phe Glu Phe Lys Gly Glu Asp Leu Thr Glu
    130                 135                 140

Glu Glu Asp Gly Gly Ile Ile Arg Arg Ile Gln Thr Arg Gly Glu Gly
145                 150                 155                 160

Tyr Ala Lys Pro Asn Glu Gly Ala Ile Val Glu Val Ala Leu Glu Gly
                165                 170                 175

Tyr Tyr Lys Asp Lys Leu Phe Asp Gln Arg Glu Leu Arg Phe Glu Ile
            180                 185                 190

Gly Glu Gly Glu Asn Leu Asp Leu Pro Tyr Gly Leu Glu Arg Ala Ile
        195                 200                 205

Gln Arg Met Glu Lys Gly Glu His Ser Ile Val Tyr Leu Lys Pro Ser
    210                 215                 220

Tyr Ala Phe Gly Ser Val Gly Lys Glu Lys Phe Gln Ile Pro Pro Asn
225                 230                 235                 240

Ala Glu Leu Lys Tyr Glu Leu His Leu Lys Ser Phe Glu Lys Ala Lys
                245                 250                 255

Glu Ser Trp Glu Met Asn Ser Glu Glu Lys Leu Glu Gln Ser Thr Ile
            260                 265                 270

Val Lys Glu Arg Gly Thr Val Tyr Phe Lys Glu Gly Lys Tyr Lys Gln
        275                 280                 285

Ala Leu Leu Gln Tyr Lys Lys Ile Val Ser Trp Leu Glu Tyr Glu Ser
    290                 295                 300

Ser Phe Ser Asn Glu Glu Ala Gln Lys Ala Gln Ala Leu Arg Leu Ala
305                 310                 315                 320

Ser His Leu Asn Leu Ala Met Cys His Leu Lys Leu Gln Ala Phe Ser
                325                 330                 335
```

```
Ala Ala Ile Glu Ser Cys Asn Lys Ala Leu Glu Leu Asp Ser Asn Asn
            340                 345                 350

Glu Lys Gly Leu Phe Arg Arg Gly Glu Ala His Leu Ala Val Asn Asp
        355                 360                 365

Phe Glu Leu Ala Arg Ala Asp Phe Gln Lys Val Leu Gln Leu Tyr Pro
    370                 375                 380

Asn Asn Lys Ala Ala Lys Thr Gln Leu Ala Val Cys Gln Gln Arg Ile
385                 390                 395                 400

Arg Arg Gln Leu Ala Arg Glu Lys Lys Leu Tyr Ala Asn Met Phe Glu
                405                 410                 415

Arg Leu Ala Glu Glu Glu Asn Lys Ala Lys Ala Glu Ala Ser Ser Gly
            420                 425                 430

Asp His Pro Thr Asp Thr Glu Met Lys Glu Glu Gln Lys Ser Asn Thr
        435                 440                 445

Ala Gly Ser Gln Ser Gln Val Glu Thr Glu Ala
    450                 455

<210> SEQ ID NO 15
<211> LENGTH: 13546
<212> TYPE: DNA
<213> ORGANISM: Homo sapiens

<400> SEQUENCE: 15
ggaggtcggc gcagctgccc ctttgggctt tggctctgga ctggagcgca gcatccttcg      60
aggctgcagc cgccacggct gttgccgtaa gcaatcctcc tgcctcagcc tcccgagtag     120
ctgggactcg ggaccagcct cccgagtatt ggtcagatga catttaccat caccgttttc     180
ttcttctttc atcatcatca tcatcaccat tgccactacc accacctcca aggccactac     240
caccacagca tctctgttcc tccatcagag ctcttcaagt tctgtaaagg cagattctct     300
aaaggcatgc ctggtggcat cacgtttttc acatctccgc atctggaccc tgcccaagcg     360
aaggctgatc taggcagtct cattgctgga gatgactgtc agctgctttc tctgcatagc     420
caccatcaca tgcctcacca ctggagcctg gaagcctga  ccacaaaccg catctccaa     480 ggcatgaata attaggtagg cataatggaa ggcactcatt gtaccctcca attgcataag     540
cccattacgg aactctgcta catcagcttc tgtcttccaa agggggaagt cagaggattt     600
tcatacaagg gcactgtaac tctagacaga tccaataaag gttttcataa ctgctaccaa     660
gtcagggagg agtcagacat catcagcctc agccaggagc cggacgaaca tccaggcgac     720 atattttca agcagactcc cacgaaagac attctaactg agctgtacaa actcacaaca     780
gagagggaga gactgctaac caatctcctg agctcagacc acatcctggg gatcacgatg     840
gggaaccagg aggggaagct gcaagagctg tccgtgagcc tggcccccga ggatgactgt     900
ttccagagtg ctggtgactg gcagggagag ctccccgtgg gccctctcaa taagaggagc     960
acccacggga caaaaagcc tcggaggtct agtggaagga gagagagctt tggggcccctt    1020 ccacagaaga ggaccaaaag aaaagggcgt ggaggccgag aatcagctcc tctgatgggc    1080
aaggacaaga tctgttccag ccactccctt cctctttcta gaacaaggcc taacctttgg    1140
gtactagagg agaaaggaaa tctgctcccg aatggggcac ttgcctgctc cctgcagagg    1200
agagagagct gccccccaga tattcccaag acgccagaca cagaccttgg ctttgggagc    1260
tttgagacgg ctttcaagga cactgggctt ggaagagaag tgctgccccc tgactgcagc    1320
tccacagagg caggagggga tggcattcgg aggccgccga gcgggctgga gcatcagcaa    1380
acaggtttgt ctgaaagtca ccaggaccct gagaagcatc cagaggcaga aaaggatgag    1440
```

```
atggagaagc cggctaagcg gacttgcaag cagaaacctg tctccaaagt ggtggccaaa    1500
gttcaggacc tgtcctccca ggtacaaaga gtagttaaaa cgcattctaa gggtaaggag    1560
acgattgcca ttcgcccagc agcccacgct gagtttgtac ccaaagccga cttgctcacc    1620
ctcccgggag ctgaggctgg ggctcatggc tccaggcggc agggcaagga gcggcaaggg    1680
gataggtcat cgcagtcgcc agccggggaa acagcctcca tttctagtgt gtcggccagt    1740
gccgaggggg ccgtgaacaa ggtcccoctg aaggtgatag agagtgagaa gttagatgaa    1800
gcccctgagg ggaaaagact gggcttccct gtccacacga gtgtccctca cactcgccca    1860
gaaacgagaa acaagaggag agccgggttg ccccttggtg ccacaagtc cttgtttctg    1920 gatctgcccc acaaagtagg tcctgactcc tcacaaccca gaggtgataa aagaagcca    1980 tccccaccag caccggcagc tcttggcaag gtgtttaata attcagcctc gcagtccagc    2040
acacacaaac agacgtcacc tgttccctcg cctctgtctc caaggctccc cagccctcag    2100
cagcatcaca ggatcctccg gctccctgca ttgcctggtg agagggaagc tgctcttaat    2160
gactctcctt gtagaaagag ccgtgtcttc tctgggtgcg tctctgctga caccttggag    2220
ccaccatcct ctgcaaaggt cacggagacc aaaggagcca gcccggcctt cctcagagca    2280
ggccaacctc ggttggtgcc tggggaaact ttggaaaaga gcttggggcc agggaagacc    2340
acagctgagc cccagcacca gtcacctcca ggtatctcct ctgagggctt ccctgggac    2400 ggcttcaatg agcagacacc taaagacctt cccaacagag atggaggcgc gtgggttctg    2460
ggctacagag cgggaccagc ctgtccattt ttgcttcatg aggaaaggga gaagtcaaac    2520
aggagcgaat tgtacttgga tctccatcct gaccacagcc tgactgagca ggatgacagg    2580
actcctggca gacttcaagc tgtctggcca ccccaaaga caaagacac agaagaaaaa    2640 gtgggactga agtacactga agcagaatac caagctgcta ttttacactt gaagagggag    2700
cacaaagaag aaattgaaaa cctgcaggca cagtttgaac ttcgggcatt tcatatccgg    2760
ggcgagcatg caatgataac agcgagacta gaagaaacca ttgaaaatct gaaacacgag    2820
ctagaacaca gatggcgagg gggttgtgaa gagaggaaag atgtgtgcat ttccaccgat    2880
gatgactgcc ctccaaagac cttcagaaat gtgtgcgtcc agacagacag agagaccttc    2940
ctcaagccct gtgaaagtga aagcaagaca accagaagta atcaattagt acccaaaaag    3000
ctgaatatct cctctttaag ccagctctca cccccaaatg accacaaaga catccatgca    3060
gcactccagc caatggaggg catggcatca aatcagcaga aggcattgcc tccgcctccc    3120
gcatccatcc ctcccoctcc gccoctcccc tcaggacttg gatctttgtc tccogcacct    3180 ccaatgccac ctgtgagtgc tgggccaccg ctaccacctc cgcctcctcc accgccacct    3240
ctacctccac cttcaagtgc tggacctcca ccacccccac cccaccccc acttcctaac    3300 tcccctgccc cacccaaccc tggagggcct cctcctgctc caccaccccc aggacttgca    3360 ccoccacctc cccctggact cttctttgga cttggctctt cttccagtca atgtcctcga    3420
aaaccagcca tcgagcccag ttgtcccatg aagcctttat attggactag gatacaaata    3480
agtgatagga gccaaaatgc tacaccaacc ttatgggact ccttagaaga acctgacatt    3540
cgggacccca gtgaatttga gtattttattc tccaaagaca caactcaaca gaagaaaaaa    3600
cctctgtcag agacttatga gaagaaaaac aaggtcaaaa agatcatcaa attgttggat    3660
ggaaaacgat ctcaaactgt gggaatcttg atatctagtt tacatttaga aatgaaggat    3720
atccaacagg ccattttcaa tgtggatgac tccgtggttg atctggagac cctggcagcc    3780
```

```
ttatatgaaa acagagccca agaggatgag ctggttaaaa taagaaagta ttacgagaca    3840
tccaaagaag aagaactgaa gctgctggat aaacctgagc aattttttaca tgagttagcc   3900 cagattccta attttgctga acgtgcccag tgcataatct tcagatctgt cttttctgag    3960
ggtatcacct ccttgcacag aaaggtagag atcatcacgc gagcttctaa ggacttgctg    4020
cacgtgaaga gcgtgaagga tattttagct ctcatcttgg cttttggaaa ttatatgaat    4080
ggaggaaata ggactcgggg acaagccgat ggatatagct tagaaattct gcccaaactc    4140
aaggatgtca aaagtcggga taatgggatt aatctggtgg actacgttgt taagtattac    4200
ctgcgttact atgatcagga agctggaaca gaaaagagtg ttttccccctt gccggaacca    4260 caggatttct ttctggcctc ccaagtcaag tttgaagacc tcataaaaga tttgagaaaa    4320
ctgaagaggc aactagaagc aagtgagaaa cagatggtgg tggtgtgcaa ggagtcccca    4380
aaggagtatc tccagccttt caaggacaaa ctagaggagt tcttccaaaa agccaaaaaa    4440
gagcataaga tggaagaaag tcacttggag aatgcacaga aaagttttga acaacagta    4500 cgatattttg ggatgaagcc aaagtctggt gagaaggaga tcacacccag ctacgtgttt    4560
atggtgtggt atgagttctg cagtgacttc aagacaattt ggaaacggga gagtaaaaac    4620
atatctaaag aaagattgaa aatggctcag gaatcagtca gcaagttgac ttcagagaag    4680
aaagtggaga caaagaaaat caatcccact gctagcctga agaaagact gcgtcagaag    4740 gaagccagtg tgaccactaa ctaagatgaa acacatgga aatgatgca ctggaggtgg     4800 aggaccttgc acgcatactc tttgtgacca cagggttgca ggacgttctt gaaagatgtg   4860
tcactaaatg tttgttttg ctcatctctt tctgaggtca tctgcagaga gtgccccatg    4920
ccttctttaa gaagtccctc attaagccgc aggaacaatg gaaaactatt taagggaaca   4980
ttgcagaaat atttgatgac tgtttcttgt ggaagcccaa agtccactct aagagcagaa    5040
gaaataccaa aatgtttcca aaatttttt aaaagctgag atttccagct ttataaccaa    5100
agcttgatat atgtcacatt gtcacagaag agagaaaaga tcattgagga cagttgcctt    5160
gggagagttc aagtctttgt cgttacacac tgctgttttg attattggtc ttagttttga   5220
tcctgttgca gcaaaatcct gcagcatctt tctctccaat aatgttgcaa ctcaccaaaa    5280
ctattcttga agaggtccaa gaacatgtat tatccagact aaaaaaatga ttttttgttg   5340
ttatggttta cgtgatgaaa aggagaaaaa acagaatcat acctgggtgg agagagggag   5400
acaaatagcc ataaacttca tcctggagaa caagttacca tgcaaggagt tgacatcagt    5460
tgttaagtga ggcccattct tgttttaca tcggtccttt gtggttttc tgggccagca     5520 gagattctgc accccaactc ccaggagaaa atgtaatacc tgagcaagca cagccttggg   5580
tgtgcttgga caagaccccc agcggcagag caccttttac attttggacc gttcatgaat   5640
gggcaatgtt gtgttgatac gcagccgagt tctacgttat gtgctgtgac tgtgcagctg    5700
gacgaccccc atcccccagga ggcagttttcc agacaggaga gcaaatgcaa ctcacagcac    5760
ctgctcatga ccttggctga taggcatgtg aagtaggatg aagcaggact ctttaatgtc    5820
aaaaaaactg aagggcagaa aaaaggttcc ttacatcaaa atgaaagtaa ttacattaat    5880
agaaaacttc caagtggaat attgttcaca ggcagctctt tctgaccctg gctcttgagt    5940
cacataagga aaccacctttt gacctctctg acactttgt ctttaagcca cgtctctgaa    6000
atcttgtgag gggtgaagaa agaggactgg agatgaatgg acaatatgat caaagactca    6060
tttttaggcc ttgaagaggc cgagctttct ccccccaatt ggtggaggac agtccagaga    6120
tgagcagaaa tcttaaattc cttcctgatc cagcctccac atgtggcctg cccttgccc    6180
```

```
cagcatctttt ccagaacccc tggacttgcc aggtgcctga gcatcttccc aggatatgcc    6240
tgccagccag cagcccctca ggaatgcttc tataatagat ccagtaatga aagcagcacc    6300
atatcctaat ctaatgtcag cttcgagaat gaagactgca gtcaggatca aatcaagtca    6360
cagaagccat attcatgcag gtgctaaccg ccttttctac tggtgcaact gaaaggaata    6420
tggtaacatg gttggatttt taaaattcac aatgaaggaa cgagacaagc aaaacagaaa    6480
agccgagaag gaacatgcat gactaaaaag gcttgaagtt gcttgtgagc aagaagcttt    6540
ttatgctgct ttcttacata gtttctcttc attttcactt aactctgaag acaaccaaaa    6600
gaacggatca attaaaaact gattccactt ataaccattg tatgctccct ctagtgttat    6660
catgcacaag aaaagtgcca gttttaccca tgccatataa ttcagctctt ttgagttatg    6720
tggggccagc agaagtctca atccttatag gcttgatggt gagagcagcg ggaggtttga    6780
ggtgtactca ttgcagtcca ctttggtctg taagtaggat gcttacgaga aatcagtgaa    6840
ggtaagcagg gctgccactg tggccacgta acccttcagg aaccagtgct gaagaataat    6900
gagtgagaac acttaatttg agagttagac aaatacagcc cactttggat ttcatcctag    6960
tgaacagact aaaactttgc agtaaaatac ctatttctac aaagcaaggt ttgcctgcct    7020
cggttgggga aacctagtgg ttttgtcaca ctagtcgatg tatgatgtta gtgttgtaag    7080
acaccatggc agaatcttca ttattctcac ctattctgaa ccctgcatca tgtatctggg    7140
atgccccctc ccaagtccac caatgtacca cgttgctgac acagccttca tttttaactc    7200
aaattgatgc tcagtaaagg tcaatgacaa tttgttcaag gaagttcatc taaaataatc    7260
tggaggcctt gaaaatgatc cctctaaaat gctgttgagc ttgtgttcag tgtagcagga    7320
ggatctgaac ttttcctgga gaggaggtga tcgggatgcc atttggcagc ttaagcacat    7380
cctgccagca ggctttaagt ggctgttcta ggcatagccc tccctgaact agaaaggaga    7440
gtaaccagtt tgctatgctg catctaacca gacacacctg acttagtagt aactctaaga    7500
acccttaact tacaaacaac tttgtctcct cttagacaat attcattaaa tctgaggaca    7560
cagtttgaca gtagttcaga ttcttgcatg agcaattgac agcatcagag cacacaatat    7620
cataagttac ataaattaca caaagtacat cataaattac actacagaca cgttaggtaa    7680
aaagcatcag gcccgggccg ggcgtggtgg ctcatgccta taatcccagc actttgggag    7740
gccaagcggg ggcggatcac gaggtcagga gattgagacc atcctggcta acacggtgaa    7800
accccatctc tactaaaaat acaaaaaatt agccgggcgt ggtggtgggc gcctgtagtc    7860
ccagctactc gggaggctga ggcaggagaa tggcgtgaac ccaggaggtg gagcttgcag    7920
ctagccgaga tagcaccact gcactccagc ctgggcgaca gtgagactcc gtttcaaaaa    7980
aaaaagcatc aggcccatga agtatcaaaa accaggttag gaggtgtgct gtatggcttt    8040
tatctcaata agtggcagct tactgggaaa aagaaataa gaaaaagtgt ggccaagcag    8100
aagtggatgt ttatgatgac ggtgggggcc cagaggtcat aggtgatggt cctactgccc    8160
aacagttgcc ttttgaatcc ttatgttgat gatggtgtct ttctacacac tcactgcaac    8220
tactcaggaa ttataaagat tttctgaaat ctgagaagtg gaataaggaa acccagtgga    8280
gctattacac ttttaaatgt tctagccaaa acaaattgcc agtatggttg aggaattgaa    8340
tatcagatgg catgcagtct cccctcccct ccctatcaa ggacagtaga agctgcaaac    8400
ctcttctcag cctccttcag gcacctcctg ttttcataag caccatgaag aatggtgttt    8460
cctaaatgaa aagttcagat actgctggta aagaaactgg aaaaactgaa ggaaggaata    8520
```

```
aaatatgttg gtggtattaa cacctccagt aagataagtc attggtacgg ttttctaag    8580
ggccgcagtg agatgtagca gaagaaatat gtttattttg ggcaaagatt tgcttattgg    8640
cctgggattg cacattttct ctatgatgtt tgcaacagag aaattttcat tttaatgata    8700
ctcttccttt cttgaaagtt acatgtcctc atttctgttt ctgcttctcc cttggccagt    8760
gtcattgatg cagatcattg catacaacag cacagcaaat tgcgccaagt cagtgtgtga    8820
atgggaatta gcaatgcacg cttgcaggct cttttccag gaaccaggct gtaacattga    8880
ccggggaacc tcttcattcc ctgacatact aaattggtca attttgtagt actcatctcc    8940
atccacaaaa acaacaaaga taaaatcaat ttggagcttt atatgacaaa aaggaagaag    9000
tccaaaaata tatagccttc cccctccca catatctgat ccaaatatta aatatctgat    9060
tttataaaac agtttaaatt gtctttttaa attgctaaca agcatcagtt atatttgagc    9120
ttcatttttc ttttatcctg tctgtcctaa taaaacaaa aatggccaaa aagtggagag    9180
gaaagaaaaa gcttccactt tttaaaattt gttttgtatt agttatttta cctttaggga    9240
ccctacaact gaagagagtg gagagaataa agaagtgaac tttcattcat gtctgctact    9300
ttgacctcat aaagaaatct gcaacacaga tgaaaccagt ctgtgtggcc aagctgatgg    9360
gatttgaaaa gagtggataa tttttagcct ttccaaaatg caaataactt ggatatattt    9420
ccatttccca gctatagaga gaaacaatcc agctgcctgg aaactgttat tagtatagaa    9480
gtggcttaaa gaaaagcatc ttcaaatact tgacttagca tatctttctt ctttagactt    9540
acataatgat attcatctct ccattagcaa ttgaatccag gcataaccgg gctcagttac    9600
acagcttgtc tgtgactggg aagcccattt tgtgtcattt ctgcacacct gtccgctgtt    9660
gacaccttat tagaggcact gcattttggt ttcacaattc ttcatctccc ttcccaagga    9720
atgggcaatc tactgaactt ccagatcaat gctttgttgg aaagtgatga atttaagaga    9780
gttttaacat gtcaaatttg aagccaattc agtatcctta tttgttccaa gactcttaac    9840
caatactgtg atataaagtt aggatttggg aaacgtgtag ttaacaactt ggaaacatga    9900
agatattaaa atggcagctg gctaactgtc tcttaagcca ctatgcaatt tctaccaatg    9960
gagagattag ggaagcaaat taagcctcat tcagtaggtc tgctgtctgg tggaacttac   10020
ggaactcatt tcctcctcta tccccagccc ttctcctaac tatggtgata accagggcca   10080
tagaagacct tttctctctt acctttctct gataggatcg tgtccttcag tcaagagctc   10140
atgtgaactc cagactttat attacatctc tgaagttctt gatgtgggga agattgactt   10200
ttattccatt tttatatgaa ggtgttagat atagccatca atttattttt ctacattccc   10260
tctacgctta tgtaattttc tattttaaa tcttctctta aatatactga gaatctctag   10320
tctcctttc taaaggctga tccaactaca cttgtgggct atttttccaa gctttgtgtg   10380
aaacttgatg acattgggcc agcaaaatgc aaagaagact atagtttcag gcagaaaatc   10440
acgtccaaag aatttggcat ggattaaaca acctctacca cactatagct ctcacatagg   10500
ctgaacattt tcctaaattc tacctgtgca gacactgagg ggctctctac ctttgaaact   10560
atgagaacgt cttaaattaa tatgaatatt tctctccatg tatagtgtga gctgccaatg   10620
cattatctta atacatcaag aaggaaatca gatttcaggc acacattagc aattgtttgt   10680
taatgtcctt ggcaaacgtg tacctgcttt ccttcattgt tctcttcagg ggcttcttc    10740
cactttcctc ttatgaaacg aatgtgtttt tgactgttaa ctgggttcgc tttccagatc   10800
tgtctttccc aaatgaaagg ttagtcccat agaccactgg ctattcaggg aaattactct   10860
ctacctcccc atgacatgga tgataagtgt tgagggatga acactctgga aactcttagc   10920
```

-continued

```
atggattttg aattccagat ttctttatag gagatgtata aaaaggagtt tatagcatac    10980
aaaaattata ctgctcttcc cagtaaggga ctaaaaggac atttgaaatc tttacatttt    11040
agatgttttt gtgaattata aatatctcct ttttcctcgc ttcatgctaa cttgtctcta    11100
gataaaatct tatttcttca tacattggac cacaaggcat aaagaaggta gctcagcgcc    11160
actgagattg tgttctgcat aatatttgga aggcttccat ttccattgaa aacaaatcca    11220
tgagtgagag ggaaagtcta gtatcaattc ttctgtttgc tcgcaatgac acaaataggt    11280
tttggggatc tacctaaggg ataggtctac tccaaaatta ttaaatttat aattgtgcaa    11340
ttctgtaatt tcccaaggca taagtaatat gaccctactg tcagctagat gtcttatctt    11400
caaagagagt atgcattaat aaaaagaact tccctttaaa gaaccaatct aaaatactaa    11460
aaaggcagaa acttttaaaa ttagaaattg gataattttt aagaatcttt agagaaaaca    11520
ttggtttatc atagtctttt tctttcattg agttttcatt tagactagca tggcaagcag    11580
ggtggccttg gactttgatt tagggggatcg tgctttggcc tggaaaataa gcactggcct    11640
gcatgcctag aacctgagtg aaggcagtca acatcctagt atgaatcaga cctagcagaa    11700
atgtaaatta tttcaagtac ttcagggttt agttttctta gtgacaccct ggaccctgga    11760
tgctgctttc taaagtgcac ctgatccatg cagttttatg tcttcatata actggtatct    11820
tgtgagtttg caagcaatgg gatgagcaag aaaaaaagga cgcatggagg agaaaaattt    11880
gaacgaggct agtgcaatgt tttgctgata gattacattg ttagggagct ggtgattttt    11940
tgccatggtc gtatcgtgga cagcttttcc gtggaaattc aaggcatctg tattaggcaa    12000
atgtgagtgc ccttgatctt gtattgatca gtgccaatgt actgggaaag caggtacccc    12060
agtgaaactg gtctgtgctt ggtttaacag ctccaacaat ttcagatcca tggggctgct    12120
tgaccataga ccctgtttac tccatgcctg ttcaaaagtc attttgactt ctagctttgt    12180
ttcactttct tctttcaata cttctgtttc ctcgtccttt tccttcatat tccatggcta    12240
tttctttcct actttacagt ttcccccaga cccagatttt ttcacacctc tgcatcatag    12300
acaactgagt agctcccttg gccctcctc catcctctca cccctgtgc tccgttcctc    12360
agccgtttgg acagggagct ccgctgtcac caaggagccc atgtgagaca cactgctgtg    12420
actgcctctt gttaatgtca gcatcacctc atcacttaag caaaaaggaa aatccataaa    12480
agagatggaa aatacgtctc ttttttatttt atttttaagaa gattgggcgg ggtgggggg    12540
gggttcttat tctaggcctt ctcaatttct catagatttt accttaaact aattaaggcc    12600
attctcttga taaatttgta catcagaccg ggtcaccagc tatgatgcag aacgccagat    12660
ttttgaatct caagtaactt tctgtggtgc tggacaaatt gacttaattc tgtgcaggca    12720
aacactttga atcataagga ttttattgc cgctccattc ttactactat tcatgattca    12780
aacatctacc cctgttctga atcaggatgt tgacacttct tggttatttt cagatgaaca    12840
gtaactgcta cactcttgaa agcacttaaa agtgcaagca tgtcctaaat agccatttaa    12900
cctggtaaaa cataggcttt tctgtttaat taagtattag accagtctgt agatataatc    12960
tgaaaagatt gtaggcagta atgaagacag ttggggaaag gagaaggccc tttaaagaca    13020
tgaaaccttta cacgctcttg ggatatttttt aagcataata agctcattgg attcaggtat    13080
ttttcccttt gcattttttaa aaatacgtat ttctaatttg tttgcatatt taattttgtc    13140
aaagctgaga aatgctcatg agttgaattt ataaatgtca tttgcaacca aatgaagtat    13200
ttattttttaa aaagagagtg aaggaaccaa cactgatttg tacataataa aaatgtgtgt    13260
```

-continued

```
attatatata tatattttttt cctccttgac agtacttggt cacaatatca agtgtatttt    13320
tgtacataat atatattgat tagaaaaacg tcaattgtct attcaaaaaa ttctatctct    13380
gtgatagatt atatttatcc taatctgttg atacctctgt taatttgttt taagagaatt    13440 atatttttg gaattacag agaattgcat tcatggcttt caattgtaaa tatgctaagg      13500 gtatttaat aaatcttggt ttcatgtcca aaaaaaaaaa aaaaa                     13546
```

<210> SEQ ID NO 16
<211> LENGTH: 1419
<212> TYPE: PRT
<213> ORGANISM: Homo sapiens

<400> SEQUENCE: 16

| Met | Glu | Gly | Thr | His | Cys | Thr | Leu | Gln | Leu | His | Lys | Pro | Ile | Thr | Glu |
|---|---|---|---|---|---|---|---|---|---|---|---|---|---|---|---|
| 1 | | | | 5 | | | | | 10 | | | | | 15 | |

| Leu | Cys | Tyr | Ile | Ser | Phe | Cys | Leu | Pro | Lys | Gly | Glu | Val | Arg | Gly | Phe |
|---|---|---|---|---|---|---|---|---|---|---|---|---|---|---|---|
| | | | 20 | | | | | 25 | | | | | 30 | | |

| Ser | Tyr | Lys | Gly | Thr | Val | Thr | Leu | Asp | Arg | Ser | Asn | Lys | Gly | Phe | His |
|---|---|---|---|---|---|---|---|---|---|---|---|---|---|---|---|
| | | | 35 | | | | | 40 | | | | | 45 | | |

| Asn | Cys | Tyr | Gln | Val | Arg | Glu | Glu | Ser | Asp | Ile | Ile | Ser | Leu | Ser | Gln |
|---|---|---|---|---|---|---|---|---|---|---|---|---|---|---|---|
| 50 | | | | | 55 | | | | | 60 | | | | | |

| Glu | Pro | Asp | Glu | His | Pro | Gly | Asp | Ile | Phe | Phe | Lys | Gln | Thr | Pro | Thr |
|---|---|---|---|---|---|---|---|---|---|---|---|---|---|---|---|
| 65 | | | | | 70 | | | | | 75 | | | | | 80 |

| Lys | Asp | Ile | Leu | Thr | Glu | Leu | Tyr | Lys | Leu | Thr | Thr | Glu | Arg | Glu | Arg |
|---|---|---|---|---|---|---|---|---|---|---|---|---|---|---|---|
| | | | | 85 | | | | | 90 | | | | | 95 | |

| Leu | Leu | Thr | Asn | Leu | Leu | Ser | Ser | Asp | His | Ile | Leu | Gly | Ile | Thr | Met |
|---|---|---|---|---|---|---|---|---|---|---|---|---|---|---|---|
| | | | 100 | | | | | 105 | | | | | 110 | | |

| Gly | Asn | Gln | Glu | Gly | Lys | Leu | Gln | Glu | Leu | Ser | Val | Ser | Leu | Ala | Pro |
|---|---|---|---|---|---|---|---|---|---|---|---|---|---|---|---|
| | | | 115 | | | | | 120 | | | | | 125 | | |

| Glu | Asp | Asp | Cys | Phe | Gln | Ser | Ala | Gly | Asp | Trp | Gln | Gly | Glu | Leu | Pro |
|---|---|---|---|---|---|---|---|---|---|---|---|---|---|---|---|
| 130 | | | | | 135 | | | | | 140 | | | | | |

| Val | Gly | Pro | Leu | Asn | Lys | Arg | Ser | Thr | His | Gly | Asn | Lys | Lys | Pro | Arg |
|---|---|---|---|---|---|---|---|---|---|---|---|---|---|---|---|
| 145 | | | | | 150 | | | | | 155 | | | | | 160 |

| Arg | Ser | Ser | Gly | Arg | Arg | Glu | Ser | Phe | Gly | Ala | Leu | Pro | Gln | Lys | Arg |
|---|---|---|---|---|---|---|---|---|---|---|---|---|---|---|---|
| | | | | 165 | | | | | 170 | | | | | 175 | |

| Thr | Lys | Arg | Lys | Gly | Arg | Gly | Arg | Glu | Ser | Ala | Pro | Leu | Met | Gly |
|---|---|---|---|---|---|---|---|---|---|---|---|---|---|---|
| | | | 180 | | | | | 185 | | | | | 190 | |

| Lys | Asp | Lys | Ile | Cys | Ser | Ser | His | Ser | Leu | Pro | Leu | Ser | Arg | Thr | Arg |
|---|---|---|---|---|---|---|---|---|---|---|---|---|---|---|---|
| | | | 195 | | | | | 200 | | | | | 205 | | |

| Pro | Asn | Leu | Trp | Val | Leu | Glu | Glu | Lys | Gly | Asn | Leu | Leu | Pro | Asn | Gly |
|---|---|---|---|---|---|---|---|---|---|---|---|---|---|---|---|
| | | | 210 | | | | | 215 | | | | | 220 | | |

| Ala | Leu | Ala | Cys | Ser | Leu | Gln | Arg | Arg | Glu | Ser | Cys | Pro | Pro | Asp | Ile |
|---|---|---|---|---|---|---|---|---|---|---|---|---|---|---|---|
| 225 | | | | | 230 | | | | | 235 | | | | | 240 |

| Pro | Lys | Thr | Pro | Asp | Thr | Asp | Leu | Gly | Phe | Gly | Ser | Phe | Glu | Thr | Ala |
|---|---|---|---|---|---|---|---|---|---|---|---|---|---|---|---|
| | | | | 245 | | | | | 250 | | | | | 255 | |

| Phe | Lys | Asp | Thr | Gly | Leu | Gly | Arg | Glu | Val | Leu | Pro | Pro | Asp | Cys | Ser |
|---|---|---|---|---|---|---|---|---|---|---|---|---|---|---|---|
| | | | 260 | | | | | 265 | | | | | 270 | | |

| Ser | Thr | Glu | Ala | Gly | Gly | Asp | Gly | Ile | Arg | Arg | Pro | Pro | Ser | Gly | Leu |
|---|---|---|---|---|---|---|---|---|---|---|---|---|---|---|---|
| | | | 275 | | | | | 280 | | | | | 285 | | |

| Glu | His | Gln | Gln | Thr | Gly | Leu | Ser | Glu | Ser | His | Gln | Asp | Pro | Glu | Lys |
|---|---|---|---|---|---|---|---|---|---|---|---|---|---|---|---|
| | | | 290 | | | | | 295 | | | | | 300 | | |

| His | Pro | Glu | Ala | Glu | Lys | Asp | Glu | Met | Glu | Lys | Pro | Ala | Lys | Arg | Thr |
|---|---|---|---|---|---|---|---|---|---|---|---|---|---|---|---|
| 305 | | | | | 310 | | | | | 315 | | | | | 320 |

| Cys | Lys | Gln | Lys | Pro | Val | Ser | Lys | Val | Val | Ala | Lys | Val | Gln | Asp | Leu |
|---|---|---|---|---|---|---|---|---|---|---|---|---|---|---|---|

```
            325                 330                 335
Ser Ser Gln Val Gln Arg Val Val Lys Thr His Ser Lys Gly Lys Glu
            340                 345                 350
Thr Ile Ala Ile Arg Pro Ala Ala His Ala Glu Phe Val Pro Lys Ala
            355                 360                 365
Asp Leu Leu Thr Leu Pro Gly Ala Glu Ala Gly Ala His Gly Ser Arg
            370                 375                 380
Arg Gln Gly Lys Glu Arg Gln Gly Asp Arg Ser Ser Gln Ser Pro Ala
385                 390                 395                 400
Gly Glu Thr Ala Ser Ile Ser Ser Val Ser Ala Ser Ala Glu Gly Ala
            405                 410                 415
Val Asn Lys Val Pro Leu Lys Val Ile Glu Ser Glu Lys Leu Asp Glu
            420                 425                 430
Ala Pro Glu Gly Lys Arg Leu Gly Phe Pro Val His Thr Ser Val Pro
            435                 440                 445
His Thr Arg Pro Glu Thr Arg Asn Lys Arg Arg Ala Gly Leu Pro Leu
            450                 455                 460
Gly Gly His Lys Ser Leu Phe Leu Asp Leu Pro His Lys Val Gly Pro
465                 470                 475                 480
Asp Ser Ser Gln Pro Arg Gly Asp Lys Lys Pro Ser Pro Pro Ala
            485                 490                 495
Pro Ala Ala Leu Gly Lys Val Phe Asn Asn Ser Ala Ser Gln Ser Ser
            500                 505                 510
Thr His Lys Gln Thr Ser Pro Val Pro Ser Pro Leu Ser Pro Arg Leu
            515                 520                 525
Pro Ser Pro Gln Gln His His Arg Ile Leu Arg Leu Pro Ala Leu Pro
            530                 535                 540
Gly Glu Arg Glu Ala Ala Leu Asn Asp Ser Pro Cys Arg Lys Ser Arg
545                 550                 555                 560
Val Phe Ser Gly Cys Val Ser Ala Asp Thr Leu Glu Pro Pro Ser Ser
                    565                 570                 575
Ala Lys Val Thr Glu Thr Lys Gly Ala Ser Pro Ala Phe Leu Arg Ala
            580                 585                 590
Gly Gln Pro Arg Leu Val Pro Gly Glu Thr Leu Glu Lys Ser Leu Gly
            595                 600                 605
Pro Gly Lys Thr Thr Ala Glu Pro Gln His Gln Ser Pro Pro Gly Ile
            610                 615                 620
Ser Ser Glu Gly Phe Pro Trp Asp Gly Phe Asn Glu Gln Thr Pro Lys
625                 630                 635                 640
Asp Leu Pro Asn Arg Asp Gly Gly Ala Trp Val Leu Gly Tyr Arg Ala
                    645                 650                 655
Gly Pro Ala Cys Pro Phe Leu Leu His Glu Glu Arg Glu Lys Ser Asn
                    660                 665                 670
Arg Ser Glu Leu Tyr Leu Asp Leu His Pro Asp His Ser Leu Thr Glu
            675                 680                 685
Gln Asp Asp Arg Thr Pro Gly Arg Leu Gln Ala Val Trp Pro Pro Pro
            690                 695                 700
Lys Thr Lys Asp Thr Glu Glu Lys Val Gly Leu Lys Tyr Thr Glu Ala
705                 710                 715                 720
Glu Tyr Gln Ala Ala Ile Leu His Leu Lys Arg Glu His Lys Glu Glu
                    725                 730                 735
Ile Glu Asn Leu Gln Ala Gln Phe Glu Leu Arg Ala Phe His Ile Arg
            740                 745                 750
```

```
Gly Glu His Ala Met Ile Thr Ala Arg Leu Glu Glu Thr Ile Glu Asn
            755                 760                 765

Leu Lys His Glu Leu Glu His Arg Trp Arg Gly Gly Cys Glu Glu Arg
        770                 775                 780

Lys Asp Val Cys Ile Ser Thr Asp Asp Cys Pro Pro Lys Thr Phe
785                 790                 795                 800

Arg Asn Val Cys Val Gln Thr Asp Arg Glu Thr Phe Leu Lys Pro Cys
                805                 810                 815

Glu Ser Glu Ser Lys Thr Thr Arg Ser Asn Gln Leu Val Pro Lys Lys
            820                 825                 830

Leu Asn Ile Ser Ser Leu Ser Gln Leu Ser Pro Pro Asn Asp His Lys
            835                 840                 845

Asp Ile His Ala Ala Leu Gln Pro Met Glu Gly Met Ala Ser Asn Gln
850                 855                 860

Gln Lys Ala Leu Pro Pro Pro Ala Ser Ile Pro Pro Pro Pro
865                 870                 875                 880

Leu Pro Ser Gly Leu Gly Ser Leu Ser Pro Ala Pro Met Pro Pro
                885                 890                 895

Val Ser Ala Gly Pro Pro Leu Pro Pro Pro Pro Pro Pro Pro
                900                 905                 910

Leu Pro Pro Pro Ser Ser Ala Gly Pro Pro Pro Pro Pro Pro
        915                 920                 925

Pro Leu Pro Asn Ser Pro Ala Pro Pro Asn Pro Gly Gly Pro Pro Pro
    930                 935                 940

Ala Pro Pro Pro Pro Gly Leu Ala Pro Pro Pro Pro Gly Leu Phe
945                 950                 955                 960

Phe Gly Leu Gly Ser Ser Ser Gln Cys Pro Arg Lys Pro Ala Ile
                965                 970                 975

Glu Pro Ser Cys Pro Met Lys Pro Leu Tyr Trp Thr Arg Ile Gln Ile
                980                 985                 990

Ser Asp Arg Ser Gln Asn Ala Thr Pro Thr Leu Trp Asp Ser Leu Glu
        995                 1000                1005

Glu Pro Asp Ile Arg Asp Pro Ser Glu Phe Glu Tyr Leu Phe Ser
    1010                1015                1020

Lys Asp Thr Thr Gln Gln Lys Lys Pro Leu Ser Glu Thr Tyr
    1025                1030                1035

Glu Lys Lys Asn Lys Val Lys Ile Ile Lys Leu Leu Asp Gly
    1040                1045                1050

Lys Arg Ser Gln Thr Val Gly Ile Leu Ile Ser Ser Leu His Leu
    1055                1060                1065

Glu Met Lys Asp Ile Gln Gln Ala Ile Phe Asn Val Asp Asp Ser
    1070                1075                1080

Val Val Asp Leu Glu Thr Leu Ala Ala Leu Tyr Glu Asn Arg Ala
1085                1090                1095

Gln Glu Asp Glu Leu Val Lys Ile Arg Lys Tyr Tyr Glu Thr Ser
    1100                1105                1110

Lys Glu Glu Glu Leu Lys Leu Leu Asp Lys Pro Glu Gln Phe Leu
    1115                1120                1125

His Glu Leu Ala Gln Ile Pro Asn Phe Ala Glu Arg Ala Gln Cys
    1130                1135                1140

Ile Ile Phe Arg Ser Val Phe Ser Glu Gly Ile Thr Ser Leu His
    1145                1150                1155
```

| | | | | | | | | | | |
|---|---|---|---|---|---|---|---|---|---|---|
| Arg | Lys | Val | Glu | Ile | Ile | Thr | Arg | Ala | Ser | Lys | Asp | Leu | Leu | His |
| | 1160 | | | | 1165 | | | | 1170 | |
| Val | Lys | Ser | Val | Lys | Asp | Ile | Leu | Ala | Leu | Ile | Leu | Ala | Phe | Gly |
| 1175 | | | | | 1180 | | | | | 1185 | |
| Asn | Tyr | Met | Asn | Gly | Gly | Asn | Arg | Thr | Arg | Gly | Gln | Ala | Asp | Gly |
| | 1190 | | | | 1195 | | | | | 1200 |
| Tyr | Ser | Leu | Glu | Ile | Leu | Pro | Lys | Leu | Lys | Asp | Val | Lys | Ser | Arg |
| 1205 | | | | | 1210 | | | | | 1215 |
| Asp | Asn | Gly | Ile | Asn | Leu | Val | Asp | Tyr | Val | Val | Lys | Tyr | Tyr | Leu |
| 1220 | | | | | 1225 | | | | | 1230 |
| Arg | Tyr | Tyr | Asp | Gln | Glu | Ala | Gly | Thr | Glu | Lys | Ser | Val | Phe | Pro |
| 1235 | | | | | 1240 | | | | | 1245 |
| Leu | Pro | Glu | Pro | Gln | Asp | Phe | Phe | Leu | Ala | Ser | Gln | Val | Lys | Phe |
| 1250 | | | | | 1255 | | | | | 1260 |
| Glu | Asp | Leu | Ile | Lys | Asp | Leu | Arg | Lys | Leu | Lys | Arg | Gln | Leu | Glu |
| 1265 | | | | | 1270 | | | | | 1275 |
| Ala | Ser | Glu | Lys | Gln | Met | Val | Val | Cys | Lys | Glu | Ser | Pro | Lys |
| 1280 | | | | | 1285 | | | | | 1290 |
| Glu | Tyr | Leu | Gln | Pro | Phe | Lys | Asp | Lys | Leu | Glu | Glu | Phe | Phe | Gln |
| 1295 | | | | | 1300 | | | | | 1305 |
| Lys | Ala | Lys | Lys | Glu | His | Lys | Met | Glu | Ser | His | Leu | Glu | Asn |
| 1310 | | | | | 1315 | | | | | 1320 |
| Ala | Gln | Lys | Ser | Phe | Glu | Thr | Thr | Val | Arg | Tyr | Phe | Gly | Met | Lys |
| 1325 | | | | | 1330 | | | | | 1335 |
| Pro | Lys | Ser | Gly | Glu | Lys | Glu | Ile | Thr | Pro | Ser | Tyr | Val | Phe | Met |
| 1340 | | | | | 1345 | | | | | 1350 |
| Val | Trp | Tyr | Glu | Phe | Cys | Ser | Asp | Phe | Lys | Thr | Ile | Trp | Lys | Arg |
| 1355 | | | | | 1360 | | | | | 1365 |
| Glu | Ser | Lys | Asn | Ile | Ser | Lys | Glu | Arg | Leu | Lys | Met | Ala | Gln | Glu |
| 1370 | | | | | 1375 | | | | | 1380 |
| Ser | Val | Ser | Lys | Leu | Thr | Ser | Glu | Lys | Lys | Val | Glu | Thr | Lys | Lys |
| 1385 | | | | | 1390 | | | | | 1395 |
| Ile | Asn | Pro | Thr | Ala | Ser | Leu | Lys | Glu | Arg | Leu | Arg | Gln | Lys | Glu |
| 1400 | | | | | 1405 | | | | | 1410 |
| Ala | Ser | Val | Thr | Thr | Asn |
| 1415 |

<210> SEQ ID NO 17
<211> LENGTH: 8555
<212> TYPE: DNA
<213> ORGANISM: Homo sapiens

<400> SEQUENCE: 17

```
gctaaatggt taagagatac ataaatactg cagtagagat gggattttac ctcaaagtgc      60
aaaggtaaat gaaataaagt tttttcaatg gaaggcttgc agctcttgag gacctgccaa     120
atggaagaag gacagagacc tggagcccta tggaaagttc tgacaccatg tgtggaagga     180
catggctttt aacacgtgtg gtgactggag tagctgcagc tgaggacagc cacccttttct     240
tcgtctctgc tgagcgaagg ctacacggcc cttcctcctt gcagctgttt caccttctac     300
cttgcgtgga gccaggcttt tgcaccgaat ctgagatgcc attttaaaca gaagactcca     360
tcctcttgaa gatgggaaat tcttacgctg acagctgaa gacgacacgc tttgaagagg     420
tcttgcacaa ttccatcgag gcatccctgc ggtccaacaa cctggtgccc aggcccatct     480
tttcccagct gtacctggaa gctgagcagc agcttgccgc tctagaaggt ggtagccgag     540
```

```
tggacaatga ggaagaggaa gaagagggag aaggagggct ggaaacaaat ggccccccaa      600
accctttcca gctgcaccct ctgcctgaag gatgctgtac cacagacggg ttttgccagg      660
ccgggaagga cctgcgcctt gtctccattt ccaacgagcc catggatgtc cctgcgggct      720
ttctcctcgt gggggtcaag tcccccagcc tgccggacca tctcctggtg tgcgccgttg      780
acaagaggtt cttgccagat gacaatggcc acaatgctct tcttggtttc tctgggaatt      840
gtgttggctg tggaaagaaa ggcttctgtt acttcacgga attctccaat catataaatc      900
tgaaactgac cactcaaccc aagaagcaga aacacttgaa gtattacctg gtccgtaatg      960
cacaagggac tctaaccaaa ggacctttaa tctgttggaa aggctcagag tttagaagcc     1020
ggcagatccc cgccagtact tgttccagtt ccctcttccc agccctggag agcacggctg     1080
ccttccccag cgagcccgtt cctgggacga accccagcat cctgatggga gctcagcagg     1140
caggaccagc ttctgatcac ccctcactaa acgcagcaat gggtccggct gttttcaacg     1200
gcaaagattc cccgaagtgc caacaactgg caaagaataa cctgttggcc ctgccgcgac     1260
catcggcttt aggtatcttg tcaaactccg gccccccaa aaaacgccac aaagggtggt      1320
ctccagaatc tccatcagct ccagatggtg gctgccccca aggtggtggg aacagagcta     1380
agtatgagag cgcaggcatg tcctgcgtgc cgcaggttgg cttggtggga ccagcttcag     1440
tcacctttcc agtggtggcc tctggagaac cagtgtctgt tcctgacaac ttgctgaaaa     1500
tatgcaaggc caagccagtg atatttaaag ccatgggaa cttcccttac ctctgtggga      1560
acctgaatga cgtcgtggtc agccccctct tgtacacgtg ctaccagaat cccagtctg     1620 tctcacgggc atacgagcag tacggcgcct ctgccatcca gccatctcc gaggagatgc      1680 agctcctgct taccgtctac tacctggtcc agctggccgc ggaccaggtg cccttgatgg     1740
aggacctgga gcagatcttc ctgcgctctt ggcgcgagtc gcacctgacc gagatccggc     1800
agtaccagca ggcgccgccg cagccctccc cgcccgcgcc cagcgccgcg gcacccgtga     1860
cctccgcgca gctgccctgg ctggccagcc tggccgccag ctcctgcaac gacagcgtgc     1920
acgtcatcga gtgtgcttac tccctggccg agggcctctc cgagatgttc cggctgttgg     1980
tcgagggcaa gcttgccaag accaactacg tggtcatcat ctgcgcctgc cgcagcgcgg     2040
ccatcgactc ctgcatcgcc gtcaccggaa aataccaagc ccggattctt ccgagagcc      2100 ttctcactcc tgcggagtac cagaaggaag tcaattacga gctggttacg gggaaggtag     2160
actcgctggg ggccttcttt agcaccctct gtccagaggg tgacattgac attttgctgg     2220
acaaatttca ccaggaaaat caaggccata tttcttcctc actcgctgcc tcttctgtca     2280
ctaaagcagc atccctggat gtcagtggga caccggtgtg cacaagttac aatctggagc     2340
cacacagcat ccggccctttc cagctggcag tagcgcagaa gctcctctcc catgtgtgtt     2400
ccattgcgga ttccagcacc caaaatctgg acctgggatc ctttgagaag gtggactttc     2460
tcatttgcat tccccctca gaagtgacct accagcagac tctgctccat gtgtggcatt     2520
caggggtttt gctggagctt ggtctgaaga aagagcacat gacgaagcag agggtggaac     2580
agtatgttct gaagctagac acggaggcac agacaaaatt taaggctttt ctgcaaaact     2640
ccttccagaa cccgcataca ctttttgtcc taatccatga ccatgcgcac tgggatcttg     2700
tgagtagcac tgttcataac ctctattctc aaagtgaccc gtcggtggga ttggtggacc     2760
gattgctcaa ctgcagggag gtgaaggagg ccccaacat tgtgacactt cacgtgacct      2820
ccttcccgta tgcactgcag acacagcaca ccctcatcag ccctacaac gagatccact      2880
```

```
ggcctgcctc ctgcagtaat ggagtggact tatatcatga aaataagaag tacttcgggc  2940
tgtcggagtt tattgaatcc acccttcag  gacacagcct ccccttgctc agatacgata   3000
gctcctttga ggccatggtc actgcattag gaaaaaggtt cccccgcctg cacagcgcgg   3060
tgatcaggac ctttgttctc gtgcagcact acgcggccgc cctgatgcc  gtaagcggcc   3120
tcccgcagat gaagaactac acgtcggtgg agacgctgga gatcacgcag aacctcctca   3180
actccccgaa gcagtgcccc tgcggccacg ggctcatggt cctgctgcgg gtgccctgtt   3240
cgcccctggc ggtggtggcc tatgagcggc tggcccacgt gcgggcccgg ctggcgctgg   3300
aggagcactt tgagatcatc ctgggcagtc ccagctcagg cgtcaccgtg ggaagcact   3360
tcgtaaagca gctcaggatg tggcagaaaa ttgaggatgt ggagtggaga ccccagactt   3420
acttggagct ggagggtctg ccttgcatcc tgatcttcag tgggatggac ccgcatgggg   3480
agtccttgcc gaggtctttg aggtactgtg acctgcgatt gataaactcc tcctgcttgg   3540
tgagaacagc cttggagcag gagctgggcc tggctgccta ctttgtgagc aacgaggttc   3600
ccttggagaa gggggctagg aacgaggcct tggagagtga tgctgagaag ctgagcagca   3660
cagacaacga ggatgaggag ctggggacag aaggctctac ctcggagaag agaagcccca   3720
tgaaaaggga gaggtcccgc tcccacgact cagcatcctc atccctctcc tccaaggctt   3780
ccggttcagc gctcggtggc gagtcctcgg ctcagcccac agcactcccc cagggagagc   3840
atgccaggtc gccccagccc cgtggccccg cagaggaggg cagagcccct ggtgagaaac   3900
agaggccccg ggcaagtcag gggccaccct cggccatcag caggcacagt cccgggccga   3960
cgccccagcc cgactgtagc ctcaggaccg gccagaggag cgtccaggtg tcggtcacct   4020
cgtcgtgctc ccagctgtcc tcctcctcgg gctcatcctc ctcatccgtg gcgcccgctg   4080
ccggcacgtg ggtcctgcag gcctcccagt gctccttgac caaggcctgc cgccagccac   4140
ccattgtctt cttgcccaag ctcgtgtacg acatggttgt gtccactgac agcagtggcc   4200
tgcccaaggc cgcctccctc ctgccctccc cctcggtcat gtgggccagc tctttccgcc   4260
ccctgctcag caagaccatg acatccaccg agcagtccct ctactaccgg cagtggacgg   4320
tgccccggcc cagccacatg gactacggca accgggccga gggccgcgtg gacggcttcc   4380
accccccgcag gctgctgctc agcggccccc ctcagatcgg gaagacaggt gcctacctgc   4440
agttcctcag tgtcctgtcc aggatgcttg ttcggctcac agaagtggat gtctatgacg   4500
aggaggagat caatatcaac ctcagagaag aatctgactg gcattatctc cagcttagcg   4560
accctggcc  agacctggag ctgttcaaga agttgccctt tgactacatc attcacgacc   4620
cgaagtatga agatgccagc ctgatttgtt cgcactatca gggtataaag agtgaagaca   4680
gagggatgtc ccggaagccg gaggacccttt atgtgcggcg tcagacggca cggatgagac   4740
tgtccaagta cgcagcgtac aacacttacc accactgtga gcagtgccac cagtacatgg   4800
gcttccaccc ccgctaccag ctgtatgagt ccacccctgca cgcctttgcc ttctcttact   4860
ccatgctagg agaggagatc cagctgcact tcatcatccc caagtccaag gagcaccact   4920
ttgtcttcag ccaacctgga ggccagctgg agagcatgcg actacccctc gtgacagaca   4980
agagccatga atatataaaa agtccgacat tcactccaac caccggccgt cacgaacatg   5040
ggctctttaa tctgtaccac gcaatggacg gtgccagcca tttgcacgtg ctggttgtca   5100
aggaatacga gatggcaatt tataagaaat attggcccaa ccacatcatg ctggtgctcc   5160
ccagtatctt caacagtgct ggagttggtg ctgctcattt cctcatcaag gagctgtcct   5220
accataaccct ggagctcgag cggaaccggc aggaggagct gggaatcaag ccgcaggaca   5280
```

```
tctggccttt cattgtgatc tctgatgact cctgcgtgat gtggaacgtg gtggatgtca    5340
actctgctgg ggagagaagc agggagttct cctggtcgga aaggaacgtg tctttgaagc    5400
acatcatgca gcacatcgag gcggcccccg acatcatgca ctacgccctg ctgggcctgc    5460
ggaagtggtc cagcaagacc cgggccagcg aggtgcaaga gcccttctcc cgctgccacg    5520
tgcacaactt catcatcctg aacgtggacc tgacccagaa cgtgcagtac aaccagaacc    5580
ggttcctgtg tgacgatgta gacttcaacc tgcgggtgca cagcgccggc ctcctgctct    5640
gccggttcaa ccgcttcagc gtgatgaaga agcagatcgt ggtgggcggc cacaggtcct    5700
tccacatcac atccaaggtg tctgataact ctgccgcgt cgtgccggcc cagtacatct    5760
gtgccccgga cagcaagcac acgttcctcg cagcgcccgc ccagctcctg ctggagaagt    5820
tcctgcagca ccacagccac ctcttcttcc cgctgtccct gaagaaccat gaccacccag    5880
tgctgtctgt cgactgttac ctgaacctgg gatctcagat ttctgtttgc tatgtgagct    5940
ccaggcccca ctcttttaaac atcagctgct cggacttgct gttcagtggg ctgctgctgt    6000
acctctgtga ctcttttgtg ggagctagct ttttgaaaaa gtttcatttt ctgaaaggtg    6060
cgacgttgtg tgtcatctgt caggaccgga gctcactgcg ccagacggtc gtccgcctgg    6120
agctcgagga cgagtggcag ttccggctgc gcgatgagtt ccagaccgcc aatgccaggg    6180
aagaccggcc gctctttttt ctgacgggac gacacatctg aggaagacag cggcgagttt    6240
tctgaagaga tgagtgctca gagccctcat gctgttgagg ctaaagggag gcctggaacg    6300
gtggggcgtt tgactggaat ggaccccagg gactgtccag gtgcagcccc tcctagtaca    6360
catgggcccc cgaggccgtg gtcctgggag ccaggaagac tccgcagtgg gtgagaatga    6420
aaacttgaga ctcccaagtt ctgggccagc ccattgctct gggctgtttt aaagcccatt    6480
tcacgaggaa caaagattta cttcctgtcc tgccattcgt gtgcttccat ggacaaacct    6540 gattttttc tcttagttct aaagaatctt gggttattt gtagcggtgc cagtatttca    6600
gtagatggga tttcagccaa gtaggttccc ctgtaacctc ctacaaagca atattccaaa    6660
ggaacatttt aactgtaaag gctggagaca agaaaaaata agtagatcgt tttaataaca    6720
attatttaat tgcctataag tttgctgttt cagaggctag cccaaaggca tcaaatttaa    6780
taaagttaaa caaattgatt tacttcagag caaatatgat cctattaaaa taatataggg    6840 taaatacccct acctcttaga aagggcaaaa atgcaaagaa gctttcttta aaactaaaag    6900 ggtttttttgg ggggggagtt ggcggggagg aaataaggct aacagaggtt gacctaaaat    6960
tagccttaca aaggagaaag gaccacattg cttacttgaa acagacaatg aaaacaacca    7020
aagtgatata taaaatagtt gatgagaact agacttatga ctgtagttta ctagagttta    7080
gttttcagtt gctgaagtag ctcatttct cttactaatg tttggttcct cagggaagaa    7140
tctcacttga ctagagagga ggtgggaaca gaagagagaa ggaggcaggg agatgtattt    7200
cttagggctc acccccttcac agactgacag aatggttttg ttttgttttg ttttgttttg    7260
ttttgttttt gagatggact ctagctctgt cacccaggct ggagtgcagt ggtgcgatct    7320
cggctcactg caagctccgc ctcccgggtt ctcaccattc tcctgcctca gcctcccgag    7380
tagctgggac tacaggcgcc caccaccacg cccggctaat ttttgtatt ttttagtaga    7440 gacggggttt caccatgtta gccaggatgg tctcgatctc ctgacctcgt gatccgcccg    7500
cctcggcctc ccaaagtgct gggattacag gcgtgagcca ccgtgcctgc cccagaatgg    7560
tttttaaagc cacagttgag aggccaccca ttgcccggcg cctggacagt gatcatcttg    7620
```

-continued

```
ttcatcttgt tcagtcctttt cttgtgtgat tggaattatt catccccttt gaaagatgag       7680
aaggttgaga tgcaaagagt ctacctttcc aagttctcac tgctggaaag agctagaagc       7740
acagttcaaa gttctggctt ctggactctg cagtccaggt ctcccttctc ccacttgcct       7800
accctcaatg ccacactgtt tttgaagtgg cccataactt gaaggaaaag tttaaagaca       7860
gttcaattta atcatcagaa tgcattcttt ttttttttcgg agacggagtt tcactcttgc       7920
tgcccaggct ggagtgcaat ggtgcaatga cctcggctca ctgcaacctc tgcctcctgg       7980
gttcaagtga ttctccagcc tcagcctccc gagtagctgg gattatgggc gcccaccacc       8040
atgcccagct aattttttgta ttttttttttt ttagtagaga tggggtttcg ccaggttggc       8100
caggctggtc ttgtgaactc ctggcctcag gtgatctgcc cacctcatcc tccaaaagtg       8160
ctgggattac aggcatgagc cactgcgcct ggcctcagaa tgcattctta cacatctatc       8220
ctagacattt ataagcactc taatggataa caatccaaga ataaatgatt gtaaaagatg       8280
atgccgaaga gttgatgtca atcttttttt cctaagaaaa aaagtccgcg agtattaaat       8340
atttagatca atgtttataa aatgattact ttgtatatct cattattcct attttggaat       8400
aaaaactgac cttctttaat catatacttg tcttttgtaa atagcagctt ttgtgtcatt       8460
ctccccactt tattagttaa tttaaattgg aaaaaacccct caaactaata ttcttgtctg       8520
ttccagtctt ataaataaaa cttataatgc atgta                                   8555
```

<210> SEQ ID NO 18
<211> LENGTH: 1949
<212> TYPE: PRT
<213> ORGANISM: Homo sapiens

<400> SEQUENCE: 18

```
Met Gly Asn Ser Tyr Ala Gly Gln Leu Lys Thr Thr Arg Phe Glu Glu
1               5                   10                  15

Val Leu His Asn Ser Ile Glu Ala Ser Leu Arg Ser Asn Asn Leu Val
            20                  25                  30

Pro Arg Pro Ile Phe Ser Gln Leu Tyr Leu Glu Ala Glu Gln Gln Leu
        35                  40                  45

Ala Ala Leu Glu Gly Gly Ser Arg Val Asp Asn Glu Glu Glu Glu Glu
    50                  55                  60

Glu Gly Glu Gly Gly Leu Glu Thr Asn Gly Pro Pro Asn Pro Phe Gln
65                  70                  75                  80

Leu His Pro Leu Pro Glu Gly Cys Cys Thr Thr Asp Gly Phe Cys Gln
                85                  90                  95

Ala Gly Lys Asp Leu Arg Leu Val Ser Ile Ser Asn Glu Pro Met Asp
            100                 105                 110

Val Pro Ala Gly Phe Leu Leu Val Gly Val Lys Ser Pro Ser Leu Pro
        115                 120                 125

Asp His Leu Leu Val Cys Ala Val Asp Lys Arg Phe Leu Pro Asp Asp
    130                 135                 140

Asn Gly His Asn Ala Leu Leu Gly Phe Ser Asn Cys Val Gly Cys
145                 150                 155                 160

Gly Lys Lys Gly Phe Cys Tyr Phe Thr Glu Phe Ser Asn His Ile Asn
                165                 170                 175

Leu Lys Leu Thr Thr Gln Pro Lys Lys Gln Lys His Leu Lys Tyr Tyr
            180                 185                 190

Leu Val Arg Asn Ala Gln Gly Thr Leu Thr Lys Gly Pro Leu Ile Cys
        195                 200                 205
```

```
Trp Lys Gly Ser Glu Phe Arg Ser Arg Gln Ile Pro Ala Ser Thr Cys
    210                 215                 220

Ser Ser Ser Leu Phe Pro Ala Leu Glu Ser Thr Ala Ala Phe Pro Ser
225                 230                 235                 240

Glu Pro Val Pro Gly Thr Asn Pro Ser Ile Leu Met Gly Ala Gln Gln
                245                 250                 255

Ala Gly Pro Ala Ser Asp His Pro Ser Leu Asn Ala Ala Met Gly Pro
            260                 265                 270

Ala Val Phe Asn Gly Lys Asp Ser Pro Lys Cys Gln Gln Leu Ala Lys
        275                 280                 285

Asn Asn Leu Leu Ala Leu Pro Arg Pro Ser Ala Leu Gly Ile Leu Ser
    290                 295                 300

Asn Ser Gly Pro Pro Lys Lys Arg His Lys Gly Trp Ser Pro Glu Ser
305                 310                 315                 320

Pro Ser Ala Pro Asp Gly Gly Cys Pro Gln Gly Gly Gly Asn Arg Ala
                325                 330                 335

Lys Tyr Glu Ser Ala Gly Met Ser Cys Val Pro Gln Val Gly Leu Val
            340                 345                 350

Gly Pro Ala Ser Val Thr Phe Pro Val Val Ala Ser Gly Glu Pro Val
        355                 360                 365

Ser Val Pro Asp Asn Leu Leu Lys Ile Cys Lys Ala Lys Pro Val Ile
    370                 375                 380

Phe Lys Gly His Gly Asn Phe Pro Tyr Leu Cys Gly Asn Leu Asn Asp
385                 390                 395                 400

Val Val Val Ser Pro Leu Leu Tyr Thr Cys Tyr Gln Asn Ser Gln Ser
                405                 410                 415

Val Ser Arg Ala Tyr Glu Gln Tyr Gly Ala Ser Ala Ile Gln Pro Ile
            420                 425                 430

Ser Glu Glu Met Gln Leu Leu Leu Thr Val Tyr Tyr Leu Val Gln Leu
        435                 440                 445

Ala Ala Asp Gln Val Pro Leu Met Glu Asp Leu Glu Gln Ile Phe Leu
    450                 455                 460

Arg Ser Trp Arg Glu Ser His Leu Thr Glu Ile Arg Gln Tyr Gln Gln
465                 470                 475                 480

Ala Pro Pro Gln Pro Phe Pro Ala Pro Ser Ala Ala Pro Val
                485                 490                 495

Thr Ser Ala Gln Leu Pro Trp Leu Ala Ser Leu Ala Ala Ser Ser Cys
            500                 505                 510

Asn Asp Ser Val His Val Ile Glu Cys Ala Tyr Ser Leu Ala Glu Gly
        515                 520                 525

Leu Ser Glu Met Phe Arg Leu Leu Val Glu Gly Lys Leu Ala Lys Thr
    530                 535                 540

Asn Tyr Val Val Ile Ile Cys Ala Cys Arg Ser Ala Ala Ile Asp Ser
545                 550                 555                 560

Cys Ile Ala Val Thr Gly Lys Tyr Gln Ala Arg Ile Leu Ser Glu Ser
                565                 570                 575

Leu Leu Thr Pro Ala Glu Tyr Gln Lys Glu Val Asn Tyr Glu Leu Val
            580                 585                 590

Thr Gly Lys Val Asp Ser Leu Gly Ala Phe Phe Ser Thr Leu Cys Pro
        595                 600                 605

Glu Gly Asp Ile Asp Ile Leu Leu Asp Lys Phe His Gln Glu Asn Gln
    610                 615                 620

Gly His Ile Ser Ser Ser Leu Ala Ala Ser Ser Val Thr Lys Ala Ala
```

-continued

```
625                 630                 635                 640
Ser Leu Asp Val Ser Gly Thr Pro Val Cys Thr Ser Tyr Asn Leu Glu
                645                 650                 655

Pro His Ser Ile Arg Pro Phe Gln Leu Ala Val Ala Gln Lys Leu Leu
                660                 665                 670

Ser His Val Cys Ser Ile Ala Asp Ser Ser Thr Gln Asn Leu Asp Leu
                675                 680                 685

Gly Ser Phe Glu Lys Val Asp Phe Leu Ile Cys Ile Pro Pro Ser Glu
    690                 695                 700

Val Thr Tyr Gln Gln Thr Leu Leu His Val Trp His Ser Gly Val Leu
705                 710                 715                 720

Leu Glu Leu Gly Leu Lys Lys Glu His Met Thr Lys Gln Arg Val Glu
                725                 730                 735

Gln Tyr Val Leu Lys Leu Asp Thr Glu Ala Gln Thr Lys Phe Lys Ala
                740                 745                 750

Phe Leu Gln Asn Ser Phe Gln Asn Pro His Thr Leu Phe Val Leu Ile
            755                 760                 765

His Asp His Ala His Trp Asp Leu Val Ser Ser Thr Val His Asn Leu
    770                 775                 780

Tyr Ser Gln Ser Asp Pro Ser Val Gly Leu Val Asp Arg Leu Leu Asn
785                 790                 795                 800

Cys Arg Glu Val Lys Glu Ala Pro Asn Ile Val Thr Leu His Val Thr
                805                 810                 815

Ser Phe Pro Tyr Ala Leu Gln Thr Gln His Thr Leu Ile Ser Pro Tyr
                820                 825                 830

Asn Glu Ile His Trp Pro Ala Ser Cys Ser Asn Gly Val Asp Leu Tyr
            835                 840                 845

His Glu Asn Lys Lys Tyr Phe Gly Leu Ser Glu Phe Ile Glu Ser Thr
        850                 855                 860

Leu Ser Gly His Ser Leu Pro Leu Leu Arg Tyr Asp Ser Ser Phe Glu
865                 870                 875                 880

Ala Met Val Thr Ala Leu Gly Lys Arg Phe Pro Arg Leu His Ser Ala
                885                 890                 895

Val Ile Arg Thr Phe Val Leu Val Gln His Tyr Ala Ala Leu Met
                900                 905                 910

Ala Val Ser Gly Leu Pro Gln Met Lys Asn Tyr Thr Ser Val Glu Thr
        915                 920                 925

Leu Glu Ile Thr Gln Asn Leu Leu Asn Ser Pro Lys Gln Cys Pro Cys
    930                 935                 940

Gly His Gly Leu Met Val Leu Arg Val Pro Cys Ser Pro Leu Ala
945                 950                 955                 960

Val Val Ala Tyr Glu Arg Leu Ala His Val Arg Ala Arg Leu Ala Leu
                965                 970                 975

Glu Glu His Phe Glu Ile Ile Leu Gly Ser Pro Ser Ser Gly Val Thr
            980                 985                 990

Val Gly Lys His Phe Val Lys Gln Leu Arg Met Trp Gln Lys Ile Glu
        995                 1000                1005

Asp Val Glu Trp Arg Pro Gln Thr Tyr Leu Glu Leu Glu Gly Leu
    1010                1015                1020

Pro Cys Ile Leu Ile Phe Ser Gly Met Asp Pro His Gly Glu Ser
    1025                1030                1035

Leu Pro Arg Ser Leu Arg Tyr Cys Asp Leu Arg Leu Ile Asn Ser
    1040                1045                1050
```

-continued

```
Ser Cys Leu Val Arg Thr Ala Leu Glu Gln Glu Leu Gly Leu Ala
    1055                1060                1065

Ala Tyr Phe Val Ser Asn Glu Val Pro Leu Glu Lys Gly Ala Arg
    1070                1075                1080

Asn Glu Ala Leu Glu Ser Asp Ala Glu Lys Leu Ser Ser Thr Asp
    1085                1090                1095

Asn Glu Asp Glu Glu Leu Gly Thr Glu Gly Ser Thr Ser Glu Lys
    1100                1105                1110

Arg Ser Pro Met Lys Arg Glu Arg Ser Arg Ser His Asp Ser Ala
    1115                1120                1125

Ser Ser Ser Leu Ser Ser Lys Ala Ser Gly Ser Ala Leu Gly Gly
    1130                1135                1140

Glu Ser Ser Ala Gln Pro Thr Ala Leu Pro Gln Gly Glu His Ala
    1145                1150                1155

Arg Ser Pro Gln Pro Arg Gly Pro Ala Glu Gly Arg Ala Pro
    1160                1165                1170

Gly Glu Lys Gln Arg Pro Arg Ala Ser Gln Gly Pro Pro Ser Ala
    1175                1180                1185

Ile Ser Arg His Ser Pro Gly Pro Thr Pro Gln Pro Asp Cys Ser
    1190                1195                1200

Leu Arg Thr Gly Gln Arg Ser Val Gln Val Ser Val Thr Ser Ser
    1205                1210                1215

Cys Ser Gln Leu Ser Ser Ser Gly Ser Ser Ser Ser Ser Val
    1220                1225                1230

Ala Pro Ala Ala Gly Thr Trp Val Leu Gln Ala Ser Gln Cys Ser
    1235                1240                1245

Leu Thr Lys Ala Cys Arg Gln Pro Pro Ile Val Phe Leu Pro Lys
    1250                1255                1260

Leu Val Tyr Asp Met Val Val Ser Thr Asp Ser Ser Gly Leu Pro
    1265                1270                1275

Lys Ala Ala Ser Leu Leu Pro Ser Pro Ser Val Met Trp Ala Ser
    1280                1285                1290

Ser Phe Arg Pro Leu Leu Ser Lys Thr Met Thr Ser Thr Glu Gln
    1295                1300                1305

Ser Leu Tyr Tyr Arg Gln Trp Thr Val Pro Arg Pro Ser His Met
    1310                1315                1320

Asp Tyr Gly Asn Arg Ala Glu Gly Arg Val Asp Gly Phe His Pro
    1325                1330                1335

Arg Arg Leu Leu Leu Ser Gly Pro Pro Gln Ile Gly Lys Thr Gly
    1340                1345                1350

Ala Tyr Leu Gln Phe Leu Ser Val Leu Ser Arg Met Leu Val Arg
    1355                1360                1365

Leu Thr Glu Val Asp Val Tyr Asp Glu Glu Glu Ile Asn Ile Asn
    1370                1375                1380

Leu Arg Glu Glu Ser Asp Trp His Tyr Leu Gln Leu Ser Asp Pro
    1385                1390                1395

Trp Pro Asp Leu Glu Leu Phe Lys Lys Leu Pro Phe Asp Tyr Ile
    1400                1405                1410

Ile His Asp Pro Lys Tyr Glu Asp Ala Ser Leu Ile Cys Ser His
    1415                1420                1425

Tyr Gln Gly Ile Lys Ser Glu Asp Arg Gly Met Ser Arg Lys Pro
    1430                1435                1440
```

-continued

```
Glu Asp Leu Tyr Val Arg Arg Gln Thr Ala Arg Met Arg Leu Ser
1445                1450                1455

Lys Tyr Ala Ala Tyr Asn Thr Tyr His His Cys Glu Gln Cys His
1460                1465                1470

Gln Tyr Met Gly Phe His Pro Arg Tyr Gln Leu Tyr Glu Ser Thr
1475                1480                1485

Leu His Ala Phe Ala Phe Ser Tyr Ser Met Leu Gly Glu Glu Ile
1490                1495                1500

Gln Leu His Phe Ile Ile Pro Lys Ser Lys Glu His His Phe Val
1505                1510                1515

Phe Ser Gln Pro Gly Gly Gln Leu Glu Ser Met Arg Leu Pro Leu
1520                1525                1530

Val Thr Asp Lys Ser His Glu Tyr Ile Lys Ser Pro Thr Phe Thr
1535                1540                1545

Pro Thr Thr Gly Arg His Glu His Gly Leu Phe Asn Leu Tyr His
1550                1555                1560

Ala Met Asp Gly Ala Ser His Leu His Val Leu Val Lys Glu
1565                1570                1575

Tyr Glu Met Ala Ile Tyr Lys Lys Tyr Trp Pro Asn His Ile Met
1580                1585                1590

Leu Val Leu Pro Ser Ile Phe Asn Ser Ala Gly Val Gly Ala Ala
1595                1600                1605

His Phe Leu Ile Lys Glu Leu Ser Tyr His Asn Leu Glu Leu Glu
1610                1615                1620

Arg Asn Arg Gln Glu Glu Leu Gly Ile Lys Pro Gln Asp Ile Trp
1625                1630                1635

Pro Phe Ile Val Ile Ser Asp Asp Ser Cys Val Met Trp Asn Val
1640                1645                1650

Val Asp Val Asn Ser Ala Gly Glu Arg Ser Arg Glu Phe Ser Trp
1655                1660                1665

Ser Glu Arg Asn Val Ser Leu Lys His Ile Met Gln His Ile Glu
1670                1675                1680

Ala Ala Pro Asp Ile Met His Tyr Ala Leu Leu Gly Leu Arg Lys
1685                1690                1695

Trp Ser Ser Lys Thr Arg Ala Ser Glu Val Gln Glu Pro Phe Ser
1700                1705                1710

Arg Cys His Val His Asn Phe Ile Ile Leu Asn Val Asp Leu Thr
1715                1720                1725

Gln Asn Val Gln Tyr Asn Gln Asn Arg Phe Leu Cys Asp Asp Val
1730                1735                1740

Asp Phe Asn Leu Arg Val His Ser Ala Gly Leu Leu Leu Cys Arg
1745                1750                1755

Phe Asn Arg Phe Ser Val Met Lys Lys Gln Ile Val Val Gly Gly
1760                1765                1770

His Arg Ser Phe His Ile Thr Ser Lys Val Ser Asp Asn Ser Ala
1775                1780                1785

Ala Val Val Pro Ala Gln Tyr Ile Cys Ala Pro Asp Ser Lys His
1790                1795                1800

Thr Phe Leu Ala Ala Pro Ala Gln Leu Leu Leu Glu Lys Phe Leu
1805                1810                1815

Gln His His Ser His Leu Phe Phe Pro Leu Ser Leu Lys Asn His
1820                1825                1830

Asp His Pro Val Leu Ser Val Asp Cys Tyr Leu Asn Leu Gly Ser
```

```
                1835                1840                1845
Gln Ile Ser Val Cys Tyr Val Ser Ser Arg Pro His Ser Leu Asn
        1850                1855                1860
Ile Ser Cys Ser Asp Leu Leu Phe Ser Gly Leu Leu Leu Tyr Leu
        1865                1870                1875
Cys Asp Ser Phe Val Gly Ala Ser Phe Leu Lys Lys Phe His Phe
        1880                1885                1890
Leu Lys Gly Ala Thr Leu Cys Val Ile Cys Gln Asp Arg Ser Ser
        1895                1900                1905
Leu Arg Gln Thr Val Val Arg Leu Glu Leu Glu Asp Glu Trp Gln
        1910                1915                1920
Phe Arg Leu Arg Asp Glu Phe Gln Thr Ala Asn Ala Arg Glu Asp
        1925                1930                1935
Arg Pro Leu Phe Phe Leu Thr Gly Arg His Ile
        1940                1945

<210> SEQ ID NO 19
<211> LENGTH: 2246
<212> TYPE: DNA
<213> ORGANISM: Homo sapiens

<400> SEQUENCE: 19
```

| | | | | | |
|---|---|---|---|---|---|
| aaagtccggg | ggagccggtc | ccgggcagcc | gctcagcccc | ctgcccctcg | ccgcccgccg | 60 |
| cctgcctggg | ccgggccgag | gatgcgcgcg | agcgcctcgg | cggccaggct | tgctcccctc | 120 |
| cggcacgcct | gctaacttcc | cccgctacgt | ccccgttcgc | ccgccgggcc | gccccgtctc | 180 |
| cccgcgccct | ccgggtcggg | tcctccagga | gcgccaggcg | ctgccgccgt | gtgccctccg | 240 |
| ccgctcgccc | gcgcgcccgc | gctccccgcc | tgcgcccagc | gccccgcgcc | cgcgcccagt | 300 |
| cctcgggcgg | tcatgctgcc | cctctgcctc | gtggccgccc | tgctgctggc | cgccgggccc | 360 |
| gggccgagcc | tgggcgacga | agccatccac | tgcccgccct | gctccgagga | gaagctggcg | 420 |
| cgctgccgcc | ccccgtggg | ctgcgaggag | ctggtgcgag | agccgggctg | cggctgttgc | 480 |
| gccacttgcg | ccctgggctt | ggggatgccc | tgcggggtgt | acacccccg | ttgcggctcg | 540 |
| ggcctgcgct | gctacccgcc | ccgaggggtg | agaagcccc | tgcacacact | gatgcacggg | 600 |
| caaggcgtgt | gcatggagct | ggcggagatc | gaggccatcc | aggaaagcct | gcagccctct | 660 |
| gacaaggacg | agggtgacca | ccccaacaac | agcttcagcc | cctgtagcgc | ccatgaccgc | 720 |
| aggtgcctgc | agaagcactt | cgccaaaatt | cgagaccgga | gcaccagtgg | gggcaagatg | 780 |
| aaggtcaatg | gggcgccccg | ggaggatgcc | cggcctgtgc | cccagggctc | ctgccagagc | 840 |
| gagctgcacc | gggcgctgga | gcggctggcc | gcttcacaga | gccgcacccc | gaggacctc | 900 |
| tacatcatcc | ccatccccaa | ctgcgaccgc | aacggcaact | tccacccaa | gcagtgtcac | 960 |
| ccagctctgg | atgggcagcg | tggcaagtgc | tggtgtgtgg | accggaagac | gggggtgaag | 1020 |
| cttccggggg | gcctggagcc | aaaggggag | ctggactgcc | accagctggc | tgacagcttt | 1080 |
| cgagagtgag | gcctgccagc | aggccaggga | ctcagcgtcc | cctgctactc | ctgtgctctg | 1140 |
| gaggctgcag | agctgaccca | gagtggagtc | tgagtctgag | tcctgtctct | gcctgcggcc | 1200 |
| cagaagtttc | cctcaaatgc | gcgtgtgcac | gtgtgcgtgt | gcgtgcgtgt | gtgtgtgttt | 1260 |
| gtgagcatgg | gtgtgcccctt | ggggtaagcc | agagcctggg | gtgttctctt | tggtgttaca | 1320 |
| cagcccaaga | ggactgagac | tggcacttag | cccaagaggt | ctgagccctg | gtgtgtttcc | 1380 |
| agatcgatcc | tggattcact | cactcactca | ttccttcact | catccagcca | cctaaaaaca | 1440 |

-continued

```
tttactgacc atgtactacg tgccagctct agttttcagc cttgggaggt tttattctga   1500
cttcctctga ttttggcatg tggagacact cctataagga gagttcaagc ctgtgggagt   1560 agaaaatct cattcccaga gtcagaggag aagagacatg taccttgacc atcgtccttc    1620
ctctcaagct agccagaggg tgggagccta aggaagcgtg gggtagcaga tggagtaatg   1680
gtcacgaggt ccagacccac tcccaaagct cagacttgcc aggctccctt tctcttcttc   1740
cccaggtcct tcctttaggt ctggttgttg caccatctgc ttggttggct ggcagctgag   1800
agccctgctg tgggagagcg aaggggggtca aggaagact tgaagcacag agggctaggg   1860
aggtggggta catttctctg agcagtcagg gtgggaagaa agaatgcaag agtggactga   1920
atgtgcctaa tggagaagac ccacgtgcta ggggatgagg ggcttcctgg gtcctgttcc   1980
ctaccccatt tgtggtcaca gccatgaagt caccgggatg aacctatcct tccagtggct   2040
cgctccctgt agctctgcct ccctctccat atctccttcc cctacacctc cctccccaca   2100
cctccctact cccctgggca tcttctggct tgactggatg gaaggagact taggaaccta   2160
ccagttggcc atgatgtctt ttcttctttt tcttttttt aacaaacag aacaaaacca    2220 aaaatgtcc agatgaaaaa aaaaaa                                         2246
```

<210> SEQ ID NO 20
<211> LENGTH: 258
<212> TYPE: PRT
<213> ORGANISM: Homo sapiens

<400> SEQUENCE: 20

```
Met Leu Pro Leu Cys Leu Val Ala Ala Leu Leu Ala Ala Gly Pro
1               5                   10                  15

Gly Pro Ser Leu Gly Asp Glu Ala Ile His Cys Pro Cys Ser Glu
                20                  25                  30

Glu Lys Leu Ala Arg Cys Arg Pro Val Gly Cys Glu Glu Leu Val
                35                  40                  45

Arg Glu Pro Gly Cys Gly Cys Cys Ala Thr Cys Ala Leu Gly Leu
            50                  55                  60

Met Pro Cys Gly Val Tyr Thr Pro Arg Cys Gly Ser Gly Leu Arg Cys
65              70                  75                      80

Tyr Pro Pro Arg Gly Val Glu Lys Pro Leu His Thr Leu Met His Gly
                85                  90                  95

Gln Gly Val Cys Met Glu Leu Ala Glu Ile Glu Ala Ile Gln Glu Ser
                100                 105                 110

Leu Gln Pro Ser Asp Lys Asp Glu Gly Asp His Pro Asn Asn Ser Phe
            115                 120                 125

Ser Pro Cys Ser Ala His Asp Arg Arg Cys Leu Gln Lys His Phe Ala
130                 135                 140

Lys Ile Arg Asp Arg Ser Thr Ser Gly Gly Lys Met Lys Val Asn Gly
145                 150                 155                 160

Ala Pro Arg Glu Asp Ala Arg Pro Val Pro Gln Gly Ser Cys Gln Ser
                165                 170                 175

Glu Leu His Arg Ala Leu Glu Arg Leu Ala Ala Ser Gln Ser Arg Thr
            180                 185                 190

His Glu Asp Leu Tyr Ile Ile Pro Ile Pro Asn Cys Asp Arg Asn Gly
        195                 200                 205

Asn Phe His Pro Lys Gln Cys His Pro Ala Leu Asp Gly Gln Arg Gly
    210                 215                 220

Lys Cys Trp Cys Val Asp Arg Lys Thr Gly Val Lys Leu Pro Gly Gly
```

```
                225                 230                 235                 240
Leu Glu Pro Lys Gly Glu Leu Asp Cys His Gln Leu Ala Asp Ser Phe
            245                 250                 255
Arg Glu
```

<210> SEQ ID NO 21
<211> LENGTH: 5016
<212> TYPE: DNA
<213> ORGANISM: Homo sapiens

<400> SEQUENCE: 21

| | | | | | |
|---|---|---|---|---|---|
| acaggaggag | ccgctcgctg | gcggctgatc | cagcgtctcc | gtgacaggca | ccctgctccg | 60 |
| ccgccaccgc | caccgccacc | gccaccgtcg | ccttttcttc | ttcgtcccgg | gcggtgcgtt | 120 |
| ccactgctct | ggggccggcg | ccgcgcccag | tcccgcttcg | gccgcaagc | cccaccgctc | 180 |
| ccctccccgg | gcaggggcgc | cgcgcagccc | gctcccgccg | ccacctcctc | ccctgccgcc | 240 |
| ctcctagccg | gcaggaattg | cgcgaccaca | gcgccgctcg | cgtcgcccgc | atcagctcag | 300 |
| cccgctgccg | ctcggccctc | ggcaccgctc | cgggtccggc | cgccgcgcgg | ccagggctcc | 360 |
| ccctgcccag | cgctcccagg | ccccgccacg | cgtcgccgcg | cccagctcca | gtctcccctc | 420 |
| cccggggtct | cgccagcccc | ttcctgcagc | cgccgcctcc | gaaggagcgg | gtccgccgcg | 480 |
| ggtaaccatg | cctagcaaaa | ccaagtacaa | ccttgtggac | gatgggcacg | acctgcggat | 540 |
| cccccttgcac | aacgaggacg | ccttccagca | cggcatctgc | tttgaggcca | agtacgtagg | 600 |
| aagcctggac | gtgccaaggc | ccaacagcag | ggtggagatc | gtggctgcca | tgcgccggat | 660 |
| acggtatgag | tttaaagcca | agaacatcaa | gaagaagaaa | gtgagcatta | tggtttcagt | 720 |
| ggatggagtg | aaagtgattc | tgaagaagaa | gaaaaagctt | cttttattgc | agaaaaagga | 780 |
| atggacgtgg | gatgagagca | agatgctggt | gatgcaggac | cccatctaca | ggatcttcta | 840 |
| tgtctctcat | gattcccaag | acttgaagat | cttcagctat | atcgctcgag | atggtgccag | 900 |
| caatatcttc | aggtgtaacg | tctttaaatc | caagaagaag | agccaagcta | tgagaatcgt | 960 |
| tcggacggtg | gggcaggcct | ttgaggtctg | ccacaagctg | agcctgcagc | acacgcagca | 1020 |
| gaatgcagat | ggccaggaag | atggagagag | cgagaggaac | agcaacagct | caggagaccc | 1080 |
| aggccgccag | ctcactggag | ccgagagggc | ctccacggcc | actgcagagg | agactgacat | 1140 |
| cgatgcggtg | gaggtcccac | ttccagggaa | tgatgtcctg | gaattcagcc | gaggtgtgac | 1200 |
| tgatctagat | gctgtaggga | aggaaggagg | ctctcacaca | ggctccaagg | tttcgcaccc | 1260 |
| ccaggagccc | atgctgacag | cctcacccag | gatgctgctc | ccttcttctt | cctcgaagcc | 1320 |
| tccaggcctg | ggcacagaga | caccgctgtc | cactcaccac | cagatgcagc | tcctccagca | 1380 |
| gctcctccag | cagcagcagc | agcagacaca | agtggctgtg | gcccaggtac | acttgctgaa | 1440 |
| ggaccagttg | gctgctgagg | ctgcggcgcg | gctggaggcc | caggctcgcg | tgcatcagct | 1500 |
| tttgctgcag | aacaaggaca | tgctccagca | catctccctg | ctggtcaagc | aggtgcaaga | 1560 |
| gctggaactg | aagctgtcag | gacagaacgc | catgggctcc | caggacagct | tgctggagat | 1620 |
| caccttccgc | tccggagccc | tgcccgtgct | ctgtgacccc | acgaccccta | agccagagga | 1680 |
| cctgcattcg | ccgccgctgg | gcgcgggctt | ggctgacttt | gcccaccctg | cgggcagccc | 1740 |
| cttaggtagg | cgcgactgct | tggtgaagct | ggagtgcttt | cgctttcttc | cgcccgagga | 1800 |
| cacccccgccc | ccagcgcagg | gcgaggcgct | cctgggcggt | ctggagctca | tcaagttccg | 1860 |
| agagtcaggc | atcgcctcgg | agtacgagtc | caacacggac | gagagcgagg | agcgcgactc | 1920 |

-continued

```
gtggtcccag gaggagctgc cgcgcctgct gaatgtcctg cagaggcagg aactgggcga    1980
cggcctggat gatgagatcg ccgtgtaggt gccgagggcg aggagatgga ggcggcggcg    2040
tggctggagg ggccgtgtct ggctgctgcc cgggtagggg atgcccagtg aatgtgcact    2100
gccgaggaga atgccagcca gggcccggga gagtgtgagg tttcaggaaa gtattgagat    2160
tctgctttgg agggtaaagt ggggaagaaa tcggattccc agaggtgaat cagctcctct    2220
cctacttgtg actagagggt ggtggaggta aggccttcca gagcccatgg cttcaggaga    2280
gggtctctct ccaggactgc caggctgctg gaggacctgc ccctacctgc tgcatcgtca    2340
ggctcccacg ctttgtccgt gatgccccc taccccctca ctctcccgt ctccatggtc     2400
ccgaccagga agggaagcca tcggtacctt ctcaggtact ttgtttctgg atatcacgat    2460
gctgcgagtt gcctaaccct cccctacct ttatgagagg aattccttct ccaggccctt    2520
gctgagattg tagagattga gtgctctgga ccgcaaaagc caggctagtc cttgtagggt    2580
gagcatggaa ttggaatgtg tcacagtgga taagcttta gaggaactga atccaaacat    2640
tttctccagc cggacattga atgttgctac aaagggagcc ttgaagcttt aacatggttc    2700
aggcccttgg tgtgagagcc caggggagg acagcttgtc tgctgctcca aatcacttag    2760
atctgattcc tgttttgaaa gtcctgccct gccttcctcc tgcctgtagc ccagcccatc    2820
taaatggaag ctgggaattg cccctcacct cccctgtgtc ctgtccagct gaagcttttg    2880
cagcacttta cctctctgaa agccccagag accagagcc cccagccta cctctcaacc     2940
tgtcccctcc actgggcagt ggtggtcagt ttttactgca aaaaaaaaa aagaaaaaag    3000
agaaagaaaa aaaagaatga atgcaagctg atagctgaga ctgtgagact gttttttgtcc   3060
actcttctga atcactgcca cttgggtcag ggaccacagc cattgccacc cttggcccat    3120
ctctctgcgt gcgtgccttg agcacacata taaaaagtgc catgtgcaat tgtcttatct    3180
tttatgatct aggctttgcc tagggatcac tactccttaa cgggctggct ggggcaatga    3240
ggaaaagctc ctttgctcct gtaaggccat aagtggctgt taacagattt tcaaatgcct    3300
gaagagattg ctgagacctg ctagagtcat atgttcgggg aattaagtct ttatcctaga    3360
caacaaggta cagatgcaaa ctgcagtgtt attggagggt caatcggcaa ggatatgatt    3420
atcccaaaat ggagttcatc gaccctagct ttccttaga ttatatataa ataaaagtgc     3480
agtcctcttc taatgccac agttggtttt cttgtagccc agaaagtcca aattaaagga     3540
aataaattca gttttatgtt agccttcctt ggtgcatcag ggtgtcagtg gaaataggat    3600
caggtggtgt gtgtgtgtgt gttttgtgtg tgtgtgtaca catgtgttta tatatacatg    3660
tgtgagggaa agtgtgtaca tatgtgtagg attgtaacca gacggaaaag aacgaggatc    3720
tccagggtgt ttgaatcagc aacagatttg tgttttctaa catgcattta gttggagagg    3780
catggttctg tttgtttgt tttgatctaa tttgccattg gaaataggta cagttacaca     3840
gagaaggaag aaccaggaaa gtgagatcca tgaaactaaa tgagcagctg tcagaatcca    3900
gtgtggctga gcctacctag cttatgaaat ctaacccagg gttccctgag tccaagacca    3960
cttagattat taagattttg aacgtccaga ggagtgaaaa gtctgttttc tgacgtaagc    4020
cggagctgag gataaagcca gaggccagtg gattaggtgt atggaatgtg gatgagagg     4080
gcttgtgtgg gatgtggcca gggagtgggt gaggaaggcc gcttctaaat ggcctgtaaa    4140
aacttgagat tggatagacg aaaggaaatg gagaaattaa agaattggag aaactagtta    4200
tctgtgttgc tgactttggg acccatccaa gactcctgcc cttggggtgt tccatggtgg    4260
tttcttcctg cctgggcgcc acccttccc cagttcaggc cctccctgga ggactagttt     4320
```

-continued

```
gtgtattggt atcctcccca gtggacccaa accagcgcat acttggtgtg tggagatggg    4380
agacaaagga cagatctagg agccttgaag gatcaccagc caccgaccct ccatcagggc    4440
caactgggca ggaaagggaa cattgcagac ctgatttccc gacgatgtca ccctgtcctc    4500
cctccttgct tcttgctctg ctaactcaac tctgccttcc tcttttcat tcttctactc     4560 tgccctatat ggaggacaaa tggacaccag gggtgctaac cttattggtg cctgccccag    4620
cctaccccag gtgccagcag actctcgtgc acaggaggct cccacagtta tggagccagg    4680
aaagaatttc tctgcactgg atggactgta tattgagatt aaaaattata ttccttatat    4740
tcctgcttat atcaatgctc tctctgtaaa acctcttcct agcctcattt ctctcaactg    4800
atcttgttta ggcgttgtat tcctttatt tactctttgc ttgactgctt cctcctaacc     4860
ctctacccac tagcactcta cttcctaaag ctgttgtgtc attaactctg ttggatcaac    4920
tctctgggaa aagattctgt taatgtaagt gcacttactc cctggatgtt gtcactagtc    4980
tagtggcttt tgctaaataa acctttctta tttcta                              5016

<210> SEQ ID NO 22
<211> LENGTH: 506
<212> TYPE: PRT
<213> ORGANISM: Homo sapiens

<400> SEQUENCE: 22

Met Pro Ser Lys Thr Lys Tyr Asn Leu Val Asp Asp Gly His Asp Leu
1               5                   10                  15

Arg Ile Pro Leu His Asn Glu Asp Ala Phe Gln His Gly Ile Cys Phe
            20                  25                  30

Glu Ala Lys Tyr Val Gly Ser Leu Asp Val Pro Arg Pro Asn Ser Arg
        35                  40                  45

Val Glu Ile Val Ala Ala Met Arg Arg Ile Arg Tyr Glu Phe Lys Ala
    50                  55                  60

Lys Asn Ile Lys Lys Lys Val Ser Ile Met Val Ser Val Asp Gly
65                  70                  75                  80

Val Lys Val Ile Leu Lys Lys Lys Lys Leu Leu Leu Gln Lys
                85                  90                  95

Lys Glu Trp Thr Trp Asp Glu Ser Lys Met Leu Val Met Gln Asp Pro
            100                 105                 110

Ile Tyr Arg Ile Phe Tyr Val Ser His Asp Ser Gln Asp Leu Lys Ile
        115                 120                 125

Phe Ser Tyr Ile Ala Arg Asp Gly Ala Ser Asn Ile Phe Arg Cys Asn
    130                 135                 140

Val Phe Lys Ser Lys Lys Ser Gln Ala Met Arg Ile Val Arg Thr
145                 150                 155                 160

Val Gly Gln Ala Phe Glu Val Cys His Lys Leu Ser Leu Gln His Thr
                165                 170                 175

Gln Gln Asn Ala Asp Gly Gln Glu Asp Gly Glu Ser Glu Arg Asn Ser
            180                 185                 190

Asn Ser Ser Gly Asp Pro Gly Arg Gln Leu Thr Gly Ala Glu Arg Ala
        195                 200                 205

Ser Thr Ala Thr Ala Glu Glu Thr Asp Ile Asp Ala Val Glu Val Pro
    210                 215                 220

Leu Pro Gly Asn Asp Val Leu Glu Phe Ser Arg Gly Val Thr Asp Leu
225                 230                 235                 240

Asp Ala Val Gly Lys Glu Gly Gly Ser His Thr Gly Ser Lys Val Ser
```

```
                245                 250                 255
His Pro Gln Glu Pro Met Leu Thr Ala Ser Pro Arg Met Leu Leu Pro
            260                 265                 270

Ser Ser Ser Ser Lys Pro Pro Gly Leu Gly Thr Glu Thr Pro Leu Ser
        275                 280                 285

Thr His His Gln Met Gln Leu Leu Gln Gln Leu Leu Gln Gln Gln Gln
    290                 295                 300

Gln Gln Thr Gln Val Ala Val Ala Gln Val His Leu Leu Lys Asp Gln
305                 310                 315                 320

Leu Ala Ala Glu Ala Ala Arg Leu Glu Ala Gln Ala Arg Val His
                325                 330                 335

Gln Leu Leu Leu Gln Asn Lys Asp Met Leu Gln His Ile Ser Leu Leu
            340                 345                 350

Val Lys Gln Val Gln Glu Leu Glu Leu Lys Leu Ser Gly Gln Asn Ala
        355                 360                 365

Met Gly Ser Gln Asp Ser Leu Leu Glu Ile Thr Phe Arg Ser Gly Ala
    370                 375                 380

Leu Pro Val Leu Cys Asp Pro Thr Thr Pro Lys Pro Glu Asp Leu His
385                 390                 395                 400

Ser Pro Pro Leu Gly Ala Gly Leu Ala Asp Phe Ala His Pro Ala Gly
                405                 410                 415

Ser Pro Leu Gly Arg Arg Asp Cys Leu Val Lys Leu Glu Cys Phe Arg
            420                 425                 430

Phe Leu Pro Pro Glu Asp Thr Pro Pro Ala Gln Gly Glu Ala Leu
        435                 440                 445

Leu Gly Gly Leu Glu Leu Ile Lys Phe Arg Glu Ser Gly Ile Ala Ser
    450                 455                 460

Glu Tyr Glu Ser Asn Thr Asp Glu Ser Glu Arg Asp Ser Trp Ser
465                 470                 475                 480

Gln Glu Glu Leu Pro Arg Leu Leu Asn Val Leu Gln Arg Gln Glu Leu
                485                 490                 495

Gly Asp Gly Leu Asp Asp Glu Ile Ala Val
            500                 505

<210> SEQ ID NO 23
<211> LENGTH: 5618
<212> TYPE: DNA
<213> ORGANISM: Homo sapiens

<400> SEQUENCE: 23
agcacatctg ggcgagagcg gcgccgctgg agccgagggg ggcgccgagc gcagatctgg     60
agcagcagag ccacggcgca gctgggaccc ttcgaggcgc tcggggcgca catctgggac    120
ctcgagcggg ggccgtgccg cgcgcagctg gaccagggga ggggggcggc ggctgcacag    180
ctggaccgaa gggggcgggg tcggccctgg gcgacccgct gaggggaggg ccgcgggccg    240
ccggggactg gagcatggga cggcgcgcct gaaggagcag gaaggggaag gaggcctggg    300
accccgaaaa gagaagggga gagcgagggg acgagagcgg aggaggaaga tgcaactgac    360 tgctgctgc ttcgtgttcc tggtgcaggg tagcctctat ctggtcatct gtggccagga    420
tgatggtcct cccggctcag aggaccctga gcgtgatgac cacgagggcc agccccggcc    480
ccgggtgcct cggaagcggg gccacatctc acctaagtcc cgccccatgg ccaattccac    540
tctcctaggc ctgctggccc cgcctgggga ggcttgggc attcttgggc agccccccaa    600
ccgcccgaac cacagccccc caccctcagc caaggtgaag aaaatctttg gctggggcga    660
```

```
cttctactcc aacatcaaga cggtggccct gaacctgctc gtcacaggga agattgtgga    720
ccatggcaat gggaccttca gcgtccactt ccaacacaat gccacaggcc agggaaacat    780
ctccatcagc ctcgtgcccc ccagtaaagc tgtagagttc caccaggaac agcagatctt    840
catcgaagcc aaggcctcca aaatcttcaa ctgccggatg gagtgggaga aggtagaacg    900
gggccgccgg acctcgcttt gcacccacga cccagccaag atctgctccc gagaccacgc    960
tcagagctca gccacctgga gctgctccca gcccttcaaa gtcgtctgtg tctacatcgc   1020
cttctacagc acggactatc ggctggtcca gaaggtgtgc ccagattaca actaccatag   1080 tgatacccccc tactacccat ctgggtgacc cggggcaggc cacagaggcc aggccagggc   1140
tggaaggaca ggcctgccca tgcaggagac catctggaca ccgggcaggg aagggggttgg   1200 gcctcaggca ggaggggggg tggagacgag gagatgccaa gtggggccag gccaagtct    1260 caagtggcag agaaagggtc ccaagtgctg gtcccaacct gaagctgtgg agtgactaga   1320
tcacaggagc actggaggag gagtgggctc tctgtgcagc ctcacagggc tttgccacgg   1380
agccacagag agatgctggg tccccgaggc ctgtgggcag gccgatcagt gtggcccccag   1440 atcaagtcat gggaggaagc taagcccttg gttcttgcca tcctgaggaa agatagcaac   1500
agggaggggg agatttcatc agtgtggaca gcctgtcaac ttaggatgga tggctgagag   1560
ggcttcctag gagccagtca gcagggtggg gtggggccag aggagctctc cagccctgcc   1620
tagtgggcgc cctcagcccc ttgtcgtgtg ctgagcatgg catgaggctg aagtggcaac   1680 cctgggggtct ttgatgtctt gacagattga ccatctgtct ccagccaggc caccccttttc   1740 caaaattccc tcttctgcca gtactccccc tgtaccaccc attgctgatg gcacacccat   1800
ccttaagcta agacaggacg attgtggtcc tcccacacta aggccacagc ccatccgcgt   1860
gctgtgtgtc cctcttccac cccaacccct gctggctcct ctgggagcat ccatgtcccg   1920
gagaggggtc cctcaacagt cagcctcacc tgtcagaccg ggttctccc ggatctggat    1980 ggcgccgccc tctcagcagc gggcacgggt ggggcggggc cgggccgcag agcatgtgct   2040
ggatctgttc tgtgtgtctg tctgtggggtg ggggagggg agggaagtct tgtgaaaccg   2100
ctgattgctg acttttgtgt gaagaatcgt gttcttggag caggaaataa agcttgcccc   2160
ggggcactgg agtcagagtt gtccaaggaa agggcctcag gcatcccttg gtccaggaag   2220
aatttctctg atggccgcag gacatttgct tgagacccaa gtggcaggga tccaaccgcc   2280
cttggcgctg atgtttgctg agggctcagg gcttccctct ccagcccgg ttccaagctg    2340 tctgatcccc cacgaggaaa cttgagcaaa caccctgggc tcggtgctgg aggagggcgt   2400
agcatcttca gaacagctc agggagggag agctagcagg tagaatgggc caatgagggt   2460
gttccttggt gtcctccctg aactgccatc tgcagaccca gcagggtcct agccccgtca   2520
ttttgctgcg tggccttggc catgtccatt ctcctctctg gctttctttc tttgtttctt   2580
cctctatgac atgaagggct tgcccagacc agggttctc aaacgcggat cacccagagg    2640
gtttgttaac acacagattt ctgggtccta cccacatttc taattcagca ggcctgggtg   2700
gggcctaaga attagaattt ctaacgagtg cccaggtcta tgctgatgct gctgctccag   2760
ggcccatgct gggagaccca ctcaaaggac cttgaagttc atctctggct atggctccgc   2820 aggagggggga gacacctcgg atgtgatttc ccagctgtaa tttccatctg cttctcctgg   2880
ggaagggggc tttcagagaa tcggggctat tgtattggat tttcaatctg accacatgcc   2940
agtgaaggaa caggctggag tggggtgtgg acacagggcc tgcgtcagtc actcccctcc   3000
```

```
tgcagctagt aagaggcctc agaatggcca gctgccagtg gcaccttgtc tgggagttag    3060
ttgggccctt tgggactctg tgaagggaag acactaccaa ggtcacagtg ccttctggag    3120
gtcattctaa gtcggctctc ttgggagggc agcactcagg gccctttggg ccctcttgag    3180
gagaggagag tcctggcagt aaggtaagat gggcttgcca cccccacct ttcgcccctg     3240 cccaccagcg ctccgcgcaa actggtcccc tcatactgca gcgcagagtt gggtggggct    3300
gagaagccat ctggttacag cccaccttgt aggaaatgac ccagcttgtt tcccccacat    3360
catgcttcca ggggccgtct ctcctgagtg gagatgtgag acacacaccc ctcctccaga    3420
ccaccctccg ctccccaccc tggaggcttg agactgctgg cactgagcca gcccaccaat    3480
ggacacccac cgtgtgccgt tcagcctccc acagtgctgt ggagactgca ggaaggagga    3540
ggaagcaatg gggccagagg ccctgggcgc cctccccacc tcccctggct gaactctcag    3600
caggcactgg gggcactttg accccctcc tgctcctctc ctcctgtgga gagccagatg     3660
ctggcgacag ctggagggcc cggccttcct ggcacacagt tctgcctgca ccagggatgg    3720
attcatttta ataacttcat ttcacccca tgcacactgc cgcctcatcc ctcctttcca     3780
ccttccccag tagcctggct gctctcctca gctaggactt cgctaacaga tttcctccca    3840
aaccttaatt ctttggaata gccctctggt ccctactgtt cttgccagat acttctgtgc    3900
ccgcttggtc ctcacaaggg caaggggtcc atccaacttc ctctggctaa gaagacgtca    3960
cctctgcccc attggcgagc agtgtcccca tggtgatgcc ccccaccat cacgacgaag     4020 tgcgctggcc tcccactctt gccatgcaca cactcacagg agattcctct gaagaaacct    4080
gtccccactc tgcccagacc ccaaagggcc aggtcctact cacactccaa cccgttgacc    4140
ttccccatcc actgcccttc aaggcagtct gaaatgccct cagaccgttt agcggtcccg    4200
tggtcctcca ccctaacccc tcagcccagc tgggggctgc cggggggcctt gtctcctcca    4260 tcagtggagc ctctgggaca agtttaccag gctgggggtt cttaaggac acagcttgga     4320 tctccccatc aggctgggga acacctaggg ccggggcca tgcctccctc atcagactga     4380
ggacaccctg atgtcagggg ctggatggcc ccttagactg ggggtccctg agggcagaag    4440
ctatgcctcc cctcatcaga ctggagtctc cctgagggca agaactgtgc tatggatggg    4500
agggggacag cttgcctttt cctaggcatc agagcacctg gaggctgcct ctgcccttca    4560
gctttgctca aaggcgctgt ctgggtctca gcattccttt ctcaagtagg gtgaatctcc    4620
tagcactctg tgaagctaat aaggggggatt accccgttagg tcaactggta gcaatgcccg    4680
agtctccttc tcgatgaagc ttaaggcaaa agcaaatgaa tatctaggtc ccttccccc     4740 cttccccct tcccttcct gggatgagca agcgggaact gagtcaccct gttccccatc      4800
cttggcagga atgctggtga ccttgcattg tggcagattc aggtggcgag gcccattgct    4860
cgagatgcac ctggtgggtg ggtggcaggg atcctggggg agtgtttatg gggacggagg    4920
cagctgaagg gcaggagggg gtgaccaggt gctgggatca tcgagtgagt atgtgcagga    4980
gggattgtag agacacaatg aaacagttgc tctgtgttgg gaagtgatcc agtgtcatcg    5040
ctgggagtgg gagacagaaa tgttacttcc aaagattccg agtcctgtgg tactgccagg    5100
agaaccgggg gctggggtga tgggtaagga gaggcaccat tagccccgcc aggcagaggc    5160
aagatggggt gggggcggca cctgccaatt atgccaaagt cttggagtgg cagctggcac    5220
catcaccaag gcacaaatgc cagcagagac ctggcactca cctgggttgt gattccatag    5280
ggcccctgtc tcctgttggt ctcccaggct caaaggctga cctgataatt caagtgaagg    5340
atgcctagtt caaggcctcc cagttcctca tcccaggcca cctggtcagg tggtcccaag    5400
```

```
ggacaagcta ggtcctcctg aactgcagag gctgccaata aactggcaac acaggtgttg    5460
caggaagata tagctgggtc ctcatcctgg gtctgtaatt tattagacgt gtggctttgg    5520
acaaatgaca taatttccca gagcctcctt agataaaaaa ctagggcttt gcttaccttg    5580
gcgtattgtt aggaaaatta aatgagttgc tcaataaa                            5618
```

<210> SEQ ID NO 24
<211> LENGTH: 252
<212> TYPE: PRT
<213> ORGANISM: Homo sapiens

<400> SEQUENCE: 24

```
Met Gln Leu Thr Arg Cys Cys Phe Val Phe Leu Val Gln Gly Ser Leu
1               5                   10                  15

Tyr Leu Val Ile Cys Gly Gln Asp Asp Gly Pro Pro Gly Ser Glu Asp
                20                  25                  30

Pro Glu Arg Asp Asp His Glu Gly Gln Pro Arg Pro Arg Val Pro Arg
            35                  40                  45

Lys Arg Gly His Ile Ser Pro Lys Ser Arg Pro Met Ala Asn Ser Thr
        50                  55                  60

Leu Leu Gly Leu Leu Ala Pro Pro Gly Glu Ala Trp Gly Ile Leu Gly
65                  70                  75                  80

Gln Pro Pro Asn Arg Pro Asn His Ser Pro Pro Ser Ala Lys Val
                85                  90                  95

Lys Lys Ile Phe Gly Trp Gly Asp Phe Tyr Ser Asn Ile Lys Thr Val
            100                 105                 110

Ala Leu Asn Leu Leu Val Thr Gly Lys Ile Val Asp His Gly Asn Gly
        115                 120                 125

Thr Phe Ser Val His Phe Gln His Asn Ala Thr Gly Gln Gly Asn Ile
    130                 135                 140

Ser Ile Ser Leu Val Pro Pro Ser Lys Ala Val Glu Phe His Gln Glu
145                 150                 155                 160

Gln Gln Ile Phe Ile Glu Ala Lys Ala Ser Lys Ile Phe Asn Cys Arg
                165                 170                 175

Met Glu Trp Glu Lys Val Glu Arg Gly Arg Arg Thr Ser Leu Cys Thr
            180                 185                 190

His Asp Pro Ala Lys Ile Cys Ser Arg Asp His Ala Gln Ser Ser Ala
        195                 200                 205

Thr Trp Ser Cys Ser Gln Pro Phe Lys Val Val Cys Val Tyr Ile Ala
    210                 215                 220

Phe Tyr Ser Thr Asp Tyr Arg Leu Val Gln Lys Val Cys Pro Asp Tyr
225                 230                 235                 240

Asn Tyr His Ser Asp Thr Pro Tyr Tyr Pro Ser Gly
                245                 250
```

<210> SEQ ID NO 25
<211> LENGTH: 2608
<212> TYPE: DNA
<213> ORGANISM: Homo sapiens

<400> SEQUENCE: 25

```
agacgcgccg gaaccgggac gcgataaata tgcagagcgg aggcttcgcg cagcagagcc     60
cgcgcgccgc ccgctccggg tgctgaatcc aggcgtgggg acacgagcca ggcgccgccg    120
ccggagccag cggagccggg gccagagccg gagcgcgtcc gcgtccacgc agccgccggc    180
```

```
cggccagcac ccagggccct gcatgccagg tcgttggagg tggcagcgag acatgcaccc    240
ggcccggaag ctcctcagcc tcctcttcct catcctgatg ggcactgaac tcactcaagt    300
gctgcccacc aaccctgagg agagctggca ggtgtacagc tctgcccagg acagcgaggg    360
caggtgtatc tgcacagtgg tcgctccaca gcagaccatg tgttcacggg atgcccgcac    420
aaaacagctg aggcagctac tggagaaggt gcagaacatg tctcaatcca tagaggtctt    480
ggacaggcgg acccagagag acttgcagta cgtggagaag atggagaacc aaatgaaagg    540
actggagtcc aagttcaaac aggtggagga gagtcataag caacacctgg ccaggcagtt    600
taaggcgata aaagcgaaaa tggatgaact taggcctttg atacctgtgt tggaagagta    660
caaggccgat gccaaattgg tattgcagtt taaagaggag gtccagaatc tgacgtcagt    720
gcttaacgag ctgcaagagg aaattggcgc ctatgactac gatgaacttc agagcagagt    780
gtccaatctt gaagaaggc tccgtgcatg catgcaaaaa ctagcttgcg ggaagttgac    840
gggcatcagt gaccccgtga ctgtcaagac ctccggctcg aggttcggat cctggatgac    900
agaccctctc gcccctgaag gcgataaccg ggtgtgtac atggacggct atcacaacaa    960
ccgcttcgta cgtgagtaca agtccatggt tgacttcatg aacacggaca atttcacctc   1020
ccaccgtctc ccccaccct ggtcgggcac ggggcaggtg gtctacaacg gttctatcta   1080
cttcaacaag ttccagagcc acatcatcat caggtttgac ctgaagacag agaccatcct   1140
caagacccgc agcctggact atgccggtta caacaacatg taccactacg cctggggtgg   1200
ccactcggac atcgacctca tggtggacga gagcgggctg tgggccgtgt acgccaccaa   1260
ccagaacgct ggcaacatcg tggtcagtag gctggacccc gtgtccctgc agaccctgca   1320
gacctggaac acgagctacc ccaagcgcag cgccggggag gccttcatca tctgcggcac   1380
gctgtacgtc accaacggct actcagggg taccaaggtc cactatgcat accagaccaa   1440
tgcctccacc tatgaataca tcgacatccc attccagaac aaatactccc acatctccat   1500
gctggactac aaccccaagg accgggccct gtatgcctgg aacaacgccc accagatcct   1560
ctacaacgtg accctcttcc acgtcatccg ctccgacgag ttgtagctcc ctcctcctgg   1620
aagccaaggg cccacgtcct caccacaaag ggactcctgt gaaactgctg ccaaaaagat   1680
accaataaca ctaacaatac cgatcttgaa aaatcatcag cagtgcggat tctgacatcg   1740
agggatggca ttacctccgt gtttctccct ttcgagccgg cgggccacag acgtcggaag   1800
aaactcccgt atttgcagct ggaactgcag cccacggcgc cccggttttc ctccccgccc   1860
tgtccctctc tggtcaaaca acatactaaa gaggcgaggc aatgactgtt ggccagttct   1920
caccggggaa aaacccactg ttaggatggc atgaacattt ccttagatcg tggtcagctc   1980
cgaggaatgt ggcgtccagg ctctttgaga gccatgggct gcacccggcc gtaggctagt   2040
gtaactcgca tcccattgca gtgccgtttc ttgactgtgt tgctgtctct tagattaacc   2100
gtgctgaggc tccacatagc tcctggacct gtgtctagta catactgaag cgatggtcag   2160
agtgtgtaga gtgaagttgc tgtgcccaca ttgtttgaac tcgcgtaccc cgtagataca   2220
ttgtgcaacg ttcttctgtt attcccttga ggtggtaact tcgtatgttc agtttatgcg   2280
atgattgttg taaatgcaat gccgtagttt ggattaataa gtggatggtt tttgtttcta   2340
aaaagaaaaa aaaaatcagt gttcaccctt atagagacat agtcaagttc atgttgataa   2400
taatcaaagg aattactctc ttcttgttaa attagctaaa tcatgtaacc gcagatagga   2460
agggctcgcc tggggaaact ctggtttccg atgggacagg aaagtcatac gggcaacagt   2520
atgcggaaag tacgttttt aagtaaaaaa caaaggcaaa cttttgtacta tccagttatc   2580
```

-continued

```
taaggaacaa taaaaacatt aggagatc                                          2608
```

<210> SEQ ID NO 26
<211> LENGTH: 485
<212> TYPE: PRT
<213> ORGANISM: Homo sapiens

<400> SEQUENCE: 26

```
Met Ser Val Pro Leu Leu Lys Ile Gly Val Val Leu Ser Thr Met Ala
1               5                   10                  15

Met Ile Thr Asn Trp Met Ser Gln Thr Leu Pro Ser Leu Val Gly Leu
            20                  25                  30

Asn Thr Thr Lys Leu Ser Ala Ala Gly Gly Gly Thr Leu Asp Arg Ser
        35                  40                  45

Thr Gly Val Leu Pro Thr Asn Pro Glu Glu Ser Trp Gln Val Tyr Ser
    50                  55                  60

Ser Ala Gln Asp Ser Glu Gly Arg Cys Ile Cys Thr Val Val Ala Pro
65                  70                  75                  80

Gln Gln Thr Met Cys Ser Arg Asp Ala Arg Thr Lys Gln Leu Arg Gln
                85                  90                  95

Leu Leu Glu Lys Val Gln Asn Met Ser Gln Ser Ile Glu Val Leu Asp
                100                 105                 110

Arg Arg Thr Gln Arg Asp Leu Gln Tyr Val Glu Lys Met Glu Asn Gln
            115                 120                 125

Met Lys Gly Leu Glu Ser Lys Phe Lys Gln Val Glu Glu Ser His Lys
        130                 135                 140

Gln His Leu Ala Arg Gln Phe Lys Ala Ile Lys Ala Lys Met Asp Glu
145                 150                 155                 160

Leu Arg Pro Leu Ile Pro Val Leu Glu Glu Tyr Lys Ala Asp Ala Lys
                165                 170                 175

Leu Val Leu Gln Phe Lys Glu Glu Val Gln Asn Leu Thr Ser Val Leu
                180                 185                 190

Asn Glu Leu Gln Glu Glu Ile Gly Ala Tyr Asp Tyr Asp Glu Leu Gln
            195                 200                 205

Ser Arg Val Ser Asn Leu Glu Glu Arg Leu Arg Ala Cys Met Gln Lys
        210                 215                 220

Leu Ala Cys Gly Lys Leu Thr Gly Ile Ser Asp Pro Val Thr Val Lys
225                 230                 235                 240

Thr Ser Gly Ser Arg Phe Gly Ser Trp Met Thr Asp Pro Leu Ala Pro
                245                 250                 255

Glu Gly Asp Asn Arg Val Trp Tyr Met Asp Gly Tyr His Asn Asn Arg
            260                 265                 270

Phe Val Arg Glu Tyr Lys Ser Met Val Asp Phe Met Asn Thr Asp Asn
        275                 280                 285

Phe Thr Ser His Arg Leu Pro His Pro Trp Ser Gly Thr Gly Gln Val
    290                 295                 300

Val Tyr Asn Gly Ser Ile Tyr Phe Asn Lys Phe Gln Ser His Ile Ile
305                 310                 315                 320

Ile Arg Phe Asp Leu Lys Thr Glu Thr Ile Leu Lys Thr Arg Ser Leu
                325                 330                 335

Asp Tyr Ala Gly Tyr Asn Asn Met Tyr His Tyr Ala Trp Gly Gly His
            340                 345                 350

Ser Asp Ile Asp Leu Met Val Asp Glu Ser Gly Leu Trp Ala Val Tyr
        355                 360                 365
```

```
Ala Thr Asn Gln Asn Ala Gly Asn Ile Val Val Ser Arg Leu Asp Pro
    370                 375                 380

Val Ser Leu Gln Thr Leu Gln Thr Trp Asn Thr Ser Tyr Pro Lys Arg
385                 390                 395                 400

Ser Ala Gly Glu Ala Phe Ile Ile Cys Gly Thr Leu Tyr Val Thr Asn
                405                 410                 415

Gly Tyr Ser Gly Gly Thr Lys Val His Tyr Ala Tyr Gln Thr Asn Ala
                420                 425                 430

Ser Thr Tyr Glu Tyr Ile Asp Ile Pro Phe Gln Asn Lys Tyr Ser His
            435                 440                 445

Ile Ser Met Leu Asp Tyr Asn Pro Lys Asp Arg Ala Leu Tyr Ala Trp
        450                 455                 460

Asn Asn Gly His Gln Ile Leu Tyr Asn Val Thr Leu Phe His Val Ile
465                 470                 475                 480

Arg Ser Asp Glu Leu
            485

<210> SEQ ID NO 27
<211> LENGTH: 13037
<212> TYPE: DNA
<213> ORGANISM: Homo sapiens

<400> SEQUENCE: 27
agtccacagc tgtcactaat cggggtaagc cttgttgtat ttgtgcgtgt gggtggcatt      60
ctcaatgaga actagcttca cttgtcattt gagtgaaatc tacaacccga ggcggctagt     120
gctcccgcac tactgggatc tgagatcttc ggagatgact gtcgcccgca gtacggagcc     180
agcagaagtc cgacccttcc tgggaatggg ctgtaccgag aggtccgact agccccaggg     240
ttttagtgag ggggcagtgg aactcagcga gggactgaga gcttcacagc atgcacgagt     300
ttgatgccag agaaaaagtc gggagataaa ggagccgcgt gtcactaaat tgccgtcgca     360
gccgcagcca ctcaagtgcc ggacttgtga gtactctgcg tctccagtcc tcggacagaa     420
gttggagaac tctcttggag aactccccga gttaggagac gagatctcct aacaattact     480 acttttttctt gcgctcccca cttgccgctc gctgggacaa cgacagcca cagttcccct      540 gacgacagga tggaggccaa gggcaggagc tgaccagcgc cgccctcccc cgccccgac      600 ccaggaggtg gagatccctc cggtccagcc acattcaaca cccactttct cctccctctg     660
cccctatatt cccgaaaccc cctcctcctt cccttttccc tcctcctgga cgggggag      720 gagaaagggg gagtccagtc gtcatgactg agctgaaggc aaagggtccc cgggctcccc     780
acgtggcggg cggccgccc tccccgagg tcggatcccc actgctgtgt cgcccagccg      840
caggtccgtt cccggggagc cagacctcgg acaccttgcc tgaagtttcg gcatacccta     900
tctccctgga cgggctactc ttccctcggc cctgccaggg acaggacccc tccgacgaaa     960
agacgcagga ccagcagtcg ctgtcggacg tggagggcgc atattccaga gctgaagcta    1020 caagggtgc tggaggcagc agttctagtc ccccagaaaa ggacagcgga ctgctggaca    1080
gtgtcttgga cactctgttg gcgccctcag gtcccgggca gagccaaccc agccctcccg    1140
cctgcgaggt caccagctct tggtgcctgt ttggccccga acttcccgaa gatccaccgg    1200
ctgcccccgc cacccagcgg gtgttgtccc cgctcatgag ccggtccggg tgcaaggttg    1260
gagacagctc cggacggca gctgcccata aagtgctgcc ccggggcctg tcaccagccc    1320
ggcagctgct gctcccggcc tctgagagcc ctcactggtc cggggcccca gtgaagccgt    1380
```

```
ctccgcaggc cgctgcggtg gaggttgagg aggaggatgg ctctgagtcc gaggagtctg  1440
cgggtccgct tctgaagggc aaacctcggg ctctgggtgg cgcggcggct ggaggaggag  1500
ccgcggctgt cccgccgggg gcggcagcag gaggcgtcgc cctggtcccc aaggaagatt  1560
cccgcttctc agcgcccagg gtcgccctgg tggagcagga cgcgccgatg cgcccgggc   1620 gctccccgct ggccaccacg gtgatggatt tcatccacgt gcctatcctg cctctcaatc  1680
acgccttatt ggcagcccgc actcggcagc tgctggaaga cgaaagttac gacggcgggg  1740
ccggggctgc cagcgccttt gccccgccgc ggagttcacc ctgtgcctcg tccacccgg   1800 tcgctgtagg cgacttcccc gactgcgcgt accgcccga cgccgagccc aaggacgacg   1860
cgtaccctct ctatagcgac ttccagccgc ccgctctaaa gataaaggag gaggaggaag  1920
gcgcggaggc ctccgcgcgc tccccgcgtt cctaccttgt ggccggtgcc aaccccgcag  1980
ccttcccgga tttccgttg  gggccaccgc ccccgctgcc gccgcgagcg accccatcca  2040
gacccgggga gcggcggtg  acggccgcac ccgccagtgc ctcagtctcg tctgcgtcct  2100
cctcggggtc gaccctggag tgcatcctgt acaaagcgga gggcgcgccg cccagcagg   2160 gcccgttcgc gccgccgccc tgcaaggcgc cgggcgcgag cggctgcctg ctcccgcggg  2220
acggcctgcc ctccacctcc gcctctgccg ccgccgccgg ggcggccccc gcgctctacc  2280
ctgcactcgg cctcaacggg ctcccgcagc tcggctacca ggccgccgtg ctcaaggagg  2340
gcctgccgca ggtctacccg ccctatctca actacctgag gccggattca gaagccagcc  2400
agagcccaca atacagcttc gagtcattac ctcagaagat ttgtttaatc tgtgggatg   2460 aagcatcagg ctgtcattat ggtgtcctta cctgtgggag ctgtaaggtc ttctttaaga  2520
gggcaatgga agggcagcac aactacttat gtgctggaag aaatgactgc atcgttgata  2580
aaatccgcag aaaaaactgc ccagcatgtc gccttagaaa gtgctgtcag gctggcatgg  2640
tccttggagg tcgaaaattt aaaaagttca ataaagtcag agttgtgaga gcactggatg  2700
ctgttgctct cccacagcca gtgggcgttc caaatgaaag ccaagcccta agccagagat  2760
tcactttttc accaggtcaa gacatacagt tgattccacc actgatcaac ctgttaatga  2820
gcattgaacc agatgtgatc tatgcaggac atgacaacac aaaacctgac acctccagtt  2880
ctttgctgac aagtcttaat caactaggcg agaggcaact tctttcagta gtcaagtggt  2940
ctaaatcatt gccaggtttt cgaaacttac atattgatga ccagataact ctcattcagt  3000
attcttggat gagcttaatg gtgtttggtc taggatggag atcctacaaa cacgtcagtg  3060
ggcagatgct gtatttttgca cctgatctaa tactaaatga acagcggatg aaagaatcat  3120
cattctattc attatgcctt accatgtggc agatcccaca ggagtttgtc aagcttcaag  3180
ttagccaaga agagttcctc tgtatgaaag tattgttact tcttaataca attcctttgg  3240
aagggctacg aagtcaaacc cagtttgagg agatgaggtc aagctacatt agagagctca  3300
tcaaggcaat tggtttgagg caaaaggag ttgtgtcgag ctcacagcgt ttctatcaac   3360
ttacaaaact tcttgataac ttgcatgatc ttgtcaaaca acttcatctg tactgcttga  3420
atacatttat ccagtcccgg gcactgagtg ttgaatttcc agaaatgatg tctgaagtta  3480
ttgctgcaca attacccaag atattggcag ggatggtgaa accccttctc tttcataaaa  3540
agtgaatgtc atcttttct  tttaaagaat taaattttgt ggtatgtctt tttgttttgg  3600
tcaggattat gaggtcttga gtttttataa tgttcttctg aaagccttac atttataaca  3660
tcatagtgtg taaatttaaa agaaaaattg tgaggttcta attattttct tttataaagt  3720
ataattagaa tgtttaactg ttttgtttac ccatattttc ttgaagaatt tacaagattg  3780
```

```
aaaaagtact aaaattgtta aagtaaacta tcttatccat attatttcat accatgtagg    3840
tgaggatttt taacttttgc atctaacaaa tcatcgactt aagagaaaaa atcttacatg    3900
taataacaca aagctattat atgttatttc taggtaactc cctttgtgtc aattatattt    3960
ccaaaaatga acctttaaaa tggtatgcaa aattttgtct atatatattt gtgtgaggag    4020
gaaattcata actttcctca gattttcaaa agtatttta  atgcaaaaaa tgtagaaaga    4080
gtttaaaacc actaaaatag attgatgttc ttcaaactag gcaaacaac  tcatatgtta    4140
agaccatttt ccagattgga aacacaaatc tcttaggaag ttaataagta gattcatatc    4200
attatgcaaa tagtattgtg ggttttgtag gttttaaaa  taacctttt  tggggagaga    4260
attgtcctct aatgaggtat tgcgagtgga cataagaaat cagaagatta tggcctaact    4320
gtactcctta ccaactgtgg catgctgaaa gttagtcact cttactgatt ctcaattctc    4380
tcacctttga aagtagtaaa atatctttcc tgccaattgc tcctttgggt cagagcttat    4440
taacatcttt tcaaatcaaa ggaaagaaga aagggagagg aggaggaggg aggtatcaat    4500
tcacatacct ttctcctctt tatcctccac tatcatgaat tcatattatg tttcagccat    4560
gcaaatcttt ttaccatgaa atttcttcca gaattttccc cctttgacac aaattccatg    4620
catgtttcaa ccttcgagac tcagccaaat gtcatttctg taaaatcttc cctgagtctt    4680
ccaagcagta atttgccttc tcctagagtt tacctgccat tttgtgcaca tttgagttac    4740
agtagcatgt tattttacaa ttgtgactct cctgggagtc tgggagccat ataaagtggt    4800
caatagtgtt tgctgactga gagttgaatg acattttctc tctgtcttgg tattactgta    4860
gatttcgatc attctttggt tacatttctg catatttctg tacccatgac tttatcactt    4920
tcttctccca tgctttatct ccatcaatta tcttcattac ttttaaattt tccacctttg    4980
cttcctactt tgtgagatct ctcccttac  tgactataac atagaagaat agaagtgtat    5040
tttatgtgtc ttaaggacaa tactttagat tccttgttct aagttttaa  actgaatgaa    5100
tggaatatta tttctctccc taagcaaaat tccacaaaac aattatttct tatgtttatg    5160
tagcctaaaa ttgttttgta ctgtaaacct cagcataaaa actttcttca tttctaattt    5220
cattcaacaa atattgattg aatacctggt attagcacaa gaaaaatgtg ctaataagcc    5280
ttatgagaat ttggagctga agaaagacat ataactcagg aaagttacag tccagtagta    5340
ggtataaatt acagtgcctg ataaataggc attttaatat ttgtacactc aacgtatact    5400
aggtaggtgc aaaacattta catataattt tactgatacc catgcagcac aaaggtacta    5460
actttaaata ttaaataaca cctttatgtg tcagtaattc atttgcatta aatcttattg    5520
aaaaggcttt caatatattt tccccacaaa tgtcatccca agaaaaaagt attttttaaca   5580
tctcccaaat ataatagtta caggaaatct acctctgtga gagtgacacc tctcagaatg    5640
aactgtgtga cacaagaaaa tgaatgtagg tctatccaaa aaaaccccca agaaacaaaa    5700
acaatattat tagcccttta tgcttaagtg atggactcag ggaacagttg atgttgtgat    5760
catttttatta tctgattctt gttactttga attaaaccaa tattttgatg atataaatca    5820
tttccaccag catatattta atttccataa taacttaaaa attttctaat ttcactcaac    5880
tatgagggaa tagaatgtgg tggccacagg tttggctttt gttaaaatgt ttgatatctt    5940
cgatgttgat ctctgtctgc aatgtagatg tctaaacact aggatttaat atttaaggct    6000
aagctttaaa aataaagtac cttttttaaaa agaatatggc ttcaccaaat ggaaaatacc    6060
taatttctaa atctttttct ctacaaagtc ctatctacta atgtctccat tactatttag    6120
```

```
tcatcataac cattatcttc attttacatg tcgtgttctt tctggtagct ctaaaatgac   6180
actaaatcat aagaagacag gttacatatc aggaaatact tgaaggttac tgaaatagat   6240
tcttgagtta atgaaaatat tttctgtaaa aaggtttgaa aagccatttg agtctaaagc   6300
attatacctc cattatcagt agttatgtga caattgtgtg tgtgtttaat gtttaaagat   6360
gtggcacttt ttaataaggc aatgctatgc tattttttcc catttaacat taagataatt   6420
tattgctata cagatgatat ggaaatatga tgaacaatat tttttttgcc aaaactatgc   6480
cttgtaagta gccatggaat gtcaacctgt aacttaaatt atccacagat agtcatgtgt   6540
ttgatgatgg gcactgtgga gataactgac ataggactgt gcccccttc tctgccactt    6600 actagctgga tgagattaag caagtcattt aactgctctg attaaacctg cctttcccaa   6660
gtgctttgta atgaatagaa atggaaacca aaaaaaacgt atacaggcct tcagaaatag   6720
taattgctac tattttgttt tcattaagcc atagttctgg ctataatttt atcaaactca   6780
ccagctatat tctacagtga aagcaggatt ctagaaagtc tcactgtttt atttatgtca   6840
ccatgtgcta tgatatattt ggttgaattc atttgaaatt agggctggaa gtattcaagt   6900
aatttcttct gctgaaaaaa tacagtgttt tgagtttagg gcctgtttta tcaaagttct   6960
aaagagccta tcactcttcc attgtagaca ttttaaaata atgacactga ttttaacatt   7020
tttaagtgtc tttttagaac agagagcctg actagaacac agcccctcca aaaacccatg   7080
ctcaaattat ttttactatg gcagcaattc cacaaagggg aacaatgggt ttagaaatta   7140
caatgaagtc atcaacccaa aaaacatccc tatccctaag aaggttatga tataaaatgc   7200
ccacaagaaa tctatgtctg ctttaatctg tcttttattg ctttggaagg atggctatta   7260 cattttagt ttttgctgtg aatacctgag cagtttctct catccatact tatccttcac    7320
acatcagaag tcaggataga atatgaatca ttttaaaaac ttttacaact ccagagccat   7380
gtgcataaga agcattcaaa acttgccaaa acatacatt ttttttcaaat ttaaagatac    7440 tctatttttg tattcaatag ctcaacaact gtggtcccca ctgataaagt gaagtggaca   7500
aggagacaag taatggcata agtttgtttt tcccaaagta tgcctgttca atagccattg   7560
gatgtgggaa atttctacat ctcttaaaat tttacagaaa atacatagcc agatagtcta   7620
gcaaaagttc accaagtcct aaattgctta tccttacttc actaagtcat gaaatcattt   7680
taatgaaaag aacatcacct aggttttgtg gtttcttttt ttcttattca tggctgagtg   7740
aaaacaacaa tctctgtttc tccctagcat ctgtggacta tttaatgtac cattattcca   7800
cactctatgg tccttactaa atacaaaatt gaacaaaaag cagtaaaaca actgactctt   7860
cacccatatt ataaaatata atccaagcca gattagtcaa catccataag atgaatccaa   7920
gctgaactgg gcctagatta ttgagttcag gttggatcac atccctattt attaataaac   7980
ttaggaaaga aggccttaca gaccatcagt tagctggagc taatagaacc tacacttcta   8040
aagttcggcc tagaatcaat gtggccttaa aagctgaaaa gaagcaggaa agaacagttt   8100
tcttcaataa tttgtccacc ctgtcactgg agaaaattta agaatttggg ggtgttggta   8160
gtaagttaaa cacagcagct gttcatggca gaaattattc aatacatacc ttctctgaat   8220
atcctataac caaagcaaag aaaaacacca aggggtttgt tctcctcctt ggagttgacc   8280
tcattccaag gcagagctca ggtcacaggc acaggggctg cgcccaagct tgtccgcagc   8340
cttatgcagc tgtggagtct ggaagactgt tgcaggactg ctggcctagt cccagaatgt   8400
cagcctcatt ttcgatttac tggctcttgt tgctgtatgt catgctgacc ttattgttaa   8460
acacaggttt gtttgctttt tttccactca tggagacatg ggagaggcat tattttaag   8520
```

```
ctggttgaaa gctttaaccg ataaagcatt tttagagaaa tgtgaatcag gcagctaaga    8580
aagcatactc tgtccattac ggtaaagaaa atgcacagat tattaactct gcagtgtggc    8640
attagtgtcc tggtcaatat tcggatagat atgaataaaa tatttaaatg gtattgtaaa    8700
tagttttcag gacatatgct atagcttatt tttattatct tttgaaattg ctcttaatac    8760
atcaaatcct gatgtattca atttatcaga tataaattat tctaaatgaa gcccagttaa    8820 atgttttgt cttgtcagtt atatgttaag tttctgatct ctttgtctat gacgtttact     8880
aatctgcatt tttactgtta tgaattattt tagacagcag tggtttcaag cttttgcca    8940 ctaaaaatac ctttattt ctcctccccc agaaaagtct ataccttgaa gtatctatcc      9000
accaaactgt acttctatta agaaatagtt attgtgtttt cttaatgttt tgttattcaa    9060
agacatatca atgaaagctg ctgagcagca tgaataacaa ttatatccac acagatttga    9120
tatattttgt gcagccttaa cttgatagta taaaatgtca ttgcttttta aataatagtt    9180
agtcaatgga cttctatcat agcttttccta aactaggtta agatccagag ctttggggtc   9240
ataatatatt acatacaatt aagttatctt tttctaaggg ctttaaaatt catgagaata    9300
accaaaaaag gtatgtggag agttaataca aacataccat attcttgttg aaacagagat    9360
gtggctctgc ttgttctcca taaggtagaa atactttcca gaatttgcct aaactagtaa    9420
gccctgaatt tgctatgatt agggatagga agagattttc acatggcaga ctttagaatt    9480
cttcacttta gccagtaaag tatctccttt tgatcttagt attctgtgta ttttaacttt    9540
tctgagttgt gcatgtttat aagaaaaatc agcacaaagg gtttaagtta aagccttttt    9600
actgaaattt gaaagaaaca gaagaaaata tcaaagttct ttgtattttg agaggattaa    9660
atatgattta caaagttac atggagggct ctctaaaaca ttaaattaat tatttttgt      9720 tgaaaagtct tactttaggc atcattttat tcctcagcaa ctagctgtga agcctttact    9780
gtgctgtatg ccagtcactc tgctagattg tggagattac cagtgttccc gtcttctccg    9840
agcttagagt tggatgggga ataaagacag gtaaacagat agctacaata ttgtactgtg    9900
aatgcttatg ctggaggaag tacagggaac tattggagca cctaagagga gcacctacct    9960
tgaatttagg ggttagcaga ggcatcctga aaaagtcaa agctaagcca caatctataa    10020
gcagtttagg aattagcaga acgtgcgtgg tgaggagatg ccaaaggcaa gaagagaaga   10080
gtattccaaa caggagggat tccaaagaga gaagagtatc ccaaacaaca tttgcacaaa   10140
cctgatgggg agagagaatg tggggtgggg atggatgatg agactgaaga agaaagccag   10200
gtctagataa tcagtggcct tgtacaccat gttaaagagt gtagacttga ttctgttgta   10260
aacaggaaag cagcacaatt catatgaata ttttagaaga ctcccactgg aatatggaga   10320
ataaagttgg agatgactaa tcctggaagc agggagaaca ttttttgagga agttgcacta   10380 ttttggtgaa aatgatgatc ataaacatga agaattgtag gtgatcatga cctcctctct   10440 aatttttccag aagggttttg gaagatataa cataggaaca ttgacaggac tgacgaaagg   10500
agatgaaata caccatataa attgtcaaac acaaggccag atgtctaatt attttgctta   10560
tgtgttgaaa ttacaaatttt ttcatcagga aaccaaaaac tacaaaactt agttttccca   10620
agtcccagaa ttctatctgt ccaaacaatc tgtaccactc cacctatatc cctacctttg   10680
catgtctgtc caacctcaaa gtccaggtct atacacacgg gtaagactag agcagttcaa   10740
gtttcagaaa atgagaaaga ggaactgagt tgtgctgaac ccatacaaaa taaacacatt   10800
ctttgtatag attcttggaa cctcgagagg aattcaccta actcataggt atttgatggt   10860
```

```
atgaatccat ggctgggctc ggcttttaaa aagccttatc tgggattcct tctatggaac   10920
caagttccat caaagcccat ttaaaagcct acattaaaaa caaaattctt gctgcattgt   10980
atacaaataa tgatgtcatg atcaaataat cagatgccat tatcaagtgg aattacaaaa   11040
tggtataccc actccaaaaa aaaaaaaaaa gctaaattct cagtagaaca ttgtgacttc   11100
atgagccctc cacagccttg gagctgagga gggagcactg gtgagcagta ggttgaagag   11160
aaaacttggc gcttaataat ctatccatgt ttttcatct aaaagagcct tcttttgga    11220
ttaccttatt caatttccat caaggaaatt gttagttcca ctaaccagac agcagctggg   11280
aaggcagaag cttactgtat gtacatggta gctgtgggaa ggaggtttct ttctccaggt   11340
cctcactggc catacaccag tcccttgtta gttatgcctg gtcatagacc cccgttgcta   11400
tcatctcata tttaagtctt tggcttgtga atttatctat tctttcagct tcagcactgc   11460
agagtgctgg gactttgcta acttccattt cttgctggct tagcacattc ctcataggcc   11520
cagctctttt ctcatctggc cctgctgtgg agtcaccttg cccccttcagg agagccatgg   11580
cttaccactg cctgctaagc ctccactcag ctgccaccac actaaatcca gcttctcta   11640
agatgttgca gactttacag gcaagcataa aaggcttgat cttcctggac ttcccttac    11700
ttgtctgaat ctcacctcct tcaactttca gtctcagaat gtaggcattt gtcctctttg   11760
ccctacatct tccttcttct gaatcatgaa agcctctcac ttcctcttgc tatgtgctgg   11820
aggcttctgt caggttttag aatgagttct catctagtcc tagtagcttt tgatgcttaa   11880
gtccaccttt taaggatacc tttgagattt agaccatgtt tttcgcttga gaaagcccta   11940
atctccagac ttgccttct gtggatttca aagaccaact gaggaagtca aaagctgaat    12000
gttgactttc tttgaacatt tccgctataa caattccaat tctcctcaga gcaatatgcc   12060
tgcctccaac tgaccaggag aaaggtccag tgccaaagag aaaaacacaa agattaatta   12120
tttcagttga gcacatactt tcaaagtggt ttgggtattc atatgaggtt ttctgtcaag   12180
agggtgagac tcttcatcta tccatgtgtg cctgacagtt ctcctggcac tggctggtaa   12240
cagatgcaaa actgtaaaaa ttaagtgatc atgtatttta acgatatcat cacatactta   12300
ttttctatgt aatgttttaa atttcccta acatactttg actgttttgc acatggtaga    12360
tattcacatt ttttgtgtt gaagttgatg caatcttcaa agttatctac cccgttgctt    12420
attagtaaaa ctagtgttaa tacttggcaa gagatgcagg gaatcttct catgactcac    12480
gccctattta gttattaatg ctactaccct attttgagta agtagtaggt ccctaagtac   12540
attgtccaga gttatacttt taaagatatt tagccccata tacttcttga atctaaagtc   12600
atacaccttg ctcctcattt ctgagtggga aagacatttg agagtatgtt gacaattgtt   12660
ctgaaggttt ttgccaagaa ggtgaaactg tcctttcatc tgtgtatgcc tggggctggg   12720
tccctggcag tgatggggtg acaatgcaaa gctgtaaaaa ctaggtgcta gtgggcacct   12780
aatatcatca tcatatactt atttcaagc taatatgcaa atcccatct ctgtttttaa     12840
actaagtgta gatttcagag aaaatatttt gtggttcaca taagaaaaca gtctactcag   12900
cttgacaagt gttttatgtt aaattggctg gtggtttgaa atgaatcatc ttcacataat   12960
gttttcttta aaaatattgt gaatttaact ctaattcttg ttattctgtg tgataataaa   13020
gaataaacta atttcta                                                  13037
```

<210> SEQ ID NO 28
<211> LENGTH: 933
<212> TYPE: PRT
<213> ORGANISM: Homo sapiens

<400> SEQUENCE: 28

```
Met Thr Glu Leu Lys Ala Lys Gly Pro Arg Ala Pro His Val Ala Gly
1               5                   10                  15

Gly Pro Pro Ser Pro Glu Val Gly Ser Pro Leu Leu Cys Arg Pro Ala
            20                  25                  30

Ala Gly Pro Phe Pro Gly Ser Gln Thr Ser Asp Thr Leu Pro Glu Val
        35                  40                  45

Ser Ala Ile Pro Ile Ser Leu Asp Gly Leu Leu Phe Pro Arg Pro Cys
    50                  55                  60

Gln Gly Gln Asp Pro Ser Asp Glu Lys Thr Gln Asp Gln Gln Ser Leu
65                  70                  75                  80

Ser Asp Val Glu Gly Ala Tyr Ser Arg Ala Glu Ala Thr Arg Gly Ala
                85                  90                  95

Gly Gly Ser Ser Ser Pro Pro Glu Lys Asp Ser Gly Leu Leu Asp
            100                 105                 110

Ser Val Leu Asp Thr Leu Leu Ala Pro Ser Gly Pro Gly Gln Ser Gln
            115                 120                 125

Pro Ser Pro Pro Ala Cys Glu Val Thr Ser Ser Trp Cys Leu Phe Gly
        130                 135                 140

Pro Glu Leu Pro Glu Asp Pro Pro Ala Ala Pro Ala Thr Gln Arg Val
145                 150                 155                 160

Leu Ser Pro Leu Met Ser Arg Ser Gly Cys Lys Val Gly Asp Ser Ser
                165                 170                 175

Gly Thr Ala Ala Ala His Lys Val Leu Pro Arg Gly Leu Ser Pro Ala
            180                 185                 190

Arg Gln Leu Leu Leu Pro Ala Ser Glu Ser Pro His Trp Ser Gly Ala
        195                 200                 205

Pro Val Lys Pro Ser Pro Gln Ala Ala Ala Val Glu Val Glu Glu Glu
    210                 215                 220

Asp Gly Ser Glu Ser Glu Glu Ser Ala Gly Pro Leu Leu Lys Gly Lys
225                 230                 235                 240

Pro Arg Ala Leu Gly Gly Ala Ala Ala Gly Gly Gly Ala Ala Ala Val
                245                 250                 255

Pro Pro Gly Ala Ala Ala Gly Gly Val Ala Leu Val Pro Lys Glu Asp
            260                 265                 270

Ser Arg Phe Ser Ala Pro Arg Val Ala Leu Val Glu Gln Asp Ala Pro
        275                 280                 285

Met Ala Pro Gly Arg Ser Pro Leu Ala Thr Thr Val Met Asp Phe Ile
    290                 295                 300

His Val Pro Ile Leu Pro Leu Asn His Ala Leu Leu Ala Ala Arg Thr
305                 310                 315                 320

Arg Gln Leu Leu Glu Asp Glu Ser Tyr Asp Gly Gly Ala Gly Ala Ala
                325                 330                 335

Ser Ala Phe Ala Pro Pro Arg Ser Ser Pro Cys Ala Ser Ser Thr Pro
            340                 345                 350

Val Ala Val Gly Asp Phe Pro Asp Cys Ala Tyr Pro Pro Asp Ala Glu
        355                 360                 365

Pro Lys Asp Asp Ala Tyr Pro Leu Tyr Ser Asp Phe Gln Pro Pro Ala
    370                 375                 380

Leu Lys Ile Lys Glu Glu Glu Glu Gly Ala Glu Ala Ser Ala Arg Ser
385                 390                 395                 400

Pro Arg Ser Tyr Leu Val Ala Gly Ala Asn Pro Ala Ala Phe Pro Asp
```

```
            405                 410                 415
Phe Pro Leu Gly Pro Pro Pro Leu Pro Pro Arg Ala Thr Pro Ser
            420                 425                 430

Arg Pro Gly Glu Ala Ala Val Thr Ala Ala Pro Ala Ser Ala Ser Val
            435                 440                 445

Ser Ser Ala Ser Ser Ser Gly Ser Thr Leu Glu Cys Ile Leu Tyr Lys
        450                 455                 460

Ala Glu Gly Ala Pro Pro Gln Gln Gly Pro Phe Ala Pro Pro Pro Cys
465                 470                 475                 480

Lys Ala Pro Gly Ala Ser Gly Cys Leu Leu Pro Arg Asp Gly Leu Pro
                485                 490                 495

Ser Thr Ser Ala Ser Ala Ala Ala Gly Ala Ala Pro Ala Leu Tyr
            500                 505                 510

Pro Ala Leu Gly Leu Asn Gly Leu Pro Gln Leu Gly Tyr Gln Ala Ala
            515                 520                 525

Val Leu Lys Glu Gly Leu Pro Gln Val Tyr Pro Pro Tyr Leu Asn Tyr
        530                 535                 540

Leu Arg Pro Asp Ser Glu Ala Ser Gln Ser Pro Gln Tyr Ser Phe Glu
545                 550                 555                 560

Ser Leu Pro Gln Lys Ile Cys Leu Ile Cys Gly Asp Glu Ala Ser Gly
                565                 570                 575

Cys His Tyr Gly Val Leu Thr Cys Gly Ser Cys Lys Val Phe Phe Lys
            580                 585                 590

Arg Ala Met Glu Gly Gln His Asn Tyr Leu Cys Ala Gly Arg Asn Asp
            595                 600                 605

Cys Ile Val Asp Lys Ile Arg Arg Lys Asn Cys Pro Ala Cys Arg Leu
        610                 615                 620

Arg Lys Cys Cys Gln Ala Gly Met Val Leu Gly Gly Arg Lys Phe Lys
625                 630                 635                 640

Lys Phe Asn Lys Val Arg Val Arg Ala Leu Asp Ala Val Ala Leu
                645                 650                 655

Pro Gln Pro Val Gly Val Pro Asn Glu Ser Gln Ala Leu Ser Gln Arg
            660                 665                 670

Phe Thr Phe Ser Pro Gly Gln Asp Ile Gln Leu Ile Pro Pro Leu Ile
            675                 680                 685

Asn Leu Leu Met Ser Ile Glu Pro Asp Val Ile Tyr Ala Gly His Asp
        690                 695                 700

Asn Thr Lys Pro Asp Thr Ser Ser Ser Leu Leu Thr Ser Leu Asn Gln
705                 710                 715                 720

Leu Gly Glu Arg Gln Leu Leu Ser Val Val Lys Trp Ser Lys Ser Leu
                725                 730                 735

Pro Gly Phe Arg Asn Leu His Ile Asp Asp Gln Ile Thr Leu Ile Gln
            740                 745                 750

Tyr Ser Trp Met Ser Leu Met Val Phe Gly Leu Gly Trp Arg Ser Tyr
            755                 760                 765

Lys His Val Ser Gly Gln Met Leu Tyr Phe Ala Pro Asp Leu Ile Leu
        770                 775                 780

Asn Glu Gln Arg Met Lys Glu Ser Ser Phe Tyr Ser Leu Cys Leu Thr
785                 790                 795                 800

Met Trp Gln Ile Pro Gln Glu Phe Val Lys Leu Gln Val Ser Gln Glu
                805                 810                 815

Glu Phe Leu Cys Met Lys Val Leu Leu Leu Leu Asn Thr Ile Pro Leu
            820                 825                 830
```

```
Glu Gly Leu Arg Ser Gln Thr Gln Phe Glu Glu Met Arg Ser Ser Tyr
        835                 840                 845
Ile Arg Glu Leu Ile Lys Ala Ile Gly Leu Arg Gln Lys Gly Val Val
    850                 855                 860
Ser Ser Ser Gln Arg Phe Tyr Gln Leu Thr Lys Leu Leu Asp Asn Leu
865                 870                 875                 880
His Asp Leu Val Lys Gln Leu His Leu Tyr Cys Leu Asn Thr Phe Ile
                885                 890                 895
Gln Ser Arg Ala Leu Ser Val Glu Phe Pro Glu Met Met Ser Glu Val
            900                 905                 910
Ile Ala Ala Gln Leu Pro Lys Ile Leu Ala Gly Met Val Lys Pro Leu
        915                 920                 925
Leu Phe His Lys Lys
    930

<210> SEQ ID NO 29
<211> LENGTH: 1762
<212> TYPE: DNA
<213> ORGANISM: Homo sapiens

<400> SEQUENCE: 29
cggccgaggg cggggcaggg aggcagcatg ctaaaccggg tgcgctcggc cgtggcgcac      60
ctggtgagct ccggggcgc tccgcctccg cgccccaaat ccccggacct gcccaacgcc     120
gcctcggcgc cgcccgccgc cgctccagaa gcgcccagga gccctcccgc gaaggctggg     180
agcgggagcg cgacgcccgc gaaggctgtt gaggctcgag cgagcttctc cagaccgacc     240
tttctgcagc tgagccccgg ggggctgcga cgcgccgatg accacgcggg ccgggctgtg     300
caaagccccc cggacacggg ccgccgcctg ccctggagca caggctacgc cgaggtcatc     360
aatgctggca agagtcggca caatgaggac caggcttgct gtgaagtggt gtatgtggaa     420
ggtcggagga gtgttacagg agtacctagg gagcctagcc gaggccaggg actctgcttc     480
tactactggg gcctatttga tgggcatgca gggggcggag ctgctgaaat ggcctcacgg     540
ctcctgcatc gccatatccg agagcagcta aaggacctgg tagagatact tcaggaccct     600
tcgccaccac ccctctgcct cccaaccact ccggggaccc cagattcctc cgatccctct     660
cacttgcttg gccctcagtc ctgctggtct tcacagaagg aagtgagcca cgagagcctg     720
gtagtggggg ccgttgagaa tgccttccag ctcatggatg agcagatggc ccgggagcgg     780
cgtggccacc aagtggaggg gggctgctgt gcactggttg tgatctacct gctaggcaag     840
gtgtacgtgg ccaatgcagg cgatagcagg gccatcattg tccggaatgg tgaaatcatt     900
ccaatgtccc gggagtttac cccggagact gagcgccagc gtcttcagct gcttggcttc     960
ctgaaaccag agctgctagg cagtgaattc acccaccttg agttccccg cagagttctg    1020
cccaaggagc tggggcagag gatgttgtac cgggaccaga acatgaccgg ctgggcctac    1080
aaaaagatcg agctggagga tctcaggttt cctctggtct gtgggagggg caaaaaggct    1140
cgggtgatgg ccaccattgg ggtgacccga ggcttgggag accacagcct taaggtctgc    1200
agttccaccc tgcccatcaa gccctttctc tcctgcttcc ctgaggtacg agtgtatgac    1260
ctgacacaat atgagcactg cccagatgat gtgctagtcc tgggaacaga tggcctgtgg    1320
gatgtcacta ctgactgtga ggtagctgcc actgtggaca gggtgctgtc ggcctatgag    1380
cctaatgacc acagcaggta tacagctctg gcccaagctc tggtcctggg ggcccggggt    1440
acccccgag accgtggctg gcgtctcccc aacaacaagc tgggttccgg ggatgacatc    1500
```

-continued

```
tctgtcttcg tcatcccccct gggagggcca ggcagttact cctgaggggc tgaacaccat    1560
ccctcccact agcctctcca tacttactcc tctcacagcc caaattctga agttgtctcc    1620 ctgaccttc tttagtggca acttaactga agaagggatg tccgctatat ccaaaattac    1680
agctattggc aaataaacga gatggataaa ggtgaaaaaa aaaaaaaaaa aaaaaaaaaa    1740
aaaaaaaaaa aaaaaaaaaa aa                                             1762
```

<210> SEQ ID NO 30
<211> LENGTH: 505
<212> TYPE: PRT
<213> ORGANISM: Homo sapiens

<400> SEQUENCE: 30

```
Met Leu Asn Arg Val Arg Ser Ala Val Ala His Leu Val Ser Ser Gly
1               5                   10                  15

Gly Ala Pro Pro Arg Pro Lys Ser Pro Asp Leu Pro Asn Ala Ala
                20                  25                  30

Ser Ala Pro Ala Ala Ala Pro Glu Ala Pro Arg Ser Pro Pro Ala
            35                  40                  45

Lys Ala Gly Ser Gly Ser Ala Thr Pro Ala Lys Ala Val Glu Ala Arg
50                  55                  60

Ala Ser Phe Ser Arg Pro Thr Phe Leu Gln Leu Ser Pro Gly Gly Leu
65                  70                  75                  80

Arg Arg Ala Asp Asp His Ala Gly Arg Ala Val Gln Ser Pro Pro Asp
                85                  90                  95

Thr Gly Arg Arg Leu Pro Trp Ser Thr Gly Tyr Ala Glu Val Ile Asn
            100                 105                 110

Ala Gly Lys Ser Arg His Asn Glu Asp Gln Ala Cys Cys Glu Val Val
        115                 120                 125

Tyr Val Glu Gly Arg Arg Ser Val Thr Gly Val Pro Arg Glu Pro Ser
130                 135                 140

Arg Gly Gln Gly Leu Cys Phe Tyr Tyr Trp Gly Leu Phe Asp Gly His
145                 150                 155                 160

Ala Gly Gly Gly Ala Ala Glu Met Ala Ser Arg Leu Leu His Arg His
                165                 170                 175

Ile Arg Glu Gln Leu Lys Asp Leu Val Glu Ile Leu Gln Asp Pro Ser
            180                 185                 190

Pro Pro Pro Leu Cys Leu Pro Thr Thr Pro Gly Thr Pro Asp Ser Ser
        195                 200                 205

Asp Pro Ser His Leu Leu Gly Pro Gln Ser Cys Trp Ser Ser Gln Lys
210                 215                 220

Glu Val Ser His Glu Ser Leu Val Val Gly Ala Val Glu Asn Ala Phe
225                 230                 235                 240

Gln Leu Met Asp Glu Gln Met Ala Arg Glu Arg Arg Gly His Gln Val
                245                 250                 255

Glu Gly Gly Cys Cys Ala Leu Val Val Ile Tyr Leu Leu Gly Lys Val
            260                 265                 270

Tyr Val Ala Asn Ala Gly Asp Ser Arg Ala Ile Ile Val Arg Asn Gly
        275                 280                 285

Glu Ile Ile Pro Met Ser Arg Glu Phe Thr Pro Glu Thr Glu Arg Gln
    290                 295                 300

Arg Leu Gln Leu Leu Gly Phe Leu Lys Pro Glu Leu Leu Gly Ser Glu
305                 310                 315                 320
```

```
Phe Thr His Leu Glu Phe Pro Arg Arg Val Leu Pro Lys Glu Leu Gly
                325                 330                 335

Gln Arg Met Leu Tyr Arg Asp Gln Asn Met Thr Gly Trp Ala Tyr Lys
            340                 345                 350

Lys Ile Glu Leu Glu Asp Leu Arg Phe Pro Leu Val Cys Gly Glu Gly
        355                 360                 365

Lys Lys Ala Arg Val Met Ala Thr Ile Gly Val Thr Arg Gly Leu Gly
    370                 375                 380

Asp His Ser Leu Lys Val Cys Ser Ser Thr Leu Pro Ile Lys Pro Phe
385                 390                 395                 400

Leu Ser Cys Phe Pro Glu Val Arg Val Tyr Asp Leu Thr Gln Tyr Glu
                405                 410                 415

His Cys Pro Asp Asp Val Leu Val Leu Gly Thr Asp Gly Leu Trp Asp
            420                 425                 430

Val Thr Thr Asp Cys Glu Val Ala Ala Thr Val Asp Arg Val Leu Ser
        435                 440                 445

Ala Tyr Glu Pro Asn Asp His Ser Arg Tyr Thr Ala Leu Ala Gln Ala
    450                 455                 460

Leu Val Leu Gly Ala Arg Gly Thr Pro Arg Asp Arg Gly Trp Arg Leu
465                 470                 475                 480

Pro Asn Asn Lys Leu Gly Ser Gly Asp Asp Ile Ser Val Phe Val Ile
                485                 490                 495

Pro Leu Gly Gly Pro Gly Ser Tyr Ser
            500                 505

<210> SEQ ID NO 31
<211> LENGTH: 3468
<212> TYPE: DNA
<213> ORGANISM: Homo sapiens

<400> SEQUENCE: 31
attgtgccct accagagagg acagatgggc accgcctcca gtggcaatgc taattcaccc      60
aagaggcctt cccagctctt ctcacagaag gaagataaac tccacatatt tctatatcct     120
gctggatgac attgtcctta cccattctct cttcctcccg acggagaaat ttctgcagga     180
gctacaccag tactttgttc gggcaggagg catggagggc cctgaagggc tgggccggaa     240
gcaagcctgt ctagccatgc ttctccattt cttggacacc taccaggggc tgcttcaaga     300
ggaagagggg gccggccaca tcatcaagga tctatacctg ctaattatga aggacgagtc     360
cctttaccag ggcctccgag aggacactct gaggctgcac cagctggtgg agacggtgga     420
actaaagatt ccagaggaga accagccacc cagcaagcag gtgaagccac tcttccgcca     480
cttccgccgg atagactcct gtctgcagac ccgggtggcc ttccggggct ctgatgagat     540
cttctgccgt gtatacatgc tgaccactc ttatgtgacc atacgcagcc gcctttcagc     600
atctgtgcag acattctgg gctctgtgac ggagaaactt caatattcag aggagcccgc     660
ggggcgtgag gattccctca tcctggtagc tgtgtcctcc tctggagaga aggtccttct     720
ccagcccact gaggactgtg ttttcaccgc actgggcatc aacagccacc tgtttgcctg     780
tactcgggac agctatgagg ctctggtgcc cctccccgag gagatccagg tctcccctgg     840
agacacagag atccaccgag tggagcctga ggacgttgcc aaccacctaa ctgccttcca     900
ctggagctg ttccgatgtg tgcatgagct ggagttcgtg gactacgtgt ccacgggga     960
gcgcggccgc cgggagacgg ccaacttgga gctgctgctg cagcgctgca gcaggtcac    1020
gcactgggtg gccaccgaag tgctgctctg cgaggccccg ggcaagcgcg cgcagctgct    1080
```

```
caagaagttc atcaagatcg cggccctctg caagcagaac caggacctgc tgtctttcta   1140
cgccgtggtc atggggctgg acaacgccgc tgtcagccgc cttcgactca cctgggagaa   1200
gctgccaggg aaattcaaga acttgtttcg caaatttgag aacctgacgg acccctgcag   1260
gaaccacaaa agctaccgag aagtgatctc caaaatgaag cccctgtga ttcccttcgt   1320
gcctctgatc ctcaaagacc tgactttcct gcacgaaggg agtaagaccc ttgtagatgg   1380
tttggtgaac atcgagaagc tgcattcagt ggccgaaaaa gtgaggacaa tccgcaaata   1440
ccggagccgg ccccttttgcc tggacatgga ggcatccccc aatcacctgc agaccaaggc   1500
ctatgtgcgc cagtttcagg tcatcgacaa ccagaacctc ctcttcgagc tctcctacaa   1560
gctggaggca aacagtcagt gagagtggag gctccagtca gacccgccag atccttgggc   1620
acctggcact caagcacttt gcacgatgtc tcaaccaaca tctgacatct ttcccgtgga   1680
gcaacttcct gctccacggg aaagaggtcg atggatttac ccctggaccc ataagtctgt   1740
tcatcctgct gaagtcccct ccccattgct ccttcaagcc aaaactacac tttgctggtt   1800
cctgtcccct ctgagaaagg ggatagaaag ctccttcctc tatgtcctcc catcgagatc   1860
tgttctgggg atggagcttc caacttcctc ttgcagcagg aaagaatgct gctcacccctt   1920
ctgtcttgca gagtgggatt gtgggaggga ttggcagcct tcttctccac cacctgtcca   1980
gcttcttcct ggtcagggct gggaccccca ggaatattat gttgccgtgt gtgtgtgtgt   2040
gtgtgtgtgt gtgtgtgtgt gtgtgtgtgt gtgtgtgtgt gtgtcttctt ttagggagca   2100
ggagtgcatc tggtaattga gggtggatgt tgtgtgtgct ggggaggggt ccttctgttt   2160
ggtgctaccc ttgtctactc tgcccctgga tggtgcgggg tgctttctcc accccacac   2220
tccctgctca gctcctcgtg ctgccctgca tgcccaggct tgtgagccaa gctgcttttt   2280
ggggcaggga gtagcagcag gtgggagggg ttacccatca gcccttgcaa gtcccccact   2340
caggcctctg gaaggtccag ggatgggctc tgatgagagg gtaaaagatg ctcagggaaa   2400
cacaggcctc agctgcctag aggaccctcc ccctgccttg cagtgggctc gggtagagca   2460
gtatcaggag ctagggttgt ctgctgccca cactcctgct ttttgggata tctaactgct   2520
aaggagggag ttgacatccc ccttctggct catgtgtctg acaccaacaa catggtctct   2580
gtccctctct ctttgactct ccctttgtcc tccccataga gctggggtgg ggtggatccc   2640
tatacctggg gcaggcagcc ccaaagtggg ggaggggat ggcagagact gtaaaggcgc   2700
cactggactc tggcaaggcc tttattacct ttactcccct ccctctccca tcaccagcct   2760
caaggcctga ggggtgcagg ggctcctggc agctactggg tgaggtttcc tggcacagac   2820
tcacccttct ttctggcacc acctctttcc cttttgaaga cacagcaaca gccgtagcaa   2880
aagcagctgc tgctcctgct atgagggtgt atatatttt tacccaaagc tctggaattg   2940
tacatttatt ttttaaaact caaagaggga aagagccttg tatcatatgt gaacattgta   3000
tcataggtaa tgttgtacag acccttttat acagtgatct gtcttgttcc tgcagcaaaa   3060
atcctctatg gacataggag gtgctgtgtc ccatgccctc ttgccctgac agtgtcccat   3120
gggccccctt ctgctccctg cccctccct gctactgctg atgcactctc ctctccctgc   3180
agcccctggc ttcccagcct tcctcctgac cccttccaac agccttggaa ctccagctgc   3240
caccaccctc tgggtcggac actgggaccc actggcccag tcttggctgc tgcttacccc   3300
tagccttgat gcctgcccag ggacccccag ccccctcccg ttgccctgca gctttaacag   3360
agtgaaccat gtgtattgta caggcgcggt tgtcattgca gaaaccgctg ggtggagaag   3420
```
aagccgataa agtctatgaa tcaacctgcc aaaaaaaaaa aaaaaaaa        3468

<210> SEQ ID NO 32
<211> LENGTH: 662
<212> TYPE: PRT
<213> ORGANISM: Homo sapiens

<400> SEQUENCE: 32

```
Met Lys Pro Leu Glu Lys Phe Leu Lys Gln Thr Ser Gln Leu Ala
1               5                   10                  15

Gly Arg Thr Val Ala Gly Gly Pro Gly Gly Leu Gly Ser Cys Gly
                20                  25                  30

Gly Pro Gly Gly Gly Gly Pro Gly Gly Gly Gly Pro Ala Gly
            35                  40                  45

Gly Gln Arg Ser Leu Gln Arg Arg Gln Ser Val Ser Arg Leu Leu Leu
        50                  55                  60

Pro Ala Phe Leu Arg Glu Pro Pro Ala Glu Pro Gly Leu Glu Pro Pro
65                  70                  75                  80

Val Pro Glu Glu Gly Gly Pro Ala Gly Val Ala Glu Pro Gly
                    85                  90                  95

Ser Gly Gly Pro Cys Trp Leu Gln Leu Glu Glu Val Pro Gly Pro Gly
                100                 105                 110

Pro Leu Gly Gly Gly Gly Pro Leu Arg Ser Pro Ser Ser Tyr Ser Ser
            115                 120                 125

Asp Glu Leu Ser Pro Gly Glu Pro Leu Thr Ser Pro Pro Trp Ala Pro
130                 135                 140

Leu Gly Ala Pro Glu Arg Pro Glu His Leu Leu Asn Arg Val Leu Glu
145                 150                 155                 160

Arg Leu Ala Gly Gly Ala Thr Arg Asp Ser Ala Ala Ser Asp Ile Leu
                165                 170                 175

Leu Asp Asp Ile Val Leu Thr His Ser Leu Phe Leu Pro Thr Glu Lys
            180                 185                 190

Phe Leu Gln Glu Leu His Gln Tyr Phe Val Arg Ala Gly Gly Met Glu
        195                 200                 205

Gly Pro Glu Gly Leu Gly Arg Lys Gln Ala Cys Leu Ala Met Leu Leu
210                 215                 220

His Phe Leu Asp Thr Tyr Gln Gly Leu Leu Gln Glu Glu Gly Ala
225                 230                 235                 240

Gly His Ile Ile Lys Asp Leu Tyr Leu Leu Ile Met Lys Asp Glu Ser
                245                 250                 255

Leu Tyr Gln Gly Leu Arg Glu Asp Thr Leu Arg Leu His Gln Leu Val
            260                 265                 270

Glu Thr Val Glu Leu Lys Ile Pro Glu Glu Asn Gln Pro Pro Ser Lys
        275                 280                 285

Gln Val Lys Pro Leu Phe Arg His Phe Arg Arg Ile Asp Ser Cys Leu
290                 295                 300

Gln Thr Arg Val Ala Phe Arg Gly Ser Asp Glu Ile Phe Cys Arg Val
305                 310                 315                 320

Tyr Met Pro Asp His Ser Tyr Val Thr Ile Arg Ser Arg Leu Ser Ala
                325                 330                 335

Ser Val Gln Asp Ile Leu Gly Ser Val Thr Glu Lys Leu Gln Tyr Ser
            340                 345                 350

Glu Glu Pro Ala Gly Arg Glu Asp Ser Leu Ile Leu Val Ala Val Ser
        355                 360                 365
```

Ser Ser Gly Glu Lys Val Leu Leu Gln Pro Thr Glu Asp Cys Val Phe
370              375                 380

Thr Ala Leu Gly Ile Asn Ser His Leu Phe Ala Cys Thr Arg Asp Ser
385              390                 395                 400

Tyr Glu Ala Leu Val Pro Leu Pro Glu Ile Gln Val Ser Pro Gly
        405                 410                 415

Asp Thr Glu Ile His Arg Val Glu Pro Glu Asp Val Ala Asn His Leu
        420                 425                 430

Thr Ala Phe His Trp Glu Leu Phe Arg Cys Val His Glu Leu Glu Phe
            435                 440                 445

Val Asp Tyr Val Phe His Gly Glu Arg Gly Arg Glu Thr Ala Asn
450                 455                 460

Leu Glu Leu Leu Leu Gln Arg Cys Ser Glu Val Thr His Trp Val Ala
465              470                 475                 480

Thr Glu Val Leu Leu Cys Glu Ala Pro Gly Lys Arg Ala Gln Leu Leu
                485                 490                 495

Lys Lys Phe Ile Lys Ile Ala Ala Leu Cys Lys Gln Asn Gln Asp Leu
            500                 505                 510

Leu Ser Phe Tyr Ala Val Val Met Gly Leu Asp Asn Ala Ala Val Ser
            515                 520                 525

Arg Leu Arg Leu Thr Trp Glu Lys Leu Pro Gly Lys Phe Lys Asn Leu
530              535                 540

Phe Arg Lys Phe Glu Asn Leu Thr Asp Pro Cys Arg Asn His Lys Ser
545              550                 555                 560

Tyr Arg Glu Val Ile Ser Lys Met Lys Pro Pro Val Ile Pro Phe Val
                565                 570                 575

Pro Leu Ile Leu Lys Asp Leu Thr Phe Leu His Glu Gly Ser Lys Thr
            580                 585                 590

Leu Val Asp Gly Leu Val Asn Ile Glu Lys Leu His Ser Val Ala Glu
            595                 600                 605

Lys Val Arg Thr Ile Arg Lys Tyr Arg Ser Arg Pro Leu Cys Leu Asp
610                 615                 620

Met Glu Ala Ser Pro Asn His Leu Gln Thr Lys Ala Tyr Val Arg Gln
625                 630                 635                 640

Phe Gln Val Ile Asp Asn Gln Asn Leu Leu Phe Glu Leu Ser Tyr Lys
                645                 650                 655

Leu Glu Ala Asn Ser Gln
            660

<210> SEQ ID NO 33
<211> LENGTH: 2467
<212> TYPE: DNA
<213> ORGANISM: Homo sapiens

<400> SEQUENCE: 33
gaagatgcac acgacccaga aggacacgac gtacaccaag atcttcgtcg gggggctgcc     60
ctaccacacc accgacgcca gcctgcgcaa gtacttcgag gtcttcggcg agatcgagga    120
ggcggtggtc atcaccgacc ggcagacggg caagtcccgg ggctatggat ttgtcaccat    180
ggctgaccgg gctgctgccg aaagggcctg caaggatccc aatccatca ttgatggcag     240 aaaggccaac gtgaacctgg catacttagg agcaaaacca aggatcatgc aaccaggttt    300
tgcctttggt gttcaacaac ttcatccagc ccttatacaa agacctttcg ggatacctgc    360
ccactatgtc tatccgcagg cttttgtgca gccgggagtg gtcattccac acgtccagcc    420

```
gacagcagct gccgcctcca ccaccccttta cattgattac actggagctg catacgcaca    480
atactcagca gctgctgctg ctgccgccgc cgctgctgcc tatgaccagt accctatgc      540
agcctctcca gctgctgcag gatatgttac tgctgggggc tatggctacg cagtccagca    600
gccaatcacc gcagcggcac ctgggacagc tgccgccgcc gctgcagcag ctgctgccgc    660
tgcagcattt ggccagtacc agcctcagca gctgcagaca gaccgaatgc aatagaccag    720
ccatctgatc aaagttgaat tgttttctct ttccctccca attttccaat ttttagtagc    780
taataagaga gttaacattg acttaacagc tttaaaaaaa aaaacagcca tgctattgtg    840
aagcagagtt attattttt ttatactcca ggtagtgttc tagatgagaa agaggtaaga     900
atgaggggaa tgggcacaat tttggaaatc aatcccaaag agcctgagta atgaaaggc     960
cactacgaaa tgacgccagg agtaacaacg gaacttcact tttgtaacgg gatttttatt   1020
tttgctcttt ttatagtatc agggaagcaa actgccttt acaagttaga aaatgctgtt    1080
tgaatctagt tgaaccaggg aatacagagc gagcaatatg tagcttgaat tacatttaaa   1140
agcagatttt ttacaaacaa aatggcgaaa gcactgattg tcattttag cagtcactta    1200
aggcctatag aactttttc aagtcggaag gtcctgttct tactatctca aaaatgggca    1260
tcgaacaatc aatctaggag cgtggcagtg ggtaaaatgg tggacaggca ccaaagctat   1320
tttctcatct gtcctgtgga tgagtggaac tgtggaacaa gtgatgtgga attaatgggt   1380
gcaacagctg tacagacaat caataacaca cacagttctg gaaagaacac atcacttgtg   1440
cttgtttgat gagcttgtca cattctaatc cctctcccca tcctgtttca atttttgggaa  1500
acttgtatct gctggtgtca gcaattctga ttctgaaata ggatcaggct tttactacaa   1560
cagccttctc tttctatttta ttgtgtcgac tcgtggctta tgaataaagg caggcaaagt  1620
ttgcagaact gtcttaagga catttatttt ttttcccttt ttaagtaatt ttacactta    1680
gtatctatt cagagtcata tttaaaacta tttattagtg actacagtac atgagacaac    1740
aaggttactg agattacaat tcttcaaagg ttaatgataa tgtggtttat actgtgcctt   1800
aatagtaatg ctatttaaga tatttatttt taagtttac tatgctgcac tctaaagaaa    1860
ggaactttag atgtgacact gtaaaattat gtattcatct catggcataa attatttagt   1920
aagtctagat gtagcgtatt aaatattaac ctattcaact aaagatgttg acttggattt   1980
atttaaattc atatgtgcac tgtataagag agtactctta cattaacaca ttttagttta   2040
gttttagat ttttttttaa acgatatatt gctagtttca tgcttcctcc tctgattttg    2100
cctgtgtaga tttcatttat tggtaattca ttagtttaac actattatgt agttttaaa   2160
tgctgcttta cattttttctt ctgaaactgc aatacttgca attttttattc ttaaactaaa 2220
ttgaatacta ttttacactg tattggattt ttatacttga acaatttcat acaagggaag  2280
acaggttagc attttttatgg actttctcca ttatcactgg atttacttta agtattccca  2340
tactagacag tgttatgtaa tgtagacatg actctcctgt gcaaattatt tattcgttgt   2400
gtatattgct ttataacatt tcagatcttc taatctattc acttgtatta aatataattt   2460
ttaaaaaa                                                            2467
```

<210> SEQ ID NO 34
<211> LENGTH: 236
<212> TYPE: PRT
<213> ORGANISM: Homo sapiens

<400> SEQUENCE: 34

Met His Thr Thr Gln Lys Asp Thr Thr Tyr Thr Lys Ile Phe Val Gly

```
              1               5              10              15
Gly Leu Pro Tyr His Thr Thr Asp Ala Ser Leu Arg Lys Tyr Phe Glu
                       20                  25                  30
Val Phe Gly Glu Ile Glu Glu Ala Val Val Ile Thr Asp Arg Gln Thr
                35                  40                  45
Gly Lys Ser Arg Gly Tyr Gly Phe Val Thr Met Ala Asp Arg Ala Ala
         50                  55                  60
Ala Glu Arg Ala Cys Lys Asp Pro Asn Pro Ile Ile Asp Gly Arg Lys
65                  70                  75                  80
Ala Asn Val Asn Leu Ala Tyr Leu Gly Ala Lys Pro Arg Ile Met Gln
                        85                  90                  95
Pro Gly Phe Ala Phe Gly Val Gln Gln Leu His Pro Ala Leu Ile Gln
                100                 105                 110
Arg Pro Phe Gly Ile Pro Ala His Tyr Val Tyr Pro Gln Ala Phe Val
                115                 120                 125
Gln Pro Gly Val Val Ile Pro His Val Gln Pro Thr Ala Ala Ala Ala
                130                 135                 140
Ser Thr Thr Pro Tyr Ile Asp Tyr Thr Gly Ala Ala Tyr Ala Gln Tyr
145                 150                 155                 160
Ser Ala Ala Ala Ala Ala Ala Ala Ala Ala Tyr Asp Gln Tyr
                165                 170                 175
Pro Tyr Ala Ala Ser Pro Ala Ala Gly Tyr Val Thr Ala Gly Gly
                180                 185                 190
Tyr Gly Tyr Ala Val Gln Gln Pro Ile Thr Ala Ala Pro Gly Thr
                195                 200                 205
Ala Ala Ala Ala Ala Ala Ala Ala Ala Ala Phe Gly Gln
                210                 215                 220
Tyr Gln Pro Gln Gln Leu Gln Thr Asp Arg Met Gln
225                 230                 235

<210> SEQ ID NO 35
<211> LENGTH: 2264
<212> TYPE: DNA
<213> ORGANISM: Homo sapiens

<400> SEQUENCE: 35
gcagtccctc cgccgctagt cggagcgagc gcgagtgagg agaccccgc cgggccactg     60 gcacttgctt ctgcggcgag tcccacccac gaccgcagcc cagcaactcg caaacgcaac    120
ctgaagcctg gctgcgcag tgtgggaggg cttcgcgatc ttgggggacc cattccgaac    180
ttgcagagga ccgtagctct cctggcctgg agagtgtgaa caggattgtg gactcttcca    240
agattcacaa tgtatggtg aatccaaaga ctggaaccaa aaagatttac tcagtgcttt    300
agttttaaca acagtaaatt gtctaccaac acccatcatg gctaaaagtg cggaggtcaa    360
actggcaata tttgggagag caggcgtggg caagtcagct cttgtagtga gatttctgac    420
caaacggttc atctgggaat atgatcccac cctcgaatca acctaccgac accaagcaac    480
catcgatgat gaagttgttt ccatggagat actagacact gctggtcagg aagataccat    540
tcagagggag gggcacatgc gatgggggga aggctttgtg ctggtctacg acattactga    600
ccgaggaagt tttgaggaag tgctgccact taagaacatc ctagatgaga tcaaaaagcc    660
caagaatgtg actctcatct tggttggaaa caaagctgac ttggaccact ccaggcaggt    720
tagcacagaa gaggagaga agctggccac agaattggct tgtgcttttt acgagtgctc    780
tgcctgcact ggagaaggga acatcacaga gatattctat gaattgtgtc gagaggtgcg    840
```

```
tcgccggagg atggtgcagg gcaagacgag gcgacgcagc tccaccacgc atgtcaagca    900
agccattaac aagatgctca ccaaaatcag tagttaggca gcccagctga ggtggaccaa    960
ctaattggaa acactcttcc ccttctgttc cccttttcaaa aataaaacaa aatattgcat   1020
tctttgtttg gattctgaga aatgtctggg cttcccattg tttctggcct ctaataggtt   1080
gggaagtttt agcgtgtttt atgcaatttc agtgctaaca atttcttcct ttcctgcttg   1140
aataagatac actctaatgg catttgaaca tgtaatcacc agagattctg aaatgactgg   1200
tttatgttaa gctattttta ggcatcttca ccttgcttta agtaggttga agttttgca    1260 aaggcattta aaaattcaat ttcttgtcag atactacaaa taattttctt aaaagtctaa   1320
gatagcagaa aatacagtaa aaacacagga gaagaagctg agctattgga acaggaaata   1380
gaaggaactc tagtttctgt ttgaagtgag gattttctga attatctaat atcatctagg   1440
ttttctttaa aattttattt tgttcttcag ttcaagcatc ttctcactaa tgttttccac   1500
tataacagag aattcatttc aatttgagtt ggttctctca atgatctatt gatcattaca   1560
ccctaactct ccttccttgg ctcaaacaat attttcccta taacaaaggc aataggacac   1620
aaaattcaca tcctgctggg ccttttttca tcaagtcagg gtgatataaa aacattggaa   1680
gtcttttcac caaaccctga ctttattgaa tgctagtaga agatgtagaa ttagagacat   1740
ctgatttgtt tatcacctta gcagaaaaac cacagtccaa aagacaagca aattaagaat   1800
ggagcttaac catgcctcca ttgggaagtc tagactttga gccaggtaca gtaagaaaaa   1860
ttagcctctg attcattaag tttgccacat gacttatttt gatattttgg atacattaac   1920
tcacttagga gaattcagaa aagaatgggt gattaaagtt cattacagct gaataaatgt   1980
gtctaaaaca gactcttgta ttctgaaagt acagtctaca actgataaaa ccttatgatt   2040
cttttctccc ccattatgcc cctatatata tcaagatttg ggtactttat tttagtagaa   2100
aatatatatc ttttacatat gtatgtattt ataaatgcat agatatatgt ataaaaattt   2160
gtaagcgtta gcggcattaa ttcaccaatg catttggaca acttgatgta actgactta    2220 ttttatgtga ctataataaa aagcataatt ttctcattct gtca                   2264
```

<210> SEQ ID NO 36
<211> LENGTH: 199
<212> TYPE: PRT
<213> ORGANISM: Homo sapiens

<400> SEQUENCE: 36

```
Met Ala Lys Ser Ala Glu Val Lys Leu Ala Ile Phe Gly Arg Ala Gly
1               5                   10                  15

Val Gly Lys Ser Ala Leu Val Val Arg Phe Leu Thr Lys Arg Phe Ile
            20                  25                  30

Trp Glu Tyr Asp Pro Thr Leu Glu Ser Thr Tyr Arg His Gln Ala Thr
        35                  40                  45

Ile Asp Asp Glu Val Val Ser Met Glu Ile Leu Asp Thr Ala Gly Gln
    50                  55                  60

Glu Asp Thr Ile Gln Arg Glu Gly His Met Arg Trp Gly Glu Gly Phe
65                  70                  75                  80

Val Leu Val Tyr Asp Ile Thr Asp Arg Gly Ser Phe Glu Glu Val Leu
                85                  90                  95

Pro Leu Lys Asn Ile Leu Asp Glu Ile Lys Lys Pro Lys Asn Val Thr
            100                 105                 110

Leu Ile Leu Val Gly Asn Lys Ala Asp Leu Asp His Ser Arg Gln Val
```

```
                    115                 120                 125
Ser Thr Glu Glu Gly Glu Lys Leu Ala Thr Glu Leu Ala Cys Ala Phe
    130                 135                 140

Tyr Glu Cys Ser Ala Cys Thr Gly Glu Gly Asn Ile Thr Glu Ile Phe
145                 150                 155                 160

Tyr Glu Leu Cys Arg Glu Val Arg Arg Arg Met Val Gln Gly Lys
                165                 170                 175

Thr Arg Arg Arg Ser Ser Thr Thr His Val Lys Gln Ala Ile Asn Lys
            180                 185                 190

Met Leu Thr Lys Ile Ser Ser
        195

<210> SEQ ID NO 37
<211> LENGTH: 5617
<212> TYPE: DNA
<213> ORGANISM: Homo sapiens

<400> SEQUENCE: 37
agtcccgcga ccgaagcagg gcgcgcagca gcgctgagtg ccccggaacg tgcgtcgcgc      60
ccccagtgtc cgtcgcgtcc gccgcgcccc gggcggggat ggggcggcca gactgagcgc     120
cgcacccgcc atccagaccc gccggcccta gccgcagtcc ctccagccgt ggccccagcg     180
cgcacgggcg atggcgaagg cgacgtccgg tgccgcgggg ctgcgtctgc tgttgctgct     240
gctgctgccg ctgctaggca agtggcattg ggcctctac ttctcgaggg atgcttactg      300
ggagaagctg tatgtggacc aggcagccgg cacgcccttg ctgtacgtcc atgccctgcg     360
ggacgcccct gaggaggtgc ccagcttccg cctgggccag catctctacg gcacgtaccg     420
cacacggctg catgagaaca actggatctg catccaggag gacaccggcc tcctctacct     480
taaccggagc ctggaccata gctcctggga gaagctcagt gtccgcaacc gcggctttcc     540
cctgctcacc gtctacctca aggtcttcct gtcacccaca tcccttcgtg agggcgagtg     600
ccagtggcca ggctgtgccc gcgtatactt ctccttcttc aacacctcct ttccagcctg     660
cagctccctc aagccccggg agctctgctt cccagagaca aggccctcct tccgcattcg     720
ggagaaccga cccccaggca ccttccacca gttccgcctg ctgcctgtgc agttcttgtg     780
ccccaacatc agcgtggcct acaggctcct ggagggtgag ggtctgccct tccgctgcgc     840
cccggacagc tggaggtga gcacgcgctg ggccctggac cgcgagcagc gggagaagta     900
cgagctggtg gccgtgtgca ccgtgcacgc cggcgcgcgc gaggaggtgg tgatggtgcc     960
cttcccggtg accgtgtacg acgaggacga ctcggcgccc accttccccg cgggcgtcga    1020
caccgccagc gccgtggtgg agttcaagcg gaaggaggac accgtggtgg ccacgctgcg    1080
tgtcttcgat gcagacgtgg tacctgcatc agggagctg gtgaggcggt acacaagcac    1140
gctgctcccc ggggacacct gggcccagca gaccttccgg gtggaacact ggcccaacga    1200
gacctcggtc caggccaacg gcagcttcgt gcgggcgacc gtacatgact ataggctggt    1260
tctcaaccgg aacctctcca tctcggagaa ccgcaccatg cagctggcgg tgctggtcaa    1320
tgactcagac ttccagggcc caggagcggg cgtcctcttg ctccacttca acgtgtcggt    1380
gctgccggtc agcctgcacc tgcccagtac ctactccctc tccgtgagca ggagggctcg    1440
ccgatttgcc cagatcggga aagtctgtgt ggaaaactgc caggcattca gtggcatcaa    1500
cgtccagtac aagctgcatt cctctggtgc caactgcagc acgctagggg tggtcacctc    1560
agccgaggac acctcgggga tcctgtttgt gaatgacacc aaggccctgc ggcggcccaa    1620
```

```
gtgtgccgaa cttcactaca tggtggtggc caccgaccag cagacctcta ggcaggccca   1680
ggcccagctg cttgtaacag tggaggggtc atatgtggcc gagaggcgg  gctgcccct    1740 gtcctgtgca gtcagcaaga gacggctgga gtgtgaggag tgtggcggcc tgggctcccc   1800
aacaggcagg tgtgagtgga ggcaaggaga tggcaagggg atcaccagga acttctccac   1860
ctgctctccc agcaccaaga cctgccccga cggccactgc gatgttgtgg agacccaaga   1920
catcaacatt tgccctcagg actgcctccg gggcagcatt gttggggac  acgagcctgg   1980 ggagccccgg gggattaaag ctggctatgg cacctgcaac tgcttccctg aggaggagaa   2040
gtgcttctgc gagcccgaag acatccagga tccactgtgc gacgagctgt gccgcacggt   2100
gatcgcagcc gctgtcctct tctccttcat cgtctcggtg ctgctgtctg ccttctgcat   2160
ccactgctac cacaagtttg cccacaagcc acccatctcc tcagctgaga tgaccttccg   2220
gaggcccgcc caggccttcc cggtcagcta ctcctcttcc ggtgcccgcc ggccctcgct   2280
ggactccatg gagaaccagg tctccgtgga tgccttcaag atcctggagg atccaaagtg   2340
ggaattccct cggaagaact tggttcttgg aaaaactcta ggagaaggcg aatttggaaa   2400
agtggtcaag gcaacggcct tccatctgaa aggcagagca gggtacacca cggtggccgt   2460
gaagatgctg aaagagaacg cctccccgag tgagctgcga gacctgctgt cagagttcaa   2520
cgtcctgaag caggtcaacc acccacatgt catcaaattg tatggggcct gcagccagga   2580
tggcccgctc ctcctcatcg tggagtacgc caaatacggc tccctgcggg gcttcctccg   2640
cgagagccgc aaagtggggc ctggctacct gggcagtgga ggcagccgca actccagctc   2700
cctggaccac ccgatgagc  gggccctcac catgggcgac ctcatctcat ttgcctggca   2760
gatctcacag gggatgcagt atctggccga gatgaagctc gttcatcggg acttggcagc   2820
cagaaacatc ctggtagctg aggggcgaa  gatgaagatt tcggatttcg gcttgtcccg   2880
agatgtttat gaagaggatt cctacgtgaa gaggagccag ggtcggattc agttaaatg    2940 gatggcaatt gaatccctt  ttgatcatat ctacaccacg caaagtgatg tatggtcttt   3000
tggtgtcctg ctgtgggaga tcgtgaccct aggggaaac  ccctatcctg ggattcctcc   3060
tgagcggctc ttcaaccttc tgaagaccgg ccaccggatg gagaggccag acaactgcag   3120
cgaggagatg taccgcctga tgctgcaatg ctggaagcag gagccggaca aaaggccggt   3180
gtttgcggac atcagcaaag acctggaaa  gatgatggtt aagaggagag actacttgga   3240
ccttgcggcg tccactccat ctgactccct gatttatgac gacggcctct cagaggagga   3300
gacaccgctg gtggactgta ataatgcccc cctccctcga gccctcccctt ccacatggat   3360 tgaaaacaaa ctctatggca tgtcagaccc gaactggcct ggagagagtc ctgtaccact   3420
cacgagagct gatggcacta acactgggtt tccaagatat ccaaatgata gtgtatatgc   3480
taactggatg ctttcacct  cagcggcaaa attaatggac acgtttgata gttaacattt   3540
ctttgtgaaa ggtaatggac tcacaagggg aagaaacatg ctgagaatgg aaagtctacc   3600 ggcccttct  ttgtgaacgt cacattggcc gagccgtgtt cagttcccag gtggcagact   3660 cgttttggt  agtttgtttt aacttccaag gtggttttac ttctgatagc cggtgatttt   3720
ccctcctagc agacatgcca caccgggtaa gagctctgag tcttagtggt taagcattcc   3780
tttctcttca gtgcccagca gcacccagtg ttggtctgtg tccatcagtg accaccaaca   3840
ttctgtgttc acatgtgtgg gtccaacact tactacctgg tgtatgaaat tggacctgaa   3900
ctgttggatt tttctagttg ccgccaaaca aggcaaaaaa atttaaacat gaagcacaca   3960
cacaaaaaag gcagtaggaa aaatgctggc cctgatgacc tgtccttatt cagaatgaga   4020
```

-continued

```
gactgcgggg ggggcctggg ggtagtgtca atgcccctcc agggctggag gggaagaggg      4080
gccccgagga tgggcctggg ctcagcattc gagatcttga gaatgatttt ttttaaatca      4140 tgcaacctttt ccttaggaag acatttggtt ttcatcatga ttaagatgat tcctagattt     4200
agcacaatgg agagattcca tgccatcttt actatgtgga tggtggtatc agggaagagg      4260
gctcacaaga cacatttgtc ccccgggccc accacatcat cctcacgtgt tcggtactga      4320
gcagccacta cccctgatga aacagtatg aagaagggg gctgttggag tcccagaatt        4380
gctgacagca gaggctttgc tgctgtgaat cccacctgcc accagcctgc agcacacccc      4440
acagccaagt agaggcgaaa gcagtggctc atcctacctg ttaggagcag gtagggcttg      4500
tactcacttt aatttgaatc ttatcaactt actcataaag ggacaggcta gctagctgtg      4560
ttagaagtag caatgacaat gaccaaggac tgctacacct ctgattacaa ttctgatgtg      4620
aaaaagatgg tgtttggctc ttatagagcc tgtgtgaaag gcccatggat cagctcttcc     4680
tgtgtttgta atttaatgct gctacaagat gtttctgttt cttagattct gaccatgact      4740
cataagcttc ttgtcattct tcattgcttg tttgtggtca cagatgcaca acactcctcc      4800
agtcttgtgg gggcagcttt tgggaagtct cagcagctct tctggctgtg ttgtcagcac      4860
tgtaacttcg cagaaaagag tcggattacc aaaacactgc ctgctcttca gacttaaagc      4920
actgatagga cttaaaatag tctcattcaa atactgtatt ttatataggc atttcacaaa      4980
aacagcaaaa ttgtggcatt ttgtgaggcc aaggcttgga tgcgtgtgta atagagcctt     5040
gtggtgtgtg cgcacacacc cagagggaga gtttgaaaaa tgcttattgg acacgtaacc     5100
tggctctaat ttgggctgtt tttcagatac actgtgataa gttcttttac aaatatctat      5160
agacatggta aacttttggt tttcagatat gcttaatgat agtcttacta aatgcagaaa      5220
taagaataaa ctttctcaaa ttattaaaaa tgcctacaca gtaagtgtga attgctgcaa      5280
caggtttgtt ctcaggaggg taagaactcc aggtctaaac agctgaccca gtgatgggga     5340
atttatcctt gaccaattta tccttgacca ataacctaat tgtctattcc tgagttataa     5400
aagtccccat ccttattagc tctactggaa ttttcataca cgtaaatgca gaagttacta     5460
agtattaagt attactgagt attaagtagt aatctgtcag ttattaaaat ttgtaaaatc      5520
tatttatgaa aggtcattaa accagatcat gttccttttt ttgtaatcaa ggtgactaag     5580
aaaatcagtt gtgtaaataa aatcatgtat cataaaa                              5617
```

<210> SEQ ID NO 38
<211> LENGTH: 1114
<212> TYPE: PRT
<213> ORGANISM: Homo sapiens

<400> SEQUENCE: 38

```
Met Ala Lys Ala Thr Ser Gly Ala Ala Gly Leu Arg Leu Leu Leu Leu
1               5                   10                  15

Leu Leu Pro Leu Leu Gly Lys Val Ala Leu Gly Leu Tyr Phe Ser
            20                  25                  30

Arg Asp Ala Tyr Trp Glu Lys Leu Tyr Val Asp Gln Ala Ala Gly Thr
        35                  40                  45

Pro Leu Tyr Val His Ala Leu Arg Asp Ala Pro Glu Glu Val Pro
    50                  55                  60

Ser Phe Arg Leu Gly Gln His Leu Tyr Gly Thr Tyr Arg Thr Arg Leu
65                  70                  75                  80

His Glu Asn Asn Trp Ile Cys Ile Gln Glu Asp Thr Gly Leu Leu Tyr
```

```
            85                  90                  95
Leu Asn Arg Ser Leu Asp His Ser Ser Trp Glu Lys Leu Ser Val Arg
            100                 105                 110

Asn Arg Gly Phe Pro Leu Leu Thr Val Tyr Leu Lys Val Phe Leu Ser
            115                 120                 125

Pro Thr Ser Leu Arg Glu Gly Glu Cys Gln Trp Pro Gly Cys Ala Arg
            130                 135                 140

Val Tyr Phe Ser Phe Phe Asn Thr Ser Phe Pro Ala Cys Ser Ser Leu
145                 150                 155                 160

Lys Pro Arg Glu Leu Cys Phe Pro Gly Thr Arg Pro Ser Phe Arg Ile
            165                 170                 175

Arg Glu Asn Arg Pro Pro Gly Thr Phe His Gln Phe Arg Leu Leu Pro
            180                 185                 190

Val Gln Phe Leu Cys Pro Asn Ile Ser Val Ala Tyr Arg Leu Leu Glu
            195                 200                 205

Gly Glu Gly Leu Pro Phe Arg Cys Ala Pro Asp Ser Leu Glu Val Ser
            210                 215                 220

Thr Arg Trp Ala Leu Asp Arg Glu Gln Arg Glu Lys Tyr Glu Leu Val
225                 230                 235                 240

Ala Val Cys Thr Val His Ala Gly Ala Arg Glu Val Val Met Val
            245                 250                 255

Pro Phe Pro Val Thr Val Tyr Asp Glu Asp Ser Ala Pro Thr Phe
            260                 265                 270

Pro Ala Gly Val Asp Thr Ala Ser Ala Val Glu Phe Lys Arg Lys
            275                 280                 285

Glu Asp Thr Val Val Ala Thr Leu Arg Val Phe Asp Ala Asp Val Val
290                 295                 300

Pro Ala Ser Gly Glu Leu Val Arg Arg Tyr Thr Ser Thr Leu Leu Pro
305                 310                 315                 320

Gly Asp Thr Trp Ala Gln Gln Thr Phe Arg Val Glu His Trp Pro Asn
            325                 330                 335

Glu Thr Ser Val Gln Ala Asn Gly Ser Phe Val Arg Ala Thr Val His
            340                 345                 350

Asp Tyr Arg Leu Val Leu Asn Arg Asn Leu Ser Ile Ser Glu Asn Arg
            355                 360                 365

Thr Met Gln Leu Ala Val Leu Val Asn Asp Ser Asp Phe Gln Gly Pro
            370                 375                 380

Gly Ala Gly Val Leu Leu Leu His Phe Asn Val Ser Val Leu Pro Val
385                 390                 395                 400

Ser Leu His Leu Pro Ser Thr Tyr Ser Leu Ser Val Ser Arg Arg Ala
            405                 410                 415

Arg Arg Phe Ala Gln Ile Gly Lys Val Cys Val Glu Asn Cys Gln Ala
            420                 425                 430

Phe Ser Gly Ile Asn Val Gln Tyr Lys Leu His Ser Ser Gly Ala Asn
            435                 440                 445

Cys Ser Thr Leu Gly Val Val Thr Ser Ala Glu Asp Thr Ser Gly Ile
            450                 455                 460

Leu Phe Val Asn Asp Thr Lys Ala Leu Arg Arg Pro Lys Cys Ala Glu
465                 470                 475                 480

Leu His Tyr Met Val Val Ala Thr Asp Gln Gln Thr Ser Arg Gln Ala
            485                 490                 495

Gln Ala Gln Leu Leu Val Thr Val Glu Gly Ser Tyr Val Ala Glu Glu
            500                 505                 510
```

```
Ala Gly Cys Pro Leu Ser Cys Ala Val Ser Lys Arg Arg Leu Glu Cys
        515                 520                 525

Glu Glu Cys Gly Gly Leu Gly Ser Pro Thr Gly Arg Cys Glu Trp Arg
        530                 535                 540

Gln Gly Asp Gly Lys Gly Ile Thr Arg Asn Phe Ser Thr Cys Ser Pro
545                 550                 555                 560

Ser Thr Lys Thr Cys Pro Asp Gly His Cys Asp Val Val Glu Thr Gln
                565                 570                 575

Asp Ile Asn Ile Cys Pro Gln Asp Cys Leu Arg Gly Ser Ile Val Gly
                580                 585                 590

Gly His Glu Pro Gly Glu Pro Arg Gly Ile Lys Ala Gly Tyr Gly Thr
        595                 600                 605

Cys Asn Cys Phe Pro Glu Glu Lys Cys Phe Cys Glu Pro Glu Asp
        610                 615                 620

Ile Gln Asp Pro Leu Cys Asp Glu Leu Cys Arg Thr Val Ile Ala Ala
625                 630                 635                 640

Ala Val Leu Phe Ser Phe Ile Val Ser Val Leu Leu Ser Ala Phe Cys
                645                 650                 655

Ile His Cys Tyr His Lys Phe Ala His Lys Pro Pro Ile Ser Ser Ala
                660                 665                 670

Glu Met Thr Phe Arg Arg Pro Ala Gln Ala Phe Pro Val Ser Tyr Ser
        675                 680                 685

Ser Ser Gly Ala Arg Arg Pro Ser Leu Asp Ser Met Glu Asn Gln Val
        690                 695                 700

Ser Val Asp Ala Phe Lys Ile Leu Glu Asp Pro Lys Trp Glu Phe Pro
705                 710                 715                 720

Arg Lys Asn Leu Val Leu Gly Lys Thr Leu Gly Glu Gly Glu Phe Gly
                725                 730                 735

Lys Val Val Lys Ala Thr Ala Phe His Leu Lys Gly Arg Ala Gly Tyr
                740                 745                 750

Thr Thr Val Ala Val Lys Met Leu Lys Glu Asn Ala Ser Pro Ser Glu
        755                 760                 765

Leu Arg Asp Leu Leu Ser Glu Phe Asn Val Leu Lys Gln Val Asn His
        770                 775                 780

Pro His Val Ile Lys Leu Tyr Gly Ala Cys Ser Gln Asp Gly Pro Leu
785                 790                 795                 800

Leu Leu Ile Val Glu Tyr Ala Lys Tyr Gly Ser Leu Arg Gly Phe Leu
                805                 810                 815

Arg Glu Ser Arg Lys Val Gly Pro Gly Tyr Leu Gly Ser Gly Gly Ser
        820                 825                 830

Arg Asn Ser Ser Ser Leu Asp His Pro Asp Glu Arg Ala Leu Thr Met
        835                 840                 845

Gly Asp Leu Ile Ser Phe Ala Trp Gln Ile Ser Gln Gly Met Gln Tyr
850                 855                 860

Leu Ala Glu Met Lys Leu Val His Arg Asp Leu Ala Ala Arg Asn Ile
865                 870                 875                 880

Leu Val Ala Glu Gly Arg Lys Met Lys Ile Ser Asp Phe Gly Leu Ser
                885                 890                 895

Arg Asp Val Tyr Glu Glu Asp Ser Tyr Val Lys Arg Ser Gln Gly Arg
                900                 905                 910

Ile Pro Val Lys Trp Met Ala Ile Glu Ser Leu Phe Asp His Ile Tyr
                915                 920                 925
```

Thr Thr Gln Ser Asp Val Trp Ser Phe Gly Val Leu Leu Trp Glu Ile
    930                 935                 940

Val Thr Leu Gly Gly Asn Pro Tyr Pro Gly Ile Pro Pro Glu Arg Leu
945                 950                 955                 960

Phe Asn Leu Leu Lys Thr Gly His Arg Met Glu Arg Pro Asp Asn Cys
                965                 970                 975

Ser Glu Glu Met Tyr Arg Leu Met Leu Gln Cys Trp Lys Gln Glu Pro
            980                 985                 990

Asp Lys Arg Pro Val Phe Ala Asp Ile Ser Lys Asp Leu Glu Lys Met
        995                 1000                1005

Met Val Lys Arg Arg Asp Tyr Leu Asp Leu Ala Ala Ser Thr Pro
    1010                1015                1020

Ser Asp Ser Leu Ile Tyr Asp Asp Gly Leu Ser Glu Glu Thr
    1025                1030                1035

Pro Leu Val Asp Cys Asn Asn Ala Pro Leu Pro Arg Ala Leu Pro
    1040                1045                1050

Ser Thr Trp Ile Glu Asn Lys Leu Tyr Gly Met Ser Asp Pro Asn
    1055                1060                1065

Trp Pro Gly Glu Ser Pro Val Pro Leu Thr Arg Ala Asp Gly Thr
    1070                1075                1080

Asn Thr Gly Phe Pro Arg Tyr Pro Asn Asp Ser Val Tyr Ala Asn
    1085                1090                1095

Trp Met Leu Ser Pro Ser Ala Ala Lys Leu Met Asp Thr Phe Asp
    1100                1105                1110

Ser

<210> SEQ ID NO 39
<211> LENGTH: 4483
<212> TYPE: DNA
<213> ORGANISM: Homo sapiens

<400> SEQUENCE: 39

```
actgcgggcg gagcagaggg aaacaccaga gtctgtgact ccagacagga cccactgtgt      60
cctcttgaac tttgcacagc gcgtgacggg ggcagacggt gcaccgtggc ccggcctttc     120
gcggggtcc tcgggaaga gagaggagcg cgggtttcct cggaggcctg agcgggacgc       180
agcctgcagc cctcccccgc acgggctgcc cccggcccgc cgctcgcgcc gctctgctgg     240
gatccggcgc cttccccggc tgtcctcggc ctcccgcgcg ctccgcggga ggagccgcca     300
gcggccgtga cgcgtcaagg aggaaacgcc ggcgcccggc ggccctgccg ggaaggagga     360
agcgcagtgc gttcggctcc gcgcccgccg cgccgggagc agcaccgcgg ggccaggttg     420
catgatggaa tttgaacatt acttcaagag gttttgtatt ttggattagt taattgggtt     480
tgtcctctgc tgactgtttc ttcggatgca ttttttggtg tgctcttgag ggattaaatg     540
caaagagatc acaccatgga ctacaaggaa agctgcccaa gtgtaagcat tcccagctcc     600
gatgaacaca gagagaaaaa gaagaggttt actgtttata agttctggt ttcagtggga      660
agaagtgaat ggtttgtctt caggagatat gcagagtttg ataaacttta taacacttta     720
aaaaaacagt ttcctgctat ggccctgaag attcctgcca agagaatatt tggtgataat     780
tttgatccag attttattaa acaaagacga gcaggactaa acgaattcat tcagaaccta     840
gttaggtatc cagaacttta taaccatcca gatgtcagag cattccttca aatggacagt     900
ccaaaacacc agtcagatcc atctgaagat gaggatgaaa aagttctca gaagctacac     960
tctacctcac agaacatcaa cctgggaccg tctggaaatc ctcatgccaa accaactgac    1020
```

-continued

| | |
|---|---|
| tttgatttct taaaagttat tggaaaaggc agctttggca aggttcttct tgcaaaacgg | 1080 |
| aaactggatg gaaaatttta tgctgtcaaa gtgttacaga aaaaaatagt tctcaacaga | 1140 |
| aaagagcaaa aacatattat ggctgaacgt aatgtgctct tgaaaaatgt gaaacatccg | 1200 |
| tttttggttg gattgcatta ttccttccaa acaactgaaa agctttatttt tgttctggat | 1260 |
| tttgttaatg gagggagct ttttttccac ttacaaagag aacggtcctt tcctgagcac | 1320 |
| agagctaggt tttacgctgc tgaaattgct agtgcattgg gttacttaca ttccatcaaa | 1380 |
| atagtataca gagacttgaa accagaaaat attcttttgg attcagtagg acatgttgtc | 1440 |
| ttaacagatt tgggctttg taaagaagga attgctattt ctgacaccac taccacattt | 1500 |
| tgtgggacac cagagtatct tgcacctgaa gtaattagaa acagcccta tgacaatact | 1560 |
| gtagattggt ggtgccttgg ggctgttctg tatgaaatgc tgtatggatt gcctccttt | 1620 |
| tattgccgag atgttgctga atgtatgac aatatccttc acaaacccct aagtttgagg | 1680 |
| ccaggagtga gtcttacagc ctggtccatt ctggaagaac tcctagaaaa agacaggcaa | 1740 |
| aatcgacttg gtgccaagga agactttctt gaaattcaga atcatccttt ttttgaatca | 1800 |
| ctcagctggg ctgaccttgt acaaaagaag attccaccac catttaatcc taatgtggct | 1860 |
| ggaccagatg atatcagaaa ctttgacaca gcatttacag aagaaacagt tccatattct | 1920 |
| gtgtgtgtat cttctgacta ttctatagtg aatgccagtg tattggaggc agatgatgca | 1980 |
| ttcgttggtt tctcttatgc acctccttca gaagacttat ttttgtgagc agtttgccat | 2040 |
| tcagaaacca ttgagcaaaa taagtctata gatgggactg aaacttctat ttgtgtgaat | 2100 |
| atattcaaat atgtataact agtgcctcat ttttatatgt aatgatgaaa actatgaaaa | 2160 |
| aatgtatttt cttctatgtg caagaaaaat agggcatttc aaagagctgt tttgattaaa | 2220 |
| atttatattc ttgtttaata agcttatttt taaacaattt aaaagctatt attcttagca | 2280 |
| ttaacctatt tttaaagaaa ccttttttgc tattgactgt ttttcctc taagtttaca | 2340 |
| ctaacatcta cccaagatag actgttttt aacagtcaat tcagttcag ctaacatata | 2400 |
| ttaataccctt tgtaactctt tgctatggct tttgttatca caccaaaact atgcaattgg | 2460 |
| tacatggttg tttaagaaga aaccgtattt ttccatgata aatcactgtt tgaaatattt | 2520 |
| ggttcatggt atgatcgaaa tgtaaaagca taattaacac attggctgct agttaacaat | 2580 |
| tggaataact ttattctgca gatcatttaa gaagtaacag gccgggcgcg gtggctcacg | 2640 |
| cctgtaatcc cagcactttg ggaggctgag gcgggcagat cacctgaggt caggagttgg | 2700 |
| agaccagcct gaccaacatg gacaaacccc gtctctacta aaaatacaaa attggcaggg | 2760 |
| tgtggtggca catgcctata atcccagcta cttgggaggc taaggcagga gaatcgcttg | 2820 |
| aacccgggag gcggaggttg cagtgagccg agatcgcacc attgcactcc tgcctgggca | 2880 |
| acaagagtga aactccatct ccaaaaaaaa aagaaaaag taacaaaagg aaattatttg | 2940 |
| tttttgaaat accagttcaa ctttgtggat tatttttcct ctgaaggaaa agaaaaggct | 3000 |
| taatggttag dattttttaag tattcccaaa gatctgaagg gtaataaaat gtactggatt | 3060 |
| ttttaaggtg gtaccaaaaa tgaatgtctg tcatatattt atattacaaa tacattatat | 3120 |
| ttatgttcta ttcatctttt gaatgtttag tatgctatta agtcattctg aatctttgta | 3180 |
| tttgcttttg caaataggta tttcaaagct cttttcctaa ctggttaagt aaaataaaaa | 3240 |
| attgagcttt ctagaatatt tgcctaattg ggaattaaaa agtaaaataa taggccaggc | 3300 |
| atggtggctc atgcctataa gcaccctggg aggccgaggc aggcagatta tttgagctca | 3360 |

```
ggagtttgag accatcctgg gcaacatggc gaaaccctat ctctacaaaa aatacaaaaa      3420
ttagccagac atggtggcac atgcctttag tcccagctac tctggaggct gaagttggag      3480
gatggcttga gcccacgaga tggaagttgc agtgaactga aattgtgcca ctgcactttt      3540
cagcctgggt gccacagcga gaccctagtt aagagaaaaa aaaagtaaaa acaaattgtg      3600
ggtcaaagta aatgtataca gttttattac aatgtaacaa aagttgaaaa tcaggcagat      3660
gtgtattcag tatccaattc aatatatctt agaaaaagca caggaaacag accttaaaat      3720
tgtaacctac caactaactt acatgcttat aaaagtaaag gagaataact ggccgggcac      3780
ggtggctcat gcctataaaa ttccagcact tgggaggcc aaggcaggag atcacttga       3840 gcctatgagt tcaagaccag cctaggcaat gtagtgacac ctcatttcta tttattttaa      3900
aaaaaagaga gagtaactac agaagaactt taaaaaataa aaaataagct taccttggat      3960
tcttggctta gagtagaggt ttttttttaag ttatggagga acatttttg taaaagttta     4020 atgacccact ttagatgctc caagaacaag catcccttcc atgtatgtct tgagaaagaa      4080
atcacagaag catttctcac caatactctt tggcttaaaa tgttcagcag aattgggcag      4140
tgggggtgac ttttcttata ttaataatat ttacatccaa tacactgaat cttcctttag      4200
aggtaagact ttaatatcta tactgtaaat atttggttta tttggcacta ctgtaagttt      4260 tgttttttcac aaagctctta ttatgaagca aataaaaat tctagtttct tgtatgattt      4320
tttgtactca ttcattcctg ttaagctgcc aaaaattaaa gtgcaatatt gtatatttt      4380 aagaacaaat ttaaaataga attttgatgt ttctcagatc acaagaaata caaatctata      4440
tagtataata aaatcagcaa aaagatcaaa aaaaaaaaa aaa                        4483
```

<210> SEQ ID NO 40
<211> LENGTH: 496
<212> TYPE: PRT
<213> ORGANISM: Homo sapiens

<400> SEQUENCE: 40

Met Gln Arg Asp His Thr Met Asp Tyr Lys Glu Ser Cys Pro Ser Val
1               5                   10                  15

Ser Ile Pro Ser Ser Asp Glu His Arg Glu Lys Lys Arg Phe Thr
            20                  25                  30

Val Tyr Lys Val Leu Val Ser Val Gly Arg Ser Glu Trp Phe Val Phe
        35                  40                  45

Arg Arg Tyr Ala Glu Phe Asp Lys Leu Tyr Asn Thr Leu Lys Lys Gln
    50                  55                  60

Phe Pro Ala Met Ala Leu Lys Ile Pro Ala Lys Arg Ile Phe Gly Asp
65                  70                  75                  80

Asn Phe Asp Pro Asp Phe Ile Lys Gln Arg Arg Ala Gly Leu Asn Glu
                85                  90                  95

Phe Ile Gln Asn Leu Val Arg Tyr Pro Glu Leu Tyr Asn His Pro Asp
            100                 105                 110

Val Arg Ala Phe Leu Gln Met Asp Ser Pro Lys His Gln Ser Asp Pro
        115                 120                 125

Ser Glu Asp Glu Asp Glu Arg Ser Ser Gln Lys Leu His Ser Thr Ser
    130                 135                 140

Gln Asn Ile Asn Leu Gly Pro Ser Gly Asn Pro His Ala Lys Pro Thr
145                 150                 155                 160

Asp Phe Asp Phe Leu Lys Val Ile Gly Lys Gly Ser Phe Gly Lys Val
                165                 170                 175

```
Leu Leu Ala Lys Arg Lys Leu Asp Gly Lys Phe Tyr Ala Val Lys Val
            180                 185                 190

Leu Gln Lys Lys Ile Val Leu Asn Arg Lys Glu Gln Lys His Ile Met
        195                 200                 205

Ala Glu Arg Asn Val Leu Leu Lys Asn Val Lys His Pro Phe Leu Val
    210                 215                 220

Gly Leu His Tyr Ser Phe Gln Thr Thr Glu Lys Leu Tyr Phe Val Leu
225                 230                 235                 240

Asp Phe Val Asn Gly Gly Glu Leu Phe Phe His Leu Gln Arg Glu Arg
                245                 250                 255

Ser Phe Pro Glu His Arg Ala Arg Phe Tyr Ala Ala Glu Ile Ala Ser
            260                 265                 270

Ala Leu Gly Tyr Leu His Ser Ile Lys Ile Val Tyr Arg Asp Leu Lys
        275                 280                 285

Pro Glu Asn Ile Leu Leu Asp Ser Val Gly His Val Val Leu Thr Asp
    290                 295                 300

Phe Gly Leu Cys Lys Glu Gly Ile Ala Ile Ser Asp Thr Thr Thr Thr
305                 310                 315                 320

Phe Cys Gly Thr Pro Glu Tyr Leu Ala Pro Glu Val Ile Arg Lys Gln
                325                 330                 335

Pro Tyr Asp Asn Thr Val Asp Trp Trp Cys Leu Gly Ala Val Leu Tyr
            340                 345                 350

Glu Met Leu Tyr Gly Leu Pro Pro Phe Tyr Cys Arg Asp Val Ala Glu
        355                 360                 365

Met Tyr Asp Asn Ile Leu His Lys Pro Leu Ser Leu Arg Pro Gly Val
370                 375                 380

Ser Leu Thr Ala Trp Ser Ile Leu Glu Glu Leu Leu Glu Lys Asp Arg
385                 390                 395                 400

Gln Asn Arg Leu Gly Ala Lys Glu Asp Phe Leu Glu Ile Gln Asn His
                405                 410                 415

Pro Phe Phe Glu Ser Leu Ser Trp Ala Asp Leu Val Gln Lys Lys Ile
            420                 425                 430

Pro Pro Pro Phe Asn Pro Asn Val Ala Gly Pro Asp Asp Ile Arg Asn
        435                 440                 445

Phe Asp Thr Ala Phe Thr Glu Glu Thr Val Pro Tyr Ser Val Cys Val
    450                 455                 460

Ser Ser Asp Tyr Ser Ile Val Asn Ala Ser Val Leu Glu Ala Asp Asp
465                 470                 475                 480

Ala Phe Val Gly Phe Ser Tyr Ala Pro Pro Ser Glu Asp Leu Phe Leu
                485                 490                 495

<210> SEQ ID NO 41
<211> LENGTH: 2032
<212> TYPE: DNA
<213> ORGANISM: Homo sapiens

<400> SEQUENCE: 41
ggactctggg acgctcagac gccgcgcggg cggggattg gtctgtggtc ctctctcggc     60
tcctcgcggc tcgcggcggc cgacggttcc tgggacacct gcttgcttgg cccgtccggc    120
ggctcagggc ttctctgctg cgctcccggt tcgctggacg ggaagaaggg ctgggccgtc    180
ccgtcccgtc cccatcggaa ccccaagtcg cgccgctgac ccgtcgcagg gcgagatgag    240
cgcggacgca gcggccgggg cgcccctgcc ccggctctgc tgcctggaga agggtccgaa    300
cggctacggc ttccacctgc acggggagaa gggcaagttg ggccagtaca tccggctggt    360
```

```
ggagcccggc tcgccggccg agaaggcggg gctgctggcg ggggaccggc tggtggaggt    420
gaacggcgaa aacgtggaga aggagaccca ccagcaggtg gtgagccgca tccgcgccgc    480
actcaacgcc gtgcgcctgc tggtggtcga ccccgagacg gacgagcagc tgcagaagct    540
cggcgtccag gtccgagagg agctgctgcg cgcccaggaa gcgccggggc aggccgagcc    600
gccggccgcc gccgaggtgc aggggggctgg caacgaaaat gagcctcgcg aggccgacaa    660
gagccacccg gagcagcgcg agcttcggcc tcggctctgt accatgaaga agggccccag    720
tggctatggc ttcaacctgc acagcgacaa gtccaagcca ggccagttca tccggtcagt    780
ggacccagac tccccggctg aggcttcagg gctcccgggcc caggatcgca ttgtggaggt    840
gaacggggtc tgcatggagg ggaagcagca tggggacgtg gtgtccgcca tcagggctgg    900
cggggacgag accaagctgc tggtggtgga caggaaaact gacgagttct tcaagaaatg    960
cagagtgatc ccatctcagg agcacctgaa tggtcccctg cctgtgccct tcaccaatgg   1020
ggagatacag aaggagaaca gtcgtgaagc cctggcagag gcagccttgg agagccccag   1080
gccagccctg gtgagatccg cctccagtga caccagcgag gagctgaatt cccaagacag   1140 cccccccaaaa caggactcca cagcgccctc gtctacctcc tcctccgacc ccatcctaga   1200
cttcaacatc tccctggcca tggccaaaga gagggcccac cagaaacgca gcagcaaacg   1260
ggccccgcag atggactgga gcaagaaaaa cgaactcttc agcaacctct gagcgccctg   1320
ctgccaccca gtgactggca gggccgagcc agcattccac cccacctttt tccttctccc   1380
caattactcc cctgaatcaa tgtacaaatc agcacccaca tcccctttct tgacaaatga   1440
tttttctaga gaactatgtt cttccctgac tttagggaag gtgaatgtgt tcccgtcctc   1500
ccgcagtcag aaaggagact ctgcctccct cctcctcact gagtgcctca tcctaccggg   1560
tgtccctttg ccaccctgcc tgggacatcg ctggaacctg caccatgcca ggatcatggg   1620
accaggcgag agggcaccct cccttcctcc cccatgtgat aaatgggtcc agggctgatc   1680
aaagaactct gactgcagaa ctgccgctct cagtggacag ggcatctgtt accctgagac   1740
ctgtggcaga cacgtcttgt tttcatttga tttttgttaa gagtgcagta ttgcagagtc   1800
tagaggaatt tttgtttcct tgattaacat gattttcctg gttgttacat ccagggcatg   1860
gcagtggcct cagccttaaa cttttgttcc tactcccacc ctcagcgaac tgggcagcac   1920
ggggagggtt tggctacccc tgcccatccc tgagccaggt accaccattg taaggaaaca   1980
ctttcagaaa ttcagctggt tcctccaaac ccttcaaaaa aaaaaaaaaa aa            2032
```

<210> SEQ ID NO 42
<211> LENGTH: 358
<212> TYPE: PRT
<213> ORGANISM: Homo sapiens

<400> SEQUENCE: 42

```
Met Ser Ala Asp Ala Ala Ala Gly Ala Pro Leu Pro Arg Leu Cys Cys
1               5                   10                  15

Leu Glu Lys Gly Pro Asn Gly Tyr Gly Phe His Leu His Gly Glu Lys
            20                  25                  30

Gly Lys Leu Gly Gln Tyr Ile Arg Leu Val Glu Pro Gly Ser Pro Ala
        35                  40                  45

Glu Lys Ala Gly Leu Leu Ala Gly Asp Arg Leu Val Glu Val Asn Gly
    50                  55                  60

Glu Asn Val Glu Lys Glu Thr His Gln Gln Val Val Ser Arg Ile Arg
65                  70                  75                  80
```

Ala Ala Leu Asn Ala Val Arg Leu Leu Val Val Asp Pro Glu Thr Asp
                 85                  90                  95

Glu Gln Leu Gln Lys Leu Gly Val Gln Val Arg Glu Glu Leu Leu Arg
            100                 105                 110

Ala Gln Glu Ala Pro Gly Gln Ala Glu Pro Pro Ala Ala Ala Glu Val
            115                 120                 125

Gln Gly Ala Gly Asn Glu Asn Glu Pro Arg Glu Ala Asp Lys Ser His
        130                 135                 140

Pro Glu Gln Arg Glu Leu Arg Pro Arg Leu Cys Thr Met Lys Lys Gly
145                 150                 155                 160

Pro Ser Gly Tyr Gly Phe Asn Leu His Ser Asp Lys Ser Lys Pro Gly
                165                 170                 175

Gln Phe Ile Arg Ser Val Asp Pro Asp Ser Pro Ala Glu Ala Ser Gly
            180                 185                 190

Leu Arg Ala Gln Asp Arg Ile Val Glu Val Asn Gly Val Cys Met Glu
        195                 200                 205

Gly Lys Gln His Gly Asp Val Val Ser Ala Ile Arg Ala Gly Gly Asp
    210                 215                 220

Glu Thr Lys Leu Leu Val Val Asp Arg Glu Thr Asp Glu Phe Phe Lys
225                 230                 235                 240

Lys Cys Arg Val Ile Pro Ser Gln Glu His Leu Asn Gly Pro Leu Pro
                245                 250                 255

Val Pro Phe Thr Asn Gly Glu Ile Gln Lys Glu Asn Ser Arg Glu Ala
            260                 265                 270

Leu Ala Glu Ala Ala Leu Glu Ser Pro Arg Pro Ala Leu Val Arg Ser
        275                 280                 285

Ala Ser Ser Asp Thr Ser Glu Glu Leu Asn Ser Gln Asp Ser Pro Pro
    290                 295                 300

Lys Gln Asp Ser Thr Ala Pro Ser Ser Thr Ser Ser Asp Pro Ile
305                 310                 315                 320

Leu Asp Phe Asn Ile Ser Leu Ala Met Ala Lys Glu Arg Ala His Gln
                325                 330                 335

Lys Arg Ser Ser Lys Arg Ala Pro Gln Met Asp Trp Ser Lys Lys Asn
            340                 345                 350

Glu Leu Phe Ser Asn Leu
        355

<210> SEQ ID NO 43
<211> LENGTH: 492
<212> TYPE: DNA
<213> ORGANISM: Homo sapiens

<400> SEQUENCE: 43
atccctgact cggggtcgcc tttggagcag agaggaggca atggccacca tggagaacaa      60
ggtgatctgc gccctggtcc tggtgtccat gctggccctc ggcaccctgg ccgaggccca     120
gacagagacg tgtacagtgg ccccccgtga agacagaat tgtggttttc ctggtgtcac     180
gccctcccag tgtgcaaata agggctgctg tttcgacgac accgttcgtg gggtcccctg     240
gtgcttctat cctaatacca tcgacgtccc tccagaagag gagtgtgaat tttagacact     300
tctgcaggga tctgcctgca tcctgacgcg gtgccgtccc cagcacggtg attagtccca     360
gagctcggct gccacctcca ccggacacct cagacacgct tctgcagctg tgcctcggct     420
cacaacacag attgactgct ctgactttga ctactcaaaa ttggcctaaa aattaaaaga     480

```
gatcgatatt aa                                                          492
```

<210> SEQ ID NO 44
<211> LENGTH: 84
<212> TYPE: PRT
<213> ORGANISM: Homo sapiens

<400> SEQUENCE: 44

```
Met Ala Thr Met Glu Asn Lys Val Ile Cys Ala Leu Val Leu Val Ser
1               5                   10                  15

Met Leu Ala Leu Gly Thr Leu Ala Glu Ala Gln Thr Glu Thr Cys Thr
            20                  25                  30

Val Ala Pro Arg Glu Arg Gln Asn Cys Gly Phe Pro Gly Val Thr Pro
        35                  40                  45

Ser Gln Cys Ala Asn Lys Gly Cys Cys Phe Asp Asp Thr Val Arg Gly
    50                  55                  60

Val Pro Trp Cys Phe Tyr Pro Asn Thr Ile Asp Val Pro Pro Glu Glu
65                  70                  75                  80

Glu Cys Glu Phe
```

<210> SEQ ID NO 45
<211> LENGTH: 3316
<212> TYPE: DNA
<213> ORGANISM: Homo sapiens

<400> SEQUENCE: 45

```
ggttttttgtg ttgctagccg gggccagcgg cggtggcggc ggcggcggag gcgtcggtgg    60
aggaggggag gcggcgagga ggcgcagctc ccgctgcacc gcgatcgacg ctgcggagcg   120
agcccacccg ccccgggagc tcgcctcccc ggtgctcccc cgccctcccc gcccccccag   180
cggcgctgcc tcctccaaat gagcgattcg cccgctggat ctaacccaag acacccgaa    240 agcagcggca gcggcagcgg cggcggcggg aagaggccgg cggtgccggc agcggtgtcc   300
ctcttgccac cggcggaccc cctgcgccag gcgaaccggc tcccgatcag ggtcctgaag   360
atgctgagcg ctcacaccgg tcacctcctg caccggagt acctgcagcc gctgtcctcc   420
actcccgtca gccccattga gctggacgcc aagaagagcc ccttggcgct gctggctcag   480
acctgctcgc agatcggcaa gccggacccg ccgccctcct ccaaactcaa ctcggtggcg   540
gcggcggcca acgggctggg agcggagaag gaccccggcc gctcagcccc gggcgccgcc   600
tccgcagccg cggccctgaa gcagctgggg gactcaccgg ccgaggacaa gtccagcttc   660 aagcccttact ccaagggctc cggcggcggc gactcccgca agacagcggc ctcctcctcg   720
gtgtcttcca cctcctcctc gtcctcctcg tccccgggag acaaggcggg cttcagggtc   780
cccagcgccg cctgcccgcc ctttcccccg catggagcgc cggtctccgc atcctcgtcc   840
tcgtcgtcgc ccggcggctc ccgcggcggc tccccgcacc actctgactg caagaacggc   900
ggcggggttg gcgcggggga gctggacaag aaagaccagg agcccaagcc cagcccggag   960
ccggcagccg tgagccgcgg cggcgtgggg gagcccgggg cgcacggtgg cgccgagtcc  1020 gggggcctccg ggcgcaagtc cgagccgccc tcggcgctgg tggggggccgg ccacgtggcg  1080 ccggtgtctc cctacaagcc gggccactcg gtgttcccgc tgccgccctc cagcattggc  1140
taccacggct ccatcgtggg cgcctacgcc ggctacccgt ctcagttcgt gcctggcctg  1200
gatcctagca gtccggggcct cgtggggaggc cagctgtctg gggggcctggg cctgccgccg  1260 ggcaagcccc ccagctccag cccgctcacc gggggcctccc cgcccctcctt cctgcaggga  1320
```

```
ttatgccgcg accoctattg cttgggaggt taccacggcg cctcgcacct cggcggctcc    1380
agctgctcca cctgcagcgc gcacgaccct gccgggccca gcctgaaggc gggggggctac   1440
ccgctggtgt accccgggca cccgctgcag cccgccgcgc tctcgtccag cgccgcccag   1500
gccgcgctcc ccggccaccc gctctacacc tacggcttca tgctgcagaa cgaaccgctg   1560
ccgcacagct gcaactgggt ggcagccagt gggccgtgcg acaagcgctt cgccacctcg   1620
gaggagctgc tcagccacct acggacccac acggccctgc cgggagccga gaaacttctg   1680
gccgcctacc ccggggcctc gggcctgggc agcgccgccg ccgccgccgc cgccgccgcc   1740
tcctgccatc tgcacctccc ccgcccgcc gccccggca gccccgggtc gctgtccttg     1800
cggaatccac acactttggg cctaagccgg taccaccoct atggcaagag ccacttatcc   1860
acagcggggg gcctggccgt gccgtccctc cccacagccg gacoctacta ttcgccatac    1920
gcgctgtatg gacagagact agcttcagcc tcggcgctgg gataccagta actacagctc   1980
ttcctccacc ccagcccct caccctcctc cctctccctc ctcctccctc cccacctgcc   2040
gtcgccgctg caacctccac tactgcttga ccctgccggg attccccacc cagcccttcc   2100
ccaccggact gtgtattat ttactataat gttagcttac aagctgggaa tataagtgca    2160
ttaacgcccc acatgagtca atggtatgca aaaagtctgt gttctcccaa ataataatat   2220
taatcccaca aataacgaca tgatccccgc ccctgttcct ttctgttatt ttttcttaga   2280
tataagtttt acatttttta ttccttttcc tcttttttg gttttgattg gtttggtttg    2340
agggagagtt ggggtctttg ggtcttcta gacgttttgt tttccctccc tggggagttt    2400
cttgcatgag tcttaactta aaactacgtt tccgccttct cttttccct cttccccctt    2460
cattcotct tgtttccttc catttgcggt tctgttttg ttttttgtt tgttttgttt      2520
tgtttttcc tttgttgtac aagtaacaga gaggaggttt tttttgtaac tcattttggg   2580
ggtggagggg gccacctggg tggcagggc cctggagctc tattgacctg gtacactgct   2640
ccgggactcc tcccccgcca ccctccgcgc atagggtcct tggtctggac cctgcccccc   2700
aaaagtaggg cttgctcct ctaccttgct ctgagcacgg agagccctga ccccaccagt    2760
aggctcgccc ccagaagggc ccaagtggcc gtctaccgtc accttccaga ctcccgcccc   2820
taacacccag tggctacagt gcgcctgtcg gggcacctgg agcgctcacc tggttgaatt   2880
caaagtccca gaaggccccg ctggcgtgaa gccggcccct tacattttgc gaagtgcatt   2940
atagtccttg tttttctctc cctcgtgggg gcaacgaccc ctcccctggc agtaggggtg   3000
gggtaggtga ctctcgctag atccctccaa agcagaccgg tggcgatgtc agcggatgtc   3060
acgagctcgt tagctgcgtt cggggaaggt tggggcgtca gggagctctc ggatcacagc   3120
agccccgcc ctctcctagg cctggccgg cagagccccc agagtggacc cccagcgac     3180
tggggtcttc tccccactcc tccctccttc tggtctgatg cggcagcgcg ggggctgcgg   3240
ggcctgtttg ggacgaacag agctctccct tggtaagact tattttgtta ataaatggaa   3300
tacttggcta tattca                                                   3316
```

<210> SEQ ID NO 46
<211> LENGTH: 590
<212> TYPE: PRT
<213> ORGANISM: Homo sapiens

<400> SEQUENCE: 46

Met Ser Asp Ser Pro Ala Gly Ser Asn Pro Arg Thr Pro Glu Ser Ser
1               5                   10                  15

```
Gly Ser Gly Ser Gly Gly Gly Lys Arg Pro Ala Val Pro Ala Ala
            20                  25                  30

Val Ser Leu Leu Pro Pro Ala Asp Pro Leu Arg Gln Ala Asn Arg Leu
        35                  40                  45

Pro Ile Arg Val Leu Lys Met Leu Ser Ala His Thr Gly His Leu Leu
    50                  55                  60

His Pro Glu Tyr Leu Gln Pro Leu Ser Ser Thr Pro Val Ser Pro Ile
65                  70                  75                  80

Glu Leu Asp Ala Lys Lys Ser Pro Leu Ala Leu Leu Ala Gln Thr Cys
                85                  90                  95

Ser Gln Ile Gly Lys Pro Asp Pro Pro Ser Ser Lys Leu Asn Ser
            100                 105                 110

Val Ala Ala Ala Asn Gly Leu Gly Ala Glu Lys Asp Pro Gly Arg
        115                 120                 125

Ser Ala Pro Gly Ala Ala Ser Ala Ala Ala Leu Lys Gln Leu Gly
        130                 135                 140

Asp Ser Pro Ala Glu Asp Lys Ser Ser Phe Lys Pro Tyr Ser Lys Gly
145                 150                 155                 160

Ser Gly Gly Gly Asp Ser Arg Lys Asp Ser Gly Ser Ser Val Ser
            165                 170                 175

Ser Thr Ser Ser Ser Ser Ser Ser Pro Gly Asp Lys Ala Gly Phe
        180                 185                 190

Arg Val Pro Ser Ala Ala Cys Pro Pro Phe Pro Pro His Gly Ala Pro
        195                 200                 205

Val Ser Ala Ser Ser Ser Ser Ser Pro Gly Gly Ser Arg Gly Gly
        210                 215                 220

Ser Pro His His Ser Asp Cys Lys Asn Gly Gly Val Gly Gly Gly
225                 230                 235                 240

Glu Leu Asp Lys Lys Asp Gln Glu Pro Lys Pro Ser Pro Glu Pro Ala
            245                 250                 255

Ala Val Ser Arg Gly Gly Gly Glu Pro Gly Ala His Gly Gly Ala
        260                 265                 270

Glu Ser Gly Ala Ser Gly Arg Lys Ser Glu Pro Pro Ser Ala Leu Val
        275                 280                 285

Gly Ala Gly His Val Ala Pro Val Ser Pro Tyr Lys Pro Gly His Ser
        290                 295                 300

Val Phe Pro Leu Pro Pro Ser Ser Ile Gly Tyr His Gly Ser Ile Val
305                 310                 315                 320

Gly Ala Tyr Ala Gly Tyr Pro Ser Gln Phe Val Pro Gly Leu Asp Pro
            325                 330                 335

Ser Lys Ser Gly Leu Val Gly Gly Gln Leu Ser Gly Gly Leu Gly Leu
        340                 345                 350

Pro Pro Gly Lys Pro Pro Ser Ser Ser Pro Leu Thr Gly Ala Ser Pro
        355                 360                 365

Pro Ser Phe Leu Gln Gly Leu Cys Arg Asp Pro Tyr Cys Leu Gly Gly
        370                 375                 380

Tyr His Gly Ala Ser His Leu Gly Gly Ser Ser Cys Ser Thr Cys Ser
385                 390                 395                 400

Ala His Asp Pro Ala Gly Pro Ser Leu Lys Ala Gly Gly Tyr Pro Leu
                405                 410                 415

Val Tyr Pro Gly His Pro Leu Gln Pro Ala Ala Leu Ser Ser Ser Ala
        420                 425                 430

Ala Gln Ala Ala Leu Pro Gly His Pro Leu Tyr Thr Tyr Gly Phe Met
```

```
                    435                 440                 445
Leu Gln Asn Glu Pro Leu Pro His Ser Cys Asn Trp Val Ala Ala Ser
    450                 455                 460

Gly Pro Cys Asp Lys Arg Phe Ala Thr Ser Glu Glu Leu Leu Ser His
465                 470                 475                 480

Leu Arg Thr His Thr Ala Leu Pro Gly Ala Glu Lys Leu Leu Ala Ala
                485                 490                 495

Tyr Pro Gly Ala Ser Gly Leu Gly Ser Ala Ala Ala Ala Ala Ala
            500                 505                 510

Ala Ala Ser Cys His Leu His Leu Pro Pro Ala Ala Pro Gly Ser
        515                 520                 525

Pro Gly Ser Leu Ser Leu Arg Asn Pro His Thr Leu Gly Leu Ser Arg
    530                 535                 540

Tyr His Pro Tyr Gly Lys Ser His Leu Ser Thr Ala Gly Gly Leu Ala
545                 550                 555                 560

Val Pro Ser Leu Pro Thr Ala Gly Pro Tyr Tyr Ser Pro Tyr Ala Leu
                565                 570                 575

Tyr Gly Gln Arg Leu Ala Ser Ala Ser Ala Leu Gly Tyr Gln
            580                 585                 590

<210> SEQ ID NO 47
<211> LENGTH: 1691
<212> TYPE: DNA
<213> ORGANISM: Homo sapiens

<400> SEQUENCE: 47
gggctggcgc gggcgggagc tgcggcggat acccttgcgt gctgtggaga ccctactctc    60
ttcgctgaga acggccgcta gcggggactg aaggccggga gcccactccc gacccggggc   120
tagcgtgcgt ccctagagtc gagcggggca agggagccag tggccgccga cgggggaccg   180
ggaaactttt ctgggctcct gggcgcgccc tgtagccgcg ctccatgctc cggcagcggc   240
ccgaaaccca gccccgccgc tgacggcgcc cgccgctccg gcagggccc atgccctgcg    300 cgctccgggg gtcgtaggct gccgccgagc cggggctccg gaagccggcg ggggcgccgc   360
ggccgtgcgg ggcgtcaatg gatcgccact ccagctacat cttcatctgg ctgcagctgg   420
agctctgcgc catggccgtg ctgctcacca aaggtgaaat tcgatgctac tgtgatgctg   480
cccactgtgt agccactggt tatatgtgta aatctgagct cagcgcctgc ttctctagac   540
ttcttgatcc tcagaactca aattccccac tcacccatgg ctgcctggac tctcttgcaa   600
gcacgacaga catctgccaa gccaaacagg cccgaaacca ctctggcacc accataccca   660
cattggaatg ctgtcatgaa gacatgtgca attacagagg gctgcacgat gttctctctc   720
ctcccagggg tgaggcctca ggacaaggaa acaggtatca gcatgatggt agcagaaacc   780
ttatcaccaa ggtgcaggag ctgacttctt ccaaagagtt gtggttccgg gcagcggtca   840
ttgccgtgcc cattgctgga gggctgattt tagtgttgct tattatgttg gccctgagga   900
tgcttcgaag tgaaaataag aggctgcagg atcagcggca acagatgctc tcccgtttgc   960
actacagctt tcacggacac cattccaaaa aggggcaggt tgcaaagtta gacttggaat  1020
gcatggtgcc ggtcagtggg cacgagaact gctgtctgac ctgtgataaa atgagacaag  1080
cagacctcag caacgataag atcctctcgc ttgttcactg gggcatgtac agtgggcacg  1140
ggaagctgga attcgtatga cggagtctta tctgaactac acttactgaa cagcttgaag  1200 gcctttgag ttctgctgga caggagcact ttatctgaag acaaactcat ttaatcatct   1260
```

-continued

```
ttgagagaca aaatgacctc tgcaaacaga atcttggata tttcttctga aggattattt    1320
gcacagactt aaatacagtt aaatgtgtta tttgctttta aaattataaa aagcaaagag    1380
aagactttgt acacactgtc accagggtta tttgcatcca agggagctgg aattgagtac    1440
ctaaataaac aaaaatgtgc cctatgtaag cttctacatc ttgatttatt gtaaagattt    1500
aaaagaaata tatatatttt gtctgaaatt taatagtgtc tttcataaat ttaactggga    1560
aacgtgagac agtacatgtt aattatacaa atggccattt gctgttaata atttgttctc    1620
aactctagga tgtggcttgg ttttttttt tctctttct tttttaaaca agaccaagat    1680
cttgcttatt c                                                        1691
```

<210> SEQ ID NO 48
<211> LENGTH: 260
<212> TYPE: PRT
<213> ORGANISM: Homo sapiens

<400> SEQUENCE: 48

```
Met Asp Arg His Ser Ser Tyr Ile Phe Ile Trp Leu Gln Leu Glu Leu
1               5                   10                  15

Cys Ala Met Ala Val Leu Leu Thr Lys Gly Glu Ile Arg Cys Tyr Cys
            20                  25                  30

Asp Ala Ala His Cys Val Ala Thr Gly Tyr Met Cys Lys Ser Glu Leu
        35                  40                  45

Ser Ala Cys Phe Ser Arg Leu Leu Asp Pro Gln Asn Ser Asn Ser Pro
    50                  55                  60

Leu Thr His Gly Cys Leu Asp Ser Leu Ala Ser Thr Thr Asp Ile Cys
65                  70                  75                  80

Gln Ala Lys Gln Ala Arg Asn His Ser Gly Thr Thr Ile Pro Thr Leu
                85                  90                  95

Glu Cys Cys His Glu Asp Met Cys Asn Tyr Arg Gly Leu His Asp Val
            100                 105                 110

Leu Ser Pro Pro Arg Gly Glu Ala Ser Gly Gln Gly Asn Arg Tyr Gln
        115                 120                 125

His Asp Gly Ser Arg Asn Leu Ile Thr Lys Val Gln Glu Leu Thr Ser
    130                 135                 140

Ser Lys Glu Leu Trp Phe Arg Ala Ala Ile Ala Val Pro Ile Ala
145                 150                 155                 160

Gly Gly Leu Ile Leu Val Leu Leu Ile Met Leu Ala Leu Arg Met Leu
                165                 170                 175

Arg Ser Glu Asn Lys Arg Leu Gln Asp Gln Arg Gln Gln Met Leu Ser
            180                 185                 190

Arg Leu His Tyr Ser Phe His Gly His His Ser Lys Lys Gly Gln Val
        195                 200                 205

Ala Lys Leu Asp Leu Glu Cys Met Val Pro Val Ser Gly His Glu Asn
    210                 215                 220

Cys Cys Leu Thr Cys Asp Lys Met Arg Gln Ala Asp Leu Ser Asn Asp
225                 230                 235                 240

Lys Ile Leu Ser Leu Val His Trp Gly Met Tyr Ser Gly His Gly Lys
                245                 250                 255

Leu Glu Phe Val
            260
```

<210> SEQ ID NO 49
<211> LENGTH: 3490
<212> TYPE: DNA

<213> ORGANISM: Homo sapiens

<400> SEQUENCE: 49

| | | | | | |
|---|---|---|---|---|---|
| actgggtaga | atacttgggg | tgccagggag | gcattaatgc | gagaggagtc | aggtgctcag | 60 |
| tttttattgg | agttgggagg | gcagccccac | atcaggaaga | gaacctgttt | ctgcaggatg | 120 |
| gtccggggag | aagggaggac | tccacccagg | cttgtgtttg | ccctgctctg | tgtattcagc | 180 |
| cagcaggctc | tgcacaagga | agcaaagtgc | agggagccag | gctccaccga | cagccaggca | 240 |
| ctgggcagca | cgcactggag | acccaggacc | ctgtgcagga | gcagctccgg | gtgacacgag | 300 |
| gggactgaag | atactcccac | aggggctcag | caggagcaat | gggtaaccaa | atgagtgttc | 360 |
| cccaaagagt | tgaagaccaa | gagaatgaac | cagaagcaga | gacttaccag | gacaacgcgt | 420 |
| ctgctctgaa | cggggttcca | gtggtggtgt | cgacccacac | agttcagcac | ttagaggaag | 480 |
| tcgacttggg | aataagtgtc | aagacggata | atgtggccac | ttcttccccc | gagacaacgg | 540 |
| agataagtgc | tgttgcggat | gccaacgaaa | agaatcttgg | gaaagaggcc | aaacccgagg | 600 |
| caccagctgc | taaatctcgt | tttttcttga | tgctctctcg | gcctgtacca | ggacgtaccg | 660 |
| gagaccaagc | cgcagattca | tcccttggat | cagtgaagct | tgatgtcagc | tccaataaag | 720 |
| ctccagcgaa | caaagaccca | agtgagagct | ggacacttcc | ggtggcagct | ggaccggggc | 780 |
| aggacacaga | taaaacccca | gggcacgccc | cggcccaaga | caaggtcctc | tctgccgcca | 840 |
| gggatcccac | gcttctccca | cctgagacag | ggggagcagg | aggagaagct | ccctccaagc | 900 |
| ccaaggactc | cagcttttt | gacaaattct | tcaagctgga | caagggacag | gaaaaggtgc | 960 |
| caggtgacag | ccaacaggaa | gccaagaggg | cagagcatca | agacaaggtg | gatgaggttc | 1020 |
| ctggcttatc | agggcagtcc | gatgatgtcc | ctgcaggaa | ggacatagtt | gacggcaagg | 1080 |
| aaaaagaagg | acaagaactt | ggaactgcgg | attgctctgt | ccctggggac | ccagaaggac | 1140 |
| tggagactgc | aaaggacgat | tcccaggcag | cagctatagc | agagaataat | aattccatca | 1200 |
| tgagtttctt | taaaactctg | gtttcaccta | acaaagctga | aacaaaaaag | gacccagaag | 1260 |
| acacgggtgc | tgaaaagtca | cccaccactt | cagctgacct | taagtcagac | aaagccaact | 1320 |
| ttacatccca | ggagacccaa | ggggctggca | agaattccaa | aggatgcaac | ccatcggggc | 1380 |
| acacacagtc | cgtgacaacc | cctgaacctg | cgaaggaagg | caccaaggag | aaatcaggac | 1440 |
| ccacctctct | gcctctgggc | aaactgtttt | ggaaaaagtc | agttaaagag | gactcagtcc | 1500 |
| ccacaggtgc | ggaggagaat | gtggtgtgtg | agtcaccagt | agagattata | aagtccaagg | 1560 |
| aagtagaatc | agccttacaa | acagtggacc | tcaacgaagg | agatgctgca | cctgaaccca | 1620 |
| cagaagcgaa | actcaaaaga | gaagaaagca | aaccaagaac | ctctctgatg | gcgtttctca | 1680 |
| gacaaatgtc | agtgaaaggg | gatggaggga | tcacccactc | agaagaaata | aatgggaaag | 1740 |
| actccagctg | ccaaacatca | gactccacag | aaaagactat | cacaccgcca | gagcctgaac | 1800 |
| caacaggagc | accacagaag | ggtaaagagg | gctcctcgaa | ggacaagaag | tcagcagccg | 1860 |
| agatgaacaa | gcagaagagc | aacaagcagg | aagccaaaga | accagcccag | tgcacagagc | 1920 |
| aggccacggt | ggacacgaac | tcactgcaga | atggggacaa | gctccaaaag | agacctgaga | 1980 |
| agcggcagca | gtcccttggg | ggcttcttta | aggcctggg | accaaagcgg | atgttggatg | 2040 |
| ctcaagtgca | aacagaccca | gtatccatcg | gaccagttgg | caaatccaag | taaacaaatc | 2100 |
| agcacggttc | ccaccaggtt | ctcctgccac | caagatgtgt | tctccttact | ccatctcctc | 2160 |
| cccaaacacg | ctccatgtat | atattcttct | gatggccagc | aaatgaaatt | ctgcctagaa | 2220 |
| attaagcccg | agctgttgta | tattgaggtg | tattatttac | gtctctggtc | cagtcttttc | 2280 |

-continued

```
tggcaaataa cagtaaagat ggtttagcag gtcacctagt tgggtcagaa gagtcgatga    2340
tcaccaagca ggaaagggag ggaatagagg aatgtgttcg ggttaagtga tgaaaatggc    2400
agtggtggcc gggcgtggtg gctctcgcct gtaatctcag cactttggga ggccgaggca    2460
ggtggatcac ctgaggtcag gagttcaaga ctagcctggc caacatcatg aaaccccgtc    2520
tctactaaaa atacaaaaat tagccaggca tggtggcaca cacctgtagt cccagctact    2580
cgggagccca acgcacgaga accgcttgta cccaggaggt ggaggttgca gtgagccgaa    2640
gttgcaccat tgcactccac cctgggcgac agagcaagat tctatcaaaa aaaaaaaaag    2700
gcagtggcaa gtaagttata gaagagaaat gctgctagaa ggaattaagc gttgtagtaa    2760
atgcgtgctt atcctctaag cttgaagaag ggagacgaaa atccatttgt ttaaattcac    2820
atctcaagga gggagaaccc gggctgtgtt gggtggttgc caatttccta gaacggaatg    2880
tgtggggtat agaaaaagga atgaataagc gttgttttc aaatagggtc cttgtaagtt    2940
attgatgaga gggaaaagat tgactgggga gggcttaaaa tgatttggga aaacaattgc    3000
ttttgaggct cagtgacaac ggcaaagatt acaacttaaa aaaaaaaat aaataaaaaa    3060 taaaggaagt tgcacggtta ttttgcaaca caaggggcg gcaaggtccc cattttatc    3120 ctgtaatact gtatccctaa caaagatttg gtctctgcta tcttacatta ttaatgtttc    3180
tcagatggct gagggctcg cttcatctgt tccgtctgac acttatctca agtgtgtctg    3240
tcattcctaa tgttctcagg atgtgctctg ataaaccct ccccataacc tcagttaata    3300
aaaatttaca gaagacttct caaatacctg agttgttttt aatacctgta caaaggagta    3360
aataggaccc tgagtctatt aaaatgtaat tcaaagtagc atatgattga ctgacagtca    3420
tgtaaactgt atctttcttt ttctgattta ataaaaaata catttacttc taaagtaaaa    3480
aaaaaaaaaa                                                          3490
```

<210> SEQ ID NO 50
<211> LENGTH: 584
<212> TYPE: PRT
<213> ORGANISM: Homo sapiens

<400> SEQUENCE: 50

Met Gly Asn Gln Met Ser Val Pro Gln Arg Val Glu Asp Gln Glu Asn
1               5                   10                  15

Glu Pro Glu Ala Glu Thr Tyr Gln Asp Asn Ala Ser Ala Leu Asn Gly
                20                  25                  30

Val Pro Val Val Val Ser Thr His Thr Val Gln His Leu Glu Glu Val
            35                  40                  45

Asp Leu Gly Ile Ser Val Lys Thr Asp Asn Val Ala Thr Ser Ser Pro
        50                  55                  60

Glu Thr Thr Glu Ile Ser Ala Val Ala Asp Ala Asn Gly Lys Asn Leu
65                  70                  75                  80

Gly Lys Glu Ala Lys Pro Glu Ala Pro Ala Lys Ser Arg Phe Phe
                85                  90                  95

Leu Met Leu Ser Arg Pro Val Pro Gly Arg Thr Gly Asp Gln Ala Ala
                100                 105                 110

Asp Ser Ser Leu Gly Ser Val Lys Leu Asp Val Ser Ser Asn Lys Ala
            115                 120                 125

Pro Ala Asn Lys Asp Pro Ser Glu Ser Trp Thr Leu Pro Val Ala Ala
        130                 135                 140

Gly Pro Gly Gln Asp Thr Asp Lys Thr Pro Gly His Ala Pro Ala Gln

```
            145                 150                 155                 160
Asp Lys Val Leu Ser Ala Ala Arg Asp Pro Thr Leu Leu Pro Pro Glu
                165                 170                 175
Thr Gly Gly Ala Gly Gly Glu Ala Pro Ser Lys Pro Lys Asp Ser Ser
                180                 185                 190
Phe Phe Asp Lys Phe Phe Lys Leu Asp Lys Gly Gln Glu Lys Val Pro
                195                 200                 205
Gly Asp Ser Gln Gln Glu Ala Lys Arg Ala Glu His Gln Asp Lys Val
210                 215                 220
Asp Glu Val Pro Gly Leu Ser Gly Gln Ser Asp Asp Val Pro Ala Gly
225                 230                 235                 240
Lys Asp Ile Val Asp Gly Lys Glu Lys Glu Gly Gln Glu Leu Gly Thr
                245                 250                 255
Ala Asp Cys Ser Val Pro Gly Asp Pro Glu Gly Leu Glu Thr Ala Lys
                260                 265                 270
Asp Asp Ser Gln Ala Ala Ala Ile Ala Glu Asn Asn Asn Ser Ile Met
                275                 280                 285
Ser Phe Phe Lys Thr Leu Val Ser Pro Asn Lys Ala Glu Thr Lys Lys
                290                 295                 300
Asp Pro Glu Asp Thr Gly Ala Glu Lys Ser Pro Thr Thr Ser Ala Asp
305                 310                 315                 320
Leu Lys Ser Asp Lys Ala Asn Phe Thr Ser Gln Glu Thr Gln Gly Ala
                325                 330                 335
Gly Lys Asn Ser Lys Gly Cys Asn Pro Ser Gly His Thr Gln Ser Val
                340                 345                 350
Thr Thr Pro Glu Pro Ala Lys Glu Gly Thr Lys Glu Lys Ser Gly Pro
                355                 360                 365
Thr Ser Leu Pro Leu Gly Lys Leu Phe Trp Lys Lys Ser Val Lys Glu
                370                 375                 380
Asp Ser Val Pro Thr Gly Ala Glu Glu Asn Val Val Cys Glu Ser Pro
385                 390                 395                 400
Val Glu Ile Ile Lys Ser Lys Glu Val Glu Ser Ala Leu Gln Thr Val
                405                 410                 415
Asp Leu Asn Glu Gly Asp Ala Ala Pro Glu Pro Thr Glu Ala Lys Leu
                420                 425                 430
Lys Arg Glu Glu Ser Lys Pro Arg Thr Ser Leu Met Ala Phe Leu Arg
                435                 440                 445
Gln Met Ser Val Lys Gly Asp Gly Gly Ile Thr His Ser Glu Glu Ile
                450                 455                 460
Asn Gly Lys Asp Ser Ser Cys Gln Thr Ser Asp Ser Thr Glu Lys Thr
465                 470                 475                 480
Ile Thr Pro Pro Glu Pro Glu Pro Thr Gly Ala Pro Gln Lys Gly Lys
                485                 490                 495
Glu Gly Ser Ser Lys Asp Lys Ser Ala Ala Glu Met Asn Lys Gln
                500                 505                 510
Lys Ser Asn Lys Gln Glu Ala Lys Glu Pro Ala Gln Cys Thr Glu Gln
                515                 520                 525
Ala Thr Val Asp Thr Asn Ser Leu Gln Asn Gly Asp Lys Leu Gln Lys
                530                 535                 540
Arg Pro Glu Lys Arg Gln Gln Ser Leu Gly Gly Phe Phe Lys Gly Leu
545                 550                 555                 560
Gly Pro Lys Arg Met Leu Asp Ala Gln Val Gln Thr Asp Pro Val Ser
                565                 570                 575
```

Ile Gly Pro Val Gly Lys Ser Lys
            580

<210> SEQ ID NO 51
<211> LENGTH: 2767
<212> TYPE: DNA
<213> ORGANISM: Homo sapiens

<400> SEQUENCE: 51

| | | | | | |
|---|---|---|---|---|---|
| cgccgtgggt | ttctttgttc | gtggtgggga | ctgtgggctt | tgaggaggtt | ggtaccatgc | 60 |
| gagtgcctcg | gtgctgcctg | ctcctcatcc | gctggagcga | ccagggtgct | gccctcagcc | 120 |
| ccagccccgg | ggggagctgg | cgcccgcgat | ggacagatag | atgctcgtgg | ggtggaagga | 180 |
| ggttgcgact | aggttaaggg | cagtctccgc | ctcggtgccc | ccgcccccg | ctcgtgttgt | 240 |
| cacggggact | tgctggcgtg | gtgcttctcg | aattgacagc | cccggggctc | tgcagagttg | 300 |
| tggggccccg | gcatcagtgg | gtggacgggt | gttgtcccta | cgggcgcggg | gcgggcgggc | 360 |
| tggactggac | ttctctcccc | ggaccgtagc | cgggtgtgcc | gcgccacccc | agggctcctg | 420 |
| ggacggggt | atccgcctct | cggatgaagg | atttggggc | agagcacttg | gcaggtcatg | 480 |
| aagggtcca | acttctcggg | ttgttgaacg | tctacctgga | acaagaagag | agattccaac | 540 |
| ctcgagaaaa | agggctgagt | ttgattgagg | ctaccccgga | gaatgataac | actttgtgtc | 600 |
| caggattgag | aaatgccaaa | gttgaagatt | taaggagttt | agccaacttt | tttgatcttt | 660 |
| gcactgaaac | ttttgtcctg | gctgtcaata | ttttggacag | gttcttggct | cttatgaagg | 720 |
| tgaaacctaa | acatttgtct | tgcattggag | tctgttcttt | tttgctggct | gctagaatag | 780 |
| ttgaagaaga | ctgcaatatt | ccatccactc | atgatgtgat | ccggattagt | cagtgtaaat | 840 |
| gtactgcttc | tgcataaaaa | cggatggaaa | aaataatttc | agaaaaattg | cactatgaat | 900 |
| tggaagctac | tactgcctta | aacttttttgc | acttatacca | tactattata | ctttgtcata | 960 |
| cttcagaaag | gaaagaaata | ctgagccttg | ataaactaga | agctcagctg | aaagcttgca | 1020 |
| actgccgact | catcttttca | aaagcaaaac | catctgtatt | agccttgtgc | cttctcaatt | 1080 |
| tggaagtgga | aactttgaaa | tctgttgaat | tactggaaat | tctcttgcta | gttaaaaaac | 1140 |
| attccaagat | taatgacact | gagttcttct | actggagaga | gttggtttct | aaatgcctag | 1200 |
| ccgagtattc | ttctcctgaa | tgttgcaaac | cagatcttaa | gaagttggtt | tggatcgttt | 1260 |
| caaggcgcac | agcccagaac | ctccacaaca | gctactatag | tgttcctgag | ctgccaacga | 1320 |
| tacctgaggg | gggttgtttt | gatgaaagtg | aaagtgagga | ctcttgtgaa | gatatgagtt | 1380 |
| gtggagagga | gagtctcagc | agctctcctc | ccagtgatca | agagtgcacc | ttcttttca | 1440 |
| acttcaaagt | ggcacaaaca | ctgtgctttc | catcttagaa | atctgattgt | tctgtcagaa | 1500 |
| tttatattta | caggtttcaa | agcaataaat | ggggaatag | gtagtttcct | ggtttagccc | 1560 |
| ccatctagtc | aggaattaat | atactggaat | acctacctc | tatttgttat | tcagatcaga | 1620 |
| tctggcctat | tttcatattt | atcctaagcc | atcaaatggg | gtagtgcctc | ttaaaccatt | 1680 |
| aacagtactt | tagacattgg | cactttattt | ttctcgtaga | tctttagcta | ctttggggag | 1740 |
| gagggaaggt | gctgataccc | tcaatttgtt | acttttcaag | atttttaaaa | ataactagtg | 1800 |
| tagcttatct | taaacatttt | ataaaacctt | cagatgtctt | taagcagatt | ggaagtatgc | 1860 |
| aagtgcttcc | ttagcaggga | cagtggataa | tccttaatgg | tttatcatag | atttcaccct | 1920 |
| ccccccttct | cagaagagtg | agtatgctct | taaatgtcaa | acacattttt | gttgtttttgt | 1980 |
| tttttaaatg | atcagtgtct | atttgatgtg | atgcagatct | tataaatttg | ggaattataa | 2040 |

-continued

```
tattgacatt tctgtgattt ttatatatgt aatgtcttaa ttgagatttc tgttaaggca    2100
gaaataatta ggctagggct cttagttttc attcctattg cccaagtatt gtcaaactat    2160
ggtattattt taatgttact ttaaaaatcc ataatctgct agttttgcat gtacttatat    2220
gaaaacagtg cagtaagttg aaaactcagt atctatggaa ttgataaatg ttgatctggt    2280
gtagtatatt ttatcgcatt ttcttatatt aaaaaatgtc tgcatgatta cattttattt    2340
cctttgtaat ttacatttca gaatagtgta ttgctatatg ggtgccaaga ttgaatgaa    2400 agaacccgag tgtttgtagt attatagttt taagcaaatc tgtgtggtga tacagccata    2460
agaatggggc ttatataaac tctgtacatg taagattttg tacagagaat ttttaacttt    2520
ataaattgta tatgaacatg taaatctttt aaaatgtaca taaaatactg tatttttta     2580 ccttgtgtgt gatagtctag tcattgcatg taaatataat ttattatgta ttctgtagta    2640
taaatcatac attgatgact tacattttta ctggtaagtc aacatccgtt ggatgttttc    2700
tgaagtggct ctttttgaag tgataataga ttgtaattca aaataaaatt attaatgaat    2760
tctcctt                                                              2767
```

```
<210> SEQ ID NO 52
<211> LENGTH: 344
<212> TYPE: PRT
<213> ORGANISM: Homo sapiens

<400> SEQUENCE: 52
```

| | | | | | | | | | | | | | | |
|---|---|---|---|---|---|---|---|---|---|---|---|---|---|---|
| Met | Lys | Asp | Leu | Gly | Ala | Glu | His | Leu | Ala | Gly | His | Glu | Gly | Val | Gln |
| 1 | | | | 5 | | | | | 10 | | | | | 15 | |
| Leu | Leu | Gly | Leu | Leu | Asn | Val | Tyr | Leu | Glu | Gln | Glu | Glu | Arg | Phe | Gln |
| | | | 20 | | | | | 25 | | | | | 30 | | |
| Pro | Arg | Glu | Lys | Gly | Leu | Ser | Leu | Ile | Glu | Ala | Thr | Pro | Glu | Asn | Asp |
| | | 35 | | | | | 40 | | | | | 45 | | | |
| Asn | Thr | Leu | Cys | Pro | Gly | Leu | Arg | Asn | Ala | Lys | Val | Glu | Asp | Leu | Arg |
| | 50 | | | | | 55 | | | | | 60 | | | | |
| Ser | Leu | Ala | Asn | Phe | Phe | Gly | Ser | Cys | Thr | Glu | Thr | Phe | Val | Leu | Ala |
| 65 | | | | | 70 | | | | | 75 | | | | | 80 |
| Val | Asn | Ile | Leu | Asp | Arg | Phe | Leu | Ala | Leu | Met | Lys | Val | Lys | Pro | Lys |
| | | | | 85 | | | | | 90 | | | | | 95 | |
| His | Leu | Ser | Cys | Ile | Gly | Val | Cys | Ser | Phe | Leu | Leu | Ala | Ala | Arg | Ile |
| | | | 100 | | | | | 105 | | | | | 110 | | |
| Val | Glu | Glu | Asp | Cys | Asn | Ile | Pro | Ser | Thr | His | Asp | Val | Ile | Arg | Ile |
| | | 115 | | | | | 120 | | | | | 125 | | | |
| Ser | Gln | Cys | Lys | Cys | Thr | Ala | Ser | Asp | Ile | Lys | Arg | Met | Glu | Lys | Ile |
| | 130 | | | | | 135 | | | | | 140 | | | | |
| Ile | Ser | Glu | Lys | Leu | His | Tyr | Glu | Leu | Glu | Ala | Thr | Thr | Ala | Leu | Asn |
| 145 | | | | | 150 | | | | | 155 | | | | | 160 |
| Phe | Leu | His | Leu | Tyr | His | Thr | Ile | Ile | Leu | Cys | His | Thr | Ser | Glu | Arg |
| | | | | 165 | | | | | 170 | | | | | 175 | |
| Lys | Glu | Ile | Leu | Ser | Leu | Asp | Lys | Leu | Glu | Ala | Gln | Leu | Lys | Ala | Cys |
| | | | 180 | | | | | 185 | | | | | 190 | | |
| Asn | Cys | Arg | Leu | Ile | Phe | Ser | Lys | Ala | Lys | Pro | Ser | Val | Leu | Ala | Leu |
| | | 195 | | | | | 200 | | | | | 205 | | | |
| Cys | Leu | Leu | Asn | Leu | Glu | Val | Glu | Thr | Leu | Lys | Ser | Val | Glu | Leu | Leu |
| | 210 | | | | | 215 | | | | | 220 | | | | |
| Glu | Ile | Leu | Leu | Leu | Val | Lys | Lys | His | Ser | Lys | Ile | Asn | Asp | Thr | Glu |
| 225 | | | | | 230 | | | | | 235 | | | | | 240 |

```
    Phe Phe Tyr Trp Arg Glu Leu Val Ser Lys Cys Leu Ala Glu Tyr Ser
                245                 250                 255

Ser Pro Glu Cys Cys Lys Pro Asp Leu Lys Lys Leu Val Trp Ile Val
            260                 265                 270

Ser Arg Arg Thr Ala Gln Asn Leu His Asn Ser Tyr Tyr Ser Val Pro
        275                 280                 285

Glu Leu Pro Thr Ile Pro Glu Gly Gly Cys Phe Asp Glu Ser Glu Ser
        290                 295                 300

Glu Asp Ser Cys Glu Asp Met Ser Cys Gly Glu Glu Ser Leu Ser Ser
    305                 310                 315                 320

Ser Pro Pro Ser Asp Gln Glu Cys Thr Phe Phe Phe Asn Phe Lys Val
                325                 330                 335

Ala Gln Thr Leu Cys Phe Pro Ser
                340

<210> SEQ ID NO 53
<211> LENGTH: 1744
<212> TYPE: DNA
<213> ORGANISM: Homo sapiens

<400> SEQUENCE: 53
gcagcaggcc aagggggagg tgcgagcgtg gacctgggac gggtctgggc ggctctcggt        60
ggttggcacg ggttcgcaca cccattcaag cggcaggacg cacttgtctt agcagttctc       120
gctgaccgcg ctagctgcgg cttctacgct ccggcactct gagttcatca gcaaacgccc       180
tggcgtctgt cctcaccatg cctagccttt gggaccgctt ctcgtcgtcg tccacctcct       240
cttcgccctc gtccttgccc cgaactccca ccccagatcg gccgccgcgc tcagcctggg       300
ggtcggcgac ccgggaggag gggtttgacc gctccacgag cctggagagc tcggactgcg       360
agtccctgga cagcagcaac agtggcttcg gccggagga agacacggct tacctggatg       420
gggtgtcgtt gcccgacttc gagctgctca gtgaccctga ggatgaacac ttgtgtgcca       480
acctgatgca gctgctgcag gagagcctgg cccaggcgcg gctgggctct cgacgccctg       540
cgcgcctgct gatgcctagc cagttggtaa gccaggtggg caaagaacta ctgcgcctgg       600
cctacagcga gccgtgcggc ctgcgggggg cgctgctgga cgtctgcgtg gagcagggca       660
agagctgcca gcgtgggc cagctggcac tcgaccccag cctggtgccc accttccagc       720
tgaccctcgt gctgcgcctg gactcacgac tctggcccaa gatccagggg ctgtttagct       780
ccgccaactc tcccttcctc cctggcttca gccagtccct gacgctgagc actggcttcc       840
gagtcatcaa gaagaagctg tacagctcgg aacagctgct cattgaggag tgttgaactt       900
caacctgagg gggccgacag tgccctccaa gacagacg actgaacttt tggggtggag       960
actagaggca ggagctgagg gactgattcc tgtggttgga aaactgaggc agccacctaa      1020
ggtggaggtg ggggaatagt gtttcccagg aagctcattg agttgtgtgc gggtggctgt      1080
gcattgggga cacatacccc tcagtactgt agcatgaaac aaaggcttag gggccaacaa      1140
ggcttccagc tggatgtgtg tgtagcatgt accttattat ttttgttact gacagttaac      1200
agtggtgtga catccagaga gcagctgggc tgctcccgcc ccagcccggc ccagggtgaa      1260
ggaagaggca cgtgctcctc agagcagccg gagggagggg ggaggtcgga ggtcgtggag      1320
gtggtttgtg tatcttactg gtctgaaggg accaagtgtg tttgttgttt gttttgtatc      1380 ttgttttttct gatcggagca tcactactga cctgttgtag gcagctatct tacagacgca      1440
tgaatgtaag agtaggaagg ggtgggtgtc aggatcact tgggatcttt gacacttgaa       1500
```

```
aaattacacc tggcagctgc gtttaagcct tcccccatcg tgtactgcag agttgagctg   1560
gcaggggagg ggctgagagg gtgggggctg gaacccctcc ccgggaggag tgccatctgg   1620
gtcttccatc tagaactgtt tacatgaaga taagatactc actgttcatg aatacacttg   1680
atgttcaagt attaagacct atgcaatatt ttttactttt ctaataaaca tgtttgttaa   1740
aaca                                                                1744
```

<210> SEQ ID NO 54
<211> LENGTH: 232
<212> TYPE: PRT
<213> ORGANISM: Homo sapiens

<400> SEQUENCE: 54

```
Met Pro Ser Leu Trp Asp Arg Phe Ser Ser Ser Thr Ser Ser Ser
1               5                   10                  15

Pro Ser Ser Leu Pro Arg Thr Pro Thr Pro Asp Arg Pro Arg Ser
                20                  25                  30

Ala Trp Gly Ser Ala Thr Arg Glu Glu Gly Phe Asp Arg Ser Thr Ser
            35                  40                  45

Leu Glu Ser Ser Asp Cys Glu Ser Leu Asp Ser Ser Asn Ser Gly Phe
    50                  55                  60

Gly Pro Glu Glu Asp Thr Ala Tyr Leu Asp Gly Val Ser Leu Pro Asp
65                  70                  75                  80

Phe Glu Leu Leu Ser Asp Pro Glu Asp Glu His Leu Cys Ala Asn Leu
                85                  90                  95

Met Gln Leu Leu Gln Glu Ser Leu Ala Gln Ala Arg Leu Gly Ser Arg
            100                 105                 110

Arg Pro Ala Arg Leu Leu Met Pro Ser Gln Leu Val Ser Gln Val Gly
        115                 120                 125

Lys Glu Leu Leu Arg Leu Ala Tyr Ser Glu Pro Cys Gly Leu Arg Gly
    130                 135                 140

Ala Leu Leu Asp Val Cys Val Glu Gln Gly Lys Ser Cys His Ser Val
145                 150                 155                 160

Gly Gln Leu Ala Leu Asp Pro Ser Leu Val Pro Thr Phe Gln Leu Thr
                165                 170                 175

Leu Val Leu Arg Leu Asp Ser Arg Leu Trp Pro Lys Ile Gln Gly Leu
            180                 185                 190

Phe Ser Ser Ala Asn Ser Pro Phe Leu Pro Gly Phe Ser Gln Ser Leu
        195                 200                 205

Thr Leu Ser Thr Gly Phe Arg Val Ile Lys Lys Leu Tyr Ser Ser
    210                 215                 220

Glu Gln Leu Leu Ile Glu Glu Cys
225                 230
```

<210> SEQ ID NO 55
<211> LENGTH: 2722
<212> TYPE: DNA
<213> ORGANISM: Homo sapiens

<400> SEQUENCE: 55

```
gagtctggcc gcagtcgcgg cagtggtggc ttcccatccc caaaggcgcg cctccgactc     60
cttgcgccgc actgctcgcc gggccagtcc ggaaacgggt cgtggagctc cgcaccactc    120
ccgctggttc ccgaaggcag atcccttctc ccgagagttg cgagaaactt tcccttgtcc    180
ccgacgctgc agcggctcgg gtaccgtggc agccgcaggt ttctgaaccc cgggccacgc    240
```

-continued

```
tccccgcgcc tcggcttcgc gctcgtgtag atcgttccct ctctggttgc acgctgggga    300
tcccggacct cgattctgcg ggcgagatgc ccctgggaca catcatgagg ctggacctgg    360
agaaaattgc cctggagtac atcgtgccct gtctgcacga ggtgggcttc tgctacctgg    420
acaacttcct gggcgaggtg gtgggcgact gcgtcctgga gcgcgtcaag cagctgcact    480
gcaccggggc cctgcgggac ggccagctgg cggggccgcg cgccggcgtc tccaagcgac    540
acctgcgggg cgaccagatc acgtggatcg ggggcaacga ggagggctgc gaggccatca    600
gcttcctcct gtccctcatc gacaggctgg tcctctactg cgggagccgg ctgggcaaat    660
actacgtcaa ggagaggtct aaggcaatgg tggcttgcta ccgggaaat ggaacaggtt    720
atgttcgcca cgtggacaac cccaacggtg atggtcgctg catcacctgc atctactatc    780
tgaacaagaa ttgggatgcc aagctacatg gtgggatcct gcggatattt ccagagggga    840
aatcattcat agcagatgtg gagcccattt ttgacagact cctgttcttc tggtcagatc    900
gtaggaaccc acacgaagtg cagccctctt acgcaaccag atatgctatg actgtctggt    960
actttgatgc tgaagaaagg gcagaagcca aaagaaatt caggaattta actaggaaaa   1020
ctgaatctgc cctcactgaa gactgaccgt gctctgaaat ctgctggcct tgttcatttt   1080
agtaacggtt cctgaattct cttaaattct ttgagatcca agatggcct cttcagtgac   1140
aacaatctcc ctgctacttc ttgcatcctt cacatccctg tcttgtgtgt ggtacttcat   1200
gttttcttgc caagactgtg ttgatcttca gatactctct ttgccagatg aagttacttg   1260
ctaactccag aaattcctgc agacatccta ctcggccagc ggtttacctg atagattcgg   1320
taatactatc aagagaagag cctaggagca cagcgaggga atgaacctta cttgcacttt   1380
atgtatactt cctgatttga aggaggagg tttgaaaaga aaaaaatgga ggtggtagat   1440
gccacagaga ggcatcacgg aagccttaac agcaggaaac agagaaattt gtgtcatctg   1500
aacaatttcc agatgttctt aatccagggc tgttggggtt tctggagaat atcacaacc   1560
taatgacatt aatacctcta gaaagggctg ctgtcatagt gaacaattta taagtgtccc   1620
atggggcaga cactccttt ttcccagtcc tgcaacctgg attttctgcc tcagccccat   1680
tttgctgaaa ataatgactt tctgaataaa gatggcaaca caattttttc tccattttca   1740
gttcttacct gggaacctaa ttccccagaa gctaaaaaac tagacattag ttgttttggt   1800
tgctttgttg gaatgaatt taaatttaaa tgaaaggaaa aatatatccc tggtagtttt   1860
gtgttaacca ctgataactg tggaaagagc taggtctact gatatacaat aaacatgtgt   1920
gcatcttgaa caatttgaga ggggaggtgg agttggaaat gtgggtgttc ctgttttttt   1980
tttttttttt ttttagtttt tccttttaa tgagctcacc ctttaacaca aaaaagcaa   2040
ggtgatgtat tttaaaaag gaagtggaaa taaaaaaatc tcaaagctat ttgagttctc   2100
gtctgtccct agcagtcttt cttcagctca cttggctctc tagatccact gtggttggca   2160
gtatgaccag aatcatggaa tttgctagaa ctgtggaagc ttctactcct gcagtaagca   2220
cagatcgcac tgcctcaata acttggtatt gagcacgtat tttgcaaaag ctacttttcc   2280
tagttttcag tattactttc atgttttaaa aatcccttta atttcttgct tgaaaatccc   2340
atgaacatta aagagccaga aatatttttcc tttgttatgt acggatatat atatatatag   2400
tcttccaaga tagaagttta ctttttcctc ttctggtttt ggaaaatttc cagataagac   2460
atgtcaccat taattctcaa cgactgctct attttgttgt acggtaatag ttatcacctt   2520
ctaaattact atgtaattta ttcacttatt atgtttattg tcttgtatcc tttctctgga   2580
```

```
gtgtaagcac aatgaagaca ggaattttgt atatttttaa ccaatgcaac atactctcag    2640
cacctaaaat agtgccggga acatagtaag ggctcagtaa atacttgttg aataaactca    2700
gtctcctaca ttagcattct aa                                             2722
```

<210> SEQ ID NO 56
<211> LENGTH: 239
<212> TYPE: PRT
<213> ORGANISM: Homo sapiens

<400> SEQUENCE: 56

```
Met Pro Leu Gly His Ile Met Arg Leu Asp Leu Glu Lys Ile Ala Leu
1               5                   10                  15

Glu Tyr Ile Val Pro Cys Leu His Glu Val Gly Phe Cys Tyr Leu Asp
            20                  25                  30

Asn Phe Leu Gly Glu Val Val Gly Asp Cys Val Leu Glu Arg Val Lys
        35                  40                  45

Gln Leu His Cys Thr Gly Ala Leu Arg Asp Gly Gln Leu Ala Gly Pro
    50                  55                  60

Arg Ala Gly Val Ser Lys Arg His Leu Arg Gly Asp Gln Ile Thr Trp
65                  70                  75                  80

Ile Gly Gly Asn Glu Glu Gly Cys Glu Ala Ile Ser Phe Leu Leu Ser
                85                  90                  95

Leu Ile Asp Arg Leu Val Leu Tyr Cys Gly Ser Arg Leu Gly Lys Tyr
            100                 105                 110

Tyr Val Lys Glu Arg Ser Lys Ala Met Val Ala Cys Tyr Pro Gly Asn
        115                 120                 125

Gly Thr Gly Tyr Val Arg His Val Asp Asn Pro Asn Gly Asp Gly Arg
    130                 135                 140

Cys Ile Thr Cys Ile Tyr Tyr Leu Asn Lys Asn Trp Asp Ala Lys Leu
145                 150                 155                 160

His Gly Gly Ile Leu Arg Ile Phe Pro Glu Gly Lys Ser Phe Ile Ala
                165                 170                 175

Asp Val Glu Pro Ile Phe Asp Arg Leu Leu Phe Phe Trp Ser Asp Arg
            180                 185                 190

Arg Asn Pro His Glu Val Gln Pro Ser Tyr Ala Thr Arg Tyr Ala Met
        195                 200                 205

Thr Val Trp Tyr Phe Asp Ala Glu Glu Arg Ala Glu Ala Lys Lys Lys
    210                 215                 220

Phe Arg Asn Leu Thr Arg Lys Thr Glu Ser Ala Leu Thr Glu Asp
225                 230                 235
```

<210> SEQ ID NO 57
<211> LENGTH: 5731
<212> TYPE: DNA
<213> ORGANISM: Homo sapiens

<400> SEQUENCE: 57

```
gcagattgcg cgaggggggag cgagcgagcg ggcgctgcca ggagcccgca gccctggcgc     60
ccgccgccgc ccggagcccc gcaatatgcc gccgcggccc tctggctcta ggccatggcg    120
aggctctgcc ggcgtgtccc ctgcaccctg cttctcggcc tggccgtggt gctgctgaaa    180
gcgcggctgg tccccgcggc cgccagagcg gaactcagcc gctccgacct cagcctcatc    240
caacagcagc agcagcagca gcaacaacaa caacaacagc aaaagcagct ggaggaggct    300
gaggaggaga ggacagaggt gcctggggca acctccacct tgacggttcc agtgtctgta    360
```

-continued

```
tttatgttga aagtccaggt gaatgacatc atcagtcgtc agtacctgag ccaagcagtt    420
gtagaagtgt ttgtaaacta cacgaagaca aattccacag taactaaaag caatggagca    480
gtgctgataa aagtacccta caaattagga cttagtttaa ctattattgc ttacaaagat    540
ggctacgtgt tgacccctct gccttggaaa accagaagaa tgccaatata ttcatcagtt    600
acactttcac tgttcccgca aagccaagca aatatatggc tatttgaaga cactgtttta    660
attactggaa aattagctga tgccaagtct caaccaagtg ttcagttttc aaaagcctta    720
attaaacttc ctgacaacca tcatattagc aacgttactg gctatcttac agttctacaa    780
cagttttga aagtggacaa ttttctgcat acaactggaa ttactctcaa taaaccaggt    840
tttgaaaaca ttgaattgac tcctcttgct gcaatatgtg tgaaaatata ttctggagga    900
aaagaactaa aggtcaatgg ctctattcaa gtttctcttc ctcttctacg tctgaatgat    960
ataagtgcag gggatcgcat acctgcttgg acatttgata tgaacacagg tgcttgggta   1020
aatcatggtc ggggaatggt caaggaacat aacaatcatt taatctggac atatgatgca   1080
ccacatttgg ggtactggat agcagctcca cttccaggaa ctagaggttc aggtataaat   1140
gaagattcca aggacataac tgcctaccac acagtgtttc ttacagccat attaggagga   1200
acaatagtca ttgtcattgg attttttgct gtactacttt gttattgcag ggacaagtgt   1260
ggtactccac agaaaagaga aagaaatatc actaaacttg aggtcctcaa gagagaccag   1320
acaacttcaa caacacacat aaatcatatc agtacagtta aagttgcatt aaaagctgag   1380
gacaagtcgc agttattcaa tgccaaaaac tcctcatata gtcctcagaa aaaggaacca   1440
tcaaaggcag aaacagaaga aagagtttcc atggtaaaaa ctcgggacga ttttaaaatc   1500
tacaatgaag atgtttcatt tctatcagtc aatcaaaata attactcaag aaacccaaca   1560
cagtctttgg agcccaatgt agggtccaaa caacctaaac atattaacaa caatctatct   1620
tcatctctag gtgatgctca agatgaaaag aggtatctca caggtaatga ggaggcgtat   1680
gggcgttccc atattcctga acagcttatg catatttaca gccaacccat tgccatcctt   1740
caaacatctg acctttttctc cacaccggaa caattacata ctgctaagtc agctactttg   1800
ccaagaaagg gacagttagt ctatggccaa ttgatggaac cagtaaatcg agagaacttt   1860
acgcagacct tgcccaaaat gccaattcat tctcatgcac agcccccaga tgccagggaa   1920
gaggatatca tacttgaagg tcaacagagc ctgccatccc aggcttcaga ttggagccga   1980
tactcaagca gcttactgga atccgtctct gttcctggaa cactaaatga ggctgttgta   2040
atgactccat tttcatcgga acttcaagga atttcagaac agaccctcct ggagctgtcc   2100
aaaggaaagc cctccccgca tcccagagcc tggtttgtgt ctcttgatgg aaagccagtt   2160
gcacaagtga ggcactcctt tatagacctg aaaaagggca agagaaccca gagcaatgac   2220
accagtctgg actctggggt ggacatgaat gagcttcact caagtagaaa gctcgagagg   2280
gagaaaacat tcatcaaaag catgcatcag cccaagatcc tttacttaga agatttagac   2340
ctaagcagca gtgagagtgg aaccaccgtc tgttccctg aggacccagc tttaaggcac   2400
atcctagatg gagggagtgg agtgatcatg gagcaccctg agaagagtc gccaggaagg   2460
aaaagcactg ttgaagattt tgaagctaat acatcccca ctaaaagaag gggcagacca   2520
ccactagcca aaagagatag caagactaac atctggaaga gcgagagga acgcccactg   2580
attcccataa attaactcca atggggattg tgtgtctgct gtctcgtgct gtttattctt   2640
gcttcttgtt gtaaattgca gtacgaactt aagaaaatga gactgagcaa tctcatggtt   2700
cttggacatg tctcaagcag agtaaatggt aattcagtaa tcagagagaa agataccaag   2760
```

```
gaatgctttt tctggcctat tcatttattt ttgggtgatg aatttacagt atctaagttt   2820
tcaaaatgta aaatagcttc aagatgttag ttatctgaaa atgttgctca gccagccagt   2880
ttggccttga ctctcttaag aataacagtg aaatatatac tcctcaagtt gcctccaaaa   2940
atgttgcctc taccatggtg actacccat ggaacattta gaaacaaaac tgacttcagg    3000
catcatatta ttttaaatgt tactattacg tcttcttctg cctatactta aaaataactt   3060
gataaatgac ttggactgat gttactctgg agttatcaca agaaaatgt tgtttggtct    3120 ttaaagagca tgtgtattgt atcatcccaa acgtaaatcc tacatttata taagatgggc   3180
aagaagctac ttggtcatta gagagggaga caccagctct ttggttgttt ttggatataa   3240
ctttacaaaa taagtaagat gttaatttag aaatttgaga aattaatgct ctaatactga   3300
gtttttattt aaaaattatt ttttcttccc ctcaacaatg aagcaagctt agctgtcaag   3360
ggaaactttt tacaaatctg aaaaaaacaa tctatgactt tggtttaagg ctcactgata   3420
cttttaggct aaattggttt taatatattt cttctattct aaaaacctga actcagtcac   3480
ttaaaggcta tgaaatttaa aaaaaagtc gatgtgaaag tttcttttga acactaaaat    3540
aaaatatgtg cagataaaat atacattgat ttgttttct taaatgttga tgagaagaaa    3600
aagagatgcc attttcctga ggctcaaaaa taccttcagg atagttgtat atccagttat   3660
tgattttctt aaaagatgtg taaggaaaac agtttcaatt tcaggggaaa agtaaaagtt   3720
tttccctaag tcacttaaag cctttgcaac ttctttttc agttttgtaa gtaatatatc    3780
tatgttcttt tcattatagc aagcattcaa tgtgaacaac ttttaatta actctgaatt    3840 accattcata catcctaaaa ataaaagctc gttattcatt aaaatcaact gatcccattt   3900
ttcttaaaat ttccctgaag gcaaatgtct gaagcaccttt tcccttgtgg gggtaaaaat  3960
cctaaattgc tttattttc attccctcct attcaacatg ggagcagcat agagacccaa    4020
accatgtaaa caagttcagt gaaccaaaac agccacatta gcttcagtaa aattatagct   4080
agatgtgcaa tttttcctc caacttctaa cgtgtcaaat aaccttccta ctgttctgtg    4140
ttaactgaaa gaacataaag accctaggca aatatttgct atatattacc ccaatccata   4200
gaagaaataa tgttttgggt aatacctagg cttccttttt ttttttttt ttttttttt    4260 agtgataagg ctcataacaa ttaattagag aaggcttctt attggtctta cacagaaaga   4320
tacatcaaaa gcagcatgac tcaaaatgat ttggaaaagg ttaaagttag tgctctgctg   4380
aagtgccttt gatatagact tgcattatta gaaggatata acatctttt taagtgtgca    4440 ttttctttca gttaaccaaa ttaaacagat gtgcagtttt attaaaaata tagacctagt   4500
gtttcatgtt ggaacaataa atattgcatg tgagtagtat ttcttgtttt ttgaatacag   4560
tatatattga taaattgttt atgttggaat gaagttagaa actatatagc aaaacattat   4620
attttaagtg tttatttttc ccacctttaa ataaaaatgt ttcatctcag cttggtaatg   4680
aaatacacat attggtataa gggtatacca ttcaggtatg ccacttattt tattcatttt   4740
tgtgtaaggg aaatgagatg atgtatccca agggcttttc tagaactact tgtttgcttt   4800
cagaataaaa ccttattatt ttttacactg cacatgctgt tctcaattgg taattatagg   4860
caatttatct tttctaatga tcaaaagagt gtgacttctc atttgtgagt agttcacaaa   4920
tttcctgtta aaaagctgaa accatctact ttttcttaac ccaagtgata ataaacaata   4980
ttcacaactt tcttaaattt ttaaattgaa accaaggtt ttttcaaata taaacctaga    5040
tgattttggt cacaaattgt taacatttgt cgatcctttg tatatacttt ggatatatat   5100
```

```
taaaggcaaa actatctctt gactaactga tggattcatt tactaaagca cagctgtatg   5160
tatttttgaa tacatattat gatcttgaga ctttataaat caatttttat gactttatgc   5220
agttgtatag ggattatgcc ctttcagttc tatagggatt atgccctttt ataatacata   5280 ataccaca gagattacaa atgttgagga atgaaagcac ttctttgctt tggcaatcat     5340
tttcagacca ctatgtgttt gaatcctctg gtatcaatac gtattatagg gttttagaga   5400
tctgtgggtc aaatgatgtc cctcaaaact tcctaaaaag gtgaagctca aagtcacaca   5460
ttcttataag gcgcatgagt ttctcatttt cccatgtacg agcattgtaa aggaattcag   5520
ctgtattaat ttctatttca gatctagaat tgacattttg ccttcttgtt tccaggtgtt   5580 tctattttt gtattctttc agagaaatct catatttcgg tgtatttatt gctgttacta   5640
ctatatttac tgctgaaaac tgtaacaacc tgaagatttg taaaatgtta aacatagttc   5700
attaaaaata taaaataaa tctaaaatgt a                                   5731
```

<210> SEQ ID NO 58
<211> LENGTH: 826
<212> TYPE: PRT
<213> ORGANISM: Homo sapiens

<400> SEQUENCE: 58

```
Met Ala Arg Leu Cys Arg Arg Val Pro Cys Thr Leu Leu Gly Leu
1               5                   10                  15

Ala Val Val Leu Lys Ala Arg Leu Val Pro Ala Ala Ala Arg Ala
                20                  25                  30

Glu Leu Ser Arg Ser Asp Leu Ser Leu Ile Gln Gln Gln Gln Gln
            35                  40                  45

Gln Gln Gln Gln Gln Gln Gln Lys Gln Leu Glu Glu Ala Glu Glu
        50                  55                  60

Glu Arg Thr Glu Val Pro Gly Ala Thr Ser Thr Leu Thr Val Pro Val
65                  70                  75                  80

Ser Val Phe Met Leu Lys Val Gln Val Asn Asp Ile Ile Ser Arg Gln
                85                  90                  95

Tyr Leu Ser Gln Ala Val Val Glu Val Phe Val Asn Tyr Thr Lys Thr
            100                 105                 110

Asn Ser Thr Val Thr Lys Ser Asn Gly Ala Val Leu Ile Lys Val Pro
        115                 120                 125

Tyr Lys Leu Gly Leu Ser Leu Thr Ile Ile Ala Tyr Lys Asp Gly Tyr
    130                 135                 140

Val Leu Thr Pro Leu Pro Trp Lys Thr Arg Arg Met Pro Ile Tyr Ser
145                 150                 155                 160

Ser Val Thr Leu Ser Leu Phe Pro Gln Ser Gln Ala Asn Ile Trp Leu
                165                 170                 175

Phe Glu Asp Thr Val Leu Ile Thr Gly Lys Leu Ala Asp Ala Lys Ser
            180                 185                 190

Gln Pro Ser Val Gln Phe Ser Lys Ala Leu Ile Lys Leu Pro Asp Asn
        195                 200                 205

His His Ile Ser Asn Val Thr Gly Tyr Leu Thr Val Leu Gln Gln Phe
    210                 215                 220

Leu Lys Val Asp Asn Phe Leu His Thr Thr Gly Ile Thr Leu Asn Lys
225                 230                 235                 240

Pro Gly Phe Glu Asn Ile Glu Leu Thr Pro Leu Ala Ala Ile Cys Val
                245                 250                 255

Lys Ile Tyr Ser Gly Gly Lys Glu Leu Lys Val Asn Gly Ser Ile Gln
```

-continued

```
                260                 265                 270
Val Ser Leu Pro Leu Arg Leu Asn Asp Ile Ser Ala Gly Asp Arg
        275                 280                 285
Ile Pro Ala Trp Thr Phe Asp Met Asn Thr Gly Ala Trp Val Asn His
        290                 295                 300
Gly Arg Gly Met Val Lys Glu His Asn Asn His Leu Ile Trp Thr Tyr
305                 310                 315                 320
Asp Ala Pro His Leu Gly Tyr Trp Ile Ala Ala Pro Leu Pro Gly Thr
                325                 330                 335
Arg Gly Ser Gly Ile Asn Glu Asp Ser Lys Asp Ile Thr Ala Tyr His
                340                 345                 350
Thr Val Phe Leu Thr Ala Ile Leu Gly Gly Thr Ile Val Ile
                355                 360                 365
Gly Phe Phe Ala Val Leu Leu Cys Tyr Cys Arg Asp Lys Cys Gly Thr
        370                 375                 380
Pro Gln Lys Arg Glu Arg Asn Ile Thr Lys Leu Glu Val Leu Lys Arg
385                 390                 395                 400
Asp Gln Thr Thr Ser Thr Thr His Ile Asn His Ile Ser Thr Val Lys
                405                 410                 415
Val Ala Leu Lys Ala Glu Asp Lys Ser Gln Leu Phe Asn Ala Lys Asn
                420                 425                 430
Ser Ser Tyr Ser Pro Gln Lys Lys Glu Pro Ser Lys Ala Glu Thr Glu
        435                 440                 445
Glu Arg Val Ser Met Val Lys Thr Arg Asp Asp Phe Lys Ile Tyr Asn
        450                 455                 460
Glu Asp Val Ser Phe Leu Ser Val Asn Gln Asn Asn Tyr Ser Arg Asn
465                 470                 475                 480
Pro Thr Gln Ser Leu Glu Pro Asn Val Gly Ser Lys Gln Pro Lys His
                485                 490                 495
Ile Asn Asn Asn Leu Ser Ser Ser Leu Gly Asp Ala Gln Asp Glu Lys
                500                 505                 510
Arg Tyr Leu Thr Gly Asn Glu Glu Ala Tyr Gly Arg Ser His Ile Pro
        515                 520                 525
Glu Gln Leu Met His Ile Tyr Ser Gln Pro Ile Ala Ile Leu Gln Thr
        530                 535                 540
Ser Asp Leu Phe Ser Thr Pro Glu Gln Leu His Thr Ala Lys Ser Ala
545                 550                 555                 560
Thr Leu Pro Arg Lys Gly Gln Leu Val Tyr Gly Gln Leu Met Glu Pro
                565                 570                 575
Val Asn Arg Glu Asn Phe Thr Gln Thr Leu Pro Lys Met Pro Ile His
                580                 585                 590
Ser His Ala Gln Pro Pro Asp Ala Arg Glu Glu Asp Ile Ile Leu Glu
                595                 600                 605
Gly Gln Gln Ser Leu Pro Ser Gln Ala Ser Asp Trp Ser Arg Tyr Ser
        610                 615                 620
Ser Ser Leu Leu Glu Ser Val Ser Val Pro Gly Thr Leu Asn Glu Ala
625                 630                 635                 640
Val Val Met Thr Pro Phe Ser Ser Glu Leu Gln Gly Ile Ser Glu Gln
                645                 650                 655
Thr Leu Leu Glu Leu Ser Lys Gly Lys Pro Ser Pro His Pro Arg Ala
                660                 665                 670
Trp Phe Val Ser Leu Asp Gly Lys Pro Val Ala Gln Val Arg His Ser
                675                 680                 685
```

```
Phe Ile Asp Leu Lys Lys Gly Lys Arg Thr Gln Ser Asn Asp Thr Ser
    690                 695                 700
Leu Asp Ser Gly Val Asp Met Asn Glu Leu His Ser Ser Arg Lys Leu
705                 710                 715                 720
Glu Arg Glu Lys Thr Phe Ile Lys Ser Met His Gln Pro Lys Ile Leu
                725                 730                 735
Tyr Leu Glu Asp Leu Asp Leu Ser Ser Ser Glu Ser Gly Thr Thr Val
            740                 745                 750
Cys Ser Pro Glu Asp Pro Ala Leu Arg His Ile Leu Asp Gly Gly Ser
        755                 760                 765
Gly Val Ile Met Glu His Pro Gly Glu Glu Ser Pro Gly Arg Lys Ser
    770                 775                 780
Thr Val Glu Asp Phe Glu Ala Asn Thr Ser Pro Thr Lys Arg Arg Gly
785                 790                 795                 800
Arg Pro Pro Leu Ala Lys Arg Asp Ser Lys Thr Asn Ile Trp Lys Lys
                805                 810                 815
Arg Glu Glu Arg Pro Leu Ile Pro Ile Asn
            820                 825

<210> SEQ ID NO 59
<211> LENGTH: 7368
<212> TYPE: DNA
<213> ORGANISM: Homo sapiens

<400> SEQUENCE: 59
```

| | | | | | |
|---|---|---|---|---|---|
| gctgtacttt | tctgggtgtg | tgttagggag | gctatgttcc | tgaccctccc | cctctggggt | 60 |
| gagaagggt | ccccgccatg | tcctcggggt | tggtaggagg | agaggattgg | agctgttttc | 120 |
| tccttgatgc | caagatacgc | caagctagga | gcattctgcc | ctttccacag | tcatccaccg | 180 |
| agaacaggcc | tgcaggacgg | gacaaggatc | agagccttcc | tgcaaccccg | gccactgcct | 240 |
| gctgtctgtg | ggcctggact | gtgcgggcaa | ctgtgcttgg | cccgagtgac | aaggaggtgg | 300 |
| gagagggtag | cagcatgggc | tacgcggttg | gctgccctca | gtcccctgc | tgctgaagct | 360 |
| gccctgccca | tgcccaccca | ggccgtgggg | ccaggggcct | gccagggcta | ggagtgggcc | 420 |
| tgccgttcat | gggtctctag | ggatttccga | gatgcctggg | aagagaggct | tgggctggtg | 480 |
| gtgggcccgg | ctgcccctt | gcctgctcct | cagcctttac | ggcccctgga | tgccttcctc | 540 |
| cctgggaaag | cccaaaggcc | accctcacat | gaattccatc | cgcatagatg | gggacatcac | 600 |
| actgggaggc | ctgttcccgg | tgcatggccg | gggctcagag | ggcaagccct | gtggagaact | 660 |
| taagaaggaa | aagggcatcc | accggctgga | ggccatgctg | ttcgccctgg | atcgcatcaa | 720 |
| caacgacccg | gacctgctgc | ctaacatcac | gctgggcgcc | cgcattctgg | acacctgctc | 780 |
| cagggacacc | catgccctcg | agcagtcgct | gacctttgtg | caggcgctca | tcgagaagga | 840 |
| tggcacagag | gtccgctgtg | gcagtggcgg | cccaccatc | atcaccaagc | tgaacgtgt | 900 |
| ggtgggtgtc | atcggtgctt | cagggagctc | ggtctccatc | atggtggcca | acatccttcg | 960 |
| cctcttcaag | ataccccaga | tcagctacgc | ctccacagcg | ccagacctga | gtgacaacag | 1020 |
| ccgctacgac | ttcttctccc | gcgtggtgcc | ctcggacacg | taccaggccc | aggccatggt | 1080 |
| ggacatcgtc | cgtgccctca | gtggaactac | tgtgtccaca | gtggcctcgg | agggcagcta | 1140 |
| tggtgagagc | ggtgtggagg | ccttcatcca | gaagtcccgt | gaggacgggg | gcgtgtgcat | 1200 |
| cgcccagtcg | gtgaagatac | cacgggagcc | caaggcaggc | gagttcgaca | agatcatccg | 1260 |
| ccgcctcctg | gagacttcga | acgccagggc | agtcatcatc | tttgccaacg | aggatgacat | 1320 |

-continued

```
caggcgtgtg ctggaggcag cacgaagggc caaccagaca ggccatttct tctggatggg      1380
ctctgacagc tggggctcca agattgcacc tgtgctgcac ctggaggagg tggctgaggg      1440
tgctgtcacg atcctcccca agaggatgtc cgtacgaggc ttcgaccgct acttctccag      1500
ccgcacgctg gacaacaacc ggcgcaacat ctggtttgcc gagttctggg aggacaactt      1560
ccactgcaag ctgagccgcc acgccctcaa gagggcagc cacgtcaaga agtgcaccaa       1620
ccgtgagcga attgggcagg attcagctta tgagcaggag gggaaggtgc agtttgtgat      1680
cgatgccgtg tacgccatgg ccacgcgct gcacgccatg caccgtgacc tgtgtcccgg       1740
ccgcgtgggg ctctgcccgc gcatggaccc tgtagatggc acccagctgc ttaagtacat      1800
ccgaaacgtc aacttctcag gcatcgcagg gaaccctgtg accttcaatg agaatggaga      1860
tgcgcctggg cgctatgaca tctaccaata ccagctgcgc aacgattctg ccagtacaa       1920 ggtcattggc tcctggactg accacctgca ccttagaata gagcggatgc actggccggg     1980
gagcgggcag cagctgcccc gctccatctg cagcctgccc tgccaaccgg gtgagcggaa     2040
gaagacagtg aagggcatgc cttgctgctg gcactgcgag ccttgcacag gtaccagta     2100 ccaggtggac cgctacacct gtaagacgtg tccctatgac atgcggccca cagagaaccg     2160
cacgggctgc cggcccatcc ccatcatcaa gcttgagtgg ggctcgccct gggccgtgct     2220 gccctcttc ctggccgtgg tgggcatcgc tgccacgttg ttcgtggtga tcaccttttgt      2280 gcgctacaac gacacgccca tcgtcaaggc ctcgggccgt gaactgagct acgtgctgct     2340
ggcaggcatc ttcctgtgct atgccaccac cttcctcatg atcgctgagc ccgaccttgg     2400
cacctgctcg ctgcgccgaa tcttcctggg actagggatg agcatcagct atgcagccct     2460
gctcaccaag accaaccgca tctaccgcat cttcgagcag ggcaagcgct cggtcagtgc     2520
cccacgcttc atcagccccg cctcacagct ggccatcacc ttcagcctca tctcgctgca     2580
gctgctgggc atctgtgtgt ggtttgtggt ggacccctcc cactcggtgg tggacttcca      2640
ggaccagcgg acactcgacc cccgcttcgc caggggtgtg ctcaagtgtg acatctcgga     2700
cctgtcgctc atctgcctgc tgggctacag catgctgctc atggtcacgt gcaccgtgta     2760
tgccatcaag acacgcggcg tgcccgagac cttcaatgag gccaagccca ttggcttcac     2820
catgtacacc acttgcatcg tctggctggc cttcatcccc atcttctttg gcacctcgca     2880
gtcggccgac aagctgtaca tccagacgac gacgctgacg gtctcggtga gtctgagcgc     2940
ctcggtgtcc ctgggaatgc tctacatgcc caaagtctac atcatcctct ccacccgga      3000 gcagaacgtg cccaagcgca agcgcagcct caaagccgtc gttacggcgg ccaccatgtc     3060
caacaagttc acgcagaagg gcaacttccg gcccaacgga gaggccaagt ctgagctctg     3120
cgagaacctt gaggccccag cgctggccac caaacagact tacgtcactt acaccaacca     3180
tgcaatctag cgagtccatg gagctgagca gcaggaggag gagccgtgac cctgtggaag     3240
gtgcgtcggg ccagggccac acccaagggc ccagctgtct tgcctgcccg tgggcaccca     3300
cggacgtggc ttggtgctga ggatagcaga gcccccagcc atcactgctg gcagcctggg     3360
caaaccgggt gagcaacagg aggacgaggg gccggggcgg tgccaggcta ccacaagaac     3420
ctgcgtcttg gaccattgcc cctcccgccc ccaaaccaca ggggctcagg tcgtgtgggc     3480
cccagtgcta gatctctccc tcccttcgtc tctgtctgtg ctgttggcga ccctctgtc     3540 tgtctccagc cctgtctttc tgttctctta tctctttgtt tcacctttttc cctctctggc    3600 gtccccggct gcttgtactc ttggcctttt ctgtgtctcc tttctggctc ttgcctccgc     3660
```

```
ctctctctct catcctcttt gtcctcagct cctcctgctt tcttgggtcc caccagtgtc    3720
acttttctgc cgttttcttt cctgttctcc tctgcttcat tctcgtccag ccattgctcc    3780
cctctccctg ccacccttcc ccagttcacc aaaccttaca tgttgcaaaa gagaaaaaag    3840 gaaaaaaat caaacacaa aaaagccaaa acgaaaacaa atctcgagtg tgttgccaag      3900
tgctgcgtcc tcctggtggc ctctgtgtgt gtccctgtgg cccgcagcct gcccgcctgc    3960
cccgcccatc tgccgtgtgt cttgcccgcc tgccccgccc gtctgccgtc tgtcttgccc    4020
gcctgcccgc ctgcccctcc tgccgaccac acggagttca gtgcctgggt gtttggtgat    4080
ggttattgac gacaatgtgt agcgcatgat tgttttttata ccaagaacat ttctaataaa    4140
aataaacaca tggttttgca cccgggctcc acatccactg agggtcctgc catgggacca    4200
caggctcagc ctgcagctgg agggcttaga cctagaggga agcgggaact gggctctgga    4260
gacccagggc ttgggggctg tggagactgc tccctaggct gggatctagt gtggtgtggt    4320
gaggccttgg gcatgagggg gccagattcc caggtaaggg gcaggacat tgcaggaaat     4380 tccaggaatc agcacctagt agtcccctaa ttaggggta tgctctgtcc cctgccctgc     4440
agccctggga gggtaacatt tctgccttgc ctgtcctctg tctcacaccc ctcacacctg    4500
ggactgccct tccaccctg cccccataac ctgtgcctct ctccttccag ccaggaagtc     4560
ctcttcttga aagttagct tcccgggctg ccagcactca tagccgtccc ctcctgcttg     4620
tgttggctcc aggctcgggt gctaagaaga tgtgtgtctg tcctggagat cagtgtgttg    4680
ttatgtgtcc acgtgggccc acaagtgcac ggcacaggca tggccgtgtg gctgtgttgg    4740
ctgtgttggc tgtgtgtctg tgtgcacgtc cagcgcctcc atgcgcatgc gtgcctgtct    4800
tgtttgcgtg tctgatcatc tgtttgggcc ccggtggctc atgcagatgc ctgtctcagg    4860
cccatggcga gtgttcacct cagctggctt ccctggcagg ttgggaggtg ggaaacagga    4920
gcgcttaggg gctgggctct ggctggggta aattatagag ccagaaacac aatgaggcca    4980
taggcagcag ctggagcctg ggctgcctgt gccgtcccct cctgccctgc ccctgggtcc    5040
tgcaccccct cccacctcca ggctagctga cagcgctatg gagcacagtg aagggactg     5100 gaggaacct aggcaggggg ccacgcaggg acagagtatg agagtgtgtg tataactgag     5160
gctgggacat tgaatcatgc caggtatgtc ttctccatca gcccactctt actcctggcc    5220
tgggcatctc acacatctgt gcataggaaa tctcttcttc cctggggtct gtgtgcagca    5280
cctagtagat gctcaataaa tgtttgtgtg agggaaggag acaggaaagg aagtgtctcg    5340
ctgatcatct tgcggaatgg ttcctaagac ctctgcccag gaaagattcc acccagtgct    5400
ccagcccggt caggcagaac taggttgcca gatcaagggt atctcccaaa agcttccagg    5460
gcagttgggg gtgggggggt gggggtagg gatgggaat gcagaagcgg gtgcagccag      5520
ctctccccca gggtgactct ggcagcaccc ccatcctggg caccctgcct gctctgtggc    5580
tcacgcccct cctgaagtga ctgatgctct gaggcccaag gctaggtcca gggcagggcc    5640 tgcagggtt tcatgctcag tccaggactt gcctaggtcc cctacatct gtggggcccc      5700 catctaggtt ctaacaggag aatcacctct ccaagggga tgctgcccct cggctcccct    5760
tggctctcag gaggggccct cagggactac cagtcccctg ccagtgggaa gaaatagccc    5820
tgccctcagg gagcttccag tgtgatgggg gagatacagc agactgtgtc ccaaagtaaa    5880
atgactgtta gaatgaggtg ggtggaggag ggaagccttg ggtgggtgtg actttgggca    5940
tctgagcctg gggtgcagag gtgggctctg tgggcctgag gtggacagga gggaaccagg    6000
ccctagcaag acttttgcca gctagacctg ctgcagcagt tgggagggtg ggtgctgctg    6060
```

```
gagtcctggg tccatcacct agaaggctca ggccagtgca gccagggctg gggcccacag    6120
ctggcctggg tgggacctgc cctgatgccc atgcaggag ggacgcctgg cccttcacaa     6180
ttggcttggc tgctcacctt tgctctcatc ctcaattatt aatgactgga gaaagctgct    6240
aagtatcttc agaatgttag atttcaacaa gatggggggt tcagggtccc tggcaccctg    6300
gatagggagc cagcggcccc tagagacctt tgctgtgtgc aggggggtatg tgctcacccc   6360 cgtggcctca gcctcctcaa tgtctgaatg aaggattggg ctagcagaca tcccacccca   6420
cagcacactt tctaaccagc aggggaactt ctagacaata gagacgctgg gctccctcca   6480
gaacactgga cctgaacttc tggggggagg gctgggcacg ggcatatttt aaaagctccc   6540
cagcagatgg gccgtgcagt caagtgggcc aagagtggca ccagactttg gggcttgtga   6600
agtcaggagg gagcaacagt gcccactcga gcttgcctgg ggctcaagcc caaggctggg   6660
ctgctgccag cctgagcaga cacccaggag cttccaggcc agctggatgc acagggcacc   6720
tttgtggaac tcctaggacc ctggggagac ccacctcagg agcagagtct caggtccctt   6780
ccggctctga ggggctgttc tgagctctaa tgtcttatgg tctgcccctc ccatccttac   6840
ttctcaggcc ctggaggcag aggcatagag ccagcagga cagaggtctc agtgggccac    6900
atgccagctg cccccacact gcctcagcct ccaggcctcc aaggggtcct ggggagcccc   6960
tgagaagatg ctgagcctgc ataaggctgg gcgcccctct ttctgacacc ctcactggct   7020
ccacggctcc cccttcccat cccaggtttc catctgccca ctgaacaggg aggggaaact   7080
gaggcactcc cctggcactg agggctcctt ctgtcatcct gcctgccctg gatggtcctg   7140
gctgcccctc agggcttggc cctggcactg tgagcctcac agggctcaga cccccacccc   7200
caacccagca ctaaatggca ctcggcacca gaatctcact tcagttggca aaagcagcaa   7260
ttagcatgta atgaggcttc ttgctttatt tttaggtaac ctccaaggcc ctgcctgtgt   7320
aattcagccc gccattgctc ggtggataat taaagcatgt caccataa                7368
```

<210> SEQ ID NO 60
<211> LENGTH: 912
<212> TYPE: PRT
<213> ORGANISM: Homo sapiens

<400> SEQUENCE: 60

```
Met Pro Gly Lys Arg Gly Leu Gly Trp Trp Ala Arg Leu Pro Leu
1               5                   10                  15

Cys Leu Leu Leu Ser Leu Tyr Gly Pro Trp Met Pro Ser Ser Leu Gly
            20                  25                  30

Lys Pro Lys Gly His Pro His Met Asn Ser Ile Arg Ile Asp Gly Asp
        35                  40                  45

Ile Thr Leu Gly Gly Leu Phe Pro Val His Gly Arg Gly Ser Glu Gly
    50                  55                  60

Lys Pro Cys Gly Glu Leu Lys Lys Glu Lys Gly Ile His Arg Leu Glu
65                  70                  75                  80

Ala Met Leu Phe Ala Leu Asp Arg Ile Asn Asn Asp Pro Asp Leu Leu
                85                  90                  95

Pro Asn Ile Thr Leu Gly Ala Arg Ile Leu Asp Thr Cys Ser Arg Asp
            100                 105                 110

Thr His Ala Leu Glu Gln Ser Leu Thr Phe Val Gln Ala Leu Ile Glu
        115                 120                 125

Lys Asp Gly Thr Glu Val Arg Cys Gly Ser Gly Gly Pro Pro Ile Ile
    130                 135                 140
```

-continued

```
Thr Lys Pro Glu Arg Val Val Gly Val Ile Gly Ala Ser Gly Ser Ser
145                 150                 155                 160

Val Ser Ile Met Val Ala Asn Ile Leu Arg Leu Phe Lys Ile Pro Gln
                165                 170                 175

Ile Ser Tyr Ala Ser Thr Ala Pro Asp Leu Ser Asp Asn Ser Arg Tyr
            180                 185                 190

Asp Phe Phe Ser Arg Val Val Pro Ser Asp Thr Tyr Gln Ala Gln Ala
        195                 200                 205

Met Val Asp Ile Val Arg Ala Leu Lys Trp Asn Tyr Val Ser Thr Val
    210                 215                 220

Ala Ser Glu Gly Ser Tyr Gly Glu Ser Gly Val Glu Ala Phe Ile Gln
225                 230                 235                 240

Lys Ser Arg Glu Asp Gly Gly Val Cys Ile Ala Gln Ser Val Lys Ile
                245                 250                 255

Pro Arg Glu Pro Lys Ala Gly Glu Phe Asp Lys Ile Ile Arg Arg Leu
                260                 265                 270

Leu Glu Thr Ser Asn Ala Arg Ala Val Ile Ile Phe Ala Asn Glu Asp
        275                 280                 285

Asp Ile Arg Arg Val Leu Glu Ala Ala Arg Arg Ala Asn Gln Thr Gly
    290                 295                 300

His Phe Phe Trp Met Gly Ser Asp Ser Trp Gly Ser Lys Ile Ala Pro
305                 310                 315                 320

Val Leu His Leu Glu Glu Val Ala Glu Gly Ala Val Thr Ile Leu Pro
                325                 330                 335

Lys Arg Met Ser Val Arg Gly Phe Asp Arg Tyr Phe Ser Ser Arg Thr
                340                 345                 350

Leu Asp Asn Asn Arg Arg Asn Ile Trp Phe Ala Glu Phe Trp Glu Asp
        355                 360                 365

Asn Phe His Cys Lys Leu Ser Arg His Ala Leu Lys Lys Gly Ser His
    370                 375                 380

Val Lys Lys Cys Thr Asn Arg Glu Arg Ile Gly Gln Asp Ser Ala Tyr
385                 390                 395                 400

Glu Gln Glu Gly Lys Val Gln Phe Val Ile Asp Ala Val Tyr Ala Met
                405                 410                 415

Gly His Ala Leu His Ala Met His Arg Asp Leu Cys Pro Gly Arg Val
                420                 425                 430

Gly Leu Cys Pro Arg Met Asp Pro Val Asp Gly Thr Gln Leu Leu Lys
        435                 440                 445

Tyr Ile Arg Asn Val Asn Phe Ser Gly Ile Ala Gly Asn Pro Val Thr
    450                 455                 460

Phe Asn Glu Asn Gly Asp Ala Pro Gly Arg Tyr Asp Ile Tyr Gln Tyr
465                 470                 475                 480

Gln Leu Arg Asn Asp Ser Ala Glu Tyr Lys Val Ile Gly Ser Trp Thr
                485                 490                 495

Asp His Leu His Leu Arg Ile Glu Arg Met His Trp Pro Gly Ser Gly
                500                 505                 510

Gln Gln Leu Pro Arg Ser Ile Cys Ser Leu Pro Cys Gln Pro Gly Glu
        515                 520                 525

Arg Lys Lys Thr Val Lys Gly Met Pro Cys Cys Trp His Cys Glu Pro
    530                 535                 540

Cys Thr Gly Tyr Gln Tyr Gln Val Asp Arg Tyr Thr Cys Lys Thr Cys
545                 550                 555                 560
```

| | | | | | | | | | | | |
|---|---|---|---|---|---|---|---|---|---|---|---|
| Pro | Tyr | Asp | Met | Arg | Pro | Thr | Glu | Asn | Arg | Thr | Gly | Cys | Arg | Pro | Ile |
| | | | | 565 | | | | | 570 | | | | | 575 | |

Pro Tyr Asp Met Arg Pro Thr Glu Asn Arg Thr Gly Cys Arg Pro Ile
            565                 570                 575

Pro Ile Ile Lys Leu Glu Trp Gly Ser Pro Trp Ala Val Leu Pro Leu
            580                 585                 590

Phe Leu Ala Val Val Gly Ile Ala Ala Thr Leu Phe Val Val Ile Thr
            595                 600                 605

Phe Val Arg Tyr Asn Asp Thr Pro Ile Val Lys Ala Ser Gly Arg Glu
        610                 615                 620

Leu Ser Tyr Val Leu Leu Ala Gly Ile Phe Leu Cys Tyr Ala Thr Thr
625                 630                 635                 640

Phe Leu Met Ile Ala Glu Pro Asp Leu Gly Thr Cys Ser Leu Arg Arg
            645                 650                 655

Ile Phe Leu Gly Leu Gly Met Ser Ile Ser Tyr Ala Ala Leu Leu Thr
            660                 665                 670

Lys Thr Asn Arg Ile Tyr Arg Ile Phe Glu Gln Gly Lys Arg Ser Val
            675                 680                 685

Ser Ala Pro Arg Phe Ile Ser Pro Ala Ser Gln Leu Ala Ile Thr Phe
            690                 695                 700

Ser Leu Ile Ser Leu Gln Leu Leu Gly Ile Cys Val Trp Phe Val Val
705                 710                 715                 720

Asp Pro Ser His Ser Val Val Asp Phe Gln Asp Gln Arg Thr Leu Asp
            725                 730                 735

Pro Arg Phe Ala Arg Gly Val Leu Lys Cys Asp Ile Ser Asp Leu Ser
            740                 745                 750

Leu Ile Cys Leu Leu Gly Tyr Ser Met Leu Leu Met Val Thr Cys Thr
            755                 760                 765

Val Tyr Ala Ile Lys Thr Arg Gly Val Pro Glu Thr Phe Asn Glu Ala
770                 775                 780

Lys Pro Ile Gly Phe Thr Met Tyr Thr Thr Cys Ile Val Trp Leu Ala
785                 790                 795                 800

Phe Ile Pro Ile Phe Phe Gly Thr Ser Gln Ser Ala Asp Lys Leu Tyr
            805                 810                 815

Ile Gln Thr Thr Thr Leu Thr Val Ser Val Ser Leu Ser Ala Ser Val
            820                 825                 830

Ser Leu Gly Met Leu Tyr Met Pro Lys Val Tyr Ile Ile Leu Phe His
            835                 840                 845

Pro Glu Gln Asn Val Pro Lys Arg Lys Arg Ser Leu Lys Ala Val Val
            850                 855                 860

Thr Ala Ala Thr Met Ser Asn Lys Phe Thr Gln Lys Gly Asn Phe Arg
865                 870                 875                 880

Pro Asn Gly Glu Ala Lys Ser Glu Leu Cys Glu Asn Leu Glu Ala Pro
            885                 890                 895

Ala Leu Ala Thr Lys Gln Thr Tyr Val Thr Tyr Thr Asn His Ala Ile
            900                 905                 910

<210> SEQ ID NO 61
<211> LENGTH: 4959
<212> TYPE: DNA
<213> ORGANISM: Homo sapiens

<400> SEQUENCE: 61
acttgtatct tttcatatca aaaatgggag gtgacaccca gtttaaggaa aattccaagg     60
catttgtctc gactaatgtg aaagatgatt acagtggcca gaggactgcc aaggctcctt    120
ctcaagctgc ttgagtcaat gagggtagac gcaccctctg aagatggtga ctccctcctg    180

```
agaagctgga ccccttggta aaagacaagg ccttctccaa gaagaatatg aaagtgttac      240
tcagacttat ttgtttcata gctctactga tttcttctct ggaggctgat aaatgcaagg      300
aacgtgaaga aaaataatt ttagtgtcat ctgcaaatga aattgatgtt cgtccctgtc       360
ctcttaaccc aaatgaacac aaaggcacta aacttggta taaagatgac agcaagacac       420
ctgtatctac agaacaagcc tccaggattc atcaacacaa agagaaactt tggtttgttc      480
ctgctaaggt ggaggattca ggacattact attgcgtggt aagaaattca tcttactgcc      540
tcagaattaa aataagtgca aaatttgtgg agaatgagcc taacttatgt tataatgcac      600
aagccatatt taagcagaaa ctacccgttg caggagacgg aggacttgtg tgcccttata      660
tggagttttt taaaaatgaa aataatgagt tacctaaatt acagtggtat aaggattgca      720
aacctctact tcttgacaat atacactta gtggagtcaa agataggctc atcgtgatga       780
atgtggctga aaagcataga gggaactata cttgtcatgc atcctacaca tacttgggca     840
agcaatatcc tattcccgg gtaatagaat ttattactct agaggaaaac aaacccacaa       900
ggcctgtgat tgtgagccca gctaatgaga caatggaagt agacttggga tcccagatac     960
aattgatctg taatgtcacc ggccagttga gtgacattgc ttactggaag tggaatgggt     1020
cagtaattga tgaagatgac ccagtgctag gggaagacta ttacagtgtg gaaaatcctg     1080
caaacaaaag aaggagtacc ctcatcacag tgcttaatat atcggaaatt gaaagtagat     1140
tttataaaca tccatttacc tgttttgcca agaatacaca tggtatagat gcagcatata     1200
tccagttaat atatccagtc actaatttcc agaagcacat gattggtata tgtgtcacgt     1260
tgacagtcat aattgtgtgt tctgttttca tctataaaat cttcaagatt gacattgtgc     1320
tttggtacag ggattcctgc tatgattttc tcccaataaa agtcttgcct gaggtcttgg     1380
aaaaacagtg tggatataag ctgttcattt atggaaggga tgactacgtt ggggaagaca     1440
ttgttgaggt cattaatgaa aacgtaaaga aaagcagaag actgattatc attttagtca     1500
gagaaacatc aggcttcagc tggctgggtg gttcatctga agagcaaata gccatgtata     1560
atgctcttgt tcaggatgga attaaagttg tcctgcttga gctggagaaa atccaagact     1620
atgagaaaat gccagaatcg attaaattca ttaagcagaa acatgggggct atccgctggt    1680 cagggggactt tacacaggga ccacagtctg caaagacaag gttctggaag aatgtcaggt    1740 accacacatgcc agtccagcga cggtcacctt catctaaaca ccagttactg tcaccagcca   1800
ctaaggagaa actgcaaaga gaggctcacg tgcctctcgg gtagcatgga gaagttgcca     1860
agagttcttt aggtgcctcc tgtcttatgg cgttgcaggc caggttatgc ctcatgctga     1920
cttgcagagt tcatggaatg taactatatc atcctttatc cctgaggtca cctggaatca     1980
gattattaag gaataagcc atgacgtcaa tagcagccca gggcacttca gagtagaggg      2040
cttgggaaga tcttttaaaa aggcagtagg cccggtgtgg tggctcacgc ctataatccc     2100
agcactttgg gaggctgaag tgggtggatc cagaggtc aggagttcga ccagcccag         2160 gccaacatgg caaacccca tctctactaa aaatacaaaa atgagctagg catggtggca       2220
cacgcctgta atcccagcta cacctgaggc tgaggcagga gaattgcttg aaccggggag     2280
acggaggttg cagtgagccg agtttgggcc actgcactct agcctggcaa cagagcaaga     2340
ctccgtctca aaaaagggc aataaatgcc ctctctgaat gtttgaactg ccaagaaaag      2400
gcatggagac agcgaactag aagaaggggc aagaaggaaa tagccaccgt ctacagatgg     2460
cttagttaag tcatccacag cccaagggcg gggctatgcc ttgtctgggg accctgtaga     2520
```

```
gtcactgacc ctggagcggc tctcctgaga ggtgctgcag gcaaagtgag actgacacct    2580
cactgaggaa gggagacata ttcttggaga actttccatc tgcttgtatt ttccatacac    2640
atccccagcc agaagttagt gtccgaagac cgaattttat tttacagagc ttgaaaactc    2700
acttcaatga acaagggat tctccaggat tccaaagttt tgaagtcatc ttagcttttcc    2760
acaggaggga gagaacttaa aaaagcaaca gtagcaggga attgatccac ttcttaatgc    2820
tttcctccct ggcatgacca tcctgtcctt tgttattatc ctgcatttta cgtctttgga    2880
ggaacagctc cctagtggct tcctccgtct gcaatgtccc ttgcacagcc cacacatgaa    2940
ccatccttcc catgatgccg ctcttctgtc atcccgctcc tgctgaaaca cctcccaggg    3000
gctccacctg ttcaggagct gaagcccatg ctttcccacc agcatgtcac tcccagacca    3060
cctcctgcc ctgtcctcca gcttcccctc gctgtcctgc tgtgtgaatt cccaggttgg    3120
cctggtggcc atgtcgcctg ccccccagcac tcctctgtct ctgctcttgc ctgcacccctt   3180
cctcctcctt tgcctaggag gccttctcgc attttctcta gctgatcaga attttaccaa    3240
aattcagaac atcctccaat tccacagtct ctgggagact ttccctaaga ggcgacttcc    3300
tctccagcct tctctctctg gtcaggccca ctgcagagat ggtggtgagc acatctggga    3360
ggctggtctc cctccagctg gaattgctgc tctctgaggg agaggctgtg gtggctgtct    3420
ctgtccctca ctgccttcca ggagcaattt gcacatgtaa catagattta tgtaatgctt    3480
tatgtttaaa acattcccc aattatctta tttaattttt gcaattattc taattttata    3540
tatagagaaa gtgacctatt ttttaaaaaa atcacactct aagttctatt gaacctagga    3600
cttgagcctc catttctggc ttctagtctg gtgttctgag tacttgattt caggtcaata    3660
acggtccccc ctcactccac actggcacgt ttgtgagaag aaatgacatt tgctaggaa     3720
gtgaccgagt ctaggaatgc ttttattcaa gacaccaaat tccaaacttc taaatgttgg    3780
aattttcaaa aattgtgttt agattttatg aaaaactctt ctactttcat ctattctttc    3840
cctagaggca aacatttctt aaaatgtttc attttcatta aaaatgaaag ccaaatttat    3900
atgccaccga ttgcaggaca caagcacagt tttaagagtt gtatgaacat ggagaggact    3960
tttggtttt atatttctcg tatttaatat gggtgaacac caactttat ttggaataat      4020
aatttttcctc ctaaacaaaa acacattgag tttaagtctc tgactcttgc ctttccacct   4080
gctttctcct gggcccgctt tgcctgcttg aaggaacagt gctgttctgg agctgctgtt    4140
ccaacagaca gggcctagct ttcatttgac acacagacta cagccagaag cccatggagc    4200
agggatgtca cgtcttgaaa agcctattag atgttttaca aatttaattt tgcagattat    4260
tttagtctgt catccagaaa atgtgtcagc atgcatagtg ctaagaaagc aagccaattt    4320
ggaaacttag gttagtgaca aaattggcca gagagtgggg gtgatgatga ccaagaatta    4380
caagtagaat ggcagctgga atttaaggag ggacaagaat caatggataa gcgtgggtgg    4440
aggaagatcc aaacagaaaa gtgcaaagtt attccccatc ttccaagggt tgaattctgg    4500
aggaagaaga cacattccta gttccccgtg aacttccttt gacttattgt ccccactaaa    4560
acaaaacaaa aaacttttaa tgccttccac attaattaga ttttcttgca gtttttttat   4620
ggcatttttt taaagatgcc ctaagtgttg aagaagagtt tgcaaatgca acaaaatatt    4680
taattaccgg ttgttaaaac tggtttagca caatttatat tttccctctc ttgcctttct   4740
tatttgcaat aaaaggtatt gagccatttt ttaaatgaca ttttgataa attatgtttg    4800
tactagttga tgaaggagtt ttttttaacc tgtttatata attttgcagc agaagccaaa   4860
ttttttgtat attaaagcac caaattcatg tacagcatgc atcacggatc aatagactgt    4920
```

```
acttattttc caataaaatt ttcaaacttt gtactgtta                                  4959
```

<210> SEQ ID NO 62
<211> LENGTH: 569
<212> TYPE: PRT
<213> ORGANISM: Homo sapiens

<400> SEQUENCE: 62

| | | | | | | | | | | | | | | |
|---|---|---|---|---|---|---|---|---|---|---|---|---|---|---|
| Met | Lys | Val | Leu | Leu | Arg | Leu | Ile | Cys | Phe | Ile | Ala | Leu | Leu | Ile | Ser |
| 1 | | | | 5 | | | | | 10 | | | | | 15 | |
| Ser | Leu | Glu | Ala | Asp | Lys | Cys | Lys | Glu | Arg | Glu | Lys | Ile | Ile | Leu | |
| | | | 20 | | | | | 25 | | | | | 30 | | |
| Val | Ser | Ser | Ala | Asn | Glu | Ile | Asp | Val | Arg | Pro | Cys | Pro | Leu | Asn | Pro |
| | | 35 | | | | | 40 | | | | | 45 | | | |
| Asn | Glu | His | Lys | Gly | Thr | Ile | Thr | Trp | Tyr | Lys | Asp | Asp | Ser | Lys | Thr |
| | 50 | | | | | 55 | | | | | 60 | | | | |
| Pro | Val | Ser | Thr | Glu | Gln | Ala | Ser | Arg | Ile | His | Gln | His | Lys | Glu | Lys |
| 65 | | | | | 70 | | | | | 75 | | | | | 80 |
| Leu | Trp | Phe | Val | Pro | Ala | Lys | Val | Glu | Asp | Ser | Gly | His | Tyr | Tyr | Cys |
| | | | | 85 | | | | | 90 | | | | | 95 | |
| Val | Val | Arg | Asn | Ser | Ser | Tyr | Cys | Leu | Arg | Ile | Lys | Ile | Ser | Ala | Lys |
| | | | 100 | | | | | 105 | | | | | 110 | | |
| Phe | Val | Glu | Asn | Glu | Pro | Asn | Leu | Cys | Tyr | Asn | Ala | Gln | Ala | Ile | Phe |
| | | | 115 | | | | | 120 | | | | | 125 | | |
| Lys | Gln | Lys | Leu | Pro | Val | Ala | Gly | Asp | Gly | Gly | Leu | Val | Cys | Pro | Tyr |
| | 130 | | | | | 135 | | | | | 140 | | | | |
| Met | Glu | Phe | Phe | Lys | Asn | Glu | Asn | Asn | Glu | Leu | Pro | Lys | Leu | Gln | Trp |
| 145 | | | | | 150 | | | | | 155 | | | | | 160 |
| Tyr | Lys | Asp | Cys | Lys | Pro | Leu | Leu | Leu | Asp | Asn | Ile | His | Phe | Ser | Gly |
| | | | | 165 | | | | | 170 | | | | | 175 | |
| Val | Lys | Asp | Arg | Leu | Ile | Val | Met | Asn | Val | Ala | Glu | Lys | His | Arg | Gly |
| | | | 180 | | | | | 185 | | | | | 190 | | |
| Asn | Tyr | Thr | Cys | His | Ala | Ser | Tyr | Thr | Tyr | Leu | Gly | Lys | Gln | Tyr | Pro |
| | | | 195 | | | | | 200 | | | | | 205 | | |
| Ile | Thr | Arg | Val | Ile | Glu | Phe | Ile | Thr | Leu | Glu | Glu | Asn | Lys | Pro | Thr |
| | 210 | | | | | 215 | | | | | 220 | | | | |
| Arg | Pro | Val | Ile | Val | Ser | Pro | Ala | Asn | Glu | Thr | Met | Glu | Val | Asp | Leu |
| 225 | | | | | 230 | | | | | 235 | | | | | 240 |
| Gly | Ser | Gln | Ile | Gln | Leu | Ile | Cys | Asn | Val | Thr | Gly | Gln | Leu | Ser | Asp |
| | | | | 245 | | | | | 250 | | | | | 255 | |
| Ile | Ala | Tyr | Trp | Lys | Trp | Asn | Gly | Ser | Val | Ile | Asp | Glu | Asp | Asp | Pro |
| | | | 260 | | | | | 265 | | | | | 270 | | |
| Val | Leu | Gly | Glu | Asp | Tyr | Tyr | Ser | Val | Glu | Asn | Pro | Ala | Asn | Lys | Arg |
| | | | 275 | | | | | 280 | | | | | 285 | | |
| Arg | Ser | Thr | Leu | Ile | Thr | Val | Leu | Asn | Ile | Ser | Glu | Ile | Glu | Ser | Arg |
| | 290 | | | | | 295 | | | | | 300 | | | | |
| Phe | Tyr | Lys | His | Pro | Phe | Thr | Cys | Phe | Ala | Lys | Asn | Thr | His | Gly | Ile |
| 305 | | | | | 310 | | | | | 315 | | | | | 320 |
| Asp | Ala | Ala | Tyr | Ile | Gln | Leu | Ile | Tyr | Pro | Val | Thr | Asn | Phe | Gln | Lys |
| | | | | 325 | | | | | 330 | | | | | 335 | |
| His | Met | Ile | Gly | Ile | Cys | Val | Thr | Leu | Thr | Val | Ile | Ile | Val | Cys | Ser |
| | | | 340 | | | | | 345 | | | | | 350 | | |
| Val | Phe | Ile | Tyr | Lys | Ile | Phe | Lys | Ile | Asp | Ile | Val | Leu | Trp | Tyr | Arg |
| | | | 355 | | | | | 360 | | | | | 365 | | |

```
Asp Ser Cys Tyr Asp Phe Leu Pro Ile Lys Ala Ser Asp Gly Lys Thr
        370                 375                 380

Tyr Asp Ala Tyr Ile Leu Tyr Pro Lys Thr Val Gly Glu Gly Ser Thr
385                 390                 395                 400

Ser Asp Cys Asp Ile Phe Val Phe Lys Val Leu Pro Glu Val Leu Glu
                405                 410                 415

Lys Gln Cys Gly Tyr Lys Leu Phe Ile Tyr Gly Arg Asp Asp Tyr Val
                420                 425                 430

Gly Glu Asp Ile Val Glu Val Ile Asn Glu Asn Val Lys Lys Ser Arg
                435                 440                 445

Arg Leu Ile Ile Ile Leu Val Arg Glu Thr Ser Gly Phe Ser Trp Leu
        450                 455                 460

Gly Gly Ser Ser Glu Glu Gln Ile Ala Met Tyr Asn Ala Leu Val Gln
465                 470                 475                 480

Asp Gly Ile Lys Val Val Leu Leu Glu Leu Glu Lys Ile Gln Asp Tyr
                485                 490                 495

Glu Lys Met Pro Glu Ser Ile Lys Phe Ile Lys Gln Lys His Gly Ala
                500                 505                 510

Ile Arg Trp Ser Gly Asp Phe Thr Gln Gly Pro Gln Ser Ala Lys Thr
        515                 520                 525

Arg Phe Trp Lys Asn Val Arg Tyr His Met Pro Val Gln Arg Arg Ser
530                 535                 540

Pro Ser Ser Lys His Gln Leu Leu Ser Pro Ala Thr Lys Glu Lys Leu
545                 550                 555                 560

Gln Arg Glu Ala His Val Pro Leu Gly
                565

<210> SEQ ID NO 63
<211> LENGTH: 3142
<212> TYPE: DNA
<213> ORGANISM: Homo sapiens

<400> SEQUENCE: 63
aacttcctgt tgtcaccaca cctctgagtc gtctgagctc actgtgagca aaatcccaca      60
gtggaaactc ttaagcctct gcgaagtaaa tcattcttgt gaatgtgaca cacgatctct     120
ccagtttcca tatgttgaga ttctacttat tcatcagttt gttgtgcttg tcaagatcag     180
acgcagaaga acatgtcctt cattcacca ggctgagctt tcacagtgca gtggttggta     240
cgggactaaa tgtgaggctg atgctctaca caaggaaaaa cctgacctgc gcacaaacca     300
tcaactcctc agcttttggg aacttgaatg tgaccaagaa aaccaccttc attgtccatg     360
gattcaggcc aacaggctcc cctcctgttt ggatggatga cttagtaaag gtttgctct      420 ctgttgaaga catgaacgta gttgttgttg attggaatcg aggagctaca actttaatat     480
atacccatgc tctagtaag accagaaaag tagccatggt cttgaaggaa tttattgacc     540
agatgttggc agaaggagct tctcttgatg acatttacat gatcggagta agtctaggag     600
cccacatatc tgggtttgtt ggagagatgt acgatggatg gctggggaga attacaggcc     660
tcgaccctgc aggccctta ttcaacggga aacctcacca agacagatta gatcccagtg      720
atgcgcagtt tgttgatgtc atccattccg acactgatgg atttcagtat tttaaatgtg     780
accaccagag gtctgtatac ctgtacctgt cttccctgag agagagctgc accatcactg     840
cgtatccctg tgactcctac caggattata ggaatggcaa gtgtgtcagc tgcggcacgt     900
cacaaaaaga gtcctgtccc cttctgggct attatgctga taattggaaa gaccatctaa     960
```

```
ggggggaaaga tcctccaatg acgaaggcat tctttgacac agctgaggag agcccattct    1020
gcatgtatca ttactttgtg gatattataa catggaacaa gaatgtaaga agagggaca     1080 ttaccatcaa attgagagac aaagctggaa acaccacaga atccaaaatc aatcatgaac    1140
ccaccacatt tcagaaatat caccaagtga gtctacttgc aagatttaat caagatctgg    1200
ataaagtggc tgcaatttcc ttgatgttct ctacaggatc tctaataggc ccaaggtaca    1260
agctcaggat tctccgaatg aagttaaggt cccttgccca tccggagagg cctcagctgt    1320
gtcggtatga tcttgtcctg atggaaaacg ttgaaacagt cttccaacct attctttgcc    1380
cagagttgca gttgtaactg ttgccaggac acatggccat aaataataga aagaaagcta    1440
caaccacagg ctgtttgaaa gcttcacctc acctttctgc aaggcagaaa agtatgaaa     1500 aaaaccaagg cttttttcag tagcgtccta tggatgtcac attgtacatc aaacaacctt    1560
gtgattataa aacgatcctg ggaaggagcc cctaactagg gcaagtcaga aatagccagg    1620
ctcgcagcag cgcagcgctg tgtctgctgt gtcctgggc ctcccttgtt ccgacctgtc    1680
aattctgctg cctgtcacgc gggtggttct gcccatcgcg gctgcgggtc aagcatcttc    1740
aagggaagga cggactggag gcctcaccgt ggactcaact ctgcattctc cgtgccacat    1800
tcctccagtt cccacacgta aagggaacg aaactgacgt ctacctcatg gggctgctgt    1860
gtgggtttgg gaggcaaaaa tctatgaagg gttttttgaa atcccatagg tgccacatct    1920
atgagatgtt tgataaatgt gaatatgctt ttacatttgg gcttatctaa tttgcaataa    1980
gagagcctct ctctatcaac accagcttct ctctcgggct gtttgctcag ggaaggcaag    2040
aaagccacgt gctggccctc tgccttctct aaagtgctgt tggagcatgg aggagctgga    2100
ggagatgggg atggactgac agctaagagg gcggctgctg ggactagata gtggatgaag    2160
aaagaaggac gaggaagccg tggggcagcc tcttcacatg gggacagggg atggagcatg    2220
aggcaaggga aggaaaagca gagcttattt ttcacctaag gtggagaagg atcactttac    2280
aggcaacgct catttaagc aaccccttaag aaatgtttat gtttctttat taccaatgta    2340
atctatgatt attgaaggaa atttagaaaa tgcgtagata caaaattaaa aaaaaatact    2400
gtccacgatc ctattagagg taattaatgt tagccttttg gaacaaggct gtcacctatt    2460
ttgccaacac gtgaattcaa aacatgaacc ggtttgcttt tggagaatct gaagactcca    2520
gtttgaggaa tcctttgctt ccctggaggt agatgctgtc tgcaaatcta gaatgacagc    2580
aggagtccag tcaagaggtc ctgtcaggcc aaggccagaa agaagggagg acaatccctg    2640
gggccagatg cccagtgtga ggggaggcat gatctgtccc atggctgtgg ccactgcagg    2700
aaggtctgtg aaaaggaggt gacaggccca gtcacctcct cttcacccaa gtgattgctc    2760
cttcaactgc tatctgtgaa aatagccttt gttatgaaga aattgactct ctctctcttt    2820 ttttttttt ggagttgcct aggctggagt gcaatggtac gatctcagct cactgcaacc    2880
tccacctccc aggttcaatt gattctcctg cctcagcctc ctgagtagct gggattacag    2940
gcatgtgcca ccacccggg ctaatttttg tatttttatt agagacaggg tttcaccacg    3000
ttagccaggc tcgtctcgaa ctcctgtcct caggtgacta cccgtctcgg cctcccaaag    3060
tgctgggatt acaggcatga gccaccacac ccggccaaaa atggattctc tatgtcataa    3120
attaaagaaa tctataaatg ta                                             3142
```

<210> SEQ ID NO 64
<211> LENGTH: 451
<212> TYPE: PRT

<213> ORGANISM: Homo sapiens

<400> SEQUENCE: 64

| Met | Leu | Arg | Phe | Tyr | Leu | Phe | Ile | Ser | Leu | Leu | Cys | Leu | Ser | Arg | Ser |
|---|---|---|---|---|---|---|---|---|---|---|---|---|---|---|---|
| 1 | | | | 5 | | | | | 10 | | | | | 15 | |

| Asp | Ala | Glu | Glu | Thr | Cys | Pro | Ser | Phe | Thr | Arg | Leu | Ser | Phe | His | Ser |
|---|---|---|---|---|---|---|---|---|---|---|---|---|---|---|---|
| | | | 20 | | | | | 25 | | | | | 30 | | |

| Ala | Val | Val | Gly | Thr | Gly | Leu | Asn | Val | Arg | Leu | Met | Leu | Tyr | Thr | Arg |
|---|---|---|---|---|---|---|---|---|---|---|---|---|---|---|---|
| | | 35 | | | | | 40 | | | | | 45 | | | |

| Lys | Asn | Leu | Thr | Cys | Ala | Gln | Thr | Ile | Asn | Ser | Ser | Ala | Phe | Gly | Asn |
|---|---|---|---|---|---|---|---|---|---|---|---|---|---|---|---|
| 50 | | | | | 55 | | | | | 60 | | | | | |

| Leu | Asn | Val | Thr | Lys | Lys | Thr | Thr | Phe | Ile | Val | His | Gly | Phe | Arg | Pro |
|---|---|---|---|---|---|---|---|---|---|---|---|---|---|---|---|
| 65 | | | | | 70 | | | | | 75 | | | | | 80 |

| Thr | Gly | Ser | Pro | Pro | Val | Trp | Met | Asp | Asp | Leu | Val | Lys | Gly | Leu | Leu |
|---|---|---|---|---|---|---|---|---|---|---|---|---|---|---|---|
| | | | 85 | | | | | 90 | | | | | 95 | | |

| Ser | Val | Glu | Asp | Met | Asn | Val | Val | Val | Asp | Trp | Asn | Arg | Gly | Ala |
|---|---|---|---|---|---|---|---|---|---|---|---|---|---|---|
| | | 100 | | | | | 105 | | | | | 110 | | |

| Thr | Thr | Leu | Ile | Tyr | Thr | His | Ala | Ser | Ser | Lys | Thr | Arg | Lys | Val | Ala |
|---|---|---|---|---|---|---|---|---|---|---|---|---|---|---|---|
| | | | 115 | | | | | 120 | | | | | 125 | | |

| Met | Val | Leu | Lys | Glu | Phe | Ile | Asp | Gln | Met | Leu | Ala | Glu | Gly | Ala | Ser |
|---|---|---|---|---|---|---|---|---|---|---|---|---|---|---|---|
| | 130 | | | | | 135 | | | | | 140 | | | | |

| Leu | Asp | Asp | Ile | Tyr | Met | Ile | Gly | Val | Ser | Leu | Gly | Ala | His | Ile | Ser |
|---|---|---|---|---|---|---|---|---|---|---|---|---|---|---|---|
| 145 | | | | | 150 | | | | | 155 | | | | | 160 |

| Gly | Phe | Val | Gly | Glu | Met | Tyr | Asp | Gly | Trp | Leu | Gly | Arg | Ile | Thr | Gly |
|---|---|---|---|---|---|---|---|---|---|---|---|---|---|---|---|
| | | | | 165 | | | | | 170 | | | | | 175 | |

| Leu | Asp | Pro | Ala | Gly | Pro | Leu | Phe | Asn | Gly | Lys | Pro | His | Gln | Asp | Arg |
|---|---|---|---|---|---|---|---|---|---|---|---|---|---|---|---|
| | | | 180 | | | | | 185 | | | | | 190 | | |

| Leu | Asp | Pro | Ser | Asp | Ala | Gln | Phe | Val | Asp | Val | Ile | His | Ser | Asp | Thr |
|---|---|---|---|---|---|---|---|---|---|---|---|---|---|---|---|
| | | 195 | | | | | 200 | | | | | 205 | | | |

| Asp | Ala | Leu | Gly | Tyr | Lys | Glu | Pro | Leu | Gly | Asn | Ile | Asp | Phe | Tyr | Pro |
|---|---|---|---|---|---|---|---|---|---|---|---|---|---|---|---|
| 210 | | | | | 215 | | | | | 220 | | | | | |

| Asn | Gly | Gly | Leu | Asp | Gln | Pro | Gly | Cys | Pro | Lys | Thr | Ile | Leu | Gly | Gly |
|---|---|---|---|---|---|---|---|---|---|---|---|---|---|---|---|
| 225 | | | | | 230 | | | | | 235 | | | | | 240 |

| Phe | Gln | Tyr | Phe | Lys | Cys | Asp | His | Gln | Arg | Ser | Val | Tyr | Leu | Tyr | Leu |
|---|---|---|---|---|---|---|---|---|---|---|---|---|---|---|---|
| | | | | 245 | | | | | 250 | | | | | 255 | |

| Ser | Ser | Leu | Arg | Glu | Ser | Cys | Thr | Ile | Thr | Ala | Tyr | Pro | Cys | Asp | Ser |
|---|---|---|---|---|---|---|---|---|---|---|---|---|---|---|---|
| | | | 260 | | | | | 265 | | | | | 270 | | |

| Tyr | Gln | Asp | Tyr | Arg | Asn | Gly | Lys | Cys | Val | Ser | Cys | Gly | Thr | Ser | Gln |
|---|---|---|---|---|---|---|---|---|---|---|---|---|---|---|---|
| | | 275 | | | | | 280 | | | | | 285 | | | |

| Lys | Glu | Ser | Cys | Pro | Leu | Leu | Gly | Tyr | Tyr | Ala | Asp | Asn | Trp | Lys | Asp |
|---|---|---|---|---|---|---|---|---|---|---|---|---|---|---|---|
| | 290 | | | | | 295 | | | | | 300 | | | | |

| His | Leu | Arg | Gly | Lys | Asp | Pro | Pro | Met | Thr | Lys | Ala | Phe | Phe | Asp | Thr |
|---|---|---|---|---|---|---|---|---|---|---|---|---|---|---|---|
| 305 | | | | | 310 | | | | | 315 | | | | | 320 |

| Ala | Glu | Glu | Ser | Pro | Phe | Cys | Met | Tyr | His | Tyr | Phe | Val | Asp | Ile | Ile |
|---|---|---|---|---|---|---|---|---|---|---|---|---|---|---|---|
| | | | | 325 | | | | | 330 | | | | | 335 | |

| Thr | Trp | Asn | Lys | Asn | Val | Arg | Arg | Gly | Asp | Ile | Thr | Ile | Lys | Leu | Arg |
|---|---|---|---|---|---|---|---|---|---|---|---|---|---|---|---|
| | | | 340 | | | | | 345 | | | | | 350 | | |

| Asp | Lys | Ala | Gly | Asn | Thr | Thr | Glu | Ser | Lys | Ile | Asn | His | Glu | Pro | Thr |
|---|---|---|---|---|---|---|---|---|---|---|---|---|---|---|---|
| | | 355 | | | | | 360 | | | | | 365 | | | |

| Thr | Phe | Gln | Lys | Tyr | His | Gln | Val | Ser | Leu | Leu | Ala | Arg | Phe | Asn | Gln |
|---|---|---|---|---|---|---|---|---|---|---|---|---|---|---|---|
| | 370 | | | | | 375 | | | | | 380 | | | | |

| Asp | Leu | Asp | Lys | Val | Ala | Ala | Ile | Ser | Leu | Met | Phe | Ser | Thr | Gly | Ser |
|---|---|---|---|---|---|---|---|---|---|---|---|---|---|---|---|
| 385 | | | | | 390 | | | | | 395 | | | | | 400 |

```
Leu Ile Gly Pro Arg Tyr Lys Leu Arg Ile Leu Arg Met Lys Leu Arg
            405                 410                 415

Ser Leu Ala His Pro Glu Arg Pro Gln Leu Cys Arg Tyr Asp Leu Val
        420                 425                 430

Leu Met Glu Asn Val Glu Thr Val Phe Gln Pro Ile Leu Cys Pro Glu
    435                 440                 445

Leu Gln Leu
    450

<210> SEQ ID NO 65
<211> LENGTH: 11140
<212> TYPE: DNA
<213> ORGANISM: Homo sapiens

<400> SEQUENCE: 65
```

| | | | | | |
|---|---|---|---|---|---|
| aggcagggggg | cggcaacatg | gcggagtgag | cggcggcgtc | ggggcttcac | aacaacagtg | 60 |
| gtggccgtag | cagcggcggc | agcagcgtca | atagcatcgg | ccacagcctg | agcttcagca | 120 |
| ccggccagcg | tcgtggccag | ctgctcgcgt | cctcgggctt | tcggagcgg | ctgcagcatc | 180 |
| tccgcggggg | gcgggccggg | ccggacagac | cgggagaggg | agagagcaga | ggcagcggcg | 240 |
| gcggcagcgg | cagcggcagc | ggcacacctg | ctgggcgggc | acagccgctt | gcccggcagc | 300 |
| ggttagcggt | accgccaccg | ccgagaataa | gcctgcggat | ccccgccgc | ctccgcgggg | 360 |
| gagagcgccg | gagcgggccg | ggctgaggcg | caggcgggga | gcgggcccgg | cgccgcggcg | 420 |
| ctggtggatg | ctggggctcc | gaggcgacgg | ccggggggcg | ggggccgagg | caggtataac | 480 |
| ggtaccggcg | gcgcagcgc | cgctgctctt | cccttctcct | caggaggggg | gccaatggct | 540 |
| agcgagaagc | cgggcccggg | cccggggctc | gagcctcagc | ccgtggggct | cattgccgtc | 600 |
| ggggccgctg | gcggaggcgg | cggggggcagc | ggtggtggcg | gcaccggggg | cagcgggatg | 660 |
| ggggagctaa | gggggggcgtc | cggctccggc | tcggtgatgc | tccccgcggg | gatgattaac | 720 |
| ccttcggtgc | cgatccgcaa | catccggatg | aaattcgcag | tgttgattgg | actcatacag | 780 |
| gtcggagagg | tcagcaacag | ggacatcgtg | gagacggtgc | tcaacctgct | ggttggtgga | 840 |
| gaatttgact | tggagatgaa | ctttattatc | caggatgctg | agagtataac | atgtatgaca | 900 |
| gagcttttgg | agcactgtga | tgtaacatgt | caagcagaaa | tatggagcat | gtttacagcc | 960 |
| attctacgaa | aaagtgttcg | gaatttacag | actagcacag | aagttgggct | aattgaacaa | 1020 |
| gtattgctga | aaatgagtgc | tgtagatgac | atgatagcag | atcttctagt | tgatatgttg | 1080 |
| ggggttcttg | ccagctacag | catcactgtc | aaggagttga | agcttttgtt | cagcatgctt | 1140 |
| cgaggagaaa | gtggaatctg | gccaagacat | gcagtaaaat | tattatcagt | tcttaatcag | 1200 |
| atgccacaga | gacacggtcc | tgatactttt | ttcaatttcc | ctggttgtag | cgctgcggca | 1260 |
| attgccttgc | ctcctattgc | aaagtggcct | tatcagaatg | gcttcacctt | aaacacttgg | 1320 |
| tttcgtatgg | atccattaaa | taatattaat | gttgataagg | ataaacctta | tctttattgt | 1380 |
| tttcgtacta | gcaaaggagt | tggttactct | gctcattttg | ttggcaactg | tttaatagtc | 1440 |
| acatcattga | agtccaaagg | aaaaggtttt | cagcattgtg | tgaaatatga | ttttcaacca | 1500 |
| cgcaagtggt | acatgatcag | cattgtccac | atttacaatc | gatggaggaa | cagtgaaatt | 1560 |
| cggtgttatg | ttaatggaca | actggtatct | tatggtgata | tggcttggca | tgttaacaca | 1620 |
| aatgatagct | atgacaagtg | ctttcttgga | tcatcagaaa | ctgctgatgc | aaatagggta | 1680 |
| ttctgtggtc | aacttggtgc | cgtgtatgtg | ttcagtgaag | cactcaaccc | agcacagata | 1740 |
| tttgcaattc | atcagttagg | acctggatat | aagagtacct | tcaagtttaa | atctgagagt | 1800 |

```
gatattcatt tggcagaaca tcataaacag gtgttatatg atgggaaact tgcaagtagc    1860
attgccttta catataatgc taaggccact gatgctcagc tctgcctgga atcatcacca    1920
aaagagaatg catcaatttt tgtgcattcc ccacatgctc taatgcttca ggatgtgaaa    1980
gcgatagtaa cacattcaat tcatagtgca attcattcaa ttggagggat tcaagtgctt    2040
tttccacttt ttgcccaatt ggataatagg cagctcaatg acagtcaagt ggaaacaact    2100
gtctgtgcta ctctgttggc attcctggtt gaactactta aaagttcagt agccatgcaa    2160
gaacagatgc tgggtggaaa aggcttttta gtcattggct acttacttga aaagtcatca    2220
agagttcata taactagagc tgtcctggag caatttttat cttttgcaaa ataccttgat    2280
ggtttatctc atggagcacc tttgctgaag cagctttgtg atcacatttt atttaaccca    2340
gccatctgga tacatacacc tgcaaaggtt cagctttccc tatacacata tttgtctgct    2400
gaatttattg gaactgctac catctacacc accatacgca gagtaggaac agtattacag    2460
ctaatgcaca ccttaaaata ttactactgg gttattaatc ctgctgacag tagtggcatt    2520
acacctaaag gattagatgg tccccggcca tcacaaaaag aaattatatc actgagggca    2580
tttatgctac tttttctgaa acagctgata ctaaaggatc gaggggtcaa ggaagatgaa    2640
cttcagagta tattaaatta cctacttacg atgcatgagg atgaaaatat tcatgatgtg    2700
ctacagttac tggtggcttt aatgtcggaa cacccagcct caatgatacc agcatttgat    2760
caaagaaatg gaataagggt gatctacaaa ttattggctt ctaaaagtga agtatttgg    2820
gttcaagctt tgaaggttct gggatacttt ctgaagcatt taggtcacaa gagaaaagtt    2880
gaaattatgc acacccatag tcttttcact cttcttggag aaaggctgat gttgcataca    2940
aacactgtga ctgtcaccac atacaacaca ctttatgaga tcttgacaga acaagtatgt    3000
actcaggtcg tacacaaacc acatccagag ccagattcta cagtgaaaat tcagaatcca    3060
atgattctta agtggtggc aactttgtta aaaaactcta caccaagtgc agagctgatg    3120
gaagttcgtc gtttattttt atctgatatg ataaaacttt tcagtaacag ccgtgaaaat    3180
agaagatgct tattgcagtg ttcagtgtgg caggattgga tgttttctct tggctatatc    3240
aatcctaaaa attctgagga acagaagatt accgaaatgg tctacaatat cttccggatt    3300
cttttgtatc atgcaataaa atatgaatgg ggaggctgga gagtctgggt ggatacctc    3360
tcaatagccc attccaaggt cacttatgaa gctcataagg aatacctagc caaaatgtat    3420
gaggaatatc aaagacaaga ggaggaaaac attaaaaagg gaaagaaagg gaatgtgagc    3480
accatctctg gtctttcatc acagacaaca ggagcaaaag gtggaatgga aattcgagag    3540
atagaagatc tttcacaaag ccagagccca gaaagtgaga ccgattaccc tgtcagcaca    3600
gatactcgag acttactcat gtcaacaaaa gtgtcagatg atattcttgg aaattcagat    3660
agaccaggaa gtggtgtaca tgtggaagta catgatcttt tagtagatat aaaagcagag    3720
aaagtggaag caacagaagt aaagctcgat gatatgqatt tatcaccqga ctttagta    3780
ggtggagaga atggtgccct tgtggaggtt gaatctctgt tggataatgt atatagtgct    3840
gctgttgaga aactccagaa caatgtacat ggaagtgttg gtatcattaa aaaaaatgaa    3900
gaaaaggata atggtccatt gataacatta gcagatgaga agaagacct tcccaatagt    3960
agtacatcat ttctctttga taaaatacccc aaacaggagg aaaaactact tcctgaactt    4020
tctagcaatc acattattcc aaatattcag gacacacaag tacatcttgg tgttagtgat    4080
gatcttggat tgcttgctca catgaccggt agcgtagact taacttgtac atccagtata    4140
```

```
atagaagaaa aagaattcaa aatccataca acttcagatg gaatgagcag tatttctgaa    4200
agagacttag cgtcatcaac taaggggctg gagtatgctg aaatgactgc tacaactctg    4260
gaaactgagt cttctagtag caaaattgta ccaaatattg atgcaggaag tataatttca    4320
gatactgaaa ggtctgacga tggcaaagaa tcaggaaaag aaatccgaaa atccaaaca    4380 actactacga cacaagctgt gcagggtcgg tctatcaccc aacaagaccg agatctccga    4440
gttgatttag gatttcgagg aatgccaatg actgaggaac agcgacgcca gtttagccca    4500
ggtccacgga ctacaatgtt tcgtattcct gagtttaaat ggtctccaat gcaccagcgg    4560
cttctcactg atttactatt tgcattagaa actgatgtac atgtttggag gagccattct    4620
acaaagtctg taatggattt tgtcaatagc aatgaaaata ttatttttgt acataacaca    4680
attcacctca tttcccaaat ggtagacaac atcatcattg cttgtggagg aattttacct    4740
ttgctctctg ctgctacatc accaactggt tctaagacgg aattggaaaa tattgaagtg    4800
acacaaggca tgtcagctga cagcagta actttcctca gccggctgat ggctatggtt    4860
gatgtacttg tgtttgcaag ctctctaaat tttagtgaga ttgaagctga gaaaaacatg    4920
tcttctggag gtttaatgcg acagtgccta agattagttt gttgtgttgc tgtgagaaac    4980
tgtttagaat gtcggcaaag acagagagac aggggaaata aatcttccca tggaagcagt    5040
aaacctcagg aagttcctca aagtgtgact gctacagcag cttcgaagac tccattggaa    5100
aatgttccag gtaacctttc tcctattaag gatccggata gacttcttca ggatgttgat    5160
atcaatcgcc ttcgtgctgt tgtctttcgg gatgtggatg atagcaaaca agcacagttc    5220
ttagctctgg ctgttgttta cttcatttcg gttctgatgg tttccaagta tcgtgacata    5280
ttagaacccc agagagagac tacaagaact ggaagccaac caggtagaaa catcaggcaa    5340
gaaataaatt caccaacaag tacagttgtg gtcataccat ctatccctca tccaagtttg    5400
aaccatggat tccttgccaa gttaattcct gagcagagct ttggccactc atttttacaaa    5460 gaaacacctg ctgcatttcc agacaccata aaagaaaaag aaacaccaac tcctggtgaa    5520
gatattcagg tagaaagttc aattccccat acagattcag gaattggaga ggagcaagtg    5580
gctagcatcc tgaatggggc agaattagaa acaagtacag gccctgatgc catgagtgaa    5640
ctcttatcca ctttgtcatc cgaagtgaag aaatcacaag agagcttaac tgaaaatcct    5700
agtgaaacgt tgaagcctgc aacatccata tctagcatta gtcaaaccaa aggcatcaat    5760
gtgaaggaaa tactgaaaag tcttgtggct gctccagttg aaatagcaga atgtggccct    5820
gaacctatcc catacccaga tccagcattg aagagagaaa cacaagctat tcttcctatg    5880
cagtttcatt cctttgacag gagtgttgtg gtgcctgtaa agaaaccacc tccaggtagt    5940
ttagctgtaa ccactgtggg agccactact gctggaagtg ggctgccaac aggcagtacc    6000
tctaatatat ttgctgctac tggagctaca ccaaaaagta tgattaatac aacaggtgcc    6060
gtggattcag ggtcctcctc ctcttcctcc tcttctagtt ttgtgaatgg tgctactagc    6120
aaaaaccttc cagctgtaca aactgttgct ccaatgccag aagattcagc tgaaaatatg    6180
agcatcactg caaaacttga agagcgtta gaaaaagttg ctcctcttct tcgtgaaatt    6240
tttgtagact ttgccccatt cctatctcgt acacttcttg gcagtcatgg acaagagcta    6300
ttgatagaag gccttgtttg tatgaagtcc agcacatctg tggttgagct tgttatgctg    6360 cttttgttctc aggaatggca aaactctatt cagaagaatg caggacttgc atttattgag    6420
ctcatcaatg aaggaagatt actgtgccat gctatgaagg accatatagt ccgtgttgca    6480
aatgaagctg agtttatttt gaacagacaa agagccgagg atgtacataa acatgcagag    6540
```

```
tttgagtcac agtgtgccca atatgctgct gatagaagag aggaagaaaa gatgtgtgac   6600
catcttatca gtgctgctaa acatcgagat catgtaacag caaatcagct gaaacagaag   6660
attctcaata ttctcacaaa taaacatggt gcttggggag cagtttctca tagccaattg   6720
catgatttct ggcgtttgga ttactgggaa gatgatcttc gtcgaaggag acgatttgtt   6780
cgcaatgcat ttggctccac tcatgctgaa gcattgctga agctgcaat agaatatggc   6840
acggaagaag atgtagtaaa gtcaaagaaa acattcagaa gtcaagcaat agtgaaccaa   6900
aatgcagaga cagaacttat gctggaagga gacgatgatg cagtcagtct gctacaggag   6960
aaagaaattg acaaccttgc aggcccagtg gttctcagca cccctgccca gctcatcgct   7020
cccgtggtgg tggccaaggg gactctctcc atcaccacga cagaaatcta cttcgaggta   7080
gatgaggatg attctgcctt caagaagatc gacacgaaag ttcttgcata cactgaggga   7140
cttcacggaa aatggatgtt cagcgagata cgagctgtat tttcaagacg ttaccttcta   7200
caaaacactg ctttggaagt atttatggca aaccgaacct cagttatgtt taatttccct   7260
gatcaagcaa cagtaaaaaa agttgtctat agcttgcctc gggttggagt agggaccagc   7320
tatggtctgc cacaagccag gaggatatca ttggccactc ctcgacagct ttataaatct   7380
tccaatatga ctcagcgctg gcaaagaagg gaaatttcaa acttcgaata tttgatgttc   7440
cttaatacta ttgcaggacg gacatataat gatctgaacc aatatccagt gtttccgtgg   7500
gtgttaacca actatgaatc agaagagttg gacctgactc ttccaggaaa cttcagggat   7560
ctatcaaagc caattggtgc tttgaacccc aagagagctg tgttttatgc agagcgttat   7620
gagacatggg aagatgatca aagcccaccc taccattata atacccatta ttcaacagca   7680
acatctactt tatcctggct tgttcgaatt gaaccttca caaccttctt cctcaatgca   7740
aatgatggaa aatttgatca tccagatcga accttctcat ccgttgcaag gtcttggaga   7800
actagtcaga gagatacttc tgatgtaaag gaactaattc cagagttcta ctacctacca   7860
gagatgtttg tcaacagtaa tggatataat cttggagtca gagaagatga agtagtggta   7920
aatgatgttg atcttcccccc ttgggcaaaa aaacctgaag actttgtgcg gatcaacagg   7980
atggccctag aaagtgaatt tgtttcttgc caacttcatc agtggatcga ccttatattt   8040
ggctataagc agcgaggacc agaagcagtt cgtgctctga atgtttttca ctacttgact   8100
tatgaaggct ctgtgaacct ggatagtatc actgatcctg tgctcaggga ggccatggag   8160
gcacagatac agaactttgg acagacgcca tctcagttgc ttattgagcc acatccgcct   8220
cggagctctg ccatgcacct gtgtttcctt ccacagagtc cgctcatgtt taaagatcag   8280
atgcaacagg atgtgataat ggtgctgaag tttccttcaa attctccagt aacccatgtg   8340
gcagccaaca ctctgcccca cttgaccatc cccgcagtgg tgacagtgac ttgcagccga   8400
ctctttgcag tgaatagatg gcacaacaca gtaggcctca gaggagctcc aggatactcc   8460
ttggatcaag cccaccatct tcccattgaa atggatccat aatagccaa taattcaggt   8520
gtaaacaaac ggcagatcac agacctcgtt gaccagagta tacaaatcaa tgcacattgt   8580
tttgtggtaa cagcagataa tcgctatatt cttatctgtg gattctggga taagagcttc   8640
agagtttatt ctacagaaac agggaaattg actcagattg tatttggcca ttgggatgtg   8700
gtcacttgct tggccaggtc cgagtcatac attggtgggg actgctacat cgtgtccgga   8760
tctcgagatg ccaccctgct gctctggtac tggagtgggc ggcaccatat cataggagac   8820
aaccctaaca gcagtgacta tccggcacca agagccgtcc tcacaggcca tgaccatgaa   8880
```

```
gttgtctgtg tttctgtctg tgcagaactt gggcttgtta tcagtggtgc taaagagggc    8940
ccttgccttg tccacaccat cactggagat ttgctgagag cccttgaagg accagaaaac    9000
tgcttattcc cacgcttgat atctgtctcc agcgaaggcc actgtatcat atactatgaa    9060
cgagggcgat tcagtaattt cagcattaat gggaaacttt tggctcaaat ggagatcaat    9120
gattcaacac gggccattct cctgagcagt gacggccaga acctggtcac cggaggggac    9180
aatggggtag tagaggtctg gcaggcctgt gacttcaagc aactgtacat ttaccctgga    9240
tgtgatgctg gcattagagc aatggacttg tcccatgacc agaggactct gatcactggc    9300
atggcttctg gtagcattgt agcttttaat atagatttta atcggtggca ttatgagcat    9360
cagaacagat actgaagata aggaagaac caaaagccaa gttaaagctg agagcacaag     9420
tgctgcatgg aaaggcaata tctctggtgg aaaaaactcg tctacatcga cctccgtttg    9480
tacattccat cacacccagc aatagctgta cattgtagtc agcaaccatt ttactttgtg    9540
tgttttttca cgactgaaca ccagctgcta tcaagcaagc ttatatcatg taaattatat    9600
gaattaggag atgttttggt aattatttca tatattgttg tttattgaga aaggttgta    9660 ggatgtgtca caagagactt ttgacaattc tgaggaacct tgtgtccagt tgttacaaag    9720
tttaagcttt gaacctaacc tgcatcccat ttccagcctc ttttcaagct gagaaaaaaa    9780 aaaaaaaca cgtttgatac tttgtacatc agatgcatct tatttaaaag ggatactttt    9840
gtaaaagtaa aaccttgtat aaagaacaaa atgtttctta attttattgt ggagttacaa    9900
cttgcatgtt ccttactcct gttggcttga tggaacaggt gcattcacac tatgaaacag    9960
aaagatctgt ccaaggacac agcttgtatg aaagggttga atttgggctc catcagtaat   10020
ttttgacatt tcaccaaaa tatagtttgc acttttaat ctaaagtcat cccttctgag    10080
tgaaatttgc tcataaagca tttggatact aagccattat ttgccatttt gggtacttta   10140
tacaaagaaa attcagccct accctgcata atttgaagac acagcagaaa ggggcttag   10200 ggatgaggtc ctggtttttc ttgtataaat aggagtcatg ggcgttagtt ctgtagtaat   10260
aacttcccag cacctggaca tctcttccag agttatccca ctggcttggt gtgtatacat   10320
taggggagga taatctgatg ctaactttt ttttctcttt ggttcttgaa agcttagtt    10380 tctttaataa caagtcaaac tttattacaa caataactga agttattctt ttaggttctc   10440
gtgaaattct cactgaaagc cacattctta gcctaaggca tttcatcttt tatgatataa   10500
aatgatggct atcaaatgat tttccataca ttgtactgat caagttatac acccaggggt   10560
atatacactt tcttcatgtt tcttctttgt atatttggtg actgtatcgt catagatgta   10620
catattgtgt cggtagggct atgaggcatg ttacaggaat gtaattttct cagaatttac   10680
actcactcgc agtcatttat ttaaaaagat aaaacaagat aatgggttct ttgtattggc   10740
actttgcacc agaaacatat cattatttat tgatgtgatt acttatttgt tatccaccctt  10800 gtactagtaa gttttagcac tgaattcctt cttcactgtt gtttgtattt atgaaattct   10860
gaaattatgg ggaatcagcg taatgattaa gttattcatc accaggctgt aagcaatatc   10920
ttgagtttgt agcttagaat tgggaggata cttaacatct ggaagacaag ttcatttcat   10980
cttgagatca tggtgaaata ttttggatat ataaattcct taagctattg taaccatgtt   11040
ttattgcaaa gatgtaaaat atgccagatg tgtgtgagtt ggaaatcaaa aaagaaaaa   11100 taaaatatgc aagaattca aaaaaaaaa aaaaaaaaa                          11140
```

<210> SEQ ID NO 66
<211> LENGTH: 2946

```
<212> TYPE: PRT
<213> ORGANISM: Homo sapiens

<400> SEQUENCE: 66

Met Ala Ser Glu Lys Pro Gly Pro Gly Leu Glu Pro Gln Pro
1               5                   10                  15

Val Gly Leu Ile Ala Val Gly Ala Gly Gly Gly Gly Gly Ser
                20                  25                  30

Gly Gly Gly Gly Thr Gly Gly Ser Gly Met Gly Glu Leu Arg Gly Ala
                35                  40                  45

Ser Gly Ser Gly Ser Val Met Leu Pro Ala Gly Met Ile Asn Pro Ser
50                  55                      60

Val Pro Ile Arg Asn Ile Arg Met Lys Phe Ala Val Leu Ile Gly Leu
65                  70                  75                  80

Ile Gln Val Gly Glu Val Ser Asn Arg Asp Ile Val Glu Thr Val Leu
                85                  90                  95

Asn Leu Leu Val Gly Gly Glu Phe Asp Leu Glu Met Asn Phe Ile Ile
                100                 105                 110

Gln Asp Ala Glu Ser Ile Thr Cys Met Thr Glu Leu Leu Glu His Cys
                115                 120                 125

Asp Val Thr Cys Gln Ala Glu Ile Trp Ser Met Phe Thr Ala Ile Leu
                130                 135                 140

Arg Lys Ser Val Arg Asn Leu Gln Thr Ser Thr Glu Val Gly Leu Ile
145                 150                 155                 160

Glu Gln Val Leu Leu Lys Met Ser Ala Val Asp Asp Met Ile Ala Asp
                165                 170                 175

Leu Leu Val Asp Met Leu Gly Val Leu Ala Ser Tyr Ser Ile Thr Val
                180                 185                 190

Lys Glu Leu Lys Leu Leu Phe Ser Met Leu Arg Gly Leu Ser Gly Ile
                195                 200                 205

Trp Pro Arg His Ala Val Lys Leu Leu Ser Val Leu Asn Gln Met Pro
210                 215                 220

Gln Arg His Gly Pro Asp Thr Phe Phe Asn Phe Pro Gly Cys Ser Ala
225                 230                 235                 240

Ala Ala Ile Ala Leu Pro Pro Ile Ala Lys Trp Pro Tyr Gln Asn Gly
                245                 250                 255

Phe Thr Leu Asn Thr Trp Phe Arg Met Asp Pro Leu Asn Asn Ile Asn
                260                 265                 270

Val Asp Lys Asp Lys Pro Tyr Leu Tyr Cys Phe Arg Thr Ser Lys Gly
                275                 280                 285

Val Gly Tyr Ser Ala His Phe Val Gly Asn Cys Leu Ile Val Thr Ser
                290                 295                 300

Leu Lys Ser Lys Gly Lys Gly Phe Gln His Cys Val Lys Tyr Asp Phe
305                 310                 315                 320

Gln Pro Arg Lys Trp Tyr Met Ile Ser Ile Val His Ile Tyr Asn Arg
                325                 330                 335

Trp Arg Asn Ser Glu Ile Arg Cys Tyr Val Asn Gly Gln Leu Val Ser
                340                 345                 350

Tyr Gly Asp Met Ala Trp His Val Asn Thr Asn Asp Ser Tyr Asp Lys
                355                 360                 365

Cys Phe Leu Gly Ser Ser Glu Thr Ala Asp Ala Asn Arg Val Phe Cys
                370                 375                 380

Gly Gln Leu Gly Ala Val Tyr Val Phe Ser Glu Ala Leu Asn Pro Ala
385                 390                 395                 400
```

```
Gln Ile Phe Ala Ile His Gln Leu Gly Pro Gly Tyr Lys Ser Thr Phe
            405                 410                 415
Lys Phe Lys Ser Glu Ser Asp Ile His Leu Ala Glu His His Lys Gln
            420                 425                 430
Val Leu Tyr Asp Gly Lys Leu Ala Ser Ser Ile Ala Phe Thr Tyr Asn
            435                 440                 445
Ala Lys Ala Thr Asp Ala Gln Leu Cys Leu Glu Ser Ser Pro Lys Glu
450                 455                 460
Asn Ala Ser Ile Phe Val His Ser Pro His Ala Leu Met Leu Gln Asp
465                 470                 475                 480
Val Lys Ala Ile Val Thr His Ser Ile His Ser Ala Ile His Ser Ile
            485                 490                 495
Gly Gly Ile Gln Val Leu Phe Pro Leu Phe Ala Gln Leu Asp Asn Arg
            500                 505                 510
Gln Leu Asn Asp Ser Gln Val Glu Thr Thr Val Cys Ala Thr Leu Leu
            515                 520                 525
Ala Phe Leu Val Glu Leu Leu Lys Ser Ser Val Ala Met Gln Glu Gln
            530                 535                 540
Met Leu Gly Gly Lys Gly Phe Leu Val Ile Gly Tyr Leu Leu Glu Lys
545                 550                 555                 560
Ser Ser Arg Val His Ile Thr Arg Ala Val Leu Glu Gln Phe Leu Ser
            565                 570                 575
Phe Ala Lys Tyr Leu Asp Gly Leu Ser His Gly Ala Pro Leu Leu Lys
            580                 585                 590
Gln Leu Cys Asp His Ile Leu Phe Asn Pro Ala Ile Trp Ile His Thr
            595                 600                 605
Pro Ala Lys Val Gln Leu Ser Leu Tyr Thr Tyr Leu Ser Ala Glu Phe
610                 615                 620
Ile Gly Thr Ala Thr Ile Tyr Thr Thr Ile Arg Arg Val Gly Thr Val
625                 630                 635                 640
Leu Gln Leu Met His Thr Leu Lys Tyr Tyr Tyr Trp Val Ile Asn Pro
            645                 650                 655
Ala Asp Ser Ser Gly Ile Thr Pro Lys Gly Leu Asp Gly Pro Arg Pro
            660                 665                 670
Ser Gln Lys Glu Ile Ile Ser Leu Arg Ala Phe Met Leu Leu Phe Leu
            675                 680                 685
Lys Gln Leu Ile Leu Lys Asp Arg Gly Val Lys Glu Asp Glu Leu Gln
            690                 695                 700
Ser Ile Leu Asn Tyr Leu Leu Thr Met His Glu Asp Glu Asn Ile His
705                 710                 715                 720
Asp Val Leu Gln Leu Leu Val Ala Leu Met Ser Glu His Pro Ala Ser
            725                 730                 735
Met Ile Pro Ala Phe Asp Gln Arg Asn Gly Ile Arg Val Ile Tyr Lys
            740                 745                 750
Leu Leu Ala Ser Lys Ser Glu Ser Ile Trp Val Gln Ala Leu Lys Val
            755                 760                 765
Leu Gly Tyr Phe Leu Lys His Leu Gly His Lys Arg Lys Val Glu Ile
            770                 775                 780
Met His Thr His Ser Leu Phe Thr Leu Leu Gly Glu Arg Leu Met Leu
785                 790                 795                 800
His Thr Asn Thr Val Thr Val Thr Thr Tyr Asn Thr Leu Tyr Glu Ile
            805                 810                 815
```

```
Leu Thr Glu Gln Val Cys Thr Gln Val Val His Lys Pro His Pro Glu
            820                 825                 830

Pro Asp Ser Thr Val Lys Ile Gln Asn Pro Met Ile Leu Lys Val Val
        835                 840                 845

Ala Thr Leu Leu Lys Asn Ser Thr Pro Ser Ala Glu Leu Met Glu Val
850                 855                 860

Arg Arg Leu Phe Leu Ser Asp Met Ile Lys Leu Phe Ser Asn Ser Arg
865                 870                 875                 880

Glu Asn Arg Arg Cys Leu Leu Gln Cys Ser Val Trp Gln Asp Trp Met
                885                 890                 895

Phe Ser Leu Gly Tyr Ile Asn Pro Lys Asn Ser Glu Glu Gln Lys Ile
            900                 905                 910

Thr Glu Met Val Tyr Asn Ile Phe Arg Ile Leu Leu Tyr His Ala Ile
            915                 920                 925

Lys Tyr Glu Trp Gly Gly Trp Arg Val Trp Val Asp Thr Leu Ser Ile
        930                 935                 940

Ala His Ser Lys Val Thr Tyr Glu Ala His Lys Glu Tyr Leu Ala Lys
945                 950                 955                 960

Met Tyr Glu Glu Tyr Gln Arg Gln Glu Glu Glu Asn Ile Lys Lys Gly
                965                 970                 975

Lys Lys Gly Asn Val Ser Thr Ile Ser Gly Leu Ser Ser Gln Thr Thr
            980                 985                 990

Gly Ala Lys Gly Gly Met Glu Ile  Arg Glu Ile Glu Asp  Leu Ser Gln
            995                 1000                1005

Ser Gln Ser Pro Glu Ser Glu  Thr Asp Tyr Pro Val  Ser Thr Asp
    1010                1015                1020

Thr Arg Asp Leu Leu Met Ser  Thr Lys Val Ser Asp  Asp Ile Leu
    1025                1030                1035

Gly Asn Ser Asp Arg Pro Gly  Ser Gly Val His Val  Glu Val His
    1040                1045                1050

Asp Leu Leu Val Asp Ile Lys  Ala Glu Lys Val Glu  Ala Thr Glu
    1055                1060                1065

Val Lys Leu Asp Asp Met Asp  Leu Ser Pro Glu Thr  Leu Val Gly
    1070                1075                1080

Gly Glu Asn Gly Ala Leu Val  Glu Val Glu Ser Leu  Leu Asp Asn
    1085                1090                1095

Val Tyr Ser Ala Ala Val Glu  Lys Leu Gln Asn Asn  Val His Gly
    1100                1105                1110

Ser Val Gly Ile Ile Lys Lys  Asn Glu Glu Lys Asp  Asn Gly Pro
    1115                1120                1125

Leu Ile Thr Leu Ala Asp Glu  Lys Glu Asp Leu Pro  Asn Ser Ser
    1130                1135                1140

Thr Ser Phe Leu Phe Asp Lys  Ile Pro Lys Gln Glu  Glu Lys Leu
    1145                1150                1155

Leu Pro Glu Leu Ser Ser Asn  His Ile Ile Pro Asn  Ile Gln Asp
    1160                1165                1170

Thr Gln Val His Leu Gly Val  Ser Asp Asp Leu Gly  Leu Leu Ala
    1175                1180                1185

His Met Thr Gly Ser Val Asp  Leu Thr Cys Thr Ser  Ser Ile Ile
    1190                1195                1200

Glu Glu Lys Glu Phe Lys Ile  His Thr Thr Ser Asp  Gly Met Ser
    1205                1210                1215

Ser Ile Ser Glu Arg Asp Leu  Ala Ser Ser Thr Lys  Gly Leu Glu
```

-continued

```
            1220                1225                1230

Tyr Ala Glu Met Thr Ala Thr Thr Leu Glu Thr Glu Ser Ser Ser
            1235                1240                1245

Ser Lys Ile Val Pro Asn Ile Asp Ala Gly Ser Ile Ile Ser Asp
            1250                1255                1260

Thr Glu Arg Ser Asp Asp Gly Lys Glu Ser Gly Lys Glu Ile Arg
            1265                1270                1275

Lys Ile Gln Thr Thr Thr Thr Gln Ala Val Gln Gly Arg Ser
            1280                1285                1290

Ile Thr Gln Gln Asp Arg Asp Leu Arg Val Asp Leu Gly Phe Arg
            1295                1300                1305

Gly Met Pro Met Thr Glu Glu Gln Arg Arg Gln Phe Ser Pro Gly
            1310                1315                1320

Pro Arg Thr Thr Met Phe Arg Ile Pro Glu Phe Lys Trp Ser Pro
            1325                1330                1335

Met His Gln Arg Leu Leu Thr Asp Leu Leu Phe Ala Leu Glu Thr
            1340                1345                1350

Asp Val His Val Trp Arg Ser His Ser Thr Lys Ser Val Met Asp
            1355                1360                1365

Phe Val Asn Ser Asn Glu Asn Ile Ile Phe Val His Asn Thr Ile
            1370                1375                1380

His Leu Ile Ser Gln Met Val Asp Asn Ile Ile Ile Ala Cys Gly
            1385                1390                1395

Gly Ile Leu Pro Leu Leu Ser Ala Ala Thr Ser Pro Thr Gly Ser
            1400                1405                1410

Lys Thr Glu Leu Glu Asn Ile Glu Val Thr Gln Gly Met Ser Ala
            1415                1420                1425

Glu Thr Ala Val Thr Phe Leu Ser Arg Leu Met Ala Met Val Asp
            1430                1435                1440

Val Leu Val Phe Ala Ser Ser Leu Asn Phe Ser Glu Ile Glu Ala
            1445                1450                1455

Glu Lys Asn Met Ser Ser Gly Gly Leu Met Arg Gln Cys Leu Arg
            1460                1465                1470

Leu Val Cys Cys Val Ala Val Arg Asn Cys Leu Glu Cys Arg Gln
            1475                1480                1485

Arg Gln Arg Asp Arg Gly Asn Lys Ser Ser His Gly Ser Ser Lys
            1490                1495                1500

Pro Gln Glu Val Pro Gln Ser Val Thr Ala Thr Ala Ser Lys
            1505                1510                1515

Thr Pro Leu Glu Asn Val Pro Gly Asn Leu Ser Pro Ile Lys Asp
            1520                1525                1530

Pro Asp Arg Leu Leu Gln Asp Val Asp Ile Asn Arg Leu Arg Ala
            1535                1540                1545

Val Val Phe Arg Asp Val Asp Ser Lys Gln Ala Gln Phe Leu
            1550                1555                1560

Ala Leu Ala Val Val Tyr Phe Ile Ser Val Leu Met Val Ser Lys
            1565                1570                1575

Tyr Arg Asp Ile Leu Glu Pro Gln Arg Glu Thr Thr Arg Thr Gly
            1580                1585                1590

Ser Gln Pro Gly Arg Asn Ile Arg Gln Glu Ile Asn Ser Pro Thr
            1595                1600                1605

Ser Thr Val Val Val Ile Pro Ser Ile Pro His Pro Ser Leu Asn
            1610                1615                1620
```

-continued

```
His Gly Phe Leu Ala Lys Leu Ile Pro Glu Gln Ser Phe Gly His
    1625              1630                1635

Ser Phe Tyr Lys Glu Thr Pro Ala Ala Phe Pro Asp Thr Ile Lys
    1640              1645                1650

Glu Lys Glu Thr Pro Thr Pro Gly Glu Asp Ile Gln Val Glu Ser
    1655              1660                1665

Ser Ile Pro His Thr Asp Ser Gly Ile Gly Glu Gln Val Ala
    1670              1675                1680

Ser Ile Leu Asn Gly Ala Glu Leu Glu Thr Ser Thr Gly Pro Asp
    1685              1690                1695

Ala Met Ser Glu Leu Leu Ser Thr Leu Ser Ser Glu Val Lys Lys
    1700              1705                1710

Ser Gln Glu Ser Leu Thr Glu Asn Pro Ser Glu Thr Leu Lys Pro
    1715              1720                1725

Ala Thr Ser Ile Ser Ser Ile Ser Gln Thr Lys Gly Ile Asn Val
    1730              1735                1740

Lys Glu Ile Leu Lys Ser Leu Val Ala Ala Pro Val Glu Ile Ala
    1745              1750                1755

Glu Cys Gly Pro Glu Pro Ile Pro Tyr Pro Asp Pro Ala Leu Lys
    1760              1765                1770

Arg Glu Thr Gln Ala Ile Leu Pro Met Gln Phe His Ser Phe Asp
    1775              1780                1785

Arg Ser Val Val Val Pro Val Lys Lys Pro Pro Gly Ser Leu
    1790              1795                1800

Ala Val Thr Thr Val Gly Ala Thr Thr Ala Gly Ser Gly Leu Pro
    1805              1810                1815

Thr Gly Ser Thr Ser Asn Ile Phe Ala Ala Thr Gly Ala Thr Pro
    1820              1825                1830

Lys Ser Met Ile Asn Thr Thr Gly Ala Val Asp Ser Gly Ser Ser
    1835              1840                1845

Ser Ser Ser Ser Ser Ser Ser Phe Val Asn Gly Ala Thr Ser Lys
    1850              1855                1860

Asn Leu Pro Ala Val Gln Thr Val Ala Pro Met Pro Glu Asp Ser
    1865              1870                1875

Ala Glu Asn Met Ser Ile Thr Ala Lys Leu Glu Arg Ala Leu Glu
    1880              1885                1890

Lys Val Ala Pro Leu Leu Arg Glu Ile Phe Val Asp Phe Ala Pro
    1895              1900                1905

Phe Leu Ser Arg Thr Leu Leu Gly Ser His Gly Gln Glu Leu Leu
    1910              1915                1920

Ile Glu Gly Leu Val Cys Met Lys Ser Ser Thr Ser Val Val Glu
    1925              1930                1935

Leu Val Met Leu Leu Cys Ser Gln Glu Trp Gln Asn Ser Ile Gln
    1940              1945                1950

Lys Asn Ala Gly Leu Ala Phe Ile Glu Leu Ile Asn Glu Gly Arg
    1955              1960                1965

Leu Leu Cys His Ala Met Lys Asp His Ile Val Arg Val Ala Asn
    1970              1975                1980

Glu Ala Glu Phe Ile Leu Asn Arg Gln Arg Ala Glu Asp Val His
    1985              1990                1995

Lys His Ala Glu Phe Glu Ser Gln Cys Ala Gln Tyr Ala Ala Asp
    2000              2005                2010
```

```
Arg Arg Glu Glu Glu Lys Met Cys Asp His Leu Ile Ser Ala Ala
    2015                2020                2025

Lys His Arg Asp His Val Thr Ala Asn Gln Leu Lys Gln Lys Ile
    2030                2035                2040

Leu Asn Ile Leu Thr Asn Lys His Gly Ala Trp Gly Ala Val Ser
    2045                2050                2055

His Ser Gln Leu His Asp Phe Trp Arg Leu Asp Tyr Trp Glu Asp
    2060                2065                2070

Asp Leu Arg Arg Arg Arg Phe Val Arg Asn Ala Phe Gly Ser
    2075                2080                2085

Thr His Ala Glu Ala Leu Leu Lys Ala Ala Ile Glu Tyr Gly Thr
    2090                2095                2100

Glu Glu Asp Val Val Lys Ser Lys Lys Thr Phe Arg Ser Gln Ala
    2105                2110                2115

Ile Val Asn Gln Asn Ala Glu Thr Glu Leu Met Leu Glu Gly Asp
    2120                2125                2130

Asp Asp Ala Val Ser Leu Leu Gln Glu Lys Glu Ile Asp Asn Leu
    2135                2140                2145

Ala Gly Pro Val Val Leu Ser Thr Pro Ala Gln Leu Ile Ala Pro
    2150                2155                2160

Val Val Val Ala Lys Gly Thr Leu Ser Ile Thr Thr Thr Glu Ile
    2165                2170                2175

Tyr Phe Glu Val Asp Glu Asp Ser Ala Phe Lys Lys Ile Asp
    2180                2185                2190

Thr Lys Val Leu Ala Tyr Thr Glu Gly Leu His Gly Lys Trp Met
    2195                2200                2205

Phe Ser Glu Ile Arg Ala Val Phe Ser Arg Arg Tyr Leu Leu Gln
    2210                2215                2220

Asn Thr Ala Leu Glu Val Phe Met Ala Asn Arg Thr Ser Val Met
    2225                2230                2235

Phe Asn Phe Pro Asp Gln Ala Thr Val Lys Lys Val Val Tyr Ser
    2240                2245                2250

Leu Pro Arg Val Gly Val Gly Thr Ser Tyr Gly Leu Pro Gln Ala
    2255                2260                2265

Arg Arg Ile Ser Leu Ala Thr Pro Arg Gln Leu Tyr Lys Ser Ser
    2270                2275                2280

Asn Met Thr Gln Arg Trp Gln Arg Arg Glu Ile Ser Asn Phe Glu
    2285                2290                2295

Tyr Leu Met Phe Leu Asn Thr Ile Ala Gly Arg Thr Tyr Asn Asp
    2300                2305                2310

Leu Asn Gln Tyr Pro Val Phe Pro Trp Val Leu Thr Asn Tyr Glu
    2315                2320                2325

Ser Glu Glu Leu Asp Leu Thr Leu Pro Gly Asn Phe Arg Asp Leu
    2330                2335                2340

Ser Lys Pro Ile Gly Ala Leu Asn Pro Lys Arg Ala Val Phe Tyr
    2345                2350                2355

Ala Glu Arg Tyr Glu Thr Trp Glu Asp Asp Gln Ser Pro Pro Tyr
    2360                2365                2370

His Tyr Asn Thr His Tyr Ser Thr Ala Thr Ser Thr Leu Ser Trp
    2375                2380                2385

Leu Val Arg Ile Glu Pro Phe Thr Thr Phe Phe Leu Asn Ala Asn
    2390                2395                2400

Asp Gly Lys Phe Asp His Pro Asp Arg Thr Phe Ser Ser Val Ala
```

-continued

```
              2405                2410                2415

Arg  Ser  Trp  Arg  Thr  Ser  Gln  Arg  Asp  Thr  Ser  Asp  Val  Lys  Glu
         2420                2425                2430

Leu  Ile  Pro  Glu  Phe  Tyr  Tyr  Leu  Pro  Glu  Met  Phe  Val  Asn  Ser
         2435                2440                2445

Asn  Gly  Tyr  Asn  Leu  Gly  Val  Arg  Glu  Asp  Glu  Val  Val  Val  Asn
         2450                2455                2460

Asp  Val  Asp  Leu  Pro  Pro  Trp  Ala  Lys  Lys  Pro  Glu  Asp  Phe  Val
         2465                2470                2475

Arg  Ile  Asn  Arg  Met  Ala  Leu  Glu  Ser  Glu  Phe  Val  Ser  Cys  Gln
         2480                2485                2490

Leu  His  Gln  Trp  Ile  Asp  Leu  Ile  Phe  Gly  Tyr  Lys  Gln  Arg  Gly
         2495                2500                2505

Pro  Glu  Ala  Val  Arg  Ala  Leu  Asn  Val  Phe  His  Tyr  Leu  Thr  Tyr
         2510                2515                2520

Glu  Gly  Ser  Val  Asn  Leu  Asp  Ser  Ile  Thr  Asp  Pro  Val  Leu  Arg
         2525                2530                2535

Glu  Ala  Met  Glu  Ala  Gln  Ile  Gln  Asn  Phe  Gly  Gln  Thr  Pro  Ser
         2540                2545                2550

Gln  Leu  Leu  Ile  Glu  Pro  His  Pro  Pro  Arg  Ser  Ser  Ala  Met  His
         2555                2560                2565

Leu  Cys  Phe  Leu  Pro  Gln  Ser  Pro  Leu  Met  Phe  Lys  Asp  Gln  Met
         2570                2575                2580

Gln  Gln  Asp  Val  Ile  Met  Val  Leu  Lys  Phe  Pro  Ser  Asn  Ser  Pro
         2585                2590                2595

Val  Thr  His  Val  Ala  Ala  Asn  Thr  Leu  Pro  His  Leu  Thr  Ile  Pro
         2600                2605                2610

Ala  Val  Val  Thr  Val  Thr  Cys  Ser  Arg  Leu  Phe  Ala  Val  Asn  Arg
         2615                2620                2625

Trp  His  Asn  Thr  Val  Gly  Leu  Arg  Gly  Ala  Pro  Gly  Tyr  Ser  Leu
         2630                2635                2640

Asp  Gln  Ala  His  His  Leu  Pro  Ile  Glu  Met  Asp  Pro  Leu  Ile  Ala
         2645                2650                2655

Asn  Asn  Ser  Gly  Val  Asn  Lys  Arg  Gln  Ile  Thr  Asp  Leu  Val  Asp
         2660                2665                2670

Gln  Ser  Ile  Gln  Ile  Asn  Ala  His  Cys  Phe  Val  Val  Thr  Ala  Asp
         2675                2680                2685

Asn  Arg  Tyr  Ile  Leu  Ile  Cys  Gly  Phe  Trp  Asp  Lys  Ser  Phe  Arg
         2690                2695                2700

Val  Tyr  Ser  Thr  Glu  Thr  Gly  Lys  Leu  Thr  Gln  Ile  Val  Phe  Gly
         2705                2710                2715

His  Trp  Asp  Val  Val  Thr  Cys  Leu  Ala  Arg  Ser  Glu  Ser  Tyr  Ile
         2720                2725                2730

Gly  Gly  Asp  Cys  Tyr  Ile  Val  Ser  Gly  Ser  Arg  Asp  Ala  Thr  Leu
         2735                2740                2745

Leu  Leu  Trp  Tyr  Trp  Ser  Gly  Arg  His  His  Ile  Ile  Gly  Asp  Asn
         2750                2755                2760

Pro  Asn  Ser  Ser  Asp  Tyr  Pro  Ala  Pro  Arg  Ala  Val  Leu  Thr  Gly
         2765                2770                2775

His  Asp  His  Glu  Val  Val  Cys  Val  Ser  Val  Cys  Ala  Glu  Leu  Gly
         2780                2785                2790

Leu  Val  Ile  Ser  Gly  Ala  Lys  Glu  Gly  Pro  Cys  Leu  Val  His  Thr
         2795                2800                2805
```

```
Ile Thr Gly Asp Leu Leu Arg Ala Leu Glu Gly Pro Glu Asn Cys
2810                2815                2820

Leu Phe Pro Arg Leu Ile Ser Val Ser Ser Glu Gly His Cys Ile
2825                2830                2835

Ile Tyr Tyr Glu Arg Gly Arg Phe Ser Asn Phe Ser Ile Asn Gly
2840                2845                2850

Lys Leu Leu Ala Gln Met Glu Ile Asn Asp Ser Thr Arg Ala Ile
2855                2860                2865

Leu Leu Ser Ser Asp Gly Gln Asn Leu Val Thr Gly Gly Asp Asn
2870                2875                2880

Gly Val Val Glu Val Trp Gln Ala Cys Asp Phe Lys Gln Leu Tyr
2885                2890                2895

Ile Tyr Pro Gly Cys Asp Ala Gly Ile Arg Ala Met Asp Leu Ser
2900                2905                2910

His Asp Gln Arg Thr Leu Ile Thr Gly Met Ala Ser Gly Ser Ile
2915                2920                2925

Val Ala Phe Asn Ile Asp Phe Asn Arg Trp His Tyr Glu His Gln
2930                2935                2940

Asn Arg Tyr
2945

<210> SEQ ID NO 67
<211> LENGTH: 4675
<212> TYPE: DNA
<213> ORGANISM: Homo sapiens

<400> SEQUENCE: 67
agatgacaga cacttctcaa aagacagctt ttcttcctgg agaacagact ttttcagcag    60
gattttcctt tcagtgaaac ataatttgac ttgaaaggaa cccagggaaa agtgtccagg   120
tgtgagcatg agcgggtaga ggtgtgccct tgtttgcttc aggctgtctg cttttcgccc   180
ctgactgttt tttctgtttc tggccatgga ggaagagaaa gatgacagcc acaggctga    240
cttctgcctg gcaccgcccc tgcactcttg ggactgtgg ttcacggagg aaggttcacc   300
gtccaccatg ctgacgggga ttgcagttgg agccctcctg gccctggcct tggttggtgt   360
cctcatcctt ttcatgttca gaaggcttag acaatttcga caagcacagc ccactcctca   420
gtaccggttc cggaagagag acaaagtgat gttttacggc cggaagatca tgaggaaggt   480
gaccacactc cccaacaccc ttgtggagaa cactgccctg ccccggcagc gggccaggaa   540
gaggaccaag gtgctgtctt tggccaagag gattctgcgc ttcaagaagg aatacccggc   600
cctgcagccc aaggagcccc cgccctccct gctggaggcc gacctcacgg agtttgacgt   660
gaagaattct cacctgccat cggaagttct gtacatgctg aaaaacgttc gggtcctggg   720
ccactttgag aagccgctgt tcctggagct ttgcaaacac atcgtctttg tgcagctgca   780
ggaaggggag cacgtcttcc agcccaggga gccggacccc agcatctgtg tggtgcagga   840
cgggcggctg gaggtctgca tccaggacac tgacggcacc gaggtggtgg tgaaagaggt   900
tctggcggga gacagcgtcc acagcctgct cagcatcctg gacatcatca ccggccatgc   960
tgcaccttac aaaacggtct ccgtccgcgc ggccatcccg tccaccatcc tccggcttcc  1020
agctgcggct tttcatggag ttttgagaa atatccggaa actctggtga gggtggtgca  1080
gatcatcatg gtgcggctgc agagggtgac ctttctggct ctgcacaact acctcggcct  1140
gaccacagag ctcttcaacg ctgagagcca ggccatccct ctcgtgtctg tagccagtgt  1200
```

```
ggctgccggg aaggccaaga agcaggtgtt ctatggcgaa aagagcggc ttaaaaagcc   1260
accgcggctc caggagtcct gtgactcaga tcacggggc ggccgcccgg cagctgctgg    1320
gccctgctg aagaggagcc actccgtccc cgcgccttcc attcgcaaac agatcttgga   1380
ggagctggag aagcccgggg caggtgaccc tgacccttcg gccccacaag ggggcccagg   1440
cagtgccact tctgatctgg ggatggcatg tgaccgtgcc agggtcttcc tgcactcgga   1500
cgagcacccc gggagctccg tggccagcaa gtccaggaaa agcgtgatgg ttgcagagat   1560
accctccacg gtctcccagc actcagagag tcacacggat gagaccctgg ccagcaggaa   1620
gtcggatgcc atcttcagag ctgccaagaa ggacctgctc accctgatga agctggaaga   1680
ctcatctctg ttggatggcc gggtggcgct tctgcacgtt cctgcaggca cggtggtgtc   1740
aaggcaggga gaccaggacg ccagcatcct gttcgtggtc tcgggctgc tgcacgtgta   1800
ccagcggaag atcggcagcc aggaggacac ctgcttgttc ctcacgcgcc ccggggagat   1860
ggtgggccag ctggccgtgc tcaccgggga gcctctcatc ttcaccgtca aggccaacag   1920
ggactgcagc ttcctgtcca tctccaaggc ccacttctat gaaatcatgc ggaagcagcc   1980
gaccgtcgtc ctgggtgtgg cgcacactgt ggtgaagagg atgtcgtcct tcgtgcggca   2040
aatcgacttt gccctggact gggtggaggt ggaggccggg cgagcaatat acaggcaggg   2100
ggacaagtcc gactgcacgt acatcatgct cagcggccgg ctgcgctctg tgatccggaa   2160
ggatgatggg aagaagcgcc tggccgggga gtacggccga ggagacctcg tcggcgtggt   2220
ggagacactg acccaccagg cccgggcgac cacggtgcat gccgttcggg actcagaatt   2280
ggccaagctg ccggcaggag ccctcacgtc catcaagcgc aggtacccac aggtggtgac   2340
tcggctgatt catctcttgg gtgagaagat cctgggcagc ctccagcagg acctgtgac    2400
aggccaccag cttgggctcc ccacggaggg cagcaagtgg gacttgggga acccggctgt   2460
caacctgtcc acggtggcag tgatgcccgt gtcagaggaa gtgcccctca ccgccttcgc   2520
cctggagctg gagcatgccc tcagcgccat cggcccgacc ctgctgctga ctagtgacaa   2580
cataaaacgg cgccttggct ccgctgccct ggacagtgtt cacgagtacc ggctgtccag   2640
ctggctgggg cagcaggagg acacccacag gatcgtgctc taccaggcag atggcacgct   2700
cacaccctgg acccagcgct gcgtgcgcca ggccgactgc atcctcatcg tgggcctggg   2760
tgaccaggag cccacagtgg gcgagctgga gcggatgctg gagagcacag ctgtgcgtgc   2820
ccagaagcag ctgatcctgc tgcacaggga ggagggcccg gcgccagcgc gcaccgtgga   2880
gtggctcaac atgcggagct ggtgctccgg ccacctgcac ctctgctgcc cgcgccgcgt   2940
cttctccagg aggagcctgc ccaagctggt ggagatgtac aagcatgtct tccagcggcc   3000
cccggaccga cactcagact tctcccgcct ggcgagggtg ctgacgggca cgccattgc    3060
cctggtgctt gggggagggg gagcaagagg ctgtgcccag gtgggcgttc tcaaggcctt   3120
ggcggagtgc ggcatccctg tggacatggt gggaggcacg tccatcgggg ccttcgtggg   3180
tgccctgtac tctgaggagc ggaactacag ccagatgcgg atccgggcca agcagtgggc   3240
cgagggcatg acgtccttga tgaaggccgc gctggacctc acctacccca tcacgtccat   3300
gttctccgga gccggcttca acagcagcat cttcagcgtc ttcaaggacc agcagatcga   3360
ggacctgtgg attccttatt cgccatcac caccgacatc acagcctcgg ccatgcgggt   3420
ccacaccgac ggctccctgt ggtggtacgt gcgtgccagc atgtccctgt ccggttacat   3480
gcccctctc tgtgacccga aggacggaca cctgctgatg gacgggggct acatcaacaa   3540
cctcccagcg gatgtggccc ggtccatggg ggcaaaagtg gtgatcgcca ttgacgtggg   3600
```

```
cagccgagat gagacggacc tcaccaacta tggggatgcg ctgtctgggt ggtggctgct   3660
gtggaaacgc tggaacccct tggccacgaa agtcaaggtg ttgaacatgg cagagattca   3720
gacgcgcctg gcctacgtgt gttgcgtgcg gcagctggag gtggtgaaga gcagtgacta   3780
ctgcgagtac ctgcgccccc ccatcgacag ctacagcacc ctggacttcg caagttcaa    3840 cgagatctgc gaagtgggct accagcacgg gcgcacggtg tttgacatct ggggccgcag   3900
cggcgtgctg gagaagatgc tccgcgacca gcaggggccg agcaagaagc ccgcgagtgc   3960
ggtcctcacc tgtcccaacg cctccttcac ggaccttgcc gaaattgtgt ctcgcattga   4020
gcccgccaag cccgccatgg tggatgacga atctgactac agacggagt acgaggagga    4080 gctgctggac gtccccaggg atgcatacgc agacttccag agcacctcag cccagcaggg   4140
ctcagacttg gaggacgagt cctcactgcg gcatcgacac cccagtctgg ctttcccaaa   4200
actgtctgag ggctcctctg accaggacgg gtagaggcct ctgctaaaga gcccggatgc   4260
agcgtcttcc gtgggactgt ccccaaggct gaggctcctg ccaagtccta ggggcctctg   4320
tacctgccct gctggaagcc ctgacttccc cggggcccca ggctgtgtta gggttctctg   4380
ggcctcttct ttgtaccagc agccctgcat acagggccct gtgagccccc ctgcagtcct   4440
gtgaggcccc tgaagctctg tgaggcccct gaagctctgt gaaccccctg cagccctgtg   4500 aggcccccg aagccctgtg aggcccccg aagccctgtg aaccaccgc tgccctgtga     4560 ggcccccaaa gccctgtgaa ctgcctgctg tcctgtgaac tgcctgctgc cctgtgaggt   4620
gtgggagccc tgatgctgcc gtgtgatgtt tcaataaagg tggatctcac tgttg        4675
```

<210> SEQ ID NO 68
<211> LENGTH: 1317
<212> TYPE: PRT
<213> ORGANISM: Homo sapiens

<400> SEQUENCE: 68

```
Met Glu Glu Glu Lys Asp Asp Ser Pro Gln Leu Thr Gly Ile Ala Val
1               5                   10                  15

Gly Ala Leu Leu Ala Leu Ala Leu Val Gly Val Leu Ile Leu Phe Met
            20                  25                  30

Phe Arg Arg Leu Arg Gln Phe Arg Gln Ala Gln Pro Thr Pro Gln Tyr
        35                  40                  45

Arg Phe Arg Lys Arg Asp Lys Val Met Phe Tyr Gly Arg Lys Ile Met
    50                  55                  60

Arg Lys Val Thr Thr Leu Pro Asn Thr Leu Val Glu Asn Thr Ala Leu
65                  70                  75                  80

Pro Arg Gln Arg Ala Arg Lys Arg Thr Lys Val Leu Ser Leu Ala Lys
                85                  90                  95

Arg Ile Leu Arg Phe Lys Lys Glu Tyr Pro Ala Leu Gln Pro Lys Glu
            100                 105                 110

Pro Pro Pro Ser Leu Leu Glu Ala Asp Leu Thr Glu Phe Asp Val Lys
        115                 120                 125

Asn Ser His Leu Pro Ser Glu Val Leu Tyr Met Leu Lys Asn Val Arg
    130                 135                 140

Val Leu Gly His Phe Glu Lys Pro Leu Phe Leu Glu Leu Cys Lys His
145                 150                 155                 160

Ile Val Phe Val Gln Leu Gln Glu Gly Glu His Val Phe Gln Pro Arg
                165                 170                 175

Glu Pro Asp Pro Ser Ile Cys Val Val Gln Asp Gly Arg Leu Glu Val
```

-continued

```
                180                 185                 190
Cys Ile Gln Asp Thr Asp Gly Thr Glu Val Val Lys Glu Val Leu
            195                 200                 205
Ala Gly Asp Ser Val His Ser Leu Leu Ser Ile Leu Asp Ile Ile Thr
            210                 215                 220
Gly His Ala Ala Pro Tyr Lys Thr Val Ser Val Arg Ala Ala Ile Pro
225                 230                 235                 240
Ser Thr Ile Leu Arg Leu Pro Ala Ala Ala Phe His Gly Val Phe Glu
                245                 250                 255
Lys Tyr Pro Glu Thr Leu Val Arg Val Gln Ile Ile Met Val Arg
            260                 265                 270
Leu Gln Arg Val Thr Phe Leu Ala Leu His Asn Tyr Leu Gly Leu Thr
            275                 280                 285
Thr Glu Leu Phe Asn Ala Glu Ser Gln Ala Ile Pro Leu Val Ser Val
            290                 295                 300
Ala Ser Val Ala Ala Gly Lys Ala Lys Lys Gln Val Phe Tyr Gly Glu
305                 310                 315                 320
Glu Glu Arg Leu Lys Lys Pro Pro Arg Leu Gln Glu Ser Cys Asp Ser
                325                 330                 335
Asp His Gly Gly Gly Arg Pro Ala Ala Ala Gly Pro Leu Leu Lys Arg
                340                 345                 350
Ser His Ser Val Pro Ala Pro Ser Ile Arg Lys Gln Ile Leu Glu Glu
            355                 360                 365
Leu Glu Lys Pro Gly Ala Gly Asp Pro Asp Pro Ser Ala Pro Gln Gly
            370                 375                 380
Gly Pro Gly Ser Ala Thr Ser Asp Leu Gly Met Ala Cys Asp Arg Ala
385                 390                 395                 400
Arg Val Phe Leu His Ser Asp Glu His Pro Gly Ser Ser Val Ala Ser
                405                 410                 415
Lys Ser Arg Lys Ser Val Met Val Ala Glu Ile Pro Ser Thr Val Ser
            420                 425                 430
Gln His Ser Glu Ser His Thr Asp Glu Thr Leu Ala Ser Arg Lys Ser
            435                 440                 445
Asp Ala Ile Phe Arg Ala Ala Lys Lys Asp Leu Leu Thr Leu Met Lys
450                 455                 460
Leu Glu Asp Ser Ser Leu Leu Asp Gly Arg Val Ala Leu Leu His Val
465                 470                 475                 480
Pro Ala Gly Thr Val Val Ser Arg Gln Gly Asp Gln Asp Ala Ser Ile
                485                 490                 495
Leu Phe Val Val Ser Gly Leu Leu His Val Tyr Gln Arg Lys Ile Gly
            500                 505                 510
Ser Gln Glu Asp Thr Cys Leu Phe Leu Thr Arg Pro Gly Glu Met Val
            515                 520                 525
Gly Gln Leu Ala Val Leu Thr Gly Glu Pro Leu Ile Phe Thr Val Lys
            530                 535                 540
Ala Asn Arg Asp Cys Ser Phe Leu Ser Ile Ser Lys Ala His Phe Tyr
545                 550                 555                 560
Glu Ile Met Arg Lys Gln Pro Thr Val Val Leu Gly Val Ala His Thr
                565                 570                 575
Val Val Lys Arg Met Ser Ser Phe Val Arg Gln Ile Asp Phe Ala Leu
            580                 585                 590
Asp Trp Val Glu Val Glu Ala Gly Arg Ala Ile Tyr Arg Gln Gly Asp
            595                 600                 605
```

Lys Ser Asp Cys Thr Tyr Ile Met Leu Ser Gly Arg Leu Arg Ser Val
610                 615                 620

Ile Arg Lys Asp Asp Gly Lys Lys Arg Leu Ala Gly Glu Tyr Gly Arg
625                 630                 635                 640

Gly Asp Leu Val Gly Val Val Glu Thr Leu Thr His Gln Ala Arg Ala
                645                 650                 655

Thr Thr Val His Ala Val Arg Asp Ser Glu Leu Ala Lys Leu Pro Ala
                660                 665                 670

Gly Ala Leu Thr Ser Ile Lys Arg Arg Tyr Pro Gln Val Val Thr Arg
                675                 680                 685

Leu Ile His Leu Leu Gly Glu Lys Ile Leu Gly Ser Leu Gln Gln Gly
690                 695                 700

Pro Val Thr Gly His Gln Leu Gly Leu Pro Thr Glu Gly Ser Lys Trp
705                 710                 715                 720

Asp Leu Gly Asn Pro Ala Val Asn Leu Ser Thr Val Ala Val Met Pro
                725                 730                 735

Val Ser Glu Glu Val Pro Leu Thr Ala Phe Ala Leu Glu Leu Glu His
                740                 745                 750

Ala Leu Ser Ala Ile Gly Pro Thr Leu Leu Thr Ser Asp Asn Ile
                755                 760                 765

Lys Arg Arg Leu Gly Ser Ala Ala Leu Asp Ser Val His Glu Tyr Arg
770                 775                 780

Leu Ser Ser Trp Leu Gly Gln Gln Glu Asp Thr His Arg Ile Val Leu
785                 790                 795                 800

Tyr Gln Ala Asp Gly Thr Leu Thr Pro Trp Thr Gln Arg Cys Val Arg
                805                 810                 815

Gln Ala Asp Cys Ile Leu Ile Val Gly Leu Gly Asp Gln Glu Pro Thr
                820                 825                 830

Val Gly Glu Leu Glu Arg Met Leu Glu Ser Thr Ala Val Arg Ala Gln
                835                 840                 845

Lys Gln Leu Ile Leu Leu His Arg Glu Glu Gly Pro Ala Pro Ala Arg
850                 855                 860

Thr Val Glu Trp Leu Asn Met Arg Ser Trp Cys Ser Gly His Leu His
865                 870                 875                 880

Leu Cys Cys Pro Arg Arg Val Phe Ser Arg Ser Leu Pro Lys Leu
                885                 890                 895

Val Glu Met Tyr Lys His Val Phe Gln Arg Pro Pro Asp Arg His Ser
                900                 905                 910

Asp Phe Ser Arg Leu Ala Arg Val Leu Thr Gly Asn Ala Ile Ala Leu
                915                 920                 925

Val Leu Gly Gly Gly Gly Ala Arg Gly Cys Ala Gln Val Gly Val Leu
930                 935                 940

Lys Ala Leu Ala Glu Cys Gly Ile Pro Val Asp Met Val Gly Gly Thr
945                 950                 955                 960

Ser Ile Gly Ala Phe Val Gly Ala Leu Tyr Ser Glu Glu Arg Asn Tyr
                965                 970                 975

Ser Gln Met Arg Ile Arg Ala Lys Gln Trp Ala Glu Gly Met Thr Ser
                980                 985                 990

Leu Met Lys Ala Ala Leu Asp Leu Thr Tyr Pro Ile Thr Ser Met Phe
                995                 1000                1005

Ser Gly Ala Gly Phe Asn Ser Ser Ile Phe Ser Val Phe Lys Asp
        1010                1015                1020

| | | | | | | | | | | | |
|---|---|---|---|---|---|---|---|---|---|---|---|
| Gln | Gln | Ile | Glu | Asp | Leu | Trp | Ile | Pro | Tyr | Phe | Ala | Ile | Thr | Thr |
| 1025 | | | | | 1030 | | | | | 1035 | | | | |

Gln Gln Ile Glu Asp Leu Trp Ile Pro Tyr Phe Ala Ile Thr Thr
 1025                1030               1035

Asp Ile Thr Ala Ser Ala Met Arg Val His Thr Asp Gly Ser Leu
 1040                1045               1050

Trp Trp Tyr Val Arg Ala Ser Met Ser Leu Ser Gly Tyr Met Pro
 1055                1060               1065

Pro Leu Cys Asp Pro Lys Asp Gly His Leu Leu Met Asp Gly Gly
 1070                1075               1080

Tyr Ile Asn Asn Leu Pro Ala Asp Val Ala Arg Ser Met Gly Ala
 1085                1090               1095

Lys Val Val Ile Ala Ile Asp Val Gly Ser Arg Asp Glu Thr Asp
 1100                1105               1110

Leu Thr Asn Tyr Gly Asp Ala Leu Ser Gly Trp Trp Leu Leu Trp
 1115                1120               1125

Lys Arg Trp Asn Pro Leu Ala Thr Lys Val Lys Val Leu Asn Met
 1130                1135               1140

Ala Glu Ile Gln Thr Arg Leu Ala Tyr Val Cys Cys Val Arg Gln
 1145                1150               1155

Leu Glu Val Val Lys Ser Ser Asp Tyr Cys Glu Tyr Leu Arg Pro
 1160                1165               1170

Pro Ile Asp Ser Tyr Ser Thr Leu Asp Phe Gly Lys Phe Asn Glu
 1175                1180               1185

Ile Cys Glu Val Gly Tyr Gln His Gly Arg Thr Val Phe Asp Ile
 1190                1195               1200

Trp Gly Arg Ser Gly Val Leu Glu Lys Met Leu Arg Asp Gln Gln
 1205                1210               1215

Gly Pro Ser Lys Lys Pro Ala Ser Ala Val Leu Thr Cys Pro Asn
 1220                1225               1230

Ala Ser Phe Thr Asp Leu Ala Glu Ile Val Ser Arg Ile Glu Pro
 1235                1240               1245

Ala Lys Pro Ala Met Val Asp Asp Glu Ser Asp Tyr Gln Thr Glu
 1250                1255               1260

Tyr Glu Glu Glu Leu Leu Asp Val Pro Arg Asp Ala Tyr Ala Asp
 1265                1270               1275

Phe Gln Ser Thr Ser Ala Gln Gln Gly Ser Asp Leu Glu Asp Glu
 1280                1285               1290

Ser Ser Leu Arg His Arg His Pro Ser Leu Ala Phe Pro Lys Leu
 1295                1300               1305

Ser Glu Gly Ser Ser Asp Gln Asp Gly
 1310                1315

<210> SEQ ID NO 69
<211> LENGTH: 982
<212> TYPE: DNA
<213> ORGANISM: Homo sapiens

<400> SEQUENCE: 69
acagcccacc agtgaccacg aaggctgtgc tgcttgccct gttgatggca ggcttggccc    60
tgcagccagg cactgccctg ctgtgctact cctgcaaagc ccaggtgagc aacgaggact   120
gcctgcaggt ggagaactgc acccagctgg gggagcagtg ctggaccgcg cgcatccgcg   180
cagttggcct cctgaccgtc atcagcaaag gctgcagctt gaactgcgtg gatgactcac   240
aggactacta cgtgggcaag aagaacatca cgtgctgtga caccgacttg tgcaacgcca   300
gcggggccca tgccctgcag ccggctgctg ccatccttgc gctgctccct gcactcggcc   360

```
tgctgctctg gggacccggc cagctctagg ctctgggggg ccccgctgca gcccacactg      420
ggtgtggtgc cccaggcctc tgtgccactc ctcacacacc cggcccagtg ggagcctgtc      480
ctggttcctg aggcacatcc taacgcaagt ctgaccatgt atgtctgcgc ccctgtcccc      540 cacccctgacc ctcccatggc cctctccagg actcccaccc ggcagatcgg ctctattgac     600
acagatccgc ctgcagatgg cccctccaac cctctctgct gctgtttcca tggcccagca      660
ttctccaccc ttaaccctgt gctcaggcac ctcttccccc aggaagcctt ccctgcccac      720
cccatctatg acttgagcca ggtctggtcc gtggtgtccc ccgcacccag caggggacag      780
gcactcagga gggcccggta aaggctgaga tgaagtggac tgagtagaac tggaggacag      840
gagtcgacgt gagttcctgg gagtctccag agatgggggcc tggaggcctg aggaagggg     900 ccaggcctca cattcgtggg gctccctgaa tggcagcctc agcacagcgt aggcccttaa      960
taaacacctg ttggataagc ca                                              982
```

<210> SEQ ID NO 70
<211> LENGTH: 114
<212> TYPE: PRT
<213> ORGANISM: Homo sapiens

<400> SEQUENCE: 70

```
Met Ala Gly Leu Ala Leu Gln Pro Gly Thr Ala Leu Leu Cys Tyr Ser
1               5                   10                  15

Cys Lys Ala Gln Val Ser Asn Glu Asp Cys Leu Gln Val Glu Asn Cys
            20                  25                  30

Thr Gln Leu Gly Glu Gln Cys Trp Thr Ala Arg Ile Arg Ala Val Gly
        35                  40                  45

Leu Leu Thr Val Ile Ser Lys Gly Cys Ser Leu Asn Cys Val Asp Asp
    50                  55                  60

Ser Gln Asp Tyr Tyr Val Gly Lys Lys Asn Ile Thr Cys Cys Asp Thr
65                  70                  75                  80

Asp Leu Cys Asn Ala Ser Gly Ala His Ala Leu Gln Pro Ala Ala Ala
                85                  90                  95

Ile Leu Ala Leu Leu Pro Ala Leu Gly Leu Leu Trp Gly Pro Gly Pro
            100                 105                 110

Gln Leu
```

<210> SEQ ID NO 71
<211> LENGTH: 7273
<212> TYPE: DNA
<213> ORGANISM: Homo sapiens

<400> SEQUENCE: 71

```
aaccctgcct gaactttcct gtaaacagcc actgacagac tgcatccctg ctgggtggat      60
cctgcgactc ctagagggaa tggcacttct tgttttttaat tagcaaggtg aaaggtgaat    120
taaaactagc agtttggcaa gtcagtgcaa gaggctgact tctgagaggc ttccaggagc    180
ccgaagagag gacctccacg ggagaaggga gtgcgtgtgc tcggttttgt ttttttctct    240
cttttttttt ttttttttctg aatgaacagc tttgcccaag tgactgaaaa atacagcttc   300
ttcctgaatc taccggcgta gttgctgaag agcgctctag acaggacatg gctctgaaga    360
ctcactcttt ggaatgtcct cttgctcccg gcttataaac aactgtcccg aggaaagaaa    420
ggttttacat agccaaatac agcctgacaa atggcacttc ggaactgtgc tttctgatga    480
caacgcgttc gatttctgac aaagcctctc gcacgctgcc cctggaggga agtcctaagt    540
```

```
aaaactcaga ccctccttaa agtgaggagc gagggcttgg acggtgaaca cggcagcatg    600
gcatccgcgg ggcacattat caccttgctc ctgtggggtt acttactgga gctttggaca    660
ggaggtcata cagctgatac tacccacccc cggttacgcc tgtcacataa agagctcttg    720
aatctgaaca gaacatcaat atttcatagc ccttttggat ttcttgatct ccatacaatg    780
ctgctggatg aatatcaaga gaggctcttc gtgggaggca gggaccttgt atattccctc    840
agcttggaga gaatcagtga cggctataaa gagatacact ggccgagtac agctctaaaa    900
atggaagaat gcataatgaa gggaaaagat gcgggtgaat gtgcaaatta tgttcgggtt    960
ttgcatcact ataacaggac acaccttctg acctgtggta ctggagcttt tgatccagtt   1020
tgtgccttca tcagagttgg atatcatttg gaggatcctc tgtttcacct ggaatcaccc   1080
agatctgaga gaggaagggg cagatgtcct tttgaccccca gctcctcctt catctccact   1140
ttaattggta gtgaattgtt tgctggactc tacagtgact actggagcag agacgctgcg   1200
atcttccgca gcatggggcg actggcccat atccgcactg agcatgacga tgagcgtctg   1260
ttgaaagaac caaaatttgt aggttcatac atgattcctg acaatgaaga cagagatgac   1320
aacaaagtat atttcttttt tactgagaag gcactggagg cagaaaacaa tgctcacgca   1380
atttacacca gggtcgggcg actctgtgtg aatgatgtag gagggcagag aatactggtg   1440
aataagtgga gcactttcct aaaagcgaga ctcgtttgct cagtaccagg aatgaatgga   1500
attgacacat attttgatga attagaggac gttttttttgc tacctaccag agatcataag   1560
aatccagtga tatttggact ctttaacact accagtaata ttttttcgagg gcatgctata   1620 tgtgtctatc acatgtctag cattcgggca gccttcaacg gaccatatgc acataaggaa   1680
ggacctgaat accactggtc agtctatgaa ggaaaagtcc cttatccaag gcctggttct   1740
tgtgccagca aagtaaatgg agggagatac ggaaccacca aggactatcc tgatgatgcc   1800
atccgatttg caagaagtca tccactaatg taccaggcca taaaacctgc cataaaaaaa   1860
ccaatattgg taaaaacaga tggaaaatat aacctgaaac aaatagcagt agatcgagtg   1920
gaagctgagg atggccaata tgacgtcttg tttattggga cagataatgg aattgtgctg   1980
aaagtaatca caatttacaa ccaagaaatg gaatcaatgg aagaagtaat tctagaagaa   2040
cttcagatat tcaaggatcc agttcctatt atttctatgg agatttcttc aaagcggcaa   2100
cagctgtata ttggatctgc ttctgctgtg gctcaagtca gattccatca ctgtgacatg   2160 tatgaagtg cttgtgctga ctgctgcctg gctcgagacc cttactgtgc ctgggatggc   2220
atatcctgct cccggtatta cccaacaggc acacatgcaa aaaggcgttt ccggagacaa   2280
gatgttcgac atggaaatgc agctcagcag tgctttggac aacagtttgt tggggatgct   2340
ttggataaga ctgaagaaca tctggcttat ggcatagaga caacagtac tttgctggaa   2400 tgtaccccac gatctttaca agcgaaagtt atctggtttg tacagaaagg acgtgagaca   2460
agaaaagagg aggtgaagac agatgacaga gtggttaaga tggaccttgg tttactcttc   2520
ctaaggttac acaaatcaga tgctgggacc tatttttgcc agacagtaga gcatagcttt   2580
gtccatacgg tccgtaaaat caccttggag gtagtggaag aggagaaagt cgaggatatg   2640
tttaacaagg acgatgagga ggacaggcat cacaggatgc cttgtcctgc tcagagtagc   2700
atctcgcagg gagcaaaacc atggtacaag gaattcttgc agctgatcgg ttatagcaac   2760
ttccagagag tggaagaata ctgcgagaaa gtatggtgca cagatagaaa gaggaaaaag   2820
cttaaaatgt caccctccaa gtggaagtat gccaacccctc aggaaaagaa gctccgttcc   2880
```

```
aaacctgagc attaccgcct gcccaggcac acgctggact cctgatgggg tgagactatc    2940
tactgtcttt tgaagaattt atatttggaa agtaaaaaag taaaaaaata aatcatccaa    3000
cttctttgca ttacttaaaa gagatttctg taatacagga atgactatga aggtgttata    3060
ataaattatt ctacatactc atttgactgg ataaacttta cataaaatta actaattttt    3120
taaataaatg cattgcttaa tggtttctca ttatgtttat caaaaaacaa ctgtagctgt    3180
tattttcagt acttggctgc ttttctgtga aaattattat tttacttttg gaagacaaga    3240
ttattagaat attgaagaaa aattggagac ttataatcat ggtaaatata aaactaaata    3300
tgttttaata tttctgaatt tttcttttcc atcacaatgt aagatatgca gaatacaaga    3360
tactttggca ttctcatgtg aactttctgt actctttaag gattatttta ttagtgttgt    3420
ttaagccatg agtgttaagt agcaggtgtg ttgtgagtgc tgtaacccat gaaaggaaaa    3480
atgtcattct gaggcttgtg cccttcgtaa aatattcatt aaagtacatt cacactattt    3540
ttgctttata acacagtctt taattttcac tcactgtgga aataaaaact aaggtaactt    3600
ctcagaaaga tatcaaatct cagaaagaat gtcaaatcag atgaagttat agttaggatt    3660
ctaactactg taaagatttt ttgcttcccct cttgtggtaa aaaaaattat attctcacac    3720
atttctttt tctctacaga cggatatctg tttaggaaag atttgaaagc agattatcag    3780
taggtacatg gatacatcaa gttcatttgc agaaacaaat aactgaaata aaaaacatgt    3840
taatccttgt atcatacttt aatatgaaag tattgtttat agataattta tctcacaagt    3900
caaaaatgaa gattttgcag cactgaaaat ctattaaagc tccaaatttt aagtttctaa    3960
ataatcttcg ctgaaatcta aaatatacta taacaaccgt gttttatttg tgaaaaaaat    4020
attaaagtga tttgctctca aatatcaaat tttcttctct cttttatatt aagagacaga    4080
aaattgtttc atgagttcac ttaactactg agatattcag agcatttta cctctctctt    4140
aaatgttata aaaacaatt gtattttaa gaatgtttat ttatcaaagt ctttccttct    4200
tctattaaat atttagcaat taccttccta aaatatgaaa ttttgtaaga tgttttcacc    4260
taaataaaaa ttgaaagcaa gtggattaca caggagaacc attatgaaca tttatttaga    4320
tattaatctt aaacagtgtt tatttcagtt ttcaaagtta gcttataggt tatacattta    4380
agttaaagtg ctcataatca cttgcaattt cattgtaaaa tgaacaaata cataaatatt    4440
ttaagaaaaa tttaagttta ttcagataag tcaccatgct tcaaaagatc taagaaatgc    4500
aaatatactg aaaattgaca tcctctgaaa attccacttg ctatttaccc aagaatccac    4560
tggaggtcat tactgccatt aaataataac tgaaaagact atgtagtgaa atgtattttt    4620
aaaaactata ttcagtaaaa gcctgctcaa tttggagaaa tagaaccaca aacacagatc    4680
acagggcct tacaaagttt atgtctgaac aaataagtca attaagtaca ctttattgaa    4740
aattgccttc cattaacaca caagaaagaa agcaggattt tctcctgtat ctgaattta    4800
aaattaaaaa ggcagataag acataaatag ttatcatttt aattgcaata acacagacaa    4860
gtagttaatg atgataacaa tggtgtaact tgtaaactaa atatttggta actgaagcaa    4920
taggcagagg aaaatagctt ttctatgaca caagtcataa gaagtccata tactgaagag    4980
cgtttgatta aaataaagtg actattaacc agaaagaaa cattttacat aaaatgctaa    5040
aatttattat aggaaaataa atcaaaccca agaaagttt attcaatgct aatttgaaag    5100
aaaattgata agaaaacttt gagggcccaa gtccacaatt tggtgagacc actaaatttt    5160
acatataatt atacacacac atatgtacat atatatgtat ataatcttgc ttcccgcctg    5220
tttatggcag tactgaagag aaatgggaaa gaagagggag ggagagagaa agacgaaggg    5280
```

| | | | |
|---|---|---|---|
| agagagaaag cagtttccaa ggatatgttt catgtcccac cattttctca gtttctccct | | | 5340 |
| ctctctccca acacacacac acacacaccc ctcacatact ataaataaa tcttcactgc | | | 5400 |
| cctatcaaaa tacaaataaa tcaatctatg ctgttctgtc cttcttgaga atctaaaaca | | | 5460 |
| taccacaaaa atacatcccc agtcttttgt tctgtctgag gttagaatta attcaaattc | | | 5520 |
| agaatctgtt gtgagaaatg cccaggcttt aaaaattaaa aatggatgga tcttctctga | | | 5580 |
| actcagggag ggcacatact tagataccta caagacttgg aggaattaag agttcaccct | | | 5640 |
| tcatctcacc aaattttccc cattttctc tttcttgtag aaggagagaa accatgctct | | | 5700 |
| ctagcaacat tgagcaaaaa tcataaccac tcatctaatt tctaagaggc acctccatcg | | | 5760 |
| agggccggtc tcctgcttct ttagacctct tctatctttg ttacaggaga ggacctgtgg | | | 5820 |
| atagacttag ttttgacata aaacaatgcc cattcacctc ctccttcagc acaacgtcac | | | 5880 |
| ccattgggca agagatccag atttgttaac aaaaaagatt ttacttcgtg attccacgtc | | | 5940 |
| tataattcta tattgctaat tttttctttt gtgtgaatta ctgaatattt cagagcaaag | | | 6000 |
| ctatcaactt ggagaaacag ggattaaaaa taaggataaa cactaataag agctctagaa | | | 6060 |
| aaaagggaac agaaagtctg cctgtttagt aagtggcaat tccatacata ttttagagtt | | | 6120 |
| ttttctatct aaaattagtt aaatacttag aatgtttgta atgagtgttc gatatttgct | | | 6180 |
| ataggtttta gggttttgta aatcttcata gtaattataa acatttgtaa aatttgtaaa | | | 6240 |
| atactataag tcattttgag tgttggtgtt aagcatgaaa caaacagcag ctgttgtcct | | | 6300 |
| taaaaatgaa ttgacctggc cgggcgcggt ggctcacgcc tgtaatccca gcactttggg | | | 6360 |
| aggccgaggc gggtggatca tgaggtcagg agatcgagac catcctggct aacaaggtga | | | 6420 |
| aaccccgtct ctactaaaaa tacaaaaaat tagccgggcg cggtggcggg cgcctgtagt | | | 6480 |
| cccagctact tgggaggctg aggcaggaga atggcgtgaa cccgggaagc ggagcttgca | | | 6540 |
| gtgagccgag attgcgccac tgcagtccgc agtccggcct gggcgacaga gcgagactcc | | | 6600 |
| gtctcaaaaa aaaaaaaaaa aaaaaaaaaa aaaaaaaaaa aaaaaaaaaa tgaattgacc | | | 6660 |
| tgtgacacct gtagcctaat aaacatatta agaaaagtac ttagtattgt atagatattt | | | 6720 |
| ggattccaag agaaaatgca acatttataa taagaagtcc atactctttt tcttacagca | | | 6780 |
| gagcgtcaca ctgagttcca ttttaaaaaa ggactcattt ttcaggccaa caactgttgc | | | 6840 |
| atttgaatca gatataaata atagattttc cacaaacact cagctgattg tagcagtgtt | | | 6900 |
| atttaagctg gtatgtttat tttttttttc ttggaaggat agctttatat tttggctttc | | | 6960 |
| attataaatt gtgttctgct tgtgtttaaa tggcttactt ataagctaga gcactatatg | | | 7020 |
| ggagtgttct tctctgtatg gtatccttt atttgcttgg ctgggttcat aacagtgtgt | | | 7080 |
| gccatattct ttcttttcac tgattctaag ccatgagact tattagcatc tggtggcaag | | | 7140 |
| ctgcagggac cattaacagt gtgtctcttt gactacaacg tggatctgcc actacgcgct | | | 7200 |
| atgtaccatt atgtacaatc tctatttggc tcaacttcga tgaaaagaa ataaatattt | | | 7260 |
| gctaaactct caa | | | 7273 |

<210> SEQ ID NO 72
<211> LENGTH: 775
<212> TYPE: PRT
<213> ORGANISM: Homo sapiens

<400> SEQUENCE: 72

Met Ala Ser Ala Gly His Ile Ile Thr Leu Leu Leu Trp Gly Tyr Leu
1               5                   10                  15

-continued

Leu Glu Leu Trp Thr Gly Gly His Thr Ala Asp Thr His Pro Arg
            20              25              30

Leu Arg Leu Ser His Lys Glu Leu Asn Leu Asn Arg Thr Ser Ile
        35              40              45

Phe His Ser Pro Phe Gly Phe Leu Asp Leu His Thr Met Leu Asp
50              55              60

Glu Tyr Gln Glu Arg Leu Phe Val Gly Gly Arg Asp Leu Val Tyr Ser
65              70              75              80

Leu Ser Leu Glu Arg Ile Ser Asp Gly Tyr Lys Glu Ile His Trp Pro
            85              90              95

Ser Thr Ala Leu Lys Met Glu Glu Cys Ile Met Lys Gly Lys Asp Ala
            100             105             110

Gly Glu Cys Ala Asn Tyr Val Arg Val Leu His His Tyr Asn Arg Thr
            115             120             125

His Leu Leu Thr Cys Gly Thr Gly Ala Phe Asp Pro Val Cys Ala Phe
130             135             140

Ile Arg Val Gly Tyr His Leu Glu Asp Pro Leu Phe His Leu Glu Ser
145             150             155             160

Pro Arg Ser Glu Arg Gly Arg Gly Arg Cys Pro Phe Asp Pro Ser Ser
            165             170             175

Ser Phe Ile Ser Thr Leu Ile Gly Ser Glu Leu Phe Ala Gly Leu Tyr
            180             185             190

Ser Asp Tyr Trp Ser Arg Asp Ala Ala Ile Phe Arg Ser Met Gly Arg
            195             200             205

Leu Ala His Ile Arg Thr Glu His Asp Asp Arg Leu Leu Lys Glu
210             215             220

Pro Lys Phe Val Gly Ser Tyr Met Ile Pro Asp Asn Glu Asp Arg Asp
225             230             235             240

Asp Asn Lys Val Tyr Phe Phe Thr Glu Lys Ala Leu Glu Ala Glu
            245             250             255

Asn Asn Ala His Ala Ile Tyr Thr Arg Val Gly Arg Leu Cys Val Asn
            260             265             270

Asp Val Gly Gly Gln Arg Ile Leu Val Asn Lys Trp Ser Thr Phe Leu
            275             280             285

Lys Ala Arg Leu Val Cys Ser Val Pro Gly Met Asn Gly Ile Asp Thr
290             295             300

Tyr Phe Asp Glu Leu Glu Asp Val Phe Leu Leu Pro Thr Arg Asp His
305             310             315             320

Lys Asn Pro Val Ile Phe Gly Leu Phe Asn Thr Thr Ser Asn Ile Phe
            325             330             335

Arg Gly His Ala Ile Cys Val Tyr His Met Ser Ser Ile Arg Ala Ala
            340             345             350

Phe Asn Gly Pro Tyr Ala His Lys Glu Gly Pro Glu Tyr His Trp Ser
            355             360             365

Val Tyr Glu Gly Lys Val Pro Tyr Pro Arg Pro Gly Ser Cys Ala Ser
            370             375             380

Lys Val Asn Gly Gly Arg Tyr Gly Thr Thr Lys Asp Tyr Pro Asp Asp
385             390             395             400

Ala Ile Arg Phe Ala Arg Ser His Pro Leu Met Tyr Gln Ala Ile Lys
            405             410             415

Pro Ala His Lys Lys Pro Ile Leu Val Lys Thr Asp Gly Lys Tyr Asn
            420             425             430

| | | | | | | | | | | | |
|---|---|---|---|---|---|---|---|---|---|---|---|
|Leu|Lys|Gln|Ile|Ala|Val|Asp|Arg|Val|Glu|Ala|Glu|Asp|Gly|Gln|Tyr|
| | |435| | | |440| | | |445| |

Leu Lys Gln Ile Ala Val Asp Arg Val Glu Ala Glu Asp Gly Gln Tyr
            435                 440                 445

Asp Val Leu Phe Ile Gly Thr Asp Asn Gly Ile Val Leu Lys Val Ile
450                 455                 460

Thr Ile Tyr Asn Gln Glu Met Glu Ser Met Glu Val Ile Leu Glu
465                 470                 475                 480

Glu Leu Gln Ile Phe Lys Asp Pro Val Pro Ile Ile Ser Met Glu Ile
                485                 490                 495

Ser Ser Lys Arg Gln Gln Leu Tyr Gly Ser Ala Ser Val Ala
            500                 505                 510

Gln Val Arg Phe His His Cys Asp Met Tyr Gly Ser Ala Cys Ala Asp
            515                 520                 525

Cys Cys Leu Ala Arg Asp Pro Tyr Cys Ala Trp Asp Gly Ile Ser Cys
530                 535                 540

Ser Arg Tyr Tyr Pro Thr Gly Thr His Ala Lys Arg Phe Arg Arg
545                 550                 555                 560

Gln Asp Val Arg His Gly Asn Ala Ala Gln Cys Phe Gly Gln Gln
                565                 570                 575

Phe Val Gly Asp Ala Leu Asp Lys Thr Glu Glu His Leu Ala Tyr Gly
            580                 585                 590

Ile Glu Asn Asn Ser Thr Leu Leu Glu Cys Thr Pro Arg Ser Leu Gln
            595                 600                 605

Ala Lys Val Ile Trp Phe Val Gln Lys Gly Arg Glu Thr Arg Lys Glu
            610                 615                 620

Glu Val Lys Thr Asp Asp Arg Val Val Lys Met Asp Leu Gly Leu Leu
625                 630                 635                 640

Phe Leu Arg Leu His Lys Ser Asp Ala Gly Thr Tyr Phe Cys Gln Thr
                645                 650                 655

Val Glu His Ser Phe Val His Thr Val Arg Lys Ile Thr Leu Glu Val
            660                 665                 670

Val Glu Glu Glu Lys Val Glu Asp Met Phe Asn Lys Asp Glu Glu
            675                 680                 685

Asp Arg His His Arg Met Pro Cys Pro Ala Gln Ser Ser Ile Ser Gln
            690                 695                 700

Gly Ala Lys Pro Trp Tyr Lys Glu Phe Leu Gln Leu Ile Gly Tyr Ser
705                 710                 715                 720

Asn Phe Gln Arg Val Glu Glu Tyr Cys Glu Lys Val Trp Cys Thr Asp
                725                 730                 735

Arg Lys Arg Lys Lys Leu Lys Met Ser Pro Ser Lys Trp Lys Tyr Ala
            740                 745                 750

Asn Pro Gln Glu Lys Lys Leu Arg Ser Lys Pro Glu His Tyr Arg Leu
            755                 760                 765

Pro Arg His Thr Leu Asp Ser
770                 775

<210> SEQ ID NO 73
<211> LENGTH: 15580
<212> TYPE: DNA
<213> ORGANISM: Homo sapiens

<400> SEQUENCE: 73
atgctactcc ctgccctcct ctttgggatg gcgtgggccc tggctgacgg gcggtggtgt      60
gagtggacag agaccatccg tgtggaggag gaagtggcac ccgtcagga ggacctggta     120 ccctgtgcca gcctcgacca ttacagccgc ctgggctggc ggctggacct gccctggagt     180

-continued

```
ggccgctcgg ggcttacccg gtccccagcg cctgggctct gtcctatcta caaacctcca    240
gaaacccggc ctgccaagtg aaccggaca gtgaggactt gttgcccagg ctggggggc     300 gcccactgca ctgaggccct tgccaaagcc agtcctgaag ccactgctt tgccatgtgg    360 cagtgccagc tacaggcagg ctcagctaat gcctcagcag gaagcctgga ggagtgctgc   420
gcccggccct ggggacaaag ctggtgggat ggcagctccc aggcctgccg cagctgctcc   480
agccgacacc tgccaggcag tgcctcttct ccagccctcc tgcagcccct ggcaggggct   540
gtgggccagc tctggagcca gcaccagcgt ccctcggcca cctgtgcctc ctggtcgggc   600
ttccactacc gcacctttga tggccgccac tatcacttcc tgggccgctg cacctacctg   660
ctggcgggtg ctgcggactc cacctgggct gtccacctaa cacccgggga ccgctgcccc   720
cagcctggac actgtcagcg ggtgactatg ggacccgagg aggtgctgat ccaggctgga   780
aatgtgtctg tgaaggggca gctggtacct gaagggcagt cttggctgct ccacgggctg   840
agcctgcaat ggctgggga ctggctggtg ctgtcaggag gcctggggt cgtggtgcgg    900 ctggacagga ctggctccat ctccatctct gtggaccacg agctctgggg acagacacaa   960
ggcctctgtg ggctctacaa tggctggcca gaggatgact tcatggagcc aggcggaggg  1020
ctggccatgt tagcagccac ctttggaaat tcctggaggc tccctggctc ggagtctggg  1080
tgtctggatg cagtggaggt ggcccagggc tgtgaccccc tggggctcat agacgcagat  1140
gtagaacctg gccacctgcg ggctgaagcc caggacgtgt gccatcagct gctggaaggt  1200
ccattcgggc agtgccatgc ccaggttttcc cctgctgagt accacgaggc ctgtctcttt  1260
gcctactgcg caggggccat ggcaggcagt gggcaagagg ggcggcagca ggctgtttgt  1320
gccacctttg ccagctatgt ccaggcctgt gccaggcggc acatccacat tcgctggagg  1380
aagcctggct tctgcgagcg cctgtgcccc gggggccagc tctactccga ctgcgtctcc  1440
ctctgcccac ccagctgcga ggcggtgggt cagggagagg aggagtcctg cagggaagag  1500
tgtgtgagtg gctgtgagtg cccgcgaggc ctcttctgga atggcaccct ctgtgtgcct  1560
gctgcccact gccctgcta ctactgccgc cagcgctatg tacccggtga caccgtgcgc  1620
cagctgtgta acccctgcgt gtgcagggat ggccgctggc actgtgccca ggcactgtgc  1680
cccgccgagt gtgcagtggg tggggacggg cactacctca ccttcgatgg gcggagctac  1740
tccttctggg gtggtcaagg ttgccgctac agcctggtgc aggactatgt gaagggacag  1800
ctactgatcc tactggagca tgggggcctgc gacgctggga gctgcctgca cgccatctcc  1860
gtctccctgg aggacaccca catccagctc agggactcag gagctgtgct ggtcaatggg  1920
caggatgtgg gcttgccctg gattggcgct gagggcctca gtgtgcgccg agcttcctct  1980
gcctttctgc tgctgcgctg gcctggggcc caggtgctct ggggactgtc tgaccctgta  2040
gcctacatca ccctggaccc ccgccatgcc caccaggtgc agggtctgtg tggcaccttc  2100
acccagaacc agcaggacga cttcctgaca ccagccggag atgtggaaac tagcattgct  2160
gcctttgcta gcaagttcca ggtggccggc aagggaagat gccccctctga ggacagtgcc  2220 ctgctgtctc cctgcaccac ccactcccag cgccacgcct tcgcagaggc ggcctgtgcc  2280
atcctgcaca gctctgtctt ccaggaatgc cacaggctgg tggacaaaga gccattctat  2340
ctgcgctgcc tggcagccgt gtgtggctgt gatcccggca gtgactgcct gtgcccggtg  2400
ctgtctgcct atgcgcgtcg ctgtgcccag gaaggtgcct cacctccctg gaggaaccag  2460
accctctgcc ctgttatgtg tcctggtggc caggagtacc gagagtgtgc cccagcatgc  2520
```

```
ggtcaacact gcgggaaacc agaggactgt ggagagctgg gcagctgtgt ggctggttgt    2580
aactgtcctc tggggctgct gtgggaccct gagggccagt gtgtgccccc cagcttgtgc    2640
ccctgccagc tcggagcccg tcgctatgcc cctggcagtg ccaccatgaa ggagtgcaac    2700
cgctgcatct gccaggaaag gggcctctgg aattgcacgg ctcgccactg cccttcacag    2760
gcattctgcc ccagggagct tgtctatgcc cctggtgcct gtctcctcac ctgtgacagc    2820
cccagcgcca atcactcctg ccctgcaggc agtactgatg ctgtgtctg tccaccaggc     2880 acggtgctgc tggacgagcg ctgtgtgcct cctgacctct gtcctgccg tcacagtggg     2940 cagtggtacc tgcccaacgc caccatccag gaagactgca acgtttgcgt gtgccggggc    3000
cggcagtggc actgcacagg ccagcggcgc agtgggcggt gccaggcatc aggcgccccc    3060
cactatgtga catttgacgg actggccttc acctatcctg gggcctgcga gtatctgctg    3120
gtgcgagagg ccagtggcct attcacagtc tctgcccaga acctgccctg tggggccagc    3180
ggtctcacct gcaccaaagc gctggccgtg cgtctggagg gcactgttgt gcacatgctc    3240
agaggccggg cagtgacggt gaatgggtg agcgtgacgc cccccaaggt ctacacaggc     3300
cctgggctga gcctgcgtcg tgctggcctc ttcctgctgc tctcgaccca cctgggcctc    3360
accctgctct gggatggagg gactcgggtc ctggtgcaac tgtcccctca gttccgtggt    3420
cgcgtggctg ggctgtgtgg tgactttgat ggagatgcca gtaatgatct gcggagccgc    3480
cagggcgtcc tggagcccac agctgaactg gctgcccact cctggcgcct cagccccctc    3540
tgccctgagc caggagacct gccacacccc tgcacgatga acacacaccg ggctggttgg    3600
gctcgggccc gctgtggggc gctgctgcag ccgctcttca cattatgcca cgcggaggtc    3660
cccccgcagc agcactatga gtggtgcctg tatgacgcct gcggctgcga ctcgggggt     3720 gactgtgagt gcctctgctc ggccattgcc acctatgcag atgagtgtgc ccggcatggg    3780
caccacgtgc gctggcgtag ccaggagctc tgctccctgc agtgtgaagg gggacaggta    3840
tatgaggcct gtgccccac gtgtcccccc acctgccatg agcagcatcc tgagcccggg     3900
tggcactgcc aggtggtggc ctgtgtggag gctgcttct gccccgaggg gactctgctg     3960
cacggaggag cctgcttgga gccagcttcc tgccctgtg agtggggccg caactccttc     4020 ccgccgggt ctgtgctgca aaaggactgc gggaactgca cgtgccagga aggtcaatgg     4080
cattgtgggg gtgacggtgg ccactgtgag gagcttgtgc ctgcctgtgc agagggagag    4140
gccctgtgcc aagagaatgg gcactgtgtg cccatgggt ggctttgtga caaccaggac     4200
gactgtggcg atggctctga tgaggaggt tgtgccgccc caggctgtgg ggaggggcag     4260
atgacttgca gctccggcca ctgcctgccc ctggccctgc tctgtgaccg ccaggatgac    4320
tgtggagatg gcacggatga gccgagctat ccgtgccccc agggcttgct ggcctgtgcc    4380
gatggacgct gcctgccgcc ggccctgctc tgcgatgggc atcctgactg tctggatgcc    4440
gccgacgagg agtcctgtct ggggcaggtg acctgcgtcc ccggggaggt gtcctgtgtt    4500
gatggcacct gcctgggggc catccagctg tgtgacggag tctgggactg cccagatgga    4560
gccgatgagg ggccgggaca ctgcccccta ccttctctgc ccacacctcc tgccagcacc    4620
ttgcctggcc cctccccagg ctccctggac actgcgtcaa gtccctggc cagcgccagc     4680 cctgcgccac cctgcggccc cttcgagttt cggtgcggca gcggcgagtg caccccgcgg    4740
ggctggcgct gcgaccagga ggaagactgc gccgacggca gcgacgagcg cggctgcgga    4800
gggccctgcg cgccgcacca cgcgccctgc gcccgcggcc tcactgcgt gtccccgag     4860 cagctgtgcg acggcgtgcg gcagtgtccc gacggctcgg acgagggccc cgacgcctgc    4920
```

```
gggggctgc cagccctggg aggccccaac aggacagggc ttccctgccc agaatacacc    4980
tgccccaatg gcacctgcat aggcttccag ctggtgtgtg atgggcagcc tgactgtgga    5040
aggccagggc aggtgggccc ctccccagaa gagcagggtt gtgggcctg gggcccctgg     5100
agcccatggg ggccctgcag ccggacgtgt gggccctggg gccagggccg agccgccgc     5160
tgctccccac tcggcctcct ggtgctacag aactgcccag ggcctgagca ccagtctcag    5220
gcctgcttca cggcagcctg cccagtggac ggtgaatgga gcacctggtc ccctggtct    5280
gtgtgctctg agccgtgcag gggcaccatg acgcggcaac ggcagtgcca ctcaccccag    5340
aatgggggcc gcacctgtgc tgcactgccc ggaggcctgc acagcacccg ccagaccaag    5400
ccttgccctc aggacggctg ccccaatgcc acttgctctg gggagctgat gttccagccc    5460
tgtgcccct gccactgac ctgtgatgac atctctggcc aggtcacgtg cccacctgat      5520
tggccctgcg gcagcccggg ctgctggtgc ccagaagggc aggtgctggg cagcgagggg    5580
tggtgtgtgt ggccccggca gtgccctgc ctggtggacg tgcccgcta ctggcctggg      5640
caacgcatca aggccgactg ccagctctgc atctgccaag acggacggcc ccgacgctgc    5700
cgactcaacc cggactgcgc tgtggactgt ggctggtcct cctggtcacc ctgggccaag    5760
tgcctgggcc cctgtggaag ccagagcatc cagtggtcct tccggagctc aacaacccc    5820
cgcccctccg gccgaggtcg ccagtgccgt ggcatccacc gcaaggcacg caggtgccag    5880
acggagccct gtgagggtg tgagcatcag ggccaggtcc accgtgtcgg ggaacgctgg    5940
catgggggcc cctgcagggt gtgccagtgt ctgcacaacc tcaccgcaca ctgctcaccc    6000
tactcccgc tcggcagctg ccccccaggg ctgggtcttg gtggagggac gggagaatca    6060
tgctgccact gtgccctacc tggagagaac cagacggtcc agcccatggc cactcctgcc    6120
gcagctccgg ctcccagtcc ccagatcaga ttccctttgg ccacttacat tctgcctccg    6180
tcaggagacc cctgctattc tcccctgggg ctggccggac tggctgaggg gagtctgcat    6240
gcatcgtccc agcagctgga acaccccacc caggctgccc tcctgggggc tcccacccag    6300
gggcccagcc ctcagggatg gcacgctgga ggggatgctt atgccaagtg gcacactcgg    6360
ccccattacc tgcagctgga cctgcttcag cctcggaacc tcactggcat cctagtgccg    6420
gagactggct cctccaacgc atatgccagc agcttctcac tccagttcag cagcaatggt    6480
ctacactggc atgactatcg tgacctcctg cctggcatct gcccctgcc caagctttc     6540
cccagaaact gggatgacct ggaccctgcc gtatggactt tcggccgcat ggtgcaggcg    6600
aggtttgtca gggtgtggcc ccacgatgtc caccacagcg atgtcccct gcaggtggag    6660
ctgctgggct gcgagccagg gtccccaccg gcacctctgt gcccagggt tggactccgc     6720
tgtgccagtg gtgagtgtgt cctgagaggg ggcccttgtg acgtgttct ggactgcgag     6780
gatggctcgg atgaggaggg ctgtgtgttg ctgcctgagg gcactggcag attccattcc    6840
acagccaaga ccctggccct ctcctctgcc cagccggggc agctgctgca ctggcccagg    6900
gagggcctgg cagagactga gcactggccc cctgggcagg aatcccccac gtccccgaca    6960
gagacaaggc ccgtgagtcc tggcccagcc tccggggtgc ctcaccatgg gaatctgtg    7020
cagatggtga ccaccacccc catacccag atggaggcca ggaccctgcc accaggtatg    7080
gcagctgtga cggtggtgcc cccacaccct gtgactccag cgaccctgc tggccagagc    7140
gtcgccccag gacccttccc acctgtgcag tgtggccccg ccagacgcc ctgtgaggtg     7200
ctgggctgcg tggaacaggc gcaggtgtgt gatggcaggg aggattgcct cgacggctcc    7260
```

```
gacgagaggc actgcgccag gaatctactt atgtggctcc cttctctccc tgccttgtgg   7320
gcagcgagca ctgtgcccct tcatgatgcct accatggccc tgcctgggct tccagcctca   7380
agggccctct gttccccgag ccagctgagc tgtggcagcg gggagtgtct gtctgctgag   7440
cggcgctgtg acctgcggcc tgactgccag gatggctcgg acgaggatgg ctgtgtggac   7500
tgcgtgctgg cccctggtc tgtctggagc agctgcagcc gcagctgtgg cctgggcctc   7560
accttccagc gccaggagct gctgcggcct cctctgccag ggggcagctg cccgcgtgac   7620
cggttccgaa gccagtcctg ctttgtgcag gcctgcccag tggctggggc atgggccatg   7680
tgggaggcct ggggaccctg cagcgtctcc tgcggggtg gccatcagag tcgccagaga   7740
agctgtgtgg accccccacc caagaatggc ggtgccccct gccccggggc ctcccaagag   7800
agggcaccct gcggcttgca gccctgctca ggtggcacag actgcgagct gggccgtgtg   7860
tatgtgagtg ccgatctgtg ccagaagggg ctggtgcccc catgcccacc ctcctgcctg   7920
gatcccaagg ccaacagaag ctgcagtggg cattgtgtgg aaggatgccg ctgtcccccg   7980
gggctccttc tgcatgacac tcgctgcctg ccctctctg agtgccctg cctggtgggc   8040 gaagagctga agtggccagg ggtgtccttc ctcctgggca actgcagcca atgcgtgtgt   8100 gagaagggg agttgctgtg ccaaccaggg ggctgccccc tgcctgcgg ctggtcagcc   8160 tggtcctcct gggctccctg cgaccgctcc tgtggctctg gagtgagggc caggttcagg   8220
tctccctcca cccctccggc agcctggggg ggtgccccgt gtgaaggtga ccggcaggaa   8280
ctgcagggct gccacacagt gtgtgggaca gaggtgttcg gctggacgcc ctggacttcc   8340
tggtcctcct gctcccaaag ctgccttgcc ccggaggggg gccctggctg gcgcagtcgt   8400
tcccgactct gccccagccc tggggattca tcctgcccag gagatgccac ccaggaggag   8460
ccctgcagcc cccctgtatg cccagtgcca agcatctggg gtctgtgggc tccctggtcc   8520
acttgctcag cccctgtga tggaggcatc cagacacgtg ggcgcagctg ctccagcttg   8580
gctccagggg acaccacgtg cccaggaccc cacagtcaga ccaggactg caacacgcag   8640 ccctgcacag cccagtgccc agagaacatg ttgttccgct cagcagagca gtgtcaccag   8700 gagggggtc cttgccctcg gctatgcctg acgcagggcc ccgggataga gtgtacgggc   8760
ttctgcgccc ccggctgcac ctgcccccct ggtcttttcc tgcacaatgc tagctgcctg   8820
ccccgcagcc agtgccctg ccagctgcac gggcagctct atgcatcagg agcaatggct   8880
cgcctggact cctgcaacaa ctgcacctgt gtctctggta agatggcatg cacctcggag   8940
cgctgcccag tggcctgtgg ctggagtccc tggaccctgt ggagtctctg tagctgcagc   9000
tgcaacgtgg gcattcggcg ccgcttccgg gcaggcactg cacccccagc tgccttttggg   9060 ggtgctgagt gccaaggccc caccatggag gctgaattct gcagcctgcg gccatgtcca   9120
ggtcctggtg gggagtgggg cccttggtct ccgtgctccg tgccctgtgg tggtggctac   9180
aggaaccgca cccgaggcag cagccgcagc ctcatggagt tttccacctg tggcctgcag   9240
ccctgcgcag ggcagtgcc tggcatgtgt cccagggaca agcagtggct ggactgtgcc   9300
cagggccctg cctcttgtgc agagctcagc gccccaagag ggactaacca gacctgccac   9360
cctggctgcc actgccctc tgggatgctt ctgctgaaca acgtgtgtgt gcccaccag   9420 gactgcccct gtgcccacga ggggcacctc tacccccgg gcagcactgt ggttcgtcca   9480
tgtgaaaact gctcctgtgt ctccgggctc atcgccaact gcagctcctg gccttgtgcg   9540
gagggtgagc ccacgtggtc accctggacc ccttggagcc agtgttcagc ctcctgtggc   9600
cctgcccggt gccatcggca ccggttctgt gccaggtccc ccagtgcagt gccatccacc   9660
```

```
gtggctccgc tgccctgcc agccacccc acacctctct gctcaggccc cgaggctgaa    9720
gaggagccat gtctcctgca ggggtgtgat cgagctgggg gatggggtcc atggggcc     9780
tggtcccact gtagccggag ctgtggggga ggcctgcgga gccggacccg ggcctgtgac   9840
cagccccac cccagggcct gggggattac tgcgaggggc cacgggcaca ggggaggtc    9900
tgccaggctc tgccctgccc agtgaccaac tgcactgcca ttgaaggggc cgagtatagc   9960
ccctgtggcc ctccgtgccc tcgctcctgt gatgacctag tgcactgcgt gtggcgctgc   10020
cagcctggct gctactgccc accaggccag gtactgagtt ccaacggggc catctgcgtg   10080
cagccgggtc actgcagctg cctggacctg ctgaccgggc agcggcacca tccgggtgct   10140
cggctggcaa ggcctgacgg ctgcaaccac tgcacctgcc tggagggag gctgaactgc    10200
acagacctgc cctgcccagt gcccggaggc tggtgcccgt ggtcggagtg acaatgtgc    10260
tcccagccct gcaggggcca gaccaggagc cgctccaggg cctgtgcctg ccccactcct   10320
cagcacggtg gtgccccgtg cactggagag gctgggggagg caggggccca gcatcagagg  10380
gaggcctgcc ccagctacgc cacgtgccca gtggacggag cctgggcc atggggcca     10440
tggtctccct gcgacatgtg cttggggcag tcccaccgga gccggcgtg cagccggccc   10500
cccaccctg agggaggggag gccctgccct gggaaccaca cgcagagtcg cccttgccag   10560
gaaaattcca cccagtgcac agactgcggg ggtggccaga gtctgcatcc ctgtgggcag   10620
ccctgcccc gctcctgcca ggacctgtcc cctgggagtg tgtgccagcc aggctctgtg    10680
ggctgccagc ccacttgtgg gtgccccctg ggccagctct cccaggacgg gctgtgcgtg    10740
ccccagccc actgccgctg ccagtaccag cctggagcca tggggatccc tgagaaccag   10800
agccgctcag cagggtctag gtttagctcc tgggagagcc tggaacccgg agaggtggtc   10860
actgggccat gtgacaactg cacctgtgtg gcaggcattc tgcaatgcca ggaggtgcct   10920
gactgcccgg accctggggt gtggagctct tggggcccctt gggaagactg cagtgtttcg   10980
tgtggggcg gggagcagct gcgctccgg cgctgtgctc gtcctccctg cccagggcct    11040
gcccgccaga gccgcacatg cagcacacag gtctgcagag aggcaggctg cccggctggc   11100
cgcctgtacc gtgaatgcca gcccggcgag ggatgcccct tctcctgcgc ccacgtcacg   11160
cagcaggtgg gctgcttctc tgagggctgc gaggagggct gccactgccc cgagggcacc   11220
ttccagcacc gcctggcctg tgtgcaggag tgcccttgtg tgctgacagc ctggctgctg   11280
caggagctgg gagccaccat aggtgaccct ggtcagcccc tcgggcctgg agatgagctg   11340
gactcaggcc agacacttcg tacaagctgt ggcaactgct cgtgtgcaca cgggaagctg   11400
tcttgctccc tggacgactg cttcgaggcc gatggtggtt tcggtccctg agcccgtgg    11460
ggcccgtgct cccgctcctg tggagggctg ggcaccgta cccgcagccg ccagtgtgtg    11520
ctcaccatgc ccaccctcag tggtcagggc tgccgtgggc cccgccagga cctcgagtgc   11580
cccagcccag actgccctgg ggctgaaggg tccacggtgg agccagtaac aggccttcca   11640
ggtggctggg gccatggtc ctcctggtcc ccctgctcca gaagctgcac ggaccccgct   11700
cgccctgcat ggcgcagccg cacccgcctc tgcctggcta actgcaccat ggggaccca   11760
ttacaggagc ccctgcaa cctgcctca tgcacagagc tgcccgtgtg ccctggccct    11820
ggctgtgggg ctgggaactg ttcctggacc tcctgggccc cgtgggaacc ttgctcccgc   11880
agctgcggag tggccagca cgccgcctg cgggcatacc gtcccctgg gcccggcggg     11940
cactggtgcc ccaacatcct tactgcctac caagagcgcc gcttctgcaa cctgcgagcc   12000
```

```
tgcccagtgc ccgggggctg gtcacgctgg agtccctggt cctggtgtga ccgcagctgt    12060
gggggaggcc aatccctgag aagccgcagc tgctcaagcc ccccatccaa gaacggggga    12120 gcccctgtg ctggggagcg gcaccaggcc cgcctctgca atcccatgcc ttgtgaggcc     12180
ggctgcccag caggcatgga ggtggtcacc tgtgccaacc gctgccccg ccgctgctca     12240 gacctccagg agggaattgt gtgtcaggac gaccaggtct gccagaaggg ctgccgctgc    12300
ccaaaggggt ccctggagca ggatggtggc tgcgtgccaa ttgggcactg tgactgcacc    12360
gatgcccagg ccacagctg ggccccgggg agccagcacc aggatgcctg caacaactgc    12420
tcatgccaag ctgggcagct ctcctgcacg gctcagccct gcccgcctcc cacccactgt    12480
gcctggagcc actggtcggc ctggagtccc tgcagccact catgcgggcc cagagggcag    12540
cagagccgct tccggtcctc cacgtcgggc tcgtgggccc cagagtgtcg ggaggagcag    12600
tcccagagcc agccctgccc tcagccctcg tgcccacccc tgtgcctgca gggcactcgc    12660
tcccgcaccc tggggacag ctggctgcag ggggagtgcc agcggtgctc ctgcaccccg     12720
gagggtgtga tctgcgaaga tacggagtgt gcagtgcctg aggcttggac gctgtggtcc    12780
tcctggtccg actgccctgt ctcctgtgga ggtggaaacc aggtccgaac ccgggcctgc    12840
agggccgcag cccctcacca caggagccca ccctgcctgg gccctgacac ccagaccagg    12900
cagcagcctt gcccagggct gctggaggcc tgctcctggg gccgtgggg gccctgttcc     12960 cgcagctgcg gcccgggcct ggcctctcgc tctgggtcct gccccgcct gatggccaag     13020 gccgacccca cctgcaacag caccttcctc cacctggaca cccagggctg ctactcaggg    13080 ccctgccag aggagtgtgt gtggagcagc tggagcagct ggacgcgctg ctcttgccgg     13140
gtgctggtgc agcagcgcta ccgacaccag ggcccggcgt cccgagggc cagggcaggc     13200 gcccctgca cgcggctgga tggccacttc cggccttgcc ttatcagcaa ctgctctgag     13260
gacagctgca cgcctcccct tgagttccat gcctgcggct ccccctgtgc tgggctctgt    13320
gccacacacc tgagccatca gctctgccag gacctgccac cctgccagcc gggctgctac    13380
tgccccaagg ggctgctgga gcaggctggg ggctgcattc cccagagga gtgtaactgc     13440 tggcatacct cagcagcagg agccgggatg accctggccc ctggggaccg cctgcagctg    13500
ggctgtaagg agtgtgaatg ccggcgtggg gagctgcact gcaccagcca gggctgtcaa    13560
ggtcttctgc ctctgagtga gtggtccgag tggtcgccct gtgggccctg cctgccgccc    13620
agcgccctgg cccctgcctc caggactgcc ctagaggagc actggctccg agacccaact    13680
ggcctctccc ccaccttggc cccgctgctg gcttcagagc agcaccgcca ccggctctgt    13740
ctggatcctg cgacagggag gccctggact ggagcccctc acctctgcac cgcaccctc     13800 agccagcagc gcctctgccc tgaccctgga gcctgccctg actcatgcca gtggagtctg    13860
tgggggccat ggagccctg ccaggtgccc tgcagtgggg ggttcaggct acgctggaga     13920
gaggcagagg ccctctgtgg aggaggctgc cgggagccat gggctcaaga aagctgcaac    13980
ggagggccct gcccagagtg cgaggcccaa gacactgtat tcaccctgga ctgtgccaac    14040
cagtgcccac acagctgtgc cgacctctgg gaccgcgttc agtgtctgca gggaccctgc    14100
cgcccaggct gccgctgtcc ccctggccag ctggtccagg atgggcgctg tgtgccgatc    14160
tcctcttgcc gctgtggcct ccccagtgcc aatgcctctt gggagctggc cccggcccag    14220
gcggtgcagc tggactgcca aaactgcacc tgtgtcaacg agtccctggt gtgcccacac    14280
caggagtgtc cagtccttgg gccttggtca gcctggagca gttgctcggc cccctgtggt    14340
gggggcacta tggagcgaca tcggacttgt gaggggggtc ctggggtggc accatgccag    14400
```

```
gcccaggaca cagagcaacg gcaggagtgt aacctgcagc cctgccctga gtgccccct    14460 ggccaggtgc ttagtgcctg tgccacctca tgcccgtgcc tctgctggca tctgcagcct    14520
ggtgccatct gtgtgcagga gccctgccag cctggctgtg gctgccctgg agggcagctg    14580
ctgcacaatg gcacgtgtgt gcctcccact gcctgcccct gcacccagca ttctctgccc    14640
tggggcctca ccctgaccct ggaagagcag gcccaggagc tgccccagg gactgtgctc    14700 acccggaact gcaccgctg tgtctgccac ggtggagcct tcagctgctc cctcgttgac    14760
tgtcaggtgc ccctgggga aacgtggcag caggtggccc cggggagct ggggctctgc    14820 gagcagacgt gcctggagat gaacgccaca aagacccaga gtaactgcag ttcagctcga    14880
gcctcgggct gcgtgtgcca gcccgggcac ttccgcagcc aggcaggccc ctgcgtcccc    14940
gaagaccact gcgagtgctg gcaccttggg cgtccccacc tgcctggatc tgaatggcag    15000
gaggcctgtg agagctgcct ctgcctcagt gggaggcctg tctgcaccca gcactgctcc    15060
ccactcacct gtgctcaggg cgaggagatg gtgctggagc cagggagctg ctgtccctct    15120
tgccgcaggg aggctccgga ggagcagtcg ccctcctgcc agctcctcac ggagcttcga    15180
aacttcacca aagggacctg ttacctggac caggtagaag tgagctactg cagtgggtac    15240
tgcccatcca gcacccatgt catgccagag gagccatacc tgcagagcca gtgtgactgc    15300
tgcagctacc gtctagaccc ggagagccct gtgcggatcc tgaacctgcg ctgtctgggt    15360
ggccacacag agcccgtggt gctgccggtc atccacagct gccagtgcag ctcctgccag    15420
ggtggggact tctcaaagcg ctaacaggct ccgctgggtg agtccacagc tgtccctctt    15480
gtgatcatgg gactcagcag cactgaccac gtccttccac gctctctcac ctgccccaa    15540 ctggggccc atgacttggc attagcatgt tccaaataaa    15580
```

<210> SEQ ID NO 74
<211> LENGTH: 5150
<212> TYPE: PRT
<213> ORGANISM: Homo sapiens

<400> SEQUENCE: 74

Met Leu Leu Pro Ala Leu Leu Phe Gly Met Ala Trp Ala Leu Ala Asp
1               5                   10                  15

Gly Arg Trp Cys Glu Trp Thr Glu Thr Ile Arg Val Glu Glu Glu Val
            20                  25                  30

Ala Pro Arg Gln Glu Asp Leu Val Pro Cys Ala Ser Leu Asp His Tyr
        35                  40                  45

Ser Arg Leu Gly Trp Arg Leu Asp Leu Pro Trp Ser Gly Arg Ser Gly
    50                  55                  60

Leu Thr Arg Ser Pro Ala Pro Gly Leu Cys Pro Ile Tyr Lys Pro Pro
65                  70                  75                  80

Glu Thr Arg Pro Ala Lys Trp Asn Arg Thr Val Arg Thr Cys Cys Pro
                85                  90                  95

Gly Trp Gly Gly Ala His Cys Thr Glu Ala Leu Ala Lys Ala Ser Pro
            100                 105                 110

Glu Gly His Cys Phe Ala Met Trp Gln Cys Gln Leu Gln Ala Gly Ser
        115                 120                 125

Ala Asn Ala Ser Ala Gly Ser Leu Glu Glu Cys Cys Ala Arg Pro Trp
    130                 135                 140

Gly Gln Ser Trp Trp Asp Gly Ser Ser Gln Ala Cys Arg Ser Cys Ser
145                 150                 155                 160

```
Ser Arg His Leu Pro Gly Ser Ala Ser Pro Ala Leu Leu Gln Pro
            165                 170                 175

Leu Ala Gly Ala Val Gly Gln Leu Trp Ser Gln His Gln Arg Pro Ser
            180                 185                 190

Ala Thr Cys Ala Ser Trp Ser Gly Phe His Tyr Arg Thr Phe Asp Gly
            195                 200                 205

Arg His Tyr His Phe Leu Gly Arg Cys Thr Tyr Leu Leu Ala Gly Ala
            210                 215                 220

Ala Asp Ser Thr Trp Ala Val His Leu Thr Pro Gly Asp Arg Cys Pro
225                 230                 235                 240

Gln Pro Gly His Cys Gln Arg Val Thr Met Gly Pro Glu Glu Val Leu
            245                 250                 255

Ile Gln Ala Gly Asn Val Ser Val Lys Gly Gln Leu Val Pro Glu Gly
            260                 265                 270

Gln Ser Trp Leu Leu His Gly Leu Ser Leu Gln Trp Leu Gly Asp Trp
            275                 280                 285

Leu Val Leu Ser Gly Gly Leu Gly Val Val Arg Leu Asp Arg Thr
            290                 295                 300

Gly Ser Ile Ser Ile Ser Val Asp His Glu Leu Trp Gly Gln Thr Gln
305                 310                 315                 320

Gly Leu Cys Gly Leu Tyr Asn Gly Trp Pro Glu Asp Asp Phe Met Glu
            325                 330                 335

Pro Gly Gly Gly Leu Ala Met Leu Ala Ala Thr Phe Gly Asn Ser Trp
            340                 345                 350

Arg Leu Pro Gly Ser Glu Ser Gly Cys Leu Asp Ala Val Glu Val Ala
            355                 360                 365

Gln Gly Cys Asp Ser Pro Leu Gly Leu Ile Asp Ala Asp Val Glu Pro
            370                 375                 380

Gly His Leu Arg Ala Glu Ala Gln Asp Val Cys His Gln Leu Leu Glu
385                 390                 395                 400

Gly Pro Phe Gly Gln Cys His Ala Gln Val Ser Pro Ala Glu Tyr His
            405                 410                 415

Glu Ala Cys Leu Phe Ala Tyr Cys Ala Gly Ala Met Ala Gly Ser Gly
            420                 425                 430

Gln Glu Gly Arg Gln Gln Ala Val Cys Ala Thr Phe Ala Ser Tyr Val
            435                 440                 445

Gln Ala Cys Ala Arg Arg His Ile His Ile Arg Trp Arg Lys Pro Gly
            450                 455                 460

Phe Cys Glu Arg Leu Cys Pro Gly Gly Gln Leu Tyr Ser Asp Cys Val
465                 470                 475                 480

Ser Leu Cys Pro Pro Ser Cys Glu Ala Val Gly Gln Gly Glu Glu
            485                 490                 495

Ser Cys Arg Glu Glu Cys Val Ser Gly Cys Glu Cys Pro Arg Gly Leu
            500                 505                 510

Phe Trp Asn Gly Thr Leu Cys Val Pro Ala Ala His Cys Pro Cys Tyr
            515                 520                 525

Tyr Cys Arg Gln Arg Tyr Val Pro Gly Asp Thr Val Arg Gln Leu Cys
            530                 535                 540

Asn Pro Cys Val Cys Arg Asp Gly Arg Trp His Cys Ala Gln Ala Leu
545                 550                 555                 560

Cys Pro Ala Glu Cys Ala Val Gly Gly Asp Gly His Tyr Leu Thr Phe
            565                 570                 575

Asp Gly Arg Ser Tyr Ser Phe Trp Gly Gly Gln Gly Cys Arg Tyr Ser
```

-continued

```
              580             585             590
Leu Val Gln Asp Tyr Val Lys Gly Gln Leu Leu Ile Leu Leu Glu His
            595                 600             605
Gly Ala Cys Asp Ala Gly Ser Cys Leu His Ala Ile Ser Val Ser Leu
            610                 615             620
Glu Asp Thr His Ile Gln Leu Arg Asp Ser Gly Ala Val Leu Val Asn
625             630                 635                 640
Gly Gln Asp Val Gly Leu Pro Trp Ile Gly Ala Glu Gly Leu Ser Val
                645                 650             655
Arg Arg Ala Ser Ser Ala Phe Leu Leu Leu Arg Trp Pro Gly Ala Gln
                660             665                 670
Val Leu Trp Gly Leu Ser Asp Pro Val Ala Tyr Ile Thr Leu Asp Pro
            675                 680             685
Arg His Ala His Gln Val Gln Gly Leu Cys Gly Thr Phe Thr Gln Asn
            690                 695             700
Gln Gln Asp Asp Phe Leu Thr Pro Ala Gly Asp Val Glu Thr Ser Ile
705             710                 715                 720
Ala Ala Phe Ala Ser Lys Phe Gln Val Ala Gly Lys Gly Arg Cys Pro
                725                 730             735
Ser Glu Asp Ser Ala Leu Leu Ser Pro Cys Thr Thr His Ser Gln Arg
                740             745                 750
His Ala Phe Ala Glu Ala Ala Cys Ala Ile Leu His Ser Ser Val Phe
            755                 760             765
Gln Glu Cys His Arg Leu Val Asp Lys Glu Pro Phe Tyr Leu Arg Cys
            770                 775             780
Leu Ala Val Cys Gly Cys Asp Pro Gly Ser Asp Cys Leu Cys Pro
785                 790             795                 800
Val Leu Ser Ala Tyr Ala Arg Arg Cys Ala Gln Glu Gly Ala Ser Pro
                805                 810             815
Pro Trp Arg Asn Gln Thr Leu Cys Pro Val Met Cys Pro Gly Gly Gln
                820             825                 830
Glu Tyr Arg Glu Cys Ala Pro Ala Cys Gly Gln His Cys Gly Lys Pro
            835                 840             845
Glu Asp Cys Gly Glu Leu Gly Ser Cys Val Ala Gly Cys Asn Cys Pro
            850                 855             860
Leu Gly Leu Leu Trp Asp Pro Glu Gly Gln Cys Val Pro Pro Ser Leu
865                 870             875                 880
Cys Pro Cys Gln Leu Gly Ala Arg Arg Tyr Ala Pro Gly Ser Ala Thr
                885                 890             895
Met Lys Glu Cys Asn Arg Cys Ile Cys Gln Glu Arg Gly Leu Trp Asn
                900             905                 910
Cys Thr Ala Arg His Cys Pro Ser Gln Ala Phe Cys Pro Arg Glu Leu
            915                 920             925
Val Tyr Ala Pro Gly Ala Cys Leu Leu Thr Cys Asp Ser Pro Ser Ala
            930                 935             940
Asn His Ser Cys Pro Ala Gly Ser Thr Asp Gly Cys Val Cys Pro Pro
945                 950             955                 960
Gly Thr Val Leu Leu Asp Glu Cys Val Pro Pro Asp Leu Cys Pro
                965             970                 975
Cys Arg His Ser Gly Gln Trp Tyr Leu Pro Asn Ala Thr Ile Gln Glu
                980             985                 990
Asp Cys Asn Val Cys Val Cys Arg  Gly Arg Gln Trp His  Cys Thr Gly
                995                 1000                1005
```

```
Gln Arg Arg Ser Gly Arg Cys Gln Ala Ser Gly Ala Pro His Tyr
    1010            1015            1020

Val Thr Phe Asp Gly Leu Ala Phe Thr Tyr Pro Gly Ala Cys Glu
    1025            1030            1035

Tyr Leu Leu Val Arg Glu Ala Ser Gly Leu Phe Thr Val Ser Ala
    1040            1045            1050

Gln Asn Leu Pro Cys Gly Ala Ser Gly Leu Thr Cys Thr Lys Ala
    1055            1060            1065

Leu Ala Val Arg Leu Glu Gly Thr Val Val His Met Leu Arg Gly
    1070            1075            1080

Arg Ala Val Thr Val Asn Gly Val Ser Val Thr Pro Pro Lys Val
    1085            1090            1095

Tyr Thr Gly Pro Gly Leu Ser Leu Arg Arg Ala Gly Leu Phe Leu
    1100            1105            1110

Leu Leu Ser Thr His Leu Gly Leu Thr Leu Leu Trp Asp Gly Gly
    1115            1120            1125

Thr Arg Val Leu Val Gln Leu Ser Pro Gln Phe Arg Gly Arg Val
    1130            1135            1140

Ala Gly Leu Cys Gly Asp Phe Asp Gly Asp Ala Ser Asn Asp Leu
    1145            1150            1155

Arg Ser Arg Gln Gly Val Leu Glu Pro Thr Ala Glu Leu Ala Ala
    1160            1165            1170

His Ser Trp Arg Leu Ser Pro Leu Cys Pro Glu Pro Gly Asp Leu
    1175            1180            1185

Pro His Pro Cys Thr Met Asn Thr His Arg Ala Gly Trp Ala Arg
    1190            1195            1200

Ala Arg Cys Gly Ala Leu Leu Gln Pro Leu Phe Thr Leu Cys His
    1205            1210            1215

Ala Glu Val Pro Pro Gln Gln His Tyr Glu Trp Cys Leu Tyr Asp
    1220            1225            1230

Ala Cys Gly Cys Asp Ser Gly Gly Asp Cys Glu Cys Leu Cys Ser
    1235            1240            1245

Ala Ile Ala Thr Tyr Ala Asp Glu Cys Ala Arg His Gly His His
    1250            1255            1260

Val Arg Trp Arg Ser Gln Glu Leu Cys Ser Leu Gln Cys Glu Gly
    1265            1270            1275

Gly Gln Val Tyr Glu Ala Cys Gly Pro Thr Cys Pro Pro Thr Cys
    1280            1285            1290

His Glu Gln His Pro Glu Pro Gly Trp His Cys Gln Val Val Ala
    1295            1300            1305

Cys Val Glu Gly Cys Phe Cys Pro Glu Gly Thr Leu Leu His Gly
    1310            1315            1320

Gly Ala Cys Leu Glu Pro Ala Ser Cys Pro Cys Glu Trp Gly Arg
    1325            1330            1335

Asn Ser Phe Pro Pro Gly Ser Val Leu Gln Lys Asp Cys Gly Asn
    1340            1345            1350

Cys Thr Cys Gln Glu Gly Gln Trp His Cys Gly Gly Asp Gly Gly
    1355            1360            1365

His Cys Glu Glu Leu Val Pro Ala Cys Ala Glu Gly Glu Ala Leu
    1370            1375            1380

Cys Gln Glu Asn Gly His Cys Val Pro His Gly Trp Leu Cys Asp
    1385            1390            1395
```

```
Asn Gln Asp Asp Cys Gly Asp Gly Ser Asp Glu Glu Gly Cys Ala
    1400                1405                1410

Ala Pro Gly Cys Gly Glu Gly Gln Met Thr Cys Ser Ser Gly His
    1415                1420                1425

Cys Leu Pro Leu Ala Leu Leu Cys Asp Arg Gln Asp Asp Cys Gly
    1430                1435                1440

Asp Gly Thr Asp Glu Pro Ser Tyr Pro Cys Pro Gln Gly Leu Leu
    1445                1450                1455

Ala Cys Ala Asp Gly Arg Cys Leu Pro Pro Ala Leu Leu Cys Asp
    1460                1465                1470

Gly His Pro Asp Cys Leu Asp Ala Ala Asp Glu Glu Ser Cys Leu
    1475                1480                1485

Gly Gln Val Thr Cys Val Pro Gly Glu Val Ser Cys Val Asp Gly
    1490                1495                1500

Thr Cys Leu Gly Ala Ile Gln Leu Cys Asp Gly Val Trp Asp Cys
    1505                1510                1515

Pro Asp Gly Ala Asp Glu Gly Pro Gly His Cys Pro Leu Pro Ser
    1520                1525                1530

Leu Pro Thr Pro Pro Ala Ser Thr Leu Pro Gly Pro Ser Pro Gly
    1535                1540                1545

Ser Leu Asp Thr Ala Ser Ser Pro Leu Ala Ser Ala Ser Pro Ala
    1550                1555                1560

Pro Pro Cys Gly Pro Phe Glu Phe Arg Cys Gly Ser Gly Glu Cys
    1565                1570                1575

Thr Pro Arg Gly Trp Arg Cys Asp Gln Glu Glu Asp Cys Ala Asp
    1580                1585                1590

Gly Ser Asp Glu Arg Gly Cys Gly Gly Pro Cys Ala Pro His His
    1595                1600                1605

Ala Pro Cys Ala Arg Gly Pro His Cys Val Ser Pro Glu Gln Leu
    1610                1615                1620

Cys Asp Gly Val Arg Gln Cys Pro Asp Gly Ser Asp Glu Gly Pro
    1625                1630                1635

Asp Ala Cys Gly Gly Leu Pro Ala Leu Gly Gly Pro Asn Arg Thr
    1640                1645                1650

Gly Leu Pro Cys Pro Glu Tyr Thr Cys Pro Asn Gly Thr Cys Ile
    1655                1660                1665

Gly Phe Gln Leu Val Cys Asp Gly Gln Pro Asp Cys Gly Arg Pro
    1670                1675                1680

Gly Gln Val Gly Pro Ser Pro Glu Glu Gln Gly Cys Gly Ala Trp
    1685                1690                1695

Gly Pro Trp Ser Pro Trp Gly Pro Cys Ser Arg Thr Cys Gly Pro
    1700                1705                1710

Trp Gly Gln Gly Arg Ser Arg Arg Cys Ser Pro Leu Gly Leu Leu
    1715                1720                1725

Val Leu Gln Asn Cys Pro Gly Pro Glu His Gln Ser Gln Ala Cys
    1730                1735                1740

Phe Thr Ala Ala Cys Pro Val Asp Gly Glu Trp Ser Thr Trp Ser
    1745                1750                1755

Pro Trp Ser Val Cys Ser Glu Pro Cys Arg Gly Thr Met Thr Arg
    1760                1765                1770

Gln Arg Gln Cys His Ser Pro Gln Asn Gly Gly Arg Thr Cys Ala
    1775                1780                1785

Ala Leu Pro Gly Gly Leu His Ser Thr Arg Gln Thr Lys Pro Cys
```

-continued

```
            1790                1795                1800

Pro Gln Asp Gly Cys Pro Asn Ala Thr Cys Ser Gly Glu Leu Met
    1805                1810                1815

Phe Gln Pro Cys Ala Pro Cys Pro Leu Thr Cys Asp Asp Ile Ser
    1820                1825                1830

Gly Gln Val Thr Cys Pro Pro Asp Trp Pro Cys Gly Ser Pro Gly
    1835                1840                1845

Cys Trp Cys Pro Glu Gly Gln Val Leu Gly Ser Glu Gly Trp Cys
    1850                1855                1860

Val Trp Pro Arg Gln Cys Pro Cys Leu Val Asp Gly Ala Arg Tyr
    1865                1870                1875

Trp Pro Gly Gln Arg Ile Lys Ala Asp Cys Gln Leu Cys Ile Cys
    1880                1885                1890

Gln Asp Gly Arg Pro Arg Arg Cys Arg Leu Asn Pro Asp Cys Ala
    1895                1900                1905

Val Asp Cys Gly Trp Ser Ser Trp Ser Pro Trp Ala Lys Cys Leu
    1910                1915                1920

Gly Pro Cys Gly Ser Gln Ser Ile Gln Trp Ser Phe Arg Ser Ser
    1925                1930                1935

Asn Asn Pro Arg Pro Ser Gly Arg Gly Arg Gln Cys Arg Gly Ile
    1940                1945                1950

His Arg Lys Ala Arg Arg Cys Gln Thr Glu Pro Cys Glu Gly Cys
    1955                1960                1965

Glu His Gln Gly Gln Val His Arg Val Gly Glu Arg Trp His Gly
    1970                1975                1980

Gly Pro Cys Arg Val Cys Gln Cys Leu His Asn Leu Thr Ala His
    1985                1990                1995

Cys Ser Pro Tyr Cys Pro Leu Gly Ser Cys Pro Gln Gly Trp Val
    2000                2005                2010

Leu Val Glu Gly Thr Gly Glu Ser Cys Cys His Cys Ala Leu Pro
    2015                2020                2025

Gly Glu Asn Gln Thr Val Gln Pro Met Ala Thr Pro Ala Ala Ala
    2030                2035                2040

Pro Ala Pro Ser Pro Gln Ile Arg Phe Pro Leu Ala Thr Tyr Ile
    2045                2050                2055

Leu Pro Pro Ser Gly Asp Pro Cys Tyr Ser Pro Leu Gly Leu Ala
    2060                2065                2070

Gly Leu Ala Glu Gly Ser Leu His Ala Ser Ser Gln Gln Leu Glu
    2075                2080                2085

His Pro Thr Gln Ala Ala Leu Leu Gly Ala Pro Thr Gln Gly Pro
    2090                2095                2100

Ser Pro Gln Gly Trp His Ala Gly Gly Asp Ala Tyr Ala Lys Trp
    2105                2110                2115

His Thr Arg Pro His Tyr Leu Gln Leu Asp Leu Leu Gln Pro Arg
    2120                2125                2130

Asn Leu Thr Gly Ile Leu Val Pro Glu Thr Gly Ser Ser Asn Ala
    2135                2140                2145

Tyr Ala Ser Ser Phe Ser Leu Gln Phe Ser Ser Asn Gly Leu His
    2150                2155                2160

Trp His Asp Tyr Arg Asp Leu Leu Pro Gly Ile Leu Pro Leu Pro
    2165                2170                2175

Lys Leu Phe Pro Arg Asn Trp Asp Asp Leu Asp Pro Ala Val Trp
    2180                2185                2190
```

```
Thr Phe Gly Arg Met Val Gln Ala Arg Phe Val Arg Val Trp Pro
    2195            2200                2205

His Asp Val His His Ser Asp Val Pro Leu Gln Val Glu Leu Leu
    2210            2215                2220

Gly Cys Glu Pro Gly Ser Pro Pro Ala Pro Leu Cys Pro Gly Val
    2225            2230                2235

Gly Leu Arg Cys Ala Ser Gly Glu Cys Val Leu Arg Gly Gly Pro
    2240            2245                2250

Cys Asp Gly Val Leu Asp Cys Glu Asp Gly Ser Asp Glu Glu Gly
    2255            2260                2265

Cys Val Leu Leu Pro Glu Gly Thr Gly Arg Phe His Ser Thr Ala
    2270            2275                2280

Lys Thr Leu Ala Leu Ser Ser Ala Gln Pro Gly Gln Leu Leu His
    2285            2290                2295

Trp Pro Arg Glu Gly Leu Ala Glu Thr Glu His Trp Pro Pro Gly
    2300            2305                2310

Gln Glu Ser Pro Thr Ser Pro Thr Glu Thr Arg Pro Val Ser Pro
    2315            2320                2325

Gly Pro Ala Ser Gly Val Pro His His Gly Glu Ser Val Gln Met
    2330            2335                2340

Val Thr Thr Thr Pro Ile Pro Gln Met Glu Ala Arg Thr Leu Pro
    2345            2350                2355

Pro Gly Met Ala Ala Val Thr Val Val Pro Pro His Pro Val Thr
    2360            2365                2370

Pro Ala Thr Pro Ala Gly Gln Ser Val Ala Pro Gly Pro Phe Pro
    2375            2380                2385

Pro Val Gln Cys Gly Pro Gly Gln Thr Pro Cys Glu Val Leu Gly
    2390            2395                2400

Cys Val Glu Gln Ala Gln Val Cys Asp Gly Arg Glu Asp Cys Leu
    2405            2410                2415

Asp Gly Ser Asp Glu Arg His Cys Ala Arg Asn Leu Leu Met Trp
    2420            2425                2430

Leu Pro Ser Leu Pro Ala Leu Trp Ala Ala Ser Thr Val Pro Phe
    2435            2440                2445

Met Met Pro Thr Met Ala Leu Pro Gly Leu Pro Ala Ser Arg Ala
    2450            2455                2460

Leu Cys Ser Pro Ser Gln Leu Ser Cys Gly Ser Gly Glu Cys Leu
    2465            2470                2475

Ser Ala Glu Arg Arg Cys Asp Leu Arg Pro Asp Cys Gln Asp Gly
    2480            2485                2490

Ser Asp Glu Asp Gly Cys Val Asp Cys Val Leu Ala Pro Trp Ser
    2495            2500                2505

Val Trp Ser Ser Cys Ser Arg Ser Cys Gly Leu Gly Leu Thr Phe
    2510            2515                2520

Gln Arg Gln Glu Leu Leu Arg Pro Pro Leu Pro Gly Gly Ser Cys
    2525            2530                2535

Pro Arg Asp Arg Phe Arg Ser Gln Ser Cys Phe Val Gln Ala Cys
    2540            2545                2550

Pro Val Ala Gly Ala Trp Ala Met Trp Glu Ala Trp Gly Pro Cys
    2555            2560                2565

Ser Val Ser Cys Gly Gly Gly His Gln Ser Arg Gln Arg Ser Cys
    2570            2575                2580
```

-continued

```
Val Asp Pro Pro Lys Asn Gly Gly Ala Pro Cys Pro Gly Ala
    2585              2590              2595

Ser Gln Glu Arg Ala Pro Cys Gly Leu Gln Pro Cys Ser Gly Gly
2600              2605              2610

Thr Asp Cys Glu Leu Gly Arg Val Tyr Val Ser Ala Asp Leu Cys
    2615              2620              2625

Gln Lys Gly Leu Val Pro Pro Cys Pro Ser Cys Leu Asp Pro
    2630              2635              2640

Lys Ala Asn Arg Ser Cys Ser Gly His Cys Val Glu Gly Cys Arg
    2645              2650              2655

Cys Pro Pro Gly Leu Leu His Asp Thr Arg Cys Leu Pro Leu
    2660              2665              2670

Ser Glu Cys Pro Cys Leu Val Gly Glu Glu Leu Lys Trp Pro Gly
    2675              2680              2685

Val Ser Phe Leu Leu Gly Asn Cys Ser Gln Cys Val Cys Glu Lys
    2690              2695              2700

Gly Glu Leu Leu Cys Gln Pro Gly Gly Cys Pro Leu Pro Cys Gly
    2705              2710              2715

Trp Ser Ala Trp Ser Ser Trp Ala Pro Cys Asp Arg Ser Cys Gly
    2720              2725              2730

Ser Gly Val Arg Ala Arg Phe Arg Ser Pro Ser Asn Pro Pro Ala
    2735              2740              2745

Ala Trp Gly Gly Ala Pro Cys Glu Gly Asp Arg Gln Glu Leu Gln
    2750              2755              2760

Gly Cys His Thr Val Cys Gly Thr Glu Val Phe Gly Trp Thr Pro
    2765              2770              2775

Trp Thr Ser Trp Ser Ser Cys Ser Gln Ser Cys Leu Ala Pro Gly
    2780              2785              2790

Gly Gly Pro Gly Trp Arg Ser Arg Ser Arg Leu Cys Pro Ser Pro
    2795              2800              2805

Gly Asp Ser Ser Cys Pro Gly Asp Ala Thr Gln Glu Glu Pro Cys
    2810              2815              2820

Ser Pro Pro Val Cys Pro Val Pro Ser Ile Trp Gly Leu Trp Ala
    2825              2830              2835

Pro Trp Ser Thr Cys Ser Ala Pro Cys Asp Gly Gly Ile Gln Thr
    2840              2845              2850

Arg Gly Arg Ser Cys Ser Ser Leu Ala Pro Gly Asp Thr Thr Cys
    2855              2860              2865

Pro Gly Pro His Ser Gln Thr Arg Asp Cys Asn Thr Gln Pro Cys
    2870              2875              2880

Thr Ala Gln Cys Pro Glu Asn Met Leu Phe Arg Ser Ala Glu Gln
    2885              2890              2895

Cys His Gln Glu Gly Gly Pro Cys Pro Arg Leu Cys Leu Thr Gln
    2900              2905              2910

Gly Pro Gly Ile Glu Cys Thr Gly Phe Cys Ala Pro Gly Cys Thr
    2915              2920              2925

Cys Pro Pro Gly Leu Phe Leu His Asn Ala Ser Cys Leu Pro Arg
    2930              2935              2940

Ser Gln Cys Pro Cys Gln Leu His Gly Gln Leu Tyr Ala Ser Gly
    2945              2950              2955

Ala Met Ala Arg Leu Asp Cys Asn Asn Cys Thr Cys Val Ser
    2960              2965              2970

Gly Lys Met Ala Cys Thr Ser Glu Arg Cys Pro Val Ala Cys Gly
```

|  |  |  |  |  | 2975 |  |  |  | 2980 |  |  |  | 2985 |  |
|---|---|---|---|---|---|---|---|---|---|---|---|---|---|---|

Trp Ser Pro Trp Thr Leu Trp Ser Leu Cys Ser Cys Ser Cys Asn
              2990                2995                3000

Val Gly Ile Arg Arg Phe Arg Ala Gly Thr Ala Pro Pro Ala
3005                3010                3015

Ala Phe Gly Gly Ala Glu Cys Gln Gly Pro Thr Met Glu Ala Glu
    3020                3025                3030

Phe Cys Ser Leu Arg Pro Cys Pro Gly Pro Gly Gly Glu Trp Gly
    3035                3040                3045

Pro Trp Ser Pro Cys Ser Val Pro Cys Gly Gly Gly Tyr Arg Asn
    3050                3055                3060

Arg Thr Arg Gly Ser Ser Arg Ser Leu Met Glu Phe Ser Thr Cys
    3065                3070                3075

Gly Leu Gln Pro Cys Ala Gly Pro Val Pro Gly Met Cys Pro Arg
    3080                3085                3090

Asp Lys Gln Trp Leu Asp Cys Ala Gln Gly Pro Ala Ser Cys Ala
    3095                3100                3105

Glu Leu Ser Ala Pro Arg Gly Thr Asn Gln Thr Cys His Pro Gly
    3110                3115                3120

Cys His Cys Pro Ser Gly Met Leu Leu Leu Asn Asn Val Cys Val
    3125                3130                3135

Pro Thr Gln Asp Cys Pro Cys Ala His Glu Gly His Leu Tyr Pro
    3140                3145                3150

Pro Gly Ser Thr Val Val Arg Pro Cys Glu Asn Cys Ser Cys Val
    3155                3160                3165

Ser Gly Leu Ile Ala Asn Cys Ser Ser Trp Pro Cys Ala Glu Gly
    3170                3175                3180

Glu Pro Thr Trp Ser Pro Trp Thr Pro Trp Ser Gln Cys Ser Ala
    3185                3190                3195

Ser Cys Gly Pro Ala Arg Cys His Arg His Arg Phe Cys Ala Arg
    3200                3205                3210

Ser Pro Ser Ala Val Pro Ser Thr Val Ala Pro Leu Pro Leu Pro
    3215                3220                3225

Ala Thr Pro Thr Pro Leu Cys Ser Gly Pro Glu Ala Glu Glu Glu
    3230                3235                3240

Pro Cys Leu Leu Gln Gly Cys Asp Arg Ala Gly Gly Trp Gly Pro
    3245                3250                3255

Trp Gly Pro Trp Ser His Cys Ser Arg Ser Cys Gly Gly Gly Leu
    3260                3265                3270

Arg Ser Arg Thr Arg Ala Cys Asp Gln Pro Pro Pro Gln Gly Leu
    3275                3280                3285

Gly Asp Tyr Cys Glu Gly Pro Arg Ala Gln Gly Glu Val Cys Gln
    3290                3295                3300

Ala Leu Pro Cys Pro Val Thr Asn Cys Thr Ala Ile Glu Gly Ala
    3305                3310                3315

Glu Tyr Ser Pro Cys Gly Pro Pro Cys Pro Arg Ser Cys Asp Asp
    3320                3325                3330

Leu Val His Cys Val Trp Arg Cys Gln Pro Gly Cys Tyr Cys Pro
    3335                3340                3345

Pro Gly Gln Val Leu Ser Ser Asn Gly Ala Ile Cys Val Gln Pro
    3350                3355                3360

Gly His Cys Ser Cys Leu Asp Leu Leu Thr Gly Gln Arg His His
    3365                3370                3375

| | | | | | | | | | | |
|---|---|---|---|---|---|---|---|---|---|---|
|Pro|Gly|Ala|Arg|Leu|Ala|Arg|Pro|Asp|Gly|Cys|Asn|His|Cys|Thr|
|3380| | | |3385| | | |3390| | |
|Cys|Leu|Glu|Gly|Arg|Leu|Asn|Cys|Thr|Asp|Leu|Pro|Cys|Pro|Val|
|3395| | | |3400| | | |3405| | |
|Pro|Gly|Gly|Trp|Cys|Pro|Trp|Ser|Glu|Trp|Thr|Met|Cys|Ser|Gln|
|3410| | | |3415| | | |3420| | |
|Pro|Cys|Arg|Gly|Gln|Thr|Arg|Ser|Arg|Ser|Arg|Ala|Cys|Ala|Cys|
|3425| | | |3430| | | |3435| | |
|Pro|Thr|Pro|Gln|His|Gly|Gly|Ala|Pro|Cys|Thr|Gly|Glu|Ala|Gly|
|3440| | | |3445| | | |3450| | |
|Glu|Ala|Gly|Ala|Gln|His|Gln|Arg|Glu|Ala|Cys|Pro|Ser|Tyr|Ala|
|3455| | | |3460| | | |3465| | |
|Thr|Cys|Pro|Val|Asp|Gly|Ala|Trp|Gly|Pro|Trp|Gly|Pro|Trp|Ser|
|3470| | | |3475| | | |3480| | |
|Pro|Cys|Asp|Met|Cys|Leu|Gly|Gln|Ser|His|Arg|Ser|Arg|Ala|Cys|
|3485| | | |3490| | | |3495| | |
|Ser|Arg|Pro|Pro|Thr|Pro|Glu|Gly|Gly|Arg|Pro|Cys|Pro|Gly|Asn|
|3500| | | |3505| | | |3510| | |
|His|Thr|Gln|Ser|Arg|Pro|Cys|Gln|Glu|Asn|Ser|Thr|Gln|Cys|Thr|
|3515| | | |3520| | | |3525| | |
|Asp|Cys|Gly|Gly|Gly|Gln|Ser|Leu|His|Pro|Cys|Gly|Gln|Pro|Cys|
|3530| | | |3535| | | |3540| | |
|Pro|Arg|Ser|Cys|Gln|Asp|Leu|Ser|Pro|Gly|Ser|Val|Cys|Gln|Pro|
|3545| | | |3550| | | |3555| | |
|Gly|Ser|Val|Gly|Cys|Gln|Pro|Thr|Cys|Gly|Cys|Pro|Leu|Gly|Gln|
|3560| | | |3565| | | |3570| | |
|Leu|Ser|Gln|Asp|Gly|Leu|Cys|Val|Pro|Pro|Ala|His|Cys|Arg|Cys|
|3575| | | |3580| | | |3585| | |
|Gln|Tyr|Gln|Pro|Gly|Ala|Met|Gly|Ile|Pro|Glu|Asn|Gln|Ser|Arg|
|3590| | | |3595| | | |3600| | |
|Ser|Ala|Gly|Ser|Arg|Phe|Ser|Ser|Trp|Glu|Ser|Leu|Glu|Pro|Gly|
|3605| | | |3610| | | |3615| | |
|Glu|Val|Val|Thr|Gly|Pro|Cys|Asp|Asn|Cys|Thr|Cys|Val|Ala|Gly|
|3620| | | |3625| | | |3630| | |
|Ile|Leu|Gln|Cys|Gln|Glu|Val|Pro|Asp|Cys|Pro|Asp|Pro|Gly|Val|
|3635| | | |3640| | | |3645| | |
|Trp|Ser|Ser|Trp|Gly|Pro|Trp|Glu|Asp|Cys|Ser|Val|Ser|Cys|Gly|
|3650| | | |3655| | | |3660| | |
|Gly|Gly|Glu|Gln|Leu|Arg|Ser|Arg|Arg|Cys|Ala|Arg|Pro|Pro|Cys|
|3665| | | |3670| | | |3675| | |
|Pro|Gly|Pro|Ala|Arg|Gln|Ser|Arg|Thr|Cys|Ser|Thr|Gln|Val|Cys|
|3680| | | |3685| | | |3690| | |
|Arg|Glu|Ala|Gly|Cys|Pro|Ala|Gly|Arg|Leu|Tyr|Arg|Glu|Cys|Gln|
|3695| | | |3700| | | |3705| | |
|Pro|Gly|Glu|Gly|Cys|Pro|Phe|Ser|Cys|Ala|His|Val|Thr|Gln|Gln|
|3710| | | |3715| | | |3720| | |
|Val|Gly|Cys|Phe|Ser|Glu|Gly|Cys|Glu|Glu|Gly|Cys|His|Cys|Pro|
|3725| | | |3730| | | |3735| | |
|Glu|Gly|Thr|Phe|Gln|His|Arg|Leu|Ala|Cys|Val|Gln|Glu|Cys|Pro|
|3740| | | |3745| | | |3750| | |
|Cys|Val|Leu|Thr|Ala|Trp|Leu|Leu|Gln|Glu|Leu|Gly|Ala|Thr|Ile|
|3755| | | |3760| | | |3765| | |

| | | | | | | | | | | | |
|---|---|---|---|---|---|---|---|---|---|---|---|
| Gly | Asp | Pro | Gly | Gln | Pro | Leu | Gly | Pro | Gly | Asp | Glu | Leu | Asp | Ser |
| 3770 | | | | | 3775 | | | | | 3780 | | | | |
| Gly | Gln | Thr | Leu | Arg | Thr | Ser | Cys | Gly | Asn | Cys | Ser | Cys | Ala | His |
| 3785 | | | | | 3790 | | | | | 3795 | | | | |
| Gly | Lys | Leu | Ser | Cys | Ser | Leu | Asp | Asp | Cys | Phe | Glu | Ala | Asp | Gly |
| 3800 | | | | | 3805 | | | | | 3810 | | | | |
| Gly | Phe | Gly | Pro | Trp | Ser | Pro | Trp | Gly | Pro | Cys | Ser | Arg | Ser | Cys |
| 3815 | | | | | 3820 | | | | | 3825 | | | | |
| Gly | Gly | Leu | Gly | Thr | Arg | Thr | Arg | Ser | Arg | Gln | Cys | Val | Leu | Thr |
| 3830 | | | | | 3835 | | | | | 3840 | | | | |
| Met | Pro | Thr | Leu | Ser | Gly | Gln | Gly | Cys | Arg | Gly | Pro | Arg | Gln | Asp |
| 3845 | | | | | 3850 | | | | | 3855 | | | | |
| Leu | Glu | Tyr | Cys | Pro | Ser | Pro | Asp | Cys | Pro | Gly | Ala | Glu | Gly | Ser |
| 3860 | | | | | 3865 | | | | | 3870 | | | | |
| Thr | Val | Glu | Pro | Val | Thr | Gly | Leu | Pro | Gly | Gly | Trp | Gly | Pro | Trp |
| 3875 | | | | | 3880 | | | | | 3885 | | | | |
| Ser | Ser | Trp | Ser | Pro | Cys | Ser | Arg | Ser | Cys | Thr | Asp | Pro | Ala | Arg |
| 3890 | | | | | 3895 | | | | | 3900 | | | | |
| Pro | Ala | Trp | Arg | Ser | Arg | Thr | Arg | Leu | Cys | Leu | Ala | Asn | Cys | Thr |
| 3905 | | | | | 3910 | | | | | 3915 | | | | |
| Met | Gly | Asp | Pro | Leu | Gln | Glu | Arg | Pro | Cys | Asn | Leu | Pro | Ser | Cys |
| 3920 | | | | | 3925 | | | | | 3930 | | | | |
| Thr | Glu | Leu | Pro | Val | Cys | Pro | Gly | Pro | Gly | Cys | Gly | Ala | Gly | Asn |
| 3935 | | | | | 3940 | | | | | 3945 | | | | |
| Cys | Ser | Trp | Thr | Ser | Trp | Ala | Pro | Trp | Glu | Pro | Cys | Ser | Arg | Ser |
| 3950 | | | | | 3955 | | | | | 3960 | | | | |
| Cys | Gly | Val | Gly | Gln | Gln | Arg | Arg | Leu | Arg | Ala | Tyr | Arg | Pro | Pro |
| 3965 | | | | | 3970 | | | | | 3975 | | | | |
| Gly | Pro | Gly | Gly | His | Trp | Cys | Pro | Asn | Ile | Leu | Thr | Ala | Tyr | Gln |
| 3980 | | | | | 3985 | | | | | 3990 | | | | |
| Glu | Arg | Arg | Phe | Cys | Asn | Leu | Arg | Ala | Cys | Pro | Val | Pro | Gly | Gly |
| 3995 | | | | | 4000 | | | | | 4005 | | | | |
| Trp | Ser | Arg | Trp | Ser | Pro | Trp | Ser | Trp | Cys | Asp | Arg | Ser | Cys | Gly |
| 4010 | | | | | 4015 | | | | | 4020 | | | | |
| Gly | Gly | Gln | Ser | Leu | Arg | Ser | Arg | Ser | Cys | Ser | Ser | Pro | Pro | Ser |
| 4025 | | | | | 4030 | | | | | 4035 | | | | |
| Lys | Asn | Gly | Gly | Ala | Pro | Cys | Ala | Gly | Glu | Arg | His | Gln | Ala | Arg |
| 4040 | | | | | 4045 | | | | | 4050 | | | | |
| Leu | Cys | Asn | Pro | Met | Pro | Cys | Glu | Ala | Gly | Cys | Pro | Ala | Gly | Met |
| 4055 | | | | | 4060 | | | | | 4065 | | | | |
| Glu | Val | Val | Thr | Cys | Ala | Asn | Arg | Cys | Pro | Arg | Arg | Cys | Ser | Asp |
| 4070 | | | | | 4075 | | | | | 4080 | | | | |
| Leu | Gln | Glu | Gly | Ile | Val | Cys | Gln | Asp | Asp | Gln | Val | Cys | Gln | Lys |
| 4085 | | | | | 4090 | | | | | 4095 | | | | |
| Gly | Cys | Arg | Cys | Pro | Lys | Gly | Ser | Leu | Glu | Gln | Asp | Gly | Gly | Cys |
| 4100 | | | | | 4105 | | | | | 4110 | | | | |
| Val | Pro | Ile | Gly | His | Cys | Asp | Cys | Thr | Asp | Ala | Gln | Gly | His | Ser |
| 4115 | | | | | 4120 | | | | | 4125 | | | | |
| Trp | Ala | Pro | Gly | Ser | Gln | His | Gln | Asp | Ala | Cys | Asn | Asn | Cys | Ser |
| 4130 | | | | | 4135 | | | | | 4140 | | | | |
| Cys | Gln | Ala | Gly | Gln | Leu | Ser | Cys | Thr | Ala | Gln | Pro | Cys | Pro | Pro |
| 4145 | | | | | 4150 | | | | | 4155 | | | | |
| Pro | Thr | His | Cys | Ala | Trp | Ser | His | Trp | Ser | Ala | Trp | Ser | Pro | Cys |

```
                4160              4165            4170
Ser His Ser Cys Gly Pro Arg Gly Gln Gln Ser Arg Phe Arg Ser
    4175            4180            4185
Ser Thr Ser Gly Ser Trp Ala Pro Glu Cys Arg Glu Glu Gln Ser
    4190            4195            4200
Gln Ser Gln Pro Cys Pro Gln Pro Ser Cys Pro Pro Leu Cys Leu
    4205            4210            4215
Gln Gly Thr Arg Ser Arg Thr Leu Gly Asp Ser Trp Leu Gln Gly
    4220            4225            4230
Glu Cys Gln Arg Cys Ser Cys Thr Pro Glu Gly Val Ile Cys Glu
    4235            4240            4245
Asp Thr Glu Cys Ala Val Pro Glu Ala Trp Thr Leu Trp Ser Ser
    4250            4255            4260
Trp Ser Asp Cys Pro Val Ser Cys Gly Gly Gly Asn Gln Val Arg
    4265            4270            4275
Thr Arg Ala Cys Arg Ala Ala Pro His His Arg Ser Pro Pro
    4280            4285            4290
Cys Leu Gly Pro Asp Thr Gln Thr Arg Gln Gln Pro Cys Pro Gly
    4295            4300            4305
Leu Leu Glu Ala Cys Ser Trp Gly Pro Trp Gly Pro Cys Ser Arg
    4310            4315            4320
Ser Cys Gly Pro Gly Leu Ala Ser Arg Ser Gly Ser Cys Pro Cys
    4325            4330            4335
Leu Met Ala Lys Ala Asp Pro Thr Cys Asn Ser Thr Phe Leu His
    4340            4345            4350
Leu Asp Thr Gln Gly Cys Tyr Ser Gly Pro Cys Pro Glu Glu Cys
    4355            4360            4365
Val Trp Ser Ser Trp Ser Ser Trp Thr Arg Cys Ser Cys Arg Val
    4370            4375            4380
Leu Val Gln Gln Arg Tyr Arg His Gln Gly Pro Ala Ser Arg Gly
    4385            4390            4395
Ala Arg Ala Gly Ala Pro Cys Thr Arg Leu Asp Gly His Phe Arg
    4400            4405            4410
Pro Cys Leu Ile Ser Asn Cys Ser Glu Asp Ser Cys Thr Pro Pro
    4415            4420            4425
Phe Glu Phe His Ala Cys Gly Ser Pro Cys Ala Gly Leu Cys Ala
    4430            4435            4440
Thr His Leu Ser His Gln Leu Cys Gln Asp Leu Pro Pro Cys Gln
    4445            4450            4455
Pro Gly Cys Tyr Cys Pro Lys Gly Leu Leu Glu Gln Ala Gly Gly
    4460            4465            4470
Cys Ile Pro Pro Glu Glu Cys Asn Cys Trp His Thr Ser Ala Ala
    4475            4480            4485
Gly Ala Gly Met Thr Leu Ala Pro Gly Asp Arg Leu Gln Leu Gly
    4490            4495            4500
Cys Lys Glu Cys Glu Cys Arg Arg Gly Glu Leu His Cys Thr Ser
    4505            4510            4515
Gln Gly Cys Gln Gly Leu Leu Pro Leu Ser Glu Trp Ser Glu Trp
    4520            4525            4530
Ser Pro Cys Gly Pro Cys Leu Pro Pro Ser Ala Leu Ala Pro Ala
    4535            4540            4545
Ser Arg Thr Ala Leu Glu Glu His Trp Leu Arg Asp Pro Thr Gly
    4550            4555            4560
```

```
Leu Ser Pro Thr Leu Ala Pro Leu Leu Ala Ser Glu Gln His Arg
4565                4570                4575

His Arg Leu Cys Leu Asp Pro Ala Thr Gly Arg Pro Trp Thr Gly
4580                4585                4590

Ala Pro His Leu Cys Thr Ala Pro Leu Ser Gln Gln Arg Leu Cys
4595                4600                4605

Pro Asp Pro Gly Ala Cys Pro Asp Ser Cys Gln Trp Ser Leu Trp
4610                4615                4620

Gly Pro Trp Ser Pro Cys Gln Val Pro Cys Ser Gly Gly Phe Arg
4625                4630                4635

Leu Arg Trp Arg Glu Ala Glu Ala Leu Cys Gly Gly Gly Cys Arg
4640                4645                4650

Glu Pro Trp Ala Gln Glu Ser Cys Asn Gly Gly Pro Cys Pro Glu
4655                4660                4665

Ser Cys Glu Ala Gln Asp Thr Val Phe Thr Leu Asp Cys Ala Asn
4670                4675                4680

Gln Cys Pro His Ser Cys Ala Asp Leu Trp Asp Arg Val Gln Cys
4685                4690                4695

Leu Gln Gly Pro Cys Arg Pro Gly Cys Arg Cys Pro Pro Gly Gln
4700                4705                4710

Leu Val Gln Asp Gly Arg Cys Val Pro Ile Ser Ser Cys Arg Cys
4715                4720                4725

Gly Leu Pro Ser Ala Asn Ala Ser Trp Glu Leu Ala Pro Ala Gln
4730                4735                4740

Ala Val Gln Leu Asp Cys Gln Asn Cys Thr Cys Val Asn Glu Ser
4745                4750                4755

Leu Val Cys Pro His Gln Glu Cys Pro Val Leu Gly Pro Trp Ser
4760                4765                4770

Ala Trp Ser Ser Cys Ser Ala Pro Cys Gly Gly Gly Thr Met Glu
4775                4780                4785

Arg His Arg Thr Cys Glu Gly Gly Pro Gly Val Ala Pro Cys Gln
4790                4795                4800

Ala Gln Asp Thr Glu Gln Arg Gln Glu Cys Asn Leu Gln Pro Cys
4805                4810                4815

Pro Glu Cys Pro Pro Gly Gln Val Leu Ser Ala Cys Ala Thr Ser
4820                4825                4830

Cys Pro Cys Leu Cys Trp His Leu Gln Pro Gly Ala Ile Cys Val
4835                4840                4845

Gln Glu Pro Cys Gln Pro Gly Cys Gly Cys Pro Gly Gly Gln Leu
4850                4855                4860

Leu His Asn Gly Thr Cys Val Pro Pro Thr Ala Cys Pro Cys Thr
4865                4870                4875

Gln His Ser Leu Pro Trp Gly Leu Thr Leu Thr Leu Glu Glu Gln
4880                4885                4890

Ala Gln Glu Leu Pro Pro Gly Thr Val Leu Thr Arg Asn Cys Thr
4895                4900                4905

Arg Cys Val Cys His Gly Gly Ala Phe Ser Cys Ser Leu Val Asp
4910                4915                4920

Cys Gln Val Pro Pro Gly Glu Thr Trp Gln Gln Val Ala Pro Gly
4925                4930                4935

Glu Leu Gly Leu Cys Glu Gln Thr Cys Leu Glu Met Asn Ala Thr
4940                4945                4950
```

| | | | | | | | | | | | |
|---|---|---|---|---|---|---|---|---|---|---|---|
| Lys | Thr | Gln | Ser | Asn | Cys | Ser | Ser | Ala | Arg | Ala | Ser | Gly | Cys | Val |
| | 4955 | | | | 4960 | | | | | 4965 | | | | |

Lys Thr Gln Ser Asn Cys Ser Ser Ala Arg Ala Ser Gly Cys Val
    4955                      4960                          4965

Cys Gln Pro Gly His Phe Arg Ser Gln Ala Gly Pro Cys Val Pro
    4970                      4975                          4980

Glu Asp His Cys Glu Cys Trp His Leu Gly Arg Pro His Leu Pro
    4985                      4990                          4995

Gly Ser Glu Trp Gln Glu Ala Cys Glu Ser Cys Leu Cys Leu Ser
    5000                      5005                          5010

Gly Arg Pro Val Cys Thr Gln His Cys Ser Pro Leu Thr Cys Ala
    5015                      5020                          5025

Gln Gly Glu Glu Met Val Leu Glu Pro Gly Ser Cys Cys Pro Ser
    5030                      5035                          5040

Cys Arg Arg Glu Ala Pro Glu Glu Gln Ser Pro Ser Cys Gln Leu
    5045                      5050                          5055

Leu Thr Glu Leu Arg Asn Phe Thr Lys Gly Thr Cys Tyr Leu Asp
    5060                      5065                          5070

Gln Val Glu Val Ser Tyr Cys Ser Gly Tyr Cys Pro Ser Ser Thr
    5075                      5080                          5085

His Val Met Pro Glu Glu Pro Tyr Leu Gln Ser Gln Cys Asp Cys
    5090                      5095                          5100

Cys Ser Tyr Arg Leu Asp Pro Glu Ser Pro Val Arg Ile Leu Asn
    5105                      5110                          5115

Leu Arg Cys Leu Gly Gly His Thr Glu Pro Val Val Leu Pro Val
    5120                      5125                          5130

Ile His Ser Cys Gln Cys Ser Ser Cys Gln Gly Gly Asp Phe Ser
    5135                      5140                          5145

Lys Arg
    5150

<210> SEQ ID NO 75
<211> LENGTH: 5651
<212> TYPE: DNA
<213> ORGANISM: Homo sapiens

<400> SEQUENCE: 75

```
ctggtgtggc tggctgcggc cagaatcgga gccccaaccg cgctgccgct cggaccttag      60
cctgtgcctg cagcccggag tcccctcctg ccctggaagg caaggagcca ggccacgggg     120
ccacagccgc gggggccacc acactggccc aaatatttcc tgcagagtca acctatttga     180
tttcttgaca agaccacaat ctgatcccaa agatgtgctc acaaatccaa ggcaaatggg     240
tcacctttga tgatgatcct gctgttcaat cttctcaaaa gtcaaagaat ttcctctgg      300 agaatcaagg tgtctgtaga ccaaatggac tgaagctgaa ccttcctggc ctcagggaat     360
ttcccagtgg atcttcctcc accagcagca ctcctctctc ctcccccatt gtagattttt     420
atttcagtcc aggacctcca agtaactctc tctttctac acctaccaaa gacttcccag      480
gttttcctgg catccccaaa gcagggactc atgtgcttta tcctattcca gaatcatctt     540
cagacagccc actcgcaata tcaggaggag aatcttcctt actgcctacc agaccaacat     600
gtttatccca tgcctgtta cccagtgacc actcatgtac acatccaact cccaaagtag      660
gtcttccaga tgaagttaat cctcaacagg ctgaaagcct aggattccaa agtgatgatc     720
tcccccagtt tcagtatttt cgagaggact gtgcttttc aagtccattt tggaaagatg      780
aaggcagtga ttcccatttc acccttgacc caccaggaag caaaaagatg ttctcatcaa     840
gaaacaagga gatgcctatt gaccaaaaaa gcctaaataa gtgttcactc aactatatct     900
```

```
gtgagaagct tgaacatctc cagtcagctg agaaccaaga ctcacttaga agtttgtcta    960
tgcactgtct atgtgctgaa gaaaatgcct cttcctttgt cccccacaca ctcttcagga   1020
gtcagccaaa atccggatgg tctttcatgc tgagaattcc tgagaagaag aatatgatgt   1080
cttcccggca atgggaccca attttttctga aagttttgcc tggaggaatt ttgcagatgt   1140
attatgaaca gggattagaa aaaccatttta aagagataca gcttgatcca tattgtaggc   1200
tttctgaacc caaggttgag aacttcagtg tagcaggaaa aatccacact gtgaagattg   1260
aacatgtgtc ttacacagaa aaaggaaat accattctaa gacagaagta gttcatgaac    1320
ctgacataga gcagatgctg aagttggggt ccacatcgta ccatgacttc cttgactttc   1380
tgactactgt ggaggaggag ctgatgaagt tgccagctgt ttcaaaacca aaaaagaact   1440
acgaggagca agaaatttcc ttggaaattg tggacaactt tgggggtaaa gtcacaaaag   1500
aaggaaaatt tgttgaaagt gctgtgataa ctcaaattta ttgcctctgc tttgtgaatg   1560
ggaacctgga atgctttttta accttgaatg accttgagtt gccgaagcga gatgaatcct   1620
attatgagaa ggactcagaa aaaaagggga ttgatattct tgactaccat tttcataagt   1680
gtgtgaatgt acaagaattt gagcaatcaa gaatcattaa gtttgtacct ctggatgcct   1740
gccggtttga gctgatgcgt ttcaagactt tgtataatgg ggataatctt cccttttcct   1800
tgaagtctgt agtggttgtc cagggagcat acgtggaact tcaggctttt gtcaacatgg   1860
cctcattggc gcagaggtca tcctatgctg gttccttaag gtcctgtgac aatataagga   1920
tacactttcc tgtcccatcg cagtggatca aggcccttg gaccatgaac ctccagaggc    1980
agaagtctct gaaagctaaa atgaaccgcc gagcatgtct ggggagttta caggaacttg   2040
aatctgaacc tgtcattcaa gtcactgtgg ggtcagcaaa atatgagagt gcctaccagg   2100
cagtggtatg gaagatagat cggcttccag acaaaaattc aagtctagat catccccatt   2160
gtctgtcata caaattagag cttggatcag accaagaaat tccctctgat tggtatccat   2220
ttgctactgt tcagtttttcc gtgcctgaca cctgtgcctc aaggacagag gtcaggtctc   2280
tgggagtgga gagtgatgtc cagccacaga aacatgttca gcagcgagct tgctacaaca   2340
tccaggttga aatagaaaag aagtggatta aaatcgatgg agaagaccca gataaaattg   2400
gtgactgcat aactcagtag gagtagcaag agtttatgat gacagcccac ttgtcaaata   2460
tgtaattcac cgaaaccaca ccaagtcctg ctactgtaga gtggaaatga cttctgaata   2520
gcggttttag gacaggtctg atggctgtgt ttagagaagt ttagacctaa aaccgaacaa   2580
tctgtatttt ttgctttttca tgtgttttttg tcctaggggt tcgatctaaa atgtttctat   2640
aattcgtgtg atgttttgct tcctattgaa actcaaaggc actgttactc gttgtgtgac   2700
cccgcagcca gtatgatttt tgattactca gtggctgact gttttgctct ctggattact   2760
gaggtgccgt cttcatttct tcccatctct tcttgctgct tagtgtctgt actagagggt   2820
aagggaatca aaggagacat aaaccaaaat agttaatttt ccctctttct tgcctctgaa   2880
atgtggctag gtgtagaatg atgttgaaac cacaggctaa aatgtagatc tggaagtatc   2940
tgtgcttttg aattacttat ttacctgtcc tcttaccgtt ggtaaataat aattggctat   3000
atttggtacc tgtctctctc ctactgtatt gtcattttca aaatgtgttt gttttctggc   3060
gcgtgctgca aagaagctat ttctgttgtc ctacatattt tagtataaat cactaagaca   3120
tatttccttt cacttggcag gattcctttc aaaatggaat ctgagtatta gacactagtt   3180
aacatatttg tgtatattaa atatgaattt ttaaaattta taaatactat tttccaaaag   3240
```

```
tacagactct aaggacatat tttgataaag tattatttgt aatgaacaca agcctctctt    3300
gagtagaagt ctaaatcaca ttatgattat tttatactag ttctgctatc atgctgtttt    3360
atgctaattc tgcttatttt agagtatttt tcattaaaag gtgagcaaag tgaaagatac    3420
ttggtatttt acccagattt ctaagtggca acatttttat tcttcagagt caggtaaatg    3480
actataatag tttggtttct aatgaaaagt caatagcatt agcagttata attctgttta    3540
taatttcctt tcagcattta cagtgaaaag tgagaatttt aaaatttatg aaatctatat    3600
tccaggtatt gttttagtc tgaaaaacaa actcccccat gtggtattaa ataccttca     3660 atttatgttg agtcttaaac ataattagga gatattttc tctatttgct agatttgttt    3720
tgagtcaaaa ctgatttagt gttcttccaa acaacattta tgtgttggcc tacagagttt    3780
atttcatgtg ttttttttaa tatttaatat tatattacat tcattgaaat ctgttcaaaa    3840
acagattaag acaaacattt atgatggtct gtatcaatca gcagatttta ttgcttttca    3900
ttattttact gtaaaggcaa agaatgcaat aggtgatggt tggttgaaag gaattgttat    3960
tgctgttttt attttttact tttttgaga cagagtctca ctctgttgcc cagcctggag    4020
tgcagtgtgt catcttggct cactgcaacc tccgcctcct gggttcaagg gattctcctg    4080
cctcagcctc caactagctg ggattacagg cacaagccac catgcctggc taaaattctt    4140 ttgtatttt actacagacg gagtttcccc atgttggccg gctagtctc gaactcctga    4200 cctcaggtga tccaccagcc tcggcctccc aaagttctgg gattaaatgc gtgagccacc    4260
atgcccggcc gctattgctc tttttaactt catttgatgc cttgcttata atatcatatg    4320
cttgaggctc actgttgatg tagagtaggg caaatctgtg tgtgtatgtc attaaaaaaa    4380
ttctaccatc tttctttatc atctggtgtg ggcgcactct acagtgactt cagtctgctc    4440
agaacgaatg tggaggccgg ccgaaaactga tgctgcccac agtcccagtg aagttaggtg    4500
ggttaattac tgccattcct ttctaagtgt gttttatggc atcctgccca caagaactc     4560 acagtctgat taggatgaac ttaatgacta tttacacctc aaaatatatt cagcaaaggg    4620
ttcacttagt tgcccctcat gcttcacagg ttgactagta tctgtgggta cctccctgcc    4680
caggttattc actcacaagc caccgggcct tcaggacatc tcaagattca gtcttgacaa    4740
tataatagca aaagctggac taaagcccaa atggattgtc tgtggcaatg cagaagctga    4800
tagcattaac agcagggtgt tacagcataa ttgttaattc gcacatctat taggatcctt    4860
aaatattcat tacttaatgt taaattaaca ttctgtgtag ggagggagg cttattcaat    4920 tcttctgacc tcagaactgg cagaaggtca gatgtgacta cagaactcta ggtgaaaaat    4980
caggtagggt tcaaattaag tagaactgcc cttgccggaa tagtgatctt caaaaaaccc    5040
ttgcttttag gggagggaag cggggaagga aaggaatgag ggaggaaata ttcctttcta    5100
gcattcattt tgcttagatc actccattgt gagtttgacc attttggagt caaatgagca    5160
gacttccaag gagttgacca gtttgtgact agtctggtca cctttccagt tacaggatca    5220
tattaactgt gtaaatgaat tcatgggtag atgatttgtg cagatctgaa tttaagaaca    5280 tttcctttt ctgtgggaat cacaagagtt tatccactaa aaaagatat gtaaaaaga     5340 tactttccag cacataaata aaggctgaa ttttacaacc tgatgtatat attagacagt    5400
tctaggatgt tagttcctt cattccagag ctatgcttgt gatacagccc cttttcttat    5460
aaagtcagtt agaaggactt ccttaacaat gactattata atgtcttact taaaatacag    5520
ttttgtattc tgtcaatgca aatataagac aggttgagcc ttaatcatgt aacaaatat     5580 tttgtagatt acatattgat ttttcaaaaa ttaaaaatgt atttcaaact attaaaaaaa    5640
```
aaaaaaaaaa a                                                                 5651

<210> SEQ ID NO 76
<211> LENGTH: 735
<212> TYPE: PRT
<213> ORGANISM: Homo sapiens

<400> SEQUENCE: 76

Met Cys Ser Thr Asn Pro Gly Lys Trp Val Thr Phe Asp Asp Pro
1               5                   10                  15

Ala Val Gln Ser Ser Gln Lys Ser Lys Asn Phe Pro Leu Glu Asn Gln
            20                  25                  30

Gly Val Cys Arg Pro Asn Gly Leu Lys Leu Asn Leu Pro Gly Leu Arg
        35                  40                  45

Glu Phe Pro Ser Gly Ser Ser Thr Ser Ser Thr Pro Leu Ser Ser
    50                  55                  60

Pro Ile Val Asp Phe Tyr Phe Ser Pro Gly Pro Pro Ser Asn Ser Pro
65                  70                  75                  80

Leu Ser Thr Pro Thr Lys Asp Phe Pro Gly Phe Pro Gly Ile Pro Lys
                85                  90                  95

Ala Gly Thr His Val Leu Tyr Pro Ile Pro Glu Ser Ser Asp Ser
            100                 105                 110

Pro Leu Ala Ile Ser Gly Gly Glu Ser Ser Leu Leu Pro Thr Arg Pro
        115                 120                 125

Thr Cys Leu Ser His Ala Leu Leu Pro Ser Asp His Ser Cys Thr His
130                 135                 140

Pro Thr Pro Lys Val Gly Leu Pro Asp Glu Val Asn Pro Gln Gln Ala
145                 150                 155                 160

Glu Ser Leu Gly Phe Gln Ser Asp Asp Leu Pro Gln Phe Gln Tyr Phe
                165                 170                 175

Arg Glu Asp Cys Ala Phe Ser Ser Pro Phe Trp Lys Asp Glu Gly Ser
            180                 185                 190

Asp Ser His Phe Thr Leu Asp Pro Pro Gly Ser Lys Lys Met Phe Ser
        195                 200                 205

Ser Arg Asn Lys Glu Met Pro Ile Asp Gln Lys Ser Leu Asn Lys Cys
210                 215                 220

Ser Leu Asn Tyr Ile Cys Glu Lys Leu Glu His Leu Gln Ser Ala Glu
225                 230                 235                 240

Asn Gln Asp Ser Leu Arg Ser Leu Ser Met His Cys Leu Cys Ala Glu
                245                 250                 255

Glu Asn Ala Ser Ser Phe Val Pro His Thr Leu Phe Arg Ser Gln Pro
            260                 265                 270

Lys Ser Gly Trp Ser Phe Met Leu Arg Ile Pro Glu Lys Lys Asn Met
        275                 280                 285

Met Ser Ser Arg Gln Trp Gly Pro Ile Phe Leu Lys Val Leu Pro Gly
290                 295                 300

Gly Ile Leu Gln Met Tyr Tyr Glu Gln Gly Leu Glu Lys Pro Phe Lys
305                 310                 315                 320

Glu Ile Gln Leu Asp Pro Tyr Cys Arg Leu Ser Glu Pro Lys Val Glu
                325                 330                 335

Asn Phe Ser Val Ala Gly Lys Ile His Thr Val Lys Ile Glu His Val
            340                 345                 350

Ser Tyr Thr Glu Lys Arg Lys Tyr His Ser Lys Thr Glu Val Val His
        355                 360                 365

-continued

Glu Pro Asp Ile Glu Gln Met Leu Lys Leu Gly Ser Thr Ser Tyr His
    370                 375                 380

Asp Phe Leu Asp Phe Leu Thr Thr Val Glu Glu Leu Met Lys Leu
385                 390                 395                 400

Pro Ala Val Ser Lys Pro Lys Asn Tyr Glu Glu Gln Glu Ile Ser
                405                 410                 415

Leu Glu Ile Val Asp Asn Phe Trp Gly Lys Val Thr Lys Glu Gly Lys
                420                 425                 430

Phe Val Glu Ser Ala Val Ile Thr Gln Ile Tyr Cys Leu Cys Phe Val
            435                 440                 445

Asn Gly Asn Leu Glu Cys Phe Leu Thr Leu Asn Asp Leu Glu Leu Pro
450                 455                 460

Lys Arg Asp Glu Ser Tyr Tyr Glu Lys Asp Ser Glu Lys Lys Gly Ile
465                 470                 475                 480

Asp Ile Leu Asp Tyr His Phe His Lys Cys Val Asn Val Gln Glu Phe
                485                 490                 495

Glu Gln Ser Arg Ile Ile Lys Phe Val Pro Leu Asp Ala Cys Arg Phe
                500                 505                 510

Glu Leu Met Arg Phe Lys Thr Leu Tyr Asn Gly Asp Asn Leu Pro Phe
            515                 520                 525

Ser Leu Lys Ser Val Val Val Gln Gly Ala Tyr Val Glu Leu Gln
530                 535                 540

Ala Phe Val Asn Met Ala Ser Leu Ala Gln Arg Ser Ser Tyr Ala Gly
545                 550                 555                 560

Ser Leu Arg Ser Cys Asp Asn Ile Arg Ile His Phe Pro Val Pro Ser
                565                 570                 575

Gln Trp Ile Lys Ala Leu Trp Thr Met Asn Leu Gln Arg Gln Lys Ser
            580                 585                 590

Leu Lys Ala Lys Met Asn Arg Arg Ala Cys Leu Gly Ser Leu Gln Glu
            595                 600                 605

Leu Glu Ser Glu Pro Val Ile Gln Val Thr Val Gly Ser Ala Lys Tyr
    610                 615                 620

Glu Ser Ala Tyr Gln Ala Val Val Trp Lys Ile Asp Arg Leu Pro Asp
625                 630                 635                 640

Lys Asn Ser Ser Leu Asp His Pro His Cys Leu Ser Tyr Lys Leu Glu
                645                 650                 655

Leu Gly Ser Asp Gln Glu Ile Pro Ser Asp Trp Tyr Pro Phe Ala Thr
            660                 665                 670

Val Gln Phe Ser Val Pro Asp Thr Cys Ala Ser Arg Thr Glu Val Arg
            675                 680                 685

Ser Leu Gly Val Glu Ser Asp Val Gln Pro Lys His Val Gln Gln
690                 695                 700

Arg Ala Cys Tyr Asn Ile Gln Val Glu Ile Glu Lys Lys Trp Ile Lys
705                 710                 715                 720

Ile Asp Gly Glu Asp Pro Asp Lys Ile Gly Asp Cys Ile Thr Gln
                725                 730                 735

<210> SEQ ID NO 77
<211> LENGTH: 3510
<212> TYPE: DNA
<213> ORGANISM: Homo sapiens

<400> SEQUENCE: 77
aaaatttcag cagagagaaa tagagaaagc agtgtgtgtg catgtgtgtg tgtgtgagag    60

```
agagagggag aggagcgaga gggagaggga gagggagaga gagaaaggga gggaagcaga    120
gagtcaagtc caagggaatg agcgagagag gcagagacag gggaagaggc gtgcgagaga    180
aggaataaca gctttccgga gcaggcgtgc cgtgaactgg cttctatttt atttttatttt   240 tttctccttt ttatttttta aagagaagca ggggacagaa gcaatggccg aggcagaaga    300
caagccgagg tgctggtgac cctgggcgtc tgagtggatg attggggctg ctgcgctcag    360
aggcctgcct ccctgccttc caatgcatat aaccccacac cccagccaat gaagacgaga    420
ggcagcgtga acaaagtcat ttagaaagcc cccgaggaag tgtaaacaaa agagaaagca    480
tgaatggagt gcctgagaga caagtgtgtc ctgtactgcc cccacccttta gctgggccag    540 caactgcccg gcctgcttc tccccaccta ctcactggtg atctttttttt ttttactttt    600 ttttcccttt tcttttccat tctcttttct tattttcttt caaggcaagg caaggatttt     660
gattttggga cccagccatg gtccttctgc ttcttcttta aaatacccac tttctcccca    720
tcgccaagcg gcgtttggca atatcagata tccactctat ttattttttac ctaaggaaaa   780 actccagctc ccttcccact cccagctgcc ttgccacccc tcccagccct ctgcttgccc    840
tccacctggc ctgctgggag tcagagccca gcaaaacctg tttagacaca tggacaagaa    900
tcccagcgct acaaggcaca cagtccgctt cttcgtcctc agggttgcca gcgcttcctg    960
gaagtcctga agctctcgca gtgcagtgag ttcatgcacc ttcttgccaa gcctcagtct    1020
ttgggatctg gggaggccgc ctggttttcc tccctccttc tgcacgtctg ctggggtctc    1080
ttcctctcca ggccttgccg tcccctggc ctctcttccc agctcacaca tgaagatgca     1140
cttgcaaagg gctctggtgg tcctggccct gctgaacttt gccacggtca gcctctctct   1200
gtccacttgc accaccttgg acttcggcca catcaagaag aagagggtgg aagccattag    1260
gggacagatc ttgagcaagc tcaggctcac cagcccccct gagccaacgg tgatgaccca    1320
cgtcccctat caggtcctgg ccctttacaa cagcacccgg gagctgctgg aggagatgca    1380
tggggagagg gaggaaggct gcacccagga aaacaccgag tcggaatact atgccaaaga    1440
aatccataaa ttcgacatga tccagggggct ggcggagcac aacgaactgg ctgtctgccc   1500
taaaggaatt acctccaagg ttttccgctt caatgtgtcc tcagtggaga aaaatagaac    1560
caacctattc cgagcagaat tccgggtctt gcgggtgccc aaccccagct ctaagcggaa    1620
tgagcagagg atcgagctct tccagatcct tcggccagat gagcacattg ccaaacagcg    1680 ctatatcgt ggcaagaatc tgcccacacg gggcactgcc gagtggctgt cctttgatgt     1740
cactgacact gtgcgtgagt ggctgttgag aagagagtcc aacttaggtc tagaaatcag    1800
cattcactgt ccatgtcaca ccttttcagcc aatggagat atcctggaaa acattcacga    1860
ggtgatggaa atcaaattca aaggcgtgga caatgaggat gaccatggcc gtggagatct    1920
ggggcgcctc aagaagcaga aggatcacca caaccctcat ctaatcctca tgatgattcc    1980
cccacaccgg ctcgacaacc cgggccaggg gggtcagagg aagaagcggg ctttggacac    2040
caattactgc ttccgcaact tggaggagaa ctgctgtgtg cgccccctct acattgactt    2100
ccgacaggat ctgggctgga gtgggtccca tgaacctaag ggctactatg ccaacttctg    2160
ctcaggccct tgcccatacc tccgcagtgc agacacaacc cacagcacgg tgctgggact    2220
gtacaacact ctgaaccctg aagcatctgc ctcgccttgc tgcgtgcccc aggacctgga    2280 gccctgacc atcctgtact atgttgggag accccaaa gtggagcagc tctccaacat       2340
ggtggtgaag tcttgtaaat gtagctgaga ccccacgtgc gacagagaga ggggagagag    2400
```

```
aaccaccact gcctgactgc ccgctcctcg ggaaacacac aagcaacaaa cctcactgag      2460
aggcctggag cccacaacct tcggctccgg gcaaatggct gagatggagg tttccttttg      2520
gaacatttct ttcttgctgg ctctgagaat cacggtggta agaaagtgt gggtttggtt       2580 agaggaaggc tgaactcttc agaacacaca gactttctgt gacgcagaca gagggatgg       2640 ggatagagga aagggatggt aagttgagat gttgtgtggc aatgggattt gggctaccct      2700
aaagggagaa ggaagggcag agaatggctg ggtcagggcc agactggaag acacttcaga     2760
tctgaggttg gatttgctca ttgctgtacc acatctgctc tagggaatct ggattatgtt      2820
atacaaggca agcattttt ttttttttt aaagacaggt tacgaagaca aagtcccaga        2880
attgtatctc atactgtctg ggattaaggg caaatctatt acttttgcaa actgtcctct      2940
acatcaatta acatcgtggg tcactacagg gagaaaatcc aggtcatgca gttcctggcc     3000
catcaactgt attgggcctt ttggatatgc tgaacgcaga agaaagggtg gaaatcaacc      3060
ctctcctgtc tgccctctgg gtccctcctc tcacctctcc ctcgatcata tttccccttg      3120
gacacttggt tagacgcctt ccaggtcagg atgcacattt ctggattgtg gttccatgca     3180
gccttggggc attatgggtt cttccccac ttccctcca agaccctgtg ttcatttggt        3240
gttcctggaa gcaggtgcta caacatgtga ggcattcggg gaagctgcac atgtgccaca     3300
cagtgacttg gccccagacg catagactga ggtataaaga caagtatgaa tattactctc     3360
aaaatctttg tataaataaa tattttggg gcatcctgga tgattcatc ttctggaata        3420 ttgtttctag aacagtaaaa gccttattct aaggtgtatg tctgactcga taaatatcct     3480
tcaattaccc ttaaaaaaaa aaaaaaaaaa                                        3510
```

<210> SEQ ID NO 78
<211> LENGTH: 412
<212> TYPE: PRT
<213> ORGANISM: Homo sapiens

<400> SEQUENCE: 78

```
Met Lys Met His Leu Gln Arg Ala Leu Val Val Leu Ala Leu Leu Asn
1               5                   10                  15

Phe Ala Thr Val Ser Leu Ser Leu Ser Thr Cys Thr Thr Leu Asp Phe
            20                  25                  30

Gly His Ile Lys Lys Lys Arg Val Glu Ala Ile Arg Gly Gln Ile Leu
        35                  40                  45

Ser Lys Leu Arg Leu Thr Ser Pro Pro Glu Pro Thr Val Met Thr His
    50                  55                  60

Val Pro Tyr Gln Val Leu Ala Leu Tyr Asn Ser Thr Arg Glu Leu Leu
65                  70                  75                  80

Glu Glu Met His Gly Glu Arg Glu Gly Cys Thr Gln Glu Asn Thr
            85                  90                  95

Glu Ser Glu Tyr Tyr Ala Lys Glu Ile His Lys Phe Asp Met Ile Gln
            100                 105                 110

Gly Leu Ala Glu His Asn Glu Leu Ala Val Cys Pro Lys Gly Ile Thr
        115                 120                 125

Ser Lys Val Phe Arg Phe Asn Val Ser Val Glu Lys Asn Arg Thr
    130                 135                 140

Asn Leu Phe Arg Ala Glu Phe Arg Val Leu Arg Val Pro Asn Pro Ser
145                 150                 155                 160

Ser Lys Arg Asn Glu Gln Arg Ile Glu Leu Phe Gln Ile Leu Arg Pro
            165                 170                 175
```

Asp Glu His Ile Ala Lys Gln Arg Tyr Ile Gly Lys Asn Leu Pro
            180                 185                 190

Thr Arg Gly Thr Ala Glu Trp Leu Ser Phe Asp Val Thr Asp Thr Val
        195                 200                 205

Arg Glu Trp Leu Leu Arg Arg Glu Ser Asn Leu Gly Leu Glu Ile Ser
    210                 215                 220

Ile His Cys Pro Cys His Thr Phe Gln Pro Asn Gly Asp Ile Leu Glu
225                 230                 235                 240

Asn Ile His Glu Val Met Glu Ile Lys Phe Lys Gly Val Asp Asn Glu
            245                 250                 255

Asp Asp His Gly Arg Gly Asp Leu Gly Arg Leu Lys Lys Gln Lys Asp
        260                 265                 270

His His Asn Pro His Leu Ile Leu Met Met Ile Pro Pro His Arg Leu
    275                 280                 285

Asp Asn Pro Gly Gln Gly Gly Gln Arg Lys Lys Arg Ala Leu Asp Thr
290                 295                 300

Asn Tyr Cys Phe Arg Asn Leu Glu Glu Asn Cys Cys Val Arg Pro Leu
305                 310                 315                 320

Tyr Ile Asp Phe Arg Gln Asp Leu Gly Trp Lys Trp Val His Glu Pro
            325                 330                 335

Lys Gly Tyr Tyr Ala Asn Phe Cys Ser Gly Pro Cys Pro Tyr Leu Arg
        340                 345                 350

Ser Ala Asp Thr Thr His Ser Thr Val Leu Gly Leu Tyr Asn Thr Leu
    355                 360                 365

Asn Pro Glu Ala Ser Ala Ser Pro Cys Cys Val Pro Gln Asp Leu Glu
370                 375                 380

Pro Leu Thr Ile Leu Tyr Tyr Val Gly Arg Thr Pro Lys Val Glu Gln
385                 390                 395                 400

Leu Ser Asn Met Val Val Lys Ser Cys Lys Cys Ser
            405                 410

<210> SEQ ID NO 79
<211> LENGTH: 5605
<212> TYPE: DNA
<213> ORGANISM: Homo sapiens

<400> SEQUENCE: 79

| | | | | | |
|---|---|---|---|---|---|
| gttgcgagcg | ctgcacaaca | acaaaaggac | ttgactggc | cggcctgggc | gcagcgaccc | 60 |
| gagggctgga | gccggccccg | cgcctgccgt | ctgggtacct | gaacgaggtg | cagcgcagcc | 120 |
| cggcccacc | gcagctacct | cagcagtccc | gccccgcccg | cgtccttccc | cgccgagccg | 180 |
| gcggccgctc | ccttccccgc | gcagccccgc | acggcccggg | cccacgtaca | atgactcttc | 240 |
| ttgcttttca | cctaagttga | ataagcaccc | tgtgcacttt | aatctcctgt | cggtaccatt | 300 |
| gggccaacta | agacaaggt | tttgaaatct | cagctataaa | agacatccag | ccaaactctc | 360 |
| agtcttgcct | taacaatgtt | ccagaggctg | aataaaatgt | tgtgggtga | agtcagttct | 420 |
| tcctccaacc | aagaaccaga | attcaatgag | aaagaagatg | atgaatggat | tcttgttgac | 480 |
| ttcatagata | cttgcactgg | tttctcagca | gaagaagaag | aagaagagga | ggacatcagt | 540 |
| gaagagtcac | ctactgagca | cccttcagtc | ttttcctgtt | taccggcatc | tcttgagtgc | 600 |
| ttggctgata | caagtgattc | ctgctttctc | cagtttgagt | catgtccaat | ggaggagagc | 660 |
| tggtttatca | ccccacccc | atgttttact | gcaggtggat | taaccactat | caaggtggaa | 720 |
| acaagtccta | tggaaaacct | tctcattgaa | catcccagca | tgtctgtcta | tgctgtgcat | 780 |

```
aactcctgcc ctggtctcag tgaggccacc cgtgggactg atgaattaca tagcccaagt     840
agtcccagag tggaagctca aaatgaaatg gggcagcata ttcattgtta tgttgcagct     900
cttgctgctc atacaacttt tctggaacaa cccaagagct ttcgcccttc ccagtggata     960
aaagaacaca gtgaaagaca gcctcttaac agaaatagcc ttcgtcgcca aaatcttacc    1020
agggattgcc accctcggca agtcaagcac aatggctggg ttgttcatca gccctgcccg    1080
cgtcagtaca attactaata gtttcaagtt ttgttggttg gtttctcttg gtttgtgctt    1140
acatgtatgg atgtgtgtat atgtacagtg aaaatgttgt ctctttacaa ccaattgata    1200
accaatcaca tagttttatc agtgtattta gacactatct tgaaaatcag atttatatgc    1260
tgtgtatcac ataatgcctt gccttttaaca tttacttttt ttgtacactt tttcagatta    1320
tttctggaaa catatcaata taattacagt gtttgggggt gtctttaaat atattaggtt    1380
atacattagt cagcatttta aagacatttc ttcccaagta cgagaatagg catctttcat    1440
tttcatttta ttttgtatta cttaatcttt taagcaagca aaaatttatt ctcagggtca    1500
gctgtacact ttattgacca gtacttgata atctctctgt atatgatgaa tacattttta    1560
cacactaaca ttagcattaa caggtgatag ttgccatgga tataatgaaa ttatggctgg    1620
actttctttt gaaagaaaac ttgatgtatt ctgtgtgtat ggttttttccc cagattagtc    1680
atacagttca tttggaattc aggtacatta agctttagtg aagagtgcat gcagtaattc    1740
caatgtgact gcatgacgtg gtacagacat tacaggtgtt gtagacagag gcacttgtct    1800
cgtgcagagg gattaaatta gacctgtgag attatatttg gaaaaattca tgtctgtaac    1860
taacccatta gtgcagtatt taatttgtta ctattccttc ccgccaattc tgtccactcc    1920
tcacctcgca tcagctataa atttggaagt acttgtccag gcactcaagt gacttcatat    1980
ttctctctgc ccatgggaaa agagataggc tttatatttc cacagagtga aaatcctct    2040
gtcatggagc ctgtcctgcc aagtggcaag agtgtgggga ctgtctggtg atgatgtctt    2100
tcatggcatc tgagtgaaga gtgacaggtt ggctcaactt ttttctttt ttttttttaa    2160
ttgccttgta ttgtaagtat cttccctgc agtccaagtg acttttcatt ttttgttta    2220
acttcaggca aaatctttaa ccactctggc ctctgtttcc cccaccaacg gggagcagtg    2280
acatttacct ccctcacaga gtcactgtga ggattctata ctgatttgaa gtggagctgt    2340
tcagaactga accttgtagg aaattccaag ggcctttcta ctgaatctgg tgatggggtg    2400
gggccgtggc actttctctg ccacagctgt tcttcacagt gttggtgcta atgaggccag    2460
ggtgcagggt tcgattcaca cgtaggccag ttaacttaga gaaaatctat ttccttacct    2520
ctagccagtc acttccttt tccgcagttg tgatgggttt tgctgagcca tccactctga    2580
ctgattctcct ctgaagtaaa catatttaca atccaaagca attctactga cagaagtgtt    2640
gccttcataa tcaaacagct tgtttttcca tctcctctgc aaccctaatt aaatgagtac    2700
aggtctacaa aatgttttca aggagaaaag cagcatatcc ttaagtgaag tattatatttt    2760
ttcaataacc ctgtagtggc ttgatgcagg gaaccctggg ggactttcag cgaagagctg    2820
tgctctttct tgactagatt agagcgtttg gagtggaaga cgtcaaatgt gtagtgagat    2880
ggaggtttta cattgttctt ctactggctg tgatgaagtg ccagaatgtc tctttagaac    2940
aagagttaga ttcccccttt ctccttattg ccccttccgt tttgacttcc cctttattta    3000
tttgttgtct aattagggc caagtctgta aagtttgtc aaagtgagtt agaagttgtt    3060
ttctcttact atttgtgttt accagagttg ggagataaga tagtttccat gaaggtgtgt    3120
atgttttata cgatgtttgt tatagggcca tgcattggta acttgaaaat agaccagctt    3180
```

```
aatgtcttca ggatgtaaaa ctctgaatac acggcgtctc ttttcatac attgcatgta     3240 agttgttagt acctcacaag ctacagaagt tcagccatga gattttgttt ggcaacatga     3300
acagatttgt gtataactgc aatggccttt ttttccagat ttccttattg acttttgtt     3360 tgccttacct ggggctagtt ttttatgctt tgtacctaga aaacaaaaaa ttacattcgt     3420
tgggcttttt ttcaaggttg ggattaccac accacctgga atatcatact gtggtttctg     3480
cctaaaattg gcacatgtaa gtattgaaga aaatggttat ataattcagt tgaaactctt     3540
ggttattaga tgttaggcat ctcctgtatg taagacacaa ggccaaccac aacacagaac     3600
gatgttgacc tgttaagtat tctctgaaac atggccaaaa tgcattttat gagctttttt     3660
ttttgctatt gtaaatatta gtggtttaca atgcgcttta gacatatttc tttaaaatgc     3720
aagcagtgag aaataagacc tctctgaatt agtagctcta aactgttaac atagaatgtt     3780
acttggaaaa agtctggaat atgtggtgta cacaagcagt gcttcgtgaa tgagtttctt     3840
agcttttata gtgcgccatg tttctcaaag tttgttttg ttgacaaaac attttataat     3900
atatatctta tgtttatttt ttttctcaac taattgtgta ctgcactgta aggtgaaaat     3960
tagccatcca ttatttatct tctgtggcaa tgcatttata tggttgattg ggtggggaat     4020 ttttttgcaga aagatgcaaa gtgattgggt tttcgacttc ctatcgcagg gagcttttaa     4080
gaaatattaa tttcctatac attttttccaa tccccatgca aactgttcct gtttacatac     4140
cttctctgtt gtatcagtac tttgagtgag aagacagttt atttaaaact tgagcaggct     4200
gttcagcatt gtttctgctt ctgaaatctg tatagtacac tggtttgtaa tcattatgtc     4260
ttcattgaaa tccttgctac ttctcttcct cctcaatgaa atacattata tattatcttt     4320
atgtactctt aagaaaaacg agcaaggaag agtatcttca ttattctcat tttctctgag     4380
ttggaaacaa aaacatgaag gactccaact agaagacaga tatttacatt taaatagatt     4440
agtgggaaaa ctttaagagt ttccacatat tagttttcat ttttttgagtc aagagactgc     4500 tccttgtact gggagacact agtagtatat gtttgtaatg ttactttaaa attatctttt     4560
tattttataa ggcccataaa tactggttaa actctgttaa aagtgggcct tctatcttgg     4620
atggtttcac tgccatcagc catgctgata tattagaaat ggcatcccta tctacttact     4680
ttaatgctta aaattataca taaaatgctt tatttagaaa acctacatga tacagtggtg     4740
tcagccttgc catgtatcag tttcacttga aatttgagac caattaaatt tcaactgttt     4800
agggtggaga aagaggtact ggaaaacatg cagatgagga tatcttttat gtgcaacagt     4860
atcctttgca tgggaggaga gttactcttg aaaggcaggc agcttaagtg gacaatgttt     4920
tgtatatagt tgagaatttt acgacacttt taaaaattgt gtaattgtta aatgtccagt     4980
tttgctctgt tttgcctgaa gttttagtat tgtttcta ggtggacctc tgaaaaccaa     5040
accagtacct ggggaggtta gatgtgtgtt tcaggcttgg agtgtatgag tggttttgct     5100
tgtattttcc tccagagatt ttgaacttta ataattgcgt gtgttttttt tttttttaag     5160
tggctttgtt ttttttctc aagtaaaatt gtgaacatat ttcctttata ggggcagggc     5220
atgagttagg gagactgaag agtattgtag actgtacatg tgccttctta atgtgtttct     5280
cgacacattt ttttcagta acttgaaaat tcaaagggga catttggtta ggttactgta     5340
catcaatcta tgcataaatg gcagcttgtt ttcttgagcc acggtctaaa ttttgttttt     5400
atagaaattt tttatactga ttggttcata gatggtcagt tttgtacaca gactgaacaa     5460
tacagcactt tgccaaaaat gagtgtagca ttgtttaaac attgtgtgtt aacacctgtt     5520
```

```
ctttgtaatt gggttgtggt gcattttgca ctacctggag ttacagtttt caatctgtca    5580
gtaaataaag tgtcctttaa cttca                                          5605
```

<210> SEQ ID NO 80
<211> LENGTH: 240
<212> TYPE: PRT
<213> ORGANISM: Homo sapiens

<400> SEQUENCE: 80

```
Met Phe Gln Arg Leu Asn Lys Met Phe Val Gly Glu Val Ser Ser Ser
1               5                   10                  15

Ser Asn Gln Glu Pro Glu Phe Asn Glu Lys Glu Asp Asp Glu Trp Ile
            20                  25                  30

Leu Val Asp Phe Ile Asp Thr Cys Thr Gly Phe Ser Ala Glu Glu Glu
        35                  40                  45

Glu Glu Glu Asp Ile Ser Glu Ser Pro Thr Glu His Pro Ser
    50                  55                  60

Val Phe Ser Cys Leu Pro Ala Ser Leu Glu Cys Leu Ala Asp Thr Ser
65                  70                  75                  80

Asp Ser Cys Phe Leu Gln Phe Glu Ser Cys Pro Met Glu Glu Ser Trp
                85                  90                  95

Phe Ile Thr Pro Pro Cys Phe Thr Ala Gly Gly Leu Thr Thr Ile
            100                 105                 110

Lys Val Glu Thr Ser Pro Met Glu Asn Leu Leu Ile Glu His Pro Ser
        115                 120                 125

Met Ser Val Tyr Ala Val His Asn Ser Cys Pro Gly Leu Ser Glu Ala
    130                 135                 140

Thr Arg Gly Thr Asp Glu Leu His Ser Pro Ser Pro Arg Val Glu
145                 150                 155                 160

Ala Gln Asn Glu Met Gly Gln His Ile His Cys Tyr Val Ala Ala Leu
                165                 170                 175

Ala Ala His Thr Thr Phe Leu Glu Gln Pro Lys Ser Phe Arg Pro Ser
            180                 185                 190

Gln Trp Ile Lys Glu His Ser Glu Arg Gln Pro Leu Asn Arg Asn Ser
        195                 200                 205

Leu Arg Arg Gln Asn Leu Thr Arg Asp Cys His Pro Arg Gln Val Lys
    210                 215                 220

His Asn Gly Trp Val Val His Gln Pro Cys Pro Arg Gln Tyr Asn Tyr
225                 230                 235                 240
```

<210> SEQ ID NO 81
<211> LENGTH: 4127
<212> TYPE: DNA
<213> ORGANISM: Homo sapiens

<400> SEQUENCE: 81

```
gcacagactc aaagcccgc gggcgagctc agcagcccgg agcgaccgcg gccccgccgc      60 ctccccgcg agtcccggcg atgcggcccg gcctgtgagc ggccggcgac cctgggacgc     120
cccgccgcac aactacctca cgccgtgcc gccccctcc cgcccccagg gaatctctgg     180
agattggttc accttttgtg gtcctgaccc cttctgtcct cactgtacct tgaagtccta    240
gagtccaata aaatcgctgc ctcccagctg tttggatcac agagaggttt ttgcactgcc    300
atagggcgcc cccgtgaggc gcttcgcccc ccaccatgtt ccagcgcctc tccagcctct    360
tcttcagcac cccctcgccc cccgaagacc ccgactgccc ccgcgccttc gtgtcggagg    420
```

-continued

```
aggatgaagt ggacggctgg ctcatcattg acctgccgga cagctacgcg gctccaccca    480
gccccgggc cgcccctgcc cccgcgggcc gccctccgcc cgcgccctcc ttgatggacg    540
agagctggtt tgttaccct cccgcctgtt ttacggcaga ggggcctgga ctcggtcccg    600
cccgcctcca gagcagtccc ctggaggacc tcctcatcga gcaccccagc atgtccgttt    660
acgtcaccgg cagcaccata gtgctagagc ccgggtcccc ttccccgctc ccggacgcgg    720
ccctgcctga cggcgacctc agcgaagggg aattgacgcc cgcccgccgc gagccgcggg    780
ccgcgcgcca cgccgctcct ctcccagcgc gggcggcgct gctggagaag cgggccagg    840
tgcggcggct gcagcgggcc cggcagcggg cagagcgcca cgcgctgagc gccaaggcgg    900
tgcagcggca gaaccgagcc cgcgagagcc gtccgcgccg gtccaagaac cagagcagct    960
tcatctacca gccgtgccag cgccagttca actactgagc gtccaccggc cgcgccacga   1020
acccttgcc gatcccgatc cctgtcgggc tcctccgact cctcgggctg acaccgaaa   1080
cctcccttct taaagcgtgt gaggttgggt gatagccgtt ccttccccga caccctcaat   1140
ttccccatct ctgatcctct aatctgcctc tgaacccatt caccctcac cctcactcct   1200
ggtccccata cccagcatct aatcatccat gcccctact cctggccct ccatcctttc   1260
ttctctggtc cccatccctg tctctccctt tcacccttgc cctccagtcc tctacctctg   1320
gcctgcccct atttctgaaa gcttcttcca gtccctgatc tggctcattc cccaccttca   1380
actcccacct tacatgtctc acactatccc atggttggca ttacactcac tcctgttccc   1440
ttattcttca ttcccagtaa ttccctacca aatggtgggg accctgagcc cagctctgac   1500
caggtagagc ctgtgcagcc tgggctgctg tcattgccct ccagtaaggg ctcagggttt   1560
tgctttagt ctccccttcc ttctgccttg ggggcggtac tctgtggagc tgcttaggcc   1620
tggaaaggta cagtatgtag aagaggactg tgagacgtga gttagaggga gaagatggag   1680
ggaatctagg gaacgaggca gcctattgga gatgcggaca ggacagacac gttgagaagc   1740
tgcagggagc agggcaccaa gggagtgtgc actgtgcttg ctcagagagg ccaaaccctg   1800
ctcccaggct gaagcctgga gtctgccccc acttcccttt tctataatcc acccttctgc   1860
aggccctgaa atctgaaggg cttagttagt accttgccac tctaccccca acacgtcacc   1920
cgagtagaag ctgggcaagg ccctaccatc ctggccgtct gttcacaagc caaggtgct   1980
agaactagct taggagacat gcaggccaca gggcttctag gcagggaaag ggcacacacc   2040
ctaggtcagc gtgcagagca gtgatgctgg aggacacacc atggggtgaa gccatcccaa   2100
ggctgacagc tcagtcttca ccttgcctct ggccttgtat ttcacaccct gctcagtatg   2160
gctagccagc agtcctgagt aggagtccag gactcccact gtctcaatct gcaaattgtt   2220
cctatccagg ttcagggcct tcaggggcc tcttttcatt ttctcccaca ggcctctctt   2280
tctttctagg ttgctgggga gaaatgggta ccctatgatc ccctcccct tctcctccag   2340
taaatacctg gaagagggaa cctgaatccc tggggagac agaagggca ggggccacca   2400
gcctccccctt cttgtggtga gactgaattt tgggctcaga caccagcaac agcctcttgg   2460
gatgccctga gttgcttccc atttcctctt tctagccgtc cttttctagt gtgtgctcac   2520
tcttcctagg aacttttaag acttcttggt acctatgaac ataggtcctc ccctcacccc   2580
aactctaggt ttccaggcct cacagccaag ctgaagcttg gagaaaactc tgcattccca   2640
tgagggcaaa ggcagctgcc ctccctgacc ctatagcccc aggcctcatg ggggtatgt   2700
ggggaaggga tggggtatcc ccatggatgc tgggatgagg acagaggaag acctgatggg   2760
gtctcctatt ccagggaata agccaaatta acactaaaaa cggatcaaag ctcccacgcc   2820
```

```
agtccactag ggccccagta gttgacagcc ttgctcctct cccaagttct ccttcagaac   2880
ctagttgctt ttattcttcc agctaccact tgggcacttc acagccagcc tagggtcttc   2940
ggcacctcca agagctgaat ctccctccaa cccttcttgc ctactcctca ctgccagctg   3000
ggacctaggc tcagtcctgt gtggtgccca tgatccttct ggtggggggaa gagtttaagt   3060
tatagggcat ttggctcaaa ttttaaaagg cctttttgttt acctatattt ctggaggctc   3120
ctgtattcta gaacccaatc tctcacctgc ttggttgcaa ggctcatatt tttttgtacc   3180
tttcctatag attctgtagc atttgagtgt ggcaatattt taattgtgta tagatttcta   3240
agaaccaaca ctactcagtc tcctgctagt ctgactcctg aagcatcagc ccttgtcata   3300
ctgtattgac tgtgtacgtg cctttcacct tgagcatgct tcaggatttt tttttaaacc   3360
acagaacttg aatacatgag ggaaccagag ttcaaagtcc tatgcaacct taggaggggg   3420
ttagagagtc tgttttgatt gatgttttct gaggccctag aggagtttgt atcaatttgt   3480
gagtattaat gtcagtacta ccagcacttt gccaaaactg tcagagggac ccgtttctag   3540
agtgagtccc agttacatca aacagtgact tccagttatt ccccagtaag tctgagtggt   3600
tccttcaagc tgggtgtctt tccagccttt gccagtctag ccccagcagg gcaccgtgta   3660
tgaatgcagt ttggtgctgt tttagagtat gcctgctccc cagcccctg cctggaaccc   3720
tctgagcaac ttgctctgac ctataatgtc ttaggtgcaa cacggacccc accagagctc   3780
ttggataccc ccctagatcc atgtggcttt atgtgagggg actgaatgca gacacaccat   3840
agccccttc tactactttc cctctcgccc tgccacctag ttccacatgg aaccaacaag   3900
ttgagtgcat ccctgttggg tgttttgtgt tgagactggc tgaaatgagg agactttgac   3960
catgtgacgt gtcaacagac tcaaggagac aaccacctca actgggtcat gtggcatgcc   4020
tgtgtatgtg tgtaacagaa ttctgattgt tagactgtaa tgctattcct ctatgggaga   4080
aaaaaattaa tataaagaaa aacaaataaa aatatattta aagcaca             4127
```

<210> SEQ ID NO 82
<211> LENGTH: 220
<212> TYPE: PRT
<213> ORGANISM: Homo sapiens

<400> SEQUENCE: 82

Met Phe Gln Arg Leu Ser Ser Leu Phe Phe Ser Thr Pro Ser Pro Pro
1               5                   10                  15

Glu Asp Pro Asp Cys Pro Arg Ala Phe Val Ser Glu Glu Asp Glu Val
            20                  25                  30

Asp Gly Trp Leu Ile Ile Asp Leu Pro Asp Ser Tyr Ala Ala Pro Pro
        35                  40                  45

Ser Pro Gly Ala Ala Pro Pro Ala Gly Arg Pro Pro Pro Ala Pro
    50                  55                  60

Ser Leu Met Asp Glu Ser Trp Phe Val Thr Pro Pro Ala Cys Phe Thr
65                  70                  75                  80

Ala Glu Gly Pro Gly Leu Gly Pro Ala Arg Leu Gln Ser Ser Pro Leu
                85                  90                  95

Glu Asp Leu Leu Ile Glu His Pro Ser Met Ser Val Tyr Val Thr Gly
            100                 105                 110

Ser Thr Ile Val Leu Glu Pro Gly Ser Pro Ser Pro Leu Pro Asp Ala
        115                 120                 125

Ala Leu Pro Asp Gly Asp Leu Ser Glu Gly Glu Leu Thr Pro Ala Arg
    130                 135                 140

Arg Glu Pro Arg Ala Ala Arg His Ala Pro Leu Pro Ala Arg Ala
145                 150                 155                 160

Ala Leu Leu Glu Lys Ala Gly Gln Val Arg Leu Gln Arg Ala Arg
                165                 170                 175

Gln Arg Ala Glu Arg His Ala Leu Ser Ala Lys Ala Val Gln Arg Gln
            180                 185                 190

Asn Arg Ala Arg Glu Ser Arg Pro Arg Arg Ser Lys Asn Gln Ser Ser
        195                 200                 205

Phe Ile Tyr Gln Pro Cys Gln Arg Gln Phe Asn Tyr
    210                 215                 220

<210> SEQ ID NO 83
<211> LENGTH: 2199
<212> TYPE: DNA
<213> ORGANISM: Homo sapiens

<400> SEQUENCE: 83

| | |
|---|---:|
| agacggtggc cgagcggggg accgggaagc atggcccggg ggtcggcggt tgcctgggcg | 60 |
| gcgctcgggc cgttgttgtg gggctgcgcg ctggggctgc agggcgggat gctgtacccc | 120 |
| caggagagcc cgtcgcggga gtgcaaggag ctggacggcc tctggagctt ccgcgccgac | 180 |
| ttctctgaca accgacgccg gggcttcgag gagcagtggt accggcggcc gctgtgggag | 240 |
| tcaggcccca ccgtggacat gccagttccc tccagcttca tgacatcag ccaggactgg | 300 |
| cgtctgcggc attttgtcgg ctgggtgtgg tacgaacggg aggtgatcct gccggagcga | 360 |
| tggacccagg acctgcgcac aagagtggtg ctgaggattg cagtgcccca ttcctatgcc | 420 |
| atcgtgtggg tgaatggggt cgacacgcta gagcatgagg gggctaccct ccccttcgag | 480 |
| gccgacatca gcaacctggt ccaggtgggg cccctgccct cccggctccg aatcactatc | 540 |
| gccatcaaca acacactcac ccccaccacc ctgccaccag ggaccatcca atacctgact | 600 |
| gacacctcca gtatcccaa gggttacttt gtccagaaca catattttga cttttttcaac | 660 |
| tacgctggac tgcagcggtc tgtacttctg tacacgacac ccaccaccta catcgatgac | 720 |
| atcaccgtca ccaccagcgt ggagcaagac agtgggctgg tgaattacca gatctctgtc | 780 |
| aagggcagta acctgttcaa gttggaagtg cgtcttttgg atgcagaaaa caaagtcgtg | 840 |
| gcgaatggga ctgggaccca gggccaactt aaggtgccag tgtcagcct ctggtggccg | 900 |
| tacctgatgc acgaacgccc tgcctatctg tattcattgg aggtgcagct gactgcacag | 960 |
| acgtcactgg ggcctgtgtc tgacttctac acactccctg tggggatccg cactgtggct | 1020 |
| gtcaccaaga gccagttcct catcaatggg aaaccttct atttccacgg tgtcaacaag | 1080 |
| catgaggatg cggacatccg agggaagggc ttcgactggc cgctgctggt gaaggacttc | 1140 |
| aacctgcttc gctggcttgg tgccaacgct ttccgtacca gccactaccc ctatgcagag | 1200 |
| gaagtgatgc agatgtgtga ccgctatggg attgtggtca tcgatgagtg tcccggcgtg | 1260 |
| ggcctggcgc tgccgcagtt cttcaacaac gtttctctgc atcaccacat gcaggtgatg | 1320 |
| gaagaagtgg tgcgtaggga caagaaccac cccgcggtcg tgatgtggtc tgtggccaac | 1380 |
| gagcctgcgt cccacctaga atctgctggc tactacttga agatggtgat cgctcacacc | 1440 |
| aaatccttgg accctcccg gcctgtgacc tttgtgagca actctaacta tgcagcagac | 1500 |
| aagggggctc cgtatgtgga tgtgatctgt ttgaacagct actactcttg gtatcacgac | 1560 |
| tacgggcacc tggagttgat tcagctgcag ctggccaccc agtttgagaa ctggtataag | 1620 |
| aagtatcaga gcccattat tcagagcgag tatggagcag aaacgattgc agggtttcac | 1680 |

-continued

```
caggatccac ctctgatgtt cactgaagag taccagaaaa gtctgctaga gcagtaccat      1740
ctgggtctgg atcaaaaacg cagaaaatac gtggttggag agctcatttg aattttgcc       1800 gatttcatga ctgaacagtc accgacgaga gtgctgggga ataaaaaggg gatcttcact      1860
cggcagagac aaccaaaaag tgcagcgttc cttttgcgag agagatactg gaagattgcc      1920
aatgaaacca ggtatcccca ctcagtagcc aagtcacaat gtttggaaaa cagcctgttt      1980
acttgagcaa gactgatacc acctgcgtgt cccttcctcc ccgagtcagg gcgacttcca      2040
cagcagcaga acaagtgcct cctggactgt tcacggcaga ccagaacgtt tctggcctgg      2100
gttttgtggt catctattct agcagggaac actaaaggtg gaaataaaag attttctatt      2160
atggaaataa agagttggca tgaaagtggc tactgaaaa                             2199
```

<210> SEQ ID NO 84
<211> LENGTH: 651
<212> TYPE: PRT
<213> ORGANISM: Homo sapiens

<400> SEQUENCE: 84

```
Met Ala Arg Gly Ser Ala Val Ala Trp Ala Ala Leu Gly Pro Leu Leu
1               5                   10                  15

Trp Gly Cys Ala Leu Gly Leu Gln Gly Gly Met Leu Tyr Pro Gln Glu
            20                  25                  30

Ser Pro Ser Arg Glu Cys Lys Glu Leu Asp Gly Leu Trp Ser Phe Arg
        35                  40                  45

Ala Asp Phe Ser Asp Asn Arg Arg Arg Gly Phe Glu Glu Gln Trp Tyr
    50                  55                  60

Arg Arg Pro Leu Trp Glu Ser Gly Pro Thr Val Asp Met Pro Val Pro
65                  70                  75                  80

Ser Ser Phe Asn Asp Ile Ser Gln Asp Trp Arg Leu Arg His Phe Val
                85                  90                  95

Gly Trp Val Trp Tyr Glu Arg Glu Val Ile Leu Pro Glu Arg Trp Thr
            100                 105                 110

Gln Asp Leu Arg Thr Arg Val Val Leu Arg Ile Gly Ser Ala His Ser
        115                 120                 125

Tyr Ala Ile Val Trp Val Asn Gly Val Asp Thr Leu Glu His Glu Gly
    130                 135                 140

Gly Tyr Leu Pro Phe Glu Ala Asp Ile Ser Asn Leu Val Gln Val Gly
145                 150                 155                 160

Pro Leu Pro Ser Arg Leu Arg Ile Thr Ile Ala Ile Asn Asn Thr Leu
                165                 170                 175

Thr Pro Thr Thr Leu Pro Pro Gly Thr Ile Gln Tyr Leu Thr Asp Thr
            180                 185                 190

Ser Lys Tyr Pro Lys Gly Tyr Phe Val Gln Asn Thr Tyr Phe Asp Phe
        195                 200                 205

Phe Asn Tyr Ala Gly Leu Gln Arg Ser Val Leu Leu Tyr Thr Thr Pro
    210                 215                 220

Thr Thr Tyr Ile Asp Asp Ile Thr Val Thr Thr Ser Val Glu Gln Asp
225                 230                 235                 240

Ser Gly Leu Val Asn Tyr Gln Ile Ser Val Lys Gly Ser Asn Leu Phe
                245                 250                 255

Lys Leu Glu Val Arg Leu Leu Asp Ala Glu Asn Lys Val Val Ala Asn
            260                 265                 270

Gly Thr Gly Thr Gln Gly Gln Leu Lys Val Pro Gly Val Ser Leu Trp
```

```
            275                 280                 285
Trp Pro Tyr Leu Met His Glu Arg Pro Ala Tyr Leu Tyr Ser Leu Glu
        290                 295                 300
Val Gln Leu Thr Ala Gln Thr Ser Leu Gly Pro Val Ser Asp Phe Tyr
305                 310                 315                 320
Thr Leu Pro Val Gly Ile Arg Thr Val Ala Val Thr Lys Ser Gln Phe
                325                 330                 335
Leu Ile Asn Gly Lys Pro Phe Tyr Phe His Gly Val Asn Lys His Glu
            340                 345                 350
Asp Ala Asp Ile Arg Gly Lys Gly Phe Asp Trp Pro Leu Leu Val Lys
        355                 360                 365
Asp Phe Asn Leu Leu Arg Trp Leu Gly Ala Asn Ala Phe Arg Thr Ser
370                 375                 380
His Tyr Pro Tyr Ala Glu Glu Val Met Gln Met Cys Asp Arg Tyr Gly
385                 390                 395                 400
Ile Val Val Ile Asp Glu Cys Pro Gly Val Gly Leu Ala Leu Pro Gln
                405                 410                 415
Phe Phe Asn Asn Val Ser Leu His His Met Gln Val Met Glu Glu
            420                 425                 430
Val Val Arg Arg Asp Lys Asn His Pro Ala Val Val Met Trp Ser Val
        435                 440                 445
Ala Asn Glu Pro Ala Ser His Leu Glu Ser Ala Gly Tyr Tyr Leu Lys
450                 455                 460
Met Val Ile Ala His Thr Lys Ser Leu Asp Pro Ser Arg Pro Val Thr
465                 470                 475                 480
Phe Val Ser Asn Ser Asn Tyr Ala Ala Asp Lys Gly Ala Pro Tyr Val
                485                 490                 495
Asp Val Ile Cys Leu Asn Ser Tyr Tyr Ser Trp Tyr His Asp Tyr Gly
            500                 505                 510
His Leu Glu Leu Ile Gln Leu Gln Leu Ala Thr Gln Phe Glu Asn Trp
        515                 520                 525
Tyr Lys Lys Tyr Gln Lys Pro Ile Ile Gln Ser Glu Tyr Gly Ala Glu
530                 535                 540
Thr Ile Ala Gly Phe His Gln Asp Pro Pro Leu Met Phe Thr Glu Glu
545                 550                 555                 560
Tyr Gln Lys Ser Leu Leu Glu Gln Tyr His Leu Gly Leu Asp Gln Lys
                565                 570                 575
Arg Arg Lys Tyr Val Val Gly Glu Leu Ile Trp Asn Phe Ala Asp Phe
            580                 585                 590
Met Thr Glu Gln Ser Pro Thr Arg Val Leu Gly Asn Lys Lys Gly Ile
        595                 600                 605
Phe Thr Arg Gln Arg Gln Pro Lys Ser Ala Ala Phe Leu Leu Arg Glu
610                 615                 620
Arg Tyr Trp Lys Ile Ala Asn Glu Thr Arg Tyr Pro His Ser Val Ala
625                 630                 635                 640
Lys Ser Gln Cys Leu Glu Asn Ser Leu Phe Thr
                645                 650

<210> SEQ ID NO 85
<211> LENGTH: 2237
<212> TYPE: DNA
<213> ORGANISM: Homo sapiens

<400> SEQUENCE: 85
```

```
gttttgcaga cgccaccgcc gaggaaaacc gtgtactatt agccatggtc aaccccaccg    60
tgttcttcga cattgccgtc gacggcgagc ccttgggccg cgtctccttt gagctgtttg   120
cagacaaggt cccaaagaca gcagaaaatt tcgtgctct gagcactgga gagaaaggat    180
ttggttataa gggttcctgc tttcacagaa ttattccagg gtttatgtgt cagggtggtg   240
acttcacacg ccataatggc actggtggca agtccatcta tggggagaaa tttgaagatg   300
agaacttcat cctaaagcat acgggtcctg gcatcttgtc catggcaaat gctggaccca   360
acacaaatgg ttcccagttt ttcatctgca ctgccaagac tgagtggttg gatggcaagc   420
atgtggtgtt tggcaaagtg aaagaaggca tgaatattgt ggaggccatg gagcgctttg   480
ggtccaggaa tggcaagacc agcaagaaga tcaccattgc tgactgtgga caactcgaat   540
aagtttgact tgtgttttat cttaaccacc agatcattcc ttctgtagct caggagagca   600
cccctccacc ccatttgctc gcagtatcct agaatctttg tgctctcgct gcagttccct   660
ttgggttcca tgttttcctt gttccctccc atgcctagct ggattgcaga gttaagttta   720
tgattatgaa ataaaaacta aataacaatt gtcctcgttt gagttaagag tgttgatgta   780
ggctttattt taagcagtaa tgggttactt ctgaaacatc acttgtttgc ttaattctac   840
acagtactta gattttttt actttccagt cccaggaagt gtcaatgttt gttgagtgga   900
atattgaaaa tgtaggcagc aactgggcat ggtggctcac tgtctgtaat gtattacctg   960
aggcagaaga ccacctgagg gtaggagtca agatcagcct gggcaacata gtgagacgct  1020
gtctctacaa aaataatta gcctggcctg gtggtgcatg cctagtccta gctgatctgg  1080
aggctgacgt gggaggattg cttgagccta gagtgagcta ttatcatgcc actgtacagc  1140
ctgggtgttc acagatcttg tgtctcaaag gtaggcagag gcaggaaaag caaggagcca  1200
gaattaagag gttgggtcag tctgcagtga gttcatgcat ttagaggtgt tcttcaagat  1260
gactaatgtc aaaaattgag acatctgttg cggtttttt ttttttttt tcccctggaa   1320
tgcagtggcg tgatctcagc tcactgcagc ctccgcctcc tgggttcaag tgattctagt  1380
gcctcagcct cctgagtagc tgggataatg ggcgtgtgcc accatgccca gctaattttt  1440
gtatttttag tatagatggg gtttcatcat tttgaccagg ctggtctcaa actcttgacc  1500
tcagctgatg cgcctgcctt ggcctcccaa actgctgaga ttacagatgt gagccaccgc  1560
accctacctc atttttctgta acaaagctaa gcttgaacac tgttgatgtt cttgagggaa  1620
gcatattggg ctttaggctg taggtcaagt ttatacatct taattatggt ggaattccta  1680
tgtagagtct aaaaagccag gtacttggtg ctacagtcag tctccctgca gagggttaag  1740
gcgcagacta cctgcagtga ggaggtactg cttgtagcat atagagcctc tccctagctt  1800
tggttatgga ggctttgagg ttttgcaaac ctgaccaatt taagccataa gatctggtca  1860
aagggatacc cttcccacta aggacttggt ttctcaggaa attatatgta cagtgcttgc  1920
tggcagttag atgtcaggac aatctaagct gagaaaaccc cttctctgcc caccttaaca  1980
gacctctagg gttcttaacc cagcaatcaa gtttgcctat cctagaggtg gcggatttga  2040
tcatttggtg tgttgggcaa ttttttgtttt actgtctggt tccttctgcg tgaattacca  2100
ccaccaccac ttgtgcatct cagtcttgtg tgttgtctgg ttacgtattc cctgggtgat  2160
accattcaat gtcttaatgt acttgtggct cagacctgag tgcaaggtgg aaataaacat  2220
caaacatctt ttcatta                                                  2237

<210> SEQ ID NO 86
<211> LENGTH: 165
```

```
<212> TYPE: PRT
<213> ORGANISM: Homo sapiens

<400> SEQUENCE: 86

Met Val Asn Pro Thr Val Phe Phe Asp Ile Ala Val Asp Gly Glu Pro
1               5                   10                  15

Leu Gly Arg Val Ser Phe Glu Leu Phe Ala Asp Lys Val Pro Lys Thr
            20                  25                  30

Ala Glu Asn Phe Arg Ala Leu Ser Thr Gly Glu Lys Gly Phe Gly Tyr
        35                  40                  45

Lys Gly Ser Cys Phe His Arg Ile Ile Pro Gly Phe Met Cys Gln Gly
    50                  55                  60

Gly Asp Phe Thr Arg His Asn Gly Thr Gly Gly Lys Ser Ile Tyr Gly
65                  70                  75                  80

Glu Lys Phe Glu Asp Glu Asn Phe Ile Leu Lys His Thr Gly Pro Gly
                85                  90                  95

Ile Leu Ser Met Ala Asn Ala Gly Pro Asn Thr Asn Gly Ser Gln Phe
            100                 105                 110

Phe Ile Cys Thr Ala Lys Thr Glu Trp Leu Asp Gly Lys His Val Val
        115                 120                 125

Phe Gly Lys Val Lys Glu Gly Met Asn Ile Val Glu Ala Met Glu Arg
    130                 135                 140

Phe Gly Ser Arg Asn Gly Lys Thr Ser Lys Lys Ile Thr Ile Ala Asp
145                 150                 155                 160

Cys Gly Gln Leu Glu
                165

<210> SEQ ID NO 87
<211> LENGTH: 2193
<212> TYPE: DNA
<213> ORGANISM: Homo sapiens

<400> SEQUENCE: 87
agttccgtcg cagccgggat ttgggtcgca gttcttgttt gtggatcgct gtgatcgtca     60
cttgacaatg cagatcttcg tgaagactct gactggtaag accatcaccc tcgaggttga    120
gcccagtgac accatcgaga atgtcaaggc aaagatccaa gataaggaag catccctcc     180
tgaccagcag aggctgatct ttgctggaaa acagctggaa gatgggcgca ccctgtctga    240
ctacaacatc agaaagagt ccaccctgca cctggtgctc cgtctcagag gtgggatgca    300
aatcttcgtg aagacactca ctggcaagac catcaccctt gaggtcgagc cagtgacac    360
catcgagaac gtcaaagcaa agatccagga caaggaaggc attcctcctg accagcagag    420
gttgatcttt gccggaaagc agctggaaga tgggcgcacc ctgtctgact acaacatcca    480
gaaagagtct accctgcacc tggtgctccg tctcagaggt gggatgcaga tcttcgtgaa    540
gaccctgact ggtaagacca tcaccctcga ggtggagccc agtgacacca tcgagaatgt    600
caaggcaaag atccaagata ggaaggcat tcctcctgat cagcagaggt tgatctttgc    660
cggaaaacag ctggaagatg gtcgtaccct gtctgactac aacatccaga agagtccac    720
cttgcacctg gtactccgtc tcagaggtgg gatgcaaatc ttcgtgaaga cactcactgg    780
caagaccatc accttgagg tcgagcccag tgacactatc gagaacgtca agcaaagat    840
ccaagacaag gaaggcattc tcctgaccac gcagaggttg atctttgccg gaaagcagct    900
ggaagatggg cgcaccctgt ctgactacaa catccagaaa gagtctaccc tgcacctggt    960
gctccgtctc agaggtggga tgcagatctt cgtgaagacc ctgactggta agaccatcac   1020
```

-continued

```
tctcgaagtg gagccgagtg acaccattga gaatgtcaag gcaaagatcc aagacaagga    1080
aggcatccct cctgaccagc agaggttgat ctttgccgga aaacagctgg aagatggtcg    1140
taccctgtct gactacaaca tccagaaaga gtccaccttg cacctggtgc tccgtctcag    1200
aggtgggatg cagatcttcg tgaagaccct gactggtaag accatcactc tcgaggtgga    1260
gccgagtgac accattgaga atgtcaaggc aaagatccaa gacaaggaag catccctcc    1320
tgaccagcag aggttgatct tgctgggaa acagctggaa gatggacgca ccctgtctga    1380
ctacaacatc cagaaagagt ccaccctgca cctggtgctc cgtcttagag gtgggatgca    1440
gatcttcgtg aagaccctga ctggtaagac catcactctc gaagtggagc cgagtgacac    1500
cattgagaat gtcaaggcaa agatccaaga caaggaaggc atccctcctg accagcagag    1560
gttgatcttt gctgggaaac agctggaaga tggacgcacc ctgtctgact acaacatcca    1620
gaaagagtcc accctgcacc tggtgctccg tcttagaggt gggatgcaga tcttcgtgaa    1680
gaccctgact ggtaagacca tcactctcga agtggagccg agtgacacca ttgagaatgt    1740
caaggcaaag atccaagaca aggaaggcat ccctcctgac cagcagaggt tgatctttgc    1800
tgggaaacag ctggaagatg gacgcaccct gtctgactac aacatccaga aagagtccac    1860
cctgcacctg gtgctccgtc tcagaggtgg gatgcaaatc ttcgtgaaga ccctgactgg    1920
taagaccatc accctcgagg tggagcccag tgacaccatc gagaatgtca aggcaaagat    1980
ccaagataag gaaggcatcc ctcctgatca gcagaggttg atctttgctg ggaaacagct    2040
ggaagatgga cgcaccctgt ctgactacaa catccagaaa gagtccactc tgcacttggt    2100
cctgcgcttg agggggggtg tctaagtttc ccctttttaag gtttcaacaa atttcattgc    2160
actttccttt caataaagtt gttgcattcc caa                                 2193
```

<210> SEQ ID NO 88
<211> LENGTH: 685
<212> TYPE: PRT
<213> ORGANISM: Homo sapiens

<400> SEQUENCE: 88

```
Met Gln Ile Phe Val Lys Thr Leu Thr Gly Lys Thr Ile Thr Leu Glu
  1               5                  10                  15

Val Glu Pro Ser Asp Thr Ile Glu Asn Val Lys Ala Lys Ile Gln Asp
             20                  25                  30

Lys Glu Gly Ile Pro Pro Asp Gln Gln Arg Leu Ile Phe Ala Gly Lys
         35                  40                  45

Gln Leu Glu Asp Gly Arg Thr Leu Ser Asp Tyr Asn Ile Gln Lys Glu
     50                  55                  60

Ser Thr Leu His Leu Val Leu Arg Leu Arg Gly Gly Met Gln Ile Phe
 65                  70                  75                  80

Val Lys Thr Leu Thr Gly Lys Thr Ile Thr Leu Glu Val Glu Pro Ser
                 85                  90                  95

Asp Thr Ile Glu Asn Val Lys Ala Lys Ile Gln Asp Lys Glu Gly Ile
            100                 105                 110

Pro Pro Asp Gln Gln Arg Leu Ile Phe Ala Gly Lys Gln Leu Glu Asp
        115                 120                 125

Gly Arg Thr Leu Ser Asp Tyr Asn Ile Gln Lys Glu Ser Thr Leu His
    130                 135                 140

Leu Val Leu Arg Leu Arg Gly Gly Met Gln Ile Phe Val Lys Thr Leu
145                 150                 155                 160
```

-continued

```
Thr Gly Lys Thr Ile Thr Leu Glu Val Glu Pro Ser Asp Thr Ile Glu
            165                 170                 175
Asn Val Lys Ala Lys Ile Gln Asp Lys Glu Gly Ile Pro Pro Asp Gln
        180                 185                 190
Gln Arg Leu Ile Phe Ala Gly Lys Gln Leu Glu Asp Gly Arg Thr Leu
    195                 200                 205
Ser Asp Tyr Asn Ile Gln Lys Glu Ser Thr Leu His Leu Val Leu Arg
210                 215                 220
Leu Arg Gly Gly Met Gln Ile Phe Val Lys Thr Leu Thr Gly Lys Thr
225                 230                 235                 240
Ile Thr Leu Glu Val Glu Pro Ser Asp Thr Ile Glu Asn Val Lys Ala
                245                 250                 255
Lys Ile Gln Asp Lys Glu Gly Ile Pro Pro Asp Gln Gln Arg Leu Ile
            260                 265                 270
Phe Ala Gly Lys Gln Leu Glu Asp Gly Arg Thr Leu Ser Asp Tyr Asn
        275                 280                 285
Ile Gln Lys Glu Ser Thr Leu His Leu Val Leu Arg Leu Arg Gly Gly
    290                 295                 300
Met Gln Ile Phe Val Lys Thr Leu Thr Gly Lys Thr Ile Thr Leu Glu
305                 310                 315                 320
Val Glu Pro Ser Asp Thr Ile Glu Asn Val Lys Ala Lys Ile Gln Asp
                325                 330                 335
Lys Glu Gly Ile Pro Pro Asp Gln Gln Arg Leu Ile Phe Ala Gly Lys
            340                 345                 350
Gln Leu Glu Asp Gly Arg Thr Leu Ser Asp Tyr Asn Ile Gln Lys Glu
        355                 360                 365
Ser Thr Leu His Leu Val Leu Arg Leu Arg Gly Gly Met Gln Ile Phe
    370                 375                 380
Val Lys Thr Leu Thr Gly Lys Thr Ile Thr Leu Glu Val Glu Pro Ser
385                 390                 395                 400
Asp Thr Ile Glu Asn Val Lys Ala Lys Ile Gln Asp Lys Glu Gly Ile
                405                 410                 415
Pro Pro Asp Gln Gln Arg Leu Ile Phe Ala Gly Lys Gln Leu Glu Asp
            420                 425                 430
Gly Arg Thr Leu Ser Asp Tyr Asn Ile Gln Lys Glu Ser Thr Leu His
        435                 440                 445
Leu Val Leu Arg Leu Arg Gly Gly Met Gln Ile Phe Val Lys Thr Leu
    450                 455                 460
Thr Gly Lys Thr Ile Thr Leu Glu Val Glu Pro Ser Asp Thr Ile Glu
465                 470                 475                 480
Asn Val Lys Ala Lys Ile Gln Asp Lys Glu Gly Ile Pro Pro Asp Gln
                485                 490                 495
Gln Arg Leu Ile Phe Ala Gly Lys Gln Leu Glu Asp Gly Arg Thr Leu
            500                 505                 510
Ser Asp Tyr Asn Ile Gln Lys Glu Ser Thr Leu His Leu Val Leu Arg
        515                 520                 525
Leu Arg Gly Gly Met Gln Ile Phe Val Lys Thr Leu Thr Gly Lys Thr
    530                 535                 540
Ile Thr Leu Glu Val Glu Pro Ser Asp Thr Ile Glu Asn Val Lys Ala
545                 550                 555                 560
Lys Ile Gln Asp Lys Glu Gly Ile Pro Pro Asp Gln Gln Arg Leu Ile
                565                 570                 575
Phe Ala Gly Lys Gln Leu Glu Asp Gly Arg Thr Leu Ser Asp Tyr Asn
```

|  |  |  | 580 |  |  |  | 585 |  |  |  | 590 |  |
|---|---|---|---|---|---|---|---|---|---|---|---|---|

Ile Gln Lys Glu Ser Thr Leu His Leu Val Leu Arg Leu Arg Gly Gly
                   595                         600                       605

Met Gln Ile Phe Val Lys Thr Leu Thr Gly Lys Thr Ile Thr Leu Glu
    610                             615                       620

Val Glu Pro Ser Asp Thr Ile Glu Asn Val Lys Ala Lys Ile Gln Asp
625                       630                       635                       640

Lys Glu Gly Ile Pro Pro Asp Gln Gln Arg Leu Ile Phe Ala Gly Lys
                 645                       650                       655

Gln Leu Glu Asp Gly Arg Thr Leu Ser Asp Tyr Asn Ile Gln Lys Glu
                    660                       665                       670

Ser Thr Leu His Leu Val Leu Arg Leu Arg Gly Gly Val
             675                       680                       685

<210> SEQ ID NO 89
<211> LENGTH: 2547
<212> TYPE: DNA
<213> ORGANISM: Homo sapiens

<400> SEQUENCE: 89

| actgcagccc | cgctcgactc | cggcgtggtg | cgcaggcgcg | gtatcccccc | tcccccgcca | 60 |
| gctcgacccc | ggtgtggtgc | gcaggcgcag | tctgcgcagg | gactggcggg | actgcgcggc | 120 |
| ggcaacagca | gacatgtcgg | gggtccgggg | cctgtcgcgg | ctgctgagcg | ctcggcgcct | 180 |
| ggcgctggcc | aaggcgtggc | caacagtgtt | gcaaacagga | acccgaggtt | ttcacttcac | 240 |
| tgttgatggg | aacaagaggg | catctgctaa | agtttcagat | tccatttctg | ctcagtatcc | 300 |
| agtagtggat | catgaatttg | atgcagtggt | ggtaggcgct | ggaggggcag | gcttgcgagc | 360 |
| tgcatttggc | ctttctgagg | cagggtttaa | tacagcatgt | gttaccaagc | tgtttcctac | 420 |
| caggtcacac | actgttgcag | cacagggagg | aatcaatgct | gctctgggga | acatggagga | 480 |
| ggacaactgg | aggtggcatt | tctacgacac | cgtgaagggc | tccgactggc | tgggggacca | 540 |
| ggatgccatc | cactacatga | cggagcaggc | ccccgccgcc | gtggtcgagc | tagaaaatta | 600 |
| tggcatgccg | tttagcagaa | ctgaagatgg | gaagatttat | cagcgtgcat | ttggtggaca | 660 |
| gagcctcaag | tttggaaagg | gcgggcaggc | ccatcggtgc | tgctgtgtgg | ctgatcggac | 720 |
| tggccactcg | ctattgcaca | ccttatatgg | aaggtctctg | cgatatgata | ccagctattt | 780 |
| tgtggagtat | tttgccttgg | atctcctgat | ggagaatggg | gagtgccgtg | tgtcatcgc | 840 |
| actgtgcata | gaggacgggt | ccatccatcg | cataagagca | aagaacactg | ttgttgccac | 900 |
| aggaggctac | gggcgcacct | acttcagctg | cacgtctgcc | cacaccagca | ctggcgacgg | 960 |
| cacggccatg | atcaccaggg | caggccttcc | ttgccaggac | ctagagtttg | ttcagttcca | 1020 |
| ccctacaggc | atatatggtg | ctggttgtct | cattacggaa | ggatgtcgtg | agagggagg | 1080 |
| cattctcatt | aacagtcaag | gcgaaaggtt | tatggagcga | tacgcccctg | tcgcgaagga | 1140 |
| cctggcgtct | agagatgtgg | tgtctcggtc | catgactctg | gagatccgag | aaggaagagg | 1200 |
| ctgtggccct | gagaaagatc | acgtctacct | gcagctgcac | cacctacctc | cagagcagct | 1260 |
| ggccacgcgc | ctgcctggca | tttcagagac | agccatgatc | ttcgctggcg | tggacgtcac | 1320 |
| gaaggagccg | atccctgtcc | tccccaccgt | gcattataac | atgggcggca | ttcccaccaa | 1380 |
| ctacaagggg | caggtcctga | ggcacgtgaa | tggccaggat | cagattgtgc | ccggcctgta | 1440 |
| cgcctgtggg | gaggccgcct | gtgcctcggt | acatggtgcc | aaccgcctcg | gggcaaactc | 1500 |
| gctcttggac | ctggttgtct | ttggtcgggc | atgtgccctg | agcatcgaag | agtcatgcag | 1560 |

-continued

```
gcctggagat aaagtccctc caattaaacc aaacgctggg gaagaatctg tcatgaatct    1620
tgacaaattg agatttgctg atggaagcat aagaacatcg gaactgcgac tcagcatgca    1680
gaaggtgcgg attgatgagt acgattactc caagcccatc caggggcaac agaagaagcc    1740
ctttgaggag cactggagga agcacaccct gtcctatgtg gacgttggca ctgggaaggt    1800
cactctggaa tatagacccg tgatcgacaa aactttgaac gaggctgact gtgccaccgt    1860
cccgccagcc attcgctcct actgatgaga caagatgtgg tgatgacaga atcagctttt    1920
gtaattatgt ataatagctc atgcatgtgt ccatgtcata actgtcttca tacgcttctg    1980
cactctgggg aagaaggagt acattgaagg gagattggca cctagtggct gggagcttgc    2040
caggaaccca gtggccaggg agcgtggcac ttacctttgt cccttgcttc attcttgtga    2100
gatgataaaa ctgggcacag ctcttaaata aaatataaat gaacaaactt tcttttattt    2160
ccaaatccat ttgaaatatt ttactgttgt gactttagtc atatttgttg acctaaaaat    2220
caaatgtaat ctttgtattg tgttacatca aaatccagat attttgtata gtttcttttt    2280
tcttttctt ttcttttttt ttttgagac aggatcggtg cagtagtaca atcacagctc    2340
actgcagcct caaactcctg ggcagctcag gtgatcttcc tgactcagcc ttctgagtag    2400
ttggggctac aggtgtgcac caccatgccc agctcattta ttttgtaatt gtagggacag    2460
ggtctcactg tgttgcctag gctggtctca agtgatcctc cctccttggc ctcccaaggt    2520
gctggaatta taggtgtgaa caaacca                                         2547
```

<210> SEQ ID NO 90
<211> LENGTH: 664
<212> TYPE: PRT
<213> ORGANISM: Homo sapiens

<400> SEQUENCE: 90

```
Met Ser Gly Val Arg Gly Leu Ser Arg Leu Leu Ser Ala Arg Arg Leu
1               5                   10                  15

Ala Leu Ala Lys Ala Trp Pro Thr Val Leu Gln Thr Gly Thr Arg Gly
                20                  25                  30

Phe His Phe Thr Val Asp Gly Asn Lys Arg Ala Ser Ala Lys Val Ser
            35                  40                  45

Asp Ser Ile Ser Ala Gln Tyr Pro Val Val Asp His Glu Phe Asp Ala
        50                  55                  60

Val Val Val Gly Ala Gly Gly Ala Gly Leu Arg Ala Ala Phe Gly Leu
65                  70                  75                  80

Ser Glu Ala Gly Phe Asn Thr Ala Cys Val Thr Lys Leu Phe Pro Thr
                85                  90                  95

Arg Ser His Thr Val Ala Ala Gln Gly Gly Ile Asn Ala Ala Leu Gly
            100                 105                 110

Asn Met Glu Glu Asp Asn Trp Arg Trp His Phe Tyr Asp Thr Val Lys
        115                 120                 125

Gly Ser Asp Trp Leu Gly Asp Gln Asp Ala Ile His Tyr Met Thr Glu
    130                 135                 140

Gln Ala Pro Ala Ala Val Val Glu Leu Glu Asn Tyr Gly Met Pro Phe
145                 150                 155                 160

Ser Arg Thr Glu Asp Gly Lys Ile Tyr Gln Arg Ala Phe Gly Gly Gln
                165                 170                 175

Ser Leu Lys Phe Gly Lys Gly Gly Gln Ala His Arg Cys Cys Cys Val
            180                 185                 190
```

```
Ala Asp Arg Thr Gly His Ser Leu Leu His Thr Leu Tyr Gly Arg Ser
            195                 200                 205

Leu Arg Tyr Asp Thr Ser Tyr Phe Val Glu Tyr Phe Ala Leu Asp Leu
    210                 215                 220

Leu Met Glu Asn Gly Glu Cys Arg Gly Val Ile Ala Leu Cys Ile Glu
225                 230                 235                 240

Asp Gly Ser Ile His Arg Ile Arg Ala Lys Asn Thr Val Val Ala Thr
                245                 250                 255

Gly Gly Tyr Gly Arg Thr Tyr Phe Ser Cys Thr Ser Ala His Thr Ser
            260                 265                 270

Thr Gly Asp Gly Thr Ala Met Ile Thr Arg Ala Gly Leu Pro Cys Gln
        275                 280                 285

Asp Leu Glu Phe Val Gln Phe His Pro Thr Gly Ile Tyr Gly Ala Gly
    290                 295                 300

Cys Leu Ile Thr Glu Gly Cys Arg Gly Glu Gly Gly Ile Leu Ile Asn
305                 310                 315                 320

Ser Gln Gly Glu Arg Phe Met Glu Arg Tyr Ala Pro Val Ala Lys Asp
                325                 330                 335

Leu Ala Ser Arg Asp Val Val Ser Arg Ser Met Thr Leu Glu Ile Arg
            340                 345                 350

Glu Gly Arg Gly Cys Gly Pro Glu Lys Asp His Val Tyr Leu Gln Leu
        355                 360                 365

His His Leu Pro Pro Glu Gln Leu Ala Thr Arg Leu Pro Gly Ile Ser
    370                 375                 380

Glu Thr Ala Met Ile Phe Ala Gly Val Asp Val Thr Lys Glu Pro Ile
385                 390                 395                 400

Pro Val Leu Pro Thr Val His Tyr Asn Met Gly Gly Ile Pro Thr Asn
                405                 410                 415

Tyr Lys Gly Gln Val Leu Arg His Val Asn Gly Gln Asp Gln Ile Val
            420                 425                 430

Pro Gly Leu Tyr Ala Cys Gly Glu Ala Ala Cys Ala Ser Val His Gly
        435                 440                 445

Ala Asn Arg Leu Gly Ala Asn Ser Leu Leu Asp Leu Val Val Phe Gly
    450                 455                 460

Arg Ala Cys Ala Leu Ser Ile Glu Glu Ser Cys Arg Pro Gly Asp Lys
465                 470                 475                 480

Val Pro Pro Ile Lys Pro Asn Ala Gly Glu Glu Ser Val Met Asn Leu
                485                 490                 495

Asp Lys Leu Arg Phe Ala Asp Gly Ser Ile Arg Thr Ser Glu Leu Arg
            500                 505                 510

Leu Ser Met Gln Lys Ser Met Gln Asn His Ala Ala Val Phe Arg Val
        515                 520                 525

Gly Ser Val Leu Gln Glu Gly Cys Gly Lys Ile Ser Lys Leu Tyr Gly
    530                 535                 540

Asp Leu Lys His Leu Lys Thr Phe Asp Arg Gly Met Val Trp Asn Thr
545                 550                 555                 560

Asp Leu Val Glu Thr Leu Glu Leu Gln Asn Leu Met Leu Cys Ala Leu
                565                 570                 575

Gln Thr Ile Tyr Gly Ala Glu Ala Arg Lys Glu Ser Arg Gly Ala His
            580                 585                 590

Ala Arg Glu Asp Tyr Lys Val Arg Ile Asp Glu Tyr Asp Tyr Ser Lys
        595                 600                 605

Pro Ile Gln Gly Gln Gln Lys Lys Pro Phe Glu Glu His Trp Arg Lys
```

-continued

```
            610                 615                 620
His Thr Leu Ser Tyr Val Asp Val Gly Thr Gly Lys Val Thr Leu Glu
625                     630                 635                 640

Tyr Arg Pro Val Ile Asp Lys Thr Leu Asn Glu Ala Asp Cys Ala Thr
                645                 650                 655

Val Pro Pro Ala Ile Arg Ser Tyr
            660
```

DIAGNOSTIC AND THERAPEUTIC METHODS FOR THE TREATMENT OF BREAST CANCER

CROSS-REFERENCE TO RELATED APPLICATIONS

This application is a continuation of U.S. application Ser. No. 16/542,817 filed Aug. 16, 2019, issued as U.S. Pat. No. 11,081,236, which claims priority to U.S. Application No. 62/719,545 filed Aug. 17, 2018, the disclosure of which is incorporated herein in its entirety and for all purposes.

REFERENCES TO A "SEQUENCE LISTING"

The Sequence Listing written in file 048893-517001US_SEQUENCE_LISTING_ST25.txt, 560,154 bytes, created on Aug. 13, 2019, machine format IBM-PC, MS-Windows operating system, is hereby incorporated by reference in its entirety for all purposes.

FIELD

Provided herein, inter alia, are diagnostic and therapeutic methods for the treatment of breast cancer. For example, provided are methods of predicting therapeutic responsiveness, methods of monitoring responsiveness to treatment, methods of selecting a treatment, methods of treatment, and diagnostic kits.

BACKGROUND

Cancer remains one of the most deadly threats to human health. In the U.S., cancer affects nearly 1.3 million new patients each year and is the second leading cause of death after heart disease, accounting for approximately 1 in 4 deaths. Solid tumors are responsible for most of those deaths. Although there have been significant advances in the medical treatment of certain cancers, the overall 5-year survival rate for all cancers has improved only by about 10% in the past 20 years.

The estrogen receptor ("ER") is a ligand-activated transcriptional regulatory protein that mediates induction of a variety of biological effects through its interaction with endogenous estrogens. Estrogens and estrogen receptors are implicated in cancers, such as breast cancer, lung cancer, ovarian cancer, colon cancer, prostate cancer, endometrial cancer, uterine cancer, as well as other diseases or conditions. Estrogen receptor degradation as measured by immunohistochemistry (IHC) however, is insufficient as a predictor of ER pathway activity or as a pharmacodynamics (PD) biomarker for endocrine therapy; levels of ER protein do not always correlate with ER pathway status. For example, activators of ER signaling, such as the ER ligand estradiol (E2), promote degradation of ER. Furthermore, the progesterone receptor (PR), a well-established ER target gene, is often measured as a read-out of ER pathway activity; however, PR is not always present in ER+ breast tumors, and, even if present, PR suppression may not fully capture ER pathway status.

Thus, there exists an unmet need for biomarkers (e.g., transcriptional signatures), which comprehensively reflect ER pathway activity and can be useful in both diagnostic and therapeutic methods.

SUMMARY

Provided herein, inter alia, are diagnostic methods, therapeutic methods, kits for informing the treating an individual having a breast cancer and kits for predicting of responsiveness of an individual to a treatment for breast cancer.

In an aspect is provided a method of identifying an individual having a breast cancer who may benefit from a treatment including an endocrine therapy, the method including determining an estrogen receptor (ER) pathway activity score from a sample from the individual, where an ER pathway activity score from the sample that is at or above a reference ER pathway activity score identifies the individual as one who may benefit from a treatment including an endocrine therapy.

In an aspect is provided a method for selecting a therapy for an individual having a breast cancer, the method including determining an ER pathway activity score from a sample from the individual, where an ER pathway activity score from the sample that is at or above a reference ER pathway activity score identifies the individual as one who may benefit from a treatment including an endocrine therapy.

In an aspect is provided a method of treating an individual having a breast cancer, the method including administering an effective amount of an endocrine therapy to the individual, where the individual has been identified as one who is more likely to benefit from a treatment including an endocrine therapy as described herein.

In an aspect is provided a method of treating an individual having a breast cancer, the individual being identified as having an ER pathway activity score that is at or above a reference ER pathway activity score, the method including administering to the individual an effective amount of an endocrine therapy.

In an aspect is provided a method of treating an individual having a breast cancer, the method including: (a) determining an ER pathway activity score from a sample from the individual, where the ER pathway activity score from the sample is determined to be at or above a reference ER pathway activity score; and (b) administering to the individual an effective amount of an endocrine therapy.

In an aspect is provided a method for monitoring the response of an individual having a breast cancer to treatment with an endocrine therapy, the method including: (a) determining a first ER pathway activity score from a sample from the individual at a first time point; (b) following step (a), determining a second ER pathway activity score from a sample from the individual at a second time point following administration of an endocrine therapy; and (c) comparing the first ER pathway activity score with the second ER pathway activity score, where a decrease in the second ER pathway activity score relative to the first ER pathway activity score is predictive of an individual who is likely to respond to treatment with an endocrine therapy.

In an aspect is provided a method of identifying an individual having a breast cancer who may benefit from a treatment including an endocrine therapy, the method including determining an estradiol (E2)-induced score from a sample from the individual, where an E2-induced score from the sample that is at or above a reference E2-induced score identifies the individual as one who may benefit from a treatment including an endocrine therapy.

In an aspect is provided a method for selecting a therapy for an individual having a breast cancer, the method including determining an E2-induced score from a sample from the individual, where an E2-induced score from the sample that is at or above a reference E2-induced score identifies the individual as one who may benefit from a treatment including an endocrine therapy.

In an aspect is provided a method of treating an individual having a breast cancer, the method including administering an effective amount of an endocrine therapy to the individual, where the individual has been identified as one who is more likely to benefit from a treatment including an endocrine therapy as described herein.

In an aspect is provided a method of treating an individual having a breast cancer, the individual being identified as having an E2-induced score that is at or above a reference E2-induced score, the method including administering to the individual an effective amount of an endocrine therapy.

In an aspect is provided a method of treating an individual having a breast cancer, the method including: (a) determining an E2-induced score from a sample from the individual, where the E2-induced score from the sample is determined to be at or above a reference E2-induced score; and (b) administering to the individual an effective amount of an endocrine therapy.

In an aspect is provided a method for monitoring the response of an individual having a breast cancer to treatment with an endocrine therapy, the method including: (a) determining a first E2-induced score from a sample from the individual at a first time point; (b) following step (a), determining a second E2-induced score from a sample from the individual at a second time point following administration of an endocrine therapy; and (c) comparing the first E2-induced score with the second E2-induced score, where a decrease in the second E2-induced score relative to the first E2-induced score is predictive of an individual who is likely to respond to treatment with an endocrine therapy.

In an aspect is provided a method of detecting estrogen receptor (ER) pathway activity in a subject that has breast cancer, the method including detecting an expression level of at least five genes set forth in Table 1 and at least five genes set forth in Table 4; at least five genes set forth in Table 2 and at least five genes set forth in Table 5; or at least five genes set forth in Table 3 and at least five genes set forth in Table 6.

In an aspect is provided a method, including: detecting, by one or more processors, a first expression level of at least five genes set forth in Table 1, at least five genes set forth in Table 2, or at least five genes set forth in Table 3; detecting, by the one or more processors, a second expression level of at least five genes set forth in Table 4, at least five genes set forth in Table 5 or at least five genes set forth in Table 6; and detecting, based at least on the first expression level and/or the second expression level, estrogen receptor (ER) pathway activity in a subject that has cancer.

In an aspect is provided a kit including a plurality of nucleic acids, where the plurality of nucleic acids are at least 5 nucleotides in length and are at least 95% identical to a 5 nucleotide continuous sequence within at least five genes set forth in Table 1 and at least five genes set forth in Table 4; at least five genes set forth in Table 2 and at least five genes set forth in Table 4; or at least five genes set forth in Table 3 and at least five genes set forth in Table 6, or 95% identical to a sequence complementary to the 5 nucleotide continuous sequence.

BRIEF DESCRIPTION OF THE DRAWINGS

The application file contains at least one drawing executed in color. Copies of this patent or patent application with color drawings will be provided by the Office upon request and payment of the necessary fee.

FIGS. 3B-3D are a series of reference density curves for the E2-induced score (FIG. 3B), E2-repressed score (FIG. 3C), and ER pathway activity score (FIG. 3D) in the collection of 139 HR+/HER2− breast tumors. Pre- and post-treatment with Compound B expression data for six patients are overlaid: pre-treatment scores are indicated as a diamond; post-treatment scores as a circle. Arrows show the magnitude and direction of change in ER pathway activity score per patient.

FIG. 3E is a scatter plot of pre-treatment ER pathway activity score versus pre-treatment ESR1 expression levels for six patients treated with Compound B.

FIG. 3F is a scatter plot of the treatment-induced difference in ER pathway activity pre-treatment to post-treatment versus pre-treatment ER pathway activity levels for six patients treated with Compound B.

FIG. 3G is a scatter plot of the treatment-induced difference in E2-induced score pre-treatment to post-treatment versus pre-treatment E2-induced scores for six patients treated with Compound B.

FIGS. 3H-3J are a series of reference density curves for the E2-induced score (FIG. 3H), E2-repressed score (FIG. 3I), and ER pathway activity score (FIG. 3J) in the collection of 139 HR+/HER2− breast tumors. Pre- and post-treatment with Compound A expression data for seven patients are overlaid: pre-treatment scores are indicated as a diamond; post-treatment scores as a circle. Arrows show the magnitude and direction of change in ER pathway activity score per patient.

FIG. 4J is a table showing the 41-gene signature (23 E2-induced and 18 E2-repressed genes).

FIG. 4K is a table showing the 19-gene signature (11 E2-induced and 8 E2-repressed genes).

FIG. 4L is a table showing the 14-gene signature (8 E2-induced and 6 E2-repressed genes).

DETAILED DESCRIPTION

General Techniques

Figure 1A:
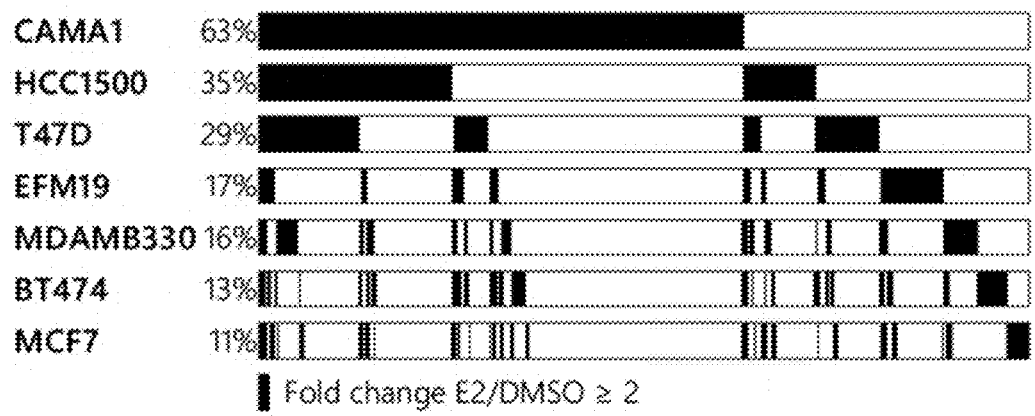
FIG. 1A is an overview of estradiol (E2)-induced genes shown in red (columns) in seven breast cancer cell lines (rows). E2 induction is defined as ≥2-fold change in expression following E2 treatment compared to treatment with DMSO (p-value ≤0.05).
Figure 1B:
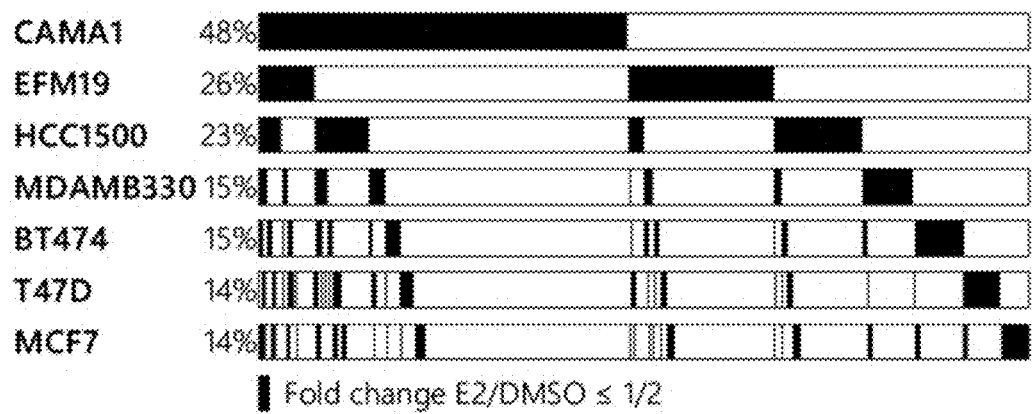
FIG. 1B is an overview of E2-repressed genes shown in blue (columns) in seven breast cancer cell lines (rows). E2 repression is defined as ≤½-fold change in expression following E2 treatment compared to treatment with DMSO (p-value ≤0.05).
Figure 1C:
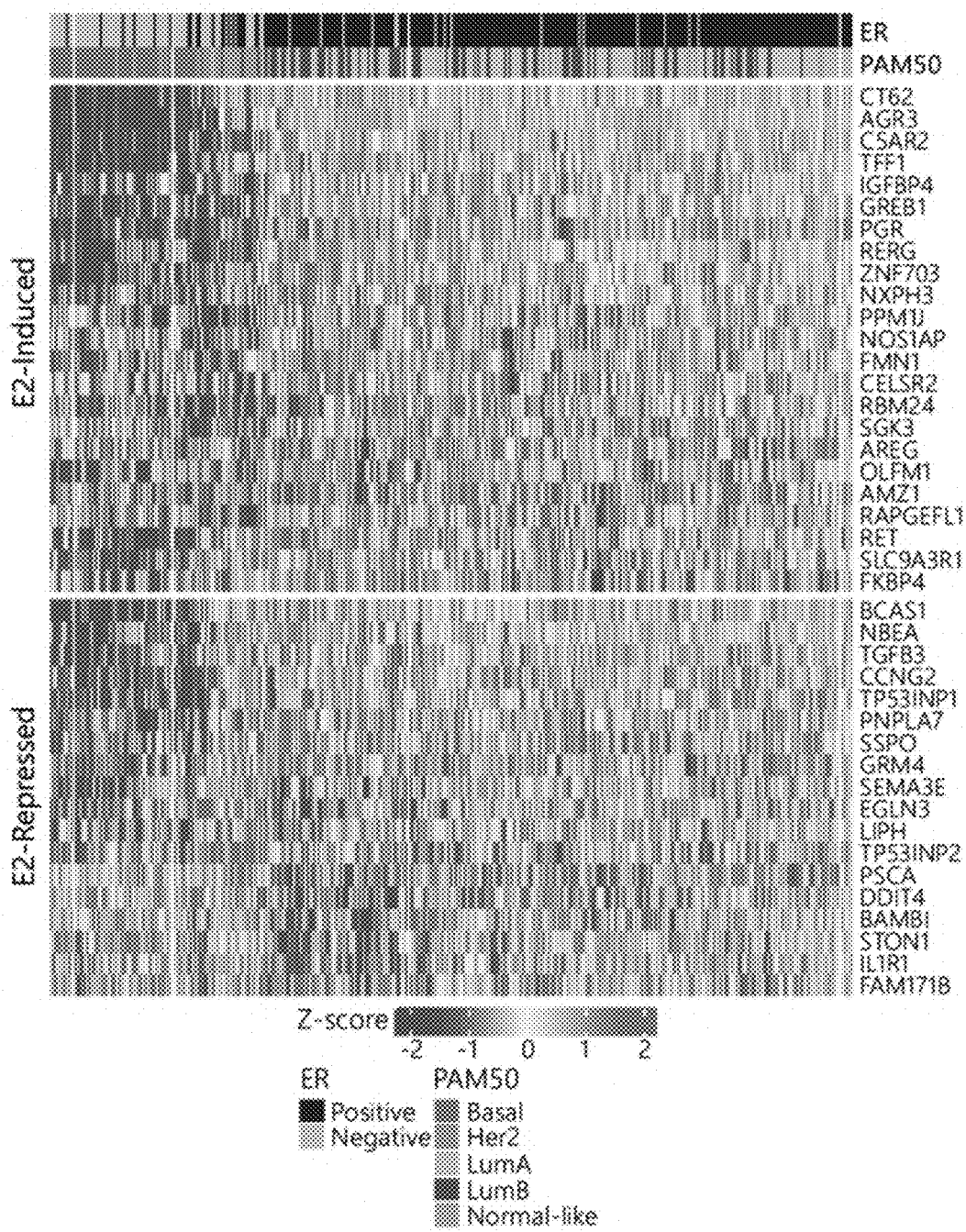
FIG. 1C is a heat map with z-scored expression of 23 E2-induced and 18 E2-repressed genes in 989 breast tumors from The Cancer Genome Atlas (TGCA), annotated by estrogen receptor (ER) immunohistochemistry (IHC) status and PAM50 subtype.

The techniques and procedures described or referenced herein are generally well understood and commonly employed using conventional methodology by those skilled in the art, such as, for example, the widely utilized methodologies described in Sambrook et al., *Molecular Cloning: A Laboratory Manual* 3d edition (2001) Cold Spring Harbor Laboratory Press, Cold Spring Harbor, N.Y.; *Current Protocols in Molecular Biology* (F. M. Ausubel, et al. eds., (2003)); the series *Methods in Enzymology* (Academic Press, Inc.): PCR 2: A Practical Approach (M. J. MacPherson, B. D. Hames and G. R. Taylor eds. (1995)), Harlow and Lane, eds. (1988) *Antibodies, A Laboratory Manual*, and *Animal Cell Culture* (R. I. Freshney, ed. (1987)); *Oligonucleotide Synthesis* (M. J. Gait, ed., 1984); *Methods in*

*Molecular Biology*, Humana Press; *Cell Biology: A Laboratory Notebook* (J. E. Cellis, ed., 1998) Academic Press; *Animal Cell Culture* (R. I. Freshney), ed., 1987); *Introduction to Cell and Tissue Culture* (J. P. Mather and P. E. Roberts, 1998) Plenum Press; *Cell and Tissue Culture: Laboratory Procedures* (A. Doyle, J. B. Griffiths, and D. G. Newell, eds., 1993-8) J. Wiley and Sons; *Handbook of Experimental Immunology* (D. M. Weir and C. C. Blackwell, eds.); *Gene Transfer Vectors for Mammalian Cells* (J. M. Miller and M. P. Calos, eds., 1987); *PCR: The Polymerase Chain Reaction*, (Mullis et al., eds., 1994); *Current Protocols in Immunology* (J. E. Coligan et al., eds., 1991); *Short Protocols in Molecular Biology* (Wiley and Sons, 1999); *Immunobiology* (C. A. Janeway and P. Travers, 1997); *Antibodies* (P. Finch, 1997); *Antibodies: A Practical Approach* (D. Catty., ed., IRL Press, 1988-1989); *Monoclonal Antibodies: A Practical Approach* (P. Shepherd and C. Dean, eds., Oxford University Press, 2000); *Using Antibodies: A Laboratory Manual* (E. Harlow and D. Lane (Cold Spring Harbor Laboratory Press, 1999); *The Antibodies* (M. Zanetti and J. D. Capra, eds., Harwood Academic Publishers, 1995); and *Cancer: Principles and Practice of Oncology* (V. T. DeVita et al., eds., J.B. Lippincott Company, 1993).

Definitions

It is to be understood that aspects and embodiments described herein include "comprising," "consisting," and "consisting essentially of" aspects and embodiments. As used herein, the singular form "a," "an," and "the" includes plural references unless indicated otherwise.

The term "about" as used herein refers to the usual error range for the respective value readily known to the skilled person in this technical field. Reference to "about" a value or parameter herein includes (and describes) embodiments that are directed to that value or parameter per se. For example, description referring to "about X" includes description of "X."

As used herein, "administering" is meant a method of giving a dosage of a compound (e.g., an endocrine therapy as described herein or a composition (e.g., a pharmaceutical composition, e.g., a pharmaceutical composition including an endocrine therapy (e.g., a selective estrogen receptor modulator (SERM) (e.g., a selective estrogen receptor degrader (SERD)), a gonadotropin-releasing hormone (GnRH) agonist, and/or an aromatase inhibitor (AI)) to a subject. The compounds and/or compositions utilized in the methods described herein can be administered, for example, orally, intramuscularly, intravenously (e.g., by intravenous infusion), subcutaneously, intradermally, percutaneously, intraarterially, intraperitoneally, intralesionally, intracranially, intraarticularly, intraprostatically, intrapleurally, intratracheally, intranasally, intravitreally, intravaginally, intrarectally, topically, intratumorally, peritoneally, subconjunctivally, intravesicularlly, mucosally, intrapericardially, intraumbilically, intraocularly, topically, locally, by inhalation, by injection, by infusion, by continuous infusion, by localized perfusion bathing target cells directly, by catheter, by lavage, in creams, or in lipid compositions. The method of administration can vary depending on various factors (e.g., the compound or composition being administered and the severity of the condition, disease, or disorder being treated).

The term "anti-cancer therapy" refers to a therapy useful for treating a cancer (e.g., a breast cancer, e.g., an HR+ breast cancer (e.g., an ER+ breast cancer (e.g., a luminal A breast cancer or a luminal B breast cancer)) and/or a metastatic or a locally advanced breast cancer). Examples of anti-cancer therapeutic agents include, but are not limited to, endocrine therapies as described herein, growth inhibitory agents, cytotoxic agents, agents used in radiation therapy, anti-angiogenesis agents, apoptotic agents, anti-tubulin agents, and other agents to treat cancer, for example, anti-CD20 antibodies, platelet derived growth factor inhibitors (e.g., GLEEVEC™ (imatinib mesylate)), a COX-2 inhibitor (e.g., celecoxib), interferons, cytokines, antagonists (e.g., neutralizing antibodies), other bioactive and organic chemical agents, and the like. Combinations thereof are also included herein. An anti-cancer therapy as used herein can also be referred to a "non-endocrine therapy" which in turn refers to any anti-cancer therapy excluding endocrine therapies as defined herein.

The term "endocrine therapy" refers to a therapy or treatment useful for modulating (e.g. regulating, reducing, blocking, or inhibiting) the effects of the expression, a level, or an amount of one or more hormones found to cause or otherwise cause progression of a breast cancer as described herein. Endocrine therapy as described herein includes non-hormone and hormone therapies such as, for example, a selective estrogen receptor modulator (SERM) as described herein and understood in the art, a selective estrogen receptor degrader (SERD) as described herein and understood in the art, a gonadotropin-releasing hormone (GnRH) agonist as described herein and understood in the art, a Selective Estrogen Receptor Covalent Antagonist (SERCA) as described herein and understood in the art, a Selective Human Estrogen Receptor Partial Agonist (ShERPA) as described herein and understood in the art; an aromatase inhibitor (AI) as described herein, or a combination thereof. In one embodiment, an endocrine therapy comprises one or more compounds from Section IV-A herein.

Additional exemplary endocrine therapies for use in the methods described herein include, but are not limited to: anti-estrogens, for example, tamoxifen (including NOLVADEX® tamoxifen), raloxifene, droloxifene, 4-hydroxytamoxifen, trioxifene, keoxifene, LY117018, onapristone, FARESTON® (toremifene citrate), nafoxidine, clomifene, anordrin, bazedoxifene, broparestrol, cyclofenil, lasofoxifene, ormeloxifene, acolbifene, elacestrant (RAD1901), clomifenoxide, etacstil, ospemifene, fulvestrant (FASLODEX®), EM800, brilanestrant (GDC-0810), LX-039, AZ9496, GDC-0927 (SRN-0927); GDC-9545, G1T48 (G1 Therapeutics), H3B 6545 (H3 Biomedicine), SAR439859 (Sanofi), aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® (exemestane), formestanie, fadrozole, RIVISOR® (vorozole), FEMARA® (letrozole), and ARIMIDEX® (anastrozole); anti-androgens such as flutamide, nilutamide, bicalutamide, leuprolide, and goserelin; as well as troxacitabine (a 1,3-dioxolane nucleoside cytosine analog); and antisense oligonucleotides, particularly those which inhibit expression of genes in signaling pathways implicated in aberrant cell proliferation, as well as combinations of two or more of the above.

Examples of chemotherapeutic agents (and as applicable non-endocrine therapies) include, but are not limited to, mammalian target of rapamycin (mTOR) inhibitors such as sirolimus (also known as rapamycin), temsirolimus (also known as CCI-779 or TORISEL®), everolimus (also known as RAD001 or AFINITOR®), ridaforolimus (also known as AP-23573, MK-8669, or deforolimus), OSI-027, AZD8055, and INK128; phosphatidylinositol 3-kinase (PI3K) inhibitors such as idelalisib (also known as GS-1101 or CAL-101), BKM120, and perifosine (also known as KRX-0401); dual phosphatidylinositol 3-kinase (PI3K)/mTOR inhibitors such as XL765, GDC-0980, BEZ235 (also known as NVP-BEZ235), BGT226, GSK2126458, PF-04691502, and PF-05212384 (also known as PKI-587); and cyclin-dependent kinase (CDK)4/6 inhibitors such as abemaciclib (VERZENIO®), palbociclib (IBRANCE®), ribociclib (KISQALI®), trilaciclib (G1T28); anthracyclines such as daunorubicin, doxorubicin, epirubicin, idarubicin, mitoxantrone, valrubicin; taxanes, including paclitaxel and docetaxel; podophyllotoxin; gemcitabine (GEMZAR®); 5-fluorouracil (5-FU); cyclophosphamide (CYTOXAN®); platinum analogs such as cisplatin and carboplatin; vinorelbine (NAVELBINE®); capecitabine (XELODA®); ixabepilone (IXEMPRA®); and eribulin (HALAVEN®); ribozymes such as a VEGF expression inhibitor (e.g., ANGIOZYME® ribozyme) and a HER2 expression inhibitor; vaccines such as gene therapy vaccines, for example, ALLOVECTIN® vaccine, LEUVECTIN® vaccine, and VAXID® vaccine; PROLEUKIN® rIL-2; LURTOTECAN® topoisomerase 1 inhibitor; ABARELIX® rmRH; Vinorelbine and Esperamicins (see U.S. Pat. No. 4,675,187), any of the compounds described in Section IV-A, below, and pharmaceutically acceptable salts, acids or derivatives of any of the above; as well as combinations of two or more of the above.

Further exemplary chemotherapeutic agents (and non-endocrine therapies) include alkylating agents such as thiotepa and cyclosphosphamide (CYTOXAN©); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN©), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin $\gamma_1^1$ and calicheamicin omega1 (see, e.g., Nicolaou et al., Angew. Chem Intl. Ed Engl., 33: 183-186 (1994)); CDP323, an oral alpha-4 integrin inhibitor; dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycins, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®), liposomal doxorubicin TLC D-99 (MYOCET®), peglylated liposomal doxorubicin (CAELYX®), and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); combretastatin; folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2''-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoid, e.g., paclitaxel (TAXOL®, Bristol-Myers Squibb Oncology, Princeton, N.J.), albumin-engineered nanoparticle formulation of paclitaxel (ABRAXANE™), and docetaxel (TAXOTERE®, Rhome-Poulene Rorer, Antony, France); chlorambucil; 6-thioguanine; mercaptopurine; methotrexate; platinum agents such as cisplatin, oxaliplatin (e.g., ELOXATIN®), and carboplatin; vincas, which prevent tubulin polymerization from forming microtubules, including vinblastine (VELBAN®), vincristine (ONCOVIN®), vindesine (ELDISINE®, FILDESIN®), and vinorelbine (NAVELBINE®); etoposide (VP-16); ifosfamide; mitoxantrone; leucovorin; novantrone; edatrexate; daunomycin; aminopterin; ibandronate; topoisomerase inhibitor RFS 2000; difluoromethylornithine (DMFO); retinoids such as retinoic acid, including bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); troxacitabine (a 1,3-dioxolane nucleoside cytosine analog); antisense oligonucleotides, particularly those that inhibit expression of genes in signaling pathways implicated in aberrant cell proliferation, such as, for example, PKC-alpha, Raf, H-Ras, and epidermal growth factor receptor (EGF-R) (e.g., erlotinib (TARCEVA™)); and VEGF-A that reduce cell proliferation; vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); rmRH (e.g., ABARELIX®); BAY439006 (sorafenib; Bayer); SU-11248 (sunitinib, SUTENT®, Pfizer); perifosine, COX-2 inhibitor (e.g., celecoxib or etoricoxib), proteosome inhibitor (e.g., PS341); bortezomib (VELCADE®); CCI-779; tipifarnib (R11577); orafenib, ABT510; Bcl-2 inhibitor such as oblimersen sodium (GENASENSE®); pixantrone; EGFR inhibitors; tyrosine kinase inhibitors; serine-threonine kinase inhibitors such as rapamycin (sirolimus, RAPAMUNE®); farnesyl-transferase inhibitors such as lonafarnib (SCH 6636, SARA-SAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXA-TIN™) combined with 5-FU and leucovorin, and pharmaceutically acceptable salts, acids or derivatives of any of the above; as well as combinations of two or more of the above.

The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Ret^{88}$, $Sm^{153}$, $Bi^{212}$, $P^{32}$, $Pb^{212}$ and radioactive isotopes of Lu); chemotherapeutic agents or drugs (e.g., methotrexate, adriamicin, *vinca* alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anti-cancer agents disclosed below. A cytotoxic agent can be a non-endocrine agent.

An "article of manufacture" is any manufacture (e.g., a package or container) or kit comprising at least one reagent, e.g., a medicament for treatment of a disease or disorder (e.g., a cancer, e.g., a breast cancer, e.g., an HR+ breast cancer (e.g., an ER+ breast cancer (e.g., luminal A breast cancer or luminal B breast cancer)), DCIS, and/or a metastatic or a locally advanced breast cancer), and/or a probe for specifically detecting a biomarker described herein. In certain embodiments, the manufacture or kit is promoted, distributed, or sold as a unit for performing the methods described herein.

The term "biomarker" as used herein refers to an indicator, e.g., a predictive, prognostic, and/or a pharmacodynamic indicator which can be detected in a sample (e.g., a tissue sample, e.g., a tumor tissue sample, e.g., a formalin-fixed and paraffin-embedded (FFPE), a fresh frozen (FF), an archival, a fresh, or a frozen tumor tissue sample). The biomarker may serve as an indicator of a particular subtype of a disease or disorder (e.g., a breast cancer, an HR+ breast cancer (e.g., an ER+ breast cancer (e.g., luminal A breast cancer or luminal B breast cancer)), DCIS, and/or a metastatic or a locally advanced breast cancer) characterized by certain molecular, pathological, histological, and/or clinical features. In some embodiments, a biomarker is a gene or a set of genes. Biomarkers include, but are not limited to, polynucleotides (e.g., DNA, and/or RNA), polynucleotide copy number alterations (e.g., DNA copy numbers), polypeptides, polypeptide and polynucleotide modifications (e.g., posttranslational modifications), carbohydrates, and/or glycolipid-based molecular markers. Exemplary sets of biomarkers are found in Tables 1-6.

The term "biomarker signature," "signature," "biomarker expression signature," or "expression signature" are used interchangeably herein and refer to a combination of biomarkers whose expression is an indicator, e.g., predictive, prognostic, and/or pharmacodynamic (e.g., the 41-gene signature (e.g., the combination of genes set forth in Tables 3 and 6), the 19-gene signature (e.g., the combination of genes set forth in Tables 2 and 5), or the 14-gene signature (e.g., the combination of genes set forth in Tables 1 and 4)). The biomarker signature may serve as an indicator of a particular subtype of a disease or disorder (e.g., cancer, e.g., breast cancer, e.g., an HR+ breast cancer (e.g., an ER+ breast cancer (e.g., luminal A breast cancer or luminal B breast cancer)), DCIS, and/or a metastatic or a locally advanced breast cancer) characterized by certain molecular, pathological, histological, and/or clinical features. In some embodiments, the biomarker signature is a "gene signature." The term "gene signature" is used interchangeably with "gene expression signature" and refers to a combination of polynucleotides whose expression is an indicator, e.g., predictive, diagnostic, and/or prognostic. In some embodiments, the biomarker signature is a "protein signature." The term "protein signature" is used interchangeably with "protein expression signature" and refers to a combination of polypeptides whose expression is an indicator, e.g., predictive, prognostic, and/or pharmacodynamic.

The term "AGR3" refers to any native Anterior Gradient 3, Protein Disulphide Isomerase Family Member from any vertebrate source, including mammals such as primates (e.g., humans) and rodents (e.g., mice and rats), unless otherwise indicated. The term encompasses "full-length," unprocessed AGR3 as well as any form of AGR3 that results from processing in the cell. The term also encompasses naturally occurring variants of AGR3, e.g., splice variants or allelic variants. AGR3 is also referred to in the art as Protein Disulfide Isomerase Family A Member 18, Breast Cancer Membrane Protein 11, BCMP11, PDIA18, HAG-3, HAG3, AG-3, AG3, and Anterior Gradient Protein 3 Homolog. The nucleic acid sequence of an exemplary human AGR3 is shown under NCBI Reference Sequence: NM_176813.4 or in SEQ ID NO: 1. The amino acid sequence of an exemplary protein encoded by human AGR3 is shown under UniProt Accession No. Q8TD06 or in SEQ ID NO: 2.

The term "AMZ1" refers to any native Archaelysin Family Metallopeptidase 1 from any vertebrate source, including mammals such as primates (e.g., humans) and rodents (e.g., mice and rats), unless otherwise indicated. The term encompasses "full-length," unprocessed AMZ1 as well as any form of AMZ1 that results from processing in the cell. The term also encompasses naturally occurring variants of AMZ1, e.g., splice variants or allelic variants. AMZ1 is also referred to in the art as Archeobacterial Metalloproteinase-Like Protein 1, Archaemetzincin-1, Metalloproteinase-Like Protein, and KIAA1950. The nucleic acid sequence of an exemplary human AMZ1 is shown under NCBI Reference Sequence: NM_133463.3 or in SEQ ID NO: 3. The amino acid sequence of an exemplary protein encoded by human AMZ1 is shown under UniProt Accession No. Q400G9 or in SEQ ID NO: 4.

The term "AREG" refers to any native Amphiregulin from any vertebrate source, including mammals such as primates (e.g., humans) and rodents (e.g., mice and rats), unless otherwise indicated. The term encompasses "full-length," unprocessed AREG as well as any form of AREG that results from processing in the cell. The term also encompasses naturally occurring variants of AREG, e.g., splice variants or allelic variants. AREG is also referred to in the art as Colorectum Cell-Derived Growth Factor, Schwannoma-Derived Growth Factor, Amphiregulin B, AREGB, CRDGF, and SDGF. The nucleic acid sequence of an exemplary human AREG is shown under NCBI Reference Sequence: NM_001657.3 or in SEQ ID NO: 5. The amino acid sequence of an exemplary protein encoded by human AREG is shown under UniProt Accession No. P15514 or in SEQ ID NO: 6.

The term "C5AR2" refers to any native Complement Component 5a Receptor 2 from any vertebrate source, including mammals such as primates (e.g., humans) and rodents (e.g., mice and rats), unless otherwise indicated. The term encompasses "full-length," unprocessed C5AR2 as well as any form of C5AR2 that results from processing in the cell. The term also encompasses naturally occurring variants of C5AR2, e.g., splice variants or allelic variants. C5AR2 is also referred to in the art as Complement Component 5a Receptor 2, G Protein-Coupled Receptor 77, GPR77, C5L2, C5a Anaphylatoxin Chemotactic Receptor C5L2, and GPF77. The nucleic acid sequence of an exemplary human C5AR2 is shown under NCBI Reference Sequence: NM_001271749.1 or in SEQ ID NO: 7. The amino acid sequence of an exemplary protein encoded by human C5AR2 is shown under UniProt Accession No. Q9P296 or in SEQ ID NO: 8.

The term "CELSR2" refers to any native Cadherin EGF LAG Seven-Pass G-Type Receptor 2 from any vertebrate source, including mammals such as primates (e.g., humans) and rodents (e.g., mice and rats), unless otherwise indicated. The term encompasses "full-length," unprocessed CELSR2 as well as any form of CELSR2 that results from processing in the cell. The term also encompasses naturally occurring variants of CELSR2, e.g., splice variants or allelic variants. CELSR2 is also referred to in the art as Multiple Epidermal Growth Factor-Like Domains Protein 3, Multiple Epidermal Growth Factor-Like Domains Protein 3, Adhesion G Protein-Coupled Receptor C2, Epidermal Growth Factor-Like Protein 2, Multiple EGF-Like Domains Protein 3, Cadherin Family Member 10, Flamingo Homolog 3, EGF-Like Protein 2, CDHF10, EGFL2, MEGF3, Flamingo1, KIAA0279, and ADGRC2. The nucleic acid sequence of an exemplary human CELSR2 is shown under NCBI Reference Sequence: NM_001408.2 or in SEQ ID NO: 9. The amino acid sequence of an exemplary protein encoded by human CELSR2 is shown under UniProt Accession No. Q9HCU4 or in SEQ ID NO: 10.

The term "CT62" refers to any native Cancer/Testis Antigen 62 from any vertebrate source, including mammals such as primates (e.g., humans) and rodents (e.g., mice and rats), unless otherwise indicated. The term encompasses "full-length," unprocessed CT62 as well as any form of CT62 that results from processing in the cell. The term also encompasses naturally occurring variants of CT62, e.g., splice variants or allelic variants. The nucleic acid sequence of an exemplary human CT62 is shown under NCBI Reference Sequence: XM_006720429 or in SEQ ID NO: 11. The amino acid sequence of an exemplary protein encoded by human CT62 is shown under UniProt Accession No. P0C5K7 or in SEQ ID NO: 12.

The term "FKBP4" refers to any native FK506 Binding Protein 4 from any vertebrate source, including mammals such as primates (e.g., humans) and rodents (e.g., mice and rats), unless otherwise indicated. The term encompasses "full-length," unprocessed FKBP4 as well as any form of FKBP4 that results from processing in the cell. The term also encompasses naturally occurring variants of FKBP4, e.g., splice variants or allelic variants. FKBP4 is also referred to in the art as Rotamase, FKBP51, FKBP52, FKBP59, HBI, Peptidyl-Prolyl Cis-Trans Isomerase FKBP4, T-Cell FK506-Binding Protein (59 kD), HSP Binding Immunophilin, Immunophilin FKBP52, PPIase FKBP4, PPIASE, Hsp56, P52, and P59. The nucleic acid sequence of an exemplary human FKBP4 is shown under NCBI Reference Sequence: NM_002014.3 or in SEQ ID NO: 13. The amino acid sequence of an exemplary protein encoded by human FKBP4 is shown under UniProt Accession No. Q02790 or in SEQ ID NO: 14.

The term "FMN1" refers to any native Formin 1 from any vertebrate source, including mammals such as primates (e.g., humans) and rodents (e.g., mice and rats), unless otherwise indicated. The term encompasses "full-length," unprocessed FMN1 as well as any form of FMN1 that results from processing in the cell. The term also encompasses naturally occurring variants of FMN1, e.g., splice variants or allelic variants. FMN1 is also referred to in the art as Limb Deformity Protein Homolog, FMN, and LD. The nucleic acid sequence of an exemplary human FMN1 is shown under NCBI Reference Sequence: NM_001277313.1 or in SEQ ID NO: 15. The amino acid sequence of an exemplary protein encoded by human FMN1 is shown under UniProt Accession No. Q68DA7 or in SEQ ID NO: 16.

The term "GREB1" refers to any native Growth Regulation By Estrogen in Breast Cancer 1 from any vertebrate source, including mammals such as primates (e.g., humans) and rodents (e.g., mice and rats), unless otherwise indicated. The term encompasses "full-length," unprocessed GREB1 as well as any form of GREB1 that results from processing in the cell. The term also encompasses naturally occurring variants of GREB1, e.g., splice variants or allelic variants. GREB1 is also referred to in the art as Gene Regulated in Breast Cancer 1 Protein and KIAA0575. The nucleic acid sequence of an exemplary human GREB1 is shown under NCBI Reference Sequence: NM_014668.3 or in SEQ ID NO: 17. The amino acid sequence of an exemplary protein encoded by human GREB1 is shown under UniProt Accession No. Q4ZG55 or in SEQ ID NO: 18.

The term "IGFBP4" refers to any native Insulin Like Growth Factor Binding Protein 4 from any vertebrate source, including mammals such as primates (e.g., humans) and rodents (e.g., mice and rats), unless otherwise indicated. The term encompasses "full-length," unprocessed IGFBP4 as well as any form of IGFBP4 that results from processing in the cell. The term also encompasses naturally occurring variants of IGFBP4, e.g., splice variants or allelic variants. IGFBP4 is also referred to in the art as IGF-Binding Protein 4, IBP-4, HT29-IGFBP, and BP-4. The nucleic acid sequence of an exemplary human IGFBP4 is shown under NCBI Reference Sequence: NM_001552.2 or in SEQ ID NO: 19. The amino acid sequence of an exemplary protein encoded by human IGFBP4 is shown under UniProt Accession No. P22692 or in SEQ ID NO: 20.

The term "NOS1AP" refers to any native Nitric Oxide Synthase 1 Adaptor Protein from any vertebrate source, including mammals such as primates (e.g., humans) and rodents (e.g., mice and rats), unless otherwise indicated. The term encompasses "full-length," unprocessed NOS1AP as well as any form of NOS1AP that results from processing in the cell. The term also encompasses naturally occurring variants of NOS1AP, e.g., splice variants or allelic variants. NOS1AP is also referred to in the art as C-Terminal PDZ Ligand of Neuronal Nitric Oxide Synthase Protein, Nitric Oxide Synthase 1 (Neuronal) Adaptor Protein, CAPON, Ligand of Neuronal Nitric Oxide Synthase with Carboxyl-Terminal PDZ Domain, 6330408P19Rik, and KIAA0464. The nucleic acid sequence of an exemplary human NOS1AP is shown under NCBI Reference Sequence: NM_014697.2 or in SEQ ID NO: 21. The amino acid sequence of an exemplary protein encoded by human NOS1AP is shown under UniProt Accession No. O75052 or in SEQ ID NO: 22.

The term "NXPH3" refers to any native Neurexophilin 3 from any vertebrate source, including mammals such as primates (e.g., humans) and rodents (e.g., mice and rats), unless otherwise indicated. The term encompasses "full-length," unprocessed NXPH3 as well as any form of NXPH3 that results from processing in the cell. The term also encompasses naturally occurring variants of NXPH3, e.g., splice variants or allelic variants. NXPH3 is also referred to in the art as NPH3 and KIAA1159. The nucleic acid sequence of an exemplary human NXPH3 is shown under NCBI Reference Sequence: NM_007225.2 or in SEQ ID NO: 23. The amino acid sequence of an exemplary protein encoded by human NXPH3 is shown under UniProt Accession No. O95157 or in SEQ ID NO: 24.

The term "OLFM1" refers to any native Olfactomedin 1 from any vertebrate source, including mammals such as primates (e.g., humans) and rodents (e.g., mice and rats), unless otherwise indicated. The term encompasses "full-length," unprocessed OLFM1 as well as any form of OLFM1 that results from processing in the cell. The term also encompasses naturally occurring variants of OLFM1, e.g., splice variants or allelic variants. OLFM1 is also referred to in the art as Neuronal Olfactomedin-Related ER Localized Protein, Noelin, NOE1, Olfactomedin Related ER Localized Protein, Neuroblastoma Protein, Pancortin 1, Pancortin, NOELIN1, NOEL1, OlfA, and AMY. The nucleic acid sequence of an exemplary human OLFM1 is shown under NCBI Reference Sequence: NM_014279.4 or in SEQ ID NO: 25. The amino acid sequence of an exemplary protein encoded by human OLFM1 is shown under UniProt Accession No. Q99784 or in SEQ ID NO: 26.

The term "PGR" refers to any native Progesterone Receptor from any vertebrate source, including mammals such as primates (e.g., humans) and rodents (e.g., mice and rats), unless otherwise indicated. The term encompasses "full-length," unprocessed PGR as well as any form of PGR that results from processing in the cell. The term also encompasses naturally occurring variants of PGR, e.g., splice variants or allelic variants. PGR is also referred to in the art as Nuclear Receptor Subfamily 3 Group C Member 3, NR3C3, and PR. The nucleic acid sequence of an exemplary human PGR is shown under NCBI Reference Sequence: NM_000926.4 or in SEQ ID NO: 27. The amino acid sequence of an exemplary protein encoded by human PGR is shown under UniProt Accession No. P06401 or in SEQ ID NO: 28.

The term "PPM1J" refers to any native Protein Phosphatase, Mg2+/Mn2+ Dependent 1J from any vertebrate source, including mammals such as primates (e.g., humans) and rodents (e.g., mice and rats), unless otherwise indicated. The term encompasses "full-length," unprocessed PPM1J as well as any form of PPM1J that results from processing in the cell. The term also encompasses naturally occurring variants of PPM1J, e.g., splice variants or allelic variants. PPM1J is also referred to in the art as Protein Phosphatase 1J (PP2C Domain Containing), Protein Phosphatase 2C Zeta, EC 3.1.3.16, PP2C-Zeta, Protein Phosphatase 2a, Catalytic Subunit, Zeta Isoform, Protein Phosphatase 1J, PP2Czeta, and PP2CZ. The nucleic acid sequence of an exemplary human PPM1J is shown under NCBI Reference Sequence: NM_005167.5 or in SEQ ID NO: 29. The amino acid sequence of an exemplary protein encoded by human PPM1J is shown under UniProt Accession No. Q5JR12 or in SEQ ID NO: 30.

The term "RAPGEFL1" refers to any native Rap Guanine Nucleotide Exchange Factor Like 1 from any vertebrate source, including mammals such as primates (e.g., humans) and rodents (e.g., mice and rats), unless otherwise indicated. The term encompasses "full-length," unprocessed RAPGEFL1 as well as any form of RAPGEFL1 that results from processing in the cell. The term also encompasses naturally occurring variants RAPGEFL1, e.g., splice variants or allelic variants. RAPGEFL1 is also referred to in the art as Link Guanine Nucleotide Exchange Factor II, Rap Guanine Nucleotide Exchange Factor (GEF)-Like 1, and Link GEFII. The nucleic acid sequence of an exemplary human RAPGEFL1 is shown under NCBI Reference Sequence: NM_001303533.1 or in SEQ ID NO: 31. The amino acid sequence of an exemplary protein encoded by human RAPGEFL1 is shown under UniProt Accession No. Q9UHV5 or in SEQ ID NO: 32.

The term "RBM24" refers to any native RNA Binding Motif Protein 24 from any vertebrate source, including mammals such as primates (e.g., humans) and rodents (e.g., mice and rats), unless otherwise indicated. The term encompasses "full-length," unprocessed RBM24 as well as any form of RBM24 that results from processing in the cell. The term also encompasses naturally occurring variants of RBM24, e.g., splice variants or allelic variants. RBM24 is also referred to in the art as RNA-Binding Region (RNP1, RRM) Containing 6, RNPC6, RNA-Binding Protein 24, and DJ259A10.1. The nucleic acid sequence of an exemplary human RBM24 is shown under NCBI Reference Sequence: NM_001143942.1 or in SEQ ID NO: 33. The amino acid sequence of an exemplary protein encoded by human RBM24 is shown under UniProt Accession No. Q9BX46 or in SEQ ID NO: 34.

The term "RERG" refers to any native RAS Like Estrogen Regulated Growth Inhibitor from any vertebrate source, including mammals such as primates (e.g., humans) and rodents (e.g., mice and rats), unless otherwise indicated. The term encompasses "full-length," unprocessed RERG as well as any form of RERG that results from processing in the cell. The term also encompasses naturally occurring variants of RERG, e.g., splice variants or allelic variants. The nucleic acid sequence of an exemplary human RERG is shown under NCBI Reference Sequence: NM_032918.2 or in SEQ ID NO: 35. The amino acid sequence of an exemplary protein encoded by human RERG is shown under UniProt Accession No. Q96A58 or in SEQ ID NO: 36.

The term "RET" refers to any native Ret Proto-Oncogene from any vertebrate source, including mammals such as primates (e.g., humans) and rodents (e.g., mice and rats), unless otherwise indicated. The term encompasses "full-length," unprocessed RET as well as any form of RET that results from processing in the cell. The term also encompasses naturally occurring variants of RET, e.g., splice variants or allelic variants. RET is also referred to in the art as Cadherin-Related Family Member 16, Rearranged During Transfection, RET Receptor Tyrosine Kinase, Cadherin Family Member 12, Proto-Oncogene C-Ret, EC 2.7.10.1, CDHF12, CDHR16, PTC, Multiple Endocrine Neoplasia And Medullary Thyroid Carcinoma 1, EC 2.7.10, RET-ELE1, HSCR1, MEN2A, MEN2B, RET51, and MTC1. The nucleic acid sequence of an exemplary human RET is shown under NCBI Reference Sequence: NM_020975.5 or in SEQ ID NO: 37. The amino acid sequence of an exemplary protein encoded by human RET is shown under UniProt Accession No. P07949 or in SEQ ID NO: 38.

The term "SGK3" refers to any native Serum/Glucocorticoid Regulated Kinase Family Member 3 from any vertebrate source, including mammals such as primates (e.g., humans) and rodents (e.g., mice and rats), unless otherwise indicated. The term encompasses "full-length," unprocessed SGK3 as well as any form of SGK3 that results from processing in the cell. The term also encompasses naturally occurring variants of SGK3, e.g., splice variants or allelic variants. SGK3 is also referred to in the art as Cytokine-Independent Survival Kinase, EC 2.7.11.1, SGKL, CISK, EC 2.7.11, Serine/Threonine-Protein Kinase Sgk3, and SGK2. The nucleic acid sequence of an exemplary human SGK3 is shown under NCBI Reference Sequence: NM_001033578.2 or in SEQ ID NO: 39. The amino acid sequence of an exemplary protein encoded by human SGK3 is shown under UniProt Accession No. Q96BR1 or in SEQ ID NO: 40.

The term "SLC9A3R1" refers to any native SLC9A3 Regulator 1 from any vertebrate source, including mammals such as primates (e.g., humans) and rodents (e.g., mice and rats), unless otherwise indicated. The term encompasses "full-length," unprocessed SLC9A3R1 as well as any form of SLC9A3R1 that results from processing in the cell. The term also encompasses naturally occurring variants of SLC9A3R1, e.g., splice variants or allelic variants. SLC9A3R1 is also referred to in the art as Solute Carrier Family 9, Subfamily A (NHE3, Cation Proton Antiporter 3), Member 3 Regulator 1, Regulatory Cofactor Of Na(+)/H(+) Exchanger, NHERF-1, EBP50, NHERF, Ezrin-Radixin-Moesin Binding Phosphoprotein-50, Sodium-Hydrogen Exchanger Regulatory Factor 1, and NPHLOP2. The nucleic acid sequence of an exemplary human SLC9A3R1 is shown under NCBI Reference Sequence: NM_004252.4 or in SEQ ID NO: 41. The amino acid sequence of an exemplary protein encoded by human SLC9A3R1 is shown under UniProt Accession No. O14745 or in SEQ ID NO: 42.

The term "TFF1" refers to any native Trefoil Factor 1 from any vertebrate source, including mammals such as primates (e.g., humans) and rodents (e.g., mice and rats), unless otherwise indicated. The term encompasses "full-length," unprocessed TFF1 as well as any form of TFF1 that results from processing in the cell. The term also encompasses naturally occurring variants of TFF1, e.g., splice variants or allelic variants. TFF1 is also referred to in the art as Breast Cancer Estrogen-Inducible Protein, Polypeptide P1A, Protein PS2, HP1.A, PNR-2, BCEI, PS2, Gastrointestinal Trefoil Protein PS2, D21S21, and HPS2 The nucleic acid sequence of an exemplary human TFF1 is shown under NCBI Reference Sequence: NM_003225.2 or in SEQ ID NO: 43. The amino acid sequence of an exemplary protein encoded by human TFF is shown under UniProt Accession No. P04155 or in SEQ ID NO: 44.

The term "ZNF703" refers to any native Zinc Finger Protein 703 from any vertebrate source, including mammals such as primates (e.g., humans) and rodents (e.g., mice and rats), unless otherwise indicated. The term encompasses "full-length," unprocessed ZNF703 as well as any form of ZNF703 that results from processing in the cell. The term also encompasses naturally occurring variants of ZNF703, e.g., splice variants or allelic variants. ZNF703 is also referred to in the art as Zinc Finger Elbow-Related Proline Domain Protein 1, ZEPPO1, ZPO1, ZNF503L, and NLZ1. The nucleic acid sequence of an exemplary human ZNF703 is shown under NCBI Reference Sequence: NM_025069.2 or in SEQ ID NO: 45. The amino acid sequence of an exemplary protein encoded by human ZNF703 is shown under UniProt Accession No. Q9H7S9 or in SEQ ID NO: 46.

The term "BAMBI" refers to any native BMP and Activin Membrane Bound Inhibitor from any vertebrate source, including mammals such as primates (e.g., humans) and rodents (e.g., mice and rats), unless otherwise indicated. The term encompasses "full-length," unprocessed BAMBI as well as any form of BAMBI that results from processing in the cell. The term also encompasses naturally occurring variants of BAMBI, e.g., splice variants or allelic variants. BAMBI is also referred to in the art as Putative Transmembrane Protein NMA, Non-Metastatic Gene A Protein, NMA, and BMP And Activin Membrane-Bound Inhibitor Homolog. The nucleic acid sequence of an exemplary human BAMBI is shown under NCBI Reference Sequence: NM_012342.2 or in SEQ ID NO: 47. The amino acid sequence of an exemplary protein encoded by human BAMBI is shown under UniProt Accession No. Q13145 or in SEQ ID NO: 48.

The term "BCAS1" refers to any native Breast Carcinoma Amplified Sequence 1 from any vertebrate source, including mammals such as primates (e.g., humans) and rodents (e.g., mice and rats), unless otherwise indicated. The term encompasses "full-length," unprocessed BCAS1 as well as any form of BCAS1 that results from processing in the cell. The term also encompasses naturally occurring variants of BCAS1, e.g., splice variants or allelic variants. BCAS1 is also referred to in the art as Amplified and Overexpressed in Breast Cancer, Novel Amplified in Breast Cancer 1, AIBC1, and NABC1. The nucleic acid sequence of an exemplary human BCAS1 is shown under NCBI Reference Sequence: NM_003657.3 or in SEQ ID NO: 49. The amino acid sequence of an exemplary protein encoded by human BCAS1 is shown under UniProt Accession No. O75363 or in SEQ ID NO: 50.

The term "CCNG2" refers to any native Cyclin G2 from any vertebrate source, including mammals such as primates (e.g., humans) and rodents (e.g., mice and rats), unless otherwise indicated. The term encompasses "full-length," unprocessed CCNG2 as well as any form of CCNG2 that results from processing in the cell. The term also encompasses naturally occurring variants of CCNG2, e.g., splice variants or allelic variants. The nucleic acid sequence of an exemplary human CCNG2 is shown under NCBI Reference Sequence: XM_011532399.2 or in SEQ ID NO: 51. The amino acid sequence of an exemplary protein encoded by human CCNG2 is shown under UniProt Accession No. Q16589 or in SEQ ID NO: 52.

The term "DDIT4" refers to any native DNA Damage Inducible Transcript 4 from any vertebrate source, including mammals such as primates (e.g., humans) and rodents (e.g., mice and rats), unless otherwise indicated. The term encompasses "full-length," unprocessed DDIT4 as well as any form of DDIT4 that results from processing in the cell. The term also encompasses naturally occurring variants of DDIT4, e.g., splice variants or allelic variants. DDIT4 is also referred to in the art as Protein Regulated in Development and DNA Damage Response 1, HIF-1 Responsive Protein RTP801, REDD1, RTP801, and Dig2. The nucleic acid sequence of an exemplary human DDIT4 is shown under NCBI Reference Sequence: NM_019058.3 or in SEQ ID NO: 53. The amino acid sequence of an exemplary protein encoded by human DDIT4 is shown under UniProt Accession No. Q9NX09 or in SEQ ID NO: 54.

The term "EGLN3" refers to any native Egl-9 Family Hypoxia Inducible Factor 3 from any vertebrate source, including mammals such as primates (e.g., humans) and rodents (e.g., mice and rats), unless otherwise indicated. The term encompasses "full-length," unprocessed EGLN3 as well as any form of EGLN3 that results from processing in the cell. The term also encompasses naturally occurring variants of EGLN3, e.g., splice variants or allelic variants. EGLN3 is also referred to in the art as Prolyl Hydroxylase Domain-Containing Protein 3, Hypoxia-Inducible Factor Prolyl Hydroxylase 3, HIF-Prolyl Hydroxylase 3, HPH-1, HPH-3, PHD3, Egl Nine-Like Protein 3 Isoform, Egl Nine Homolog 3, EC 1.14.11.29, EC 1.14.11, HIFP4H3, and HIFPH3. The nucleic acid sequence of an exemplary human EGLN3 is shown under NCBI Reference Sequence: NM_022073.3 or in SEQ ID NO: 55. The amino acid sequence of an exemplary protein encoded by human EGLN3 is shown under UniProt Accession No. Q9H6Z9 or in SEQ ID NO: 56.

The term "FAM171B" refers to any native Family With Sequence Similarity 171 Member B from any vertebrate source, including mammals such as primates (e.g., humans) and rodents (e.g., mice and rats), unless otherwise indicated. The term encompasses "full-length," unprocessed FAM171B as well as any form of FAM171B that results from processing in the cell. The term also encompasses naturally occurring variants of FAM171B, e.g., splice variants or allelic variants. FAM171B is also referred to in the art as KIAA1946 and Protein FAM171B. The nucleic acid sequence of an exemplary human FAM171B is shown under NCBI Reference Sequence: NM_177454.3 or in SEQ ID NO: 57. The amino acid sequence of an exemplary protein encoded by human FAM171B is shown under UniProt Accession No. Q6P995 or in SEQ ID NO: 58.

The term "GRM4" refers to any native Glutamate Metabotropic Receptor 4 from any vertebrate source, including mammals such as primates (e.g., humans) and rodents (e.g., mice and rats), unless otherwise indicated. The term encompasses "full-length," unprocessed GRM4 as well as any form of GRM4 that results from processing in the cell. The term also encompasses naturally occurring variants of GRM4, e.g., splice variants or allelic variants. GRM4 is also referred to in the art as GPRC1D, MGLUR4, and MGlu4. The nucleic acid sequence of an exemplary human GRM4 is shown under NCBI Reference Sequence: NM_000841.4 or in SEQ ID NO: 59. The amino acid sequence of an exemplary protein encoded by human GRM4 is shown under UniProt Accession No. Q14833 or in SEQ ID NO: 60.

The term "IL1R1" refers to any native Interleukin 1 Receptor Type 1 from any vertebrate source, including mammals such as primates (e.g., humans) and rodents (e.g., mice and rats), unless otherwise indicated. The term encompasses "full-length," unprocessed IL1R1 as well as any form of IL1R1 that results from processing in the cell. The term also encompasses naturally occurring variants of IL1R1, e.g., splice variants or allelic variants. IL1R1 is also referred to in the art as CD121 Antigen-Like Family Member A, Interleukin-1 Receptor Alpha, IL-1R-Alpha, IL1RA, IL1R, P80, CD121a Antigen, D2S1473, CD121A, and IL1RT1. The nucleic acid sequence of an exemplary human IL1R1 is shown under NCBI Reference Sequence: NM_001288706.1 or in SEQ ID NO: 61. The amino acid sequence of an exemplary protein encoded by human IL1R1 is shown under UniProt Accession No. P14778 or in SEQ ID NO: 62.

The term "LIPH" refers to any native Lipase H from any vertebrate source, including mammals such as primates (e.g., humans) and rodents (e.g., mice and rats), unless otherwise indicated. The term encompasses "full-length," unprocessed LIPH as well as any form of LIPH that results from processing in the cell. The term also encompasses naturally occurring variants of LIPH, e.g., splice variants or allelic variants. LIPH is also referred to in the art as Membrane-Associated Phosphatidic Acid-Selective Phospholipase A1-Alpha, PD Lipase-Related Protein, Phospholipase A1 Member B, MPA-PLA1 Alpha, LPDLR, Membrane-Bound Phosphatidic Acid-Selective Phospholipase A1, Lipase Member H, EC 3.1.1.3, C 3.1., ARWH2, HYPT7, LAH2, and AH. The nucleic acid sequence of an exemplary human LIPH is shown under NCBI Reference Sequence: XM_006713529.4 or in SEQ ID NO: 63. The amino acid sequence of an exemplary protein encoded by human LIPH is shown under UniProt Accession No. Q8WWY8 or in SEQ ID NO: 64.

The term "NBEA" refers to any native Neurobeachin from any vertebrate source, including mammals such as primates (e.g., humans) and rodents (e.g., mice and rats), unless otherwise indicated. The term encompasses "full-length," unprocessed NBEA as well as any form of NBEA that results from processing in the cell. The term also encompasses naturally occurring variants of NBEA, e.g., splice variants or allelic variants. NBEA is also referred to in the art as Lysosomal-Trafficking Regulator 2, BCL8B, LYST2, Protein BCL8B, EC 1.14.14.5, EC 6.1.1.11, and KIAA1544. The nucleic acid sequence of an exemplary human NBEA is shown under NCBI Reference Sequence: NM_015678.4 or in SEQ ID NO: 65. The amino acid sequence of an exemplary protein encoded by human NBEA is shown under UniProt Accession No. Q8NFP9 or in SEQ ID NO: 66.

The term "PNPLA7" refers to any native Patatin Like Phospholipase Domain Containing 7 from any vertebrate source, including mammals such as primates (e.g., humans) and rodents (e.g., mice and rats), unless otherwise indicated. The term encompasses "full-length," unprocessed PNPLA7 as well as any form of PNPLA7 that results from processing in the cell. The term also encompasses naturally occurring variants of PNPLA7, e.g., splice variants or allelic variants. PNPLA7 is also referred to in the art as C9orf111, Patatin-Like Phospholipase Domain-Containing Protein 7, Chromosome 9 Open Reading Frame 111, EC 3.1.1.5, NTE-R1, and NTEL1. The nucleic acid sequence of an exemplary human PNPLA7 is shown under NCBI Reference Sequence: NM_001098537.2 or in SEQ ID NO: 67. The amino acid sequence of an exemplary protein encoded by human PNPLA7 is shown under UniProt Accession No. Q6ZV29 or in SEQ ID NO: 68.

The term "PSCA" refers to any native Prostate Stem Cell Antigen from any vertebrate source, including mammals such as primates (e.g., humans) and rodents (e.g., mice and rats), unless otherwise indicated. The term encompasses "full-length," unprocessed PSCA as well as any form of PSCA that results from processing in the cell. The term also encompasses naturally occurring variants of PSCA, e.g., splice variants or allelic variants. PSCA is also referred to in the art as PR0232. The nucleic acid sequence of an exemplary human PSCA is shown under NCBI Reference Sequence: NM_005672.4 or in SEQ ID NO: 69. The amino acid sequence of an exemplary protein encoded by human PSCA is shown under UniProt Accession No. 043653 or in SEQ ID NO: 70.

The term "SEMA3E" refers to any native Semaphorin 3E from any vertebrate source, including mammals such as primates (e.g., humans) and rodents (e.g., mice and rats), unless otherwise indicated. The term encompasses "full-length," unprocessed SEMA3E as well as any form of SEMA3E that results from processing in the cell. The term also encompasses naturally occurring variants of SEMA3E, e.g., splice variants or allelic variants. SEMA3E is also referred to in the art as Sema Domain, Immunoglobulin Domain (Ig), Short Basic Domain, Secreted, (Semaphorin) 3E, SEMAH, Semaphorin-3E, M-Sema H, KIAA0331, M-SemaK, and Coll-5. The nucleic acid sequence of an exemplary human SEMA3E is shown under NCBI Reference Sequence: NM_012431.2 or in SEQ ID NO: 71. The amino acid sequence of an exemplary protein encoded by human SEMA3E is shown under UniProt Accession No. 015041 or in SEQ ID NO: 72.

The term "SSPO" refers to any native SCO-Spondin from any vertebrate source, including mammals such as primates (e.g., humans) and rodents (e.g., mice and rats), unless otherwise indicated. The term encompasses "full-length," unprocessed SSPO as well as any form of SSPO that results from processing in the cell. The term also encompasses naturally occurring variants of SSPO, e.g., splice variants or allelic variants. SSPO is also referred to in the art as SCO Protein, Thrombospondin Domain Containing, Subcommissural Organ Spondin, EC 3.4.24.82, EC 3.4.21.9, and KIAA2036. The nucleic acid sequence of an exemplary human SSPO is shown under NCBI Reference Sequence: BN000852.1 or in SEQ ID NO: 73. The amino acid sequence of an exemplary protein encoded by human SSPO is shown under UniProt Accession No. A2VEC9 or in SEQ ID NO: 74.

The term "STON1" refers to any native Stonin 1 from any vertebrate source, including mammals such as primates (e.g., humans) and rodents (e.g., mice and rats), unless otherwise indicated. The term encompasses "full-length," unprocessed STON1 as well as any form of STON1 that results from processing in the cell. The term also encompasses naturally occurring variants of STON1, e.g., splice variants or allelic variants. STON1 is also referred to in the art as Stoned B-Like Factor, SALF, SBLF, STN1, Stoned B Homolog 1, and STNB1. The nucleic acid sequence of an exemplary human STON1 is shown under NCBI Reference Sequence: NM_001198595.1 or in SEQ ID NO: 75. The amino acid sequence of an exemplary protein encoded by human STON1 is shown under UniProt Accession No. Q9Y6Q2 or in SEQ ID NO: 76.

The term "TGFB3" refers to any native Transforming Growth Factor Beta 3 from any vertebrate source, including mammals such as primates (e.g., humans) and rodents (e.g., mice and rats), unless otherwise indicated. The term encompasses "full-length," unprocessed TGFB3 as well as any form of TGFB3 that results from processing in the cell. The term also encompasses naturally occurring variants of TGFB3, e.g., splice variants or allelic variants. TGFB3 is also referred to in the art as Prepro-Transforming Growth Factor Beta-3, Arrhythmogenic Right Ventricular Dysplasia 1, TGF-Beta-3, ARVD1, LDS5, RNHF, and ARVD. The nucleic acid sequence of an exemplary human TGFB3 is shown under NCBI Reference Sequence: NM_003239.4 or in SEQ ID NO: 77. The amino acid sequence of an exemplary protein encoded by human TGFB3 is shown under UniProt Accession No. P10600 or in SEQ ID NO: 78.

The term "TP53INP1" refers to any native Tumor Protein P53 Inducible Nuclear Protein 1 from any vertebrate source, including mammals such as primates (e.g., humans) and rodents (e.g., mice and rats), unless otherwise indicated. The term encompasses "full-length," unprocessed TP53INP1 as well as any form of TP53INP1 that results from processing in the cell. The term also encompasses naturally occurring variants of TP53INP1, e.g., splice variants or allelic variants. TP53INP1 is also referred to in the art as P53-Dependent Damage-Inducible Nuclear Protein 1, Stress-Induced Protein, P53DINP1, SIP, P53-Inducible P53DINP1, TP53DINP1, TP53INP1A, TP53INP1B, and Teap. The nucleic acid sequence of an exemplary human TGFB3 is shown under NCBI Reference Sequence: NM_033285.3 or in SEQ ID NO: 79. The amino acid sequence of an exemplary protein encoded by human TP53INP1 is shown under UniProt Accession No. Q96A56 or in SEQ ID NO: 80.

The term "TP53INP2" refers to any native Tumor Protein P53 Inducible Nuclear Protein 2 from any vertebrate source, including mammals such as primates (e.g., humans) and rodents (e.g., mice and rats), unless otherwise indicated. The term encompasses "full-length," unprocessed TP53INP2 as well as any form of TP53INP2 that results from processing in the cell. The term also encompasses naturally occurring variants of TP53INP2, e.g., splice variants or allelic variants. TP53INP2 is also referred to in the art as P53-Inducible Protein U, C20orf110, PIG-U, PINH, DOR, Chromosome 20 Open Reading Frame 110, Diabetes And Obesity-Regulated Gene, and DJ1181N3.1. The nucleic acid sequence of an exemplary human TP53INP2 is shown under NCBI Reference Sequence: NM_021202.2 or in SEQ ID NO: 81. The amino acid sequence of an exemplary protein encoded by human TP53INP2 is shown under UniProt Accession No. Q8IXH6 or in SEQ ID NO: 82.

The term "GUSB" refers to any native Glucuronidase Beta from any vertebrate source, including mammals such as primates (e.g., humans) and rodents (e.g., mice and rats), unless otherwise indicated. The term encompasses "full-length," unprocessed GUSB as well as any form of GUSB that results from processing in the cell. The term also encompasses naturally occurring variants of GUSB, e.g., splice variants or allelic variants. GUSB is also referred to in the art as EC 3.2.1.31, Beta-G1, Beta-D-Glucuronidase, MPS7, and BG. The nucleic acid sequence of an exemplary human GUSB is shown under NCBI Reference Sequence: NM_000181.3 or in SEQ ID NO: 83. The amino acid sequence of an exemplary protein encoded by human GUSB is shown under UniProt Accession No. P08236 or in SEQ ID NO: 84.

The term "PPIA" refers to any native Peptidylprolyl Isomerase A from any vertebrate source, including mammals such as primates (e.g., humans) and rodents (e.g., mice and rats), unless otherwise indicated. The term encompasses "full-length," unprocessed PPIA as well as any form of PPIA that results from processing in the cell. The term also encompasses naturally occurring variants of PPIA, e.g., splice variants or allelic variants. PPIA is also referred to in the art as Cyclosporin A-Binding Protein, Cyclophilin A, Rotamase A, EC 5.2.1.8, PPIase A, CYPA, Epididymis Secretory Sperm Binding Protein Li 69p, Peptidyl-Prolyl Cis-Trans Isomerase A, T Cell Cyclophilin, HEL-S-69p, and CYPH. The nucleic acid sequence of an exemplary human PPIA is shown under NCBI Reference Sequence: NM_021130.4 or in SEQ ID NO: 85. The amino acid sequence of an exemplary protein encoded by human PPIA is shown under UniProt Accession No. P62937 or in SEQ ID NO: 86.

The term "UBC" refers to any native Ubiquitin C from any vertebrate source, including mammals such as primates (e.g., humans) and rodents (e.g., mice and rats), unless otherwise indicated. The term encompasses "full-length," unprocessed UBC as well as any form of UBC that results from processing in the cell. The term also encompasses naturally occurring variants of UBC, e.g., splice variants or allelic variants. UBC is also referred to in the art as Polyubiquitin-C and HMG20. The nucleic acid sequence of an exemplary human UBC is shown under NCBI Reference Sequence: NM_021009.6 or in SEQ ID NO: 87. The amino acid sequence of an exemplary protein encoded by human UBC is shown under UniProt Accession No. P0CG48 or in SEQ ID NO: 88.

The term "SDHA" refers to Succinate Dehydrogenase Complex Flavoprotein Subunit A from any vertebrate source, including mammals such as primates (e.g., humans) and rodents (e.g., mice and rats), unless otherwise indicated. The term encompasses "full-length," unprocessed SDHA as well as any form of SDHA that results from processing in the cell. The term also encompasses naturally occurring variants of SDHA, e.g., splice variants or allelic variants. The nucleic acid sequence of an exemplary human SDHA is shown under NCBI Reference Sequence: NM_001330758 or in SEQ ID NO: 89. The amino acid sequence of an exemplary protein encoded by human SDHA is shown under UniProt Accession No. P31040 or in SEQ ID NO: 90.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia or lymphoid malignancies. More particular examples of such cancers include, but are not limited to, breast cancer (e.g., an HR+ breast cancer (e.g., an ER+ breast cancer (e.g., luminal A breast cancer or luminal B breast cancer)), DCIS, and/or a metastatic or a locally advanced breast cancer)); lung cancer, including small-cell lung cancer, non-small cell lung cancer, adenocarcinoma of the lung, and squamous carcinoma of the lung; bladder cancer (e.g., urothelial bladder cancer (UBC), muscle invasive bladder cancer (MIBC), and BCG-refractory non-muscle invasive bladder cancer (NMIBC)); kidney or renal cancer (e.g., renal cell carcinoma (RCC)); cancer of the urinary tract; prostate cancer, such as castration-resistant prostate cancer (CRPC); cancer of the peritoneum; hepatocellular cancer; gastric or stomach cancer, including gastrointestinal cancer and gastrointestinal stromal cancer; pancreatic cancer; glioblastoma; cervical cancer; ovarian cancer; liver cancer; hepatoma; colon cancer; rectal cancer; colorectal cancer; endometrial or uterine carcinoma; salivary gland carcinoma; prostate cancer; vulval cancer; thyroid cancer; hepatic carcinoma; anal carcinoma; penile carcinoma; melanoma, including superficial spreading melanoma, lentigo maligna melanoma, acral lentiginous melanomas, and nodular melanomas; multiple myeloma and B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); acute myelogenous leukemia (AML); hairy cell leukemia; chronic myeloblastic leukemia (CML); post-transplant lymphoproliferative disorder (PTLD); and myelodysplastic syndromes (MDS), as well as abnormal vascular proliferation associated with phakomatoses, edema (such as that associated with brain tumors), Meigs' syndrome, brain cancer, head and neck cancer, and associated metastases.

The term "breast cancer" as used herein, refers to histologically or cytologically confirmed cancer of the breast. In some embodiments, the breast cancer is a carcinoma. In some embodiments, the breast cancer is an adenocarcinoma. In some embodiments, the breast cancer is a sarcoma. In some embodiments, the breast cancer is an HR+ breast cancer. In some embodiments, the HR+ breast cancer is an ER+ breast cancer. In some embodiments, the ER+ breast cancer is luminal A breast cancer. In some embodiments, the ER+ breast cancer is luminal B breast cancer. In some embodiments, the breast cancer is a metastatic or a locally advanced breast cancer.

The term "locally advanced breast cancer" refers to cancer that has spread from where it started in the breast to nearby tissue or lymph nodes, but not to other parts of the body.

The term "metastatic breast cancer" refers to cancer that has spread from the breast to other parts of the body, such as the bones, liver, lungs, or brain. Metastatic breast cancer may also be referred to as stage IV breast cancer.

The term "ductal carcinoma in situ breast cancer" or (DCIS cancer) refers breast cancers characterized as being intraductal, non-evasive, and pre-invasive primary tumors as understood in the art.

The terms "cell proliferative disorder" and "proliferative disorder" refer to disorders that are associated with some degree of abnormal cell proliferation. In one embodiment, the cell proliferative disorder is a breast cancer (e.g., an HR+ breast cancer (e.g., an ER+ breast cancer (e.g., luminal A breast cancer or luminal B breast cancer)), DCIS, and/or a metastatic or a locally advanced breast cancer). In another embodiment, the cell proliferative disorder is a tumor.

The term "concurrently" is used herein to refer to administration of two or more therapeutic agents, where at least part of the administration overlaps in time. Accordingly, concurrent administration includes a dosing regimen when the administration of one or more agent(s) continues after discontinuing the administration of one or more other agent(s).

As used herein, "delaying progression" of a disorder or disease means to defer, hinder, slow, retard, stabilize, and/or postpone development of the disease or disorder (e.g., a breast cancer, e.g., an HR+ breast cancer (e.g., an ER+ breast cancer (e.g., luminal A breast cancer or luminal B breast cancer)), DCIS, and/or a metastatic or a locally advanced breast cancer). This delay can be of varying lengths of time, depending on the history of the disease and/or subject being treated. As is evident to one skilled in the art, a sufficient or significant delay can, in effect, encompass prevention, in that the subject does not develop the disease.

The terms "determination," "determining," "detection," "detecting," and grammatical variations thereof include any means of determining or detecting, including direct and indirect determination or detection.

A "disorder" or "disease" is any condition that would benefit from treatment including, but not limited to, chronic and acute disorders or diseases including those pathological conditions which predispose the mammal to the disorder in question (e.g., a cancer, e.g., a breast cancer, e.g., an HR+ breast cancer (e.g., an ER+ breast cancer (e.g., luminal A breast cancer or luminal B breast cancer)), DCIS, and/or a metastatic or a locally advanced breast cancer).

The term "diagnosis" is used herein to refer to the identification or classification of a molecular or pathological state, disease, or condition (e.g., a cancer, e.g., a breast cancer, e.g., an HR+ breast cancer (e.g., an ER+ breast cancer (e.g., luminal A breast cancer or luminal B breast cancer)), DCIS, and/or a metastatic or a locally advanced breast cancer). For example, "diagnosis" may refer to identification of a particular type of breast cancer. "Diagnosis" may also refer to the classification of a particular subtype of breast cancer, e.g., by histopathological criteria, or by molecular features (e.g., a subtype characterized by expression of a combination of biomarkers (e.g., particular genes or proteins encoded by said genes)).

An "effective amount" of a compound, for example, an endocrine therapy as described herein, or a composition (e.g., pharmaceutical composition) thereof, is at least the minimum amount required to achieve the desired therapeutic or prophylactic result, such as a measurable increase in overall survival (OS) or progression-free survival (PFS) of a particular disease or disorder (e.g., a breast cancer, e.g., an HR+ breast cancer (e.g., an ER+ breast cancer (e.g., luminal A breast cancer or luminal B breast cancer)), DCIS, and/or a metastatic or a locally advanced breast cancer). An effective amount herein may vary according to factors such as the disease state, age, sex, and weight of the individual, and the ability of the antibody to elicit a desired response in the subject. An effective amount is also one in which any toxic or detrimental effects of the treatment are outweighed by the therapeutically beneficial effects. For prophylactic use, beneficial or desired results include results such as eliminating or reducing the risk, lessening the severity, or delaying the onset of the disease, including biochemical, histological and/or behavioral symptoms of the disease, its complications, and intermediate pathological phenotypes presenting during development of the disease. An effective amount can be administered in one or more administrations. For purposes provided herein, an effective amount of drug, compound, or pharmaceutical composition is an amount sufficient to accomplish prophylactic or therapeutic treatment either directly or indirectly. As is understood in the clinical context, an effective amount of a drug, compound, or pharmaceutical composition may or may not be achieved in conjunction with another drug, compound, or pharmaceutical composition. Thus, an "effective amount" may be considered in the context of administering one or more therapeutic agents, and a single agent may be considered to be given in an effective amount if, in conjunction with one or more other agents, a desirable result may be or is achieved. For example, an effective amount of an endocrine therapy as described herein as a cancer treatment may reduce the number of cancer cells; reduce the primary tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder. To the extent the drug may prevent growth and/or kill existing cancer cells, it may be cytostatic and/or cytotoxic. For cancer therapy, efficacy in vivo can, for example, be measured by assessing the duration of survival, time to disease progression (TTP), the response rates (RR), duration of response, and/or quality of life.

The "expression level," "amount," or "level," or used herein interchangeably, of a biomarker is a detectable level in a biological sample. "Expression" generally refers to the process by which information (e.g., gene-encoded and/or epigenetic) is converted into the structures present and operating in the cell. Therefore, as used herein, "expression" may refer to transcription into a polynucleotide, translation into a polypeptide, or even polynucleotide and/or polypeptide modifications (e.g., posttranslational modification of a polypeptide). Fragments of the transcribed polynucleotide, the translated polypeptide, or polynucleotide and/or polypeptide modifications (e.g., posttranslational modification of a polypeptide) shall also be regarded as expressed whether they originate from a transcript generated by alternative splicing or a degraded transcript, or from a post-translational processing of the polypeptide, e.g., by proteolysis. "Expressed genes" include those that are transcribed into a polynucleotide as mRNA and then translated into a polypeptide, and also those that are transcribed into RNA but not translated into a polypeptide (for example, transfer and ribosomal RNAs). Expression levels can be measured by methods known to one skilled in the art and also disclosed herein. The expression level or amount of a biomarker can be used to identify/characterize a subject having a breast cancer (e.g., an HR+ breast cancer (e.g., an ER+ breast cancer (e.g., luminal A breast cancer or luminal B breast cancer)), DCIS, and/or a metastatic or a locally advanced breast cancer) who may be likely to respond to, or benefit from, a particular therapy (e.g., a therapy comprising an endocrine therapy, e.g., a SERM (e.g., a SERD), a GnRH agonist, and/or an AI). The expression level or amount of a biomarker provided herein in a subject having a breast cancer described herein can also be used to determine and/or track the benefit of an administered endocrine therapy over time.

Expression levels can be measured using assays and techniques suitable for measuring RNA levels. For example, a RNA-Seq kit can be used to measure expression levels and is suitable for kits as described herein. Exemplary technologies useful in measuring expression levels herein include, but are not limited to, RNA ACCESS® protocol or TRUSEQ® RIBO-ZERO® protocol (ILLUMINA®)), RT-qPCR, qPCR, multiplex qPCR (e.g. fluidigm), nanostring technologies, RT-qPCR, microarray analysis, SAGE, or MassARRAY.

The term "E2-induced score" as used herein, refers to a numerical value that reflects an aggregated expression level of a predetermined set of genes whose induction is reflective of estrogen receptor (ER) pathway activity. For example, an E2-induced score may reflect an aggregated expression level of at least five, six, seven, or eight of the genes set forth in Table 1 (i.e., AMZ1, C5AR2, CELSR2, FKBP4, GREB1, OLFM1, SLC9A3R1, and TFF1), at least the 5, 6, 7, 8, 9, 10, or 11 of the genes set forth in Table 2 (i.e., AMZ1, AREG, C5AR2, CELSR2, FKBP4, FMN1, GREB1, OLFM1, RBM24, SLC9A3R1, and TFF1), or at least the 5, 6, 7, 8, 9, 10, 11, 12, 13, 14, 15, 16, 17, 18, 19, 20, 21, 22, or 23 of the genes set forth in Table 3 (i.e., AGR3, AMZ1, AREG, C5AR2, CELSR2, CT62, FKBP4, FMN1, GREB1, IGFBP4, NOS1AP, NXPH3, OLFM1, PGR, PPM1J, RAPGEFL1, RBM24, RERG, RET, SGK3, SLC9A3R1, TFF1, and ZNF703), whose induction is reflective of estrogen receptor (ER) pathway activity. The aggregated expression level of the predetermined set of genes may determine, for example as an average z-scored expression of the predetermined set of genes detected in a sample (e.g., a tissue sample, e.g., a tumor tissue sample, e.g., a FFPE, a FF, an archival, a fresh, or a frozen tumor tissue sample) obtained from an individual (e.g., an individual having a cancer, e.g., a breast cancer (e.g., an HR+ breast cancer (e.g., an ER+ breast cancer (e.g., luminal A breast cancer or luminal B breast cancer)), DCIS, and/or a metastatic or a locally advanced breast cancer). However, it should be understood that the aggregated expression levels can be determined using methods and known in the art such as, for example, an average expression of genes portrayed onto the space of a reference population or, for example, as an average expression of genes relative to an untreated or vehicle-treated tumor, optionally expressed as a fold change.

The "E2-repressed score" as used herein, refers to a numerical value that reflects an aggregated expression level of a predetermined set of genes whose repression is reflective of estrogen receptor (ER) pathway activity. For example, an E2-repressed score may reflect an aggregated expression level of at least the three, four, five, or six of the genes set forth in Table 4 (i.e., BCAS1, CCNG2, IL1R1, PNPLA7, SEMA3E, and STON1), at least the four, five, six, seven, or eight of the genes set forth in Table 5 (i.e., BCAS1, CCNG2, IL1R1, NBEA, PNPLA7, SEMA3E, STON1, and TP53INP1), or at least the 4, 5, 6, 7, 8, 9, 10, 11, 12, 13, 14, 15, 16, 17, or 18 of the genes set forth in Table 6 (i.e., BAMBI, BCAS1, CCNG2, DDIT4, EGLN3, FAM171B, GRM4, IL1R1, LIPH, NBEA, PNPLA7, PSCA, SEMA3E, SSPO, STON1, TGFB3, TP53INP1, and TP53INP2), whose repression is reflective of estrogen receptor (ER) pathway activity. The aggregated expression level of the predetermined set of genes can be calculated as described above for the E2-induced score.an HR+ breast cancer (e.g., an ER+ breast cancer (e.g., luminal A breast cancer or luminal B breast cancer)), DCIS, and/or a metastatic or a locally advanced breast cancer.

The terms "estrogen receptor pathway activity score," "ER pathway activity score," and "composite score for ER pathway activity," as used herein, refer to a numerical value that reflects mathematical difference between the E2-induced score and the E2-repressed score. The ER pathway activity score can be used as a predictive, prognostic, and/or pharmacodynamic biomarker (e.g., to identify an individual having a breast cancer as one who is likely to benefit from a therapy comprising an endocrine therapy or to monitor responsiveness of an individual having a breast cancer to a treatment comprising an endocrine therapy).

The terms "reference estrogen receptor pathway activity score" and "reference ER pathway activity score" refer to an ER pathway activity score against which another ER pathway activity score is compared, e.g., to make a predictive, prognostic, and/or therapeutic determination.

For example, the reference ER pathway activity score may be an ER pathway activity score in a reference sample, an ER pathway activity score in a reference population (e.g., a population of patients with HR+ breast cancer), and/or a pre-determined value. In some instances, the reference ER pathway activity score is a cut-off value that significantly separates individuals having a breast cancer with ER pathway activity from individuals having a breast cancer with low or no ER pathway activity (e.g., a reference ER pathway activity score that is at or above −1.0 (e.g., −1.0, −0.9, −0.8, −0.7, −0.6, −0.5, −0.4, −0.3, −0.2, or higher). In some instances, the reference ER pathway activity score is a cut-off value that significantly separates individuals having a breast cancer that are likely to respond to a therapy including an endocrine therapy as described herein from those who are not likely to respond to a therapy including an endocrine therapy (e.g., a reference ER pathway activity score that is at or above −1.0 (e.g., −1.0, −0.9, −0.8, −0.7, −0.6, −0.5, −0.4, −0.3, −0.2, or higher). It will be appreciated by one skilled in the art that the numerical value for the reference ER pathway activity score may vary depending on the type of breast cancer (e.g., an HR+ breast cancer (e.g., an ER+ breast cancer (e.g., luminal A breast cancer or luminal B breast cancer)), DCIS, and/or a metastatic or a locally advanced breast cancer), the methodology used to measure an ER pathway activity score, the specific gene signatures examined (e.g., the combination of genes set forth in Tables 1-6), and/or the statistical methods used to generate an ER pathway activity score. For example, the activity score described herein can be calculated by calculating a z-score for a reference population and using the formula below to re-scale the expression of each gene across the samples to a mean of 0 and a standard deviation of 1. The expression data for a given patient can then be overlayed onto the z-scored reference space as described herein.

The z score may described by the formula: $z=(x-\mu)/\sigma$, where z is the rescaled score, x is gene expression level measured, is the mean gene expression calculated from a reference population; and $\sigma$ is the standard deviation for gene expression calculated from a reference population.

In some embodiments, the reference estrogen receptor pathway activity score is calculated in reference to a standard control as defined herein.

The term "reference E2-induced activity score" refers to an E2-induced activity score against which another E2-induced activity score is compared, e.g., to make a predictive, prognostic, and/or therapeutic determination. For example, the reference E2-induced activity score may be a reference E2-induced activity score in a reference sample, a reference E2-induced activity score in a reference population (e.g., a population of patients with HR+ breast cancer), and/or a pre-determined value. In some instances, the reference E2-induced activity score is a cut-off value that significantly separates individuals having a breast cancer with E2-induced activity from individuals having a breast cancer with low or no E2-induced activity (e.g., a reference E2-induced activity score that is at or above −2.0 (e.g., −2.0, −1.9, −1.8, −1.7, −1.6, −1.5, −1.4, −1.3, −1.2, −1.1, 1.0, −0.9, −0.8, −0.7, −0.6, −0.5, −0.4, −0.3, −0.2, or higher). In some instances, the reference E2-induced activity score is a cut-off value that significantly separates individuals having a breast cancer that are likely to respond to a therapy including an endocrine therapy as described herein from those who are not likely to respond to a therapy including an endocrine therapy (e.g., a reference E2-induced activity score that is at or above −2.0 (e.g., −2.0 (e.g., −2.0, −1.9, −1.8, −1.7, −1.6, −1.5, −1.4, −1.3, −1.2, −1.1, 1.0, −0.9, −0.8, −0.7, −0.6, −0.5, −0.4, −0.3, −0.2, or higher). It will be appreciated by one skilled in the art that the numerical value for the reference E2-induced activity score may vary depending on the type of breast cancer (e.g., an HR+ breast cancer (e.g., an ER+ breast cancer (e.g., luminal A breast cancer or luminal B breast cancer)), DCIS, and/or a metastatic or a locally advanced breast cancer), the methodology used to measure an E2-induced activity score, the specific gene signatures examined (e.g., the combination of genes set forth herein and in, for example, in Tables 1-6), and/or the statistical methods used to generate an E2-induced activity score. A E2-induced activity score can be calculated as described herein for an estrogen receptor pathway activity score. In some embodiments, the E2-induced activity score is calculated in reference to a standard control as defined herein.

The ability to discriminate (e.g. calculate an activity score as defined herein) is relative to the identification/characterization/quantification of expression of the genes described herein and not by the form of the assay used to determine the level of expression of the genes.

A "reference gene" as used herein, refers to a gene or group of genes (e.g., one, two, three, or more genes) that is used for comparison purposes, such as a housekeeping gene. A "housekeeping gene" refers herein to a gene or group of genes (e.g., one, two, three, or more genes) which encode proteins whose activities are essential for the maintenance of cell function and which are typically similarly present in all cell types. Exemplary housekeeping genes include SDHA, GUSB, PPIA, and UBC.

As used herein, the terms "individual," "patient," and "subject" are used interchangeably and refer to any single animal, more preferably a mammal (including such non-human animals as, for example, dogs, cats, horses, rabbits, zoo animals, cows, pigs, sheep, and non-human primates)

for which treatment is desired. In certain embodiments, the individual, patient, or subject is a human.

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

The word "label" when used herein refers to a detectable compound or composition. The label is typically conjugated or fused directly or indirectly to a reagent, such as a polynucleotide probe or an antibody, and facilitates detection of the reagent to which it is conjugated or fused. The label may itself be detectable (e.g., radioisotope labels or fluorescent labels) or, in the case of an enzymatic label, may catalyze chemical alteration of a substrate compound or composition which results in a detectable product.

The term "modulator" as used herein, refers to an agent that interacts with a target either directly or indirectly. The interactions include, but are not limited to, the interactions of an agonist, partial agonist, an inverse agonist, antagonist, degrader, or combinations thereof. In some embodiments, a modulator is an antagonist. In some embodiments, a modulator is a degrader.

The term "degrader" as used herein, refers to an agent that binds to a nuclear hormone receptor and subsequently lowers the steady state protein levels of said receptor. In some embodiments, a degrader as described herein lowers steady state estrogen receptor levels by at least 10%, at least 20%, at least 30%, at least 40%, at least 50%, at least 60%, at least 65%, at least 70%, at least 75%, at least 80%, at least 85%, at least 90%, at least 95%, at least 96%, at least 97%, at least 98%, or at least 99%. In some embodiments, a degrader as described herein lowers steady state estrogen receptor levels by at least 65%. In some embodiments, a degrader as described herein lowers steady state estrogen receptor levels by at least 85%.

The term "nucleic acid" refers to deoxyribonucleotides or ribonucleotides and polymers thereof in either single- or double-stranded form, and complements thereof. The term "polynucleotide" refers to a linear sequence of nucleotides. The term "nucleotide" typically refers to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA (including siRNA), and hybrid molecules having mixtures of single and double stranded DNA and RNA. Nucleic acid as used herein also refers to nucleic acids that have the same basic chemical structure as a naturally occurring nucleic acid. Such analogues have modified sugars and/or modified ring substituents, but retain the same basic chemical structure as the naturally occurring nucleic acid. A nucleic acid mimetic refers to chemical compounds that have a structure that is different the general chemical structure of a nucleic acid, but that functions in a manner similar to a naturally occurring nucleic acid. Examples of such analogues include, without limitation, phosphorothioates, phosphoramidates, methyl phosphonates, chiral-methyl phosphonates, 2-O-methyl ribonucleotides, and peptide-nucleic acids (PNAs). The term "oligonucleotide" refers to a relatively short polynucleotide (e.g., less than about 250 nucleotides in length), including, without limitation, single-stranded deoxyribonucleotides, single- or double-stranded ribonucleotides, RNA:DNA hybrids and double-stranded DNAs. Oligonucleotides, such as single-stranded DNA probe oligonucleotides, are often synthesized by chemical methods, for example using automated oligonucleotide synthesizers that are commercially available. However, oligonucleotides can be made by a variety of other methods, including in vitro recombinant DNA-mediated techniques and by expression of DNAs in cells and organisms.

The term "package insert" is used to refer to instructions customarily included in commercial packages of therapeutic products, that contain information about the indications, usage, dosage, administration, combination therapy, contraindications and/or warnings concerning the use of such therapeutic products.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

The term "protein," as used herein, refers to any native protein from any vertebrate source, including mammals such as primates (e.g., humans) and rodents (e.g., mice and rats), unless otherwise indicated. The term encompasses "full-length," unprocessed protein as well as any form of the protein that results from processing in the cell. The term also encompasses naturally occurring variants of the protein, e.g., splice variants or allelic variants.

"Percent (%) sequence identity" with respect to a reference polynucleotide or polypeptide sequence is defined as the percentage of nucleic acids or amino acid residues in a candidate sequence that are identical with the nucleic acids or amino acid residues in the reference polynucleotide or polypeptide sequence, after aligning the sequences and introducing gaps, if necessary, to achieve the maximum percent sequence identity, and not considering any conservative substitutions as part of the sequence identity. Alignment for purposes of determining percent nucleic acid or amino acid sequence identity can be achieved in various ways that are within the skill in the art, for instance, using publicly available computer software such as BLAST, BLAST-2, ALIGN, or Megalign (DNASTAR) software. Those skilled in the art can determine appropriate parameters for aligning sequences, including any algorithms needed to achieve maximal alignment over the full length of the sequences being compared. For purposes herein, however, % sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for nucleic acid or amino acid sequence comparisons, the % sequence identity of a given nucleic acid or amino acid sequence A to, with, or against a given nucleic acid or amino acid sequence B (which can alternatively be phrased as a given nucleic acid or amino acid sequence A that has or comprises a certain % sequence identity to, with, or against a given nucleic acid or amino acid sequence B) is calculated as follows:

100 times the fraction X/Y, where X is the number of nucleic acid or amino acid residues scored as identical matches by the sequence alignment program ALIGN-2 in that program's alignment of A and B, and where Y is the total number of nucleic acid or amino acid residues in B. It will be appreciated that where the length of nucleic acid or amino acid sequence A is not equal to the length of nucleic acid or amino acid sequence B, the % sequence identity of A to B will not equal the % sequence identity of B to A. Unless specifically stated otherwise, all % sequence identity values used herein are obtained as described in the immediately preceding paragraph using the ALIGN-2 computer program.

By "correlate" or "correlating" is meant comparing, in any way, the performance and/or results of a first analysis or protocol with the performance and/or results of a second analysis or protocol. For example, one may use the results of a first analysis or protocol in carrying out a second protocols and/or one may use the results of a first analysis or protocol to determine whether a second analysis or protocol should be performed. With respect to the embodiment of polypeptide analysis or protocol, one may use the results of the polypeptide expression analysis or protocol to determine whether a specific therapeutic regimen should be performed. With respect to the embodiment of polynucleotide analysis or protocol, one may use the results of the polynucleotide expression analysis or protocol to determine whether a specific therapeutic regimen should be performed.

"Polynucleotide" or "nucleic acid," as used interchangeably herein, refers to polymers of nucleotides of any length, and includes DNA and RNA. The nucleotides can be deoxyribonucleotides, ribonucleotides, modified nucleotides or bases, and/or their analogs, or any substrate that can be incorporated into a polymer by DNA or RNA polymerase, or by a synthetic reaction.

A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after synthesis, such as by conjugation with a label. Other types of modifications include, for example, "caps," substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), "(O)NR2 ("amidate"), P(O)R, P(O)OR', CO or CH2 ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

The technique of "polymerase chain reaction" or "PCR" as used herein generally refers to a procedure wherein minute amounts of a specific piece of nucleic acid, RNA and/or DNA, are amplified as described in U.S. Pat. No. 4,683,195 issued 28 Jul. 1987. Generally, sequence information from the ends of the region of interest or beyond needs to be available, such that oligonucleotide primers can be designed; these primers will be identical or similar in sequence to opposite strands of the template to be amplified. The 5' terminal nucleotides of the two primers may coincide with the ends of the amplified material. PCR can be used to amplify specific RNA sequences, specific DNA sequences from total genomic DNA, and cDNA transcribed from total cellular RNA, bacteriophage or plasmid sequences, etc. See generally Mullis et al., Cold Spring Harbor *Symp. Quant. Biol.*, 51: 263 (1987); Erlich, ed., PCR Technology, (Stockton Press, N Y, 1989). As used herein, PCR is considered to be one, but not the only, example of a nucleic acid polymerase reaction method for amplifying a nucleic acid test sample, comprising the use of a known nucleic acid (DNA or RNA) as a primer and utilizes a nucleic acid polymerase to amplify or generate a specific piece of nucleic acid or to amplify or generate a specific piece of nucleic acid which is complementary to a particular nucleic acid.

As used herein, the term "reverse transcriptase polymerase chain reaction" or "RT-PCR" refers to the replication and amplification of RNA sequences. In this method, reverse transcription is coupled to PCR, e.g., as described in U.S. Pat. No. 5,322,770, herein incorporated by reference in its entirety. In RT-PCR, the RNA template is converted to cDNA due to the reverse transcriptase activity of an enzyme, and then amplified using the polymerizing activity of the same or a different enzyme. Both thermostable and thermolabile reverse transcriptase and polymerase can be used. The "reverse transcriptase" (RT) may include reverse transcriptases from retroviruses, other viruses, as well as a DNA polymerase exhibiting reverse transcriptase activity.

As used herein, the term "reverse transcriptase quantitative polymerase chain reaction" or "RT-qPCR" is a form of PCR wherein the nucleic acid to be amplified is RNA that is first reverse transcribed into cDNA and the amount of PCR product is measured at each step in a PCR reaction.

"Quantitative real time polymerase chain reaction" or "qRT-PCR" refers to a form of PCR wherein the amount of PCR product is measured at each step in a PCR reaction. This technique has been described in various publications including Cronin et al., Am. J. Pathol. 164(1):35-42 (2004); and Ma et al., Cancer Cell 5:607-616 (2004).

The term "multiplex-PCR" refers to a single PCR reaction carried out on nucleic acid obtained from a single source (e.g., an individual) using more than one primer set for the purpose of amplifying two or more DNA sequences in a single reaction.

The term "RNA-seq," also called "Whole Transcriptome Shotgun Sequencing (WTSS)," refers to the use of high-throughput sequencing technologies to sequence and/or quantify cDNA to obtain information about a sample's RNA content. Publications describing RNA-seq include: Wang et al. "RNA-Seq: a revolutionary tool for transcriptomics" *Nature Reviews Genetics* 10 (1): 57-63 (January 2009); Ryan et al. *BioTechniques* 45 (1): 81-94 (2008); and Maher et al. "Transcriptome sequencing to detect gene fusions in cancer". *Nature* 458 (7234): 97-101 (January 2009). Exemplary RNA-seq protocols include the use of RNA ACCESS® protocol or TRUSEQ® RIBO-ZERO® protocol (ILLUMINA®).

"Response to a treatment," "responsiveness to treatment," or "benefit from a treatment" can be assessed using any endpoint indicating a benefit to the individual, including, without limitation, (1) inhibition, to some extent, of disease progression (e.g., breast cancer progression), including slowing down and complete arrest; (2) a reduction in tumor size; (3) inhibition (i.e., reduction, slowing down or complete stopping) of cancer cell infiltration into adjacent peripheral organs and/or tissues; (4) inhibition (i.e. reduction, slowing down or complete stopping) of metastasis; (5) relief, to some extent, of one or more symptoms associated with the disease or disorder (e.g., cancer); (6) increase or extend in the length of survival, including recurrence free survival (RFS), disease free survival (DFS), overall survival (OS HR<1) and progression free survival (PFS HR<1); and/or (9) decreased mortality at a given point of time following treatment (e.g., a treatment including an endocrine therapy, a SERM (e.g., a SERD), a GnRH agonist, and/or an AI). Response to a treatment can also refer to a pharmacodynamic response or the response of a pathway (e.g. the ER pathway) and can be assessed using methods known in the art.

As used herein, "progression-free survival" or "PFS" refers to the length of time during and after treatment during which the disease being treated (e.g., breast cancer, e.g., HR+ breast cancer, e.g., ER+ breast cancer, e.g., luminal A or luminal B breast cancer, e.g., advanced or metastatic breast cancer) does not progress or get worse. Progression-free survival may include the amount of time individuals have experienced a complete response or a partial response, as well as the amount of time individuals have experienced stable disease.

As used herein, "overall survival" or "OS" refers to the percentage of subjects in a group who are likely to be alive after a particular duration of time (e.g., 6 months, 1 year, 2 years, 3 years, 4 years, 5 years, 10 years, 15 years, 20 years, or more than 20 years from the time of diagnosis or treatment).

As used herein "recurrence free survival" or "RFS" refers to the length of time after primary treatment ends that the patient survives without any signs, symptoms, or relapses of the tumor in the same local or regional area.

As used herein "disease free survival" or "DFS" refers to the length of time after primary treatment ends that the patient survives without any signs, symptoms, or relapses of the tumor in any area, including development of distant metastases.

As used herein, "complete response" or "CR" refers to disappearance of all signs of cancer in response to treatment. This does not necessarily mean the cancer has been cured.

As used herein, "partial response" or "PR" refers to a decrease in the size of one or more tumors or lesions, or in the extent of cancer in the body, in response to treatment.

As used herein, "hazard ratio" or "HR" is a statistical definition for rates of events. For purposes provided herein, hazard ratio is defined as representing the probability of an event (e.g., PFS or OS) in the experimental (e.g., treatment) group/arm divided by the probability of an event in the control group/arm at any specific point in time. An HR with a value of 1 indicates that the relative risk of an endpoint (e.g., death) is equal in both the "treatment" and "control" groups; a value greater than 1 indicates that the risk is greater in the treatment group relative to the control group; and a value less than 1 indicates that the risk is greater in the control group relative to the treatment group. "Hazard ratio" in progression-free survival analysis (i.e., PFS HR) is a summary of the difference between two progression-free survival curves, representing the reduction in the risk of death on treatment compared to control, over a period of follow-up. "Hazard ratio" in overall survival analysis (i.e., OS HR) is a summary of the difference between two overall survival curves, representing the reduction in the risk of death on treatment compared to control, over a period of follow-up.

By "extending survival" is meant increasing overall survival or progression free survival in a treated individual relative to an untreated individual (i.e. relative to an individual not treated with the medicament), or relative to an individual who does not express a biomarker at the designated level, and/or relative to an individual treated with an approved anti-cancer therapy. An objective response refers to a measurable response, including complete response (CR) or partial response (PR).

By "reduce or inhibit" is meant the ability to cause an overall decrease of 20%, 30%, 40%, 50%, 60%, 70%, 75%, 80%, 85%, 90%, 95%, or greater. Reduce or inhibit can refer to the symptoms of the disorder being treated (e.g., a breast cancer, e.g., an HR+ breast cancer (e.g., an ER+ breast cancer (e.g., luminal A breast cancer or luminal B breast cancer)), DCIS, and/or a metastatic or a locally advanced breast cancer), the presence or size of metastases, or the size of the primary tumor. Reduce or inhibit, when referring to a tumor pathway, refers to the reduction of expression or activity of any component of the pathway (e.g. reduction of the expression ER, reduced activity of ER, or degradation of ER).

A "reference sample," "reference cell," "reference tissue," "control sample," "control cell," or "control tissue," as used herein, refers to a sample, cell, tissue, standard, or level that is used for comparison purposes. In one embodiment, a reference sample, reference cell, reference tissue, control sample, control cell, or control tissue is obtained from the same subject or individual.

In another embodiment, a reference sample is obtained from one or more individuals who are not the subject or individual. In either of the preceding embodiments, the one or more individuals from which the reference sample, reference cell, reference tissue, control sample, control cell, or control tissue is obtained has a breast cancer (e.g., e.g., an HR+ breast cancer (e.g., an ER+ breast cancer (e.g., luminal A breast cancer or luminal B breast cancer)), DCIS, and/or a metastatic or a locally advanced breast cancer). In certain embodiments, the one or more individuals from which the reference sample, reference cell, reference tissue, control sample, control cell, or control tissue is obtained has a breast cancer and has been previously treated with an anti-cancer therapy (e.g., one or more doses of an endocrine therapy, e.g., a SERM (e.g., a SERD), a GnRH agonist, and/or an AI). In other embodiments, the one or more individuals from which the reference sample, reference cell, reference tissue, control sample, control cell, or control tissue is obtained has a breast cancer and is treatment naïve. In any of the preceding embodiments, the subject/individual and the one or more individuals who are not the subject or individual have the same breast cancer.

A "standard control" as used herein in reference to the expression level of one or more genes refers to the expression level measured in a control subject (e.g. in a sample form the control subject) or population of control subjects. In embodiments, the control subject is a healthy control subject relative to the subject being tested, wherein the healthy control subject does not have breast cancer. In embodiments, the control subject is the test subject prior to treatment of the test subject, wherein the test subject and control subject have breast cancer. For example, in embodiments, the test subject has been treated for breast cancer with an anticancer agent and the control subject is the test subject prior to treatment. In embodiments, the population of control subjects is a diverse collection of healthy subjects and diseased subjects, wherein the expression level of the test subject is compared to the expression levels of the population of control subjects (e.g. an average of expression levels of the population of control subjects). In embodiments, the population of control subjects is a collection of healthy subjects that do not have breast cancer, wherein the expression level of the test subject is compared to the expression levels of the population of control subjects (e.g. an average of expression levels of the population of control subjects). In embodiments, the population of control subjects is a collection of subjects that have been treated for breast cancer, wherein the expression level of the test subject is compared to the expression levels of the population of control subjects (e.g. an average of expression levels of the population of control subjects).

The term "sample," as used herein, refers to a composition that is obtained or derived from a subject and/or individual of interest that contains a cellular and/or other molecular entity that is to be characterized and/or identified, for example based on physical, biochemical, chemical and/ or physiological characteristics. For example, the phrase "disease sample" and variations thereof refers to any sample obtained from a subject of interest that would be expected or is known to contain the cellular and/or molecular entity that is to be characterized. Samples include, but are not limited to, tissue extracts such as homogenized tissue, tumor tissue, cellular extracts, primary or cultured cells or cell lines, cell supernatants, cell lysates, platelets, serum, plasma, vitreous fluid, lymph fluid, synovial fluid, follicular fluid, seminal fluid, amniotic fluid, milk, whole blood, blood-derived cells, urine, cerebro-spinal fluid, saliva, sputum, tears, perspiration, mucus, tumor lysates, and tissue culture medium, and combinations thereof.

By "tissue sample" or "cell sample" is meant a collection of similar cells obtained from a tissue of a subject or individual. The source of the tissue or cell sample may be solid tissue as from a FFPE, FF, fresh, frozen, and/or preserved organ, tissue sample, biopsy, and/or aspirate; blood or any blood constituents such as plasma; bodily fluids such as cerebral spinal fluid, amniotic fluid, peritoneal fluid, or interstitial fluid; cells from any time in gestation or development of the subject. The tissue sample may also be primary or cultured cells or cell lines. Optionally, the tissue or cell sample is obtained from a disease (e.g., breast cancer, e.g., e.g., an HR+ breast cancer (e.g., an ER+ breast cancer (e.g., luminal A breast cancer or luminal B breast cancer)), DCIS, and/or a metastatic or a locally advanced breast cancer) tissue/organ. The tissue sample may contain compounds which are not naturally intermixed with the tissue in nature such as preservatives, anticoagulants, buffers, fixatives, nutrients, antibiotics, or the like.

For the purposes herein a "section" of a tissue sample is meant a single part or piece of a tissue sample, e.g. a thin slice of tissue or cells cut from a tissue sample. It is understood that multiple sections of tissue samples may be taken and subjected to analysis, provided that it is understood that the same section of tissue sample may be analyzed at both morphological and molecular levels, or analyzed with respect to both polypeptides and polynucleotides.

As used herein, "treatment" (and grammatical variations thereof, such as "treat" or "treating") refers to clinical intervention in an attempt to alter the natural course of the subject being treated, and can be performed either for prophylaxis or during the course of clinical pathology. Desirable effects of treatment include, but are not limited to, preventing occurrence or recurrence of a disease (e.g., a breast cancer, e.g., e.g., an HR+ breast cancer (e.g., an ER+ breast cancer (e.g., luminal A breast cancer or luminal B breast cancer)), DCIS, and/or a metastatic or a locally advanced breast cancer), alleviation of symptoms, diminishment of any direct or indirect pathological consequences of the disease, preventing metastasis, decreasing the rate of disease progression, amelioration or palliation of the disease state, and remission or improved prognosis. In some embodiments, the treatments described herein are used to delay development of a disease or to slow the progression of a disease (e.g., a breast cancer, e.g., e.g., an HR+ breast cancer (e.g., an ER+ breast cancer (e.g., luminal A breast cancer or luminal B breast cancer)), DCIS, and/or a metastatic or a locally advanced breast cancer). In some instances, the treatment may increase overall survival (OS) (e.g., by about 20% or greater, about 25% or greater, about 30% or greater, about 35% or greater, about 40% or greater, about 45% or greater, about 50% or greater, about 55% or greater, about 60% or greater, about 65% or greater, about 70% or greater, about 75% or greater, about 80% or greater, about 85% or greater, about 90% or greater, about 95% or greater, about 96% or greater, about 97% or greater, about 98% or greater, or about 99% or greater). In some instances, the treatment may increase OS, e.g., by about 5% to about 500%, e.g., from about 10% to about 450%, e.g., from about 20% to about 400%, e.g., from about 25% to about 350%, e.g., from about 30% to about 400%, e.g., from about 35% to about 350%, e.g., from about 40% to about 300%, e.g., from about 45% to about 250%, e.g., from about 50% to about 200%, e.g., from about 55% to about 150%, e.g., from about 60% to about 100%, e.g., from about 65% to about 100%, e.g., from about 70% to about 100%, e.g., from about 75% to about 100%, e.g., from about 80% to about 100%, e.g., from about 85% to about 100%, e.g., from about 90% to about 100%, e.g., from about 95% to about 100%, e.g., from about 98% to about 100%. In some instances, the treatment may increase the progression-free survival (PFS) (e.g., by about 20% or greater, about 25% or greater, about 30% or greater, about 35% or greater, about 40% or greater, about 45% or greater, about 50% or greater, about 55% or greater, about 60% or greater, about 65% or greater, about 70% or greater, about 75% or greater, about 80% or greater, about 85% or greater, about 90% or greater, about 95% or greater, about 96% or greater, about 97% or greater, about 98% or greater, or about 99% or greater). In some instances, the treatment may increase PFS, e.g., by about 5% to about 500%, e.g., from about 10% to about 450%, e.g., from about 20% to about 400%, e.g., from about 25% to about 350%, e.g., from about 30% to about 400%, e.g., from about 35% to about 350%, e.g., from about 40% to about 300%, e.g., from about 45% to about 250%, e.g., from about 50% to about 200%, e.g., from about 55% to about 150%, e.g., from about 60% to about 100%, e.g., from about 65% to about 100%, e.g., from about 70% to about 100%, e.g., from about 75% to about 100%, e.g., from about 80% to about 100%, e.g., from about 85% to about 100%, e.g., from about 90% to about 100%, e.g., from about 95% to about 100%, e.g., from about 98% to about 100%.

"Tumor," as used herein, refers to all neoplastic cell growth and proliferation, whether malignant or benign, and all pre-cancerous and cancerous cells and tissues. The terms "cancer," "cancerous," "cell proliferative disorder," "proliferative disorder," and "tumor" are not mutually exclusive as referred to herein.

Methods

Provided herein are methods and assays for identifying an individual having a breast cancer (e.g., an HR+ breast cancer (e.g., an ER+ breast cancer (e.g., luminal A breast cancer or luminal B breast cancer)), DCIS, and/or a metastatic or a locally advanced breast cancer, an ER+ breast cancer (e.g., luminal A breast cancer or luminal B breast cancer)), DCIS, and/or a metastatic or a locally advanced breast cancer who may benefit from a treatment including an endocrine therapy as described herein; selecting a therapy for an individual having breast cancer; treating an individual having breast cancer based on a diagnostic method provided herein; and monitoring therapeutic efficacy of an endocrine therapy. In one embodiment, the endocrine therapy is a compound as set forth herein. In another embodiment, the endocrine therapy is a SERM, a SERD, an AI, or a combination thereof.

The methods and assays described herein are based on the finding that the estradiol (E2)-induced score or estrogen receptor (ER) pathway activity score determined from a sample (e.g., a tissue sample, e.g., a tumor tissue sample, e.g., a FFPE, a FF, an archival, a fresh, or a frozen tumor tissue sample) from an individual may be used to predict the therapeutic efficacy of an endocrine therapy described herein. Any of the methods may further include administering an endocrine therapy (e.g., as described in Section IV-A, below) to the individual.

Accordingly, provided herein are also methods and assays of determining an E2-induced score and/or an ER pathway activity score from a sample from the individual. Any of the methods provided herein may include administering an anti-cancer therapy other than an endocrine therapy (e.g., as described in Section IV-A, below) to the individual. Any of the methods may further include administering an effective amount of an additional therapeutic agent, as described herein, to the individual.

Diagnostic Methods and Assays

Predictive Diagnostic Methods and Assays

In particular instances, the methods and assays provided herein may be used to identify an individual having a breast cancer (e.g., an HR+ breast cancer (e.g., an ER+ breast cancer (e.g., luminal A breast cancer or luminal B breast cancer)), DCIS, and/or a metastatic or a locally advanced breast cancer) who may benefit from a treatment including an endocrine therapy as described herein, the method including determining an ER pathway activity score from a sample (e.g., a tissue sample, e.g., a tumor tissue sample, e.g., a formalin-fixed paraffin-embedded (FFPE), a fresh frozen (FF), an archival, a fresh, or a frozen tumor tissue sample) from the individual, wherein an ER pathway activity score that is at or above a reference ER pathway activity score identifies the individual as one who may benefit from a treatment including an endocrine therapy as described herein.

In particular instances, the methods and assays provided herein may be used to identify an individual having a breast cancer (e.g., an HR+ breast cancer (e.g., an ER+ breast cancer (e.g., luminal A breast cancer or luminal B breast cancer)), DCIS, and/or a metastatic or a locally advanced breast cancer) who may benefit from a treatment including an endocrine therapy as described herein, the method including determining an E2-induced score from a sample (e.g., a tissue sample, e.g., a tumor tissue sample, e.g., a FFPE, a FF, an archival, a fresh, or a frozen tumor tissue sample) from the individual, wherein an E2-induced score that is at or above a reference E2-induced score identifies the individual as one who may benefit from a treatment including an endocrine therapy as described herein.

In particular instances, the methods and assays provided herein may be used to select a therapy for an individual having a breast cancer (e.g., an HR+ breast cancer (e.g., an ER+ breast cancer (e.g., luminal A breast cancer or luminal B breast cancer)), DCIS, and/or a metastatic or a locally advanced breast cancer), the method including determining an ER pathway activity score from a sample (e.g., a tissue sample, e.g., a tumor tissue sample, e.g., a FFPE, a FF, an archival, a fresh, or a frozen tumor tissue sample) from the individual, wherein an ER pathway activity score that is at or above a reference ER pathway activity score identifies the individual as one who may benefit from a treatment including an endocrine therapy as described herein.

In particular instances, the methods and assays provided herein may be used to select a therapy for an individual having a breast cancer (e.g., an HR+ breast cancer (e.g., an ER+ breast cancer (e.g., luminal A breast cancer or luminal B breast cancer)), DCIS, and/or a metastatic or a locally advanced breast cancer), the method including determining an E2-induced score from a sample (e.g., a tissue sample, e.g., a tumor tissue sample, e.g., a FFPE, a FF, an archival, a fresh, or a frozen tumor tissue sample) from the individual, wherein an E2-induced score that is at or above a reference E2-induced score identifies the individual as one who may benefit from a treatment including an endocrine therapy as described herein.

In particular instances, the methods and assays provided herein may be used to identify an individual having a breast cancer (e.g., an HR+ breast cancer (e.g., an ER+ breast cancer (e.g., luminal A breast cancer or luminal B breast cancer)), DCIS, and/or a metastatic or a locally advanced breast cancer) who may benefit from a treatment including an endocrine therapy as described herein, the method including determining an ER pathway activity score from a sample (e.g., a tissue sample, e.g., a tumor tissue sample, e.g., a FFPE, a FF, an archival, a fresh, or a frozen tumor tissue sample) from the individual, wherein an ER pathway activity score that is below a reference ER pathway activity score identifies the individual as one who is less likely to benefit from a treatment including an endocrine therapy as described herein.

In particular instances, the methods and assays provided herein may be used to identify an individual having a breast cancer who may benefit from a treatment including an endocrine therapy as described herein, the method including determining an E2-induced score from a sample (e.g., a tissue sample, e.g., a tumor tissue sample, e.g., a FFPE, a FF, an archival, a fresh, or a frozen tumor tissue sample) from the individual, wherein an E2-induced score that is below a reference E2-induced score identifies the individual as one who is less likely to benefit from a treatment including an endocrine therapy as described herein.

In particular instances, the methods and assays provided herein may be used to select a therapy for an individual having a breast cancer (e.g., an HR+ breast cancer (e.g., an ER+ breast cancer (e.g., luminal A breast cancer or luminal B breast cancer)), DCIS, and/or a metastatic or a locally advanced breast cancer), the method including determining an ER pathway activity score from a sample (e.g., a tissue sample, e.g., a tumor tissue sample, e.g., a FFPE, a FF, an archival, a fresh, or a frozen tumor tissue sample) from the individual, wherein an ER pathway activity score that is below a reference ER pathway activity score identifies the individual as one who is less likely to benefit from a treatment including an endocrine therapy as described herein. For example, the method involves selecting an anti-cancer therapy for the individual other than an endocrine therapy.

In particular instances, the methods and assays provided herein may be used to select a therapy for an individual having a breast cancer (e.g., an HR+ breast cancer (e.g., an ER+ breast cancer (e.g., luminal A breast cancer or luminal B breast cancer)), DCIS, and/or a metastatic or a locally advanced breast cancer), the method including determining an E2-induced score from a sample (e.g., a tissue sample, e.g., a tumor tissue sample, e.g., a FFPE, a FF, an archival, a fresh, or a frozen tumor tissue sample) from the individual, wherein an E2-induced score that is below a reference E2-induced score identifies the individual as one who is less likely to benefit from a treatment including an endocrine therapy as described herein. For example, the method involves selecting an anti-cancer therapy for the individual other than an endocrine therapy.

In particular instances, the methods and assays provided herein may be used to identify an individual having a breast cancer (e.g., an HR+ breast cancer (e.g., an ER+ breast cancer (e.g., luminal A breast cancer or luminal B breast cancer)), DCIS, and/or a metastatic or a locally advanced breast cancer) who may benefit from a treatment including an anti-cancer therapy other than an endocrine therapy, the method including determining an ER pathway activity score from a sample (e.g., a tissue sample, e.g., a tumor tissue sample, e.g., a FFPE, a FF, an archival, a fresh, or a frozen tumor tissue sample) from the individual, wherein an ER pathway activity score that is below a reference ER pathway activity score identifies the individual as one who may benefit from a treatment including an anti-cancer therapy other than an endocrine therapy.

In particular instances, the methods and assays provided herein may be used to identify an individual having a breast cancer who may benefit from a treatment including an anti-cancer therapy other than an endocrine therapy, the method including determining an E2-induced score from a sample (e.g., a tissue sample, e.g., a tumor tissue sample, e.g., a FFPE, a FF, an archival, a fresh, or a frozen tumor tissue sample) from the individual, wherein an E2-induced score that is below a reference E2-induced score identifies the individual as one who may benefit from a treatment including an anti-cancer therapy other than an endocrine therapy.

In particular instances, the methods and assays provided herein may be used to select a therapy for an individual having a breast cancer (e.g., an HR+ breast cancer (e.g., an ER+ breast cancer (e.g., luminal A breast cancer or luminal B breast cancer)), DCIS, and/or a metastatic or a locally advanced breast cancer), the method including determining an ER pathway activity score from a sample (e.g., a tissue sample, e.g., a tumor tissue sample, e.g., a FFPE, a FF, an archival, a fresh, or a frozen tumor tissue sample) from the individual, wherein an ER pathway activity score that is below a reference ER pathway activity score identifies the individual as one who may benefit from a treatment including an anti-cancer therapy other than an endocrine therapy.

In particular instances, the methods and assays provided herein may be used to select a therapy for an individual having a breast cancer (e.g., an HR+ breast cancer (e.g., an ER+ breast cancer (e.g., luminal A breast cancer or luminal B breast cancer)), DCIS, and/or a metastatic or a locally advanced breast cancer), the method including determining an E2-induced score from a sample (e.g., a tissue sample, e.g., a tumor tissue sample, e.g., a FFPE, a FF, an archival, a fresh, or a frozen tumor tissue sample) from the individual, wherein an E2-induced score that is below a reference E2-induced score identifies the individual as one who may benefit from a treatment including an anti-cancer therapy other than an endocrine therapy.

In any of the preceding instances, the reference ER pathway activity score may be an ER pathway activity score in a reference population of individuals having an HR+ breast cancer (e.g., an ER+ breast cancer (e.g., luminal A breast cancer or luminal B breast cancer)), DCIS, and/or a metastatic or a locally advanced breast cancer). In some instances, the reference population is a population of individuals who have not received a treatment including an endocrine therapy as described herein. In some instances, the reference population is a population of individuals who have not received a prior endocrine therapy as described herein. In some instances, the reference population is a population of individuals who are not currently receiving an anti-cancer treatment, including an endocrine therapy as described herein. In some instances, the reference ER pathway activity score may be a pre-assigned reference ER pathway activity score. In some instances, the reference ER pathway activity score may be at or above −1.0 (e.g., −1.0, −0.9, −0.8, −0.7, −0.6, −0.5, −0.4, −0.3, −0.2, or higher). For example, in some instances, the reference ER pathway activity score may be at or above −0.9. In some instances, the reference ER pathway activity score may be at or above −0.8. In some instances, the reference ER pathway activity score may be at or above −0.7. In some instances, the reference ER pathway activity score may be at or above −0.6. In some instances, the reference ER pathway activity score may be at or above −0.5. In some instances, the reference ER pathway activity score may be at or above −0.4. In some instances, the reference ER pathway activity score may be at or above −0.3. In some instances, the reference ER pathway activity score may be at or above −0.2. In some instances, the reference ER pathway activity score may be between about −1.0 to about −0.2 (e.g., between about −0.9 to about −0.2, e.g., between about −0.8 to about −0.2, e.g., between about −0.7 to about −0.2, e.g., between about −0.6 to about −0.2, e.g., between about −0.5 to about −0.2, e.g., between about −0.4 to about −0.2, or e.g., between about −0.3 to about −0.2).

In any of the preceding instances, the ER pathway activity score from the sample (e.g., a tissue sample, e.g., a tumor tissue sample, e.g., a FFPE, a FF, an archival, a fresh, or a frozen tumor tissue sample) from the individual may be at or above −1.0 (e.g., −1.0, −0.9, −0.8, −0.7, −0.6, −0.5, −0.4, −0.3, −0.2 or higher). For example, in some instances, the ER pathway activity score may be at or above −0.9. In some instances, the ER pathway activity score may be at or above −0.8. In some instances, the ER pathway activity score may be at or above −0.7. In some instances, the ER pathway activity score may be at or above −0.6. In some instances, the ER pathway activity score may be at or above −0.5. In some instances, the ER pathway activity score may be at or above −0.4. In some instances, the ER pathway activity score may be at or above −0.3. In some instances, the ER pathway activity score may be at or above −0.2. In some instances, the ER pathway activity score may be between about −1.0 to about −0.2 (e.g., between about −0.9 to about −0.2, e.g., between about −0.8 to about −0.2, e.g., between about −0.7 to about −0.2, e.g., between about −0.6 to about −0.2, e.g., between about −0.5 to about −0.2, e.g., between about −0.4 to about −0.2, or e.g., between about −0.3 to about −0.2). In some instances, the ER activity score from the sample may be less than −1.0.

In any of the preceding instances, the reference E2-induced score may be an E2-induced score in a reference population of individuals having a hormone receptor (HR)+ breast cancer (e.g., an ER+ breast cancer (e.g., luminal A breast cancer or luminal B breast cancer)) and/or a metastatic or a locally advanced breast cancer). In some instances, the reference population is a population of individuals who have not received a treatment including an endocrine therapy as described herein. In some instances, the reference E2-induced score may be a pre-assigned reference E2-induced score. In some instances, the reference E2-induced score may be at or above −2.0 (e.g., −2.0, −1.0, −0.9, −0.8, −0.7, −0.6, −0.5, −0.4, −0.3, −0.2, or higher). For example, in some instances, the reference E2-induced score may be at or above −1.0. In some instances, the reference E2-induced score may be at or above −0.9. In some instances, the reference E2-induced score may be at or above −0.8. In some instances, the reference E2-induced score may be at or above −0.7. In some instances, the reference E2-induced score may be at or above −0.6. In some instances, the reference E2-induced score may be at or above −0.5. In some instances, the reference E2-induced score may be at or above −0.4. In some instances, the reference E2-induced score may be at or above −0.3. In some instances, the reference E2-induced score may be at or above −0.2. In some instances, the reference E2-induced score may be at or above −0.1. In some instances, the reference E2-induced score may be between about −2.0 to about −0.1 (e.g., between about −1.0 to about −0.1, e.g., between about −0.7 to about −0.1, e.g., between about −0.6 to about −0.1, e.g., between about −0.5 to about −0.1, e.g., between about −0.4 to about −0.1, e.g., between about −0.3 to about −0.1, or e.g., between about −0.2 to about −0.1).

In any of the preceding instances, the E2-induced score from the sample (e.g., a tissue sample, e.g., a tumor tissue sample, e.g., a FFPE, a FF, an archival, a fresh, or a frozen tumor tissue sample) from the individual may be at or above −2.0 (e.g., −2.0, −1.0, −0.9, −0.8, −0.7, −0.6, −0.5, −0.4, −0.3, −0.2, −0.1 or higher). For example, in some instances, the E2-induced score may be at or above −1.0. In some instances, the E2-induced score may be at or above −0.9. In some instances, the E2-induced score may be at or above −0.8. In some instances, the E2-induced score may be at or above −0.7. In some instances, the E2-induced score may be at or above −0.6. In some instances, the E2-induced score may be at or above −0.5. In some instances, the E2-induced score may be at or above −0.4. In some instances, the E2-induced score may be at or above −0.3. In some instances, the E2-induced score may be at or above −0.2. In some instances, the E2-induced score may be at or above −0.1. In some instances, the E2-induced score may be between about −2.0 to about −0.1 (e.g., between about −1.0 to about −0.1, e.g., between about −0.7 to about −0.1, e.g., between about −0.6 to about −0.1, e.g., between about −0.5 to about −0.1, e.g., between about −0.4 to about −0.1, e.g., between about −0.3 to about −0.1, or e.g., between about −0.2 to about −0.1). In some instances, the E2-induced score from the sample may be less than −2.0.

In any of the predictive methods and assays described above, the methods and assays may further include administering to the individual an endocrine therapy (e.g., as described in Section IV-A, below). In particular instances, when the ER pathway activity score from a sample (e.g., a tissue sample, e.g., a tumor tissue sample, e.g., a FFPE, a FF, an archival, a fresh, or a frozen tumor tissue sample) from an individual is at or above a reference ER pathway activity score, the method further includes administering to the individual an endocrine therapy. In particular instances, when the E2-induced score from a sample (e.g., a tissue sample, e.g., a tumor tissue sample, e.g., a FFPE, a FF, an archival, a fresh, or a frozen tumor tissue sample) from an individual) is at or above a reference E2-induced score, the method further includes administering to the individual an endocrine therapy.

In any of the predictive methods and assays described above, the methods and assays may further include administering to the individual an anti-cancer therapy other than an endocrine therapy (e.g., as described in Section IV-A, below). In particular instances, when the ER pathway activity score from a sample (e.g., a tissue sample, e.g., a tumor tissue sample, e.g., a FFPE, a FF, an archival, a fresh, or a frozen tumor tissue sample) from an individual is below a reference ER pathway activity score, the method further includes administering to the individual an anti-cancer therapy other than an endocrine therapy. In particular instances, when the E2-induced score from a sample (e.g., a tissue sample, e.g., a tumor tissue sample, e.g., a FFPE, a FF, an archival, a fresh, or a frozen tumor tissue sample) from an individual is below a reference E2-induced score, the method further includes administering to the individual an anti-cancer therapy other than an endocrine therapy.

The methods provided herein may include determining an ER pathway activity score from a sample (e.g., a tissue sample, e.g., a tumor tissue sample, e.g., a FFPE, a FF, an archival, a fresh, or a frozen tumor tissue sample) from an individual. The methods provided herein may include determining an E2-induced score from a sample (e.g., a tissue sample, e.g., a tumor tissue sample, e.g., a FFPE, a FF, an archival, a fresh, or a frozen tumor tissue sample) from an individual. In some instances, the sample may be a FFPE tumor tissue sample. In some instances, the sample may be a FF tumor tissue sample.

In any of the preceding instances, the individual may have an HR+ breast cancer. In some instances, the HR+ cancer may be an ER+ breast cancer. In some instances, the individual may have an ER+ breast cancer selected from, for example, a luminal A breast cancer or a luminal B breast cancer. In some instances, the breast cancer may be an advanced or a metastatic breast cancer.

In some instances of any of the preceding methods or assays involving determining an ER pathway activity score and/or E2-induced score from a sample (e.g., a tissue sample, e.g., a tumor tissue sample, e.g., a FFPE, a FF, an archival, a fresh, or a frozen tumor tissue sample) from an individual, the individual has been previously treated with an endocrine therapy as described herein. In other instances, the individual has not been previously treated with an endocrine therapy. In another embodiment, the individual has received one or more prior therapies prior to performing the methods and assays described herein where such therapy may be an endocrine therapy or a non-endocrine therapy as described herein.

In some instances, the methods further comprise generating a report, e.g., an electronic, web-based, or paper report, to the individual or to another person or entity, a caregiver, a physician, an oncologist, a hospital, clinic, third-party payor, insurance company, a pharmaceutical or biotechnology company, or government office. In some embodiments, the report comprises output from the method which comprises evaluation of the ER pathway activity and/or E2-induced score.

Pharmacodynamic Diagnostic Methods

Also provided herein are pharmacodynamics methods. In some instances, the methods may involve monitoring a response of an individual to treatment with an endocrine therapy as described herein.

In some instances, the method includes: (a) determining an ER pathway activity score from a sample (e.g., a tissue sample, e.g., a tumor tissue sample, e.g., a FFPE, a FF, an archival, a fresh, or a frozen tumor tissue sample) from the individual at a first time point; (b) following step (a), determining a second ER pathway activity score from a sample from the individual at a second time point following administration of an endocrine therapy as described herein; and (c) comparing the first ER pathway activity score with the second ER pathway activity score, wherein a decrease (e.g., a decrease in the ER pathway activity score of about 0.1, 0.2, 0.3, or greater) in the second ER pathway activity score relative to the first ER pathway activity score is predictive of an individual who is likely to respond to treatment with an endocrine therapy e.g., a SERM (e.g., a SERD), a GnRH agonist, and/or an AI. In some instances, a decrease in the ER pathway activity score refers to an overall decrease of the ER pathway activity score of at least 0.1. In some instances, a decrease in the ER pathway activity score refers to an overall decrease of the ER pathway activity score of at least 0.2. In some instances, a decrease in the ER pathway activity score refers to an overall decrease of the ER pathway activity score of at least 0.3.

In some instances, the method further comprises administering one or more additional doses of the endocrine therapy if the second ER pathway activity score in the sample (e.g., a tissue sample, e.g., a tumor tissue sample, e.g., a formalin-fixed paraffin-embedded (FFPE), a fresh frozen (FF), an archival, a fresh, or a frozen tumor tissue sample) from the individual is decreased relative to the first ER pathway activity score. In some instances, a decreased ER pathway activity score refers to an overall decrease of the ER pathway activity score of at least 0.1 (e.g., a decrease of 0.1, 0.2, 0.3, or greater). In some instances, a decreased ER pathway activity score refers to an overall decrease of the ER pathway activity score of at least 0.2. In some instances, a decreased ER pathway activity refers to an overall decrease of ER pathway activity score of at least 0.3.

In some instances of any of the preceding methods, the first ER pathway activity score is an ER pathway activity score determined from a sample (e.g., a tissue sample, e.g., a tumor tissue sample, e.g., a FFPE, a FF, an archival, a fresh, or a frozen tumor tissue sample) from the individual obtained prior to administration of a first dose of an endocrine therapy as described herein. In other words, the sample may be a baseline sample. In other instances, the first ER pathway activity score is an ER pathway activity score determined from a sample from the individual obtained at a previous time point, wherein the previous time point is following administration of a first dose of an endocrine therapy as described herein. In other instances, the first ER pathway activity score is an ER pathway activity score determined from a sample from the individual obtained at a previous time point, wherein the previous time point is following administration of a first dose of a non-endocrine therapy as described herein. In other instances, the first ER pathway activity score is a pre-determined ER pathway activity score.

In some instances, the method includes: (a) determining an E2-induced score from a sample (e.g., a tissue sample, e.g., a tumor tissue sample, e.g., a FFPE, a FF, an archival, a fresh, or a frozen tumor tissue sample) from the individual at a first time point; (b) following step (a), determining a second E2-induced score from a sample from the individual at a second time point following administration of an endocrine therapy as described herein; and (c) comparing the first E2-induced score with the second E2-induced score, wherein a decrease (e.g., a decrease in the E2-induced score of at least 0.1, 0.2, 0.3, or greater) in the second E2-induced score relative to the first E2-induced score is predictive of an individual who is likely to respond to treatment with an endocrine therapy as described herein. In some instances, a decrease in the E2-induced score refers to an overall decrease of at least 0.1. In some instances, a decrease in the E2-induced score refers to an overall decrease of at least 0.2. In some instances, a decrease in the E2-induced score refers to an overall decrease of at least 0.3.

In some instances, the method further comprises administering one or more additional doses of the endocrine therapy as described herein if the second E2-induced in the sample (e.g., a tissue sample, e.g., a tumor tissue sample, e.g., a FFPE, a FF, an archival, a fresh, or a frozen tumor tissue sample) is decreased relative to the first E2-induced score. In some instances, a decreased E2-induced score refers to an overall decrease of the E2-induced score of at least 0.1 (e.g., a decrease of 0.1, 0.2, 0.3, or greater). In some instances, a decreased E2-induced score refers to an overall decrease of the E2-induced score of at least 0.2. In some instances, a decreased E2-induced score refers to an overall decrease of the E2-induced score of at least 0.3.

In some instances of any of the preceding methods, the first E2-induced score is E2-induced score determined from a sample (e.g., a tissue sample, e.g., a tumor tissue sample, e.g., a FFPE, a FF, an archival, a fresh, or a frozen tumor tissue sample) from the individual obtained prior to administration of a first dose of an anti-cancer therapy (e.g., an endocrine therapy as described herein. In other words, the sample may be a baseline sample. In other instances, the first E2-induced score is an E2-induced score determined from a sample from the individual obtained at a previous time point, wherein the previous time point is following administration of a first dose of an endocrine therapy as described herein. In other instances, the first E2-induced score is a pre-determined E2-induced score.

In some instances, the second ER pathway activity score from the sample (e.g., a tissue sample, e.g., a tumor tissue sample, e.g., a FFPE, a FF, an archival, a fresh, or a frozen tumor tissue sample) from the individual is decreased relative to the first ER pathway activity score, and the method or assay further involves administering an additional dose of an endocrine therapy as described herein to the individual. In some instances, the second E2-induced score from the sample (e.g., a tissue sample, e.g., a tumor tissue sample, e.g., a FFPE, a FF, an archival, a fresh, or a frozen tumor tissue sample) from the individual is decreased relative to the first E2-induced score, and the method or assay further involves administering an additional dose of an endocrine therapy as described herein to the individual.

The methods provided herein may include determining an ER pathway activity score from a sample (e.g., a tissue sample, e.g., a tumor tissue sample, e.g., a FFPE, a FF, an archival, a fresh, or a frozen tumor tissue sample) from an individual. The methods provided herein may include determining an E2-induced score from a sample (e.g., a tissue sample, e.g., a tumor tissue sample, e.g., a FFPE, a FF, an archival, a fresh, or a frozen tumor tissue sample) from an individual. In some instances, the sample may be a FFPE tumor tissue sample. In some instances, the sample may be a FF tumor tissue sample.

In any of the preceding instances, the individual may have an HR+ breast cancer. In some instances, the HR+ cancer may be an ER+ breast cancer. In some instances, the individual may have an ER+ breast cancer selected from, for example, a luminal A breast cancer or a luminal B breast cancer. In some instances, the breast cancer may be an advanced or a metastatic breast cancer.

In some instances of any of the preceding methods or assays involving determining an ER pathway activity score and/or E2-induced score from a sample (e.g., a tissue sample, e.g., a tumor tissue sample, e.g., a FFPE, a FF, an archival, a fresh, or a frozen tumor tissue sample) from the individual, the individual has been previously treated with an endocrine therapy as described herein. In other instances, the individual has not been previously treated with an endocrine therapy. In some instances of any of the methods and assays, the sample (e.g., a tissue sample, e.g., a tumor tissue sample, e.g., a FFPE, a FF, an archival, a fresh, or a frozen tumor tissue sample) is obtained from the individual prior to (e.g., minutes, hours, days, weeks, months, or years prior to) administration of an endocrine therapy as described herein. In other words, the sample may be a baseline sample. In some instances of any of the preceding methods, the sample is obtained from the individual following (e.g., minutes, hours, or days following) administration of an endocrine therapy. In some instances, the sample from the individual is obtained within thirty hours following administration of an endocrine therapy. In some instances, multiple samples are obtained from the same individual at different time points (e.g., prior to and following administration of an endocrine therapy).

In some instances, the methods further comprise generating a report, e.g., an electronic, web-based, or paper report, to the individual or to another person or entity, a caregiver, a physician, an oncologist, a hospital, clinic, third-party payor, insurance company, a pharmaceutical or biotechnology company, or government office. In some instances, the report comprises output from the method which comprises evaluation of the ER pathway activity and/or E2-induced score.

In one aspect, a method of detecting estrogen receptor (ER) pathway activity in a subject that has breast cancer is provided. The method includes detecting an expression level of at least five genes set forth in Table 1 and at least five genes set forth in Table 4; at least five genes set forth in Table 2 and at least five genes set forth in Table 5; or at least five genes set forth in Table 3 and at least five genes set forth in Table 6.

Controls used for the methods provided herein are valuable for determining the significance of data. For example, if values for a given parameter are widely variant in controls, variation in test samples will not be considered as significant. In some examples of the disclosed methods, when the expression level of any of the genes provided in Table 1-6 is assessed, the expression level is compared with a control expression level of the gene. By control expression level is meant the expression level of a gene from a sample or subject lacking breast cancer, a sample or subject at a selected stage of breast cancer or cancer state, or in the absence of a particular variable such as a therapeutic agent. Alternatively, the control level comprises a known amount of the gene. Such a known amount correlates with an average level of subjects lacking breast cancer, at a selected stage of breast cancer or cancer state, or in the absence of a particular variable such as a therapeutic agent. A control level also includes the expression level of the gene from one or more selected samples or subjects as described herein. For example, a control level includes an assessment of the expression level of the gene in a sample from a subject that does not have breast cancer, is at a selected stage of breast cancer or cancer state, or have breast cancer but have not yet received treatment for breast cancer. Another exemplary control level includes an assessment of the expression level of the gene in samples taken from multiple subjects that do not have breast cancer, are at a selected stage of cancer, or have cancer but have not yet received treatment for breast cancer. In embodiments, a threshold for elevated gene expression levels is above the median expression level of a group of control sample, where the control sample is optionally a group of subjects who have breast cancer.

In embodiments, the method includes detecting an expression level of at least five (e.g., 5, 6, 7, 8, etc.) genes set forth in Table 1 and at least five genes set forth in Table 4. In embodiments, the method includes detecting an expression level of at least five genes set forth in Table 2 and at least five genes set forth in Table 5. In embodiments, the method includes detecting an expression level of at least five genes set forth in Table 3 and at least five genes set forth in Table 6.

In embodiments, the expression level of the at least five genes set forth in Table 1, at least five genes set forth in Table 2 or at least five genes set forth in Table 3 are greater than a standard control. In embodiments, the expression level of all the genes set forth in Table 1, all of the genes set forth in Table 2 or all of the genes set forth in Table 3 are greater than a standard control. In embodiments, the expression level of the at least five genes set forth in Table 1 are greater than a standard control. In embodiments, the expression level of all genes set forth in Table 1 are greater than a standard control. In embodiments, the expression level of the at least five genes set forth in Table 2 are greater than a standard control. In embodiments, the expression level of all genes set forth in Table 2 are greater than a standard control. In embodiments, the expression level of the at least five genes set forth in Table 3 are greater than a standard control. In embodiments, the expression level of all genes set forth in Table 3 are greater than a standard control.

In embodiments, a threshold for elevated gene expression levels (e.g., expression of any one gene set forth in Table 1-6) is above the median expression level of a group of control samples, where the control sample is optionally a group of subjects who have breast cancer. In embodiments, it is above the first quartile of gene expression in a group of control samples, where the control sample is optionally a group of subjects who have breast cancer. In embodiments, it is above the third quartile of gene expression in a group of control samples, where the control sample is optionally a group of subjects who have breast cancer. In embodiments, it is above the 5th percentile of gene expression in a group of control samples, where the control sample is optionally a group of subjects who have breast cancer. In embodiments, it is above the 10th percentile of gene expression in a group of control samples, where the control sample is optionally a group of subjects who have breast cancer. In embodiments, it is above the 20th percentile of gene expression in a group of control samples, where the control sample is optionally a group of subjects who have breast cancer. In embodiments, it is above the 30th percentile of gene expression in a group of control samples, where the control sample is optionally a group of subjects who have breast cancer.

In embodiments, it is above the 40th percentile of gene expression in a group of control samples, where the control sample is optionally a group of subjects who have breast cancer. In embodiments, it is above the 45th percentile of gene expression in a group of control samples, where the control sample is optionally a group of subjects who have breast cancer. In embodiments, it is above the 50th percentile of gene expression in a group of control samples, where the control sample is optionally a group of subjects who have breast cancer. In embodiments, it is above the 60th percentile of gene expression in a group of control samples, where the control sample is optionally a group of subjects who have breast cancer. In embodiments, it is above the 70th percentile of gene expression in a group of control samples, where the control sample is optionally a group of subjects who have breast cancer. In embodiments, it is above the 80th percentile of gene expression in a group of control samples, where the control sample is optionally a group of subjects who have breast cancer. In embodiments, it is above the 90th percentile of gene expression in a group of control samples, where the control sample is optionally a group of subjects who have breast cancer.

In embodiments, the expression level of the at least five genes set forth in Table 4, at least five genes set forth in Table 5 or at least five genes set forth in Table 6 are less than a standard control. In embodiments, the expression level of all genes set forth in Table 4, of all genes set forth in Table 5 or of all genes set forth in Table 6 are less than a standard control. In embodiments, the expression level of the at least five genes set forth in Table 4 are less than a standard control. In embodiments, the expression level of all genes set forth in Table 4 are less than a standard control. In embodiments, the expression level of the at least five genes set forth in Table 5 are less than a standard control. In embodiments, the expression level of all genes set forth in Table 5 are less than a standard control. In embodiments, the expression level of the at least five genes set forth in Table 6 are less than a standard control. In embodiments, the expression level of all genes set forth in Table 6 are less than a standard control.

In embodiments, a threshold for decreased gene expression levels (e.g., expression of any one gene set forth in Table 1-6) is below the median expression level of a group of control samples, where the control sample is optionally a group of subjects who have breast cancer. In embodiments, it is below the first quartile of gene expression in a group of control samples, where the control sample is optionally a group of subjects who have breast cancer. In embodiments, it is below the third quartile of gene expression in a group of control samples, where the control sample is optionally a group of subjects who have breast cancer. In embodiments, it is below the 5th percentile of gene expression in a group of control samples, where the control sample is optionally a group of subjects who have breast cancer. In embodiments, it is below the 10th percentile of gene expression in a group of control samples, where the control sample is optionally a group of subjects who have breast cancer. In embodiments, it is below the 20th percentile of gene expression in a group of control samples, where the control sample is optionally a group of subjects who have breast cancer. In embodiments, it is below the 30th percentile of gene expression in a group of control samples, where the control sample is optionally a group of subjects who have breast cancer. In embodiments, it is below the 40th percentile of gene expression in a group of control samples, where the control sample is optionally a group of subjects who have breast cancer. In embodiments, it is below the 45th percentile of gene expression in a group of control samples, where the control sample is optionally a group of subjects who have breast cancer. In embodiments, it is below the 50th percentile of gene expression in a group of control samples, where the control sample is optionally a group of subjects who have breast cancer. In embodiments, it is below the 60th percentile of gene expression in a group of control samples, where the control sample is optionally a group of subjects who have breast cancer. In embodiments, it is below the 70th percentile of gene expression in a group of control samples, where the control sample is optionally a group of subjects who have breast cancer. In embodiments, it is below the 80th percentile of gene expression in a group of control samples, where the control sample is optionally a group of subjects who have breast cancer. In embodiments, it is below the 90th percentile of gene expression in a group of control samples, where the control sample is optionally a group of subjects who have breast cancer.

In embodiments, the subject has been treated with an endocrine therapy prior to the detecting. In embodiments, the subject is treated with an endocrine therapy subsequent to the detecting.

In embodiments, the method includes detecting an expression level of all genes set forth in Table 1 and all genes set forth in Table 4. In embodiments, the method includes detecting an expression level of all genes set forth in Table 2 and all genes set forth in Table 5. In embodiments, the method includes detecting an expression level of all genes set forth in Table 3 and all genes set forth in Table 6. In embodiments, the method includes detecting an expression level of all genes set forth in Table 1 and all genes set forth in Table 4 and not detecting an expression level of any other genes in the subject. In embodiments, the method includes detecting an expression level of all genes set forth in Table 2 and all genes set forth in Table 5 and not detecting an expression level of any other genes in the subject. In embodiments, the method includes detecting an expression level of all genes set forth in Table 3 and all genes set forth in Table 6 and not detecting an expression level of any other genes in the subject.

In embodiments, the subject is treated with an endocrine therapy where the endocrine therapy is a selective estrogen receptor degrader.

In embodiments, the method includes determining an estrogen receptor (ER) pathway activity score from a sample from the subject. In embodiments, an ER pathway activity score from the sample that is at or above a reference ER pathway activity score identifies the individual as one who may benefit from a treatment including an endocrine therapy. In embodiments, the method includes comparing an ER pathway activity score from the sample that is at or above a reference ER pathway activity score identifies the individual as one who may benefit from a treatment including an endocrine therapy.

In one aspect a method is provided, the method includes detecting, by one or more processors, a first expression level of at least five genes set forth in Table 1, at least five genes set forth in Table 2, or at least five genes set forth in Table 3; detecting, by the one or more processors, a second expression level of at least five genes set forth in Table 4, at least five genes set forth in Table 5 or at least five genes set forth in Table 6; and detecting, based at least on the first expression level and/or the second expression level, estrogen receptor (ER) pathway activity in a subject that has cancer. In embodiments, the first expression is elevated relative to the second expression level. In embodiments, the first expression is decreased relative to the second expression level.

In embodiments, a threshold for an elevated first gene expression level (e.g., a first expression level of any one gene set forth in Table 1-6) is above the second expression level. In embodiments, it is above the first quartile of the second gene expression level. In embodiments, it is above the third quartile of the second gene expression level. In embodiments, it is above the 5th percentile of the second gene expression level. In embodiments, it is above the 10th percentile of the second gene expression level. In embodiments, it is above the 20th percentile of the second gene expression level. In embodiments, it is above the 30th percentile of the second gene expression level. In embodiments, it is above the 40th percentile of the second gene expression level. In embodiments, it is above the 45th percentile of the second gene expression level. In embodiments, it is above the 50th percentile of the second gene expression level. In embodiments, it is above the 60th percentile of the second gene expression level. In embodiments, it is above the 70th percentile of the second gene expression level. In embodiments, it is above the 80th percentile of the second gene expression level. In embodiments, it is above the 90th percentile of the second gene expression level.

In embodiments, a threshold for a decreased first gene expression level (e.g., a first expression level of any one gene set forth in Table 1-6) is below the second expression level. In embodiments, it is below the first quartile of the second gene expression level. In embodiments, it is below the third quartile of the second gene expression level. In embodiments, it is below the 5th percentile of the second gene expression level. In embodiments, it is below the 10th percentile of the second gene expression level. In embodiments, it is below the 20th percentile of the second gene expression level. In embodiments, it is below the 30th percentile of the second gene expression level. In embodiments, it is below the 40th percentile of the second gene expression level. In embodiments, it is below the 45th percentile of the second gene expression level. In embodiments, it is below the 50th percentile of the second gene expression level. In embodiments, it is below the 60th percentile of the second gene expression level. In embodiments, it is below the 70th percentile of the second gene expression level. In embodiments, it is below the 80th percentile of the second gene expression level. In embodiments, it is below the 90th percentile of the second gene expression level.

In embodiments, the expression level of the at least five genes set forth in Table 1, at least five genes set forth in Table 2 or at least five genes set forth in Table 3 are greater than a standard control. In embodiments, the expression level of the at least five genes set forth in Table 4, at least five genes set forth in Table 5 or at least five genes set forth in Table 6 are less than a standard control.

In embodiments, the method includes treating the subject with an endocrine therapy prior to the detecting. In embodiments, the method includes treating, based at least on the estrogen receptor (ER) pathway activity detected in the subject, the subject with an endocrine therapy.

Therapeutic Methods

Also provided herein are methods for treating an individual having a breast cancer (e.g., an HR+ breast cancer (e.g., an ER+ breast cancer (e.g., luminal A breast cancer or luminal B breast cancer)), DCIS, and/or a metastatic or a locally advanced breast cancer). Accordingly, in some instances, the methods provided herein include administering to the individual an endocrine therapy as described herein. In other instances, the methods provided herein include administering to the individual an anti-cancer agent other than an endocrine therapy. Any of the anti-cancer agents described herein (e.g., in Section IV, below), or known in the art may be used in connection with the methods.

Provided herein is a method of treating an individual having a breast cancer (e.g., an HR+ breast cancer (e.g., an ER+ breast cancer (e.g., luminal A breast cancer or luminal B breast cancer)), DCIS, and/or a metastatic or a locally advanced breast cancer) that includes (i) determining an ER pathway activity score from a sample (e.g., a tissue sample, e.g., a tumor tissue sample, e.g., a FFPE, a FF, an archival, a fresh, or a frozen tumor tissue sample) from the individual, wherein the ER pathway activity score is determined to be at or above a reference ER pathway activity score (e.g., a reference ER pathway activity score in a reference population, e.g., a reference ER pathway activity score at or above −1.0); and (ii) administering to the individual an effective amount of an endocrine therapy as described herein.

Provided herein is a method of treating an individual having a breast cancer (e.g., an HR+ breast cancer (e.g., an ER+ breast cancer (e.g., luminal A breast cancer or luminal B breast cancer)), DCIS, and/or a metastatic or a locally advanced breast cancer), that includes administering to the individual an endocrine therapy as described herein, wherein the individual has been identified to be more likely to benefit from a treatment comprising an endocrine therapy by one or more of the predictive diagnostic methods described in Section III-A, above.

Provided herein is a method of treating an individual having a breast cancer (e.g., an HR+ breast cancer (e.g., an ER+ breast cancer (e.g., luminal A breast cancer or luminal B breast cancer)), DCIS, and/or a metastatic or a locally advanced breast cancer), that includes administering to the individual an endocrine therapy as described herein, wherein the individual has been identified as having an ER pathway activity score that is at or above a reference ER pathway activity score by any of the predictive diagnostic methods described in Section III-A, above.

Provided herein is a method of treating an individual having a breast cancer (e.g., an HR+ breast cancer (e.g., an ER+ breast cancer (e.g., luminal A breast cancer or luminal B breast cancer)), DCIS, and/or a metastatic or a locally advanced breast cancer) that includes (i) determining an E2-induced score from a sample (e.g., a tissue sample, e.g., a tumor tissue sample, e.g., a FFPE, a FF, an archival, a fresh, or a frozen tumor tissue sample) from the individual, wherein the E2-induced score is determined to be at or above a reference E2-induced score (e.g., a reference E2-induced score in a reference population, e.g., a reference E2-induced score at or above −2.0); and (ii) administering to the individual an effective amount of an endocrine therapy as described herein.

Provided herein is a method of treating an individual having a breast cancer (e.g., an HR+ breast cancer (e.g., an ER+ breast cancer (e.g., luminal A breast cancer or luminal B breast cancer)), DCIS, and/or a metastatic or a locally advanced breast cancer), that includes administering to the individual an endocrine therapy as described herein, wherein the individual has been identified as having an E2-induced score that is at or above a reference E2-induced score by any of the predictive diagnostic methods described in Section III-A, above.

Also provided herein is a method of treating an individual having a breast cancer (e.g., an HR+ breast cancer (e.g., an ER+ breast cancer (e.g., luminal A breast cancer or luminal B breast cancer)), DCIS, and/or a metastatic or a locally advanced breast cancer) that includes (i) determining an ER pathway activity score from a sample (e.g., a tissue sample, e.g., a tumor tissue sample, e.g., a FFPE, a FF, an archival, a fresh, or a frozen tumor tissue sample) from the individual, wherein the ER pathway activity score is determined to be below a reference ER pathway activity score (e.g., a reference ER pathway activity score in a reference population, e.g., a reference ER pathway activity score below $-1.0$); and (ii) administering to the individual an effective amount of an anti-cancer therapy other than endocrine therapy.

Provided herein is a method of treating an individual having a breast cancer (e.g., an HR+ breast cancer (e.g., an ER+ breast cancer (e.g., luminal A breast cancer or luminal B breast cancer)), DCIS, and/or a metastatic or a locally advanced breast cancer), that includes administering to the individual an effective amount of an anti-cancer therapy other than endocrine therapy, wherein the individual has been identified to be less likely to benefit from a treatment comprising an endocrine therapy by one or more of the predictive diagnostic methods described in Section III-A, above.

Provided herein is a method of treating an individual having a breast cancer (e.g., an HR+ breast cancer (e.g., an ER+ breast cancer (e.g., luminal A breast cancer or luminal B breast cancer)), DCIS, and/or a metastatic or a locally advanced breast cancer), that includes administering to the individual an anti-cancer therapy other than an endocrine therapy, wherein the individual has been identified to be more likely to benefit from a treatment comprising an anti-cancer therapy other than an endocrine therapy by one or more of the predictive diagnostic methods described in Section III-A, above.

Provided herein is a method of treating an individual having a breast cancer (e.g., an HR+ breast cancer (e.g., an ER+ breast cancer (e.g., luminal A breast cancer or luminal B breast cancer)), DCIS, and/or a metastatic or a locally advanced breast cancer), that includes administering to the individual an effective amount of an anti-cancer therapy other than endocrine therapy, wherein the individual has been identified as having an ER pathway activity score that is below a reference ER pathway activity score by any of the predictive diagnostic methods described in Section III-A, above.

Provided herein is a method of treating an individual having a breast cancer (e.g., an HR+ breast cancer (e.g., an ER+ breast cancer (e.g., luminal A breast cancer or luminal B breast cancer)), DCIS, and/or a metastatic or a locally advanced breast cancer) that includes (i) determining an E2-induced score from a sample (e.g., a tissue sample, e.g., a tumor tissue sample, e.g., a FFPE, a FF, an archival, a fresh, or a frozen tumor tissue sample) from the individual, wherein the E2-induced score is determined to be below a reference E2-induced score (e.g., a reference E2-induced score in a reference population, e.g., a reference E2-induced score below $-2.0$); and (ii) administering to the individual an effective amount of an effective amount of an anti-cancer therapy other than endocrine therapy.

Provided herein is a method of treating an individual having a breast cancer (e.g., an HR+ breast cancer (e.g., an ER+ breast cancer (e.g., luminal A breast cancer or luminal B breast cancer)), DCIS, and/or a metastatic or a locally advanced breast cancer), that includes administering to the individual an effective amount of an anti-cancer therapy other than endocrine therapy, wherein the individual has been identified as having an E2-induced score that is below a reference E2-induced score by any of the predictive diagnostic methods described in Section III-A, above.

In any of the preceding instances, the reference ER pathway activity score may be an ER pathway activity score in a reference population of individuals having an HR+ breast cancer (e.g., an ER+ breast cancer (e.g., luminal A breast cancer or luminal B breast cancer)), DCIS, and/or a metastatic or a locally advanced breast cancer). In some instances, the reference population is a population of individuals who have not received a treatment including an endocrine therapy, including those described herein. In some instances, the reference ER pathway activity score may be a pre-assigned reference ER pathway activity score. In some instances, the reference ER pathway activity score may be at or above $-1.0$ (e.g., $-1.0$, $-0.9$, $-0.8$, $-0.7$, $-0.6$, $-0.5$, $-0.4$, $-0.3$, and $-0.2$, or higher). For example, in some instances, the reference ER pathway activity score may be at or above $-0.9$. In some instances, the reference ER pathway activity score may be at or above $-0.8$. In some instances, the reference ER pathway activity score may be at or above $-0.7$. In some instances, the reference ER pathway activity score may be at or above $-0.6$. In some instances, the reference ER pathway activity score may be at or above $-0.5$. In some instances, the reference ER pathway activity score may be at or above $-0.4$. In some instances, the reference ER pathway activity score may be at or above $-0.3$. In some instances, the reference ER pathway activity score may be at or above $-0.2$. In some instances, the reference ER pathway activity score may be between about $-1.0$ to about $-0.2$ (e.g., between about $-0.9$ to about $-0.2$, e.g., between about $-0.8$ to about $-0.2$, e.g., between about $-0.7$ to about $-0.2$, e.g., between about $-0.6$ to about $-0.2$, e.g., between about $-0.5$ to about $-0.2$, e.g., between about $-0.4$ to about $-0.2$, or e.g., between about $-0.3$ to about $-0.2$).

In any of the preceding instances, the ER pathway activity score from the sample (e.g., a tissue sample, e.g., a tumor tissue sample, e.g., a formalin-fixed paraffin-embedded (FFPE), a fresh frozen (FF), an archival, a fresh, or a frozen tumor tissue sample) from the individual may be at, or above $-1.0$ (e.g., $-1.0$, $-0.9$, $-0.8$, $-0.7$, $-0.6$, $-0.5$, $-0.4$, $-0.3$, $-0.2$ or higher). For example, in some instances, the ER pathway activity score may be at or above $-0.9$. In some instances, the ER pathway activity score may be at or above $-0.8$. In some instances, the ER pathway activity score may be at or above $-0.7$. In some instances, the ER pathway activity score may be at or above $-0.6$. In some instances, the ER pathway activity score may be at or above $-0.5$. In some instances, the ER pathway activity score may be at or above $-0.4$. In some instances, the ER pathway activity score may be at or above $-0.3$. In some instances, the ER pathway activity score may be at or above $-0.2$. In some instances, the ER pathway activity score may be between about $-1.0$ to about $-0.2$ (e.g., between about $-0.9$ to about $-0.2$, e.g., between about $-0.8$ to about $-0.2$, e.g., between about $-0.7$ to about $-0.2$, e.g., between about $-0.6$ to about $-0.2$, e.g., between about $-0.5$ to about $-0.2$, e.g., between about −0.4 to about −0.2, or e.g., between about −0.3 to about −0.2). In some instances, the ER activity score from the sample may be less than −1.0.

In any of the preceding instances, the reference E2-induced score may be an E2-induced score in a reference population of individuals having an HR+ breast cancer (e.g., an ER+ breast cancer (e.g., luminal A breast cancer or luminal B breast cancer)), DCIS, and/or a metastatic or a locally advanced breast cancer). In some instances, the reference population is a population of individuals who have not received a treatment including an endocrine therapy as described herein. In some instances, the reference E2-induced score may be a pre-assigned reference E2-induced score. In some instances, the reference E2-induced score may be at or above −2.0 (e.g., −2.0, −1.0, −0.9, −0.8, −0.7, −0.6, −0.5, −0.4, −0.3, −0.2, or higher). For example, in some instances, the reference E2-induced score may be at or above −1.0. In some instances, the reference E2-induced score may be at or above −0.9. In some instances, the reference E2-induced score may be at or above −0.8. In some instances, the reference E2-induced score may be at or above −0.7. In some instances, the reference E2-induced score may be at or above −0.6. In some instances, the reference E2-induced score may be at or above −0.5. In some instances, the reference E2-induced score may be at or above −0.4. In some instances, the reference E2-induced score may be at or above −0.3. In some instances, the reference E2-induced score may be at or above −0.2. In some instances, the reference E2-induced score may be at or above −0.1. In some instances, the reference E2-induced score may be between about −2.0 to about −0.1 (e.g., between about −1.0 to about −0.1, e.g., between about −0.7 to about −0.1, e.g., between about −0.6 to about −0.1, e.g., between about −0.5 to about −0.1, e.g., between about −0.4 to about −0.1, e.g., between about −0.3 to about −0.1, or e.g., between about −0.2 to about −0.1).

In any of the preceding instances, the E2-induced score from the sample (e.g., a tissue sample, e.g., a tumor tissue sample, e.g., a formalin-fixed paraffin-embedded (FFPE), a fresh frozen (FF), an archival, a fresh, or a frozen tumor tissue sample) from the individual may be at, or above −2.0 (e.g., −2.0, −1.0, −0.9, −0.8, −0.7, −0.6, −0.5, −0.4, −0.3, −0.2, −0.1 or higher). In some instances, the E2-induced score may be at or above −1.0. In some instances, the E2-induced score may be at or above −0.9. In some instances, the E2-induced score may be at or above −0.8. For example, in some instances, the E2-induced score may be at or above −0.7. In some instances, the E2-induced score may be at or above −0.6. In some instances, the E2-induced score may be at or above −0.5. In some instances, the E2-induced score may be at or above −0.4. In some instances, the E2-induced score may be at or above −0.3. In some instances, the E2-induced score may be at or above −0.2. In some instances, the E2-induced score may be at or above −0.1. In some instances, the E2-induced score may be between about −2.0 to about −0.1 (e.g., between about −1.0 to about −0.1, e.g., between about −0.7 to about −0.1, e.g., between about −0.6 to about −0.1, e.g., between about −0.5 to about −0.1, e.g., between about −0.4 to about −0.1, e.g., between about −0.3 to about −0.1, or e.g., between about −0.2 to about −0.1). In some instances, the E2-induced score from the sample may be less than −2.0.

The methods provided herein may include determining an ER pathway activity score from a sample (e.g., a tissue sample, e.g., a tumor tissue sample, e.g., a FFPE, a FF, an archival, a fresh, or a frozen tumor tissue sample) from an individual. The methods provided herein may include determining an E2-induced score from a sample (e.g., a tissue sample, e.g., a tumor tissue sample, e.g., a FFPE, a FF, an archival, a fresh, or a frozen tumor tissue sample) from an individual. In some instances, the sample may be a FFPE tumor tissue sample. In some instances, the sample may be a FF tumor tissue sample.

In any of the preceding instances, the individual may have an HR+ breast cancer. In some instances, the HR+ cancer may be an ER+ breast cancer. In some instances, the individual may have an ER+ breast cancer selected from, for example, a luminal A breast cancer or a luminal B breast cancer. In some instances, the breast cancer may be an advanced or a metastatic breast cancer.

In some instances of any of the preceding methods or assays involving determining an ER pathway activity score and/or E2-induced score in a sample (e.g., a tissue sample, e.g., a tumor tissue sample, e.g., a formalin-fixed paraffin-embedded (FFPE), a fresh frozen (FF), an archival, a fresh, or a frozen tumor tissue sample) from the individual, the individual has been previously treated with an endocrine therapy as described herein. In other instances, the individual has not been previously treated with an endocrine therapy.

In some instances, the methods further comprise generating a report, e.g., an electronic, web-based, or paper report, to the individual or to another person or entity, a caregiver, a physician, an oncologist, a hospital, clinic, third-party payor, insurance company, a pharmaceutical or biotechnology company, or government office. In some instances, the report comprises output from the method which comprises evaluation of the ER pathway activity and/or E2-induced score.

Exemplary Methods for Determination of an E2-Induced, E2-Repressed, and ER Pathway Activity Scores The methods and assays provided herein may include determining an E2-induced, an E2-repressed, and/or an ER pathway activity score based on an expression level of a predetermined set of genes (e.g., a biomarker) in a sample (e.g., a tissue sample, e.g., a tumor tissue sample, e.g., a FFPE, a FF, an archival, a fresh, or a frozen tumor tissue sample) from an individual (e.g., an individual having a breast cancer (e.g., an HR+ breast cancer (e.g., an ER+ breast cancer (e.g., luminal A breast cancer or luminal B breast cancer)), DCIS, and/or a metastatic or a locally advanced breast cancer)). In some instances, the predetermined set of genes is the set of genes listed in any one of Tables 1-3. In some instances, the pre-determined set of genes are the sets of genes listed in Table 1 and Table 4 (e.g., the 14-gene signature). In some instances, the pre-determined set of genes are the sets of genes listed in Table 2 and Table 5 (e.g., the 19-gene signature). In some instances, the pre-determined set of genes are the sets of genes listed in Table 3 and Table 6 (e.g., the 41-gene signature). In some instances, the pre-determined set of genes are the sets of genes listed in Table 1 and Table 4 (e.g., the 14-gene signature) and no other genes. In some instances, the pre-determined set of genes are the sets of genes listed in Table 2 and Table 5 (e.g., the 19-gene signature) and no other genes. In some instances, the pre-determined set of genes are the sets of genes listed in Table 3 and Table 6 (e.g., the 41-gene signature) and no other genes.

In some embodiments, the ER pathway activity score is calculated using an 8-gene signature by subtracting an E2-repressed score, determined from the average z-scored expression of three of the E2-repressed genes set forth in Table 6, from an E2-induced score, determined from the average z-scored expression of five of the E2-induced genes set forth in Table 3.

In some embodiments, the ER pathway activity score is calculated using a 9-gene signature by subtracting an E2-repressed score, determined from the average z-scored expression of four of the E2-repressed genes set forth in Table 6, from an E2-induced score, determined from the average z-scored expression of five of the E2-induced genes set forth in Table 3. In some embodiments, the ER pathway activity score is calculated using a 9-gene signature by subtracting an E2-repressed score, determined from the average z-scored expression of three of the E2-repressed genes set forth in Table 6, from an E2-induced score, determined from the average z-scored expression of six of the E2-induced genes set forth in Table 3.

In some embodiments, the ER pathway activity score is calculated using a 10-gene signature by subtracting an E2-repressed score, determined from the average z-scored expression of three of the E2-repressed genes set forth in Table 6, from an E2-induced score, determined from the average z-scored expression of seven of the E2-induced genes set forth in Table 3. In some embodiments, the ER pathway activity score is calculated using a 10-gene signature by subtracting an E2-repressed score, determined from the average z-scored expression of four of the E2-repressed genes set forth in Table 6, from an E2-induced score, determined from the average z-scored expression of six of the E2-induced genes set forth in Table 3. In some embodiments, the ER pathway activity score is calculated using a 10-gene signature by subtracting an E2-repressed score, determined from the average z-scored expression of five of the E2-repressed genes set forth in Table 6, from an E2-induced score, determined from the average z-scored expression of five of the E2-induced genes set forth in Table 3.

In some embodiments, the ER pathway activity score is calculated using an 11-gene signature by subtracting an E2-repressed score, determined from the average z-scored expression of three of the E2-repressed genes set forth in Table 6, from an E2-induced score, determined from the average z-scored expression of eight of the E2-induced genes set forth in Table 3. In some embodiments, the ER pathway activity score is calculated using an 11-gene signature by subtracting an E2-repressed score, determined from the average z-scored expression of four of the E2-repressed genes set forth in Table 6, from an E2-induced score, determined from the average z-scored expression of seven of the E2-induced genes set forth in Table 3. In some embodiments, the ER pathway activity score is calculated using an 11-gene signature by subtracting an E2-repressed score, determined from the average z-scored expression of five of the E2-repressed genes set forth in Table 6, from an E2-induced score, determined from the average z-scored expression of six of the E2-induced genes set forth in Table 3.

In some embodiments, the ER pathway activity score is calculated using a 12-gene signature by subtracting an E2-repressed score, determined from the average z-scored expression of three of the E2-repressed genes set forth in Table 6, from an E2-induced score, determined from the average z-scored expression of nine of the E2-induced genes set forth in Table 3. In some embodiments, the ER pathway activity score is calculated using a 12-gene signature by subtracting an E2-repressed score, determined from the average z-scored expression of four of the E2-repressed genes set forth in Table 6, from an E2-induced score, determined from the average z-scored expression of eight of the E2-induced genes set forth in Table 3. In some embodiments, the ER pathway activity score is calculated using a 12-gene signature by subtracting an E2-repressed score, determined from the average z-scored expression of five of the E2-repressed genes set forth in Table 6, from an E2-induced score, determined from the average z-scored expression of seven of the E2-induced genes set forth in Table 3. In some embodiments, the ER pathway activity score is calculated using a 12-gene signature by subtracting an E2-repressed score, determined from the average z-scored expression of six of the E2-repressed genes set forth in Table 6, from an E2-induced score, determined from the average z-scored expression of six of the E2-induced genes set forth in Table 3.

In some embodiments, the ER pathway activity score is calculated using a 13-gene signature by subtracting an E2-repressed score, determined from the average z-scored expression of three of the E2-repressed genes set forth in Table 6, from an E2-induced score, determined from the average z-scored expression of ten of the E2-induced genes set forth in Table 3. In some embodiments, the ER pathway activity score is calculated using a 13-gene signature by subtracting an E2-repressed score, determined from the average z-scored expression of four of the E2-repressed genes set forth in Table 6, from an E2-induced score, determined from the average z-scored expression of nine of the E2-induced genes set forth in Table 3. In some embodiments, the ER pathway activity score is calculated using a 13-gene signature by subtracting an E2-repressed score, determined from the average z-scored expression of five of the E2-repressed genes set forth in Table 6, from an E2-induced score, determined from the average z-scored expression of eight of the E2-induced genes set forth in Table 3. In some embodiments, the ER pathway activity score is calculated using a 13-gene signature by subtracting an E2-repressed score, determined from the average z-scored expression of six of the E2-repressed genes set forth in Table 6, from an E2-induced score, determined from the average z-scored expression of seven of the E2-induced genes set forth in Table 3.

In some embodiments, the ER pathway activity score is calculated using a 14-gene signature by subtracting an E2-repressed score, determined from the average z-scored expression of 3 E2-repressed genes set forth in Table 6, from an E2-induced score, determined from the average z-scored expression of 11 E2-induced genes set forth in Table 3. In some embodiments, the ER pathway activity score is calculated using a 14-gene signature by subtracting an E2-repressed score, determined from the average z-scored expression of 4 E2-repressed genes set forth in Table 6, from an E2-induced score, determined from the average z-scored expression of 10 E2-induced genes set forth in Table 3. In some embodiments, the ER pathway activity score is calculated using a 14-gene signature by subtracting an E2-repressed score, determined from the average z-scored expression of 5 E2-repressed genes set forth in Table 6, from an E2-induced score, determined from the average z-scored expression of 9 E2-induced genes set forth in Table 3. In some embodiments, the ER pathway activity score is calculated using a 14-gene signature by subtracting an E2-repressed score, determined from the average z-scored expression of 6 E2-repressed genes set forth in Table 6, from an E2-induced score, determined from the average z-scored expression of the 8 E2-induced genes set forth in Table 3. In some embodiments, the ER pathway activity score is calculated using a 14-gene signature by subtracting an E2-repressed score, determined from the average z-scored expression of the 6 E2-repressed genes set forth in Table 4, from an E2-induced score, determined from the average z-scored expression of the 8 E2-induced genes set forth in Table 1. In some embodiments, the ER pathway activity score is calculated using a 14-gene signature by subtracting an E2-repressed score, determined from the average z-scored expression of 7 E2-repressed genes set forth in Table 6, from an E2-induced score, determined from the average z-scored expression of 7 E2-induced genes set forth in Table 3.

In some embodiments, the ER pathway activity score is calculated using a 15-gene signature by subtracting an E2-repressed score, determined from the average z-scored expression of 3 of the E2-repressed genes set forth in Table 6, from an E2-induced score, determined from the average z-scored expression of 12 of the E2-induced genes set forth in Table 3. In some embodiments, the ER pathway activity score is calculated using a 15-gene signature by subtracting an E2-repressed score, determined from the average z-scored expression of 4 of the E2-repressed genes set forth in Table 6, from an E2-induced score, determined from the average z-scored expression of 11 of the E2-induced genes set forth in Table 3. In some embodiments, the ER pathway activity score is calculated using a 15-gene signature by subtracting an E2-repressed score, determined from the average z-scored expression of 5 of the E2-repressed genes set forth in Table 6, from an E2-induced score, determined from the average z-scored expression of 10 of the E2-induced genes set forth in Table 3. In some embodiments, the ER pathway activity score is calculated using a 15-gene signature by subtracting an E2-repressed score, determined from the average z-scored expression of 6 of the E2-repressed genes set forth in Table 6, from an E2-induced score, determined from the average z-scored expression of 9 of the E2-induced genes set forth in Table 3. In some embodiments, the ER pathway activity score is calculated using a 15-gene signature by subtracting an E2-repressed score, determined from the average z-scored expression of 7 of the E2-repressed genes set forth in Table 6, from an E2-induced score, determined from the average z-scored expression of 8 of the E2-induced genes set forth in Table 3.

In some embodiments, the ER pathway activity score is calculated using a 16-gene signature by subtracting an E2-repressed score, determined from the average z-scored expression of 3 of the E2-repressed genes set forth in Table 6, from an E2-induced score, determined from the average z-scored expression of 13 of the E2-induced genes set forth in Table 3. In some embodiments, the ER pathway activity score is calculated using a 16-gene signature by subtracting an E2-repressed score, determined from the average z-scored expression of 4 of the E2-repressed genes set forth in Table 6, from an E2-induced score, determined from the average z-scored expression of 12 of the E2-induced genes set forth in Table 3. In some embodiments, the ER pathway activity score is calculated using a 16-gene signature by subtracting an E2-repressed score, determined from the average z-scored expression of 5 of the E2-repressed genes set forth in Table 6, from an E2-induced score, determined from the average z-scored expression of 11 of the E2-induced genes set forth in Table 3. In some embodiments, the ER pathway activity score is calculated using a 16-gene signature by subtracting an E2-repressed score, determined from the average z-scored expression of 6 of the E2-repressed genes set forth in Table 6, from an E2-induced score, determined from the average z-scored expression of 10 of the E2-induced genes set forth in Table 3. In some embodiments, the ER pathway activity score is calculated using a 16-gene signature by subtracting an E2-repressed score, determined from the average z-scored expression of 7 of the E2-repressed genes set forth in Table 6, from an E2-induced score, determined from the average z-scored expression of 9 of the E2-induced genes set forth in Table 3. In some embodiments, the ER pathway activity score is calculated using a 16-gene signature by subtracting an E2-repressed score, determined from the average z-scored expression of 8 of the E2-repressed genes set forth in Table 6, from an E2-induced score, determined from the average z-scored expression of 8 of the E2-induced genes set forth in Table 3.

In some embodiments, the ER pathway activity score is calculated using a 17-gene signature by subtracting an E2-repressed score, determined from the average z-scored expression of 3 of the E2-repressed genes set forth in Table 6, from an E2-induced score, determined from the average z-scored expression of 14 of the E2-induced genes set forth in Table 3. In some embodiments, the ER pathway activity score is calculated using a 17-gene signature by subtracting an E2-repressed score, determined from the average z-scored expression of 4 of the E2-repressed genes set forth in Table 6, from an E2-induced score, determined from the average z-scored expression of 13 of the E2-induced genes set forth in Table 3. In some embodiments, the ER pathway activity score is calculated using a 17-gene signature by subtracting an E2-repressed score, determined from the average z-scored expression of 5 of the E2-repressed genes set forth in Table 6, from an E2-induced score, determined from the average z-scored expression of 12 of the E2-induced genes set forth in Table 3. In some embodiments, the ER pathway activity score is calculated using a 17-gene signature by subtracting an E2-repressed score, determined from the average z-scored expression of 6 of the E2-repressed genes set forth in Table 6, from an E2-induced score, determined from the average z-scored expression of 11 of the E2-induced genes set forth in Table 3. In some embodiments, the ER pathway activity score is calculated using a 17-gene signature by subtracting an E2-repressed score, determined from the average z-scored expression of 7 of the E2-repressed genes set forth in Table 6, from an E2-induced score, determined from the average z-scored expression of 10 of the E2-induced genes set forth in Table 3. In some embodiments, the ER pathway activity score is calculated using a 17-gene signature by subtracting an E2-repressed score, determined from the average z-scored expression of 8 of the E2-repressed genes set forth in Table 6, from an E2-induced score, determined from the average z-scored expression of 9 of the E2-induced genes set forth in Table 3.

In some embodiments, the ER pathway activity score is calculated using an 18-gene signature by subtracting an E2-repressed score, determined from the average z-scored expression of 3 of the E2-repressed genes set forth in Table 6, from an E2-induced score, determined from the average z-scored expression of 15 of the E2-induced genes set forth in Table 3. In some embodiments, the ER pathway activity score is calculated using an 18-gene signature by subtracting an E2-repressed score, determined from the average z-scored expression of 4 of the E2-repressed genes set forth in Table 6, from an E2-induced score, determined from the average z-scored expression of 14 of the E2-induced genes set forth in Table 3. In some embodiments, the ER pathway activity score is calculated using an 18-gene signature by subtracting an E2-repressed score, determined from the average z-scored expression of 5 of the E2-repressed genes set forth in Table 6, from an E2-induced score, determined from the average z-scored expression of 13 of the E2-induced genes set forth in Table 3. In some embodiments, the ER pathway activity score is calculated using an 18-gene signature by subtracting an E2-repressed score, determined from the average z-scored expression of 6 of the E2-repressed genes set forth in Table 6, from an E2-induced score, determined from the average z-scored expression of 12 of the E2-induced genes set forth in Table 3. In some embodiments, the ER pathway activity score is calculated using an 18-gene signature by subtracting an E2-repressed score, determined from the average z-scored expression of 7 of the E2-repressed genes set forth in Table 6, from an E2-induced score, determined from the average z-scored expression of 11 of the E2-induced genes set forth in Table 3. In some embodiments, the ER pathway activity score is calculated using an 18-gene signature by subtracting an E2-repressed score, determined from the average z-scored expression of 8 of the E2-repressed genes set forth in Table 6, from an E2-induced score, determined from the average z-scored expression of 10 of the E2-induced genes set forth in Table 3. In some embodiments, the ER pathway activity score is calculated using an 18-gene signature by subtracting an E2-repressed score, determined from the average z-scored expression of 9 of the E2-repressed genes set forth in Table 6, from an E2-induced score, determined from the average z-scored expression of 9 of the E2-induced genes set forth in Table 3.

In some embodiments, the ER pathway activity score is calculated using a 19-gene signature by subtracting an E2-repressed score, determined from the average z-scored expression of 3 of the E2-repressed genes set forth in Table 6, from an E2-induced score, determined from the average z-scored expression of 16 of the E2-induced genes set forth in Table 3. In some embodiments, the ER pathway activity score is calculated using a 19-gene signature by subtracting an E2-repressed score, determined from the average z-scored expression of 4 of the E2-repressed genes set forth in Table 6, from an E2-induced score, determined from the average z-scored expression of 15 of the E2-induced genes set forth in Table 3. In some embodiments, the ER pathway activity score is calculated using a 19-gene signature by subtracting an E2-repressed score, determined from the average z-scored expression of 5 of the E2-repressed genes set forth in Table 6, from an E2-induced score, determined from the average z-scored expression of 14 of the E2-induced genes set forth in Table 3. In some embodiments, the ER pathway activity score is calculated using a 19-gene signature by subtracting an E2-repressed score, determined from the average z-scored expression of 6 of the E2-repressed genes set forth in Table 6, from an E2-induced score, determined from the average z-scored expression of 13 of the E2-induced genes set forth in Table 3. In some embodiments, the ER pathway activity score is calculated using a 19-gene signature by subtracting an E2-repressed score, determined from the average z-scored expression of 7 of the E2-repressed genes set forth in Table 6, from an E2-induced score, determined from the average z-scored expression of 12 of the E2-induced genes set forth in Table 3. In some embodiments, the ER pathway activity score is calculated using a 19-gene signature by subtracting an E2-repressed score, determined from the average z-scored expression of 8 of the E2-repressed genes set forth in Table 6, from an E2-induced score, determined from the average z-scored expression of 11 of the E2-induced genes set forth in Table 3. In some embodiments, the ER pathway activity score is calculated using a 19-gene signature by subtracting an E2-repressed score, determined from the average z-scored expression of the 8 E2-repressed genes set forth in Table 5, from an E2-induced score, determined from the average z-scored expression of the 11 E2-induced genes set forth in Table 2. In some embodiments, the ER pathway activity score is calculated using a 19-gene signature by subtracting an E2-repressed score, determined from the average z-scored expression of 9 of the E2-repressed genes set forth in Table 6, from an E2-induced score, determined from the average z-scored expression of 10 of the E2-induced genes set forth in Table 3.

In some embodiments, the ER pathway activity score is calculated using a 20-gene signature by subtracting an E2-repressed score, determined from the average z-scored expression of 3 of the E2-repressed genes set forth in Table 6, from an E2-induced score, determined from the average z-scored expression of 17 of the E2-induced genes set forth in Table 3. In some embodiments, the ER pathway activity score is calculated using a 20-gene signature by subtracting an E2-repressed score, determined from the average z-scored expression of 4 of the E2-repressed genes set forth in Table 6, from an E2-induced score, determined from the average z-scored expression of 16 of the E2-induced genes set forth in Table 3. In some embodiments, the ER pathway activity score is calculated using a 20-gene signature by subtracting an E2-repressed score, determined from the average z-scored expression of 5 of the E2-repressed genes set forth in Table 6, from an E2-induced score, determined from the average z-scored expression of 15 of the E2-induced genes set forth in Table 3. In some embodiments, the ER pathway activity score is calculated using a 20-gene signature by subtracting an E2-repressed score, determined from the average z-scored expression of 6 of the E2-repressed genes set forth in Table 6, from an E2-induced score, determined from the average z-scored expression of 14 of the E2-induced genes set forth in Table 3. In some embodiments, the ER pathway activity score is calculated using a 20-gene signature by subtracting an E2-repressed score, determined from the average z-scored expression of 7 of the E2-repressed genes set forth in Table 6, from an E2-induced score, determined from the average z-scored expression of 13 of the E2-induced genes set forth in Table 3. In some embodiments, the ER pathway activity score is calculated using a 20-gene signature by subtracting an E2-repressed score, determined from the average z-scored expression of 8 of the E2-repressed genes set forth in Table 6, from an E2-induced score, determined from the average z-scored expression of 12 of the E2-induced genes set forth in Table 3. In some embodiments, the ER pathway activity score is calculated using a 20-gene signature by subtracting an E2-repressed score, determined from the average z-scored expression of 9 of the E2-repressed genes set forth in Table 6, from an E2-induced score, determined from the average z-scored expression of 11 of the E2-induced genes set forth in Table 3. In some embodiments, the ER pathway activity score is calculated using a 20-gene signature by subtracting an E2-repressed score, determined from the average z-scored expression of 10 of the E2-repressed genes set forth in Table 6, from an E2-induced score, determined from the average z-scored expression of 10 of the E2-induced genes set forth in Table 3.

In some embodiments, the ER pathway activity score is calculated using a 21-gene signature by subtracting an E2-repressed score, determined from the average z-scored expression of 3 of the E2-repressed genes set forth in Table 6, from an E2-induced score, determined from the average z-scored expression of 18 of the E2-induced genes set forth in Table 3. In some embodiments, the ER pathway activity score is calculated using a 21-gene signature by subtracting an E2-repressed score, determined from the average z-scored expression of 4 of the E2-repressed genes set forth in Table 6, from an E2-induced score, determined from the average z-scored expression of 17 of the E2-induced genes set forth in Table 3. In some embodiments, the ER pathway activity score is calculated using a 21-gene signature by subtracting an E2-repressed score, determined from the average z-scored expression of 5 of the E2-repressed genes set forth in Table 6, from an E2-induced score, determined from the average z-scored expression of 16 of the E2-induced genes set forth in Table 3. In some embodiments, the ER pathway activity score is calculated using a 21-gene signature by subtracting an E2-repressed score, determined from the average z-scored expression of 6 of the E2-repressed genes set forth in Table 6, from an E2-induced score, determined from the average z-scored expression of 15 of the E2-induced genes set forth in Table 3. In some embodiments, the ER pathway activity score is calculated using a 21-gene signature by subtracting an E2-repressed score, determined from the average z-scored expression of 7 of the E2-repressed genes set forth in Table 6, from an E2-induced score, determined from the average z-scored expression of 14 of the E2-induced genes set forth in Table 3. In some embodiments, the ER pathway activity score is calculated using a 21-gene signature by subtracting an E2-repressed score, determined from the average z-scored expression of 8 of the E2-repressed genes set forth in Table 6, from an E2-induced score, determined from the average z-scored expression of 13 of the E2-induced genes set forth in Table 3. In some embodiments, the ER pathway activity score is calculated using a 21-gene signature by subtracting an E2-repressed score, determined from the average z-scored expression of 9 of the E2-repressed genes set forth in Table 6, from an E2-induced score, determined from the average z-scored expression of 12 of the E2-induced genes set forth in Table 3. In some embodiments, the ER pathway activity score is calculated using a 21-gene signature by subtracting an E2-repressed score, determined from the average z-scored expression of 10 of the E2-repressed genes set forth in Table 6, from an E2-induced score, determined from the average z-scored expression of 11 of the E2-induced genes set forth in Table 3.

In some embodiments, the ER pathway activity score is calculated using a 22-gene signature by subtracting an E2-repressed score, determined from the average z-scored expression of 3 of the E2-repressed genes set forth in Table 6, from an E2-induced score, determined from the average z-scored expression of 19 of the E2-induced genes set forth in Table 3. In some embodiments, the ER pathway activity score is calculated using a 22-gene signature by subtracting an E2-repressed score, determined from the average z-scored expression of 4 of the E2-repressed genes set forth in Table 6, from an E2-induced score, determined from the average z-scored expression of 18 of the E2-induced genes set forth in Table 3. In some embodiments, the ER pathway activity score is calculated using a 22-gene signature by subtracting an E2-repressed score, determined from the average z-scored expression of 5 of the E2-repressed genes set forth in Table 6, from an E2-induced score, determined from the average z-scored expression of 17 of the E2-induced genes set forth in Table 3. In some embodiments, the ER pathway activity score is calculated using a 22-gene signature by subtracting an E2-repressed score, determined from the average z-scored expression of 6 of the E2-repressed genes set forth in Table 6, from an E2-induced score, determined from the average z-scored expression of 16 of the E2-induced genes set forth in Table 3. In some embodiments, the ER pathway activity score is calculated using a 22-gene signature by subtracting an E2-repressed score, determined from the average z-scored expression of 7 of the E2-repressed genes set forth in Table 6, from an E2-induced score, determined from the average z-scored expression of 15 of the E2-induced genes set forth in Table 3. In some embodiments, the ER pathway activity score is calculated using a 22-gene signature by subtracting an E2-repressed score, determined from the average z-scored expression of 8 of the E2-repressed genes set forth in Table 6, from an E2-induced score, determined from the average z-scored expression of 14 of the E2-induced genes set forth in Table 3. In some embodiments, the ER pathway activity score is calculated using a 22-gene signature by subtracting an E2-repressed score, determined from the average z-scored expression of 9 of the E2-repressed genes set forth in Table 6, from an E2-induced score, determined from the average z-scored expression of 13 of the E2-induced genes set forth in Table 3. In some embodiments, the ER pathway activity score is calculated using a 22-gene signature by subtracting an E2-repressed score, determined from the average z-scored expression of 10 of the E2-repressed genes set forth in Table 6, from an E2-induced score, determined from the average z-scored expression of 12 of the E2-induced genes set forth in Table 3. In some embodiments, the ER pathway activity score is calculated using a 22-gene signature by subtracting an E2-repressed score, determined from the average z-scored expression of 11 of the E2-repressed genes set forth in Table 6, from an E2-induced score, determined from the average z-scored expression of 11 of the E2-induced genes set forth in Table 3.

In some embodiments, the ER pathway activity score is calculated using a 23-gene signature by subtracting an E2-repressed score, determined from the average z-scored expression of 3 of the E2-repressed genes set forth in Table 6, from an E2-induced score, determined from the average z-scored expression of 20 of the E2-induced genes set forth in Table 3. In some embodiments, the ER pathway activity score is calculated using a 23-gene signature by subtracting an E2-repressed score, determined from the average z-scored expression of 4 of the E2-repressed genes set forth in Table 6, from an E2-induced score, determined from the average z-scored expression of 19 of the E2-induced genes set forth in Table 3. In some embodiments, the ER pathway activity score is calculated using a 23-gene signature by subtracting an E2-repressed score, determined from the average z-scored expression of 5 of the E2-repressed genes set forth in Table 6, from an E2-induced score, determined from the average z-scored expression of 18 of the E2-induced genes set forth in Table 3. In some embodiments, the ER pathway activity score is calculated using a 23-gene signature by subtracting an E2-repressed score, determined from the average z-scored expression of 6 of the E2-repressed genes set forth in Table 6, from an E2-induced score, determined from the average z-scored expression of 17 of the E2-induced genes set forth in Table 3. In some embodiments, the ER pathway activity score is calculated using a 23-gene signature by subtracting an E2-repressed score, determined from the average z-scored expression of 7 of the E2-repressed genes set forth in Table 6, from an E2-induced score, determined from the average z-scored expression of 16 of the E2-induced genes set forth in Table 3. In some embodiments, the ER pathway activity score is calculated using a 23-gene signature by subtracting an E2-repressed score, determined from the average z-scored expression of 8 of the E2-repressed genes set forth in Table 6, from an E2-induced score, determined from the average z-scored expression of 15 of the E2-induced genes set forth in Table 3. In some embodiments, the ER pathway activity score is calculated using a 23-gene signature by subtracting an E2-repressed score, determined from the average z-scored expression of 9 of the E2-repressed genes set forth in Table 6, from an E2-induced score, determined from the average z-scored expression of 14 of the E2-induced genes set forth in Table 3. In some embodiments, the ER pathway activity score is calculated using a 23-gene signature by subtracting an E2-repressed score, determined from the average z-scored expression of 10 of the E2-repressed genes set forth in Table 6, from an E2-induced score, determined from the average z-scored expression of 13 of the E2-induced genes set forth in Table 3. In some embodiments, the ER pathway activity score is calculated using a 23-gene signature by subtracting an E2-repressed score, determined from the average z-scored expression of 11 of the E2-repressed genes set forth in Table 6, from an E2-induced score, determined from the average z-scored expression of 12 of the E2-induced genes set forth in Table 3.

In some embodiments, the ER pathway activity score is calculated using a 24-gene signature by subtracting an E2-repressed score, determined from the average z-scored expression of 3 of the E2-repressed genes set forth in Table 6, from an E2-induced score, determined from the average z-scored expression of 21 of the E2-induced genes set forth in Table 3. In some embodiments, the ER pathway activity score is calculated using a 24-gene signature by subtracting an E2-repressed score, determined from the average z-scored expression of 4 of the E2-repressed genes set forth in Table 6, from an E2-induced score, determined from the average z-scored expression of 20 of the E2-induced genes set forth in Table 3. In some embodiments, the ER pathway activity score is calculated using a 24-gene signature by subtracting an E2-repressed score, determined from the average z-scored expression of 5 of the E2-repressed genes set forth in Table 6, from an E2-induced score, determined from the average z-scored expression of 19 of the E2-induced genes set forth in Table 3. In some embodiments, the ER pathway activity score is calculated using a 24-gene signature by subtracting an E2-repressed score, determined from the average z-scored expression of 6 of the E2-repressed genes set forth in Table 6, from an E2-induced score, determined from the average z-scored expression of 18 of the E2-induced genes set forth in Table 3. In some embodiments, the ER pathway activity score is calculated using a 24-gene signature by subtracting an E2-repressed score, determined from the average z-scored expression of 7 of the E2-repressed genes set forth in Table 6, from an E2-induced score, determined from the average z-scored expression of 17 of the E2-induced genes set forth in Table 3. In some embodiments, the ER pathway activity score is calculated using a 24-gene signature by subtracting an E2-repressed score, determined from the average z-scored expression of 8 of the E2-repressed genes set forth in Table 6, from an E2-induced score, determined from the average z-scored expression of 16 of the E2-induced genes set forth in Table 3. In some embodiments, the ER pathway activity score is calculated using a 24-gene signature by subtracting an E2-repressed score, determined from the average z-scored expression of 9 of the E2-repressed genes set forth in Table 6, from an E2-induced score, determined from the average z-scored expression of 15 of the E2-induced genes set forth in Table 3. In some embodiments, the ER pathway activity score is calculated using a 24-gene signature by subtracting an E2-repressed score, determined from the average z-scored expression of 10 of the E2-repressed genes set forth in Table 6, from an E2-induced score, determined from the average z-scored expression of 14 of the E2-induced genes set forth in Table 3. In some embodiments, the ER pathway activity score is calculated using a 24-gene signature by subtracting an E2-repressed score, determined from the average z-scored expression of 11 of the E2-repressed genes set forth in Table 6, from an E2-induced score, determined from the average z-scored expression of 13 of the E2-induced genes set forth in Table 3. In some embodiments, the ER pathway activity score is calculated using a 24-gene signature by subtracting an E2-repressed score, determined from the average z-scored expression of 12 of the E2-repressed genes set forth in Table 6, from an E2-induced score, determined from the average z-scored expression of 12 of the E2-induced genes set forth in Table 3.

In some embodiments, the ER pathway activity score is calculated using a 25-gene signature by subtracting an E2-repressed score, determined from the average z-scored expression of 3 of the E2-repressed genes set forth in Table 6, from an E2-induced score, determined from the average z-scored expression of 22 of the E2-induced genes set forth in Table 3. In some embodiments, the ER pathway activity score is calculated using a 25-gene signature by subtracting an E2-repressed score, determined from the average z-scored expression of 4 of the E2-repressed genes set forth in Table 6, from an E2-induced score, determined from the average z-scored expression of 21 of the E2-induced genes set forth in Table 3. In some embodiments, the ER pathway activity score is calculated using a 25-gene signature by subtracting an E2-repressed score, determined from the average z-scored expression of 5 of the E2-repressed genes set forth in Table 6, from an E2-induced score, determined from the average z-scored expression of 20 of the E2-induced genes set forth in Table 3. In some embodiments, the ER pathway activity score is calculated using a 25-gene signature by subtracting an E2-repressed score, determined from the average z-scored expression of 6 of the E2-repressed genes set forth in Table 6, from an E2-induced score, determined from the average z-scored expression of 19 of the E2-induced genes set forth in Table 3. In some embodiments, the ER pathway activity score is calculated using a 25-gene signature by subtracting an E2-repressed score, determined from the average z-scored expression of 7 of the E2-repressed genes set forth in Table 6, from an E2-induced score, determined from the average z-scored expression of 18 of the E2-induced genes set forth in Table 3. In some embodiments, the ER pathway activity score is calculated using a 25-gene signature by subtracting an E2-repressed score, determined from the average z-scored expression of 8 of the E2-repressed genes set forth in Table 6, from an E2-induced score, determined from the average z-scored expression of 17 of the E2-induced genes set forth in Table 3. In some embodiments, the ER pathway activity score is calculated using a 25-gene signature by subtracting an E2-repressed score, determined from the average z-scored expression of 9 of the E2-repressed genes set forth in Table 6, from an E2-induced score, determined from the average z-scored expression of 16 of the E2-induced genes set forth in Table 3. In some embodiments, the ER pathway activity score is calculated using a 25-gene signature by subtracting an E2-repressed score, determined from the average z-scored expression of 10 of the E2-repressed genes set forth in Table 6, from an E2-induced score, determined from the average z-scored expression of 15 of the E2-induced genes set forth in Table 3. In some embodiments, the ER pathway activity score is calculated using a 25-gene signature by subtracting an E2-repressed score, determined from the average z-scored expression of 11 of the E2-repressed genes set forth in Table 6, from an E2-induced score, determined from the average z-scored expression of 14 of the E2-induced genes set forth in Table 3. In some embodiments, the ER pathway activity score is calculated using a 25-gene signature by subtracting an E2-repressed score, determined from the average z-scored expression of 12 of the E2-repressed genes set forth in Table 6, from an E2-induced score, determined from the average z-scored expression of 13 of the E2-induced genes set forth in Table 3.

In some embodiments, the ER pathway activity score is calculated using a 26-gene signature by subtracting an E2-repressed score, determined from the average z-scored expression of 3 of the E2-repressed genes set forth in Table 6, from an E2-induced score, determined from the average z-scored expression of 23 of the E2-induced genes set forth in Table 3. In some embodiments, the ER pathway activity score is calculated using a 26-gene signature by subtracting an E2-repressed score, determined from the average z-scored expression of 4 of the E2-repressed genes set forth in Table 6, from an E2-induced score, determined from the average z-scored expression of 22 of the E2-induced genes set forth in Table 3. In some embodiments, the ER pathway activity score is calculated using a 26-gene signature by subtracting an E2-repressed score, determined from the average z-scored expression of 5 of the E2-repressed genes set forth in Table 6, from an E2-induced score, determined from the average z-scored expression of 21 of the E2-induced genes set forth in Table 3. In some embodiments, the ER pathway activity score is calculated using a 26-gene signature by subtracting an E2-repressed score, determined from the average z-scored expression of 6 of the E2-repressed genes set forth in Table 6, from an E2-induced score, determined from the average z-scored expression of 20 of the E2-induced genes set forth in Table 3. In some embodiments, the ER pathway activity score is calculated using a 26-gene signature by subtracting an E2-repressed score, determined from the average z-scored expression of 7 of the E2-repressed genes set forth in Table 6, from an E2-induced score, determined from the average z-scored expression of 19 of the E2-induced genes set forth in Table 3. In some embodiments, the ER pathway activity score is calculated using a 26-gene signature by subtracting an E2-repressed score, determined from the average z-scored expression of 8 of the E2-repressed genes set forth in Table 6, from an E2-induced score, determined from the average z-scored expression of 18 of the E2-induced genes set forth in Table 3. In some embodiments, the ER pathway activity score is calculated using a 26-gene signature by subtracting an E2-repressed score, determined from the average z-scored expression of 9 of the E2-repressed genes set forth in Table 6, from an E2-induced score, determined from the average z-scored expression of 17 of the E2-induced genes set forth in Table 3. In some embodiments, the ER pathway activity score is calculated using a 26-gene signature by subtracting an E2-repressed score, determined from the average z-scored expression of 10 of the E2-repressed genes set forth in Table 6, from an E2-induced score, determined from the average z-scored expression of 16 of the E2-induced genes set forth in Table 3. In some embodiments, the ER pathway activity score is calculated using a 26-gene signature by subtracting an E2-repressed score, determined from the average z-scored expression of 11 of the E2-repressed genes set forth in Table 6, from an E2-induced score, determined from the average z-scored expression of 15 of the E2-induced genes set forth in Table 3. In some embodiments, the ER pathway activity score is calculated using a 26-gene signature by subtracting an E2-repressed score, determined from the average z-scored expression of 12 of the E2-repressed genes set forth in Table 6, from an E2-induced score, determined from the average z-scored expression of 14 of the E2-induced genes set forth in Table 3. In some embodiments, the ER pathway activity score is calculated using a 26-gene signature by subtracting an E2-repressed score, determined from the average z-scored expression of 13 of the E2-repressed genes set forth in Table 6, from an E2-induced score, determined from the average z-scored expression of 13 of the E2-induced genes set forth in Table 3.

In some embodiments, the ER pathway activity score is calculated using a 27-gene signature by subtracting an E2-repressed score, determined from the average z-scored expression of 4 of the E2-repressed genes set forth in Table 6, from an E2-induced score, determined from the average z-scored expression of 23 of the E2-induced genes set forth in Table 3.

In some embodiments, the ER pathway activity score is calculated using a 28-gene signature by subtracting an E2-repressed score, determined from the average z-scored expression of 5 of the E2-repressed genes set forth in Table 6, from an E2-induced score, determined from the average z-scored expression of 23 of the E2-induced genes set forth in Table 3.

In some embodiments, the ER pathway activity score is calculated using a 29-gene signature by subtracting an E2-repressed score, determined from the average z-scored expression of 6 of the E2-repressed genes set forth in Table 6, from an E2-induced score, determined from the average z-scored expression of 23 of the E2-induced genes set forth in Table 3.

In some embodiments, the ER pathway activity score is calculated using a 30-gene signature by subtracting an E2-repressed score, determined from the average z-scored expression of 7 of the E2-repressed genes set forth in Table 6, from an E2-induced score, determined from the average z-scored expression of 23 of the E2-induced genes set forth in Table 3.

In some embodiments, the ER pathway activity score is calculated using a 31-gene signature by subtracting an E2-repressed score, determined from the average z-scored expression of 8 of the E2-repressed genes set forth in Table 6, from an E2-induced score, determined from the average z-scored expression of 23 of the E2-induced genes set forth in Table 3.

In some embodiments, the ER pathway activity score is calculated using a 32-gene signature by subtracting an E2-repressed score, determined from the average z-scored expression of 9 of the E2-repressed genes set forth in Table 6, from an E2-induced score, determined from the average z-scored expression of 23 of the E2-induced genes set forth in Table 3.

In some embodiments, the ER pathway activity score is calculated using a 33-gene signature by subtracting an E2-repressed score, determined from the average z-scored expression of 10 of the E2-repressed genes set forth in Table 6, from an E2-induced score, determined from the average z-scored expression of 23 of the E2-induced genes set forth in Table 3.

In some embodiments, the ER pathway activity score is calculated using a 34-gene signature by subtracting an E2-repressed score, determined from the average z-scored expression of 11 of the E2-repressed genes set forth in Table 6, from an E2-induced score, determined from the average z-scored expression of 23 of the E2-induced genes set forth in Table 3.

In some embodiments, the ER pathway activity score is calculated using a 35-gene signature by subtracting an E2-repressed score, determined from the average z-scored expression of 12 of the E2-repressed genes set forth in Table 6, from an E2-induced score, determined from the average z-scored expression of 23 of the E2-induced genes set forth in Table 3.

In some embodiments, the ER pathway activity score is calculated using a 36-gene signature by subtracting an E2-repressed score, determined from the average z-scored expression of 13 of the E2-repressed genes set forth in Table 6, from an E2-induced score, determined from the average z-scored expression of 23 of the E2-induced genes set forth in Table 3.

In some embodiments, the ER pathway activity score is calculated using a 37-gene signature by subtracting an E2-repressed score, determined from the average z-scored expression of 14 of the E2-repressed genes set forth in Table 6, from an E2-induced score, determined from the average z-scored expression of 23 of the E2-induced genes set forth in Table 3.

In some embodiments, the ER pathway activity score is calculated using a 38-gene signature by subtracting an E2-repressed score, determined from the average z-scored expression of 15 of the E2-repressed genes set forth in Table 6, from an E2-induced score, determined from the average z-scored expression of 23 of the E2-induced genes set forth in Table 3.

In some embodiments, the ER pathway activity score is calculated using a 39-gene signature by subtracting an E2-repressed score, determined from the average z-scored expression of 16 of the E2-repressed genes set forth in Table 6, from an E2-induced score, determined from the average z-scored expression of 23 of the E2-induced genes set forth in Table 3.

In some embodiments, the ER pathway activity score is calculated using a 40-gene signature by subtracting an E2-repressed score, determined from the average z-scored expression of 17 of the E2-repressed genes set forth in Table 6, from an E2-induced score, determined from the average z-scored expression of 23 of the E2-induced genes set forth in Table 3.

In some embodiments, the ER pathway activity score is calculated using a 41-gene signature by subtracting an E2-repressed score, determined from the average z-scored expression of the 18 E2-repressed genes set forth in Table 6, from an E2-induced score, determined from the average z-scored expression of the 23 E2-induced genes set forth in Table 3.

In some embodiments, the ER pathway activity score is calculated using a 14-gene signature by subtracting an E2-repressed score, determined from the average z-scored expression of the six E2-repressed genes set forth in Table 4, from an E2-induced score, determined from the average z-scored expression of the eight E2-induced genes set forth in Table 1. In some embodiments, the ER pathway activity score is calculated using a 19-gene signature by subtracting an E2-repressed score, determined from the average z-scored expression of the eight E2-repressed genes set forth in Table 5, from an E2-induced score, determined from the average z-scored expression of the 11 E2-induced genes set forth in Table 2. In some embodiments, the ER pathway activity score is calculated using a 41-gene signature by subtracting an E2-repressed score, determined from the average z-scored expression of the 18 E2-repressed genes set forth in Table 6, from an E2-induced score, determined from the average z-scored expression of the 23 E2-induced genes set forth in Table 3. The ER pathway activity score can serve as a surrogate biomarker of ER pathway activity in a tumor in an individual.

In any of the methods or assays provided herein in which the expression level of a predetermined set of genes is determined in a sample (e.g., a tissue sample, e.g., a tumor tissue sample, e.g., a formalin-fixed paraffin-embedded (FFPE), a fresh frozen (FF), an archival, a fresh, or a frozen tumor tissue sample) from an individual, it is to be understood that the expression level of the predetermined set of genes may be normalized, e.g., to a reference gene, e.g., a housekeeping gene. In some instances, the reference gene is SDHA, GUSB, PPIA, and/or UBC. In some instances, an expression level for more than one gene of interest (e.g., the predetermined set of genes listed in any one of Tables 1-6) may be determined by aggregation methods known to one skilled in the art and also disclosed herein, including, for example, by calculating the median or mean of all the expression levels of the genes of interest. Before aggregation, the expression level of each gene of interest may be normalized by using statistical methods known to one skilled in the art and also disclosed herein, including, for example, normalized to the expression level of one or more housekeeping genes, to the median or mean expression level value for each gene as measured across a reference population, normalized to a total library size, or normalized to the median or mean expression level value across all genes measured. In some instances, before aggregation across multiple genes of interest, the normalized expression level of each gene of interest may be standardized by using statistical methods known to one skilled in the art and also disclosed herein, including, for example, by calculating the Z-score of the normalized expression level of each gene of interest or by, for example, scaling the normalized expression level of each gene to the respective scaling of those expression levels in a reference population.

The sample from the individual may be a FFPE sample, a FF sample, a fresh sample, frozen sample, or an archival sample. In some instances, the sample is a FFPE sample. In some instances, the sample is a FF sample. The expression level of the predetermined set of genes can be determined quantitatively based on any suitable criterion known in the art, including, but not limited to, the measurement of mRNA, DNA, cDNA, and/or gene copy number levels in an individual.

TABLE 1

Eight E2-induced genes of the 14-gene signature

E2-Induced

AMZ1
C5AR2
CELSR2
FKBP4
GREB1
OLFM1
SLC9A3R1
TFF1

TABLE 2

Eleven E2-induced genes of the 19-gene signature

E2-Induced

AMZ1
AREG
C5AR2
CELSR2
FKBP4

TABLE 2-continued

Eleven E2-induced genes of the 19-gene signature

E2-Induced

FMN1
GREB1
OLFM1
RBM24
SLC9A3R1
TFF1

TABLE 3

Twenty-three E2-induced genes of the 41 gene signature

E2-Induced

AGR3
AMZ1
AREG
C5AR2
CELSR2
CT62
FKBP4
FMN1
GREB1
IGFBP4
NOS1AP
NXPH3
OLFM1
PGR
PPM1J
RAPGEFL1
RBM24
RERG
RET
SGK3
SLC9A3R1
TFF1
ZNF703

TABLE 4

Six E2-repressed genes of the 14-gene signature

E2-repressed

BCAS1
CCNG2
IL1R1
PNPLA7
SEMA3E
STON1

TABLE 5

Eight E2-repressed genes of the 19-gene signature

E2-repressed

BCAS1
CCNG2
IL1R1
NBEA
PNPLA7
SEMA3E
STON1
TP53INP1

TABLE 6

Eighteen E2-repressed genes of the 41-gene signature

E2-repressed

BAMBI
BCAS1
CCNG2
DDIT4
EGLN3
FAM171B
GRM4
IL1R1
LIPH
NBEA
PNPLA7
PSCA
SEMA3E
SSPO
STON1
TGFB3
TP53INP1
TP53INP2

In some instances of any of the preceding methods and assays, the expression level of a gene may be a nucleic acid expression level (e.g., an RNA expression level (e.g., an mRNA expression level) or a DNA expression level). Any suitable method of determining a nucleic acid expression level may be used, for example, as described in Section VII, below. In some instances, the nucleic acid expression level is determined using RNA-seq (e.g., using an RNA ACCESS® protocol or TRUSEQ® RIBO-ZERO® protocol (ILLUMINA®)), RT-qPCR, qPCR, multiplex qPCR or RT-qPCR, microarray analysis, SAGE, MassARRAY techniques, or a combination thereof.

Methods for the evaluation of mRNAs in cells are well known and include, for example, RNA sequencing (RNA-seq), whole genome sequencing (WGS), serial analysis of gene expression (SAGE), and various nucleic acid amplification assays (such as RT-PCR (e.g., qRT-PCR) using complementary primers specific for the predetermined set of genes. In addition, such methods can include one or more steps that allow one to determine the levels of target mRNA in a biological sample (e.g., by simultaneously examining the levels of a comparative control mRNA sequence of a "housekeeping" gene such as an actin family member). Optionally, the sequence of the amplified target cDNA can be determined. Optional methods include protocols which examine or detect mRNAs, such as target mRNAs, in a tissue or cell sample by microarray technologies. Using nucleic acid microarrays, test and control mRNA samples from test and control tissue samples are reverse transcribed and labeled to generate cDNA probes. The probes are then hybridized to an array of nucleic acids immobilized on a solid support. The array is configured such that the sequence and position of each member of the array is known. For example, a selection of genes whose expression correlates with increased or reduced clinical benefit of treatment comprising an immunotherapy and a suppressive stromal antagonist may be arrayed on a solid support. Hybridization of a labeled probe with a particular array member indicates that the sample from which the probe was derived expresses that gene.

In some instances of any of the methods and assays, the sample (e.g., a tissue sample, e.g., a tumor tissue sample, e.g., a FFPE, a FF, an archival, a fresh, or a frozen tumor tissue sample) is obtained from the individual prior to (e.g., minutes, hours, days, weeks, months, or years prior to) administration of an endocrine therapy as described herein.

In other words, the sample may be a baseline sample. In some instances of any of the preceding methods, the sample is obtained from the individual following (e.g., minutes, hours, or days following) administration of an endocrine therapy. In some instances, the sample from the individual is obtained within thirty hours following administration of an endocrine therapy. In some instances, multiple samples are obtained from the same individual at different time points (e.g., prior to and following administration of an endocrine therapy.

In any of the preceding instances, the individual may have an HR+ breast cancer. In some instances, the HR+ cancer may be an ER+ breast cancer. In some instances, the individual may have an ER+ breast cancer selected from, for example, a luminal A breast cancer or a luminal B breast cancer. In some instances, the breast cancer may be an advanced or a metastatic breast cancer.

In some instances of any of the preceding methods or assays involving determining an ER pathway activity score and/or E2-induced score from a sample (e.g., a tissue sample, e.g., a tumor tissue sample, e.g., a formalin-fixed paraffin-embedded (FFPE), a fresh frozen (FF), an archival, a fresh, or a frozen tumor tissue sample) from an individual, the individual has been previously treated with an endocrine therapy as described herein. In other instances, the individual has not been previously treated with an endocrine therapy.

In some instances, the methods further comprise generating a report, e.g., an electronic, web-based, or paper report, to the individual or to another person or entity, a caregiver, a physician, an oncologist, a hospital, clinic, third-party payor, insurance company, a pharmaceutical or biotechnology company, or government office. In some instances, the report comprises output from the method which comprises evaluation of the ER pathway activity and/or E2-induced score.

Anti-Cancer Agents

Provided herein are methods for treating an individual having a breast cancer (e.g., an HR+ breast cancer (e.g., an ER+ breast cancer (e.g., luminal A cancer breast or luminal B breast cancer)) and/or a metastatic or a locally advanced breast cancer). Any of the preceding methods may be based on the determination of an E2-induced score and/or an ER pathway activity score from a sample (e.g., a tissue sample, e.g., a tumor tissue sample, e.g., a FFPE, a FF, an archival, a fresh, or a frozen tumor tissue sample) from the individual.

In some instances of any of the preceding methods, the anti-cancer therapeutic agents utilized in the methods described herein can be administered, for example, orally, intramuscularly, subcutaneously, intravenously, intradermally, percutaneously, intraarterially, intraperitoneally, intralesionally, intracranially, intraarticularly, intraprostatically, intrapleurally, intratracheally, intrathecally, intranasally, intravaginally, intrarectally, topically, intratumorally, peritoneally, subconjunctivally, intravesicularly, mucosally, intrapericardially, intraumbilically, intraocularly, intraorbitally, intravitreally (e.g., by intravitreal injection), by eye drop, topically, transdermally, parenterally, by inhalation, by injection, by implantation, by infusion, by continuous infusion, by localized perfusion bathing target cells directly, by catheter, by lavage, in creams, or in lipid compositions. In some instances of any of the preceding methods, the anti-cancer therapeutic agents utilized in the methods described herein can be administered orally. For example, in some instances, an endocrine therapy as described herein may be administered orally or intramuscularly. In some instances, a SERM may be administered orally or intramuscularly. In some instances, a SERD may be administered orally or intramuscularly. In some instances of any of the preceding methods, the anti-cancer therapeutic agents utilized in the methods described herein can be administered intramuscularly. For example, in some instances, an endocrine therapy as described herein may be administered orally. In some instances, a SERM may be administered orally. In some instances, a SERD may be administered orally. The anti-cancer therapeutic agents utilized in the methods described herein can also be administered systemically or locally. The method of administration can vary depending on various factors (e.g., the anti-cancer therapeutic agents being administered and the severity of the condition, disease, or disorder (e.g., breast cancer) being treated).

Anti-cancer agents, including endocrine agents as described herein (and any additional therapeutic agent) may be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The anti-cancer agent need not be, but is optionally formulated with and/or administered concurrently with one or more agents currently used to prevent or treat the disorder in question. The effective amount of such other agents depends on the amount of the anti-cancer present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of a breast cancer e.g., an HR+ breast cancer (e.g., an ER+ breast cancer (e.g., luminal A breast cancer or luminal B breast cancer)), DCIS, and/or a metastatic or a locally advanced breast cancer), the appropriate dosage of an anti-cancer agent (e.g., an endocrine therapy) described herein (when used alone or in combination with one or more other additional therapeutic agents) will depend on the type of disease to be treated, the severity and course of the disease, whether the anti-cancer agent is administered for preventive or therapeutic purposes, previous therapy, the individual's clinical history and response to the anti-cancer agent, and the discretion of the attending physician. The anti-cancer agent is suitably administered to the individual at one time or over a series of treatments. For repeated administrations over several days or longer, depending on the condition, the treatment would generally be sustained until a desired suppression of disease symptoms occurs. An initial higher loading dose, followed by one or more lower doses may be administered. However, other dosage regimens may be useful. The progress of this therapy is easily monitored by conventional techniques and assays. In some instances, an endocrine therapy as provided herein is dosed at an amount of about 1 mg/kg to about 100 mg/kg. In another instance, an endocrine therapy provided herein is dosed at an amount of about 100 mg/kg to about 1000 mg/kg. In still another instance, an endocrine therapy described herein is dosed at an amount of about 1000 mg/kg to about 2000 mg/kg. Certain endocrine therapies described herein can be administered in cyclic administration routines as understood in the art—for example for 20, 21, 22, 23, 24, 25, 26, 27, or 28, or more continual days followed by a rest period of 1, 2, 3, 4, 5, 6, 7, or more days. In yet another instance, an endocrine therapy described herein is administered in accordance with a package insert.

Endocrine Therapies

In some instances of any of the preceding methods, an endocrine therapy may be administered to the individual.

Exemplary endocrine therapies for use in the methods described herein include compounds that modulate the activity of the estrogen receptor. In certain instances, the compounds herein include Selective Estrogen Receptor Modulators (SERMs), Selective Estrogen Receptor Degraders (SERDs), aromatase inhibitors (AIs), or combinations thereof.

In some instances, the endocrine therapy comprises an aromatase inhibitor. The aromatase inhibitor can be an agent known in the art. For example, in one instance, the aromatase inhibitor is letrozole, anastrozole, exemestane, or testolactone, or a pharmaceutically acceptable salt thereof, or a combination thereof.

In another instance, the endocrine therapy comprises a SERM.

The endocrine therapy can comprise a compound that can be a tetra-substituted olefin compound known to have antagonist activity against ER. For example, the endocrine therapy can be tamoxifen, including derivatives thereof such as hydroxytamoxifen. In one instance, the endocrine therapy comprises nafoxidine. In another instance, the endocrine therapy comprises clomifene, toremifene, raloxifene, anordrin, bazedoxifene, broparestrol, cyclofenil, lasofoxifene, ormeloxifene, acolbifene, elacestrant, brilanestrant, clomifenoxide, droloxifene, etacstil, or ospemifene, or a pharmaceutically acceptable salt thereof, or a combination thereof. In another instance, the endocrine therapy comprises G1T48, or a pharmaceutically acceptable salt thereof.

In still another instance, the endocrine therapy comprises a SERD.

In one instance, the endocrine therapy comprises fulvestrant.

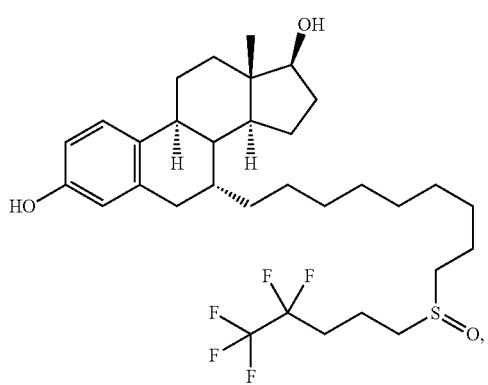

or a pharmaceutically acceptable salt thereof.

In one aspect, the endocrine therapy comprises a compound has formula (1):

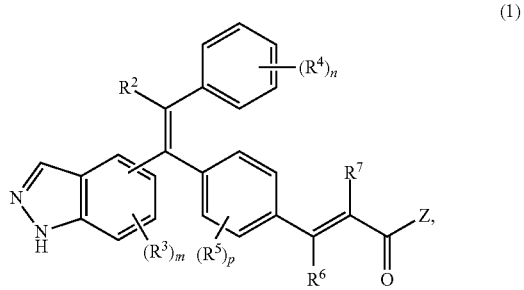

wherein; Z is —OH or —OR$^{10}$; R$^2$ is $C_{1-4}$ alkyl, $C_{1-4}$ fluoroalkyl, $C_{1-4}$ deuteroalkyl, $C_{3-6}$ cycloalkyl, or $C_{1-4}$ alkylene-W; W is hydroxy, halogen, CN, $C_{1-4}$ alkyl, $C_{1-4}$ haloalkyl, $C_{1-4}$ alkoxy, $C_{1-4}$ haloalkoxy, or $C_{3-6}$ cycloalkyl; each R$^3$ is independently halogen, $C_{1-4}$ alkyl, or $C_{1-4}$ fluoroalkyl; each R$^4$ is independently halogen, —CN, —OR$^9$, —S(O)$_2$R$^{10}$, $C_{1-4}$ alkyl, $C_{1-4}$ fluoroalkyl, or $C_{1-4}$ heteroalkyl; each R$^5$ is independently halogen, —CN, —OR$^9$, —S(O)$_2$R$^{10}$, $C_{1-4}$ alkyl, $C_{1-4}$ fluoroalkyl, or $C_{1-4}$ heteroalkyl; R$^6$ is H, $C_{1-4}$ alkyl, or halogen; R$^7$ is H, $C_{1-4}$ alkyl, or halogen; R$^9$ is H, $C_{1-6}$ alkyl, $C_{1-6}$ fluoroalkyl, or $C_{3-6}$ cycloalkyl; R$^{10}$ is $C_{1-6}$ alkyl; m is 0, 1, or 2; n is 0, 1, 2, 3, or 4; and p is 0, 1, or 2.

In another instance of the compound of formula (1), Z is —OH or —OR$^{10}$; R$^2$ is $C_{1-4}$ alkyl, $C_{1-4}$ fluoroalkyl, $C_{1-4}$ deuteroalkyl, $C_{3-6}$ cycloalkyl, or $C_{1-4}$ alkylene-W, where W is hydroxy, halogen, CN, or $C_{1-4}$ alkyl; each R$^3$ is independently halogen, $C_{1-4}$ alkyl, or $C_{1-4}$ fluoroalkyl; each R$^4$ is independently halogen, —CN, —OR$^9$, —S(O)2R$^{10}$, $C_{1-4}$ alkyl, $C_{1-4}$ fluoroalkyl, or $C_{1-4}$ heteroalkyl; each R$^5$ is independently halogen, —CN, —OR$^9$, —S(O)2R10, $C_{1-4}$ alkyl, $C_{1-4}$ fluoroalkyl, or $C_{1-4}$ heteroalkyl; R$^6$ is H, $C_{1-4}$ alkyl, or halogen; R$^7$ is H, $C_{1-4}$ alkyl, or halogen; R$^9$ is H, $C_{1-6}$ alkyl, $C_{1-6}$ fluoroalkyl, or $C_{3-6}$ cycloalkyl; R$^{10}$ is $C_{1-6}$ alkyl; m is 0, 1, or 2; n is 0, 1, 2, 3, or 4; and p is 0, 1, or 2.

In another instance of the compound of formula (1), Z is —OH. In another instance of the compound of formula (1), Z is —OR$^{10}$. In another instance of the compound of formula (1), Z is —OH, —OCH$_3$, or —OCH$_2$CH$_3$.

In another instance of the compound of formula (1), R$^6$ is H, —CH$_3$, F, or Cl. In another instance of the compound of formula (1), R$^6$ is H. In another instance of the compound of formula (1), R$^7$ is H, —CH$_3$, F, or Cl. In another instance of the compound of formula (1), R$^7$ is H.

In another instance of the compound of formula (1), R$^3$ is independently halogen, $C_{1-4}$ alkyl, or $C_{1-4}$ fluoroalkyl. In another instance of the compound of formula (1), each R$^3$ is independently F, Cl, or —CH$_3$. In another instance of the compound of formula (1), each R$^4$ is independently halogen, —CN, —OH, —OR$^9$, —S(O)$_2$R$^{10}$, $C_{1-4}$ alkyl, $C_{1-4}$ fluoroalkyl, or $C_{1-4}$ heteroalkyl.

In another instance of the compound of formula (1), each R$^4$ is independently halogen, —CN, —OH, —S(O)$_2$CH$_3$, —S(O)$_2$CH$_2$CH$_3$, —CH$_3$, —CH$_2$CH$_3$, —CF$_3$, —CH$_2$OH, —OCF$_3$, —OCH$_3$, or —OCH$_2$CH$_3$. In another instance of the compound of formula (1), each R$^4$ is independently F, Cl, —CN, —OH, —CH$_3$, —CH$_2$CH$_3$, —CF$_3$, —CH$_2$OH, —OCF$_3$, —OCH$_3$, or —OCH$_2$CH$_3$. In another instance of the compound of formula (1), each R$^4$ is independently F or Cl. In another instance of the compound of formula (1), each R$^5$ is independently halogen, $C_{1-4}$ alkyl, or $C_{1-4}$ fluoroalkyl. In another instance of the compound of formula (1), each R$^5$ is independently F, Cl, or —CH$_3$.

In another instance of the compound of formula (1), m is 0 or 1. In another instance of the compound of formula (1), m is 0. In another instance of the compound of formula (1), m is 1. In another instance of the compound of formula (1), n is 0, 1, or 2. In another instance of the compound of formula (1), n is 0. In another instance of the compound of formula (1), n is 1. In another instance of the compound of formula (1), n is 2. In another instance of the compound of formula (1), p is 0 or 1. In another instance of the compound of formula (1), p is 0. In another instance of the compound of formula (1), p is 1.

In another instance of the compound of formula (1), Z is —OH; $R^6$ is H, —CH$_3$, F, or Cl; $R^7$ is H, —CH$_3$, F, or Cl; each $R^3$ is independently halogen, $C_{1-4}$ alkyl, or $C_{1-4}$ fluoroalkyl; each $R^4$ is independently halogen, —CN, —OR$^9$, —S(O)$_2$R$^{10}$, $C_{1-4}$ alkyl, $C_{1-4}$ fluoroalkyl, or $C_{1-4}$ heteroalkyl; each $R^5$ is independently halogen, $C_{1-4}$ alkyl, or $C_{1-4}$ fluoroalkyl; m is 0 or 1; n is 0, 1, or 2; and p is 0 or 1.

In another instance of the compound of formula (1), $R^2$ is $C_{1-4}$ alkyl, $C_{1-4}$ fluoroalkyl, $C_{1-4}$ deuteroalkyl, $C_{3-6}$ cycloalkyl, or $C_{1-4}$ alkylene-W; W is hydroxy, halogen, CN, $C_{1-4}$ alkoxy, or $C_{3-6}$ cycloalkyl. In another instance of the compound of formula (1), $R^2$ is $C_{1-4}$ alkyl, $C_{1-4}$ fluoroalkyl, or $C_{1-4}$ deuteroalkyl. In another instance of the compound of formula (1), $R^2$ is $C_{1-4}$ alkyl. In another instance of the compound of formula (1), $R^2$ is —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH$_2$F, —CHF$_2$, —CF$_3$, —CH$_2$CF$_3$, —CD$_3$, —CH$_2$CD$_3$, —CD$_2$CD$_3$, cyclopropyl, cyclobutyl, cyclopentyl, cyclohexyl, —CH$_2$—W, or —CH$_2$CH$_2$—W; W is hydroxy, F, Cl, —CN, —OCH$_3$, —OCH$_2$CH$_3$, —OCH$_2$CH$_2$CH$_3$, —OCH(CH$_3$)$_2$, cyclopropyl, cyclobutyl, cyclopentyl, or cyclohexyl. In another instance of the compound of formula (1), W is hydroxy, F, Cl, —CN, cyclopropyl, cyclobutyl, cyclopentyl, or cyclohexyl. In another instance of the compound of formula (1), $R^2$ is —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH$_2$F, —CHF$_2$, —CF$_3$, —CH$_2$CF$_3$, —CD$_3$, —CH$_2$CD$_3$, —CD$_2$CD$_3$, —CH$_2$—W, or —CH$_2$CH$_2$—W. In another instance of the compound of formula (1), $R^2$ is —CH$_3$, —CH$_2$CH$_3$, —CH$_2$F, —CHF$_2$, —CF$_3$, —CH$_2$CF$_3$, —CD$_3$, —CD$_2$CD$_3$, —CH$_2$CD$_3$, or cyclopropyl.

In another instance of the compound of formula (1), Z is —OH; $R^6$ is H; $R^7$ is H; m is 0; n is 0, 1, or 2; and p is 0.

In another instance of the compound of formula (1), the compound of Formula (1) has the structure of Formula (1a), or a pharmaceutically acceptable salt, or N-oxide thereof:

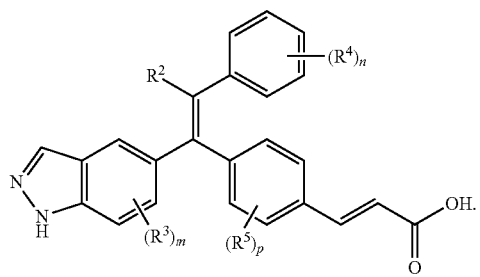

Formula (1a)

In another aspect, the endocrine therapy comprises a compound set forth in U.S. Pat. No. 8,299,112, for example in Table 1 therein, which is incorporated herein by reference in its entirety and for all purposes.

In another aspect, the endocrine therapy comprises a compound having the formula: (E)-Ethyl 3-(4-((E)-1-(1H-indazol-5-yl)-2-phenylbut-1-en-1-yl)phenyl)acrylate; (E)-3-(4-((E)-1-(1H-Indazol-5-yl)-2-phenylbut-1-en-1-yl)phenyl) acrylic acid; (E)-3-(4-((E)-1-(1H-Benzo[d][1,2,3]triazol-5-yl)-2-phenylbut-1-en-1-yl)phenyl) acrylic acid; (E)-3-(4-((E)-2-(4-Fluorophenyl)-1-(1H-indazol-5-yl)but-1-en-1-yl)phenyl)acrylic acid; (E)-3-(4-((E)-2-(4-Chlorophenyl)-1-(1H-indazol-5-yl)but-1-en-1-yl)phenyl)acrylic acid; (E)-3-(4-((E)-1-(1H-Indazol-5-yl)-2-(3-methoxyphenyl)but-1-en-1-yl)phenyl)acrylic acid; (E)-3-(4-((E)-2-(3-(Hydroxymethyl)phenyl)-1-(1H-indazol-5-yl)but-1-en-1-yl)phenyl)acrylic acid; (E)-3-(4-((E)-2-(4-(Hydroxymethyl)phenyl)-1-(1H-indazol-5-yl)but-1-en-1-yl)phenyl)acrylic acid; (E)-3-(4-((E)-2-(2-(Hydroxymethyl)phenyl)-1-(1H-indazol-5-yl)but-1-en-1-yl)phenyl)acrylic acid; (E)-3-(4-((E)-1-(1H-Indazol-5-yl)-2-(o-tolyl)but-1-en-1-yl)phenyl)acrylic acid; (E)-3-(4-((E)-1-(1H-Indazol-5-yl)-2-(m-tolyl)but-1-en-1-yl)phenyl)acrylic acid; (E)-3-(4-((E)-1-(1H-Indazol-5-yl)-2-(p-tolyl)but-1-en-1-yl)phenyl)acrylic acid; (E)-3-(4-((E)-1-(1H-Indazol-5-yl)-2-(2-methoxyphenyl)but-1-en-1-yl)phenyl)acrylic acid; (E)-3-(4-((E)-1-(1H-Indazol-5-yl)-2-(4-methoxyphenyl)but-1-en-1-yl)phenyl)acrylic acid; ((E)-3-(4-((E)-2-(2-Chlorophenyl)-1-(1H-indazol-5-yl)but-1-en-1-yl)phenyl)acrylic acid; (E)-3-(4-((E)-2-(3-Chlorophenyl)-1-(1H-indazol-5-yl)but-1-en-1-yl)phenyl)acrylic acid; (E)-3-(4-((E)-2-(2-Fluorophenyl)-1-(1H-indazol-5-yl)but-1-en-1-yl)phenyl)acrylic acid; (E)-3-(4-((E)-2-(3-Fluorophenyl)-1-(1H-indazol-5-yl)but-1-en-1-yl)phenyl)acrylic acid; (E)-3-(4-((E)-2-(2-Ethylphenyl)-1-(1H-indazol-5-yl)but-1-en-1-yl)phenyl)acrylic acid; (E)-3-(4-((E)-1-(1H-Indazol-5-yl)-2-(2-(trifluoromethyl)phenyl)but-1-en-1-yl)phenyl)acrylic acid; (E)-3-(4-((E)-4-Chloro-1-(1H-indazol-5-yl)-2-phenylbut-1-en-1-yl)phenyl)acrylic acid; (E)-3-(4-((E)-2-(2-Fluorophenyl)-1-(1H-indazol-4-yl)but-1-en-1-yl)phenyl)acrylic acid; (E)-3-(4-((E)-2-(2-Cyanophenyl)-1-(1H-indazol-5-yl)but-1-en-1-yl)phenyl)acrylic acid; (E)-3-(4-((E)-2-(2,4-Difluorophenyl)-1-(1H-indazol-5-yl)but-1-en-1-yl)phenyl) acrylic acid; (E)-3-(4-((E)-2-(2-Chloro-3-fluorophenyl)-1-(1H-indazol-5-yl)but-1-en-1-yl)phenyl)acrylic acid; (E)-3-(4-((E)-2-Cyclopropyl-1-(1H-indazol-5-yl)-2-phenylvinyl)phenyl)acrylic acid; (E)-3-(4-((E)-2-(4-Fluoro-2-methylphenyl)-1-(1H-indazol-5-yl)but-1-en-1-yl)phenyl)acrylic acid; (E)-3-(4-((E)-2-(2,6-Difluorophenyl)-1-(1H-indazol-5-yl)but-1-en-1-yl)phenyl)acrylic acid; (E)-3-(4-((E)-2-(2,6-Dichlorophenyl)-1-(1H-indazol-5-yl)but-1-en-1-yl)phenyl)acrylic acid; (E)-3-(4-((E)-4,4,4-Trideutero-1-(1H-indazol-5-yl)-2-phenylbut-1-en-1-yl)phenyl)acrylic acid; (E)-3-(4-((E)-2-(4-Fluoro-3-methylphenyl)-1-(1H-indazol-5-yl)but-1-en-1-yl)phenyl)acrylic acid; (E)-3-(4-((E)-2-(5-Fluoro-2-methylphenyl)-1-(1H-indazol-5-yl)but-1-en-1-yl)phenyl)acrylic acid; (E)-3-(4-((E)-2-(2,3-Difluorophenyl)-1-(1H-indazol-5-yl)but-1-en-1-yl)phenyl) acrylic acid; (E)-3-(4-((E)-2-(2,5-Difluorophenyl)-1-(1H-indazol-5-yl)but-1-en-1-yl)phenyl) acrylic acid; (E)-3-(4-((E)-2-(2-Chloro-5-luorophenyl)-1-(1H-indazol-5-yl)but-1-en-1-yl)phenyl)acrylic acid; (E)-3-(4-((E)-2-(2-Chloro-6-methylphenyl)-1-(1H-indazol-5-yl)but-1-en-1-yl)phenyl)acrylic acid; (E)-3-(4-((E)-1-(7-Chloro-1H-indazol-5-yl)-2-phenylbut-1-en-1-yl)phenyl)acrylic acid; (E)-3-(4-((E)-1-(4-Methyl-1H-indazol-5-yl)-2-phenylbut-1-en-1-yl)phenyl) acrylic acid; (E)-3-(4-((E)-1-(7-Methyl-1H-indazol-5-yl)-2-phenylbut-1-en-1-yl)phenyl)acrylic acid; (E)-3-(4-((E)-1-(6-Methyl-1H-indazol-5-yl)-2-phenylbut-1-en-1-yl)phenyl) acrylic acid; (E)-3-(4-((E)-1-(3-Methyl-1H-indazol-5-yl)-2- phenylbut-1-en-1-yl)phenyl)acrylic acid; (E)-3-(4-((E)-1-(3-Chloro-1H-indazol-5-yl)-2-phenylbut-1-en-1-yl)phenyl)acrylic acid; (E)-3-(4-((E)-2-(4-Chloro-2-methylphenyl)-1-(1H-indazol-5-yl)but-1-en-1-yl)phenyl)acrylic acid; (E)-3-(4-((E)-1-(1H-Indazol-5-yl)-2-phenylprop-1-en-1-yl)phenyl)acrylic acid; (E)-3-(4-((E)-1-(1H-Indazol-5-yl)-2-phenylpent-1-en-1-yl)phenyl)acrylic acid; (E)-3-(4-((E)-2-(3-Cyanophenyl)-1-(1H-indazol-5-yl)but-1-en-1-yl)phenyl)acrylic acid; (E)-3-(4-((E)-2-(4-Cyanophenyl)-1-(1H-indazol-5-yl)but-1-en-1-yl)phenyl)acrylic acid; (E)-3-(4-((E)-4-Hydroxy-1-(1H-indazol-5-yl)-2-phenylbut-1-en-1-yl)phenyl)acrylic acid; (E)-3-(4-((E)-1-(1H-Indazol-5-yl)-4-methoxy-2-phenylbut-1-en-1-yl)phenyl)acrylic acid; (E)-3-(4-((Z)-1-(1H-Indazol-5-yl)-3-methoxy-2-phenylprop-1-en-1-yl)phenyl)acrylic acid; (E)-3-(4-((E)-1-(4-Fluoro-1H-indazol-5-yl)-2-phenylbut-1-en-1-yl)phenyl)acrylic acid; (E)-3-(4-((E)-1-(1H-Indol-5-yl)-2-phenylbut-1-en-1-yl)phenyl)acrylic acid; (E)-3-(4-((E)-1-(6-Chloro-1H-indazol-5-yl)-2-phenylbut-1-en-1-yl)phenyl)acrylic acid; (E)-3-(4-((E)-1-(1H-Indazol-5-yl)-4-methyl-2-phenylpent-1-en-1-yl)phenyl)acrylic acid; (E)-3-(4-((E)-1-(1H-Benzo[d][1,2,3]triazol-5-yl)-2-(2-chloro-4-fluorophenyl)but-1-en-1-yl)phenyl)acrylic acid; (E)-3-(4-((E)-1-(4-Chloro-1H-indazol-5-yl)-2-phenylbut-1-en-1-yl)phenyl)acrylic acid; (E)-3-(4-((E)-2-Cyclopentyl-1-(1H-indazol-5-yl)-2-phenylvinyl)phenyl)acrylic acid; (E)-3-(4-((E)-2-Cyclohexyl-1-(1H-indazol-5-yl)-2-phenylvinyl)phenyl)acrylic acid; (E)-3-(4-((E)-1-(1H-Indazol-5-yl)-3-methyl-2-phenylbut-1-en-1-yl)phenyl)acrylic acid; (E)-3-(4-((E)-3-Cyclopropyl-1-(1H-indazol-5-yl)-2-phenylprop-1-en-1-yl)phenyl)acrylic acid; (E)-3-(4-((E)-2-(2-Chlorophenyl)-2-cyclopropyl-1-(1H-indazol-5-yl)vinyl)phenyl)acrylic acid; (E)-3-(4-((E)-1-(6-Fluoro-1H-indazol-5-yl)-2-phenylbut-1-en-1-yl)phenyl)acrylic acid; (E)-3-(4-((E)-1-(1H-Benzo[d]imidazol-5-yl)-2-phenylbut-1-en-1-yl)phenyl)acrylic acid; (E)-3-(4-((E)-1-(1H-Indazol-5-yl)-2-phenylhex-1-en-1-yl)phenyl)acrylic acid; (E)-3-(4-((E)-3-Cyclopentyl-1-(1H-indazol-5-yl)-2-phenylprop-1-en-1-yl)phenyl)acrylic acid; (E)-3-(4-((E)-2-(2-Chloro-4-fluorophenyl)-1-(4-fluoro-1H-indazol-5-yl)but-1-en-1-yl)phenyl)acrylic acid; (E)-3-(4-((E)-1-(7-Fluoro-1H-indazol-5-yl)-2-phenylbut-1-en-1-yl)phenyl)acrylic acid; (E)-3-(4-((E)-1-(7-Fluoro-1H-indol-5-yl)-2-phenylbut-1-en-1-yl)phenyl)acrylic acid; (E)-3-(4-((E)-2-(2-Chloro-4-fluorophenyl)-1-(1H-indazol-5-yl)-4-methylpent-1-en-1-yl)phenyl)acrylic acid; (E)-3-(4-((Z)-3,3-Difluoro-1-(1H-indazol-5-yl)-2-phenylprop-1-en-1-yl)phenyl)acrylic acid; (E)-3-(4-((E)-2-(2-Chloro-4-fluorophenyl)-1-(7-fluoro-1H-indazol-5-yl)but-1-en-1-yl)phenyl)acrylic acid; (E)-3-(4-((E)-4-Fluoro-1-(1H-indazol-5-yl)-2-phenylbut-1-en-1-yl)phenyl)acrylic acid; (E)-3-(4-((E)-4-Chloro-2-(2-chloro-4-fluorophenyl)-1-(1H-indazol-5-yl)but-1-en-1-yl)phenyl)acrylic acid; (E)-3-(4-((Z)-3,3,3-Trifluoro-1-(1H-indazol-5-yl)-2-phenylprop-1-en-1-yl)phenyl)acrylic acid; (E)-3-(4-((E)-1-(4-Fluoro-1H-indazol-5-yl)-2-(4-fluoro-2-methylphenyl)but-1-en-1-yl)phenyl)acrylic acid; (E)-3-(4-((E)-2-(4-Chloro-2-methylphenyl)-1-(4-fluoro-1H-indazol-5-yl)but-1-en-1-yl)phenyl)acrylic acid; (E)-3-(4-((E)-2-Cyclopropyl-1-(4-fluoro-1H-indazol-5-yl)-2-(4-fluoro-2-methylphenyl)vinyl)phenyl)acrylic acid; (E)-3-(4-((E)-2-(4-Chloro-2-methylphenyl)-2-cyclopropyl-1-(4-fluoro-1H-indazol-5-yl)vinyl)phenyl)acrylic acid; (E)-3-(4-((E)-1-(4-Chloro-1H-indazol-5-yl)-2-(2-chloro-4-fluorophenyl)but-1-en-1-yl)phenyl)acrylic acid; (E)-3-(4-((Z)-2-(2-Chloro-4-fluorophenyl)-3,3-difluoro-1-(1H-indazol-5-yl)prop-1-en-1-yl)phenyl)acrylic acid; (E)-3-(4-((E)-2-Cyclopropyl-1-(4-fluoro-1H-indazol-5-yl)-2-phenylvinyl)phenyl)acrylic acid; (E)-3-(4-((E)-4-Chloro-1-(4-fluoro-1H-indazol-5-yl)-2-phenylbut-1-en-1-yl)phenyl)acrylic acid; (E)-3-(4-((E)-4-Chloro-2-(2-chloro-4-fluorophenyl)-1-(4-fluoro-1H-indazol-5-yl)but-1-en-1-yl)phenyl)acrylic acid; (E)-3-(4-((E)-4-Fluoro-2-(4-fluorophenyl)-1-(1H-indazol-5-yl)but-1-en-1-yl)phenyl)acrylic acid; (E)-3-(4-((E)-4-Fluoro-1-(4-fluoro-1H-indazol-5-yl)-2-phenylbut-1-en-1-yl)phenyl)acrylic acid; (E)-3-(4-((E)-1-(1H-Indazol-5-yl)-5-methoxy-2-phenylpent-1-en-1-yl)phenyl)acrylic acid; (E)-3-(4-((E)-1-(1H-Indazol-5-yl)-6-methoxy-2-phenylhex-1-en-1-yl)phenyl)acrylic acid; (E)-3-(4-((E)-2-(2-Chloro-4-fluorophenyl)-1-(1H-indazol-5-yl)-3-methylbut-1-en-1-yl)phenyl)acrylic acid; (E)-3-(4-((E)-1-(1H-Indazol-5-yl)-2-(3-(trifluoromethoxy)phenyl)but-1-en-1-yl)phenyl)acrylic acid; (E)-3-(4-((E)-2-Cyclobutyl-1-(1H-indazol-5-yl)-2-phenylvinyl)phenyl)acrylic acid; (E)-3-(4-((E)-2-(2-Chloro-4-fluorophenyl)-2-cyclobutyl-1-(1H-indazol-5-yl)vinyl)phenyl)acrylic acid; (E)-3-(4-((E)-1-(3-Fluoro-1H-indazol-5-yl)-2-phenylbut-1-en-1-yl)phenyl)acrylic acid; (E)-3-(4-((E)-2-Cyclobutyl-1-(3-fluoro-1H-indazol-5-yl)-2-phenylvinyl)phenyl)acrylic acid; (E)-3-(4-((E)-2-(2-Chloro-4-fluorophenyl)-1-(3-fluoro-1H-indazol-5-yl)but-1-en-1-yl)phenyl)acrylic acid; (E)-3-(4-((E)-2-(2-Chloro-4-fluorophenyl)-2-cyclobutyl-1-(3-fluoro-1H-indazol-5-yl)vinyl)phenyl)acrylic acid; (E)-Ethyl 3-(4-((E)-2-(4-fluorophenyl)-1-(1H-indazol-5-yl)but-1-en-1-yl)phenyl)acrylate; (E)-Ethyl 3-(4-((E)-1-(1H-Indazol-5-yl)-2-(2-methoxyphenyl)but-1-en-1-yl)phenyl)acrylate; (E)-Ethyl 3-(4-((E)-1-(1H-Indazol-5-yl)-2-(4-methoxyphenyl)but-1-en-1-yl)phenyl)acrylate; (E)-3-(4-((E)-1-(1H-Indazol-5-yl)-2-phenylbut-1-en-1-yl)phenyl)-2-methylacrylic acid; (E)-3-(4-((Z)-1-(1H-Indazol-5-yl)-2-phenylbut-1-en-1-yl)-3-methylphenyl)acrylic acid; (E)-3-(4-((E)-1-(1H-Indazol-5-yl)-2-phenylbut-1-en-1-yl)-2-methylphenyl)acrylic acid; (E)-3-(4-((Z)-1-(1H-Indazol-5-yl)-2-phenylbut-1-en-1-yl)-2-chlorophenyl)acrylic acid; (Z)-3-(4-((E)-1-(1H-Indazol-5-yl)-2-phenylbut-1-en-1-yl)phenyl)-2-fluoroacrylic acid; (Z)-3-(4-((E)-1-(1H-Indazol-5-yl)-2-phenylbut-1-en-1-yl)phenyl)-2-chloroacrylic acid; (E)-3-(4-((Z)-1-(1H-Indazol-5-yl)-2-phenylbut-1-en-1-yl)-3-fluorophenyl)acrylic acid; (E)-3-(4-((Z)-1-(1H-Indazol-5-yl)-2-phenylbut-1-en-1-yl)-2-fluorophenyl)acrylic acid; (E)-3-(4-((Z)-1-(1H-Indazol-5-yl)-2-phenylbut-1-en-1-yl)-2-(trifluoromethyl)phenyl)acrylic acid; (E)-3-(4-((Z)-1-(1H-Indazol-5-yl)-2-phenylbut-1-en-1-yl)-3-methoxyphenyl)acrylic acid; (E)-3-(4-((Z)-1-(1H-Indazol-5-yl)-2-phenylbut-1-en-1-yl)-2-methoxyphenyl)acrylic acid; (E)-Ethyl 3-(4-((E)-2-(2-chloro-4-fluorophenyl)-1-(1H-indazol-5-yl)but-1-en-1-yl)phenyl)acrylate hydrochloride; (E)-3-(4-((E)-2-(2-Chloro-4-fluorophenyl)-1-(1H-indazol-5-yl)but-1-en-1-yl)phenyl)acrylic acid; (E)-Ethyl 3-(4-((E)-2-(2,4-dichlorophenyl)-1-(1H-indazol-5-yl)but-1-en-1-yl)phenyl)acrylate; (E)-3-(4-((E)-2-(2,4-Dichlorophenyl)-1-(1H-indazol-5-yl)but-1-en-1-yl)phenyl)acrylic acid; (E)-3-(4-((E)-2-(4-Chloro-2-(trifluoromethyl)phenyl)-1-(1H-indazol-5-yl)but-1-en-1-yl)phenyl)acrylic acid; (E)-3-(4-((E)-2-(2-Chloro-4-fluorophenyl)-2-cyclopropyl-1-(1H-indazol-5-yl)vinyl)phenyl)acrylic acid; (E)-3-(4-((E)-2-(4-Fluoro-2-(trifluoromethyl)phenyl)-1-(1H-indazol-5-yl)but-1-en-1-yl)phenyl)acrylic acid; (E)-3-(4-(1-(4-Fluoro-1H-indazol-5-yl)-2-(4-fluoro-2-(trifluoromethyl) phenyl)butyl)phenyl)acrylic acid; (E)-3-(4-((E)-2-(2,4-Dichlorophenyl)-1-(4-fluoro-1H-indazol-5-yl)but-1-en-1-yl)phenyl)acrylic acid; (E)-3-(4-((E)-2-(4-Chloro-2-(trifluoromethyl)phenyl)-1-(4-fluoro-1H-indazol-5-yl)but-1-en-1-yl)phenyl)acrylic acid; (E)-3-(4-((E)-2-(2-Chloro-4-fluorophenyl)-4-fluoro-1-(1H-indazol-5-yl)but-1-en-1-yl)phenyl)acrylic acid; (E)-3-(4-((E)-2-(2-Chloro-4-methoxyphenyl)-1-(1H-indazol-5-yl)

but-1-en-1-yl)phenyl)acrylic acid; (E)-3-(4-((E)-2-(2,4-Dichlorophenyl)-4-fluoro-1-(4-fluoro-1H-indazol-5-yl)but-1-en-1-yl)phenyl)acrylic acid; (E)-3-(4-((E)-2-Cyclopropyl-2-(2,4-dichlorophenyl)-1-(4-fluoro-1H-indazol-5-yl)vinyl)phenyl)acrylic acid; (E)-3-(4-((E)-2-(2-Chloro-4-fluorophenyl)-2-cyclopropyl-1-(4-fluoro-1H-indazol-5-yl)vinyl)phenyl)acrylic acid; (E)-3-(4-((E)-2-Cyclopropyl-2-(2,4-dichlorophenyl)-1-(1H-indazol-5-yl)vinyl)phenyl)acrylic acid; (E)-3-(4-((E)-2-(4-Chloro-2-methylphenyl)-2-cyclopropyl-1-(1H-indazol-5-yl)vinyl)phenyl)acrylic acid; (E)-3-(4-((E)-1-(1H-Indazol-5-yl)-2-(2-methyl-5-(methylsulfonyl)phenyl)but-1-en-1-yl)phenyl)acrylic acid; (E)-3-(4-((E)-1-(1H-Indazol-5-yl)-2-(4-methoxy-2-methylphenyl)but-1-en-1-yl)phenyl)acrylic acid; (E)-3-(4-((E)-2-(2-Fluoro-4-methoxyphenyl)-1-(1H-indazol-5-yl)but-1-en-1-yl)phenyl)acrylic acid; (E)-3-(4-((E)-2-(2-Chloro-5-methoxyphenyl)-1-(1H-indazol-5-yl)but-1-en-1-yl)phenyl)acrylic acid; (E)-3-(4-((E)-2-(2-Fluoro-4-(methylsulfonyl)phenyl)-1-(1H-indazol-5-yl)but-1-en-1-yl)phenyl)acrylic acid; (E)-3-(4-((E)-2-(2,4-Dichlorophenyl)-3,3,4,4,4-pentadeutero-1-(1H-indazol-5-yl)but-1-en-1-yl)phenyl)acrylic acid; (E)-3-(4-((E)-1-(1H-Indazol-5-yl)-2-(3-(methylsulfonyl)phenyl)but-1-en-1-yl)phenyl)acrylic acid; (E)-3-(4-((E)-2-(2,4-Dichlorophenyl)-1-(7-fluoro-1H-indazol-5-yl)but-1-en-1-yl)phenyl)acrylic acid; (E)-3-(4-((E)-2-(2-Chloro-3-methoxyphenyl)-1-(1H-indazol-5-yl)but-1-en-1-yl)phenyl)acrylic acid; (E)-3-(4-((E)-2-(2,4-Dichlorophenyl)-1-(7-fluoro-1H-indol-5-yl)but-1-en-1-yl)phenyl)acrylic acid; (E)-3-(4-((E)-2-(2-Chloro-4-fluorophenyl)-1-(7-fluoro-1H-indol-5-yl)but-1-en-1-yl)phenyl)acrylic acid; (E)-3-(4-((E)-2-(2-Chloro-4-fluorophenyl)-3,3,4,4,4-pentadeutero-1-(1H-indazol-5-yl)but-1-en-1-yl)phenyl)acrylic acid; (E)-3-(4-((E)-2-(4-Chloro-2-cyanophenyl)-1-(1H-indazol-5-yl)but-1-en-1-yl)phenyl)acrylic acid; (E)-3-(4-((E)-2-(2-Cyano-4-fluorophenyl)-1-(1H-indazol-5-yl)but-1-en-1-yl)phenyl)acrylic acid; (E)-3-(4-((E)-2-(2-Cyano-4-(trifluoromethyl)phenyl)-1-(1H-indazol-5-yl)but-1-en-1-yl)phenyl)acrylic acid; (E)-3-(4-((E)-2-(2-Chloro-4-cyanophenyl)-1-(1H-indazol-5-yl)but-1-en-1-yl)phenyl)acrylic acid; (E)-3-(4-((E)-2-(3-Cyano-2-methylphenyl)-1-(1H-indazol-5-yl)but-1-en-1-yl)phenyl)acrylic acid; (E)-3-(4-((E)-2-(4-Cyano-2-methylphenyl)-1-(1H-indazol-5-yl)but-1-en-1-yl)phenyl)acrylic acid; (E)-3-(4-((E)-2-(5-Cyano-2-methylphenyl)-1-(1H-indazol-5-yl)but-1-en-1-yl)phenyl)acrylic acid; (E)-3-(4-((E)-2-(2-Cyano-4-methoxyphenyl)-1-(1H-indazol-5-yl)but-1-en-1-yl)phenyl)acrylic acid; (E)-3-(4-((E)-2-(3-Hydroxyphenyl)-1-(1H-indazol-5-yl)but-1-en-1-yl)phenyl)acrylic acid; (E)-3-(4-((E)-2-(2-Hydroxyphenyl)-1-(1H-indazol-5-yl)but-1-en-1-yl)phenyl)acrylic acid; (E)-3-(4-((E)-2-(4-Hydroxyphenyl)-1-(1H-indazol-5-yl)but-1-en-1-yl)phenyl)acrylic acid; (E)-3-(4-(1-(1H-Indazol-5-yl)-2-phenylbut-1-en-1-yl)phenyl)propanoic acid; (E)-3-(4-((E)-1-(1H-Indazol-5-yl)-2-(4-(2-methoxyethoxy)phenyl)but-1-en-1-yl)phenyl)acrylic acid; (E)-3-(4-((E)-1-(1H-Indazol-5-yl)-2-(4-(3-methoxypropoxy)phenyl)but-1-en-1-yl)phenyl)acrylic acid; (E)-3-(4-((E)-1-(1H-Indazol-5-yl)-2-(3-(2-methoxyethoxy)phenyl)but-1-en-1-yl)phenyl)acrylic acid; (E)-3-(4-((E)-1-(1H-Indazol-5-yl)-2-(3-(3-methoxypropoxy)phenyl)but-1-en-1-yl)phenyl)acrylic acid; (E)-3-(4-((E)-2-(3-(Cyclohexyloxy)phenyl)-1-(4-fluoro-1H-indazol-5-yl)but-1-en-1-yl)phenyl)acrylic acid; (E)-3-(4-((E)-2-(3-Butoxyphenyl)-1-(1H-indazol-5-yl)but-1-en-1-yl)phenyl)acrylic acid; (E)-3-(4-((E)-1-(1H-Indazol-5-yl)-2-(3-(pentyloxy)phenyl)but-1-en-1-yl)phenyl)acrylic acid; (E)-3-(4-((E)-2-(3-(Hexyloxy)phenyl)-1-(1H-indazol-5-yl)but-1-en-1-yl)phenyl)acrylic acid; (E)-3-(4-((E)-2-(4-Butoxyphenyl)-1-(1H-indazol-5-yl)but-1-en-1-yl)phenyl)acrylic acid; (E)-3-(4-((E)-1-(1H-Indazol-5-yl)-2-(4-(pentyloxy)phenyl)but-1-en-1-yl)phenyl)acrylic acid; (E)-3-(4-((E)-2-(4-(Hexyloxy)phenyl)-1-(1H-indazol-5-yl)but-1-en-1-yl)phenyl)acrylic acid; (E)-3-(4-((E)-2-(4-(2-Hydroxyethoxy)phenyl)-1-(1H-indazol-5-yl)but-1-en-1-yl)phenyl)acrylic acid; (E)-3-(4-((E)-1-(1H-Indazol-5-yl)-2-(2-(methylsulfonyl)phenyl)but-1-en-1-yl)phenyl)acrylic acid; (E)-3-(4-((E)-2-(2-Chlorophenyl)-1-(1-methyl-1H-indazol-5-yl)but-1-en-1-yl)phenyl)acrylic acid; (E)-3-(4-((E)-2-Cyclobutyl-1-(1-methyl-1H-indazol-5-yl)-2-phenylvinyl)phenyl)acrylic acid; (E)-3-(4-((E)-2-(2-Chloro-4-fluorophenyl)-1-(1-methyl-1H-indazol-5-yl)but-1-en-1-yl)phenyl)acrylic acid; (E)-3-(4-((E)-2-(2-Chloro-4-fluorophenyl)-1-(1-(difluoromethyl)-1H-indazol-5-yl)but-1-en-1-yl)phenyl)acrylic acid; or a pharmaceutically acceptable salt, or N-oxide thereof, or a combination thereof.

In one instance, the endocrine therapy comprises brilanestrant (GDC-0810) having the structure:

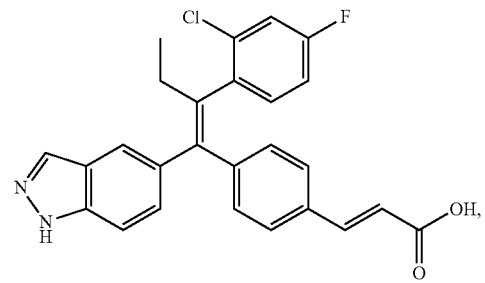 [SMILES: CC/C(=C(/c1ccc(/C=C/C(=O)O)cc1)c1ccc2[nH]ncc2c1)c1ccc(F)cc1Cl]

or a pharmaceutically acceptable salt thereof.

In another aspect, the endocrine therapy comprises a compound set forth in U.S. Pat. No. 9,499,538 or 9,586,952, each of which is incorporated herein by reference in its entirety and for all purposes.

In another aspect, the endocrine therapy comprises a compound set forth in U.S. Pat. No. 7,612,114 or 8,399,520, each of which is incorporated herein by reference in its entirety and for all purposes. In one instance, the endocrine therapy comprises elacestrant (RAD1901):

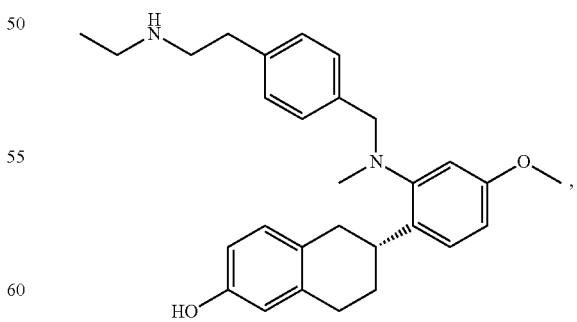

or a pharmaceutically acceptable salt thereof.

In another aspect, the endocrine therapy comprises a compound set forth in International Patent Application No. WO2018077260, for example in Table 2 therein, which is incorporated herein by reference in its entirety and for all purposes. In one instance, the endocrine therapy comprises a LX-039. In another instance, the endocrine therapy comprises a compound having the structure:

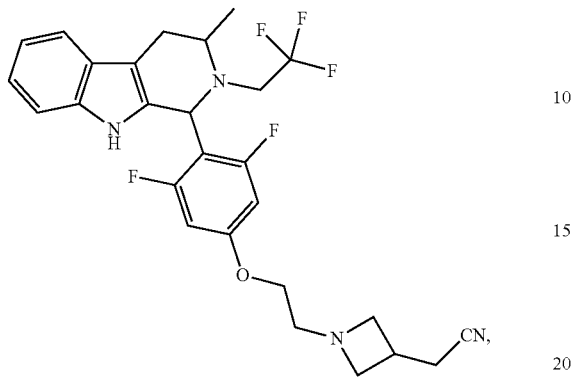

or a pharmaceutically acceptable salt thereof.

In another aspect, the endocrine therapy comprises a compound set forth in International Patent Application No. WO2017136688, WO2017162206, WO2017140669, WO2017216280, WO2017216279, WO2018091153, WO2018019793, WO2018077630, each of which is incorporated herein by reference in its entirety and for all purposes.

In another instance, the endocrine therapy comprises AZ9496 having the structure:

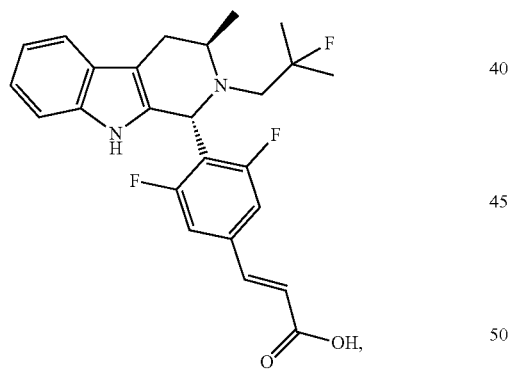

or a pharmaceutically acceptable salt thereof.

In another aspect, the endocrine therapy comprises a compound as set forth in U.S. Patent Application No. 20150284357, which is incorporated herein by reference in its entirety and for all purposes. In another aspect, the endocrine therapy comprises a compound as set forth in U.S. Pat. No. 9,475,791 which is incorporated herein by reference in its entirety and for all purposes. In still another aspect, the endocrine therapy comprises a compound as set forth in international patent application no WO2018081168 or WO2018129387, each of which is incorporated herein by reference in its entirety and for all purposes. In one aspect, the endocrine therapy comprises a compound having formula:

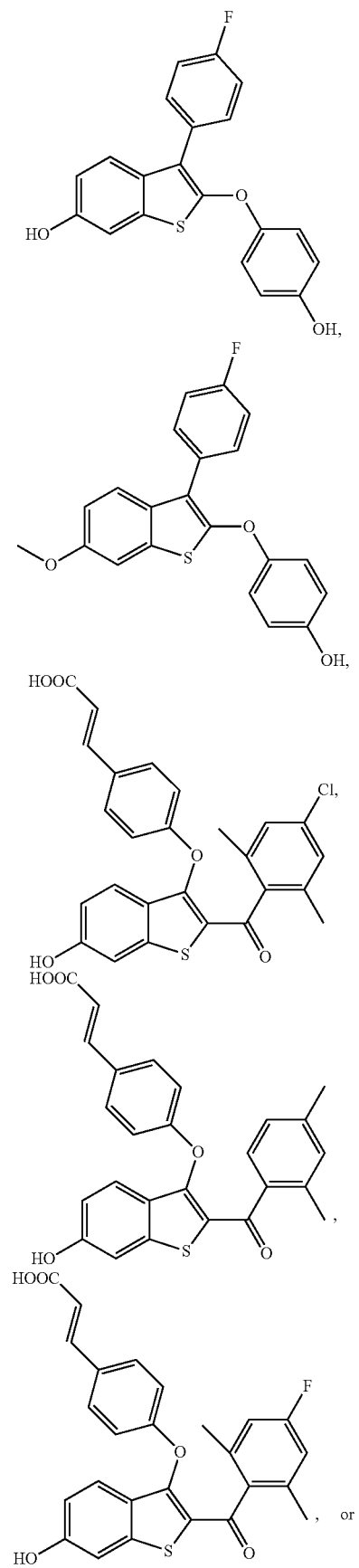

-continued

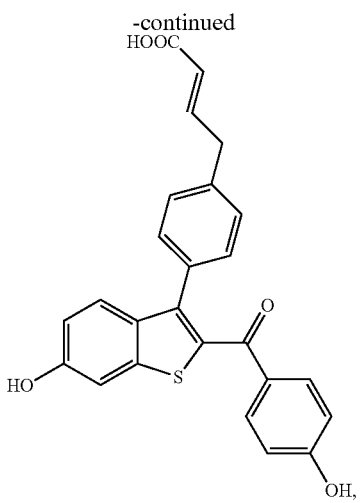

or a stereoisomer or and pharmaceutically acceptable salt thereof.

In another aspect, the endocrine therapy comprises a compound set forth in U.S. Pat. No. 8,703,810, for example in table of compounds provided therein, which is incorporated herein by reference in its entirety and for all purposes.

In one aspect, the endocrine therapy comprises a compound having formula (2):

Formula (2)

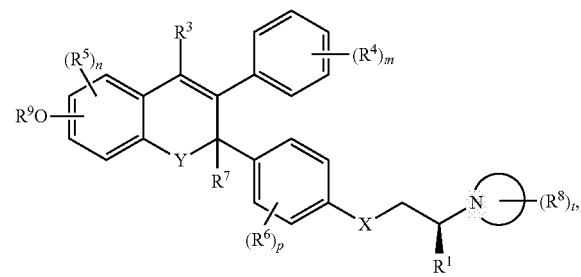

or a pharmaceutically acceptable salt thereof, wherein: $R^1$ is H, F, $C_1$-$C_4$alkyl, or $C_1$-$C_4$fluoroalkyl; $R^3$ is H, halogen, $C_1$-$C_4$alkyl, $C_3$-$C_6$cycloalkyl, or $C_1$-$C_4$fluoroalkyl; each $R^4$ is independently selected from H, halogen, —CN, —OH, —OR$^9$, —SR$^9$, —S(O)R$^{10}$, —S(O)$_2$R$^{10}$, —C(O)R$^{10}$, —C(O)OH, —C(O)OR$^{10}$, —C(O)NHR$^{10}$, —C(O)N(R$^{10}$)$_2$, substituted or unsubstituted $C_1$-$C_6$alkyl, substituted or unsubstituted $C_1$-$C_6$fluoroalkyl, substituted or unsubstituted $C_1$-$C_6$fluoroalkoxy, substituted or unsubstituted $C_1$-$C_6$alkoxy, and substituted or unsubstituted $C_1$-$C_6$heteroalkyl; each $R^5$ is independently selected from H, halogen, —CN, —OH, —OR$^9$, —SR$^9$, —S(O)R$^{10}$, —S(O)$_2$R$^{10}$, substituted or unsubstituted $C_1$-$C_6$alkyl, substituted or unsubstituted $C_1$-$C_6$fluoroalkyl, substituted or unsubstituted $C_1$-$C_6$fluoroalkoxy, substituted or unsubstituted $C_1$-$C_6$alkoxy, and substituted or unsubstituted $C_1$-$C_6$heteroalkyl; each $R^6$ is independently selected from H, halogen, —CN, —OH, —OR$^9$, —SR$^9$, —S(O)R$^{10}$, —S(O)$_2$R$^{10}$, substituted or unsubstituted $C_1$-$C_6$alkyl, substituted or unsubstituted $C_1$-$C_6$fluoroalkyl, substituted or unsubstituted $C_1$-$C_6$fluoroalkoxy, substituted or unsubstituted $C_1$-$C_6$alkoxy, and substituted or unsubstituted $C_1$-$C_6$heteroalkyl;

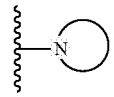

is pyrrolidinyl or azetidinyl; $R^7$ is H or $C_1$-$C_4$alkyl; each $R^8$ is independently selected from F, Cl, —CN, —OH, —OR$^9$, —SR$^9$, —S(O)R$^{10}$, —S(O)$_2$R$^{10}$, substituted or unsubstituted $C_1$-$C_6$alkyl, substituted or unsubstituted $C_1$-$C_6$fluoroalkyl, substituted or unsubstituted $C_1$-$C_6$fluoroalkoxy, substituted or unsubstituted $C_1$-$C_6$alkoxy, and substituted or unsubstituted $C_1$-$C_6$heteroalkyl; or 1 $R^8$ is taken together with $R^1$ along with the intervening atoms joining $R^8$ to $R^1$ to form a 5-, 6-, or 7-membered ring; each $R^9$ is independently selected from H, —C(O)R$^{10}$, —C(O)OR$^{10}$, —C(O)NHR$^{10}$, substituted or unsubstituted $C_1$-$C_6$alkyl, substituted or unsubstituted $C_1$-$C_6$heteroalkyl, substituted or unsubstituted $C_1$-$C_6$fluoroalkyl, substituted or unsubstituted $C_3$-$C_{10}$cycloalkyl, substituted or unsubstituted $C_2$-$C_{10}$heterocycloalkyl, substituted or unsubstituted aryl, substituted or unsubstituted heteroaryl, —$C_1$-$C_2$alkylene-(substituted or unsubstituted $C_3$-$C_{10}$cycloalkyl), —$C_1$-$C_2$alkylene-(substituted or unsubstituted $C_2$-$C_{10}$heterocycloalkyl), —$C_1$-$C_2$alkylene-(substituted or unsubstituted aryl), and —$C_1$-$C_2$alkylene-(substituted or unsubstituted heteroaryl); or each $R^{10}$ is independently selected from substituted or unsubstituted $C_1$-$C_6$alkyl, substituted or unsubstituted $C_1$-$C_6$heteroalkyl, substituted or unsubstituted $C_1$-$C_6$fluoroalkyl, substituted or unsubstituted $C_3$-$C_{10}$cycloalkyl, substituted or unsubstituted $C_2$-$C_{10}$heterocycloalkyl, substituted or unsubstituted aryl, substituted or unsubstituted heteroaryl, —$C_1$-$C_2$alkylene-(substituted or unsubstituted $C_3$-$C_{10}$cycloalkyl), —$C_1$-$C_2$alkylene-(substituted or unsubstituted $C_2$-$C_{10}$heterocycloalkyl), —$C_1$-$C_2$alkylene-(substituted or unsubstituted aryl), and —$C_1$-$C_2$alkylene-(substituted or unsubstituted heteroaryl); Y is —O—, —S—, or —NR$^{11}$—; $R^{11}$ is H, —C(O)R$^{10}$, substituted or unsubstituted $C_1$-$C_6$alkyl, substituted or unsubstituted $C_1$-$C_6$fluoroalkyl, or substituted or unsubstituted $C_1$-$C_6$heteroalkyl; X is —O—, —S—, —CH$_2$—, —NH— or —N($C_1$-$C_6$alkyl)-; m is 0, 1, 2, 3 or 4; n is 0, 1, 2, or 3; p is 0, 1, 2, 3 or 4; and t is 1, 2, 3 or 4.

In one instance, the compound of formula (2) is a compound wherein $R^1$ is H or $C_1$-$C_4$alkyl; $R^3$ is $C_1$-$C_4$alkyl or $C_1$-$C_4$fluoroalkyl; each $R^4$ is independently selected from H, halogen, —CN, —OH, —OR$^9$, —SR$^9$, —S(=O)R$^{10}$, —S(=O)$_2$R$^{10}$, $C_1$-$C_4$alkyl, $C_1$-$C_4$fluoroalkyl, $C_1$-$C_4$fluoroalkoxy, $C_1$-$C_4$alkoxy, and $C_1$-$C_4$heteroalkyl; each $R^5$ is independently selected from H, F, Cl, —OH, —CH$_3$, —CF$_3$, —OCF$_3$, and —OCH$_3$; each $R^6$ is independently selected from H, F, Cl, —OH, —CH$_3$, —CF$_3$, —OCF$_3$, and —OCH$_3$; $R^7$ is H; each $R^8$ is independently selected from H, F, Cl, —OH, $C_1$-$C_4$alkyl, $C_1$-$C_4$fluoroalkyl, $C_1$-$C_4$fluoroalkoxy, $C_1$-$C_4$alkoxy, and $C_1$-$C_4$heteroalkyl; Y is —O— or —S—; X is —O—, —S—, —CH$_2$—, —NH— or —N(CH$_3$)—; and p is 0, 1, or 2.

In another aspect, the endocrine therapy comprises a compound having formula: 3-(3-Hydroxyphenyl)-4-methyl-2-(4-((S)-2-((R)-3-methylpyrrolidin-1-yl)propoxy)phenyl)-2H-chromen-6-ol; (S)-3-(3-Hydroxyphenyl)-4-methyl-2-(4-((S)-2-((R)-3-methylpyrrolidin-1-yl)propoxy)phenyl)-2H-chromen-6-ol; (R)-3-(3-Hydroxyphenyl)-4-methyl-2-(4-((S)-2-((R)-3-methylpyrrolidin-1-yl)propoxy)phenyl)-2H- chromen-6-ol; 3-(3-Hydroxyphenyl)-4-methyl-2-(4-(2-((R)-3-methylpyrrolidin-1-yl)ethoxy)phenyl)-2H-chromen-6-ol; 3-(3-Hydroxyphenyl)-4-methyl-2-(4-((R)-2-((R)-3-methylpyrrolidin-1-yl)propoxy)phenyl)-2H-chromen-6-ol; 3-(3-Hydroxyphenyl)-4-methyl-2-(4-(2-((S)-3-methylpyrrolidin-1-yl)ethoxy)phenyl)-2H-chromen-6-ol; 3-(3-hydroxyphenyl)-4-methyl-2-(4-((S)-2-((S)-3-methylpyrrolidin-1-yl)propoxy)phenyl)-2H-chromen-6-01; 3-(3-hydroxyphenyl)-4-methyl-2-(4-((R)-2-((S)-3-methylpyrrolidin-1-yl)propoxy)phenyl)-2H-chromen-6-ol; 2-(4-((S)-2-(3,3-Dimethylpyrrolidin-1-yl)propoxy)phenyl)-3-(3-hydroxyphenyl)-4-methyl-2H-chromen-6-ol; 2-(4-(2-(3,3-Dimethylpyrrolidin-1-yl)ethoxy)phenyl)-3-(3-hydroxyphenyl)-4-methyl-2H-chromen-6-ol; 3-(3-Hydroxyphenyl)-4-methyl-2-(4-(2-((R)-2-methylpyrrolidin-1-yl)ethoxy)phenyl)-2H-chromen-6-ol; 3-(3-Hydroxyphenyl)-4-methyl-2-(4-((S)-2-((R)-2-methylpyrrolidin-1-yl)propoxy)phenyl)-2H-chromen-6-ol; 3-(3-Hydroxyphenyl)-4-methyl-2-(4-((S)-2-((S)-2-methylpyrrolidin-1-yl)propoxy)phenyl)-2H-chromen-6-ol; 3-(3-Hydroxyphenyl)-4-methyl-2-(4-((S)-2-((R)-3-methylpyrrolidin-1-yl)propoxy)phenyl)-2H-chromen-7-ol; 3-(4-Hydroxyphenyl)-4-methyl-2-(4-((S)-2-((R)-3-methylpyrrolidin-1-yl)propoxy)phenyl)-2H-chromen-7-ol; 4-Methyl-2-(4-((S)-2-((R)-3-methylpyrrolidin-1-yl)propoxy)phenyl)-3-phenyl-2H-chromen-6-ol; 3-(4-Fluorophenyl)-4-methyl-2-(4-((S)-2-((R)-3-methylpyrrolidin-1-yl)propoxy)phenyl)-2H-chromen-6-ol; (S)-3-(4-Fluorophenyl)-4-methyl-2-(4-((S)-2-((R)-3-methylpyrrolidin-1-yl)propoxy)phenyl)-2H-chromen-6-ol; (R)-3-(4-Fluorophenyl)-4-methyl-2-(4-((S)-2-((R)-3-methylpyrrolidin-1-yl)propoxy)phenyl)-2H-chromen-6-ol; 3-(4-Hydroxyphenyl)-4-methyl-2-(4-((S)-2-((R)-3-methylpyrrolidin-1-yl)propoxy)phenyl)-2H-chromen-6-ol; 3-(3-Fluorophenyl)-4-methyl-2-(4-((S)-2-((R)-3-methylpyrrolidin-1-yl)propoxy)phenyl)-2H-chromen-6-ol; 3-(3-Fluoro-4-hydroxyphenyl)-4-methyl-2-(4-((S)-2-((R)-3-methylpyrrolidin-1-yl)propoxy)phenyl)-2H-chromen-6-ol; 2-(2-Fluoro-4-((S)-2-((R)-3-methylpyrrolidin-1-yl)propoxy)phenyl)-3-(3-hydroxyphenyl)-4-methyl-2H-chromen-6-ol; 3-(3-Hydroxy-4-methylphenyl)-4-methyl-2-(4-((S)-2-((R)-3-methylpyrrolidin-1-yl)propoxy)phenyl)-2H-chromen-6-ol; 3-(3-Hydroxy-2-methylphenyl)-4-methyl-2-(4-((S)-2-((R)-3-methylpyrrolidin-1-yl)propoxy)phenyl)-2H-chromen-6-ol; 3-(4-Hydroxy-2-methylphenyl)-4-methyl-2-(4-((S)-2-((R)-3-methylpyrrolidin-1-yl)propoxy)phenyl)-2H-chromen-6-ol; 3-(4-Hydroxy-3-methylphenyl)-4-methyl-2-(4-((S)-2-((R)-3-methylpyrrolidin-1-yl)propoxy)phenyl)-2H-chromen-6-ol; 3-(3-Fluoro-5-hydroxyphenyl)-4-methyl-2-(4-((S)-2-((R)-3-methylpyrrolidin-1-yl)propoxy)phenyl)-2H-chromen-6-ol; 3-(4-Chlorophenyl)-4-methyl-2-(4-((S)-2-((R)-3-methylpyrrolidin-1-yl)propoxy)phenyl)-2H-chromen-6-ol; 3-(2-Fluoro-4-hydroxyphenyl)-4-methyl-2-(4-((S)-2-((R)-3-methylpyrrolidin-1-yl)propoxy)phenyl)-2H-chromen-6-ol; 3-(3,4-Difluorophenyl)-4-methyl-2-(4-((S)-2-((R)-3-methylpyrrolidin-1-yl)propoxy)phenyl)-2H-chromen-6-ol; 3-(3,5-Difluoro-4-hydroxyphenyl)-4-methyl-2-(4-((S)-2-((R)-3-methylpyrrolidin-1-yl)propoxy)phenyl)-2H-chromen-6-ol; 3-(2,4-Difluoro-3-hydroxyphenyl)-4-methyl-2-(4-((S)-2-((R)-3-methylpyrrolidin-1-yl)propoxy)phenyl)-2H-chromen-6-ol; 3-(3,4-Difluoro-5-hydroxyphenyl)-4-methyl-2-(4-((S)-2-((R)-3-methylpyrrolidin-1-yl)propoxy)phenyl)-2H-chromen-6-ol; 3-(2-Chloro-4-fluorophenyl)-4-methyl-2-(4-((S)-2-((R)-3-methylpyrrolidin-1-yl)propoxy)phenyl)-2H-chromen-6-ol; 3-(2,4-Difluorophenyl)-4-methyl-2-(4-((S)-2-((R)-3-methylpyrrolidin-1-yl)propoxy)phenyl)-2H-chromen-6-ol; 3-(4-Bromophenyl)-4-methyl-2-(4-((S)-2-((R)-3-methylpyrrolidin-1-yl)propoxy)phenyl)-2H-chromen-6-ol; 4-Methyl-2-(4-((S)-2-((R)-3-methylpyrrolidin-1-yl)propoxy)phenyl)-3-(o-tolyl)-2H-chromen-6-ol; 3-(4-Fluoro-3-hydroxyphenyl)-4-methyl-2-(4-((S)-2-((R)-3-methylpyrrolidin-1-yl)propoxy)phenyl)-2H-chromen-6-ol; 3-(4-Ethynylphenyl)-4-methyl-2-(4-((S)-2-((R)-3-methylpyrrolidin-1-yl)propoxy)phenyl)-2H-chromen-6-ol; 4-Methyl-2-(4-((S)-2-((R)-3-methylpyrrolidin-1-yl)propoxy)phenyl)-3-(4-(methylsulfonyl)phenyl)-2H-chromen-6-ol; 3-(2-Fluoro-3-hydroxyphenyl)-4-methyl-2-(4-((S)-2-((R)-3-methylpyrrolidin-1-yl)propoxy)phenyl)-2H-chromen-6-ol; 5-Fluoro-3-(3-hydroxyphenyl)-4-methyl-2-(4-((S)-2-((R)-3-methylpyrrolidin-1-yl)propoxy)phenyl)-2H-chromen-6-ol; 3-(2-Fluoro-5-hydroxyphenyl)-4-methyl-2-(4-((S)-2-((R)-3-methylpyrrolidin-1-yl)propoxy)phenyl)-2H-chromen-6-ol; 3-(4-Fluorophenyl)-4-methyl-2-(4-((S)-2-((R)-2-methylpyrrolidin-1-yl)propoxy)phenyl)-2H-chromen-6-ol; 2-(4-((S)-2-((R)-3-Fluoropyrrolidin-1-yl)propoxy)phenyl)-3-(3-hydroxyphenyl)-4-methyl-2H-chromen-6-ol; 3-(4-Hydroxyphenyl)-2-(4-((S)-2-((R)-3-methylpyrrolidin-1-yl)propoxy)phenyl)-4-(trifluoromethyl)-2H-chromen-6-ol; 3-(3-Hydroxyphenyl)-2-(4-((S)-2-((R)-3-methylpyrrolidin-1-yl)propoxy)phenyl)-4-(trifluoromethyl)-2H-chromen-6-ol; 3-(3-Hydroxy-4-(trifluoromethyl)phenyl)-4-methyl-2-(4-((S)-2-((R)-3-methylpyrrolidin-1-yl)propoxy)phenyl)-2H-chromen-6-ol; 3-(4-Hydroxy-3-(trifluoromethyl)phenyl)-4-methyl-2-(4-((S)-2-((R)-3-methylpyrrolidin-1-yl)propoxy)phenyl)-2H-chromen-6-ol; or a pharmaceutically acceptable salt thereof, or a combination thereof.

In one instance, the endocrine therapy comprises a GDC-0927 (SRN-0927) having the structure:

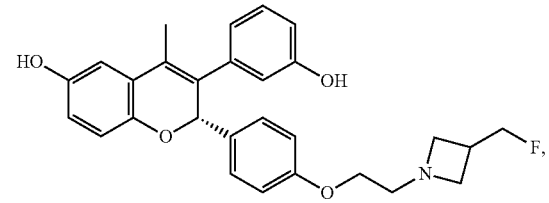 [SMILES: CC1=C(c2cccc(O)c2)[C@H](c2ccc(OCCN3CC(CF)C3)cc2)Oc2ccc(O)cc21]

or a pharmaceutically acceptable salt thereof.

In another aspect, the endocrine therapy comprises a compound set forth in U.S. Pat. No. 9,980,947, for example in Table 1 therein, which is incorporated herein by reference in its entirety and for all purposes.

In one aspect, the endocrine therapy comprises a compound of formula (3):

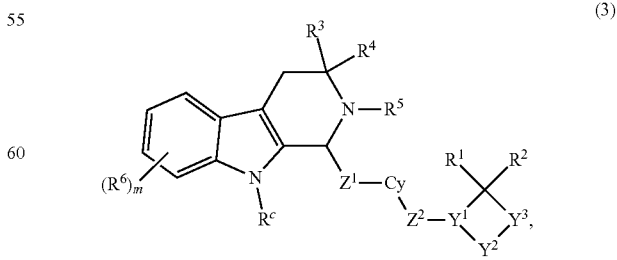

or a stereoisomer, tautomer, or pharmaceutically acceptable salt thereof, wherein: $Y^1$ is $CR^b$ or N; $Y^2$ is $—(CH_2)—$, —(CH$_2$CH$_2$)—, or NR$^a$; Y$^3$ is NR$^a$ or C(R$^b$)$_2$; where one of Y$^1$, Y$^2$ and Y$^3$ is N or NR$^a$; R$^a$ is H, C$_1$-C$_6$ alkyl, C$_2$-C$_8$ alkenyl, propargyl, C$_3$-C$_6$ cycloalkyl, or C$_3$-C$_6$ heterocyclyl, optionally substituted with one or more groups independently selected from the group consisting of F, Cl, Br, I, CN, OH, OCH$_3$, and SO$_2$CH$_3$; R$^b$ is H, —O(C$_1$-C$_3$ alkyl), C$_1$-C$_6$ alkyl, C$_2$-C$_8$ alkenyl, propargyl, —(C$_1$-C$_6$ alkyldiyl)-(C$_3$-C$_6$ cycloalkyl), C$_3$-C$_6$ cycloalkyl, or C$_3$-C$_6$ heterocyclyl, optionally substituted with one or more groups independently selected from the group consisting of F, Cl, Br, I, CN, —CH$_2$F, —CHF$_2$, —CF$_3$, —CH$_2$CF$_3$, —CH$_2$CHF$_2$, —CH$_2$CH$_2$F, OH, OCH$_3$, and SO$_2$CH$_3$; R$^c$ is H, C$_1$-C$_6$ alkyl, allyl, or propargyl, optionally substituted with one or more groups independently selected from the group consisting of F, Cl, Br, I, CN, OH, OCH$_3$, and SO$_2$CH$_3$; Z$^1$ is CR$^a$R$^b$, C(O), or a bond; Cy is C$_6$-C$_{20}$ aryldiyl, C$_3$-C$_{12}$ carbocyclyldiyl, C$_2$-C$_{20}$ heterocyclyldiyl, or C$_1$-C$_{20}$ heteroaryldiyl; Z$^2$ is O, S, NR$^a$, C$_1$-C$_6$ alkyldiyl, C$_1$-C$_6$ fluoroalkyldiyl, O—(C$_1$-C$_6$ alkyldiyl), O—(C$_1$-C$_6$ fluoroalkyldiyl), C(O), or a bond; R$^1$, R$^2$, R$^3$ and R$^4$ are independently H, F, Cl, Br, I, —CN, —CH$_3$, —CH$_2$CH$_3$, —CH(CH$_3$)$_2$, —CH$_2$CH(CH$_3$)$_2$, —CH$_2$OH, —CH$_2$OCH$_3$, —CH$_2$CH$_2$OH, —C(CH$_3$)$_2$OH, —CH(OH)CH(CH$_3$)$_2$, —C(CH$_3$)$_2$CH$_2$OH, —CH$_2$CH$_2$SO$_2$CH$_3$, —CH$_2$OP(O)(OH)$_2$, —CH$_2$F, —CHF$_2$, —CH$_2$NH$_2$, —CH$_2$NHSO$_2$CH$_3$, —CH$_2$NHCH$_3$, —CH$_2$N(CH$_3$)$_2$, —CF$_3$, —CH$_2$CF$_3$, —CH$_2$CHF$_2$, —CH(CH$_3$)CN, —C(CH$_3$)$_2$CN, —CH$_2$CN, —CO$_2$H, —COCH$_3$, —CO$_2$CH$_3$, —CO$_2$C(CH$_3$)$_3$, —COCH(OH)CH$_3$, —CONH$_2$, —CONHCH$_3$, —CONHCH$_2$CH$_3$, —CONHCH(CH$_3$)$_2$, —CON(CH$_3$)$_2$, —C(CH$_3$)$_2$CONH$_2$, —NH$_2$, —NHCH$_3$, —N(CH$_3$)$_2$, —NHCOCH$_3$, —N(CH$_3$)COCH$_3$, —NHS(O)$_2$CH$_3$, —N(CH$_3$)C(CH$_3$)$_2$CONH$_2$, —N(CH$_3$)CH$_2$CH$_2$S(O)$_2$CH$_3$, —NO$_2$, =O, —OH, —OCH$_3$, —OCH$_2$CH$_3$, —OCH$_2$CH$_2$OCH$_3$, —OCH$_2$CH$_2$OH, —OCH$_2$CH$_2$N(CH$_3$)$_2$, —OP(O)(OH)$_2$, —S(O)$_2$N(CH$_3$)$_2$, —SCH$_3$, —S(O)$_2$CH$_3$, —S(O)$_3$H, cyclopropyl, cyclopropyl amide, cyclobutyl, oxetanyl, azetidinyl, 1-methylazetidin-3-yl)oxy, N-methyl-N-oxetan-3-ylamino, azetidin-1-ylmethyl, benzyloxyphenyl, pyrrolidin-1-yl, pyrrolidin-1-yl-methanone, piperazin-1-yl, morpholinomethyl, morpholinomethanone, or morpholino; R$^5$ is H, C$_1$-C$_9$ alkyl, C$_3$-C$_9$ cycloalkyl, C$_3$-C$_9$ heterocycle, C$_6$-C$_9$ aryl, C$_6$-C$_9$ heteroaryl, —(C$_1$-C$_6$ alkyldiyl)-(C$_3$-C$_9$ cycloalkyl), —(C$_1$-C$_6$ alkyldiyl)-(C$_3$-C$_9$ heterocycle), C(O)R$^b$, C(O)NR$^a$, SO$_2$R$^a$, or SO$_2$NR$^a$, optionally substituted with one or more of halogen, CN, OR$^a$, N(R$^a$)$_2$, C$_1$-C$_9$ alkyl, C$_3$-C$_9$ cycloalkyl, C$_3$-C$_9$ heterocycle, C$_6$-C$_9$ aryl, C$_6$-C$_9$ heteroaryl, C(O)R$^b$, C(O)NR$^a$, SO$_2$R$^a$, or SO$_2$NR$^a$; R$^6$ is F, Cl, Br, I, —CN, —CH$_3$, —CH$_2$CH$_3$, —CH(CH$_3$)$_2$, —CH$_2$CH(CH$_3$)$_2$, —CH$_2$OH, —CH$_2$OCH$_3$, —CH$_2$CH$_2$OH, —C(CH$_3$)$_2$OH, —CH(OH)CH(CH$_3$)$_2$, —C(CH$_3$)$_2$CH$_2$OH, —CH$_2$CH$_2$SO$_2$CH$_3$, —CH$_2$OP(O)(OH)$_2$, —CH$_2$F, —CHF$_2$, —CH$_2$NH$_2$, —CH$_2$NHSO$_2$CH$_3$, —CH$_2$NHCH$_3$, —CH$_2$N(CH$_3$)$_2$, —CF$_3$, —CH$_2$CF$_3$, —CH$_2$CHF$_2$, —CH(CH$_3$)CN, —C(CH$_3$)$_2$CN, —CH$_2$CN, —CO$_2$H, —COCH$_3$, —CO$_2$CH$_3$, —CO$_2$C(CH$_3$)$_3$, —COCH(OH)CH$_3$, —CONH$_2$, —CONHCH$_3$, —CONHCH$_2$CH$_3$, —CONHCH(CH$_3$)$_2$, —CON(CH$_3$)$_2$, —C(CH$_3$)$_2$CONH$_2$, —NH$_2$, —NHCH$_3$, —N(CH$_3$)$_2$, —NHCOCH$_3$, —N(CH$_3$)COCH$_3$, —NHS(O)$_2$CH$_3$, —N(CH$_3$)C(CH$_3$)$_2$CONH$_2$, —N(CH$_3$)CH$_2$CH$_2$S(O)$_2$CH$_3$, —NO$_2$, =O, —OH, —OCH$_3$, —OCH$_2$CH$_3$, —OCH$_2$CH$_2$OCH$_3$, —OCH$_2$CH$_2$OH, —OCH$_2$CH$_2$N(CH$_3$)$_2$, —OP(O)(OH)$_2$, —S(O)$_2$N(CH$_3$)$_2$, —SCH$_3$, —S(O)$_2$CH$_3$, —S(O)$_3$H, cyclopropyl, cyclopropyl amide, cyclobutyl, oxetanyl, azetidinyl, 1-methylazetidin-3-yl)oxy, N-methyl-N-oxetan-3-ylamino, azetidin-1-ylmethyl, benzyloxyphenyl, pyrrolidin-1-yl, pyrrolidin-1-yl-methanone, piperazin-1-yl, morpholinomethyl, morpholinomethanone, or morpholino; and m is 0, 1, 2, 3, or 4; where alkyldiyl, fluoroalkyldiyl, aryldiyl, carbocyclyldiyl, heterocyclyldiyl, and heteroaryldiyl are optionally substituted with one or more groups independently selected from the group consisting of F, Cl, Br, I, —CN, —CH$_3$, —CH$_2$CH$_3$, —CH(CH$_3$)$_2$, —CH$_2$CH(CH$_3$)$_2$, —CH$_2$OH, —CH$_2$OCH$_3$, —CH$_2$CH$_2$OH, —C(CH$_3$)$_2$OH, —CH(OH)CH(CH$_3$)$_2$, —C(CH$_3$)$_2$CH$_2$OH, —CH$_2$CH$_2$SO$_2$CH$_3$, —CH$_2$OP(O)(OH)$_2$, —CH$_2$F, —CHF$_2$, —CF$_3$, —CH$_2$CF$_3$, —CH$_2$CHF$_2$, —CH$_2$CH$_2$F, —CH(CH$_3$)CN, —C(CH$_3$)$_2$CN, —CH$_2$CN, —CH$_2$NH$_2$, —CH$_2$NHSO$_2$CH$_3$, —CH$_2$NHCH$_3$, —CH$_2$N(CH$_3$)$_2$, —CO$_2$H, —COCH$_3$, —CO$_2$CH$_3$, —CO$_2$C(CH$_3$)$_3$, —COCH(OH)CH$_3$, —CONH$_2$, —CONHCH$_3$, —CON(CH$_3$)$_2$, —C(CH$_3$)$_2$CONH$_2$, —NH$_2$, —NHCH$_3$, —N(CH$_3$)$_2$, —NHCOCH$_3$, —N(CH$_3$)COCH$_3$, —NHS(O)$_2$CH$_3$, —N(CH$_3$)C(CH$_3$)$_2$CONH$_2$, —N(CH$_3$)CH$_2$CH$_2$S(O)$_2$CH$_3$, —NO$_2$, =O, —OH, —OCH$_3$, —OCH$_2$CH$_3$, —OCH$_2$CH$_2$OCH$_3$, —OCH$_2$CH$_2$OH, —OCH$_2$CH$_2$N(CH$_3$)$_2$, —OP(O)(OH)$_2$, —S(O)$_2$N(CH$_3$)$_2$, —SCH$_3$, —S(O)$_2$CH$_3$, —S(O)$_3$H, cyclopropyl, cyclopropyl amide, cyclobutyl, oxetanyl, azetidinyl, 1-methylazetidin-3-yl)oxy, N-methyl-N-oxetan-3-ylamino, azetidin-1-ylmethyl, benzyloxyphenyl, pyrrolidin-1-yl, pyrrolidin-1-yl-methanone, piperazin-1-yl, morpholinomethyl, morpholinomethanone, and morpholino.

In one instance of the compounds of formula (3), Y$^1$ is CR$^b$ and Y$^3$ is NR$^a$. In another instance of the compounds of formula (3), Y$^1$ is N and Y$^3$ is C(R$^b$)$_2$. In another instance of the compounds of formula (3), Y$^2$ is —(CH$_2$)—. In another instance of the compounds of formula (3), Y$^2$ is —(CH$_2$CH$_2$)—.

In another instance of the compounds of formula (3), R$^c$ is H. In another instance of the compounds of formula (3), Cy is C$_6$-C$_{20}$ aryldiyl, C$_6$-C$_{20}$ aryldiyl is phenyldiyl, and phenyldiyl is substituted with one or more F. In another instance of the compounds of formula (3), R$^1$ and R$^2$ are H. In another instance of the compounds of formula (3), R$^3$ is H, and R$^4$ is —CH$_3$. In another instance of the compounds of formula (3), R$^5$ is C$_1$-C$_6$ fluoroalkyl. In another instance of the compounds of formula (3), m is 0.

In another instance, the endocrine therapy comprises a compound of formula (3) having formula (3 a):

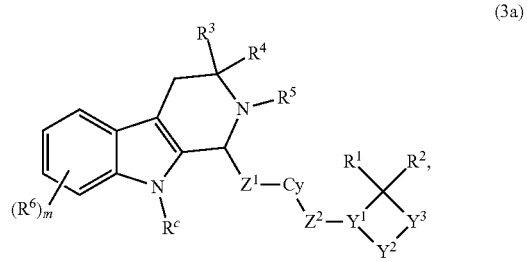

(3a)

or a stereoisomer, tautomer, or pharmaceutically acceptable salt thereof, wherein: Y$^1$ is CR$^b$ or N; Y$^2$ is —(CH$_2$)—, —(CH$_2$CH$_2$)—, or NR$^a$; Y$^3$ is NR$^a$ or C(R$^b$)$_2$; where one of Y$^1$, Y$^2$ and Y$^3$ is N or NR$^a$; R$^a$ is independently H, C$_1$-C$_6$ alkyl, C$_2$-C$_8$ alkenyl, propargyl, C$_3$-C$_6$ cycloalkyl, and C$_3$-C$_6$ heterocyclyl, optionally substituted with one or more groups independently selected from F, Cl, Br, I, CN, OH, OCH$_3$, or SO$_2$CH$_3$; R$^b$ is independently H, —O(C$_1$-C$_3$ alkyl), C$_1$-C$_6$ alkyl, C$_2$-C$_8$ alkenyl, propargyl, —(C$_1$-C$_6$ alkyldiyl)-(C$_3$-C$_6$ cycloalkyl), C$_3$-C$_6$ cycloalkyl, and C$_3$-C$_6$ heterocyclyl, optionally substituted with one or more groups independently selected from F, Cl, Br, I, CN, —CH$_2$F, —CHF$_2$, —CF$_3$, —CH$_2$CF$_3$, —CH$_2$CHF$_2$, —CH$_2$CH$_2$F, OH, OCH$_3$, or SO$_2$CH$_3$; R$^c$ is independently H, C$_1$-C$_6$ alkyl, allyl, propargyl, optionally substituted with one or more groups independently selected from F, Cl, Br, I, CN, OH, OCH$_3$, or SO$_2$CH$_3$; Z$^1$ is CR$^a$R$^b$, C(O), or a bond; Cy is C$_6$-C$_{20}$ aryldiyl, C$_3$-C$_{12}$ carbocyclyldiyl, C$_2$-C$_{20}$ heterocyclyldiyl, or C$_1$-C$_{20}$ heteroaryldiyl; Z$^2$ is O; R$^1$, R$^2$, R$^3$ and R$^4$ are each independently H, F, Cl, Br, I, —CN, —CH$_3$, —CH$_2$CH$_3$, —CH(CH$_3$)$_2$, —CH$_2$CH(CH$_3$)$_2$, —CH$_2$OH, —CH$_2$OCH$_3$, —CH$_2$CH$_2$OH, —C(CH$_3$)$_2$OH, —CH(OH)CH(CH$_3$)$_2$, —C(CH$_3$)$_2$CH$_2$OH, —CH$_2$CH$_2$SO$_2$CH$_3$, —CH$_2$OP(O)(OH)$_2$, —CH$_2$F, —CHF$_2$, —CH$_2$NH$_2$, —CH$_2$NHSO$_2$CH$_3$, —CH$_2$NHCH$_3$, —CH$_2$N(CH$_3$)$_2$, —CF$_3$, —CH$_2$CF$_3$, —CH$_2$CHF$_2$, —CH(CH$_3$)CN, —C(CH$_3$)$_2$CN, —CH$_2$CN, —CO$_2$H, —COCH$_3$, —CO$_2$CH$_3$, —CO$_2$C(CH$_3$)$_3$, —COCH(OH)CH$_3$, —CONH$_2$, —CONHCH$_3$, —CONHCH$_2$CH$_3$, —CONHCH(CH$_3$)$_2$, —CON(CH$_3$)$_2$, —C(CH$_3$)$_2$CONH$_2$, —NH$_2$, —NHCH$_3$, —N(CH$_3$)$_2$, —NHCOCH$_3$, —N(CH$_3$)COCH$_3$, —NHS(O)$_2$CH$_3$, —N(CH$_3$)C(CH$_3$)$_2$CONH$_2$, —N(CH$_3$)CH$_2$CH$_2$S(O)$_2$CH$_3$, —NO$_2$, =O, —OH, —OCH$_3$, —OCH$_2$CH$_3$, —OCH$_2$CH$_2$OCH$_3$, —OCH$_2$CH$_2$OH, —OCH$_2$CH$_2$N(CH$_3$)$_2$, —OP(O)(OH)$_2$, —S(O)$_2$N(CH$_3$)$_2$, —SCH$_3$, —S(O)$_2$CH$_3$, —S(O)$_3$H, cyclopropyl, cyclopropyl amide, cyclobutyl, oxetanyl, azetidinyl, 1-methylazetidin-3-yl)oxy, N-methyl-N-oxetan-3-ylamino, azetidin-1-ylmethyl, benzyloxyphenyl, pyrrolidin-1-yl, pyrrolidin-1-yl-methanone, piperazin-1-yl, morpholinomethyl, morpholinomethanone, or morpholino; R$^5$ is H, C$_1$-C$_9$ alkyl, C$_3$-C$_9$ cycloalkyl, C$_3$-C$_9$ heterocycle, C$_6$-C$_9$ aryl, C$_6$-C$_9$ heteroaryl, —(C$_1$-C$_6$ alkyldiyl)-(C$_3$-C$_9$ cycloalkyl), —(C$_1$-C$_6$ alkyldiyl)-(C$_3$-C$_9$ heterocycle), C(O)R$^b$, C(O)NR$^a$, SO$_2$R$^a$, and SO$_2$NR$^a$, optionally substituted with one or more of halogen, CN, OR$^a$, N(R$^a$)$_2$, C$_1$-C$_9$ alkyl, C$_3$-C$_9$ cycloalkyl, C$_3$-C$_9$ heterocycle, C$_6$-C$_9$ aryl, C$_6$-C$_9$ heteroaryl, C(O)R$^b$, C(O)NR$^a$, SO$_2$R$^a$, or SO$_2$NR$^a$; R$^6$ is F, Cl, Br, I, —CN, —CH$_3$, —CH$_2$CH$_3$, —CH(CH$_3$)$_2$, —CH$_2$CH(CH$_3$)$_2$, —CH$_2$OH, —CH$_2$OCH$_3$, —CH$_2$CH$_2$OH, —C(CH$_3$)$_2$OH, —CH(OH)CH(CH$_3$)$_2$, —C(CH$_3$)$_2$CH$_2$OH, —CH$_2$CH$_2$SO$_2$CH$_3$, —CH$_2$OP(O)(OH)$_2$, —CH$_2$F, —CHF$_2$, —CH$_2$NH$_2$, —CH$_2$NHSO$_2$CH$_3$, —CH$_2$NHCH$_3$, —CH$_2$N(CH$_3$)$_2$, —CF$_3$, —CH$_2$CF$_3$, —CH$_2$CHF$_2$, —CH$_2$CH$_2$F, —CH(CH$_3$)CN, —C(CH$_3$)$_2$CN, —CH$_2$CN, —CO$_2$H, —COCH$_3$, —CO$_2$CH$_3$, —CO$_2$C(CH$_3$)$_3$, —COCH(OH)CH$_3$, —CONH$_2$, —CONHCH$_3$, —CONHCH$_2$CH$_3$, —CONHCH(CH$_3$)$_2$, —CON(CH$_3$)$_2$, —C(CH$_3$)$_2$CONH$_2$, —NH$_2$, —NHCH$_3$, —N(CH$_3$)$_2$, —NHCOCH$_3$, —N(CH$_3$)COCH$_3$, —NHS(O)$_2$CH$_3$, —N(CH$_3$)C(CH$_3$)$_2$CONH$_2$, —N(CH$_3$)CH$_2$CH$_2$S(O)$_2$CH$_3$, —NO$_2$, =O, —OH, —OCH$_3$, —OCH$_2$CH$_3$, —OCH$_2$CH$_2$OCH$_3$, —OCH$_2$CH$_2$OH, —OCH$_2$CH$_2$N(CH$_3$)$_2$, —OP(O)(OH)$_2$, —S(O)$_2$N(CH$_3$)$_2$, —SCH$_3$, —S(O)$_2$CH$_3$, —S(O)$_3$H, cyclopropyl, cyclopropyl amide, cyclobutyl, oxetanyl, azetidinyl, 1-methylazetidin-3-yl)oxy, N-methyl-N-oxetan-3-ylamino, azetidin-1-ylmethyl, benzyloxyphenyl, pyrrolidin-1-yl, pyrrolidin-1-yl-methanone, piperazin-1-yl, morpholinomethyl, morpholino-methanone, or morpholino; and m is 0, 1, 2, 3, or 4; where alkyldiyl, fluoroalkyldiyl, aryldiyl, carbocyclyldiyl, heterocyclyldiyl, and heteroaryldiyl are optionally substituted with one or more groups independently selected from the group consisting of F, Cl, Br, I, —CN, —CH$_3$, —CH$_2$CH$_3$, —CH(CH$_3$)$_2$, —CH$_2$CH(CH$_3$)$_2$, —CH$_2$OH, —CH$_2$OCH$_3$, —CH$_2$CH$_2$OH, —C(CH$_3$)$_2$OH, —CH(OH)CH(CH$_3$)$_2$, —C(CH$_3$)$_2$CH$_2$OH, —CH$_2$CH$_2$SO$_2$CH$_3$, —CH$_2$OP(O)(OH)$_2$, —CH$_2$F, —CHF$_2$, —CF$_3$, —CH$_2$CF$_3$, —CH$_2$CHF$_2$, —CH$_2$CH$_2$F, —CH(CH$_3$)CN, —C(CH$_3$)$_2$CN, —CH$_2$CN, —CH$_2$NH$_2$, —CH$_2$NHSO$_2$CH$_3$, —CH$_2$NHCH$_3$, —CH$_2$N(CH$_3$)$_2$, —CO$_2$H, —COCH$_3$, —CO$_2$CH$_3$, —CO$_2$C(CH$_3$)$_3$, —COCH(OH)CH$_3$, —CONH$_2$, —CONHCH$_3$, —CON(CH$_3$)$_2$, —C(CH$_3$)$_2$CONH$_2$, —NH$_2$, —NHCH$_3$, —N(CH$_3$)$_2$, NHCOCH$_3$, —N(CH$_3$)COCH$_3$, —NHS(O)$_2$CH$_3$, —N(CH$_3$)C(CH$_3$)$_2$CONH$_2$, —N(CH$_3$) CH$_2$CH$_2$S(O)$_2$CH$_3$, —NO$_2$, =O, —OH, —OCH$_3$, —OCH$_2$CH$_3$, —OCH$_2$CH$_2$OCH$_3$, —OCH$_2$CH$_2$OH, —OCH$_2$CH$_2$N(CH$_3$)$_2$, —OP(O)(OH)$_2$, —S(O)$_2$N(CH$_3$)$_2$, —SCH$_3$, —S(O)$_2$CH$_3$, —S(O)$_3$H, cyclopropyl, cyclopropyl amide, cyclobutyl, oxetanyl, azetidinyl, 1-methylazetidin-3-yl)oxy, N-methyl-N-oxetan-3-ylamino, azetidin-1-ylmethyl, benzyloxyphenyl, pyrrolidin-1-yl, pyrrolidin-1-yl-methanone, piperazin-1-yl, morpholinomethyl, morpholinomethanone, and morpholino.

In one instance, the compound of formula (3 a) comprises formula (3b):

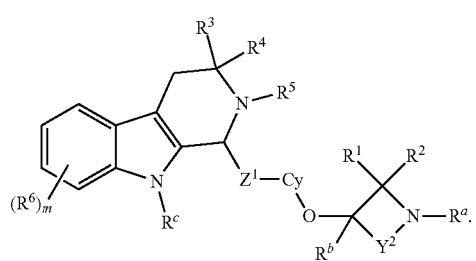

(3b)

In another instance, the compound of formula (3a) comprises formula (3c):

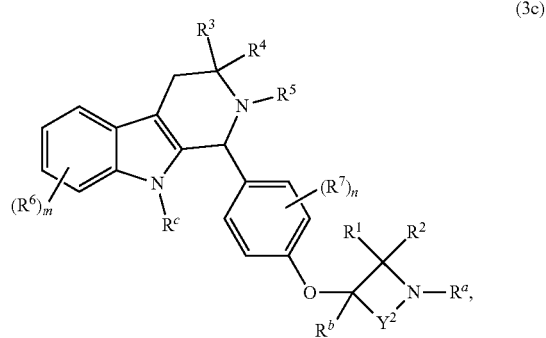

(3c)

wherein R$^7$ is F, Cl, Br, I, —CN, —CH$_3$, —CH$_2$CH$_3$, —CH(CH$_3$)$_2$, —CH$_2$CH(CH$_3$)$_2$, —CH$_2$OH, —CH$_2$OCH$_3$, —CH$_2$CH$_2$OH, —C(CH$_3$)$_2$OH, —CH(OH)CH(CH$_3$)$_2$, —C(CH$_3$)$_2$CH$_2$OH, —CH$_2$CH$_2$SO$_2$CH$_3$, —CH$_2$OP(O)(OH)$_2$, —CH$_2$F, —CHF$_2$, —CH$_2$NH$_2$, —CH$_2$NHSO$_2$CH$_3$, —CH$_2$NHCH$_3$, —CH$_2$N(CH$_3$)$_2$, —CF$_3$, —CH$_2$CF$_3$, —CH$_2$CHF$_2$, —CH(CH$_3$)CN, —C(CH$_3$)$_2$CN, —CH$_2$CN, —CO$_2$H, —COCH$_3$, —CO$_2$CH$_3$, —CO$_2$C(CH$_3$)$_3$, —COCH(OH)CH$_3$, —CONH$_2$, —CONHCH$_3$, —CONHCH$_2$CH$_3$, —CONHCH(CH$_3$)$_2$, —CON(CH$_3$)$_2$, —C(CH$_3$)$_2$CONH$_2$, —NH$_2$, —NHCH$_3$, —N(CH$_3$)$_2$, —NHCOCH$_3$, —N(CH$_3$)COCH$_3$, —NHS(O)$_2$CH$_3$, —N(CH$_3$)C(CH$_3$)$_2$CONH$_2$, —N(CH$_3$)CH$_2$CH$_2$S(O)$_2$CH$_3$, —NO$_2$, =O, —OH, —OCH$_3$, —OCH$_2$CH$_3$, —OCH₂CH₂OCH₃, —OCH₂CH₂OH, —OCH₂CH₂N(CH₃)₂, —OP(O)(OH)₂, —S(O)₂N(CH₃)₂, —SCH₃, —S(O)₂CH₃, —S(O)₃H, cyclopropyl, cyclopropylamide, oxetanyl, azetidinyl, 1-methylazetidin-3-yl)oxy, N-methyl-N-oxetan-3-ylamino, azetidin-1-ylmethyl, benzyloxyphenyl, pyrrolidin-1-yl, pyrrolidin-1-yl-methanone, piperazin-1-yl, morpholinomethyl, morpholino-methanone, or morpholino; and n is 0, 1, 2, 3, or 4.

In another instance, the compound of formula (3a) comprises formula (3d):

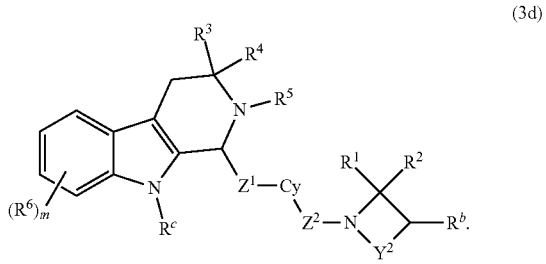

(3d)

In still another instance, the compound of formula (3a) comprises formula (3e):

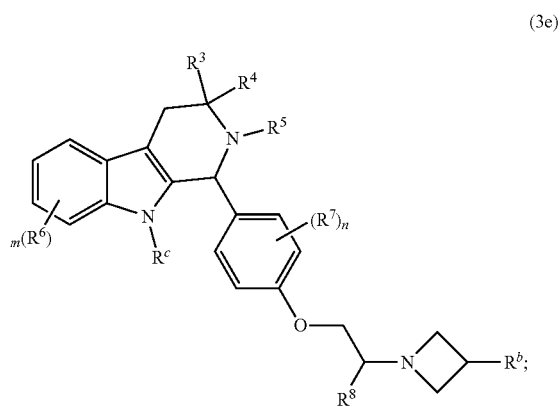

(3e)

wherein R⁸ is H or —CH₃.

In another instance of the compounds of formula (3a)-(3e), Y¹ is CR^b and Y³ is NR^a. In another instance of the compounds of formula (3a)-(3e), Y¹ is N and Y³ is C(R^b)₂. In another instance of the compounds of formula (3a)-(3e), Y² is —(CH₂)— or —(CH₂CH₂)—. In another instance of the compounds of formula (3a)-(3e), R^c is H. In another instance of the compounds of formula (3a)-(3e), Cy is phenyldiyl. In one instance of the compounds of formula (3a)-(3e), phenyldiyl is substituted with one or more F.

In another instance of the compounds of formula (3a)-(3e), R¹ and R² are H. In another instance of the compounds of formula (3a)-(3e), R³ is H, and R⁴ is —CH₃. In another instance of the compounds of formula (3a)-(3e), R⁵ is C₁-C₆ fluoroalkyl. In another instance of the compounds of formula (3a)-(3e), m is 0.

In another aspect, the endocrine therapy comprises a compound having formula: (1R,3R)-1-(2,6-difluoro-4-((1-(3-fluoropropyl)azetidin-3-yl)oxy)phenyl)-2-(2-fluoro-2-methylpropyl)-3-methyl-2,3,4,9-tetrahydro-1H-pyrido[3,4-b]indole; (1R,3R)-1-(2,6-difluoro-4-(2-(3-(fluoromethyl)azetidin-1-yl)ethoxy)phenyl)-2-(2-fluoro-2-methylpropyl)-3-methyl-2,3,4,9-tetrahydro-1H-pyrido[3,4-b]indole; 1-((1R,3R)-1-(2,6-difluoro-4-(2-(3-(fluoromethyl)azetidin-1-yl)ethoxy)phenyl)-3-methyl-3,4-dihydro-1H-pyrido[3,4-b]indol-2(9H)-yl)-2-methylpropan-1-one; 1-((1R,3R)-1-(2,6-difluoro-4-(2-(3-(fluoromethyl)azetidin-1-yl)ethoxy)phenyl)-3-methyl-3,4-dihydro-1H-pyrido[3,4-b]indol-2(9H)-yl)-2-fluoro-2-methylpropan-1-one; (1R,3R)-1-(4-(2-(3-(difluoromethyl)azetidin-1-yl)ethoxy)-2,6-difluorophenyl)-2-(2-fluoro-2-methylpropyl)-3-methyl-2,3,4,9-tetrahydro-1H-pyrido[3,4-b]indole; (1R,3R)-1-(4-((1-(3-chloropropyl)azetidin-3-yl)oxy)-2,6-difluorophenyl)-2-(2-fluoro-2-methylpropyl)-3-methyl-2,3,4,9-tetrahydro-1H-pyrido[3,4-b]indole; (1R,3R)-1-(2,6-difluoro-4-((1-propylazetidin-3-yl)oxy)phenyl)-2-(2-fluoro-2-methylpropyl)-3-methyl-2,3,4,9-tetrahydro-1H-pyrido[3,4-b]indole; (1R,3R)-1-(2,6-difluoro-4-((S)-2-((R)-3-(fluoromethyl)pyrrolidin-1-yl)propoxy)phenyl)-2-(2-fluoro-2-methylpropyl)-3-methyl-2,3,4,9-tetrahydro-1H-pyrido[3,4-b]indole; (1R,3R)-1-(2,6-difluoro-4-(2-((R)-3-(fluoromethyl)pyrrolidin-1-yl)ethoxy)phenyl)-2-(2-fluoro-2-methylpropyl)-3-methyl-2,3,4,9-tetrahydro-1H-pyrido[3,4-b]indole; (1R,3R)-2-(2-fluoro-2-methylpropyl)-1-(6-(2-(3-(fluoromethyl)azetidin-1-yl)ethoxy)pyridin-3-yl)-3-methyl-2,3,4,9-tetrahydro-1H-pyrido[3,4-b]indole; (1S,3R)-2-(2-fluoro-2-methylpropyl)-1-(3-fluoro-5-(2-(3-(fluoromethyl)azetidin-1-yl)ethoxy)pyridin-2-yl)-3-methyl-2,3,4,9-tetrahydro-1H-pyrido[3,4-b]indole; (1R,3R)-2-(cyclobutylmethyl)-1-(2,6-difluoro-4-(2-(3-(fluoromethyl)azetidin-1-yl)ethoxy)phenyl)-3-methyl-2,3,4,9-tetrahydro-1H-pyrido[3,4-b]indole; (1R,3R)-1-(2,6-difluoro-4-(2-(3-(fluoromethyl)azetidin-1-yl)ethoxy)phenyl)-3-methyl-2-((3-methyloxetan-3-yl)methyl)-2,3,4,9-tetrahydro-1H-pyrido[3,4-b]indole; (1R,3R)-1-(2,6-difluoro-4-(2-(3-(fluoromethyl)azetidin-1-yl)ethoxy)phenyl)-3-methyl-2-(oxetan-3-ylmethyl)-2,3,4,9-tetrahydro-1H-pyrido[3,4-b]indole; (1R,3R)-1-(2,6-difluoro-4-(2-(3-(fluoromethyl)azetidin-1-yl)ethoxy)phenyl)-3-methyl-2-(oxetan-3-yl)-2,3,4,9-tetrahydro-1H-pyrido[3,4-b]indole; (1R,3R)-1-(2,6-difluoro-4-(2-(pyrrolidin-1-yl)ethoxy)phenyl)-2-(2-fluoro-2-methylpropyl)-3-methyl-2,3,4,9-tetrahydro-1H-pyrido[3,4-b]indole; (1R,3R)-1-(2,6-difluoro-4-(2-(piperidin-1-yl)ethoxy)phenyl)-2-(2-fluoro-2-methylpropyl)-3-methyl-2,3,4,9-tetrahydro-1H-pyrido[3,4-b]indole; (1-(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethyl)azetidin-3-yl)methanol; (1R,3R)-2-(2-fluoro-2-methylpropyl)-1-(2-fluoro-4-(2-(3-(fluoromethyl)azetidin-1-yl)ethoxy)phenyl)-3-methyl-2,3,4,9-tetrahydro-1H-pyrido[3,4-b]indole; 1-((1R,3R)-1-(2,6-difluoro-4-(2-(3-(fluoromethyl)azetidin-1-yl)ethoxy)phenyl)-3-methyl-3,4-dihydro-1H-pyrido[3,4-b]indol-2(9H)-yl)ethanone; 1-((1R,3R)-1-(2,6-difluoro-4-(2-(3-(fluoromethyl)azetidin-1-yl)ethoxy)phenyl)-3-methyl-3,4-dihydro-1H-pyrido[3,4-b]indol-2(9H)-yl)-2-hydroxy-2-methylpropan-1-one; (R)-3-((1R,3R)-1-(2,6-difluoro-4-(2-(3-(fluoromethyl)azetidin-1-yl)ethoxy)phenyl)-3-methyl-3,4-dihydro-1H-pyrido[3,4-b]indol-2(9H)-yl)-2-methylpropan-1-ol; ((1R,3R)-1-(2,6-difluoro-4-(2-(3-(fluoromethyl)azetidin-1-yl)ethoxy)phenyl)-3-methyl-3,4-dihydro-1H-pyrido[3,4-b]indol-2(9H)-yl)((1s,3S)-3-hydroxycyclobutyl)methanone; 1-(1-(2,6-difluoro-4-(2-(3-(fluoromethyl)azetidin-1-yl)ethoxy)phenyl)-3,3-dimethyl-3,4-dihydro-1H-pyrido[3,4-b]indol-2(9H)-yl)-2-methylpropan-1-one; (1R,3R)-1-(2,6-difluoro-4-(2-(3-(fluoromethyl)azetidin-1-yl)ethoxy)phenyl)-3-methyl-2-(methylsulfonyl)-2,3,4,9-tetrahydro-1H-pyrido[3,4-b]indole; 1-[(1R,3R)-1-[2,6-difluoro-4-[2-[3-(fluoromethyl)azetidin-1-yl]ethoxy]phenyl]-3-methyl-1,3,4,9-tetrahydropyrido[3,4-b]indol-2-yl]-2-methyl-propan-2-ol;

(1R,3R)-1-[4-[2-[3-(difluoromethyl)azetidin-1-yl]ethoxy]-2,6-difluoro-phenyl]-2-(2-fluoro-2-methyl-propyl)-3-methyl-1,3,4,9-tetrahydropyrido[3,4-b]indole; (1R,3R)-1-[4-[1-(3-chloropropyl)azetidin-3-yl]oxy-2,6-difluoro-phenyl]-2-(2-fluoro-2-methyl-propyl)-3-methyl-1,3,4,9-tetrahydropyrido[3,4-b]indole; (1R,3R)-1-[2,6-difluoro-4-(1-propylazetidin-3-yl)oxy-phenyl]-2-(2-fluoro-2-methyl-propyl)-3-methyl-1,3,4,9-tetrahydropyrido[3,4-b]indole; ((1S,3R)-1-(2,6-difluoro-4-(2-(3-(fluoromethyl)azetidin-1-yl)ethoxy)phenyl)-2-(2-fluoro-2-methylpropyl)-2,3,4,9-tetrahydro-1H-pyrido[3,4-b]indol-3-yl)methanol; (1R,3R)-1-[4-(azetidin-3-yloxy)-2,6-difluoro-phenyl]-2-(2-fluoro-2-methyl-propyl)-3-methyl-1,3,4,9-tetrahydropyrido[3,4-b]indole; (1R,3R)-2-(2-fluoro-2-methylpropyl)-1-(2-fluoro-4-(2-(3-(fluoromethyl)azetidin-1-yl)ethoxy)phenyl)-3-methyl-2,3,4,9-tetrahydro-1H-pyrido[3,4-b]indole; (1R,3R)-2-cyclobutyl-1-[2,6-difluoro-4-[2-[3-(fluoromethyl)azetidin-1-yl]ethoxy]phenyl]-3-methyl-1,3,4,9-tetrahydropyrido[3,4-b]indole; (1R,3S)-1-[2,6-difluoro-4-[2-[3-(fluoromethyl)azetidin-1-yl]ethoxy]phenyl]-3-(fluoromethyl)-2-(2-fluoro-2-methyl-propyl)-1,3,4,9-tetrahydropyrido[3,4-b]indole; (1R,3R)-1-[2,6-difluoro-4-[2-[3-(fluoromethyl)azetidin-1-yl]ethoxy]phenyl]-2-[(3-fluorooxetan-3-yl)methyl]-3-methyl-1,3,4,9-tetrahydropyrido[3,4-b]indole; cyclohexyl((1R,3R)-1-(2,6-difluoro-4-(2-(3-(fluoromethyl)azetidin-1-yl)ethoxy)phenyl)-3-methyl-3,4-dihydro-1H-pyrido[3,4-b]indol-2(9H)-yl)methanone; 1-[(1R,3R)-1-[2,6-difluoro-4-[2-[3-(fluoromethyl)azetidin-1-yl]ethoxy]phenyl]-3-methyl-1,3,4,9-tetrahydropyrido[3,4-b]indol-2-yl]-2,2-dimethyl-propan-1-one; cyclopropyl((1R,3R)-1-(2,6-difluoro-4-(2-(3-(fluoromethyl)azetidin-1-yl)ethoxy)phenyl)-3-methyl-3,4-dihydro-1H-pyrido[3,4-b]indol-2(9H)-yl)methanone; (1R,3R)-1-[2,6-difluoro-4-[2-(3-methylazetidin-1-yl)ethoxy]phenyl]-2-(2-fluoro-2-methyl-propyl)-3-methyl-1,3,4,9-tetrahydropyrido[3,4-b]indole; (1R,3R)-1-(2,6-difluoro-4-(2-((R)-3-methylpyrrolidin-1-yl)ethoxy)phenyl)-2-(2-fluoro-2-methylpropyl)-3-methyl-2,3,4,9-tetrahydro-1H-pyrido[3,4-b]indole; (1R,3R)-1-[2,6-difluoro-4-[(2S)-2-pyrrolidin-1-ylpropoxy]phenyl]-2-(2-fluoro-2-methyl-propyl)-3-methyl-1,3,4,9-tetrahydropyrido[3,4-b]indole; (1R,3R)-1-[2,6-difluoro-4-[3-(fluoromethyl)azetidin-1-yl]propoxy]phenyl]-2-(2-fluoro-2-methyl-propyl)-3-methyl-1,3,4,9-tetrahydropyrido[3,4-b]indole; (1R,3R)-1-[2,6-difluoro-4-[(E)-3-[3-(fluoromethyl)azetidin-1-yl]prop-1-enyl]phenyl]-2-(2-fluoro-2-methyl-propyl)-3-methyl-1,3,4,9-tetrahydropyrido[3,4-b]indole; (1R,3R)-2-[(3,3-difluorocyclobutyl)methyl]-1-[2,6-difluoro-4-[2-[3-(fluoromethyl)azetidin-1-yl]ethoxy]phenyl]-3-methyl-1,3,4,9-tetrahydropyrido[3,4-b]indole; (1R,3R)-1-[2,6-difluoro-4-[2-[3-(fluoromethyl)azetidin-1-yl]ethoxy]phenyl]-2-(2,2-dimethylpropyl)-3-methyl-1,3,4,9-tetrahydropyrido[3,4-b]indole; cyclobutyl-[(1R,3R)-1-[2,6-difluoro-4-[2-[3-(fluoromethyl)azetidin-1-yl]ethoxy]phenyl]-3-methyl-1,3,4,9-tetrahydropyrido[3,4-b]indol-2-yl]methanone; cyclopentyl-[(1R,3R)-1-[2,6-difluoro-4-[2-[3-(fluoromethyl)azetidin-1-yl]ethoxy]phenyl]-3-methyl-1,3,4,9-tetrahydropyrido[3,4-b]indol-2-yl]methanone; (1R,3R)-1-[2,6-difluoro-4-[2-[(3S)-3-methylpyrrolidin-1-yl]ethoxy]phenyl]-2-(2-fluoro-2-methyl-propyl)-3-methyl-1,3,4,9-tetrahydropyrido[3,4-b]indole; (1R,3R)-1-[2,6-difluoro-4-[(2R)-2-pyrrolidin-1-ylpropoxy]phenyl]-2-(2-fluoro-2-methyl-propyl)-3-methyl-1,3,4,9-tetrahydropyrido[3,4-b]indole; (1R,3R)-1-[2,6-difluoro-4-[(1-propylazetidin-3-yl)methoxy]phenyl]-2-(2-fluoro-2-methyl-propyl)-3-methyl-1,3,4,9-tetrahydropyrido[3,4-b]indole; (1R,3R)-1-[2,6-difluoro-4-[2-[3-(fluoromethyl)azetidin-1-yl]ethoxy]phenyl]-2-[(1-fluorocyclobutyl)methyl]-3-methyl-1,3,4,9-tetrahydropyrido[3,4-b]indole; (S)-3-((1R,3R)-1-(2,6-difluoro-4-(2-(3-(fluoromethyl)azetidin-1-yl)ethoxy)phenyl)-3-methyl-3,4-dihydro-1H-pyrido[3,4-b]indol-2(9H)-yl)-2-fluoro-2-methylpropan-1-ol; (2R)-3-[(1R,3R)-1-[2,6-difluoro-4-[2-[3-(fluoromethyl)azetidin-1-yl]ethoxy]phenyl]-3-methyl-1,3,4,9-tetrahydropyrido[3,4-b]indol-2-yl]-2-fluoro-2-methyl-propan-1-ol; (1R,3R)-1-[4-[2-[3-(fluoromethyl)azetidin-1-yl]ethoxy]phenyl]-2-(2-fluoro-2-methyl-propyl)-3-methyl-1,3,4,9-tetrahydropyrido[3,4-b]indole; 2-cyclopropyl-1-[(1R,3R)-1-[2,6-difluoro-4-[2-[3-(fluoromethyl)azetidin-1-yl]ethoxy]phenyl]-3-methyl-1,3,4,9-tetrahydropyrido[3,4-b]indol-2-yl]ethanone; 2-cyclobutyl-1-[(1R,3R)-1-[2,6-difluoro-4-[2-[3-(fluoromethyl)azetidin-1-yl]ethoxy]phenyl]-3-methyl-1,3,4,9-tetrahydropyrido[3,4-b]indol-2-yl]ethanone; 1-[(1R,3R)-1-[2,6-difluoro-4-[2-[3-(fluoromethyl)azetidin-1-yl]ethoxy]phenyl]-3-methyl-1,3,4,9-tetrahydropyrido[3,4-b]indol-2-yl]-2,2-difluoro-propan-1-one; (1R,3R)-1-[2,6-difluoro-4-[2-[3-(fluoromethyl)-3-methyl-azetidin-1-yl]ethoxy]phenyl]-2-(2-fluoro-2-methyl-propyl)-3-methyl-1,3,4,9-tetrahydropyrido[3,4-b]indole; (1R,3R)-1-[2,6-difluoro-4-(1-methylazetidin-3-yl)oxy-phenyl]-2-(2-fluoro-2-methyl-propyl)-3-methyl-1,3,4,9-tetrahydropyrido[3,4-b]indole; (1R,3R)-1-[4-(1-ethylazetidin-3-yl)oxy-2,6-difluoro-phenyl]-2-(2-fluoro-2-methyl-propyl)-3-methyl-1,3,4,9-tetrahydropyrido[3,4-b]indole; (1R,3R)-1-[2,6-difluoro-4-(1-pentylazetidin-3-yl)oxy-phenyl]-2-(2-fluoro-2-methyl-propyl)-3-methyl-1,3,4,9-tetrahydropyrido[3,4-b]indole; (1R,3R)-1-[4-[1-(cyclopropylmethyl)azetidin-3-yl]oxy-2,6-difluoro-phenyl]-2-(2-fluoro-2-methyl-propyl)-3-methyl-1,3,4,9-tetrahydropyrido[3,4-b]indole; (1R,3R)-1-[4-[1-(cyclopentylmethyl)azetidin-3-yl]oxy-2,6-difluoro-phenyl]-2-(2-fluoro-2-methyl-propyl)-3-methyl-1,3,4,9-tetrahydropyrido[3,4-b]indole; (1R,3R)-1-[2,6-difluoro-4-[1-(2-fluoroethyl)azetidin-3-yl]oxy-phenyl]-2-(2-fluoro-2-methyl-propyl)-3-methyl-1,3,4,9-tetrahydropyrido[3,4-b]indole; (1R,3R)-1-[2,6-difluoro-4-(1-prop-2-ynylazetidin-3-yl)oxy-phenyl]-2-(2-fluoro-2-methyl-propyl)-3-methyl-1,3,4,9-tetrahydropyrido[3,4-b]indole; (1R,3R)-1-[2,6-difluoro-4-(1-isopropylazetidin-3-yl)oxy-phenyl]-2-(2-fluoro-2-methyl-propyl)-3-methyl-1,3,4,9-tetrahydropyrido[3,4-b]indole; (1R,3R)-1-[2,6-difluoro-4-(1-isobutylazetidin-3-yl)oxy-phenyl]-2-(2-fluoro-2-methyl-propyl)-3-methyl-1,3,4,9-tetrahydropyrido[3,4-b]indole; tert-butyl 3-[3,5-difluoro-4-[(1R,3R)-2-(2-fluoro-2-methyl-propyl)-3-methyl-1,3,4,9-tetrahydropyrido[3,4-b]indol-1-yl]phenoxy]azetidine-1-carboxylate; (1R,3R)-1-(2,6-difluoro-4-(2-(3-(fluoromethyl)azetidin-1-yl)ethoxy)phenyl)-3-ethyl-2-(2-fluoro-2-methylpropyl)-2,3,4,9-tetrahydro-1H-pyrido[3,4-b]indole; (1R,3S)-1-(2,6-difluoro-4-(2-(3-(fluoromethyl)azetidin-1-yl)ethoxy)phenyl)-3-ethyl-2-(2-fluoro-2-methylpropyl)-2,3,4,9-tetrahydro-1H-pyrido[3,4-b]indole; (1R,3R)-1-[2,6-difluoro-4-[2-[3-(fluoromethyl)azetidin-1-yl]ethoxy]phenyl]-3-methyl-2-[(1-methylcyclobutyl)methyl]-1,3,4,9-tetrahydropyrido[3,4-b]indole; (1R,3R)-1-[2,6-difluoro-4-[2-[3-(fluoromethyl)azetidin-1-yl]ethoxy]phenyl]-3-methyl-2-(2,2,2-trifluoroethyl)-1,3,4,9-tetrahydropyrido[3,4-b]indole; (1S,3R)-1-[2,6-difluoro-4-[2-[3-(fluoromethyl)azetidin-1-yl]ethoxy]phenyl]-3-methyl-2-(2,2,2-trifluoroethyl)-1,3,4,9-tetrahydropyrido[3,4-b]indole; (1R,3R)-1-[4-[1-(3,3-dimethoxypropyl)azetidin-3-yl]oxy-2,6-difluoro-phenyl]-2-(2-fluoro-2-methyl-propyl)-3-methyl-1,3,4,9-tetrahydropyrido[3,4-b]indole; (1R,3R)-1-[2-fluoro-4-[1-(3-fluoropropyl)azetidin-3-yl]oxy-phenyl]-2-(2-fluoro-2-methyl-propyl)-3-methyl-1,3,4,9-tetrahydropyrido[3,4-b]indole; 1-[2,6-difluoro-4-[2-

[3-(fluoromethyl)azetidin-1-yl]ethoxy]phenyl]-2-(2-fluoro-2-methyl-propyl)-1,3,4,9-tetrahydropyrido[3,4-b]indole; (1S,3R)-1-[4-[2-[3-(fluoromethyl)azetidin-1-yl]ethoxy]phenyl]-3-methyl-2-methylsulfonyl-1,3,4,9-tetrahydropyrido[3,4-b]indole; (1R,3R)-1-(4-(2-(3-(fluoromethyl)azetidin-1-yl)ethoxy)phenyl)-3-methyl-2-(methylsulfonyl)-2,3,4,9-tetrahydro-1H-pyrido[3,4-b]indole; 1-((1R,3R)-1-(2,6-difluoro-4-(2-(3-(fluoromethyl)azetidin-1-yl)ethoxy)phenyl)-3-methyl-3,4-dihydro-1H-pyrido[3,4-b]indol-2(9H)-yl)-3-hydroxy-2-methylpropan-1-one; azetidin-3-yl-[(1R,3R)-1-[2,6-difluoro-4-[2-[3-(fluoromethyl)azetidin-1-yl]ethoxy]phenyl]-3-methyl-1,3,4,9-tetrahydropyrido[3,4-b]indol-2-yl]methanone; ((1R,3R)-1-(2,6-difluoro-4-(2-(3-(fluoromethyl)azetidin-1-yl)ethoxy)phenyl)-3-methyl-3,4-dihydro-1H-pyrido[3,4-b]indol-2(9H)-yl)(2-fluorocyclopropyl)methanone; (1R,3R)-1-[2,6-difluoro-4-[(2S)-2-[(3R)-3-methylpyrrolidin-1-yl]propoxy]phenyl]-2-(2-fluoro-2-methyl-propyl)-3-methyl-1,3,4,9-tetrahydropyrido[3,4-b]indole; [(1R,3R)-1-[2,6-difluoro-4-[2-[3-(fluoromethyl)azetidin-1-yl]ethoxy]phenyl]-3-methyl-1,3,4,9-tetrahydropyrido[3,4-b]indol-2-yl]-phenyl-methanone; (1R,3R)-2-(cyclopropylmethyl)-1-[2,6-difluoro-4-[2-[3-(fluoromethyl)azetidin-1-yl]ethoxy]phenyl]-3-methyl-1,3,4,9-tetrahydropyrido[3,4-b]indole; (1R,3R)-1-[4-[1-(2-cyclopropylethyl)azetidin-3-yl]oxy-2,6-difluoro-phenyl]-2-(2-fluoro-2-methyl-propyl)-3-methyl-1,3,4,9-tetrahydropyrido[3,4-b]indole; (1R,3R)-1-[4-(1-allylazetidin-3-yl)oxy-2,6-difluoro-phenyl]-2-(2-fluoro-2-methyl-propyl)-3-methyl-1,3,4,9-tetrahydropyrido[3,4-b]indole; (1R,3R)-1-[4-[1-(cyclobutylmethyl)azetidin-3-yl]oxy-2,6-difluoro-phenyl]-2-(2-fluoro-2-methyl-propyl)-3-methyl-1,3,4,9-tetrahydropyrido[3,4-b]indole; (1R,3R)-1-[2,6-difluoro-4-(1-isopentylazetidin-3-yl)oxy-phenyl]-2-(2-fluoro-2-methyl-propyl)-3-methyl-1,3,4,9-tetrahydropyrido[3,4-b]indole; (1R,3R)-1-(2,6-difluoro-4-((1-(2-methylbutyl)azetidin-3-yl)oxy)phenyl)-2-(2-fluoro-2-methylpropyl)-3-methyl-2,3,4,9-tetrahydro-1H-pyrido[3,4-b]indole; (1R,3R)-1-(2,6-difluoro-4-((1-(pentan-2-yl)azetidin-3-yl)oxy)phenyl)-2-(2-fluoro-2-methylpropyl)-3-methyl-2,3,4,9-tetrahydro-1H-pyrido[3,4-b]indole; (1R,3R)-1-[4-(1-cyclobutylazetidin-3-yl)oxy-2,6-difluoro-phenyl]-2-(2-fluoro-2-methyl-propyl)-3-methyl-1,3,4,9-tetrahydropyrido[3,4-b]indole; (1R,3R)-1-[2,6-difluoro-4-[1-(oxetan-3-yl)azetidin-3-yl]oxy-phenyl]-2-(2-fluoro-2-methyl-propyl)-3-methyl-1,3,4,9-tetrahydropyrido[3,4-b]indole; (1R,3R)-1-[4-(1-cyclopropylazetidin-3-yl)oxy-2,6-difluoro-phenyl]-2-(2-fluoro-2-methyl-propyl)-3-methyl-1,3,4,9-tetrahydropyrido[3,4-b]indole; (1R,3R)-1-[2,6-difluoro-4-[1-(3-fluoropropyl)azetidin-3-yl]sulfanyl-phenyl]-2-(2-fluoro-2-methyl-propyl)-3-methyl-1,3,4,9-tetrahydropyrido[3,4-b]indole; (1R,3R)-1-[2,6-difluoro-4-[2-[3-(fluoromethyl)azetidin-1-yl]ethoxy]phenyl]-2-isobutyl-3-methyl-1,3,4,9-tetrahydropyrido[3,4-b]indole; (1R,3R)-1-(2,6-difluoro-4-(2-(3-(fluoromethyl)azetidin-1-yl)ethoxy)phenyl)-3-methyl-2-((R)-2-phenylpropyl)-2,3,4,9-tetrahydro-1H-pyrido[3,4-b]indole; (1R,3R)-1-(2,6-difluoro-4-(2-(3-(fluoromethyl)azetidin-1-yl)ethoxy)phenyl)-3-methyl-2-((S)-2-phenylpropyl)-2,3,4,9-tetrahydro-1H-pyrido[3,4-b]indole; (1R,3R)-1-[2,6-difluoro-4-(1-propylazetidin-3-yl)oxy-phenyl]-2-isobutyl-3-methyl-1,3,4,9-tetrahydropyrido[3,4-b]indole; (1R,3R)-2-(2-fluoro-2-methyl-propyl)-1-[4-[1-(3-fluoropropyl)azetidin-3-yl]oxyphenyl]-3-methyl-1,3,4,9-tetrahydropyrido[3,4-b]indole; (1R,3R)-1-[2,6-difluoro-4-[1-(3-fluoropropyl)azetidin-3-yl]oxy-phenyl]-3-methyl-2-methylsulfonyl-1,3,4,9-tetrahydropyrido[3,4-b]indole; 1-[2,6-difluoro-4-[2-[3-(fluoromethyl)azetidin-1-yl]ethoxy]phenyl]-3-methyl-1,3,4,9-tetrahydropyrido[3,4-b]indol-2-yl]-(3-fluorocyclobutyl)methanone; (1R,3R)-1-[4-[(2S)-2-[3-(difluoromethyl)azetidin-1-yl]propoxy]-2,6-difluoro-phenyl]-2-(2-fluoro-2-methyl-propyl)-3-methyl-1,3,4,9-tetrahydropyrido[3,4-b]indole; (1R,3R)-1-[2,6-difluoro-4-[2-[3-fluoro-3-(fluoromethyl)azetidin-1-yl]ethoxy]phenyl]-2-(2-fluoro-2-methyl-propyl)-3-methyl-1,3,4,9-tetrahydropyrido[3,4-b]indole; 4-[(1R,3R)-1-[2,6-difluoro-4-[2-[3-(fluoromethyl)azetidin-1-yl]ethoxy]phenyl]-3-methyl-1,3,4,9-tetrahydropyrido[3,4-b]indol-2-yl]-4-oxo-butanenitrile; (1R,3R)-2-(cyclohexylmethyl)-1-[2,6-difluoro-4-[2-[3-(fluoromethyl)azetidin-1-yl]ethoxy]phenyl]-3-methyl-1,3,4,9-tetrahydropyrido[3,4-b]indole; (1R,3R)-1-[2,6-difluoro-4-[1-[2-(oxetan-3-yl)ethyl]azetidin-3-yl]oxy-phenyl]-2-(2-fluoro-2-methyl-propyl)-3-methyl-1,3,4,9-tetrahydropyrido[3,4-b]indole; (1R,3R)-1-[4-[1-(cyclohexylmethyl)azetidin-3-yl]oxy-2,6-difluoro-phenyl]-2-(2-fluoro-2-methyl-propyl)-3-methyl-1,3,4,9-tetrahydropyrido[3,4-b]indole; (1R,3R)-1-[2-chloro-4-[2-[3-(fluoromethyl)azetidin-1-yl]ethoxy]phenyl]-2-(2-fluoro-2-methyl-propyl)-3-methyl-1,3,4,9-tetrahydropyrido[3,4-b]indole; (1R,3R)-1-[2-chloro-4-[1-(3-fluoropropyl)azetidin-3-yl]oxy-phenyl]-2-(2-fluoro-2-methyl-propyl)-3-methyl-1,3,4,9-tetrahydropyrido[3,4-b]indole; 1-((1R,3R)-1-(2,6-difluoro-4-(2-(3-(fluoromethyl)azetidin-1-yl)ethoxy)phenyl)-3-methyl-3,4-dihydro-1H-pyrido[3,4-b]indol-2(9H)-yl)-3-hydroxybutan-1-one; [(1R,3R)-1-[2,6-difluoro-4-[2-[3-(fluoromethyl)azetidin-1-yl]ethoxy]phenyl]-3-methyl-1,3,4,9-tetrahydropyrido[3,4-b]indol-2-yl]-(oxetan-3-yl)methanone; [(1R,3R)-1-[2,6-difluoro-4-[2-[3-(fluoromethyl)azetidin-1-yl]ethoxy]phenyl]-3-methyl-1,3,4,9-tetrahydropyrido[3,4-b]indol-2-yl]-(thietan-3-yl)methanone; (R)-1-((1R,3R)-1-(2,6-difluoro-4-(2-(3-(fluoromethyl)azetidin-1-yl)ethoxy)phenyl)-3-methyl-1,3,4,9-tetrahydro-2H-pyrido[3,4-b]indol-2-yl)-3-fluoro-2-methylpropan-1-one; (1R,3R)-2-(cyclopentylmethyl)-1-[2,6-difluoro-4-[2-[3-(fluoromethyl)azetidin-1-yl]ethoxy]phenyl]-3-methyl-1,3,4,9-tetrahydropyrido[3,4-b]indole; (1R,3R)-1-[4-[1-[(4,4-difluorocyclohexyl)methyl]azetidin-3-yl]oxy-2,6-difluoro-phenyl]-2-(2-fluoro-2-methyl-propyl)-3-methyl-1,3,4,9-tetrahydropyrido[3,4-b]indole; (S)-1-((1R,3R)-1-(2,6-difluoro-4-(2-(3-(fluoromethyl)azetidin-1-yl)ethoxy)phenyl)-3-methyl-1,3,4,9-tetrahydro-2H-pyrido[3,4-b]indol-2-yl)-3-fluoro-2-methylpropan-1-one; ((1R,3R)-1-(2,6-difluoro-4-(2-(3-(fluoromethyl)azetidin-1-yl)ethoxy)phenyl)-3-methyl-1,3,4,9-tetrahydro-2H-pyrido[3,4-b]indol-2-yl)(oxetan-2-yl)methanone; (1R,3R)-1-[2,6-difluoro-4-[2-[3-(fluoromethyl)azetidin-1-yl]ethoxy]phenyl]-3-methyl-2,3,4,9-tetrahydro-1H-pyrido[3,4-b]indole; 2-fluoro-1-[(1R,3R)-1-[4-[2-[3-(fluoromethyl)azetidin-1-yl]ethoxy]phenyl]-3-methyl-1,3,4,9-tetrahydropyrido[3,4-b]indol-2-yl]-2-methyl-propan-1-one; 1-[(1R,3R)-1-[2,6-difluoro-4-[1-(3-fluoropropyl)azetidin-3-yl]oxy-phenyl]-3-methyl-1,3,4,9-tetrahydropyrido[3,4-b]indol-2-yl]-2-fluoro-2-methyl-propan-1-one; 1-[(1R,3R)-1-[2,6-difluoro-4-[2-[3-(fluoromethyl)azetidin-1-yl]ethoxy]phenyl]-3-methyl-1,3,4,9-tetrahydropyrido[3,4-b]indol-2-yl]-2-(dimethylamino)ethanone; (1R,3R)-1-[2,6-difluoro-4-[1-[(1-fluorocyclopropyl)methyl]azetidin-3-yl]oxy-phenyl]-2-(2-fluoro-2-methyl-propyl)-3-methyl-1,3,4,9-tetrahydropyrido[3,4-b]indole; [(1R,3R)-1-[2,6-difluoro-4-[1-(3-fluoropropyl)azetidin-3-yl]oxy-phenyl]-3-methyl-1,3,4,9-tetrahydropyrido[3,4-b]indol-2-yl]-(1-fluorocyclobutyl)methanone; [(1R,3R)-1-[2,6-difluoro-4-[1-(3-fluoropropyl)azetidin-3-yl]oxy-phenyl]-3-methyl-1,3,4,9-tetrahydropyrido[3,4-b]indol-2-yl]-(1-methylcyclopropyl)methanone; (1R,3R)-1-[2,6-difluoro-4-[1-(3-fluoropropyl)

azetidin-3-yl]oxy-phenyl]-2-[[1-(fluoromethyl)cyclopropyl]methyl]-3-methyl-1,3,4,9-tetrahydropyrido[3,4-b]indole; [1-[[(1R,3R)-1-[2,6-difluoro-4-[1-(3-fluoropropyl)azetidin-3-yl]oxy-phenyl]-3-methyl-1,3,4,9-tetrahydropyrido[3,4-b]indol-2-yl]methyl]cyclopropyl]methanol; 2-fluoro-1-[(1S,3R)-1-[2-fluoro-4-[2-[3-(fluoromethyl)azetidin-1-yl]ethoxy]phenyl]-3-methyl-1,3,4,9-tetrahydropyrido[3,4-b]indol-2-yl]-2-methyl-propan-1-one; 2-fluoro-1-[(1R,3R)-1-[2-fluoro-4-[2-[3-(fluoromethyl)azetidin-1-yl]ethoxy]phenyl]-3-methyl-1,3,4,9-tetrahydropyrido[3,4-b]indol-2-yl]-2-methyl-propan-1-one; (1S,3R)-1-[2-fluoro-4-[2-[3-(fluoromethyl)azetidin-1-yl]ethoxy]phenyl]-3-methyl-2-methylsulfonyl-1,3,4,9-tetrahydropyrido[3,4-b]indole; (1R,3R)-1-[2-fluoro-4-[2-[3-(fluoromethyl)azetidin-1-yl]ethoxy]phenyl]-3-methyl-2-methylsulfonyl-1,3,4,9-tetrahydropyrido[3,4-b]indole; 3-((1R,3R)-1-(2,6-difluoro-4-((1-(3-fluoropropyl)azetidin-3-yl)oxy)phenyl)-3-methyl-1,3,4,9-tetrahydro-2H-pyrido[3,4-b]indol-2-yl)-2-fluoro-2-methylpropan-1-ol; 3-((1R,3R)-1-(2,6-difluoro-4-((1-(3-fluoropropyl)azetidin-3-yl)oxy)phenyl)-3-methyl-1,3,4,9-tetrahydro-2H-pyrido[3,4-b]indol-2-yl)-2-fluoro-2-methylpropan-1-ol; 2-fluoro-1-[(1S,3R)-1-[4-[2-[3-(fluoromethyl)azetidin-1-yl]ethoxy]phenyl]-3-methyl-1,3,4,9-tetrahydropyrido[3,4-b]indol-2-yl]-2-methyl-propan-1-one; (1R)-1-[2,6-difluoro-4-[2-[3-(fluoromethyl)azetidin-1-yl]ethoxy]phenyl]-2-(2-fluoro-2-methyl-propyl)-1,3,4,9-tetrahydropyrido[3,4-b]indole; (1S)-1-[2,6-difluoro-4-[2-[3-(fluoromethyl)azetidin-1-yl]ethoxy]phenyl]-2-(2-fluoro-2-methyl-propyl)-1,3,4,9-tetrahydropyrido[3,4-b]indole; [(1R,3R)-1-[2,6-difluoro-4-[1-(3-fluoropropyl)azetidin-3-yl]oxy-phenyl]-3-methyl-1,3,4,9-tetrahydropyrido[3,4-b]indol-2-yl]-(1-fluorocyclopropyl)methanone; (1R,3R)-6-chloro-1-(2,6-difluoro-4-((1-(3-fluoropropyl)azetidin-3-yl)oxy)phenyl)-2-(2-fluoro-2-methylpropyl)-3-methyl-2,3,4,9-tetrahydro-1H-pyrido[3,4-b]indole; (1R,3R)-1-(2,6-difluoro-4-(2-(3-(fluoromethyl)azetidin-1-yl)ethoxy)phenyl)-7-fluoro-2-(2-fluoro-2-methylpropyl)-3-methyl-2,3,4,9-tetrahydro-1H-pyrido[3,4-b]indole; (1R,3R)-1-(2,6-difluoro-4-(2-(3-(fluoromethyl)azetidin-1-yl)ethoxy)phenyl)-6-fluoro-2-(2-fluoro-2-methylpropyl)-3-methyl-2,3,4,9-tetrahydro-1H-pyrido[3,4-b]indole; (1R,3R)-1-(2,6-difluoro-4-((1-(3-fluoropropyl)azetidin-3-yl)oxy)phenyl)-6-fluoro-2-(2-fluoro-2-methylpropyl)-3-methyl-2,3,4,9-tetrahydro-1H-pyrido[3,4-b]indole; (1-(((1R,3R)-1-(2,6-difluoro-4-(2-(3-(fluoromethyl)azetidin-1-yl)ethoxy)phenyl)-3-methyl-1,3,4,9-tetrahydro-2H-pyrido[3,4-b]indol-2-yl)methyl)cyclopropyl)methanol; (1S,3S)-6-chloro-1-(2,6-difluoro-4-((1-(3-fluoropropyl)azetidin-3-yl)oxy)phenyl)-2-(2-fluoro-2-methylpropyl)-3-methyl-2,3,4,9-tetrahydro-1H-pyrido[3,4-b]indole; (1S,3S)-1-(2,6-difluoro-4-(2-(3-(fluoromethyl)azetidin-1-yl)ethoxy)phenyl)-6-fluoro-2-(2-fluoro-2-methylpropyl)-3-methyl-2,3,4,9-tetrahydro-1H-pyrido[3,4-b]indole; (1R,3R)-1-[2,6-difluoro-4-[1-(3-fluoropropyl)azetidin-3-yl]oxy-phenyl]-3-methyl-2-[(3-methyloxetan-3-yl)methyl]-1,3,4,9-tetrahydropyrido[3,4-b]indole; (1R,3R)-1-(2,6-difluoro-4-(2-(3-(fluoromethyl)azetidin-1-yl)ethoxy)phenyl)-5-fluoro-2-(2-fluoro-2-methylpropyl)-3-methyl-2,3,4,9-tetrahydro-1H-pyrido[3,4-b]indole; (1R,3R)-1-(2,6-difluoro-4-((1-(3-fluoropropyl)azetidin-3-yl)oxy)phenyl)-7-fluoro-2-(2-fluoro-2-methylpropyl)-3-methyl-2,3,4,9-tetrahydro-1H-pyrido[3,4-b]indole; (1R,3R)-1-(2,6-difluoro-4-((1-(3-fluoropropyl)azetidin-3-yl)oxy)phenyl)-5-fluoro-2-(2-fluoro-2-methylpropyl)-3-methyl-2,3,4,9-tetrahydro-1H-pyrido[3,4-b]indole; (1R,3R)-2-(2-fluoro-2-methyl-propyl)-1-[4-[2-[(3R)-3-(fluoromethyl)pyrrolidin-1-yl]ethoxy]phenyl]-3-methyl-1,3,4,9-tetrahydropyrido[3,4-b]indole; (1S,3S)-1-(2,6-difluoro-4-(2-(3-(fluoromethyl)azetidin-1-yl)ethoxy)phenyl)-5-fluoro-2-(2-fluoro-2-methylpropyl)-3-methyl-2,3,4,9-tetrahydro-1H-pyrido[3,4-b]indole; (1S,3S)-1-(2,6-difluoro-4-((1-(3-fluoropropyl)azetidin-3-yl)oxy)phenyl)-7-fluoro-2-(2-fluoro-2-methylpropyl)-3-methyl-2,3,4,9-tetrahydro-1H-pyrido[3,4-b]indole; (1S,3S)-1-(2,6-difluoro-4-((1-(3-fluoropropyl)azetidin-3-yl)oxy)phenyl)-5-fluoro-2-(2-fluoro-2-methylpropyl)-3-methyl-2,3,4,9-tetrahydro-1H-pyrido[3,4-b]indole; 2-[(1R,3R)-1-[2,6-difluoro-4-[2-[3-(fluoromethyl)azetidin-1-yl]ethoxy]phenyl]-3-methyl-1,3,4,9-tetrahydropyrido[3,4-b]indol-2-yl]-N,N-dimethyl-acetamide; 3-((1R,3R)-1-(2,6-difluoro-4-(2-(3-(fluoromethyl)azetidin-1-yl)ethoxy)phenyl)-3-methyl-1,3,4,9-tetrahydro-2H-pyrido[3,4-b]indol-2-yl)-2-fluoro-2-methylpropan-1-ol; (1R,3R)-2-(2-fluoro-2-methyl-propyl)-1-[4-[1-(3-fluoropropyl)azetidin-3-yl]oxy-2-methyl-phenyl]-3-methyl-1,3,4,9-tetrahydropyrido[3,4-b]indole; (1R)-1-[2,6-difluoro-4-[2-[3-(fluoromethyl)azetidin-1-yl]ethoxy]phenyl]-2-(2-fluoro-2-methyl-propyl)-3,3-dimethyl-4,9-dihydro-1H-pyrido[3,4-b]indole; (S)-1-(2,6-difluoro-4-(2-(3-(fluoromethyl)azetidin-1-yl)ethoxy)phenyl)-2-(2-fluoro-2-methylpropyl)-3,3-dimethyl-2,3,4,9-tetrahydro-1H-pyrido[3,4-b]indole; (1R,3R)-1-[4-[1-[(3,3-difluorocyclobutyl)methyl]azetidin-3-yl]oxy-2,6-difluoro-phenyl]-2-(2-fluoro-2-methyl-propyl)-3-methyl-1,3,4,9-tetrahydropyrido[3,4-b]indole; (1R,3R)-1-(2,6-difluoro-4-(2-(3-(fluoromethyl)azetidin-1-yl)ethoxy)phenyl)-8-fluoro-2-(2-fluoro-2-methylpropyl)-3-methyl-2,3,4,9-tetrahydro-1H-pyrido[3,4-b]indole; (1R,3R)-1-(2,6-difluoro-4-((1-(3-fluoropropyl)azetidin-3-yl)oxy)phenyl)-8-fluoro-2-(2-fluoro-2-methylpropyl)-3-methyl-2,3,4,9-tetrahydro-1H-pyrido[3,4-b]indole; (1S,3S)-1-(2,6-difluoro-4-(2-(3-(fluoromethyl)azetidin-1-yl)ethoxy)phenyl)-8-fluoro-2-(2-fluoro-2-methylpropyl)-3-methyl-2,3,4,9-tetrahydro-1H-pyrido[3,4-b]indole; (S)-1-((1R,3R)-1-(2,6-difluoro-4-((1-(3-fluoropropyl)azetidin-3-yl)oxy)phenyl)-3-methyl-1,3,4,9-tetrahydro-2H-pyrido[3,4-b]indol-2-yl)propan-2-ol; (R)-1-((1R,3R)-1-(2,6-difluoro-4-((1-(3-fluoropropyl)azetidin-3-yl)oxy)phenyl)-3-methyl-1,3,4,9-tetrahydro-2H-pyrido[3,4-b]indol-2-yl)propan-2-ol; (1R,3R)-1-[4-[2-[3-(chloromethyl)azetidin-1-yl]ethoxy]-2,6-difluoro-phenyl]-2-(2-fluoro-2-methyl-propyl)-3-methyl-1,3,4,9-tetrahydropyrido[3,4-b]indole; (1R,3R)-1-[3-chloro-4-[1-(3-fluoropropyl)azetidin-3-yl]oxy-phenyl]-2-(2-fluoro-2-methyl-propyl)-3-methyl-1,3,4,9-tetrahydropyrido[3,4-b]indole; (1R,3R)-1-[3-fluoro-4-[1-(3-fluoropropyl)azetidin-3-yl]oxy-phenyl]-2-(2-fluoro-2-methyl-propyl)-3-methyl-1,3,4,9-tetrahydropyrido[3,4-b]indole; (2R)-3-[(1R,3R)-1-[2,6-difluoro-4-[2-[3-(fluoromethyl)azetidin-1-yl]ethoxy]phenyl]-3-methyl-1,3,4,9-tetrahydropyrido[3,4-b]indol-2-yl]propane-1,2-diol; (1R,3R)-1-[2,6-difluoro-4-[1-[[(1S,2R)-2-fluorocyclopropyl]methyl]azetidin-3-yl]oxy-phenyl]-2-(2-fluoro-2-methyl-propyl)-3-methyl-1,3,4,9-tetrahydropyrido[3,4-b]indole; (1R,3R)-1-(2,6-difluoro-4-(2-(3-(fluoromethyl)azetidin-1-yl)ethoxy)phenyl)-2-((S)-3-fluoro-2-methylpropyl)-3-methyl-2,3,4,9-tetrahydro-1H-pyrido[3,4-b]indole; (S)-3-((1R,3R)-1-(2,6-difluoro-4-(2-(3-(fluoromethyl)azetidin-1-yl)ethoxy)phenyl)-3-methyl-1,3,4,9-tetrahydro-2H-pyrido[3,4-b]indol-2-yl)-2-methylpropane-1,2-diol; (1R,3R)-1-[2,6-difluoro-4-[1-(3-fluoropropyl)azetidin-3-yl]oxy-phenyl]-2-(3-fluoro-2,2-dimethyl-propyl)-3-methyl-1,3,4,9-tetrahydropyrido[3,4-b]indole; (R)-2-fluoro-3-((1R,3R)-1-(2-fluoro-4-(2-(3-(fluoromethyl)azetidin-1-yl)ethoxy)phenyl)-3-methyl-1,3,4,9-tetrahydro-2H-pyrido[3,4-b]indol-2-yl)-2-methylpropan-1-ol; (S)-2-fluoro-3-((1R,3R)-1-(2-fluoro-4-(2-(3-(fluoromethyl)azetidin-1-yl)ethoxy)phenyl)-3-methyl-1,3,4, 9-tetrahydro-2H-pyrido[3,4-b]indol-2-yl)-2-methylpropan-1-ol; (R)-2-fluoro-3-((1R,3R)-1-(4-(2-(3-(fluoromethyl)azetidin-1-yl)ethoxy)phenyl)-3-methyl-1,3,4,9-tetrahydro-2H-pyrido[3,4-b]indol-2-yl)-2-methylpropan-1-ol; (S)-2-fluoro-3-((1R,3R)-1-(4-(2-(3-(fluoromethyl)azetidin-1-yl)ethoxy)phenyl)-3-methyl-1,3,4,9-tetrahydro-2H-pyrido[3,4-b]indol-2-yl)-2-methylpropan-1-ol; (1R,3R)-1-[2,6-difluoro-4-[1-(3-fluoropropyl)azetidin-3-yl]oxy-phenyl]-3-methyl-2-(2,2,2-trifluoroethyl)-1,3,4,9-tetrahydropyrido[3,4-b]indole; (2R)-3-[(1R,3R)-1-[2,6-difluoro-4-[2-[3-(fluoromethyl)azetidin-1-yl]ethoxy]phenyl]-3-methyl-1,3,4,9-tetrahydropyrido[3,4-b]indol-2-yl]-2-methyl-propane-1,2-diol; (1R,3R)-2-(2-fluoro-2-methylpropyl)-1-(3-fluoro-4-(2-(3-(fluoromethyl)azetidin-1-yl)ethoxy)phenyl)-3-methyl-2,3,4,9-tetrahydro-1H-pyrido[3,4-b]indole; (1S,3R)-2-(2-fluoro-2-methylpropyl)-1-(3-fluoro-4-(2-(3-(fluoromethyl)azetidin-1-yl)ethoxy)phenyl)-3-methyl-2,3,4,9-tetrahydro-1H-pyrido[3,4-b]indole; (1R,3R)-1-(2,3-difluoro-4-(2-(3-(fluoromethyl)azetidin-1-yl)ethoxy)phenyl)-2-(2-fluoro-2-methylpropyl)-3-methyl-2,3,4,9-tetrahydro-1H-pyrido[3,4-b]indole; (1R,3R)-1-(2,6-difluoro-4-((1-(((1S,2S)-2-fluorocyclopropyl)methyl)azetidin-3-yl)oxy)phenyl)-2-(2-fluoro-2-methylpropyl)-3-methyl-2,3,4,9-tetrahydro-1H-pyrido[3,4-b]indole; 1-[(1R,3R)-1-[2,6-difluoro-4-[1-(3-fluoropropyl)azetidin-3-yl]oxy-phenyl]-3-methyl-1,3,4,9-tetrahydropyrido[3,4-b]indol-2-yl]propan-2-one; 3-[(1R,3R)-1-[2,6-difluoro-4-[1-(3-fluoropropyl)azetidin-3-yl]oxy-phenyl]-3-methyl-1,3,4,9-tetrahydropyrido[3,4-b]indol-2-yl]-2,2-dimethyl-propan-1-ol; (1R,3R)-1-[2,6-difluoro-4-[1-(3-fluoropropyl)azetidin-3-yl]oxy-phenyl]-2-ethylsulfonyl-3-methyl-1,3,4,9-tetrahydropyrido[3,4-b]indole; 3-[(1R,3R)-1-[2,6-difluoro-4-[2-[3-(fluoromethyl)azetidin-1-yl]ethoxy]phenyl]-3-methyl-1,3,4,9-tetrahydropyrido[3,4-b]indol-2-yl]-2,2-difluoro-propan-1-ol; 3-[(1R,3R)-1-[2,6-difluoro-4-[2-[3-(fluoromethyl)azetidin-1-yl]ethoxy]phenyl]-3-methyl-1,3,4,9-tetrahydropyrido[3,4-b]indol-2-yl]-2,2-dimethyl-propan-1-ol; 3-((1R,3R)-1-(2,6-difluoro-4-((1-(3-fluoropropyl)azetidin-3-yl)oxy)phenyl)-3-methyl-1,3,4,9-tetrahydro-2H-pyrido[3,4-b]indol-2-yl)-2-fluoro-2-methylpropan-1-ol; 1-((1S,3R)-1-(2,6-difluoro-4-((1-(3-fluoropropyl)azetidin-3-yl)oxy)phenyl)-3-methyl-1,3,4,9-tetrahydro-2H-pyrido[3,4-b]indol-2-yl)propan-2-one; (S)-3-((1R,3R)-1-(2,6-difluoro-4-(2-(3-(fluoromethyl)azetidin-1-yl)ethoxy)phenyl)-3-methyl-1,3,4,9-tetrahydro-2H-pyrido[3,4-b]indol-2-yl)-N,N,2-trimethylpropanamide; (R)-3-((1R,3R)-1-(2,6-difluoro-4-(2-(3-(fluoromethyl)azetidin-1-yl)ethoxy)phenyl)-3-methyl-1,3,4,9-tetrahydro-2H-pyrido[3,4-b]indol-2-yl)-N,N,2-trimethylpropanamide; (S)-3-((1R,3R)-1-(2,6-difluoro-4-(2-(3-(fluoromethyl)azetidin-1-yl)ethoxy)phenyl)-3-methyl-1,3,4,9-tetrahydro-2H-pyrido[3,4-b]indol-2-yl)-2-methylpropanoic acid; (R)-3-((1R,3R)-1-(2,6-difluoro-4-(2-(3-(fluoromethyl)azetidin-1-yl)ethoxy)phenyl)-3-methyl-1,3,4,9-tetrahydro-2H-pyrido[3,4-b]indol-2-yl)-2-methylpropanoic acid; (1R,3S)-1-(2,6-difluoro-4-((1-(3-fluoropropyl)azetidin-3-yl)oxy)phenyl)-2-(2-fluoro-2-methylpropyl)-3-(fluoromethyl)-2,3,4,9-tetrahydro-1H-pyrido[3,4-b]indole; 3-((1R,3R)-1-(2,6-difluoro-4-((1-(3-fluoropropyl)azetidin-3-yl)oxy)phenyl)-3-methyl-3,4-dihydro-1H-pyrido[3,4-b]indol-2(9H)-yl)-2,2-difluoropropan-1-ol; (1R,3R)-2-(2,2-difluoroethyl)-1-[2,6-difluoro-4-[1-(3-fluoropropyl)azetidin-3-yl]oxy-phenyl]-3-methyl-1,3,4,9-tetrahydropyrido[3,4-b]indole; (1R,3R)-2-(2,2-difluoroethyl)-1-[2,6-difluoro-4-[2-[3-(fluoromethyl)azetidin-1-yl]ethoxy]phenyl]-3-methyl-1,3,4,9-tetrahydropyrido[3,4-b]indole; (1S,3R)-2-(2,2-difluoroethyl)-1-[2,6-difluoro-4-[2-[3-(fluoromethyl)azetidin-1-yl]ethoxy]phenyl]-3-methyl-1,3,4,9-tetrahydropyrido[3,4-b]indole; (1R,3R)-1-[4-[1-(3,3-difluorocyclobutyl)azetidin-3-yl]oxy-2,6-difluoro-phenyl]-2-(2-fluoro-2-methyl-propyl)-3-methyl-1,3,4,9-tetrahydropyrido[3,4-b]indole; (1R,3R)-1-[2,6-difluoro-4-[1-[(E)-3-fluoroallyl]azetidin-3-yl]oxy-phenyl]-2-(2-fluoro-2-methyl-propyl)-3-methyl-1,3,4,9-tetrahydropyrido[3,4-b]indole; (1R,3R)-1-(2,6-difluoro-4-((1-(3-fluoropropyl)azetidin-3-yl)oxy)phenyl)-3-methyl-2-(2-(methylsulfonyl)propyl)-2,3,4,9-tetrahydro-1H-pyrido[3,4-b]indole; (1R,3R)-1-[4-[2-[3-(fluoromethyl)azetidin-1-yl]ethoxy]phenyl]-3-methyl-2-vinylsulfonyl-1,3,4,9-tetrahydropyrido[3,4-b]indole; (1R,3R)-1-[4-[2-[3-(fluoromethyl)azetidin-1-yl]ethoxy]phenyl]-N,3-dimethyl-1,3,4,9-tetrahydropyrido[3,4-b]indole-2-sulfonamide; 3-[(1R,3R)-1-[2,6-difluoro-4-[1-(3-fluoropropyl)azetidin-3-yl]oxy-phenyl]-3-methyl-1,3,4,9-tetrahydropyrido[3,4-b]indol-2-yl]-2,2-dimethyl-propanenitrile; (1R,3R)-1-[4-[1-(3,3-difluoroallyl)azetidin-3-yl]oxy-2,6-difluoro-phenyl]-2-(2-fluoro-2-methyl-propyl)-3-methyl-1,3,4,9-tetrahydropyrido[3,4-b]indole; (S)-2-(((1R,3R)-1-(2,6-difluoro-4-(2-(3-(fluoromethyl)azetidin-1-yl)ethoxy)phenyl)-3-methyl-1,3,4,9-tetrahydro-2H-pyrido[3,4-b]indol-2-yl)methyl)-3,3,3-trifluoropropan-1-ol; (R)-2-(((1R,3R)-1-(2,6-difluoro-4-(2-(3-(fluoromethyl)azetidin-1-yl)ethoxy)phenyl)-3-methyl-1,3,4,9-tetrahydro-2H-pyrido[3,4-b]indol-2-yl)methyl)-3,3,3-trifluoropropan-1-ol; (1R,3R)-2-ethylsulfonyl-1-[4-[2-[3-(fluoromethyl)azetidin-1-yl]ethoxy]phenyl]-3-methyl-1,3,4,9-tetrahydropyrido[3,4-b]indole; (1R,3R)-1-[4-[2-[3-(fluoromethyl)azetidin-1-yl]ethoxy]phenyl]-N,N,3-trimethyl-1,3,4,9-tetrahydropyrido[3,4-b]indole-2-sulfonamide; (1R,3R)-1-[4-[1-(3-fluoropropyl)azetidin-3-yl]oxyphenyl]-3-methyl-2-methylsulfonyl-1,3,4,9-tetrahydropyrido[3,4-b]indole; 3-[3-[3,5-difluoro-4-[(1R,3R)-2-(2-fluoro-2-methyl-propyl)-3-methyl-1,3,4,9-tetrahydropyrido[3,4-b]indol-1-yl]phenoxy]azetidin-1-yl]cyclobutanol; (1R,3R)-1-(4-(2-(3-(fluoromethyl)azetidin-1-yl)ethoxy)phenyl)-2-((S)-isopropylsulfinyl)-3-methyl-2,3,4,9-tetrahydro-1H-pyrido[3,4-b]indole; (1R,3R)-1-(4-(2-(3-(fluoromethyl)azetidin-1-yl)ethoxy)phenyl)-2-((R)-isopropylsulfinyl)-3-methyl-2,3,4,9-tetrahydro-1H-pyrido[3,4-b]indole; (1S,3s)-3-(3-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)azetidin-1-yl)cyclobutanol; (1R,3R)-1-[2,6-difluoro-4-[1-(5-fluoropentyl)azetidin-3-yl]oxy-phenyl]-2-(2-fluoro-2-methyl-propyl)-3-methyl-1,3,4,9-tetrahydropyrido[3,4-b]indole; (1R,3R)-1-[3,5-difluoro-4-[1-(3-fluoropropyl)azetidin-3-yl]oxy-phenyl]-2-(2-fluoro-2-methyl-propyl)-3-methyl-1,3,4,9-tetrahydropyrido[3,4-b]indole; (1R,3R)-1-[2,6-difluoro-4-[1-(4-fluorobutyl)azetidin-3-yl]oxy-phenyl]-2-(2-fluoro-2-methyl-propyl)-3-methyl-1,3,4,9-tetrahydropyrido[3,4-b]indole; (1R,3R)-1-[3,5-difluoro-4-[1-(5-fluoropentyl)azetidin-3-yl]oxy-phenyl]-2-(2-fluoro-2-methyl-propyl)-3-methyl-1,3,4,9-tetrahydropyrido[3,4-b]indole; (1R,3R)-1-[2,5-difluoro-4-[1-(3-fluoropropyl)azetidin-3-yl]oxy-phenyl]-2-(2-fluoro-2-methyl-propyl)-3-methyl-1,3,4,9-tetrahydropyrido[3,4-b]indole; 3-[(1R,3R)-1-[2,6-difluoro-4-[2-[3-(fluoromethyl)azetidin-1-yl]ethylamino]phenyl]-3-methyl-1,3,4,9-tetrahydropyrido[3,4-b]indol-2-yl]-2,2-difluoro-propan-1-ol; (1S,3R)-2-(2-fluoro-2-methylpropyl)-1-(5-((1-(3-fluoropropyl)azetidin-3-yl)oxy)pyrazin-2-yl)-3-methyl-2,3,4,9-tetrahydro-1H-pyrido[3,4-b]indole; (1R,3R)-1-(2,6-difluoro-4-((1-(3-fluoropropyl)-3-methylazetidin-3-yl)oxy)phenyl)-2-(2-fluoro-2-methylpropyl)-3-methyl-2,3,4,9-tetrahydro-1H-pyrido[3,4-b]indole; 2-[(1R,3R)-2-(2-fluoro-2-methylpropyl)-3-methyl-1,3,4,9-tetrahydropyrido[3,4-b]indol-1- yl]-5-[1-(3-fluoropropyl)azetidin-3-yl]oxy-benzonitrile; 4-((1R,3R)-2-(2-fluoro-2-methylpropyl)-3-methyl-2,3,4,9-tetrahydro-1H-pyrido[3,4-b]indol-1-yl)-1-(3-(3-(fluoromethyl)azetidin-1-yl)propyl)pyridin-2(1H)-one; [4-[(1R,3R)-2-(2-fluoro-2-methyl-propyl)-3-methyl-1,3,4,9-tetrahydropyrido[3,4-b]indol-1-yl]phenyl]-[1-(3-fluoropropyl)azetidin-3-yl]methanone; (R)-3-((1R,3R)-1-(2,6-difluoro-4-(2-(3-(fluoromethyl)azetidin-1-yl)ethoxy)phenyl)-3-methyl-1,3,4,9-tetrahydro-2H-pyrido[3,4-b]indol-2-yl)-2-methylpropanamide; (R)-3-((1R,3R)-1-(2,6-difluoro-4-((1-(3-fluoropropyl)azetidin-3-yl)oxy)phenyl)-3-methyl-1,3,4,9-tetrahydro-2H-pyrido[3,4-b]indol-2-yl)-2-methylpropanoic acid; (S)-3-((1R,3R)-1-(2,6-difluoro-4-((1-(3-fluoropropyl)azetidin-3-yl)oxy)phenyl)-3-methyl-1,3,4,9-tetrahydro-2H-pyrido[3,4-b]indol-2-yl)-2-methylpropanoic acid; 3-[1-[2,6-difluoro-4-[1-(3-fluoropropyl)azetidin-3-yl]oxy-phenyl]-3-methyl-1,3,4,9-tetrahydropyrido[3,4-b]indol-2-yl]-2-methyl-propanoic acid; 3-[1-[2,6-difluoro-4-[1-(3-fluoropropyl)azetidin-3-yl]oxy-phenyl]-3-methyl-1,3,4,9-tetrahydropyrido[3,4-b]indol-2-yl]-2-methyl-propanoic acid; (1S,3S)-1-(2,6-difluoro-4-(2-(3-(fluoromethyl)azetidin-1-yl)ethoxy)phenyl)-6-fluoro-3-methyl-2-(2,2,2-trifluoroethyl)-2,3,4,9-tetrahydro-1H-pyrido[3,4-b]indole; (1R,3R)-1-(2,6-difluoro-4-(2-(3-(fluoromethyl)azetidin-1-yl)ethoxy)phenyl)-6-fluoro-3-methyl-2-(2,2,2-trifluoroethyl)-2,3,4,9-tetrahydro-1H-pyrido[3,4-b]indole; (1S,3S)-1-(2,6-difluoro-4-((1-(3-fluoropropyl)azetidin-3-yl)oxy)phenyl)-6-fluoro-3-methyl-2-(2,2,2-trifluoroethyl)-2,3,4,9-tetrahydro-1H-pyrido[3,4-b]indole; (1R,3R)-1-(2,6-difluoro-4-((1-(3-fluoropropyl)azetidin-3-yl)oxy)phenyl)-6-fluoro-3-methyl-2-(2,2,2-trifluoroethyl)-2,3,4,9-tetrahydro-1H-pyrido[3,4-b]indole; 3-((1R,3R)-1-(2,6-difluoro-4-(2-(3-(fluoromethyl)azetidin-1-yl)ethoxy)phenyl)-6-fluoro-3-methyl-1,3,4,9-tetrahydro-2H-pyrido[3,4-b]indol-2-yl)-2,2-difluoropropan-1-ol; 3-((1S,3S)-1-(2,6-difluoro-4-(2-(3-(fluoromethyl)azetidin-1-yl)ethoxy)phenyl)-6-fluoro-3-methyl-1,3,4,9-tetrahydro-2H-pyrido[3,4-b]indol-2-yl)-2,2-difluoropropan-1-ol; (1R,3R)-1-[2,6-difluoro-4-[2-[3-(fluoromethyl)azetidin-1-yl]ethoxy]phenyl]-3-methyl-2-(3,3,3-trifluoropropyl)-1,3,4,9-tetrahydropyrido[3,4-b]indole; (1S,3R)-1-[2,6-difluoro-4-[2-[3-(fluoromethyl)azetidin-1-yl]ethoxy]phenyl]-3-methyl-2-(3,3,3-trifluoropropyl)-1,3,4,9-tetrahydropyrido[3,4-b]indole; 3-((1R,3R)-1-(2,6-difluoro-4-((1-(3-fluoropropyl)azetidin-3-yl)oxy)phenyl)-6-fluoro-3-methyl-1,3,4,9-tetrahydro-2H-pyrido[3,4-b]indol-2-yl)-2,2-difluoropropan-1-ol; 3-((1S,3S)-1-(2,6-difluoro-4-((1-(3-fluoropropyl)azetidin-3-yl)oxy)phenyl)-6-fluoro-3-methyl-1,3,4,9-tetrahydro-2H-pyrido[3,4-b]indol-2-yl)-2,2-difluoropropan-1-ol; 3-((1R,3R)-1-(2,6-difluoro-4-((1-(3-fluoropropyl)azetidin-3-yl)oxy)phenyl)-6-fluoro-3-methyl-1,3,4,9-tetrahydro-2H-pyrido[3,4-b]indol-2-yl)-2-fluoro-2-methylpropan-1-ol; 3-((1S,3S)-1-(2,6-difluoro-4-((1-(3-fluoropropyl)azetidin-3-yl)oxy)phenyl)-6-fluoro-3-methyl-1,3,4,9-tetrahydro-2H-pyrido[3,4-b]indol-2-yl)-2-fluoro-2-methylpropan-1-ol; 3-((1R,3R)-1-(2,6-difluoro-4-((1-(3-fluoropropyl)azetidin-3-yl)oxy)phenyl)-6-fluoro-3-methyl-1,3,4,9-tetrahydro-2H-pyrido[3,4-b]indol-2-yl)-2-fluoro-2-methylpropan-1-ol; 3-((1S,3S)-1-(2,6-difluoro-4-((1-(3-fluoropropyl)azetidin-3-yl)oxy)phenyl)-6-fluoro-3-methyl-1,3,4,9-tetrahydro-2H-pyrido[3,4-b]indol-2-yl)-2-fluoro-2-methylpropan-1-ol; 3-((1R,3R)-1-(2,6-difluoro-4-(2-(3-(fluoromethyl)azetidin-1-yl)ethoxy)phenyl)-3-methyl-1,3,4,9-tetrahydro-2H-pyrido[3,4-b]indol-2-yl)-2,2-dimethylpropanoic acid; (R)-2-(((1R,3R)-1-(2,6-difluoro-4-((1-(3-fluoropropyl)azetidin-3-yl)oxy)phenyl)-3-methyl-1,3,4,9-tetrahydro-2H-pyrido[3,4-b]indol-2-yl)methyl)-3,3,3-trifluoropropan-1-ol; (S)-2-(((1R,3R)-1-(2,6-difluoro-4-((1-(3-fluoropropyl)azetidin-3-yl)oxy)phenyl)-3-methyl-1,3,4,9-tetrahydro-2H-pyrido[3,4-b]indol-2-yl)methyl)-3,3,3-trifluoropropan-1-ol; (1R,3R)-2-(2-fluoro-2-methylpropyl)-1-(2-((1-(3-fluoropropyl)azetidin-3-yl)oxy)pyrimidin-5-yl)-3-methyl-2,3,4,9-tetrahydro-1H-pyrido[3,4-b]indole; 3-[(1S,3R)-1-[2,6-difluoro-4-[2-[3-(fluoromethyl)azetidin-1-yl]ethoxy]phenyl]-3-methyl-1,3,4,9-tetrahydropyrido[3,4-b]indol-2-yl]-2,2-dimethyl-propanoic acid; (1R,3R)-1-(2,6-difluoro-4-(2-(3-(fluoromethyl)azetidin-1-yl)ethoxy)phenyl)-2-(2,2-difluoropropyl)-3-methyl-2,3,4,9-tetrahydro-1H-pyrido[3,4-b]indole; (S)-(4-((1R,3R)-2-(2-fluoro-2-methylpropyl)-3-methyl-2,3,4,9-tetrahydro-1H-pyrido[3,4-b]indol-1-yl)phenyl)(1-(3-fluoropropyl)azetidin-3-yl)methanol; (R)-(4-((1R,3R)-2-(2-fluoro-2-methylpropyl)-3-methyl-2,3,4,9-tetrahydro-1H-pyrido[3,4-b]indol-1-yl)phenyl)(1-(3-fluoropropyl)azetidin-3-yl)methanol; (1R,3R)-1-(2,6-difluoro-4-(2-(3-(fluoromethyl)azetidin-1-yl)ethoxy)phenyl)-2-(2,2-difluoroethyl)-6-fluoro-3-methyl-2,3,4,9-tetrahydro-1H-pyrido[3,4-b]indole; (1S,3S)-1-(2,6-difluoro-4-(2-(3-(fluoromethyl)azetidin-1-yl)ethoxy)phenyl)-2-(2,2-difluoroethyl)-6-fluoro-3-methyl-2,3,4,9-tetrahydro-1H-pyrido[3,4-b]indole; (1R,3R)-1-(2,6-difluoro-4-((1-(3-fluoropropyl)azetidin-3-yl)oxy)phenyl)-2-(2,2-difluoroethyl)-6-fluoro-3-methyl-2,3,4,9-tetrahydro-1H-pyrido[3,4-b]indole; (1S,3S)-1-(2,6-difluoro-4-((1-(3-fluoropropyl)azetidin-3-yl)oxy)phenyl)-2-(2,2-difluoroethyl)-6-fluoro-3-methyl-2,3,4,9-tetrahydro-1H-pyrido[3,4-b]indole; (1R,3R)-1-(2,6-difluoro-4-((1-cis-(3-(fluoromethyl)cyclobutyl)azetidin-3-yl)oxy)phenyl)-2-(2-fluoro-2-methylpropyl)-3-methyl-2,3,4,9-tetrahydro-1H-pyrido[3,4-b]indole; (1R,3R)-1-(2,6-difluoro-4-((1-trans-(3-(fluoromethyl)cyclobutyl)azetidin-3-yl)oxy)phenyl)-2-(2-fluoro-2-methylpropyl)-3-methyl-2,3,4,9-tetrahydro-1H-pyrido[3,4-b]indole; (1R,3R)-1-(2,6-difluoro-4-((1-(3-fluoropropyl)azetidin-3-yl)oxy)phenyl)-2-((1-fluorocyclobutyl)methyl)-3-methyl-2,3,4,9-tetrahydro-1H-pyrido[3,4-b]indole; (S)-3-((1R,3R)-1-(2,6-difluoro-4-(2-(3-(fluoromethyl)azetidin-1-yl)ethoxy)phenyl)-3-methyl-3,4-dihydro-1H-pyrido[3,4-b]indol-2(9H)-yl)-2-fluoropropan-1-ol; (R)-3-((1R,3R)-1-(2,6-difluoro-4-(2-(3-(fluoromethyl)azetidin-1-yl)ethoxy)phenyl)-3-methyl-3,4-dihydro-1H-pyrido[3,4-b]indol-2(9H)-yl)-2-fluoropropan-1-ol; (R)-3-((1R,3R)-1-(2,6-difluoro-4-(2-(3-(fluoromethyl)azetidin-1-yl)ethoxy)phenyl)-3-methyl-3,4-dihydro-1H-pyrido[3,4-b]indol-2(9H)-yl)-2-(fluoromethyl)propan-1-ol; (S)-3-((1R,3R)-1-(2,6-difluoro-4-(2-(3-(fluoromethyl)azetidin-1-yl)ethoxy)phenyl)-3-methyl-3,4-dihydro-1H-pyrido[3,4-b]indol-2(9H)-yl)-2-(fluoromethyl)propan-1-ol; (1R,3R)-1-(2,6-difluoro-4-(1-(3-fluoropropyl)azetidin-3-yloxy)phenyl)-2-((3-fluorooxetan-3-yl)methyl)-3-methyl-2,3,4,9-tetrahydro-1H-pyrido[3,4-b]indole; (1R,3R)-1-(2,6-difluoro-4-(1-(3-fluoropropyl)azetidin-3-yloxy)phenyl)-6,8-difluoro-2-(2-fluoro-2-methylpropyl)-3-methyl-2,3,4,9-tetrahydro-1H-pyrido[3,4-b]indole; (1R,3R)-1-(2,6-difluoro-4-((1-((1-(fluoromethyl)cyclopropyl)methyl)azetidin-3-yl)oxy)phenyl)-2-(2-fluoro-2-methylpropyl)-3-methyl-2,3,4,9-tetrahydro-1H-pyrido[3,4-b]indole; (1R,3R)-1-(2,6-difluoro-4-(1-(3-fluoropropyl)azetidin-3-yloxy)phenyl)-6,7-difluoro-2-(2-fluoro-2-methylpropyl)-3-methyl-2,3,4,9-tetrahydro-1H-pyrido[3,4-b]indole; or (1R,3R)-2-(2-fluoro-2-methylpropyl)-1-(1-((1-(3-fluoropropyl)azetidin-3-yl)methyl)-1H-pyrazol-4-yl)-3-methyl-2,3,4,9-tetrahydro-1H-pyrido[3,4-b]indole, or a pharmaceutically acceptable salt thereof or combination thereof.

In another aspect, the endocrine therapy comprises a compound having formula:

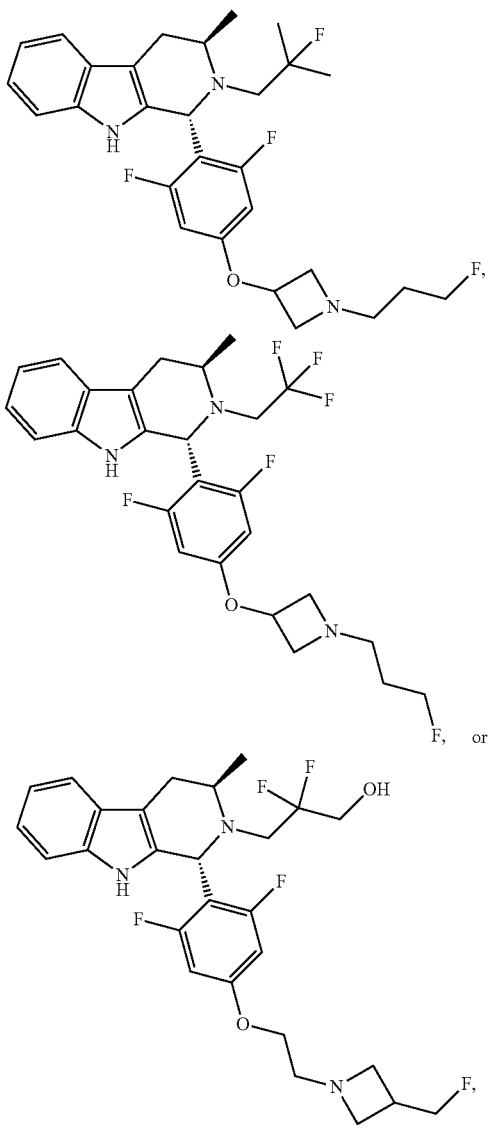

or a pharmaceutically acceptable salt thereof.

In another aspect, the endocrine therapy comprises a compound having formula (4):

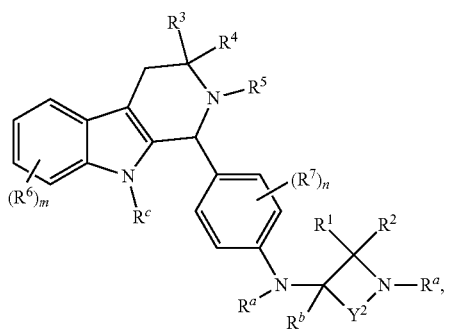

or a stereoisomer, tautomer, or pharmaceutically acceptable salt thereof, wherein: $Y^2$ is —(CH$_2$); $R^a$ is independently selected from the group consisting of H, $C_1$-$C_6$ alkyl, $C_2$-$C_8$ alkenyl, propargyl, $C_3$-$C_6$ cycloalkyl, and $C_3$-$C_6$ heterocyclyl, each optionally substituted with one or more groups independently selected from the group consisting of F, Cl, Br, I, CN, OH, OCH$_3$, and SO$_2$CH$_3$; $R^b$ is independently selected from the group consisting of H, —O($C_1$-$C_3$ alkyl), $C_1$-$C_6$ alkyl, $C_2$-$C_8$ alkenyl, and propargyl, each optionally substituted with one or more groups independently selected from the group consisting of F, Cl, Br, I, CN, —CH$_2$F, —CHF$_2$, —CF$_3$, —CH$_2$CF$_3$, —CH$_2$CHF$_2$, —CH$_2$CH$_2$F, OH, OCH$_3$, and SO$_2$CH$_3$; R is H; $R^1$, $R^2$, $R^3$ and $R^4$ are independently selected from the group consisting of H, —CH$_3$, —CH$_2$CH$_3$, —CH(CH$_3$)$_2$, —CH$_2$CH(CH$_3$)$_2$, —CH$_2$OH, —CH$_2$OCH$_3$, —CH$_2$CH$_2$OH, —C(CH$_3$)$_2$OH, —CH(OH)CH(CH$_3$)$_2$, —C(CH$_3$)$_2$CH$_2$OH, —CH$_2$CH$_2$SO$_2$CH$_3$, —CH$_2$OP(O)(OH)$_2$, —CH$_2$F, —CHF$_2$, —CH$_2$NH$_2$, —CH$_2$NHSO$_2$CH$_3$, —CH$_2$NHCH$_3$, —CH$_2$N(CH$_3$)$_2$, —CF$_3$, —CH$_2$CF$_3$, —CH$_2$CHF$_2$, —CH(CH$_3$)CN, —C(CH$_3$)$_2$CN, and —CH$_2$CN; $R^5$ is selected from the group consisting of $C_1$-$C_9$ alkyl, $C_3$-$C_9$ cycloalkyl, $C_3$-$C_9$ heterocycle, $C_6$-$C_9$ aryl, $C_6$-$C_9$ heteroaryl, —($C_1$-$C_6$ alkyldiyl)-($C_3$-$C_9$ cycloalkyl), —($C_1$-$C_6$ alkyldiyl)-($C_3$-$C_9$ heterocycle), C(O)NR$^a$, SO$_2$R$^a$, and SO$_2$NR$^a$, each optionally substituted with one or more of halogen, CN, OR$^a$, N(R$^a$)$_2$, $C_1$-$C_9$ alkyl, $C_3$-$C_9$ cycloalkyl, $C_3$-$C_9$ heterocycle, $C_6$-$C_9$ aryl, $C_6$-$C_9$ heteroaryl, C(O)R$^b$, C(O)NR$^a$, SO$_2$R$^a$, and SO$_2$NR$^a$; $R^6$ is independently F or Cl; m is 0, 1, 2, 3, or 4; wherein $R^7$ is F, Cl, Br, I, —CN, —CH$_3$, —CH$_2$CH$_3$, —CH(CH$_3$)$_2$, —CH$_2$CH(CH$_3$)$_2$, —CH$_2$OH, —CH$_2$OCH$_3$, —CH$_2$CH$_2$OH, —C(CH$_3$)$_2$OH, —CH(OH)CH(CH$_3$)$_2$, —C(CH$_3$)$_2$CH$_2$OH, —CH$_2$CH$_2$SO$_2$CH$_3$, —CH$_2$OP(O)(OH)$_2$, —CH$_2$F, —CHF$_2$, —CH$_2$NH$_2$, —CH$_2$NHSO$_2$CH$_3$, —CH$_2$NHCH$_3$, —CH$_2$N(CH$_3$)$_2$, —CF$_3$, —CH$_2$CF$_3$, —CH$_2$CHF$_2$, —CH(CH$_3$)CN, —C(CH$_3$)$_2$CN, —CH$_2$CN, —CO$_2$H, —COCH$_3$, —CO$_2$CH$_3$, —CO$_2$C(CH$_3$)$_3$, —COCH(OH)CH$_3$, —CONH$_2$, —CONHCH$_3$, —CONHCH$_2$CH$_3$, —CONHCH(CH$_3$)$_2$, —CON(CH$_3$)$_2$, —C(CH$_3$)$_2$CONH$_2$, —NH$_2$, —NHCH$_3$, —N(CH$_3$)$_2$, —NHCOCH$_3$, —N(CH$_3$)COCH$_3$, —NHS(O)$_2$CH$_3$, —N(CH$_3$)C(CH$_3$)$_2$CONH$_2$, —N(CH$_3$)CH$_2$CH$_2$S(O)$_2$CH$_3$, —NO$_2$, =O, —OH, —OCH$_3$, —OCH$_2$CH$_3$, —OCH$_2$CH$_2$OCH$_3$, —OCH$_2$CH$_2$OH, —OCH$_2$CH$_2$N(CH$_3$)$_2$, —OP(O)(OH)$_2$, —S(O)$_2$N(CH$_3$)$_2$, —SCH$_3$, —S(O)$_2$CH$_3$, —S(O)$_3$H, cyclopropyl, cyclopropylamide, oxetanyl, azetidinyl, 1-methylazetidin-3-yl)oxy, N-methyl-N-oxetan-3-ylamino, azetidin-1-ylmethyl, benzyloxyphenyl, pyrrolidin-1-yl, pyrrolidin-1-yl-methanone, piperazin-1-yl, morpholinomethyl, morpholino-methanone, or morpholino; n is 0, 1 or 2; and $R^7$ is independently halogen.

Variables $R^1$, $R^2$, $R^3$, $R^4$, $R^5$, $R^a$, $R^b$, $R^c$, m, n, and $Y^2$ are as defined herein for compounds of formula (3).

In one instance, the compound of formula (4) comprises formula (4a):

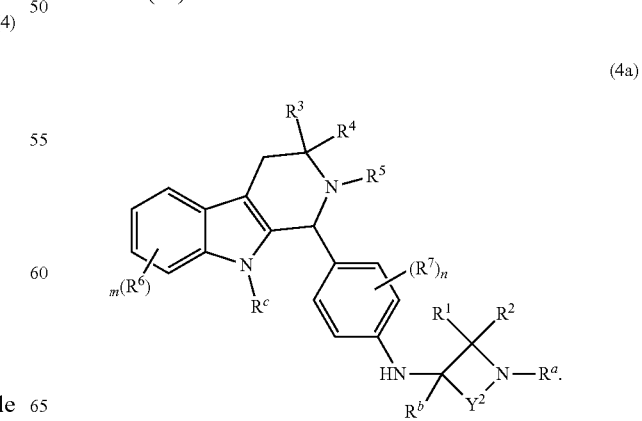

In another instance, the compound of formula (4) comprises formula (4b):

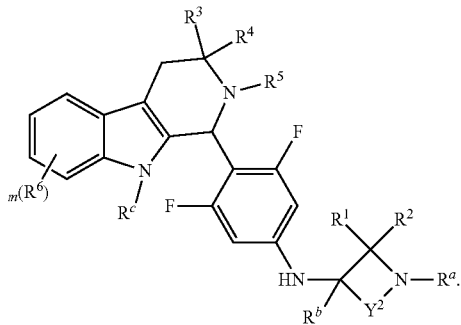

(4b)

In still another instance, the compound of formula (4) comprises formula (4c):

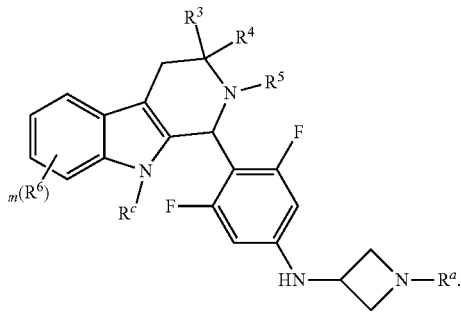

(4c)

In one instance of the compounds of formula (4a)-(4c), $R^7$ is F. In one instance of the compounds of formula (4a)-(4c), $R^1$ and $R^2$ are H. In one instance of the compounds of formula (4a)-(4c), $R^3$ is H, and $R^4$ is —CH$_3$. In one instance of the compounds of formula (4a)-(4c), $R^5$ is $C_1$-$C_6$ fluoroalkyl. In one instance of the compounds of formula (4a)-(4c), m is 0.

In another aspect, the endocrine therapy comprises a compound having formula: N-(3,5-difluoro-4-((1R,3R)-2-(2-fluoro-2-methylpropyl)-3-methyl-2,3,4,9-tetrahydro-1H-pyrido[3,4-b]indol-1-yl)phenyl)-1-(3-fluoropropyl)azetidin-3-amine; (R)-3-((1R,3R)-1-(2,6-difluoro-4-((1-(3-fluoropropyl)azetidin-3-yl)amino)phenyl)-3-methyl-1,3,4,9-tetrahydro-2H-pyrido[3,4-b]indol-2-yl)-2-fluoro-2-methylpropan-1-ol; (S)-3-((1R,3R)-1-(2,6-difluoro-4-((1-(3-fluoropropyl)azetidin-3-yl)amino)phenyl)-3-methyl-1,3,4,9-tetrahydro-2H-pyrido[3,4-b]indol-2-yl)-2-fluoro-2-methylpropan-1-ol; (R)-2-fluoro-3-((1R,3R)-1-(2-fluoro-4-((1-(3-fluoropropyl)azetidin-3-yl)amino)phenyl)-3-methyl-1,3,4,9-tetrahydro-2H-pyrido[3,4-b]indol-2-yl)-2-methylpropan-1-ol; (S)-2-fluoro-3-((1R,3R)-1-(2-fluoro-4-((1-(3-fluoropropyl)azetidin-3-yl)amino)phenyl)-3-methyl-1,3,4,9-tetrahydro-2H-pyrido[3,4-b]indol-2-yl)-2-methylpropan-1-ol; (R)-2-fluoro-3-((1R,3R)-1-(4-((1-(3-fluoropropyl)azetidin-3-yl)amino)phenyl)-3-methyl-1,3,4,9-tetrahydro-2H-pyrido[3,4-b]indol-2-yl)-2-methylpropan-1-ol; (S)-2-fluoro-3-((1R,3R)-1-(4-((1-(3-fluoropropyl)azetidin-3-yl)amino)phenyl)-3-methyl-1,3,4,9-tetrahydro-2H-pyrido[3,4-b]indol-2-yl)-2-methylpropan-1-ol; 3,5-difluoro-N-(2-(3-(fluoromethyl)azetidin-1-yl)ethyl)-4-((1R,3R)-3-methyl-2-(2,2,2-trifluoroethyl)-2,3,4,9-tetrahydro-1H-pyrido[3,4-b]indol-1-yl)aniline; N-(3,5-difluoro-4-((1R,3R)-3-methyl-2-(2,2,2-trifluoroethyl)-2,3,4,9-tetrahydro-1H-pyrido[3,4-b]indol-1-yl)phenyl)-1-(3-fluoropropyl)azetidin-3-amine; 1-(3-fluoropropyl)-N-[4-[(1R,3R)-3-methyl-2-methylsulfonyl-1,3,4,9-tetrahydropyrido[3,4-b]indol-1-yl]phenyl]azetidin-3-amine; N-[3,5-difluoro-4-[(1R,3R)-3-methyl-2-methylsulfonyl-1,3,4,9-tetrahydropyrido[3,4-b]indol-1-yl]phenyl]-1-(3-fluoropropyl)azetidin-3-amine; 1-(3-fluoropropyl)-N-[4-[(1S,3R)-3-methyl-2-methylsulfonyl-1,3,4,9-tetrahydropyrido[3,4-b]indol-1-yl]phenyl]azetidin-3-amine; N-[3,5-difluoro-4-[(1S,3R)-3-methyl-2-methylsulfonyl-1,3,4,9-tetrahydropyrido[3,4-b]indol-1-yl]phenyl]-1-(3-fluoropropyl)azetidin-3-amine; 3-((1R,3R)-1-(2,6-difluoro-4-((2-(3-(fluoromethyl)azetidin-1-yl)ethyl)amino)phenyl)-3-methyl-1,3,4,9-tetrahydro-2H-pyrido[3,4-b]indol-2-yl)-2-fluoro-2-methylpropan-1-ol; 3,5-difluoro-N-[2-[3-(fluoromethyl)azetidin-1-yl]ethyl]-4-[(1R,3R)-2-(2-fluoro-2-methyl-propyl)-3-methyl-1,3,4,9-tetrahydropyrido[3,4-b]indol-1-yl]aniline; 3-fluoro-N-[2-[3-(fluoromethyl)azetidin-1-yl]ethyl]-4-[(1R,3R)-2-(2-fluoro-2-methyl-propyl)-3-methyl-1,3,4,9-tetrahydropyrido[3,4-b]indol-1-yl]aniline; N-[2-[3-(fluoromethyl)azetidin-1-yl]ethyl]-4-[(1R,3R)-2-(2-fluoro-2-methyl-propyl)-3-methyl-1,3,4,9-tetrahydropyrido[3,4-b]indol-1-yl]aniline; N-[2-[3-(fluoromethyl)azetidin-1-yl]ethyl]-4-[(1R,3R)-3-methyl-2-methylsulfonyl-1,3,4,9-tetrahydropyrido[3,4-b]indol-1-yl]aniline; 3,5-difluoro-N-[2-[3-(fluoromethyl)azetidin-1-yl]ethyl]-4-[(1R,3R)-3-methyl-2-methylsulfonyl-1,3,4,9-tetrahydropyrido[3,4-b]indol-1-yl]aniline; 2-fluoro-3-((1R,3R)-1-(2-fluoro-4-((2-(3-(fluoromethyl)azetidin-1-yl)ethyl)amino)phenyl)-3-methyl-1,3,4,9-tetrahydro-2H-pyrido[3,4-b]indol-2-yl)-2-methylpropan-1-ol; 2-fluoro-3-((1R,3R)-1-(4-((2-(3-(fluoromethyl)azetidin-1-yl)ethyl)amino)phenyl)-3-methyl-1,3,4,9-tetrahydro-2H-pyrido[3,4-b]indol-2-yl)-2-methylpropan-1-ol; 3-[(1R,3R)-1-[2,6-difluoro-4-[[1-(3-fluoropropyl)azetidin-3-yl]amino]phenyl]-3-methyl-1,3,4,9-tetrahydropyrido[3,4-b]indol-2-yl]-2,2-difluoro-propan-1-ol; (R)-3-((1R,3R)-1-(2,6-difluoro-4-((2-(3-(fluoromethyl)azetidin-1-yl)ethyl)amino)phenyl)-3-methyl-1,3,4,9-tetrahydro-2H-pyrido[3,4-b]indol-2-yl)-2-fluoro-2-methylpropan-1-ol; (S)-3-((1R,3R)-1-(2,6-difluoro-4-((2-(3-(fluoromethyl)azetidin-1-yl)ethyl)amino)phenyl)-3-methyl-1,3,4,9-tetrahydro-2H-pyrido[3,4-b]indol-2-yl)-2-fluoro-2-methylpropan-1-ol; (2R)-3-[(1R,3R)-1-[2,6-difluoro-4-[[1-(3-fluoropropyl)azetidin-3-yl]amino]phenyl]-3-methyl-1,3,4,9-tetrahydropyrido[3,4-b]indol-2-yl]-2-methyl-propanoic acid; 3-((1R,3R)-1-(2,6-difluoro-4-((1-(3-fluoropropyl)azetidin-3-yl)amino)phenyl)-6-fluoro-3-methyl-1,3,4,9-tetrahydro-2H-pyrido[3,4-b]indol-2-yl)-2,2-difluoropropan-1-ol; 3-((1S,3S)-1-(2,6-difluoro-4-((1-(3-fluoropropyl)azetidin-3-yl)amino)phenyl)-6-fluoro-3-methyl-1,3,4,9-tetrahydro-2H-pyrido[3,4-b]indol-2-yl)-2,2-difluoropropan-1-ol; (2S)-3-[(1R,3R)-1-[2,6-difluoro-4-[[1-(3-fluoropropyl)azetidin-3-yl]amino]phenyl]-3-methyl-1,3,4,9-tetrahydropyrido[3,4-b]indol-2-yl]-2-methyl-propanoic acid; N-(3,5-difluoro-4-((1R,3R)-6-fluoro-3-methyl-2-(2,2,2-trifluoroethyl)-2,3,4,9-tetrahydro-1H-pyrido[3,4-b]indol-1-yl)phenyl)-1-(3-fluoropropyl)azetidin-3-amine; N-(3,5-difluoro-4-((1S,3S)-6-fluoro-3-methyl-2-(2,2,2-trifluoroethyl)-2,3,4,9-tetrahydro-1H-pyrido[3,4-b]indol-1-yl)phenyl)-1-(3-fluoropropyl)azetidin-3-amine; 3-((1R,3R)-1-(2,6-difluoro-4-((1-(3-fluoropropyl)azetidin-3-yl)amino)phenyl)-3-methyl-1,3,4,9-tetrahydro-2H-pyrido[3,4-b]indol-2-yl)-2,2-dimethylpropanoic acid; N-(3,5-difluoro-4-

((1R,3R)-6-fluoro-3-methyl-2-(methylsulfonyl)-2,3,4,9-tetrahydro-1H-pyrido[3,4-b]indol-1-yl)phenyl)-1-(3-fluoropropyl)azetidin-3-amine; N-(3,5-difluoro-4-((1S,3S)-6-fluoro-3-methyl-2-(methylsulfonyl)-2,3,4,9-tetrahydro-1H-pyrido[3,4-b]indol-1-yl)phenyl)-1-(3-fluoropropyl)azetidin-3-amine; N-(4-((1R,3R)-2-(2,2-difluoroethyl)-6-fluoro-3-methyl-2,3,4,9-tetrahydro-1H-pyrido[3,4-b]indol-1-yl)-3,5-difluorophenyl)-1-(3-fluoropropyl)azetidin-3-amine; N-(4-((1S,3S)-2-(2,2-difluoroethyl)-6-fluoro-3-methyl-2,3,4,9-tetrahydro-1H-pyrido[3,4-b]indol-1-yl)-3,5-difluorophenyl)-1-(3-fluoropropyl)azetidin-3-amine; N-(3,5-difluoro-4-((1R,3R)-7-fluoro-3-methyl-2-(2,2,2-trifluoroethyl)-2,3,4,9-tetrahydro-1H-pyrido[3,4-b]indol-1-yl)phenyl)-1-(3-fluoropropyl)azetidin-3-amine; N-(3,5-difluoro-4-((1S,3S)-7-fluoro-3-methyl-2-(2,2,2-trifluoroethyl)-2,3,4,9-tetrahydro-1H-pyrido[3,4-b]indol-1-yl)phenyl)-1-(3-fluoropropyl)azetidin-3-amine; (S)-3-((1R,3R)-1-(2,6-difluoro-4-((1-(3-fluoropropyl)azetidin-3-yl)amino)phenyl)-5-fluoro-3-methyl-3,4-dihydro-1H-pyrido[3,4-b]indol-2(9H)-yl)-2-fluoro-2-methylpropan-1-ol; (R)-3-((1S,3S)-1-(2,6-difluoro-4-((1-(3-fluoropropyl)azetidin-3-yl)amino)phenyl)-5-fluoro-3-methyl-3,4-dihydro-1H-pyrido[3,4-b]indol-2(9H)-yl)-2-fluoro-2-methylpropan-1-ol; (R)-3-((1R,3R)-1-(2,6-difluoro-4-((1-(3-fluoropropyl)azetidin-3-yl)amino)phenyl)-5-fluoro-3-methyl-3,4-dihydro-1H-pyrido[3,4-b]indol-2(9H)-yl)-2-fluoro-2-methylpropan-1-ol; (S)-3-((1S,3S)-1-(2,6-difluoro-4-((1-(3-fluoropropyl)azetidin-3-yl)amino)phenyl)-5-fluoro-3-methyl-3,4-dihydro-1H-pyrido[3,4-b]indol-2(9H)-yl)-2-fluoro-2-methylpropan-1-ol; N-(3,5-difluoro-4-((1R,3R)-2-(2-fluoro-2-methylpropyl)-3-methyl-2,3,4,9-tetrahydro-1H-pyrido[3,4-b]indol-1-yl)phenyl)-1-(3-fluoropropyl)-N-methylazetidin-3-amine; (R)—N-(4-(2-(2,2-difluoroethyl)-3,3-dimethyl-2,3,4,9-tetrahydro-1H-pyrido[3,4-b]indol-1-yl)-3,5-difluorophenyl)-1-(3-fluoropropyl)azetidin-3-amine; (S)—N-(4-(2-(2,2-difluoroethyl)-3,3-dimethyl-2,3,4,9-tetrahydro-1H-pyrido[3,4-b]indol-1-yl)-3,5-difluorophenyl)-1-(3-fluoropropyl)azetidin-3-amine; N-(3,5-difluoro-4-((1R,3R)-5-fluoro-3-methyl-2-(2,2,2-trifluoroethyl)-2,3,4,9-tetrahydro-1H-pyrido[3,4-b]indol-1-yl)phenyl)-1-(3-fluoropropyl)azetidin-3-amine; N-(3,5-difluoro-4-((1S,3S)-5-fluoro-3-methyl-2-(2,2,2-trifluoroethyl)-2,3,4,9-tetrahydro-1H-pyrido[3,4-b]indol-1-yl)phenyl)-1-(3-fluoropropyl)azetidin-3-amine; N-(3,5-difluoro-4-((1S,3S)-8-fluoro-3-methyl-2-(2,2,2-trifluoroethyl)-2,3,4,9-tetrahydro-1H-pyrido[3,4-b]indol-1-yl)phenyl)-1-(3-fluoropropyl)azetidin-3-amine; N-(3,5-difluoro-4-((1R,3R)-8-fluoro-3-methyl-2-(2,2,2-trifluoroethyl)-2,3,4,9-tetrahydro-1H-pyrido[3,4-b]indol-1-yl)phenyl)-1-(3-fluoropropyl)azetidin-3-amine; (S)-3-((1S,3S)-1-(2,6-difluoro-4-((1-(3-fluoropropyl)azetidin-3-yl)amino)phenyl)-7-fluoro-3-methyl-3,4-dihydro-1H-pyrido[3,4-b]indol-2(9H)-yl)-2-fluoro-2-methylpropan-1-ol; (R)-3-((1R,3R)-1-(2,6-difluoro-4-((1-(3-fluoropropyl)azetidin-3-yl)amino)phenyl)-7-fluoro-3-methyl-3,4-dihydro-1H-pyrido[3,4-b]indol-2(9H)-yl)-2-fluoro-2-methylpropan-1-ol; (S)-3-((1R,3R)-1-(2,6-difluoro-4-((1-(3-fluoropropyl)azetidin-3-yl)amino)phenyl)-7-fluoro-3-methyl-3,4-dihydro-1H-pyrido[3,4-b]indol-2(9H)-yl)-2-fluoro-2-methylpropan-1-ol; (R)-3-((1S,3S)-1-(2,6-difluoro-4-((1-(3-fluoropropyl)azetidin-3-yl)amino)phenyl)-7-fluoro-3-methyl-3,4-dihydro-1H-pyrido[3,4-b]indol-2(9H)-yl)-2-fluoro-2-methylpropan-1-ol; 3-((1R,3R)-1-(2,6-difluoro-4-((1-(3-fluoropropyl)azetidin-3-yl)amino)phenyl)-5-fluoro-3-methyl-3,4-dihydro-1H-pyrido[3,4-b]indol-2(9H)-yl)-2,2-difluoropropan-1-ol; 3-((1S,3S)-1-(2,6-difluoro-4-((1-(3-fluoropropyl)azetidin-3-yl)amino)phenyl)-5-fluoro-3-methyl-3,4-dihydro-1H-pyrido[3,4-b]indol-2(9H)-yl)-2,2-difluoropropan-1-ol; (R)-3-((1R,3R)-1-(2,6-difluoro-4-((1-(3-fluoropropyl)azetidin-3-yl)amino)phenyl)-3-methyl-3,4-dihydro-1H-pyrido[3,4-b]indol-2(9H)-yl)-2-fluoro-2-(hydroxymethyl)propanenitrile; (S)-3-((1R,3R)-1-(2,6-difluoro-4-((1-(3-fluoropropyl)azetidin-3-yl)amino)phenyl)-3-methyl-3,4-dihydro-1H-pyrido[3,4-b]indol-2(9H)-yl)-2-fluoro-2-(hydroxymethyl)propanenitrile; (R)-3-(1-(2,6-difluoro-4-((1-(3-fluoropropyl)azetidin-3-yl)amino)phenyl)-3,3-dimethyl-3,4-dihydro-1H-pyrido[3,4-b]indol-2(9H)-yl)-2,2-difluoropropan-1-ol; (S)-3-(1-(2,6-difluoro-4-((1-(3-fluoropropyl)azetidin-3-yl)amino)phenyl)-3,3-dimethyl-3,4-dihydro-1H-pyrido[3,4-b]indol-2(9H)-yl)-2,2-difluoropropan-1-ol; 3-((1S,3S)-1-(2,6-difluoro-4-((1-(3-fluoropropyl)azetidin-3-yl)amino)phenyl)-8-fluoro-3-methyl-3,4-dihydro-1H-pyrido[3,4-b]indol-2(9H)-yl)-2,2-difluoropropan-1-ol; 3-((1R,3R)-1-(2,6-difluoro-4-((1-(3-fluoropropyl)azetidin-3-yl)amino)phenyl)-8-fluoro-3-methyl-3,4-dihydro-1H-pyrido[3,4-b]indol-2(9H)-yl)-2,2-difluoropropan-1-ol; 3-((1R,3R)-1-(2,6-difluoro-4-((1-(3-fluoropropyl)azetidin-3-yl)amino)phenyl)-7-fluoro-3-methyl-3,4-dihydro-1H-pyrido[3,4-b]indol-2(9H)-yl)-2,2-difluoropropan-1-ol; 3-((1S,3S)-1-(2,6-difluoro-4-((1-(3-fluoropropyl)azetidin-3-yl)amino)phenyl)-7-fluoro-3-methyl-3,4-dihydro-1H-pyrido[3,4-b]indol-2(9H)-yl)-2,2-difluoropropan-1-ol; N-[4-[(1R,3R)-2-(2,2-difluoroethyl)-3-methyl-1,3,4,9-tetrahydropyrido[3,4-b]indol-1-yl]-3,5-difluoro-phenyl]-1-(3-fluoropropyl)azetidin-3-amine; (R)-3-((1R,3R)-1-(2,6-difluoro-4-((1-(3-fluoropropyl)azetidin-3-yl)amino)phenyl)-6-fluoro-3-methyl-1,3,4,9-tetrahydro-2H-pyrido[3,4-b]indol-2-yl)-2-fluoro-2-methylpropan-1-ol; (S)-3-((1S,3S)-1-(2,6-difluoro-4-((1-(3-fluoropropyl)azetidin-3-yl)amino)phenyl)-6-fluoro-3-methyl-1,3,4,9-tetrahydro-2H-pyrido[3,4-b]indol-2-yl)-2-fluoro-2-methylpropan-1-ol; (S)-3-((1R,3R)-1-(2,6-difluoro-4-((1-(3-fluoropropyl)azetidin-3-yl)amino)phenyl)-6-fluoro-3-methyl-1,3,4,9-tetrahydro-2H-pyrido[3,4-b]indol-2-yl)-2-fluoro-2-methylpropan-1-ol; or (R)-3-((1R,3S)-1-(2,6-difluoro-4-((1-(3-fluoropropyl)azetidin-3-yl)amino)phenyl)-6-fluoro-3-methyl-1,3,4,9-tetrahydro-2H-pyrido[3,4-b]indol-2-yl)-2-fluoro-2-methylpropan-1-ol, or a pharmaceutically acceptable salt thereof or a combination thereof.

In another aspect, the endocrine therapy comprises a compound having formula:

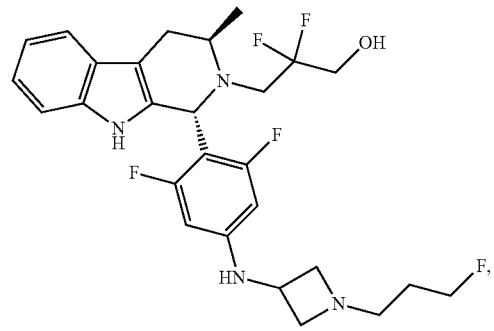 [SMILES: C[C@@H]1Cc2c([nH]c3ccccc23)[C@@H](c2c(F)cc(NC3CN(CCCF)C3)cc2F)N1CC(F)(F)CO]

or a pharmaceutically acceptable salt thereof.

In another aspect, the endocrine therapy comprises a compound having formula:

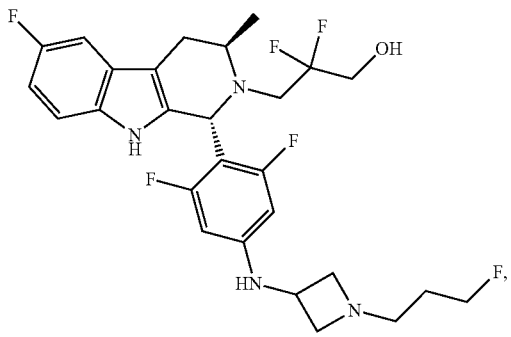 [SMILES: C[C@@H]1Cc2c([nH]c3ccc(F)cc23)[C@@H](c2c(F)cc(NC3CN(CCCF)C3)cc2F)N1CC(F)(F)CO]

or a pharmaceutically acceptable salt thereof.

In another aspect, the endocrine therapy comprises a compound having formula:

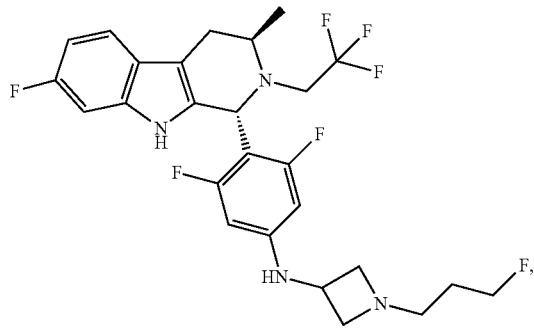 [SMILES: C[C@@H]1Cc2c([nH]c3cc(F)ccc23)[C@@H](c2c(F)cc(NC3CN(CCCF)C3)cc2F)N1CC(F)(F)F]

or a pharmaceutically acceptable salt thereof.

In another aspect, the endocrine therapy comprises a compound having formula:

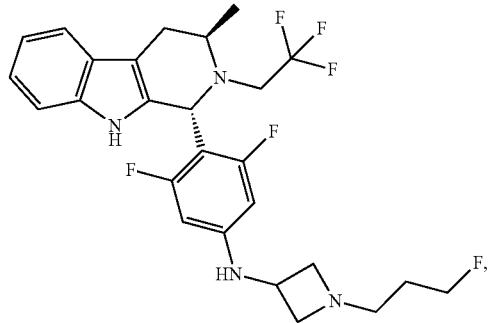 [SMILES: C[C@@H]1Cc2c([nH]c3ccccc23)[C@@H](c2c(F)cc(NC3CN(CCCF)C3)cc2F)N1CC(F)(F)F]

or a pharmaceutically acceptable salt thereof.

In another aspect, the endocrine therapy comprises a compound having formula:

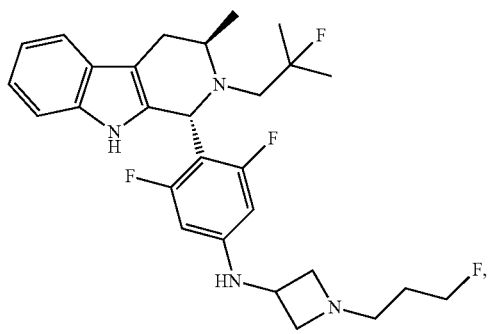 [SMILES: C[C@@H]1Cc2c([nH]c3ccccc23)[C@@H](c2c(F)cc(NC3CN(CCCF)C3)cc2F)N1CC(C)(C)F]

or a pharmaceutically acceptable salt thereof.

In another aspect, the endocrine therapy comprises a compound having formula:

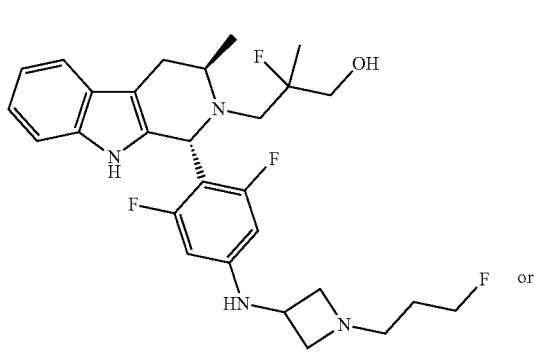

or

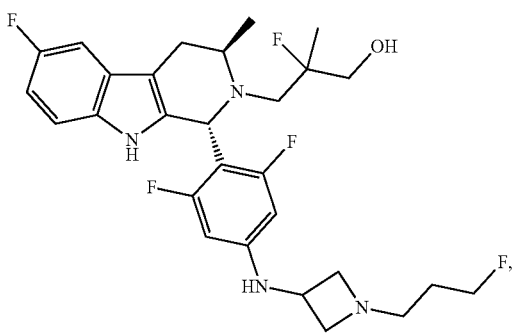

including stereoisomers thereof, or a pharmaceutically acceptable salt thereof.

In another aspect, the endocrine therapy comprises a compound set forth in U.S. Patent Application No. 20170129855, for example in Table 1 therein, which is incorporated herein by reference in its entirety and for all purposes.

In one aspect, the endocrine therapy comprises a compound of formula (5):

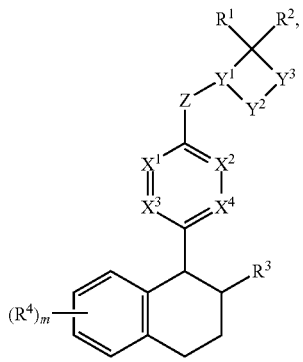

or a stereoisomer, tautomer, or pharmaceutically acceptable salt thereof, wherein: $Y^1$ is $CR^b$ or N; $Y^2$ is —($CH_2$)—, —($CH_2CH_2$)—, or $NR^a$; $Y^3$ is $NR^a$ or $C(Rb)_2$; where one of $Y^1$, $Y^2$ and $Y^3$ is N or $NR^a$; $R^a$ and $R^c$ are independently selected from H, $C_1$-$C_6$ alkyl, $C_1$-$C_6$ fluoroalkyl, allyl, propargyl, $C_3$-$C_6$ cycloalkyl, and $C_3$-$C_6$ heterocyclyl, optionally substituted with one or more groups independently selected from F, Cl, Br, I, CN, OH, $OCH_3$, and $SO_2CH_3$; $R^b$ is independently selected from H, —O($C_1$-$C_3$ alkyl), $C_1$-$C_6$ alkyl, $C_1$-$C_6$ fluoroalkyl, allyl, propargyl, $C_3$-$C_6$ cycloalkyl, and $C_3$-$C_6$ heterocyclyl, optionally substituted with one or more groups independently selected from F, Cl, Br, I, CN, OH, $OCH_3$, and $SO_2CH_3$; where at least one of $R^a$ and $R^b$ is —$CH_2Cl$, —$CH_2F$, —$CHF_2$, —$CF_3$, —$CH_2CH_2F$, —$CH_2CHF_2$, —$CH_2CF_3$, $CH_2CH_2Cl$, $CH_2CH_2CH_2F$, $CH_2CH_2CHF_2$, $CH_2CH_2CF_3$, or $CH_2CH_2CH_2Cl$; $X^1$, $X^2$, $X^3$, and $X^4$ are independently selected from CH, $CR^5$ and N; where none, one, or two of $X^1$, $X^2$, $X^3$, and $X^4$ is N; Z is selected from O, S, S(O), $S(O)_2$, C(=O), CH(OH), $C_1$-$C_6$ alkyldiyl, CH(OH)—($C_1$-$C_6$ alkyldiyl), $C_1$-$C_6$ fluoroalkyldiyl, $NR^c$, $NR^c$—($C_1$-$C_6$ alkyldiyl), $NR^c$—($C_1$-$C_6$ fluoroalkyldiyl), O—($C_1$-$C_6$ alkyldiyl), and O—($C_1$-$C_6$ fluoroalkyldiyl); $R^1$ and $R^2$ are independently selected from H, F, Cl, Br, I, —CN, —$CH_3$, —$CH_2CH_3$, —$CH(CH_3)_2$, —$CH_2CH(CH_3)_2$, —$CH_2OH$, —$CH_2OCH_3$, —$CH_2CH_2OH$, —$C(CH_3)_2OH$, —$CH(OH)CH(CH_3)_2$, —$C(CH_3)_2CH_2OH$, —$CH_2CH_2SO_2CH_3$, —$CH_2OP(O)(OH)_2$, —$CH_2Cl$, —$CH_2F$, —$CHF_2$, —$CH_2NH_2$, —$CH_2NHSO_2CH_3$, —$CH_2NHCH_3$, —$CH_2N(CH_3)_2$, —$CF_3$, —$CH_2CF_3$, —$CH_2CHF_2$, —$CH(CH_3)CN$, —$C(CH_3)_2CN$, —$CH_2CN$, —$CO_2H$, —$COCH_3$, —$CO_2CH_3$, —$CO_2C(CH_3)_3$, —$COCH(OH)CH_3$, —$CONH_2$, —$CONHCH_3$, —$CONHCH_2CH_3$, —$CONHCH(CH_3)_2$, —$CON(CH_3)_2$, —$C(CH_3)_2CONH_2$, —$NH_2$, —$NHCH_3$, —$N(CH_3)_2$, —$NHCOCH_3$, —$N(CH_3)COCH_3$, —$NHS(O)_2CH_3$, —$N(CH_3)C(CH_3)_2CONH_2$, —$N(CH_3)CH_2CH_2S(O)_2CH_3$, —$NO_2$, =O, —OH, —$OCH_3$, —$OCH_2CH_3$, —$OCH_2CH_2OCH_3$, —$OCH_2CH_2OH$, —$OCH_2CH_2N(CH_3)_2$, —$OP(O)(OH)_2$, —$S(O)_2N(CH_3)_2$, —$SCH_3$, —$S(O)_2CH_3$, —$S(O)_3H$, cyclopropyl, cyclopropylamide, cyclobutyl, oxetanyl, azetidinyl, 1-methylazetidin-3-yl)oxy, N-methyl-N-oxetan-3-ylamino, azetidin-1-ylmethyl, benzyloxyphenyl, pyrrolidin-1-yl, pyrrolidin-1-yl-methanone, piperazin-1-yl, morpholinomethyl, morpholinomethanone, and morpholino; $R^3$ is selected from $C_3$-$C_{20}$ cycloalkyl, $C_2$-$C_{20}$ heterocyclyl, $C_6$-$C_{20}$ aryl, $C_1$-$C_{20}$ heteroaryl, —($C_1$-$C_6$ alkyldiyl)-($C_3$-$C_{20}$ cycloalkyl), —($C_1$-$C_6$ alkyldiyl)-($C_2$-$C_{20}$ heterocyclyl), —($C_1$-$C_6$ alkyldiyl)-($C_6$-$C_{20}$ aryl), and —($C_1$-$C_6$ alkyldiyl)-($C_1$-$C_{20}$ heteroaryl); or $R^3$ forms a 3-6-membered spiro carbocyclic or heterocyclic group; $R^4$ and $R^5$ are independently selected from F, Cl, Br, I, —CN, —$CH_3$, —$CH_2CH_3$, —$CH(CH_3)_2$, —$CH_2CH(CH_3)_2$, —$CH_2OH$, —$CH_2OCH_3$, —$CH_2CH_2OH$, —$C(CH_3)_2OH$, —$CH(OH)CH(CH_3)_2$, —$C(CH_3)_2CH_2OH$, —$CH_2CH_2SO_2CH_3$, —$CH_2OP(O)(OH)_2$, —$CH_2F$, —$CHF_2$, —$CH_2NH_2$, —$CH_2NHSO_2CH_3$, —$CH_2NHCH_3$, —$CH_2N(CH_3)_2$, —$CF_3$, —$CH_2CF_3$, —$CH_2CHF_2$, —$CH(CH_3)CN$, —$C(CH_3)_2CN$, —$CH_2CN$, —$CO_2H$, —$COCH_3$, —$CO_2CH_3$, —$CO_2C(CH_3)_3$, —$COCH(OH)CH_3$, —$CONH_2$, —$CONHCH_3$, —$CONHCH_2CH_3$, —$CONHCH(CH_3)_2$, —$CON(CH_3)_2$, —$C(CH_3)_2CONH_2$, —$NH_2$, —$NHCH_3$, —$N(CH_3)_2$, —$NHCOCH_3$, —$N(CH_3)COCH_3$, —$NHS(O)_2CH_3$, —$N(CH_3)C(CH_3)_2CONH_2$, —$N(CH_3)CH_2CH_2S(O)_2CH_3$, —$NO_2$, =O, —OH, —$OCH_3$, —$OCH_2CH_3$, —$OCH_2CH_2OCH_3$, —$OCH_2CH_2OH$, —$OCH_2CH_2N(CH_3)_2$, —$OP(O)(OH)_2$, —$S(O)_2N(CH_3)_2$, —$SCH_3$, —$S(O)_2CH_3$, —$S(O)_3H$, cyclopropyl, cyclopropylamide, cyclobutyl, oxetanyl, azetidinyl, 1-methylazetidin-3-yl)oxy, N-methyl-N-oxetan-3-ylamino, azetidin-1-ylmethyl, benzyloxyphenyl, pyrrolidin-1-yl, pyrrolidin-1-yl-methanone, piperazin-1-yl, morpholinomethyl, morpholinomethanone, and morpholino; and m is selected from 0, 1, 2, 3, and 4; where alkyldiyl, fluoroalkyldiyl, aryl, carbocyclyl, heterocyclyl, and heteroaryl are optionally substituted with one or more groups independently selected from F, Cl, Br, I, —CN, —$CH_3$, —$CH_2CH_3$, —$CH(CH_3)_2$, —$CH_2CH(CH_3)_2$, —$CH_2OH$, —$CH_2OCH_3$, —$CH_2CH_2OH$, —$C(CH_3)_2OH$, —$CH(OH)CH(CH_3)_2$, —$C(CH_3)_2CH_2OH$, —$CH_2CH_2SO_2CH_3$, —$CH_2OP(O)(OH)_2$, —$CH_2F$, —$CHF_2$, —$CF_3$, —$CH_2CF_3$, —$CH_2CHF_2$, —$CH(CH_3)CN$, —$C(CH_3)_2CN$, —$CH_2CN$, —$CH_2NH_2$, —$CH_2NHSO_2CH_3$, —$CH_2NHCH_3$, —$CH_2N(CH_3)_2$, —$CO_2H$, —$COCH_3$, —$CO_2CH_3$, —$CO_2C(CH_3)_3$, —$COCH(OH)CH_3$, —$CONH_2$, —$CONHCH_3$, —$CON(CH_3)_2$, —$C(CH_3)_2CONH_2$, —$NH_2$, —$NHCH_3$, —$N(CH_3)_2$, —$NHCOCH_3$, —$N(CH_3)COCH_3$, —$NHS(O)_2CH_3$, —$N(CH_3)C(CH_3)_2CONH_2$, —$N(CH_3)CH_2CH_2S(O)_2CH_3$, —$NO_2$, =O, —OH, —$OCH_3$, —$OCH_2CH_3$, —$OCH_2CH_2OCH_3$, —$OCH_2CH_2OH$, —$OCH_2CH_2N(CH_3)_2$, —$OP(O)(OH)_2$, —$S(O)_2N(CH_3)_2$, —$SCH_3$, —$S(O)_2CH_3$, —$S(O)_3H$, cyclopropyl, cyclopropylamide, cyclobutyl, oxetanyl, azetidinyl, 1-methylazetidin-3-yl)oxy, N-methyl-N-oxetan-3-ylamino, azetidin-1-ylmethyl, benzyloxyphenyl, pyrrolidin-1-yl, pyrrolidin-1-yl-methanone, piperazin-1-yl, morpholinomethyl, morpholino-methanone, and morpholino.

In one instance of the compounds of formula (5), $Y^1$ is N and $Y^3$ is $C(R^b)_2$. In one instance of the compounds of formula (5), $Y^2$ is —($CH_2$)—. In one instance of the compounds of formula (5), $Y^2$ is —($CH_2CH_2$)—. In one instance of the compounds of formula (5), $Y^3$ is $NR^a$ and $R^a$ is —$CH_2Cl$, —$CH_2F$, —$CHF_2$, —$CF_3$, —$CH_2CH_2F$, —$CH_2CHF_2$, or —$CH_2CF_3$. In one instance of the compounds of formula (5), $X^1$, $X^2$, $X^3$, and $X^4$ are independently selected from CH and $CR^5$. In one instance of the compounds of formula (5), one of $X^1$, $X^2$, $X^3$, and $X^4$ is N. In one instance of the compounds of formula (5), Z is O or O—($C_1$-$C_6$ alkyldiyl). In one instance of the compounds of formula (5), $R^1$ and $R^2$ are H. In one instance of the compounds of formula (5), $R^3$ is $C_6$-$C_{20}$ aryl. In one instance of the compounds of formula (5), $C_6$-$C_{20}$ aryl is phenyl. In one instance of the compounds of formula (5), phenyl is substituted with one or more F. In one instance of the compounds of formula (5). In one instance of the compounds of formula (5), $R^4$ is OH, and m is 1. In one instance of the compounds of formula (5), $R^5$ is F and n is 2. In one instance of the compounds of formula (5), $R^5$ is H. In one instance of the compounds of formula (5), n is 0.

In one aspect, the endocrine therapy comprises a compound having formula: (1R,2S)-1-[4-[2-[3-(fluoromethyl) azetidin-1-yl]ethoxy]phenyl]-2-phenyl-tetralin-6-ol; (1S, 2R)-1-[4-[2-[3-(fluoromethyl)azetidin-1-yl]ethoxy]phenyl]-2-phenyl-tetralin-6-ol; (1S,2R)-1-[4-[2-[3-(fluoromethyl) azetidin-1-yl]ethoxy]phenyl]-2-(4-fluorophenyl)tetralin-6-ol; (1R,2R)-1-[2,6-difluoro-4-[2-[3-(fluoromethyl)azetidin-1-yl]ethoxy]phenyl]-2-phenyl-tetralin-6-ol; (1S,2S)-1-[2,6-difluoro-4-[2-[3-(fluoromethyl)azetidin-1-yl]ethoxy] phenyl]-2-phenyl-tetralin-6-ol; (1R,2S)-1-[4-[2-[3-(fluoromethyl)azetidin-1-yl]ethoxy]phenyl]-2-(4-fluorophenyl)tetralin-6-ol; (5R,6R)-5-(4-(2-(3-(fluoromethyl)azetidin-1-yl)ethoxy)phenyl)-6-(tetrahydro-2H-pyran-4-yl)-5,6,7,8-tetrahydronaphthalen-2-ol; (5S,6S)-6-(4,4-difluorocyclohexyl)-5-(4-(2-(3-(fluoromethyl) azetidin-1-yl)ethoxy)phenyl)-5,6,7,8-tetrahydronaphthalen-2-ol; (5S,6S)-5-(4-(2-(3-(fluoromethyl)azetidin-1-yl) ethoxy)phenyl)-6-(tetrahydro-2H-pyran-4-yl)-5,6,7,8-tetrahydronaphthalen-2-ol; (5R,6R)-6-(4,4-difluorocyclohexyl)-5-(4-(2-(3-(fluoromethyl)azetidin-1-yl) ethoxy)phenyl)-5,6,7,8-tetrahydronaphthalen-2-ol; (5R,6S)-5-(4-(2-(3-(fluoromethyl)pyrrolidin-1-yl)ethoxy)phenyl)-6-phenyl-5,6,7,8-tetrahydronaphthalen-2-ol; (5R,6S)-5-(4-(2-(3-(chloromethyl)azetidin-1-yl)ethoxy)phenyl)-6-phenyl-5,6,7,8-tetrahydronaphthalen-2-ol; (5S,6R)-5-(4-(2-(3-(chloromethyl)azetidin-1-yl)ethoxy)phenyl)-6-phenyl-5,6,7,8-tetrahydronaphthalen-2-ol; (5S,6R)-5-(4-(2-(3-(fluoromethyl)pyrrolidin-1-yl)ethoxy)phenyl)-6-phenyl-5,6,7,8-tetrahydronaphthalen-2-ol; (5S,6R)-5-(4-(2-(3-(fluoromethyl)azetidin-1-yl)ethoxy)phenyl)-6-(4-(methylsulfonyl)phenyl)-5,6,7,8-tetrahydronaphthalen-2-ol; (5S,6R)-5-(4-(2-(3-(difluoromethyl)azetidin-1-yl)ethoxy) phenyl)-6-phenyl-5,6,7,8-tetrahydronaphthalen-2-ol; (5R, 6S)-5-(4-(2-(3-(fluoromethyl)azetidin-1-yl)ethoxy)phenyl)-6-(4-(methylsulfonyl)phenyl)-5,6,7,8-tetrahydronaphthalen-2-ol; (5R,6S)-5-(4-(2-(3-(difluoromethyl)azetidin-1-yl)ethoxy)phenyl)-6-phenyl-5,6,7,8-tetrahydronaphthalen-2-ol; (5R,6R)-5-(2-fluoro-4-(2-(3-(fluoromethyl)azetidin-1-yl)ethoxy)phenyl)-6-phenyl-5,6,7,8-tetrahydronaphthalen-2-ol; (5S,6S)-5-(2-fluoro-4-(2-(3-(fluoromethyl)azetidin-1-yl)ethoxy)phenyl)-6-phenyl-5,6,7,8-tetrahydronaphthalen-2-ol; (S)-1'-(4-(2-(3-(fluoromethyl)azetidin-1-yl)ethoxy)phenyl)-3',4'-dihydro-1'H-spiro[cyclopentane-1,2'-naphthalen]-6'-ol; (R)-1'-(4-(2-(3-(fluoromethyl)azetidin-1-yl)ethoxy)phenyl)-3',4'-dihydro-1'H-spiro[cyclopentane-1,2'-naphthalen]-6'-ol; (5R, 6S)-5-(4-((S)-2-((R)-3-(fluoromethyl)pyrrolidin-1-yl) propoxy)phenyl)-6-phenyl-5,6,7,8-tetrahydronaphthalen-2-ol; (5S,6R)-5-(4-((S)-2-((R)-3-(fluoromethyl)pyrrolidin-1-yl)propoxy)phenyl)-6-phenyl-5,6,7,8-tetrahydronaphthalen-2-ol; (5R,6S)-5-(4-(((R)-1-((R)-3-(fluoromethyl)pyrrolidin-1-yl)propan-2-yl)oxy)phenyl)-6-phenyl-5,6,7,8-tetrahydronaphthalen-2-ol; (5S,6R)-5-(4-(((R)-1-((R)-3-(fluoromethyl)pyrrolidin-1-yl)propan-2-yl)oxy)phenyl)-6-phenyl-5,6,7,8-tetrahydronaphthalen-2-ol; (5S,6S)-5-(6-(2-(3-(fluoromethyl)azetidin-1-yl)ethoxy)pyridin-3-yl)-6-phenyl-5,6,7,8-tetrahydronaphthalen-2-ol; (5R,6R)-5-(6-(2-(3-(fluoromethyl)azetidin-1-yl)ethoxy)pyridin-3-yl)-6-phenyl-5,6,7,8-tetrahydronaphthalen-2-ol; (5S,6R)-5-(4-((1-(3-fluoropropyl)azetidin-3-yl)oxy)phenyl)-6-phenyl-5,6,7,8-tetrahydronaphthalen-2-ol; (5R,6S)-5-(4-((1-(3-fluoropropyl)azetidin-3-yl)oxy)phenyl)-6-phenyl-5,6,7,8-tetrahydronaphthalen-2-ol; (5S,6R)-5-(4-((1-(3-fluoropropyl)azetidin-3-yl)amino)phenyl)-6-phenyl-5,6,7,8-tetrahydronaphthalen-2-ol; or (5R,6S)-5-(4-((1-(3-fluoropropyl)azetidin-3-yl)amino)phenyl)-6-phenyl-5,6,7,8-tetrahydronaphthalen-2-ol, or a pharmaceutically acceptable salt thereof or combination.

Non-Endocrine Anti-Cancer Therapies

In some instances of any of the preceding methods, an anti-cancer therapy other than an endocrine therapy may be administered to the individual. Exemplary anti-cancer therapies other than endocrine therapies include, but are not limited to, mammalian target of rapamycin (mTOR) inhibitors such as sirolimus (also known as rapamycin), temsirolimus (also known as CCI-779 or TORISEL®), everolimus (also known as RAD001 or AFINITOR®), ridaforolimus (also known as AP-23573, MK-8669, or deforolimus), OSI-027, AZD8055, and INK128; phosphatidylinositol 3-kinase (PI3K) inhibitors such as idelalisib (also known as GS-1101 or CAL-101), BKM120, and perifosine (also known as KRX-0401); dual phosphatidylinositol 3-kinase (PI3K)/ mTOR inhibitors such as XL765, GDC-0980, BEZ235 (also known as NVP-BEZ235), BGT226, GSK2126458, PF-04691502, and PF-05212384 (also known as PKI-587); and cyclin-dependent kinase (CDK)$_{4/6}$ inhibitors such as abemaciclib (VERZENIO®), palbociclib (IBRANCE®), ribociclib (KISQALI®), trilaciclib (G1T28); anthracyclines such as daunorubicin, doxorubicin, epirubicin, idarubicin, mitoxantrone, valrubicin; taxanes, including paclitaxel and docetaxel; podophyllotoxin; gemcitabine (GEMZAR®); 5-fluorouracil (5-FU); cyclophosphamide (CYTOXAN®); platinum analogs such as cisplatin and carboplatin; vinorelbine (NAVELBINE®); capecitabine (XELODA®); ixabepilone (IXEMPRA®); eribulin (HALAVEN®); and pharmaceutically acceptable salts acids or derivatives thereof; as well as combinations thereof. In certain instances, an anti-cancer agent described herein can be used in combination with an endocrine therapy as described herein in the methods provided herein. For example, in one embodiment, a CDK4/6 inhibitor such as palbociclib can be administered in combination with an endocrine therapy described herein (e.g. a SERD as set forth herein). For example, in some instances, the anti-cancer therapy other than an endocrine therapy comprises a chemotherapeutic and a PI3K inhibitor.

The non-endocrine therapy can comprise administration of, for example, AKT inhibitors (e.g. Ipatasertib), angiogenic agents (e.g. Avastin), BCL-2 inhibitors (e.g. Venetoclax), HDAC inhibitors, AURK inhibitors, or cancer immunotherapy agents (e.g. anti-PD1/PDL1 agents, including for example, atezoluzimab, pembrolizumab, nivolumab, avelumab, durvalumab, and pidilizumab).

Combination Therapies

It is to be understood that the methods described herein can be used with all compounds described herein whether administered as monotherapies or in combination including, for example, double, triple, or quadruple therapy combinations. In one instance, the compounds described herein have been administered before a tested patient has had surgery. In another instance, the compounds described herein have been administered after a tested patient has had surgery. In still another instance, the compounds described herein have been administered as either a 1 L, 2 L, 3 L or more therapy. In particular instance, patients described herein may have received prior treatment with a CDK4/6 inhibitor such as, for example, palbociclib, ribociclib, or abemaciclib before, during, or after treatment with a compound described herein.

In some instances of any of the preceding methods, a combination therapy including an endocrine therapy and one or more additional anti-cancer agents may be administered to the individual. Such combination therapies noted above encompass combined administration (where two or more therapeutic agents are included in the same or separate formulations), and separate administration, in which case, administration of an endocrine therapy as described herein can occur prior to, simultaneously, and/or following, administration of the additional therapeutic agent or agents.

Compositions and Pharmaceutical Formulations

Therapeutic formulations of the therapeutic agents, including an anti-cancer agent as provided herein or an endocrine therapy as provided herein, used in accordance with the methods and compositions provided herein are prepared for storage by mixing the therapeutic agent having the desired degree of purity with optional pharmaceutically acceptable carriers, excipients, or stabilizers in the form of lyophilized formulations or aqueous solutions. For general information concerning formulations, see, e.g., Gilman et al. (eds.) *The Pharmacological Bases of Therapeutics,* 8th Ed., Pergamon Press, 1990; A. Gennaro (ed.), *Remington's Pharmaceutical Sciences,* 22nd Edition, Mack Publishing Co., Pennsylvania, 2012; Avis et al. (eds.) *Pharmaceutical Dosage Forms: Parenteral Medications* Dekker, New York, 1993; Lieberman et al. (eds.) *Pharmaceutical Dosage Forms: Tablets* Dekker, New York, 1990; Lieberman et al. (eds.), *Pharmaceutical Dosage Forms: Disperse Systems* Dekker, New York, 1990; and Walters (ed.) *Dermatological and Transdermal Formulations* (Drugs and the Pharmaceutical Sciences), Vol 119, Marcel Dekker, 2002.

Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™, or polyethylene glycol (PEG).

The formulation herein may also contain more than one active compound, preferably those with complementary activities that do not adversely affect each other. The type and effective amounts of such medicaments depend, for example, on the amount and type of therapeutic agent described herein present in the formulation, and clinical parameters of the individuals.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nanoparticles and nanocapsules) or in macroemulsions. Such techniques are disclosed in *Remington's Pharmaceutical Sciences* 16th edition, Osol, A. Ed., 1980.

Sustained-release preparations may be prepared. Suitable examples of sustained-release preparations include semipermeable matrices of solid hydrophobic polymers containing the therapeutic agent, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and 7 ethyl-L-glutamate, nondegradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

The formulations to be used for in vivo administration must be sterile. This is readily accomplished by filtration through sterile filtration membranes.

Articles of Manufacture and Kits

In another aspect, provided herein is a kit or an article of manufacture containing materials useful for the treatment, diagnosis, and/or monitoring of individuals is provided.

In some instances, such diagnostic kits including one or more reagents for identifying an individual having a breast cancer (e.g., an HR+ breast cancer (e.g., an ER+ breast cancer (e.g., luminal A breast cancer or luminal B breast cancer)), DCIS, and/or a metastatic or a locally advanced breast cancer) who may benefit from a treatment including an endocrine therapy as described herein, by determining an ER pathway activity score or an E2-induced score, as described herein, from a sample (e.g., a tissue sample, e.g., a tumor tissue sample, e.g., a FFPE, a FF, an archival, a fresh, or a frozen tumor tissue sample) from the individual. In some instances, the kit further includes one or more reagents for determining an ER pathway activity score or an E2-induced score from a sample.

Optionally, the kit may further include instructions to use the kit to select a therapy such as an endocrine therapy provided herein for treating a breast cancer if the ER pathway activity score or E2-induced score determined from the sample (e.g., a tissue sample, e.g., a tumor tissue sample, e.g., a FFPE, a FF, an archival, a fresh, or a frozen tumor tissue sample) from the individual is at or above a reference ER pathway activity score or a reference E2-induced score. In another instance, the instructions are to use the kit to select an anti-cancer therapy other than an endocrine therapy, if the ER pathway activity score or E2-induced score determined from the sample (e.g., a tissue sample, e.g., a tumor tissue sample, e.g., a FFPE, a FF, an archival, a fresh, or a frozen tumor tissue sample) from the individual is below a reference ER pathway activity score or a reference E2-induced score.

In other instances, the articles of manufacture or kits may include instructions to use the kit to monitor and/or assess the response of an individual having a breast cancer to treatment with an endocrine therapy as described herein.

In one aspect a kit including a plurality of nucleic acids is provided. The plurality of nucleic acids are at least 5 nucleotides in length and are at least 95, 98, 99, or 100% identical to a 5 nucleotide continuous sequence within at least five genes set forth in Table 1 and at least five genes set forth in Table 4; at least five genes set forth in Table 2 and at least five genes set forth in Table 4; or at least five genes set forth in Table 3 and at least five genes set forth in Table 6, or 95, 98, 99, or 100% identical to a sequence complementary to the 5 nucleotide continuous sequence.

In embodiments, the plurality of nucleic acids are attached to a solid support. In embodiments, the plurality of nucleic acids comprise a detectable label. In embodiments, the plurality of nucleic acids are at least 95, 98, 99, or 100% identical to a 5 nucleotide continuous sequence within at least five genes set forth in Table 1, at least five genes set forth in Table 2 or at least five genes set forth in Table 3 are greater than a standard control. In embodiments, the plurality of nucleic acids are at least 95, 98, 99, or 100% identical to a 5 nucleotide continuous sequence within at least five genes set forth in Table 4, at least five genes set forth in Table 5 or at least five genes set forth in Table 6 are less than a standard control. In embodiments, the plurality of nucleic acids are at least 95, 98, 99, or 100% identical to a 5 nucleotide continuous sequence within all genes set forth in Table 1 and all genes set forth in Table 4. In embodiments, the plurality of nucleic acids are at least 95, 98, 99, or 100% identical to a 5 nucleotide continuous sequence within all genes set forth in Table 2 and all genes set forth in Table 5. In embodiments, the plurality of nucleic acids are at least 95, 98, 99, or 100% identical to a 5 nucleotide continuous sequence within all genes set forth in Table 3 and all genes set forth in Table 6. In embodiments, the plurality of nucleic acids are at least 95, 98, 99, or 100% identical to a 5 nucleotide continuous sequence within all genes set forth in Table 1 and all genes set forth in Table 4 and no other genes. In embodiments, the plurality of nucleic acids are at least 95, 98, 99, or 100% identical to a 5 nucleotide continuous sequence within all genes set forth in Table 2 and all genes set forth in Table 5 and no other genes. In embodiments, the plurality of nucleic acids are at least 95, 98, 99, or 100% identical to a 5 nucleotide continuous sequence within all genes set forth in Table 3 and all genes set forth in Table 6 and no other genes in the subject.

In a further embodiment, the plurality of nucleic acids are at least 95, 98, 99, or 100% identical to a continuous nucleotide sequence comprising at least 10, 20, 25, 50, 75, 100, 150, or 200 nucleotides.

Provided herein are also articles of manufacture including, packaged together an endocrine therapy as described herein in a pharmaceutically acceptable carrier and a package insert indicating that the endocrine therapy is for treating an individual with a breast cancer as described herein based on an ER pathway activity score or an E2-induced score determined from a sample (e.g., a tissue sample, e.g., a tumor tissue sample, e.g., a FFPE, a FF, an archival, a fresh, or a frozen tumor tissue sample) from the individual.

The article of manufacture may include, for example, a container and a label or package insert on or associated with the container. Suitable containers include, for example, bottles, vials, syringes, and the like. The container may be formed from a variety of materials such as glass or plastic. The container holds or contains a composition comprising the cancer medicament as the active agent and may have a sterile access port (e.g., the container may be an intravenous solution bag or a vial having a stopper pierceable by a hypodermic injection needle).

The article of manufacture may further include a second container comprising a pharmaceutically-acceptable diluent buffer, such as bacteriostatic water for injection (BWFI), phosphate-buffered saline, Ringer's solution, and/or dextrose solution. The article of manufacture may further include other materials desirable from a commercial and user standpoint, including other buffers, diluents, filters, needles, and syringes.

The kits or articles of manufacture described herein may have a number of instances. In one instance, the kits or articles of manufacture includes a container, a label on said container, and a composition contained within said container, wherein the composition includes one or more polynucleotides that hybridize to a complement of a gene listed herein (e.g., a set of genes set forth in any one of Tables 1-6) under stringent conditions, and the label on said container indicates that the composition can be used to evaluate the presence a set of genes listed herein (e.g., a set of genes set forth in any one of Tables 1-6) in a sample, and wherein the kit includes instructions for using the polynucleotide(s) for evaluating the presence of the genes' RNA or DNA in a particular sample type.

For oligonucleotide-based articles of manufacture or kits, the article of manufacture or kit can include, for example: (1) an oligonucleotide, e.g., a detectably labeled oligonucleotide, which hybridizes to a nucleic acid sequence encoding a protein or (2) a pair of primers useful for amplifying a nucleic acid molecule. The article of manufacture or kit can also include, e.g., a buffering agent, a preservative, or a protein stabilizing agent. The article of manufacture or kit can further include components necessary for detecting the detectable label (e.g., an enzyme or a substrate). The article of manufacture or kit can also contain a control sample or a series of control samples that can be assayed and compared to the test sample. Each component of the article of manufacture or kit can be enclosed within an individual container and all of the various containers can be within a single package, along with instructions for interpreting the results of the assays performed using the kit.

The article of manufacture provided herein also includes information, for example in the form of a package insert, indicating that the composition is used for treating a breast cancer (e.g., an HR+ breast cancer (e.g., an ER+ breast cancer (e.g., luminal A breast cancer or luminal B breast cancer)), DCIS, and/or a metastatic or a locally advanced breast cancer) based on an ER pathway activity score or an E2-induced score from determined from a sample (e.g., a tissue sample, e.g., a tumor tissue sample, e.g., a FFPE, a FF, an archival, a fresh, or a frozen tumor tissue sample) from an individual as described herein. The insert or label may take any form, such as paper or on electronic media such as a magnetically recorded medium (e.g., floppy disk), a CD-ROM, a Universal Serial Bus (USB) flash drive, and the like. The label or insert may also include other information concerning the pharmaceutical compositions and dosage forms in the kit or article of manufacture.

EXAMPLES

The following are examples of the methods and compositions provided herein. It is understood that various other embodiments may be practiced, given the general description provided above.

Example 1. Identification of an ER Pathway Activity Signature

Gene expression levels in breast cancer cell lines and a breast cancer xenograft mouse model were evaluated for their association with estrogen receptor (ER) pathway activity to identify potential biomarkers for predictive purposes.

In vitro derived ER pathway activity signature. To derive a transcriptional signature of ER pathway activity, RNA sequencing was performed on seven breast cancer cell lines following treatment with either DMSO or 1 µM estradiol (E2) for 24 hours. Briefly, RNA libraries for cell lines were made with TRUSEQ® RNA sample preparation kit (ILLUMINA®) according to the manufacturer's protocol. The libraries were sequenced on an ILLUMINA® HiSeq 2000, using 1-4 lanes per cell line. RNA sequencing (RNA-seq) data were analyzed with HTSeqGenie (R package version 3.14.0) in BioConductor (Huber et al. *Nature Methods.* 112:115-21, 2015) as follows: reads were trimmed to 75 base pairs (bp), filtered for quality and rRNA/adapter contamination, and aligned to the reference genome GRCh38 using GSNAP (Wu et al. *Bioinforma Oxf Engl.* 26:873-81, 2010). Gene expression was quantified as Reads per Kilobase of exon model per Million mapped reads normalized by size factor (nRPKM), defined as number of reads aligning to a gene in a sample/(total number of uniquely mapped reads for that sample×gene length×size factor). Genes without gene symbol and genes of uncertain function (LOC and Corf symbols) were excluded.

233 to 1,390 genes were significantly induced by E2 relative to DMSO in individual cell lines (fold change ≥2, and p-value ≤0.05) (FIG. 1A), and 365 to 1,251 genes were significantly suppressed by E2 in individual cell lines (fold change ≤0.5, and p-value ≤0.05) (FIG. 1). In order to capture a core set of ER-responsive genes that are most reflective of ER pathway activity across heterogeneous tumors, and would thus likely be widely sensitive to ER perturbation, selected genes were those that were significantly and consistently induced or repressed by E2 in at least 6 out of 7 cell lines. E2-induced genes were additionally required to be higher expressed in 12 ER IHC+ breast cell lines compared to 25 ER IHC− breast cell lines (one-sided t-test p<0.05). To compare the genes in a broader panel of ER+vs. ER− breast cell lines, RNA-sequencing data from 37 breast cell lines was performed as described in Klijn et al, Nat Biotech 2015 and deposited on the European Genome-phenome Archive (http://www.ebi.ac.uk/ega/) under accession number EGAS00001000610. These data were processed in the same way as the RNAseq data for the 7 breast lines (previous paragraph). Together, this resulted in the identification of 28 E2-induced and 19 E2-repressed genes.

In order to generalize this core set of E2-induced and E2-repressed genes to patient data, RNA-seq data from 939 breast tumors from The Cancer Genome Atlas (TCGA), which included 726 ER+(by IHC) breast tumors and 213 ER− breast tumors were examined. Briefly, RNA-seq data were downloaded from the National Cancer Institute Genomic Data Commons (https://gdc.cancer.gov) and were analyzed with HTSeqGenie in BioConductor as follows: first, reads with low nucleotide qualities (70% of bases with quality <23) or rRNA and adapter contamination were removed. The reads that passed were then aligned to the reference genome GRCh38 using GSNAP. Alignments of the reads that were reported by GSNAP as "uniquely mapping" were used for subsequent analysis. Raw counts were converted to counts per million (cpm), filtered for lowly expressed genes (e.g., cpm <0.25 in over 90% of samples), normalized using TMM normalization in the edgeR package, and finally voom transformed using the limma package in R. ER IHC was available for 84% of tumors, and RNA-seq-derived PAM50 subtype labels were assigned as previously described (Daemen et al. *Breast Cancer Research.* 20:8, 2018). Genes that were on average low expressed across the 726 ER+(by IHC) breast tumors were discarded (average expression in bottom $15^{th}$ percentile).

Signature genes were required to be expressed in ER+ TCGA tumors, and E2-induced genes were required to be higher expressed in ER+ compared to ER− tumors (one-sided t-test p<0.05). This resulted in a further refinement of the signature to a 41-gene signature composed of 23 E2-induced and 18 E2-repressed genes of which are shown in Table 7 below. (See FIG. 1C).

TABLE 7

| | | ER Repressed Genes | | | | | | |
|---|---|---|---|---|---|---|---|---|
| Gene symbol | Entrez gene ID | MDA-MB-330 Log2 FC E2 vs no E2 | HCC1500 Log2 FC E2 vs no E2 | MCF7 Log2 FC E2 vs no E2 | EFM19 Log2 FC E2 vs no E2 | T47D Log2 FC E2 vs no E2 | BT474 Log2 FC E2 vs no E2 | CAMA1 Log2 FC E2 vs no E2 |
| BAMBI | 25805 | −1.352 | −1.438 | −0.572 | −1.554 | −1.354 | −1.153 | −1.072 |
| BCAS1 | 8537 | −1.772 | −2.105 | −0.981 | −2.169 | −2.539 | −1.110 | −2.311 |
| CCNG2 | 901 | −1.008 | −1.525 | −1.267 | −1.442 | −1.330 | −0.935 | −2.094 |
| DDIT4 | 54541 | −1.321 | −1.065 | −1.080 | −1.101 | −1.878 | −0.862 | −2.737 |
| EGLN3 | 112399 | −2.785 | −2.504 | −1.090 | −1.008 | −2.052 | −0.118 | −1.583 |
| FAM171B | 165215 | −2.790 | −0.683 | −1.287 | −1.910 | −1.158 | −1.279 | −2.271 |
| GRM4 | 2914 | −2.381 | −3.071 | −1.306 | −1.141 | −1.340 | −1.883 | −2.023 |
| ILIR3 | 3554 | −0.941 | −1.943 | −2.163 | −2.327 | −2.433 | −1.490 | −1.665 |
| LIPH | 200879 | −1.737 | −1.384 | −1.170 | −1.844 | −1.330 | −0.804 | −1.583 |
| NBEA | 26950 | −1.044 | −1.190 | −1.132 | −1.105 | −1.368 | −0.346 | −1.550 |
| PNPLA7 | 375775 | −1.084 | −1.376 | −1.046 | −0.901 | −1.211 | −1.427 | −2.068 |
| PSCA | 8000 | −2.529 | −1.726 | −2.196 | −1.593 | −1.253 | −1.956 | −3.517 |
| SEMA3E | 9723 | −2.427 | −1.058 | −1.034 | −1.110 | −0.741 | −1.101 | −1.374 |
| SSPO | 23145 | −1.383 | −1.304 | −1.338 | −0.605 | −1.181 | −1.739 | −2.298 |
| STON1 | 11037 | −1.081 | −1.279 | −2.067 | −1.506 | −2.304 | −0.656 | −2.609 |
| TGFB3 | 7043 | −1.111 | −1.214 | −1.707 | −1.350 | −1.263 | −0.304 | −1.444 |
| TP53INP1 | 94241 | −1.304 | −1.777 | −1.816 | −1.451 | −1.363 | −1.496 | −3.177 |
| TP53INP2 | 58476 | −1.210 | −1.073 | −1.207 | −1.373 | −0.959 | −2.069 | −2.068 |

Figures 1D, 1E, 1F:
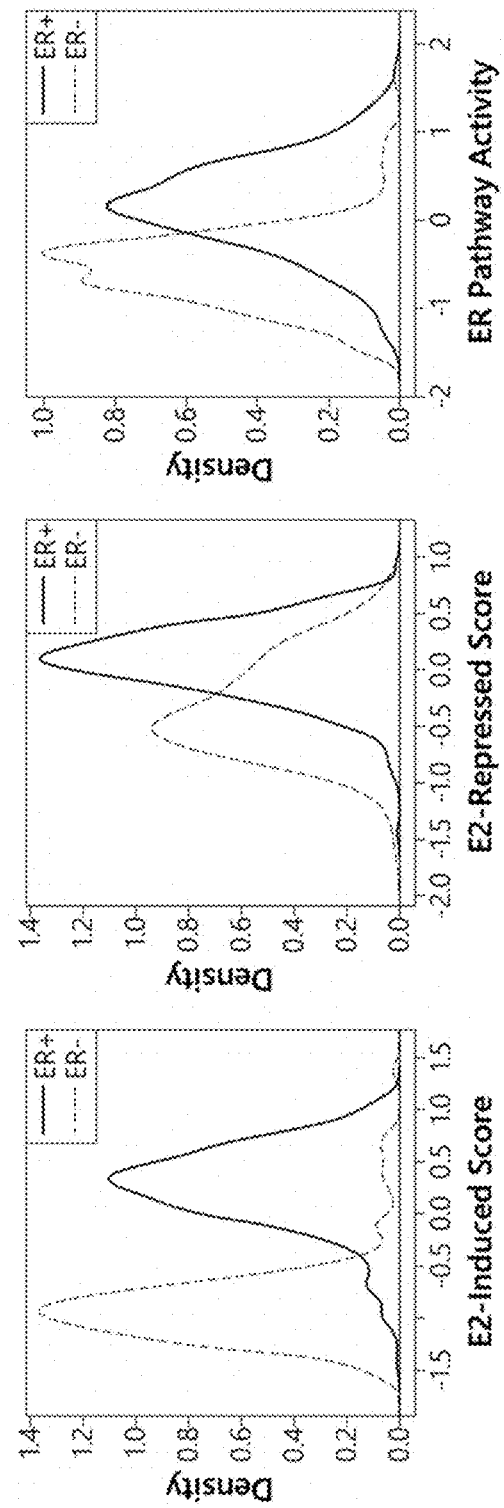
FIG. 1D is a graph showing overlaid reference density curves of the E2-induced score (defined as the average z-scored expression of the 23 E2-induced genes shown in FIG. 1C) for 726 ER IHC+ and 213 ER IHC− breast tumors from the TCGA RNA-seq data.
FIG. 1E is a graph showing overlaid reference density curves of the E2-repressed score (defined as average z-scored expression of 18 E2-repressed genes shown in FIG. 1C) in 726 ER IHC+ and 213 ER IHC− breast tumors from the TCGA RNA-seq data.
FIG. 1F is a graph showing overlaid reference density curves of the ER pathway activity score (defined as the difference between the E2-induced score and the E2-repressed score) in 726 ER IHC+ and 213 ER IHC− breast tumors from the TCGA RNA-seq data.

To assess the spectrum of ER activity across a large patient population, density curves of three scores were derived using TCGA RNA-seq data from 939 treatment-naïve, primary breast tumors. The E2-induced score was defined as the average z-scored expression of 23 E2-induced genes (FIG. 1D); the E2-repressed score was defined as the average z-scored expression of 18 E2-repressed genes (FIG. 1E); and the ER pathway activity score was defined as the difference between the E2-induced and E2-repressed score (FIG. 1F). Genes identified as being modulated by ER as contained within the signature, irrespective of whether they are induced by, or repressed by E2, were expressed at low levels in ER−/basal tumors; E2 repressed genes are thus not necessarily anticipated to be more highly expressed in ER− tumors versus ER+ tumors.

Figure 2A:
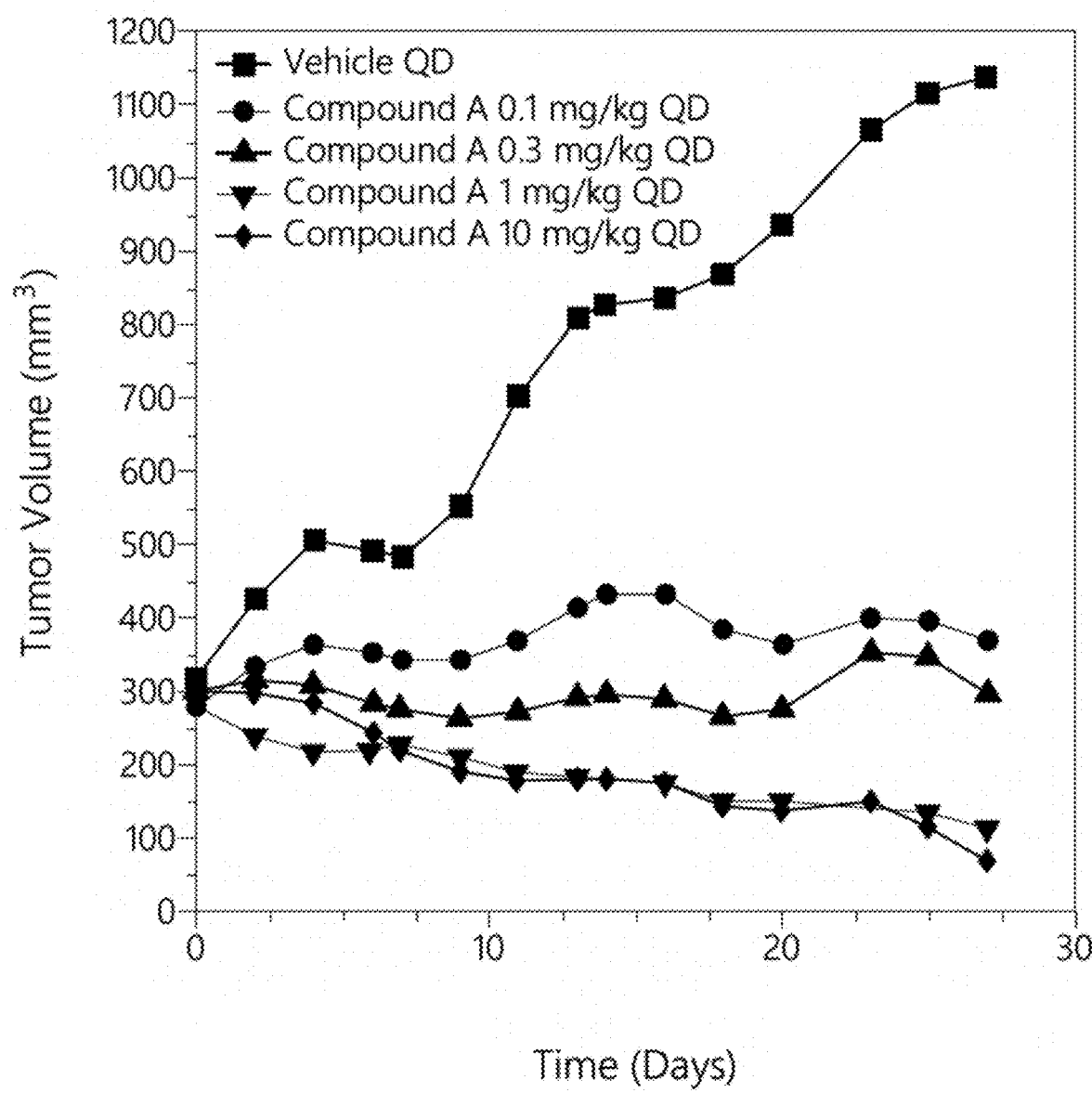
FIG. 2A is a graph showing the in vivo efficacy of treatment with Compound A, a selective estrogen receptor degrader (SERD), in a HCI-013 patient-derived xenograft (PDX) mouse model of hormone receptor (HR)-positive breast cancer, as assessed by tumor volume over time at the indicated Compound A concentrations.
Figure 2B:
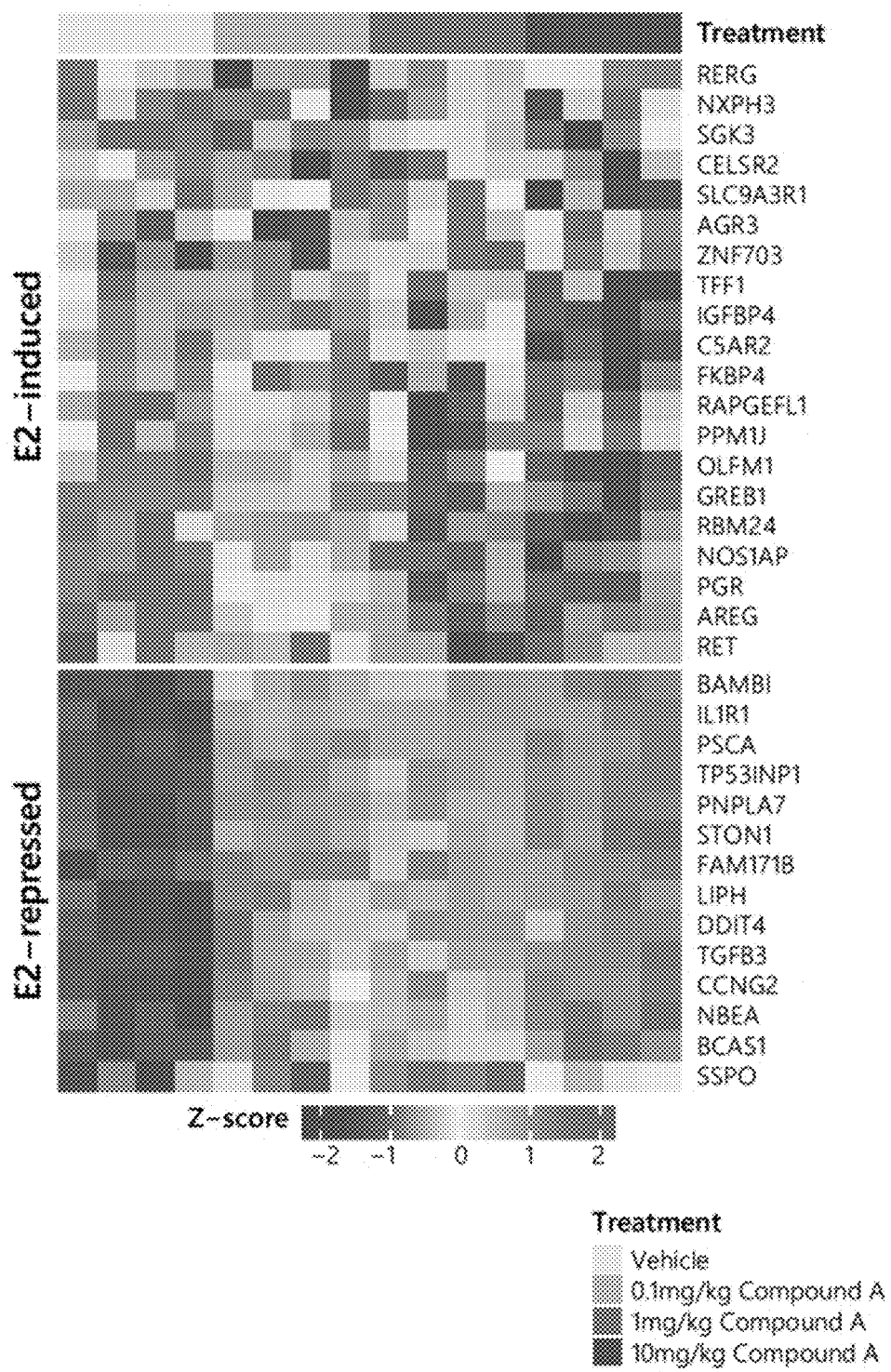
FIG. 2B is a heat map showing the relative change in z-scored expression, for the indicated 20 E2-induced and 14 E2-repressed genes in HCI-013 tumors following treatment with Compound A. Treatment regimens are annotated above.

In vivo validation of ER pathway activity signature. The HCI-013 PDX breast model was treated with vehicle or with different doses of Compound A, a selective estrogen receptor degrader (SERD), (0.1 mg/kg, 1 mg/kg, or 10 mg/kg), with four animals per treatment group (FIG. 2A). Samples were collected 8 hrs after the last dose, and expression of the 23 E2-induced genes, 18 E2-repressed genes, and housekeeping genes were measured using FLUIDIGM®, and the data processed using SPOTFIRE® software. Expression data were normalized to housekeeping genes GUSB, PPIA, and UBC. Three genes that did not meet quality control standards were excluded (GRM4, FMN1, and TP52INP2). Two E2-induced genes, AMZ1 and CT62, and two E2-repressed genes, EGLN3 and SEMA3A, that were lowly expressed across the tumors in this study (average housekeeping-normalized expression in bottom $10^{th}$ percentile of expressed genes) (FIG. 2B) were also excluded.

Figure 2C:
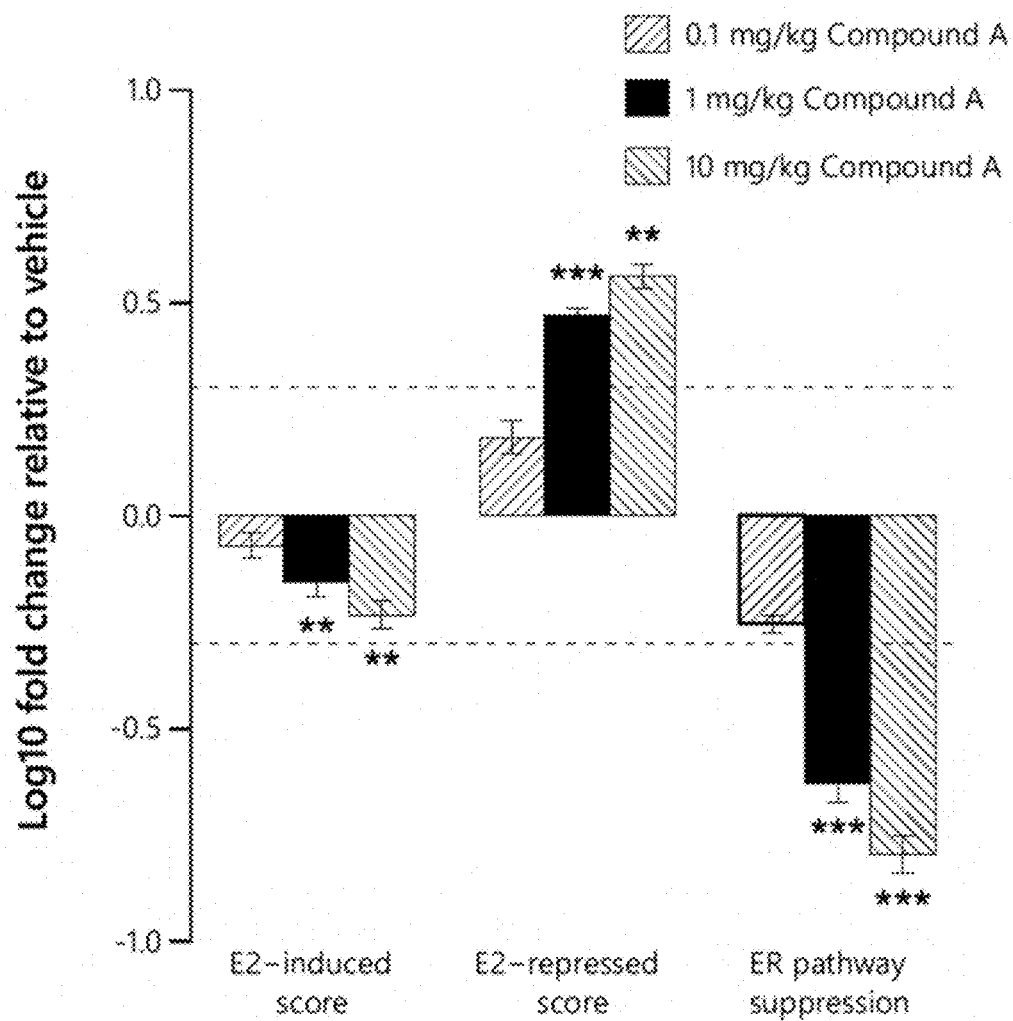
FIG. 2C is a set of bar plots of the E2-induced score, E2-repressed score, and ER pathway activity score expressed as the average $\log_{10}$-fold change, in HCI-013 tumors after Compound A exposure relative to vehicle-treated animals. Bar plots show average relative score and standard error, with n=4. One-sided t-test: *, p<0.05; , p<0.01; *, p<0.001; comparison 1 mg/kg vs. 0.1 mg/kg in black; 10 mg/kg vs. 1 mg/kg in red.

The effect of treatment with Compound A on ER pathway activity in the HCI-013 PDX model was assessed based on 20 E2-induced and 14 E2-repressed genes. The fold change in expression of each gene after Compound A exposure was calculated relative to the average expression of that gene in four vehicle treated animals. The E2-induced score was calculated as the average $\log_{10}$ fold change in expression of 20 E2-induced genes. The E2-repressed score was calculated as the average $\log_{10}$ fold change in expression of 14 E2-repressed genes. A composite score for ER pathway activity was calculated as the difference between the E2-induced score and the E2-repressed score (FIG. 2C). The three scores show a dose-response effect, with increased suppression of the ER pathway with increased dose (0.1 to 1 to 10 mg/kg).

Figure 2D:
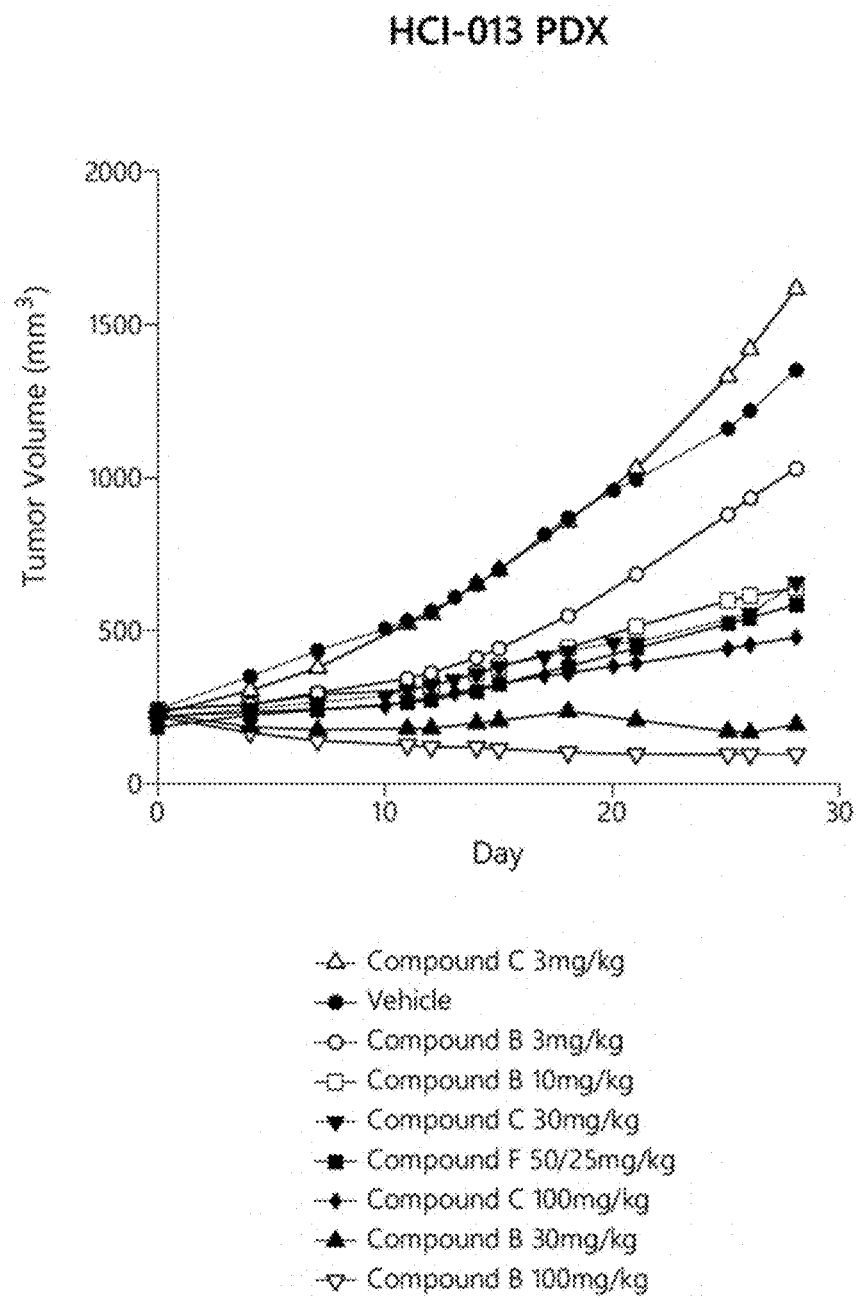
FIG. 2D is a graph showing the in vivo efficacy of treatment with vehicle, or Compound B (a SERD), Compound C (a SERD/SERM hybrid), or Compound F (a SERD) in a HCI-013 PDX mouse model of HR-positive breast cancer, as assessed by tumor volume over time at the indicated concentrations.
Figure 2E:
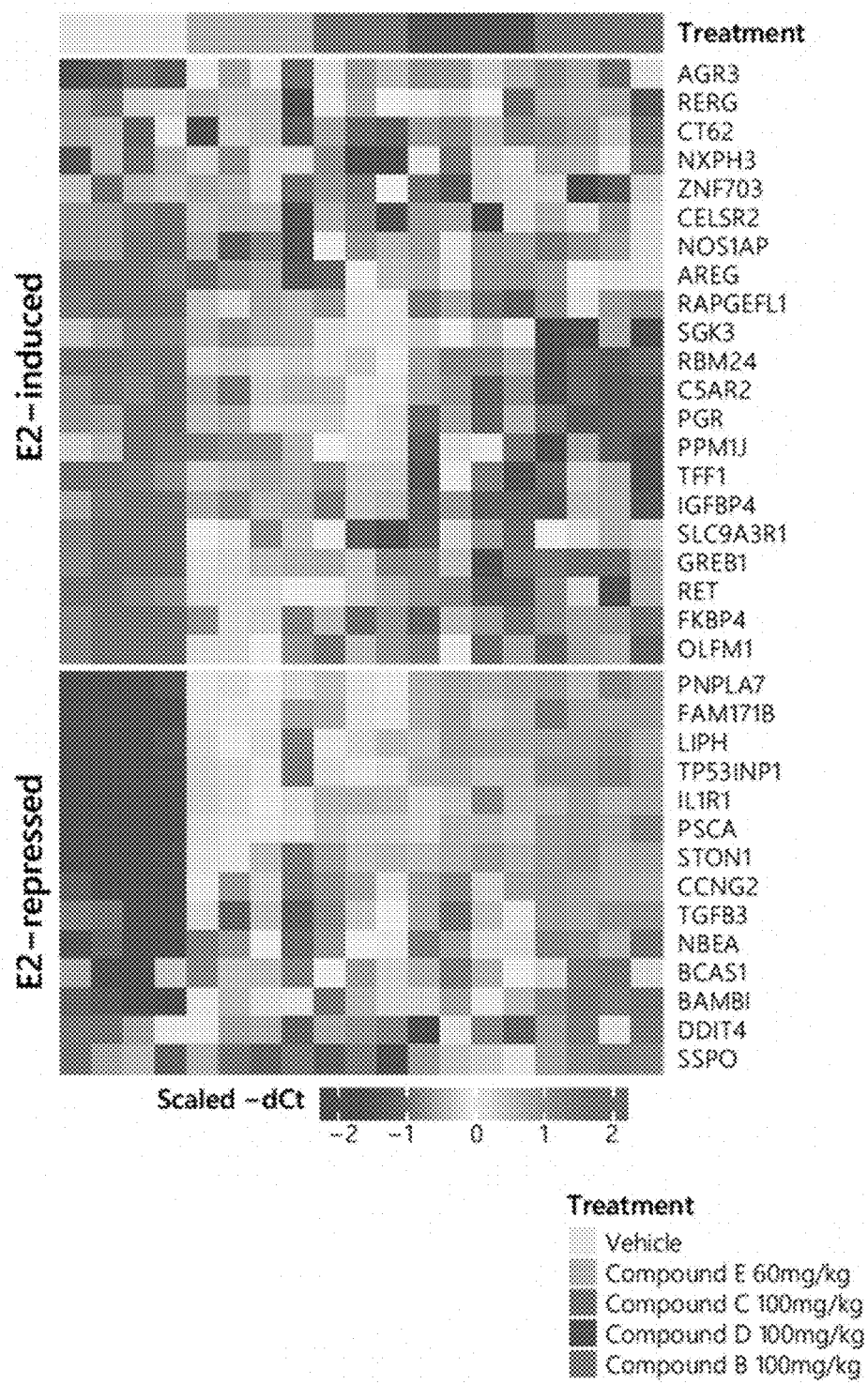
FIG. 2E is a heat map showing the relative change in z-scored expression, for the indicated 20 E2-induced and 14 E2-repressed genes in HCI-013 tumors following treatment with the indicated therapy. Treatment regimens are annotated above.
Figure 2F:
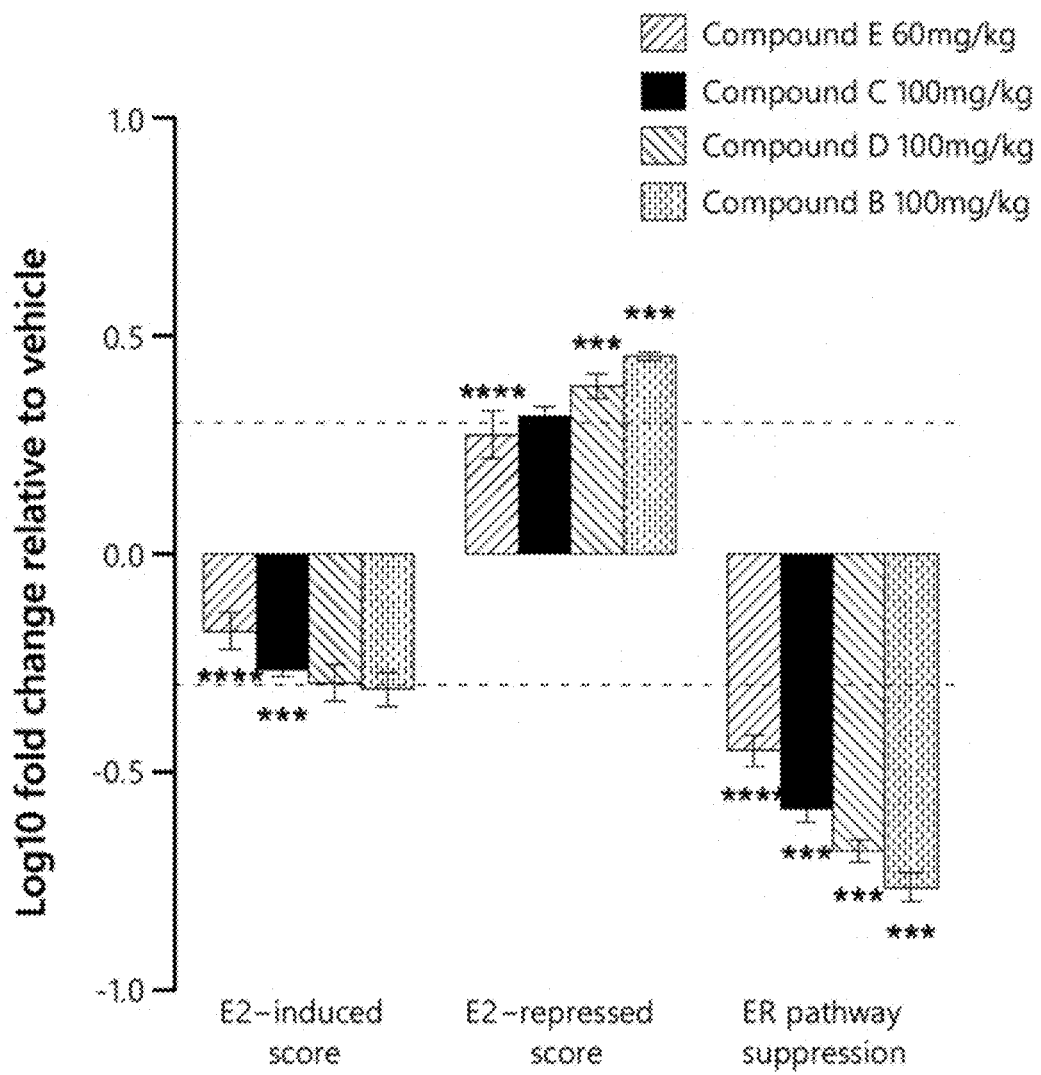
FIG. 2F is a set of bar plots of the E2-induced score, E2-repressed score, and ER pathway activity score expressed as the average $\log_{10}$-fold change, in HCI-013 tumors after exposure to the indicated compounds relative to vehicle-treated animals. Bar plots show average relative score and standard error, with n=4. One-sided t-test: *, p<0.1; , p<0.05; *, p<0.01; ****, p<0.001; comparison Compound E vs. Vehicle, Compound C vs. Compound E, Compound D vs. Compound C, and Compound B vs. Compound D.
Figure 2G:
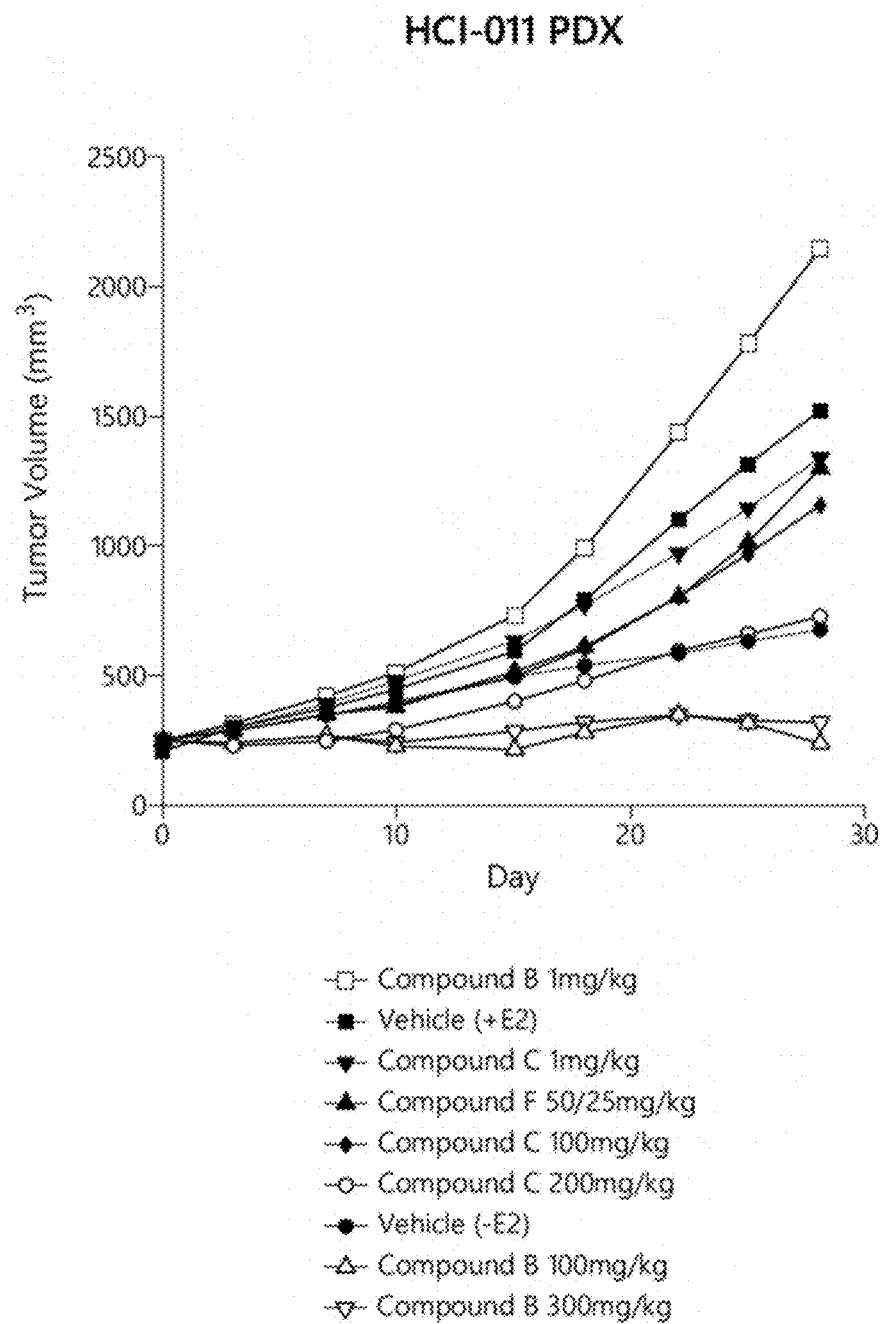
FIG. 2G is a graph showing the in vivo efficacy of treatment with vehicle, Compound B, Compound C, or Compound F in a HCI-011 PDX mouse model of HR-positive breast cancer, as assessed by tumor volume over time at the indicated endocrine therapy concentrations.
Figure 2H:
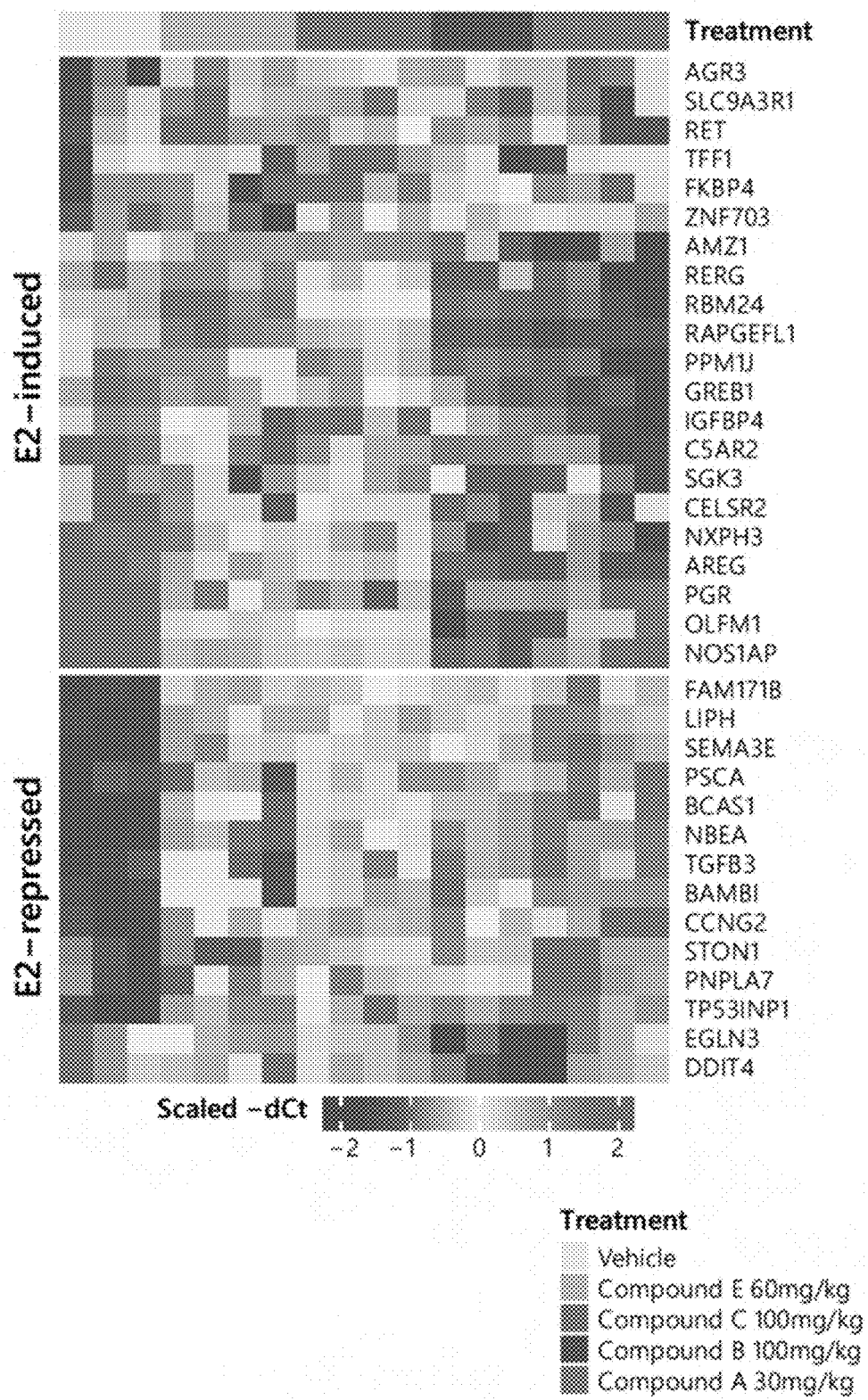
FIG. 2H is a heat map showing the relative change in z-scored expression, for the indicated 20 E2-induced and 14 E2-repressed genes in HCI-011 tumors following treatment with the indicated therapy. Treatment regimens are annotated above.
Figure 2I:
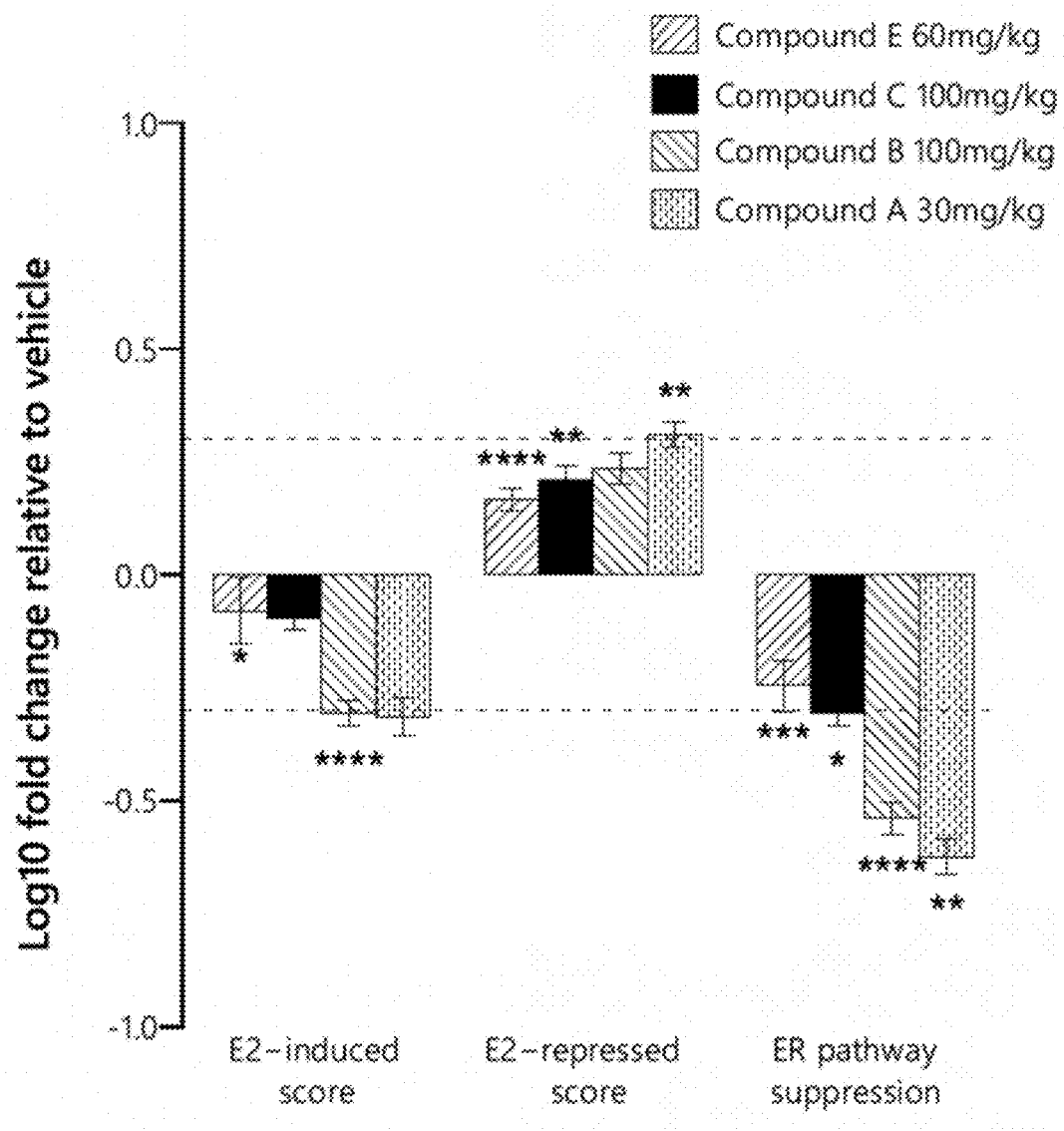
FIG. 2I is a set of bar plots of the E2-induced score, E2-repressed score, and ER pathway activity score expressed as the average $\log_{10}$-fold change, in HCI-011 tumors after exposure to the indicated compounds relative to vehicle-treated animals. Bar plots show average relative score and standard error, with n=4. One-sided t-test: *, $p<0.1$; , $p<0.05$; *, $p<0.01$; ****, $p<0.001$; comparison Compound E vs. Vehicle, Compound C vs. Compound E, Compound B vs. Compound C, and Compound A vs. Compound B.

The HCI-013 and HCI-011 PDX breast models were treated with various endocrine agents including Compound A, Compound B, Compound D, or Compound F at various doses, with four animals per treatment group. Tumor samples were collected 8 hrs after the last dose, and the expression of the 23 E2-induced genes, 18 E2-repressed genes, housekeeping genes were measured using a FLUIDIGM® assay, and genes with low expression or that did not meet quality control standards were removed from the analysis, as described above. For data shown in FIGS. 2D-2F, expression data were normalized to housekeeping genes GUSB, SDHA, and UBC. One gene that did not meet quality control standards was excluded (FMN1). One E2-induced gene, AMZ1, and four E2-repressed genes, EGLN3, GRM4, SEMA3A, and TP53INP2, that were lowly expressed across the tumors in this study (average housekeeping-normalized expression in bottom 10th percentile of expressed genes) (FIG. 2E) were also excluded. For FIGS. 2G-2I, expression data were normalized to housekeeping genes GUSB, PPIA, and UBC. Two genes that did not meet quality control standards were excluded (CXCL12 and TP52INP2). Two E2-induced genes, FMN1 and CT62, and three E2-repressed genes, GRM4, IL1R1 and SSPO, that were lowly expressed across the tumors in this study (average housekeeping-normalized expression in bottom 10th percentile of expressed genes) (FIG. 2B) were also excluded. Gene expression analysis of HCI-013 and HCI-011 tumors revealed that modulation of ER target gene expression: 21 E2-induced genes were robustly decreased by treatment with the compounds, and the 14 E2-repressed genes were significantly up-regulated by the compounds (FIGS. 2E and 2H). The degree of ER pathway suppression, as capture by the signature, associates with anti-tumor activity (FIGS. 2F and 2I).

Example 2. ER Pathway Activity Signature Captures Suppression of ER Pathway Activity in Response to SERD Treatment in Patients In clinical practice, transcriptional profiling is routinely generated from formalin-fixed paraffin-embedded (FFPE) tissue, using the RNA ACCESS® protocol.

In order to use the ER pathway activity signature as PD biomarker for SERD activity or as predictive biomarker of potential ER pathway dependency in patients, a reference distribution of ER activity was derived from RNA ACCESS® data. RNA ACCESS® data were generated from FFPE tissue of a procured collection of 139 HR+/HER2− breast tumors. Raw counts for the 139 breast tumors were converted to counts per million (cpm), filtered for lowly expressed genes (i.e. cpm <0.25 in over 90% of samples), normalized using TMM normalization in the edgeR package, and voom-transformed using the limma package in R. ER pathway signature genes with average voom-normalized expression across all 139 tumors in the bottom 5th percentile of all genes were removed from downstream analyses.

Figure 3A:
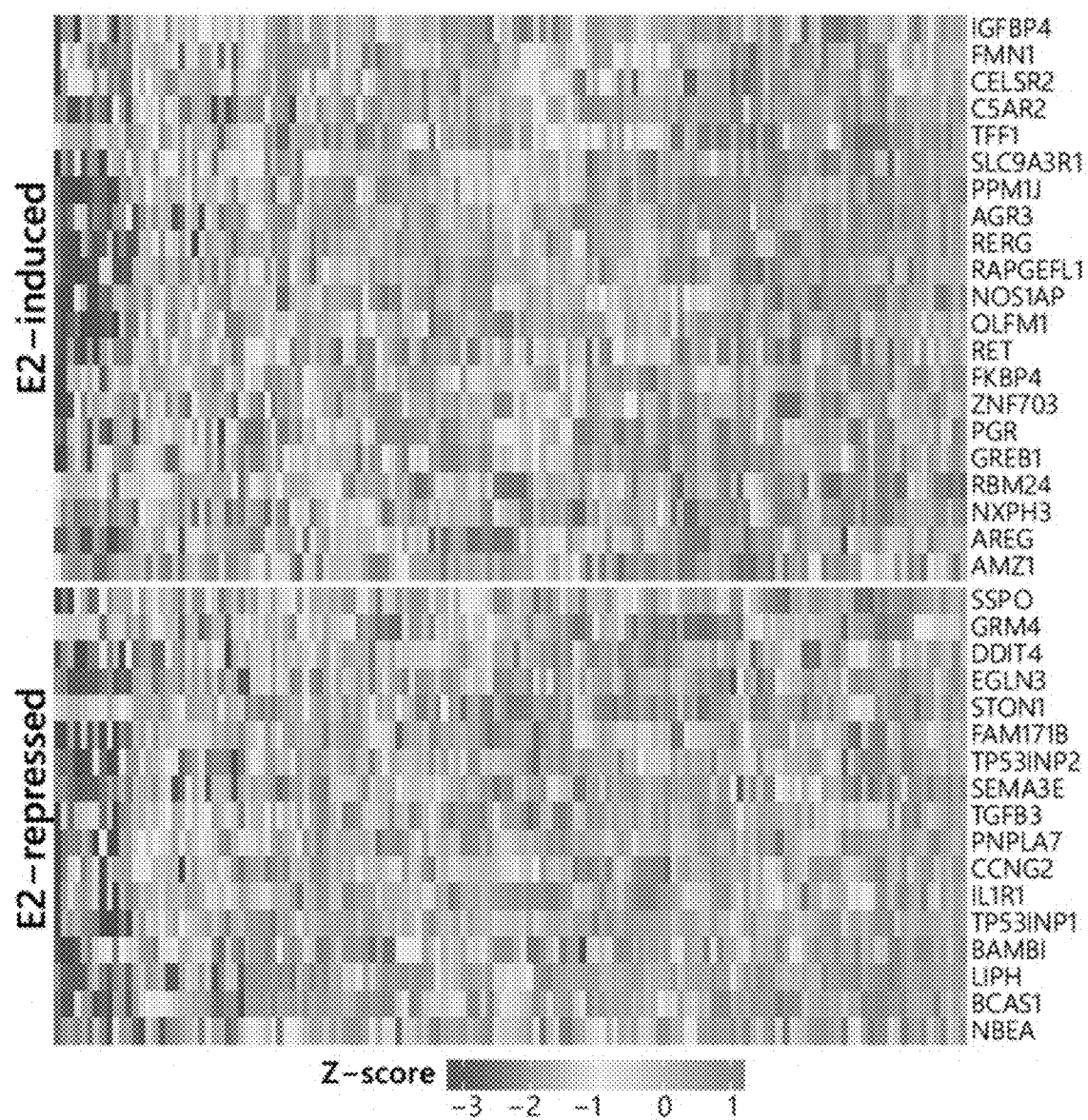
FIG. 3A is a heat map showing the relative change in z-scored expression of the 21 indicated E2-induced and 17 indicated E2-repressed genes from a collection of 139 hormone receptor-positive/human epidermal growth factor receptor 2-negative (HR+/HER2−) breast tumors.
Figures 3K, 3L, 3M:
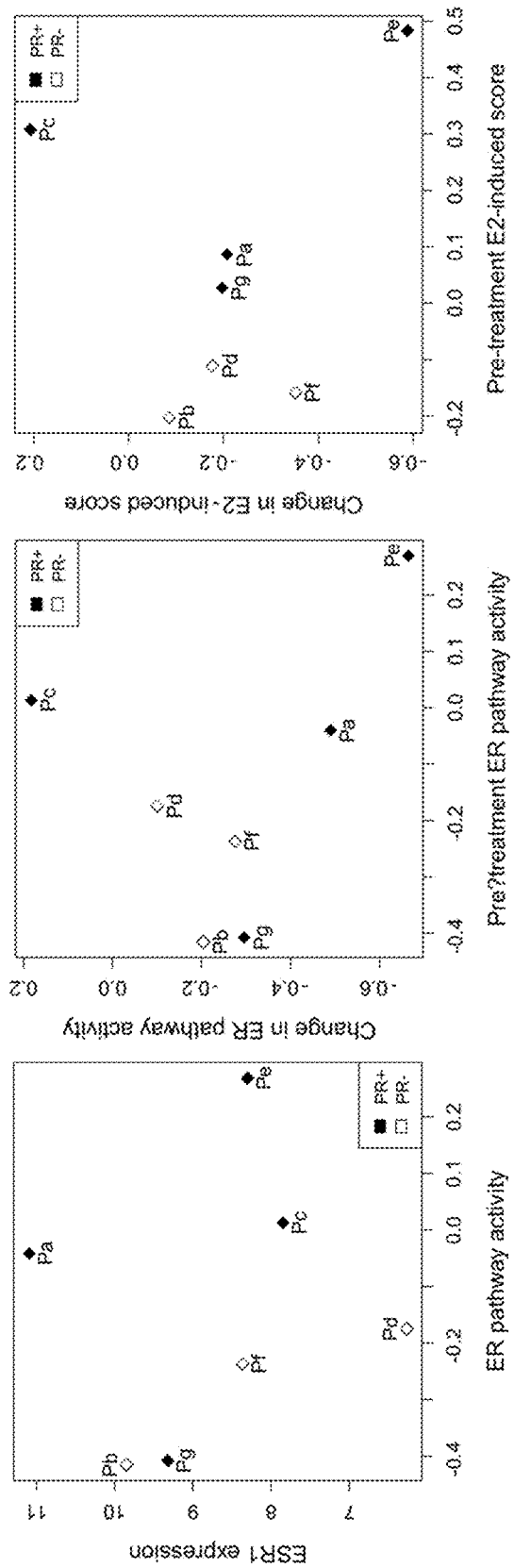
FIG. 3K is a scatter plot of pre-treatment ER pathway activity score versus pre-treatment ESR1 expression levels for seven patients treated with Compound A.
FIG. 3L is a scatter plot of the treatment-induced difference in ER pathway activity pre-treatment to post-treatment versus pre-treatment ER pathway activity levels for seven patients treated with Compound A.
FIG. 3M is a scatter plot of the treatment-induced difference in E2-induced score pre-treatment to post-treatment versus pre-treatment E2-induced scores for seven patients treated with Compound A.

Two E2-induced genes, SGK3 and CT62, were not or low expressed, and E2-repressed gene PSCA was low expressed in this reference collection. The expression of the signature genes, excluding these 3 genes, was next evaluated (FIG. 3A). RNA ACCESS® reference densities were defined for the E2-induced score, E2-repressed score, and ER pathway activity on the basis of 21 E2-induced and 17 E2-repressed genes, for the collection of 139 HR+/HER2− breast tumors (FIGS. 3B-3D, 3H-3J).

Six patients with HR+/HER2− breast cancer were treated with a SERD (Compound B), and seven patients with HR+/HER2− breast cancer were treated with another SERD (Compound A). RNA ACCESS® data were generated (as described above) from FFPE tissue collected at time of screening (pre-treatment), and during the second or third cycle of SERD treatment (post-treatment). Genes were re-centered and re-scaled, using the mean and standard deviation from the reference collection.

Signature scores for the pre- and post-treated tumors were calculated and displayed on top of the reference densities, for the six patients treated with Compound B (FIGS. 3B-3D) and for the seven patients treated with Compound A (FIGS. 3H-3J). In the first cohort of six patients treated with Compound B, ER pathway activity was suppressed by SERD treatment in 4 out of 6 patients. There was no change in ER pathway activity for the two patients with low pre-treatment ER pathway activity (patients Pb and Pf); ER pathway suppression in response to SERD-treatment is thus captured only in tumors which exhibit evidence of ER pathway activity prior to treatment (FIG. 3F). Two patients were considered PR+ (expression >4) and four patients PR−. Pre-treatment ESR1 expression levels are also an insufficient biomarker for ER pathway activity (FIG. 3E). These results were confirmed in the second cohort of seven patients treated with Compound A (FIGS. 3H-M), among which four patients with PR+ and three patients with PR− breast cancer, with an observed suppression of ER pathway activity by SERD treatment in 6 out of 7 patients. Taken together, these results show that the signature can be used as a measure of pre-treatment ER pathway activity and as a PD biomarker in both PR+ and PR− breast tumors.

Example 3: Identification of Core Signature Genes

Figure 4A:
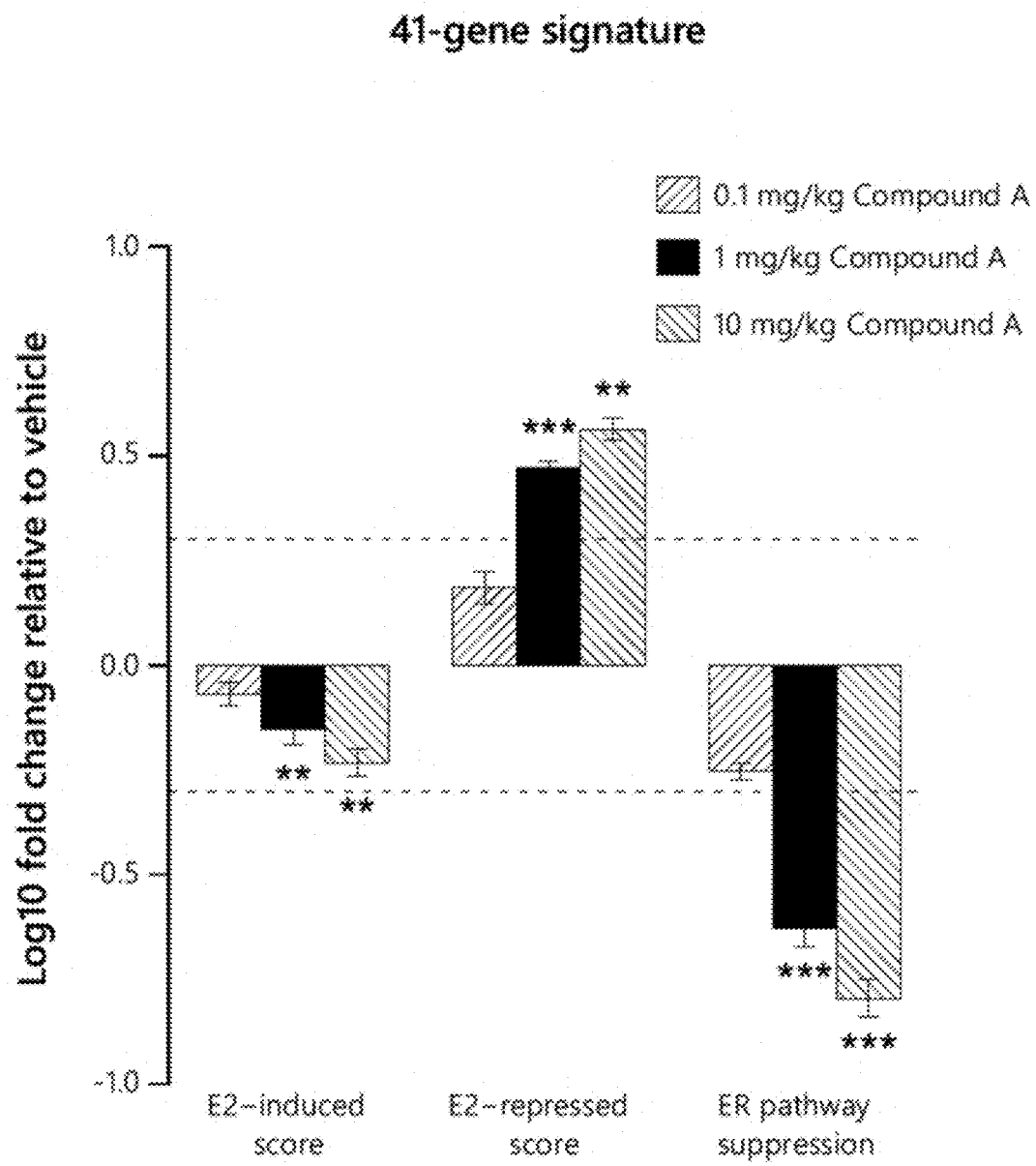
FIGS. 4A-4C are a series of bar plots of the E2-induced score, E2-repressed score, and ER pathway suppression expressed as the average $\log_{10}$-fold change, based on the complete 41-gene signature (FIG. 4A), 19-gene signature (FIG. 4B), or 14-gene signature (FIG. 4C), in HCI-013 PDX breast tumors after exposure to Compound A relative to vehicle-treated animals. Bar plots show average relative score and standard error, with n=4. One-sided t-test: *, $p<0.05$; , $p<0.01$; * $p<0.001$; comparison 1 mg/kg vs. 0.1 mg/kg in black; 10 mg/kg vs. 1 mg/kg in red.
Figure 4B:
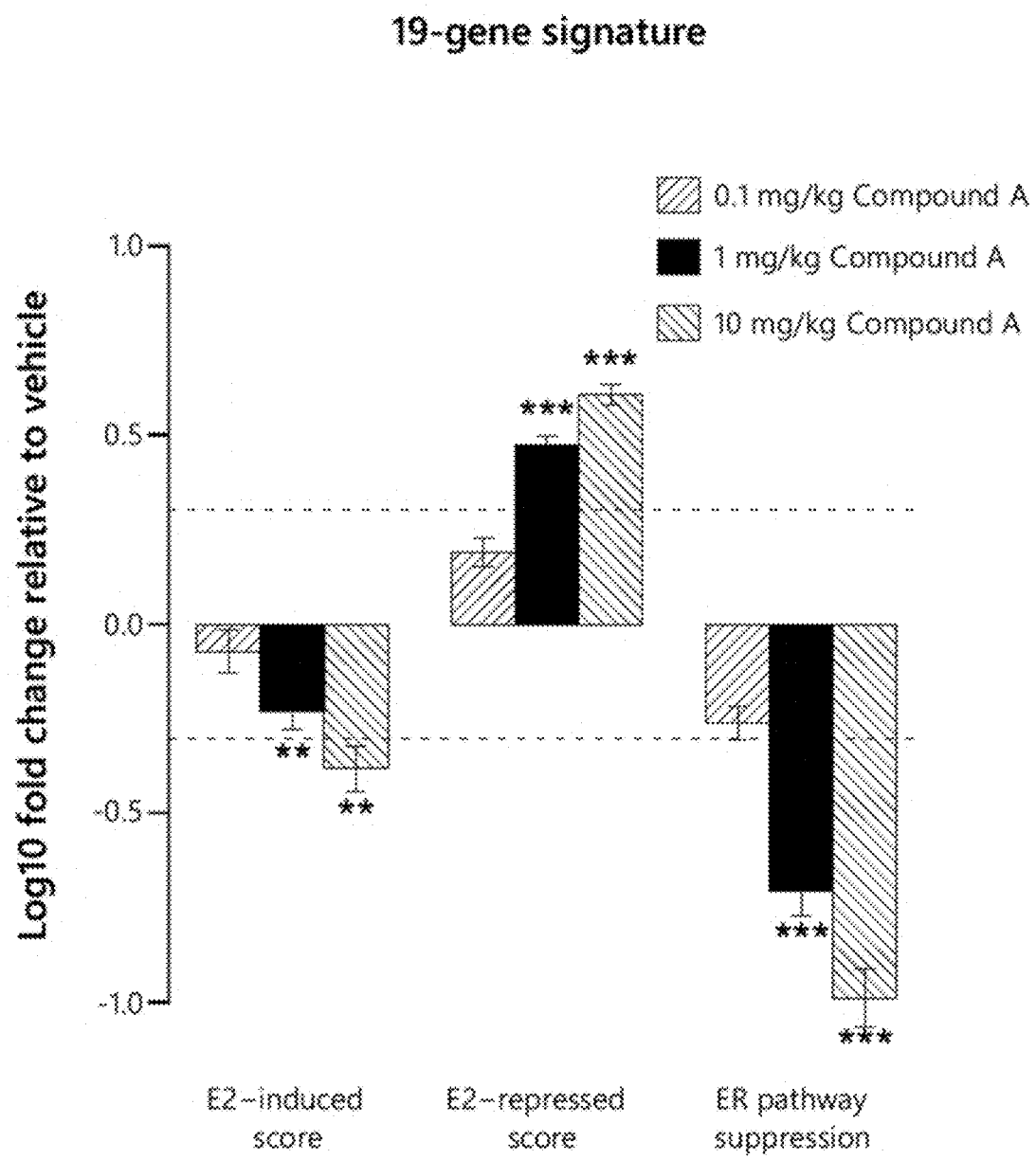
Figure 4C:
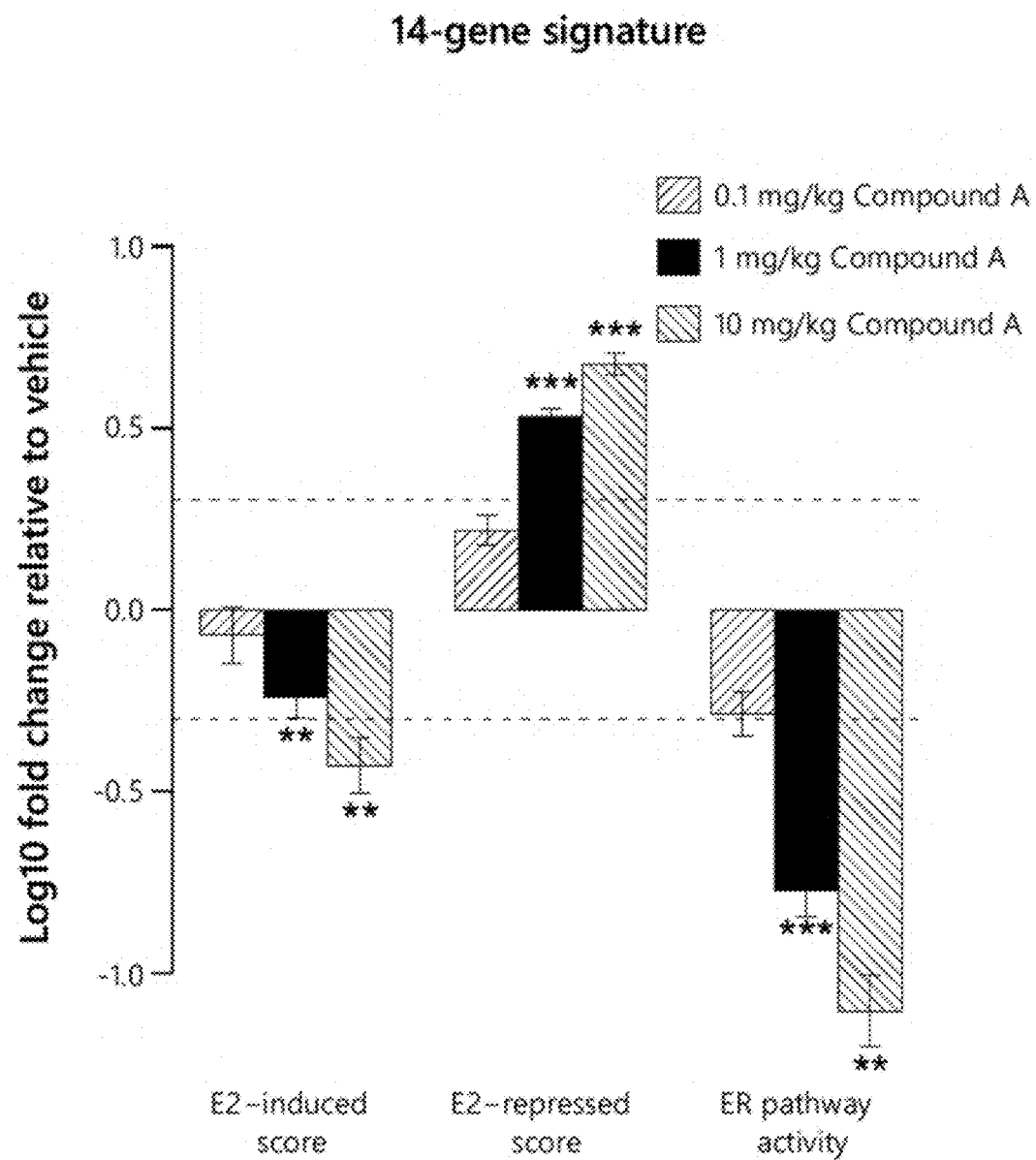
Figures 4D, 4E, 4F:
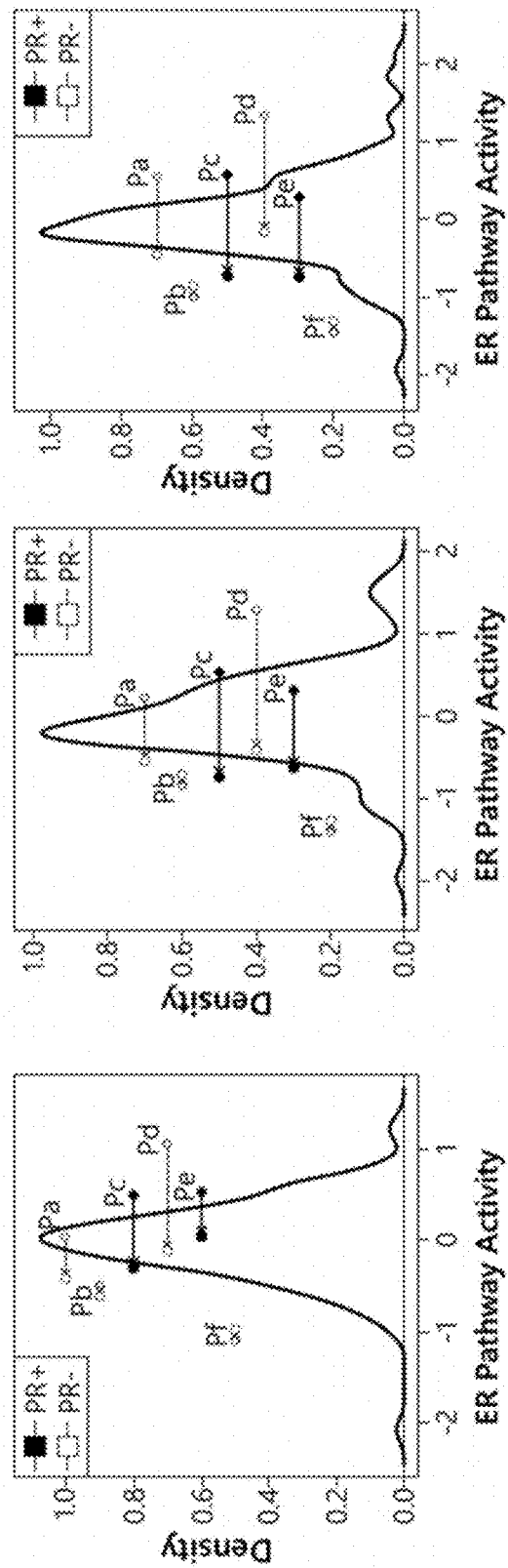
FIGS. 4D-4F are a series of reference density curves for the ER pathway activity score based on the 41-gene signature (FIG. 4D), 19-gene signature (FIG. 4E), or 14-gene signature (FIG. 4F) in the collection of 139 HR+/HER2− breast tumors. Pre- and post-treatment expression data for six patients are overlaid: pre-treatment scores are indicated as a diamond; post-treatment scores as a circle. Arrows show the magnitude and direction of change in ER pathway activity score per patient.
Figure 4I:
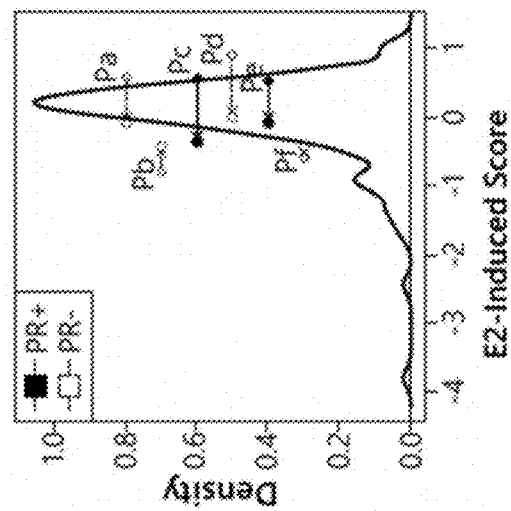
FIGS. 4G-4I are a series of reference density curves for the E2-induced score based on the 41-gene signature (FIG. 4G), 19-gene signature (FIG. 4H), or 14-gene signature (FIG. 4I) in the collection of 139 HR+/HER2− breast tumors. Pre- and post-treatment expression data for six patients are overlaid: pre-treatment scores are indicated as a diamond; post-treatment scores as a circle. Arrows show the magnitude and direction of change in E2-induced score per patient.
Figure 4H:
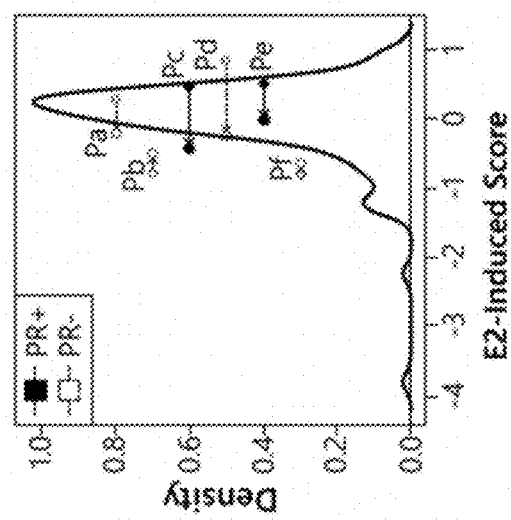
Figure 4G:
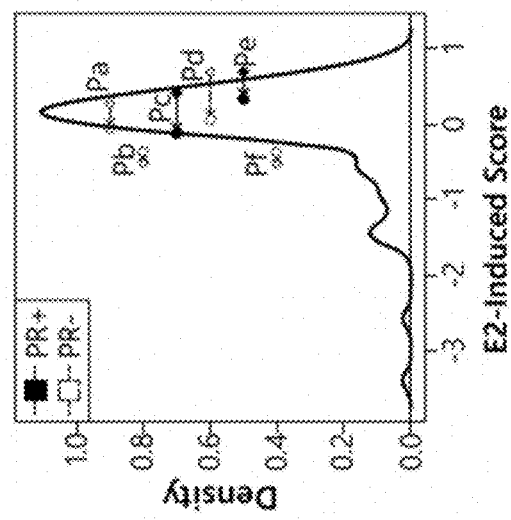

To identify a set of core genes for inclusion in the ER pathway activity score, pre- and post-treatment expression data from the 4 out of 6 patients treated with Compound B for whom Compound B was effective in suppressing the ER pathway (excluding patients Pb and Pf) were analyzed. A subset of genes among the 41 in vitro derived genes that were impacted most and most consistently by endocrine therapy treatment in those four patients was selected to create a 19-gene signature with 11 E2-induced and 8 E2-repressed genes (one-sided t-test, p<0.1) and a 14-gene signature with 8 E2-induced and 6 E2-repressed genes (one-sided t-test, p<0.05). Both reduced gene sets performed equally well in the HCI-013 PDX model treated with different doses of compound A compared to the 41-gene signature (FIGS. 4A-4C). Inclusion of both E2-induced and E2-repressed genes provided the largest dynamic range in ER pathway suppression in this in vivo model by dose. The reduced gene sets also resulted in a similar ER pathway suppression by treatment with Compound B in patients Pa through Pf as obtained with the 41-gene signature (FIGS. 4D-4F). Similar results were also observed when assessing changes in ER pathway activity based on only E2-induced genes (FIGS. 4G-4I). Signature genes are provided herein in Tables 1-6.

Figure 5:
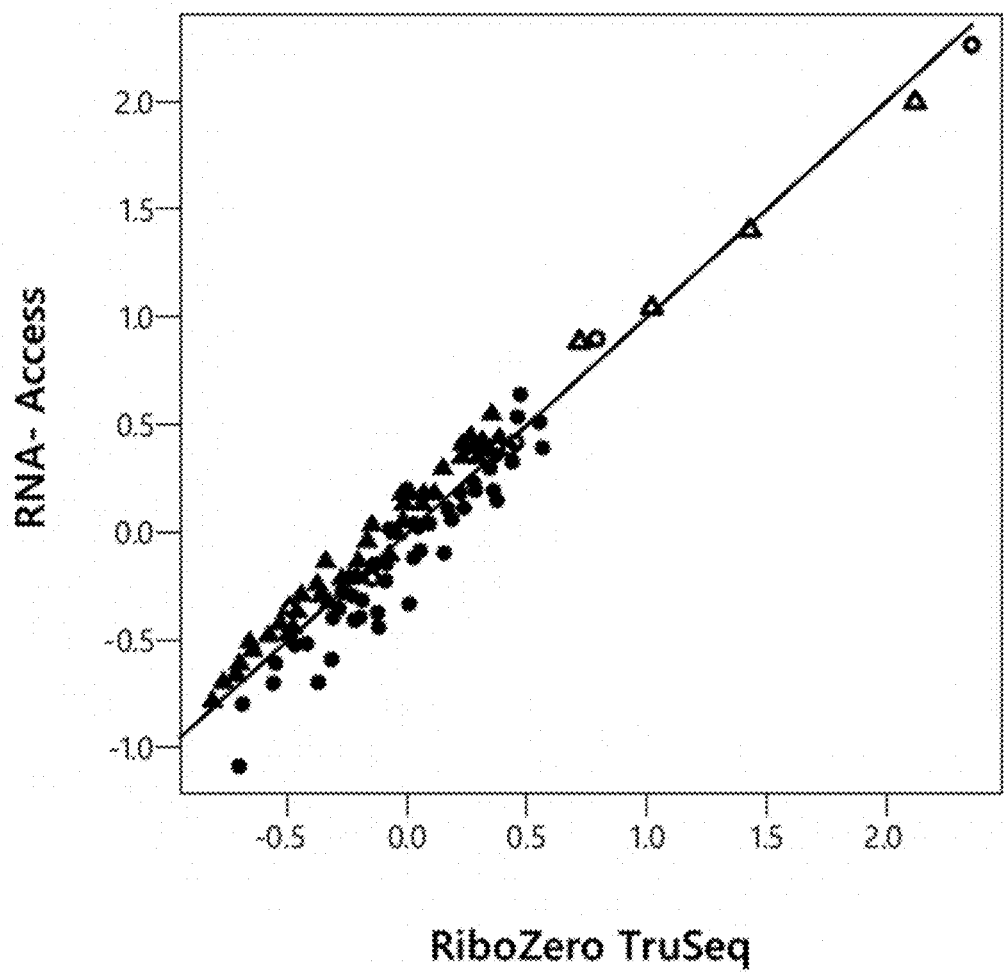
FIG. 5 is a scatterplot of ER pathway activity score in 60 tissue samples, with expression data prepared with RIBO-ZERO TRUSEQ® OR RNA ACCESS®. Formalin-fixed and paraffin-embedded (FFPE) samples are shown as triangles; fresh frozen samples are shown as circles. Breast tumors are shown in pink; other tissues are shown in black.

Example 4. ER Pathway Activity Signature Levels are Agnostic to the Sequencing Platform Employed, and to the Tissue Preparation Method The ER pathway activity scores in 30 FFPE samples, including five breast tumor samples, and in 30 FF (fresh frozen) samples, including five breast tumor samples, were determined. All breast samples were primary ER+ breast tissues, stage II or III, ductal carcinoma. RNA-sequencing data were generated for all samples using two different library kits: RNA ACCESS®, and RIBO-ZERO® TRUSEQ®. In the 60 tissue samples, ER pathway activity levels obtained with either sequencing method were highly similar (FIG. 5; Pearson correlation 0.97). Furthermore, ER pathway activity scores in breast FFPE (pink triangles) vs. breast FF samples (pink circles) were in the same range (FIG. 5). These results suggest that the signature can be used in a platform-agnostic way (RNA ACCESS®, TRUSEQ®) and in a tissue preparation-agnostic way (FFPE, FF).

Example 5. ER Inhibition and ER Transcriptional Activity

The relationship between ER pathway activity and the anti-proliferative effect of the ER antagonist fulvestrant was explored in a panel of 14 ER+/HER2− breast cancer cell lines. RNA-sequencing data was leveraged to determine the E2-induced score, determined by expression of a set of E2-induced genes (as described above), of a series of ER+/HER2− breast cancer cell lines grown under standard culture conditions, in the presence of estrogen. The effect of ER inhibition by 300 nM fulvestrant on cellular proliferation was determined in an 8-day in vitro viability assay using the GR (Growth Rate) method described by Hafner et al. (Nat Methods 13:6, 2016). The E2-induced score was then plotted against the effect of fulvestrant on cellular growth rate.

Figure 6:
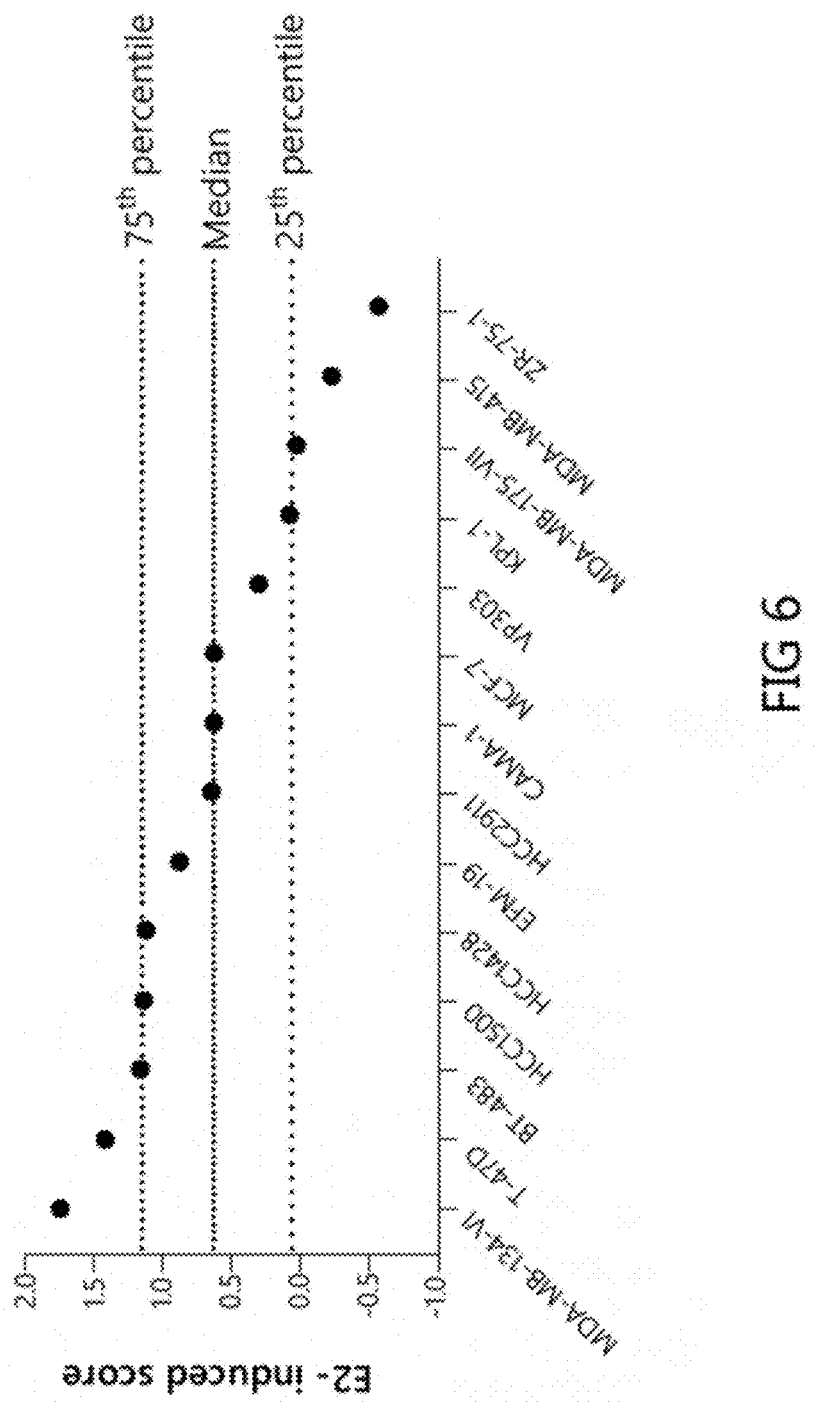
FIG. 6 is a plot of E2-induced scores of ER+/HER2− breast cancer cell lines.
Figure 7:
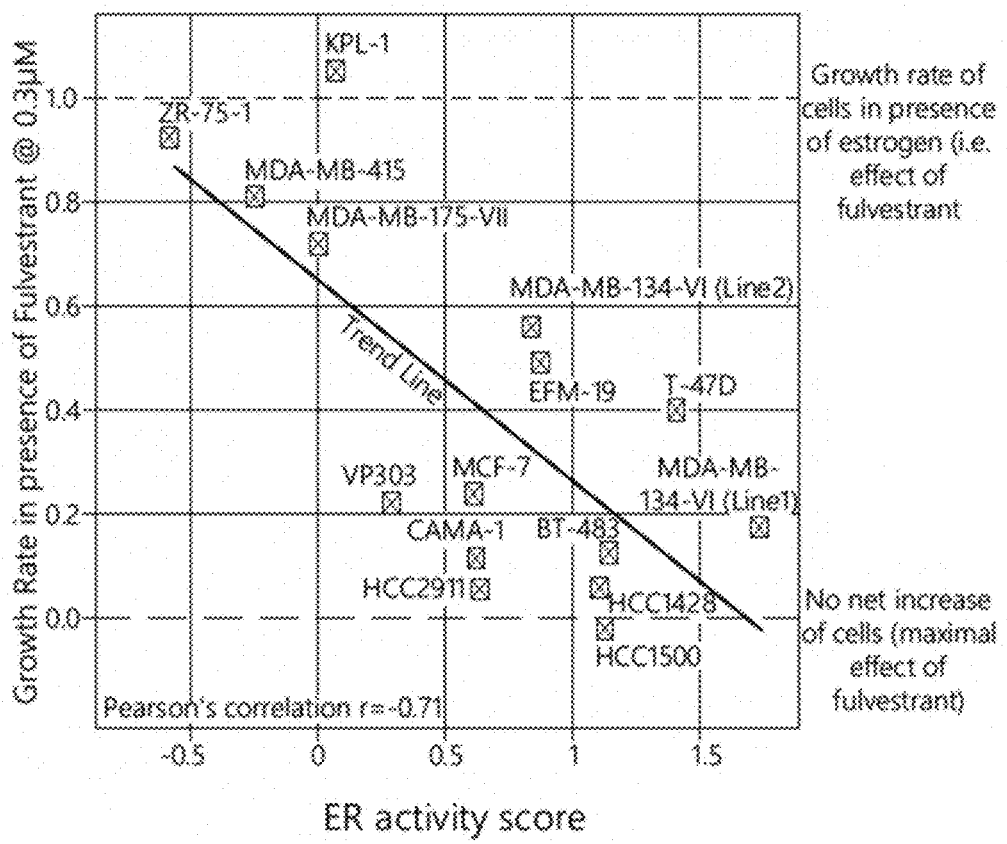
FIG. 7 is a plot of E2-induced score versus impact of fulvestrant on cellular growth rate.

ER+/HER2− breast cancer cell lines displayed E2-induced scores ranging from 1.73 to −0.57, with a median of 0.63 (FIG. 6). Fulvestrant had little impact on the growth rate of cell lines with E2-induced scores in the lowest 25th percentile for the panel of 14 cell lines (ZR-75-1, MDA-MB-415, MDA-MB-175-VII, KPL-1), while having a considerably greater impact on cell lines exhibiting higher E2-induced scores (FIG. 7). These in vitro data support the hypothesis that ER inhibition is likely to be most impactful in contexts in which gene expression profiles reflect ER transcriptional activity.

Other Embodiments

Although the foregoing methods and compositions have been described in some detail by way of illustration and example for purposes of clarity and understanding, the descriptions and examples should not be construed as limiting the scope of the methods and compositions provided herein. The disclosures of all patent and scientific literature cited herein are expressly incorporated in their entirety by reference.

EMBODIMENTS

Embodiment 1. A method of identifying an individual having a breast cancer who may benefit from a treatment comprising an endocrine therapy, the method comprising determining an estrogen receptor (ER) pathway activity score from a sample from the individual, wherein an ER pathway activity score from the sample that is at or above a reference ER pathway activity score identifies the individual as one who may benefit from a treatment comprising an endocrine therapy.

Embodiment 2. A method for selecting a therapy for an individual having a breast cancer, the method comprising determining an ER pathway activity score from a sample from the individual, wherein an ER pathway activity score from the sample that is at or above a reference ER pathway activity score identifies the individual as one who may benefit from a treatment comprising an endocrine therapy.

Embodiment 3. The method of embodiment 1 or 2, wherein the ER pathway activity score determined from the sample is at or above the reference ER pathway activity score, and the method further comprises administering to the individual an effective amount of an endocrine therapy.

Embodiment 4. The method of embodiment 1 or 2, wherein an ER pathway activity score from the sample that is below a reference ER pathway activity score identifies the individual as one who is less likely to benefit from a treatment comprising an endocrine therapy.

Embodiment 5. The method of embodiment 4, wherein the ER pathway activity score determined from the sample is below the reference ER pathway activity score, and the method further comprises administering to the individual an effective amount of an anti-cancer therapy other than an endocrine therapy.

Embodiment 6. A method of treating an individual having a breast cancer, the method comprising administering an effective amount of an endocrine therapy to the individual, wherein the individual has been identified as one who is more likely to benefit from a treatment comprising an endocrine therapy by the method of embodiment 1.

Embodiment 7. A method of treating an individual having a breast cancer, the individual being identified as having an ER pathway activity score that is at or above a reference ER pathway activity score, the method comprising administering to the individual an effective amount of an endocrine therapy.

Embodiment 8. A method of treating an individual having a breast cancer, the method comprising: (a) determining an ER pathway activity score from a sample from the individual, wherein the ER pathway activity score from the sample is determined to be at or above a reference ER pathway activity score; and (b) administering to the individual an effective amount of an endocrine therapy.

Embodiment 9. The method of any one of embodiments 1-8, wherein the reference ER pathway activity score is an ER pathway activity score in a reference population.

Embodiment 10. The method of any one of embodiments 1-3 and 6-9, wherein the ER pathway activity score in the sample is at or above −1.0.

Embodiment 11. The method of embodiment 10, wherein the ER pathway activity score in the sample is at or above −0.2.

Embodiment 12. The method of embodiment 4 or 5, wherein the ER pathway activity score in the sample is below −0.2.

Embodiment 13. The method of embodiment 4 or 5, wherein the ER pathway activity score in the sample is below −1.0.

Embodiment 14. The method of any one of embodiments 9-13, wherein the reference population is a population of individuals having hormone receptor-positive (HR+) breast cancer.

Embodiment 15. A method for monitoring the response of an individual having a breast cancer to treatment with an endocrine therapy, the method comprising: (a) determining a first ER pathway activity score from a sample from the individual at a first time point; (b) following step (a), determining a second ER pathway activity score from a sample from the individual at a second time point following administration of an endocrine therapy; and (c) comparing the first ER pathway activity score with the second ER pathway activity score, wherein a decrease in the second ER pathway activity score relative to the first ER pathway activity score is predictive of an individual who is likely to respond to treatment with an endocrine therapy.

Embodiment 16. The method of embodiment 15, wherein the second ER pathway activity score is decreased relative to the first ER pathway activity score, and the method further comprises administering an additional dose of the endocrine therapy to the individual.

Embodiment 17. The method of embodiment 15 or 16, wherein the decrease in the second ER pathway activity score relative to the first ER pathway activity score is a decrease of at least 0.1.

Embodiment 18. The method of any one of embodiments 15-17, wherein the first ER pathway activity score is: (a) an ER pathway activity score determined from a sample from the individual obtained prior to administration of a first dose of an endocrine therapy; (b) an ER pathway activity score determined from a sample from the individual at a previous time point, wherein the previous time point is following administration of a first dose of an endocrine therapy; or (c) a pre-assigned ER pathway activity score.

Embodiment 19. A method of identifying an individual having a breast cancer who may benefit from a treatment comprising an endocrine therapy, the method comprising determining an estradiol (E2)-induced score from a sample from the individual, wherein an E2-induced score from the sample that is at or above a reference E2-induced score identifies the individual as one who may benefit from a treatment comprising an endocrine therapy.

Embodiment 20. A method for selecting a therapy for an individual having a breast cancer, the method comprising determining an E2-induced score from a sample from the individual, wherein an E2-induced score from the sample that is at or above a reference E2-induced score identifies the individual as one who may benefit from a treatment comprising an endocrine therapy.

Embodiment 21. The method of embodiment 19 or 20, wherein the E2-induced score determined from the sample is at or above the reference E2-induced score, and the method further comprises administering to the individual an effective amount of an endocrine therapy.

Embodiment 22. The method of embodiment 19 or 20, wherein an E2-induced score from the sample that is below a reference E2-induced score identifies the individual as one who is less likely to benefit from a treatment comprising an endocrine therapy.

Embodiment 23. The method of embodiment 22, wherein the E2-induced score determined from the sample is below the reference E2-induced score, and the method further comprises administering to the individual an effective amount of an anti-cancer therapy other than an endocrine therapy.

Embodiment 24. A method of treating an individual having a breast cancer, the method comprising administering an effective amount of an endocrine therapy to the individual, wherein the individual has been identified as one who is more likely to benefit from a treatment comprising an endocrine therapy by the method of embodiment 19.

Embodiment 25. A method of treating an individual having a breast cancer, the individual being identified as having an E2-induced score that is at or above a reference E2-induced score, the method comprising administering to the individual an effective amount of an endocrine therapy.

Embodiment 26. A method of treating an individual having a breast cancer, the method comprising: (a) determining an E2-induced score from a sample from the individual, wherein the E2-induced score from the sample is determined to be at or above a reference E2-induced score; and (b) administering to the individual an effective amount of an endocrine therapy.

Embodiment 27. The method of any one of embodiments 19-26, wherein the reference E2-induced score is an E2-induced score in a reference population.

Embodiment 28. The method of any one of embodiments 19-21 and 24-27, wherein the E2-induced score in the sample is at or above −2.0.

Embodiment 29. The method of embodiment 28, wherein the E2-induced score in the sample is at or above −0.1.

Embodiment 30. The method of embodiment 22 or 23, wherein the E2-induced score in the sample is below −0.1.

Embodiment 31. The method of embodiment 30, wherein the E2-induced score in the sample is below −2.0.

Embodiment 32. The method of any one of embodiments 27-31, wherein the reference population is a population of individuals having HR+ breast tumors.

Embodiment 33. A method for monitoring the response of an individual having a breast cancer to treatment with an endocrine therapy, the method comprising: (a) determining a first E2-induced score from a sample from the individual at a first time point; (b) following step (a), determining a second E2-induced score from a sample from the individual at a second time point following administration of an endocrine therapy; and (c) comparing the first E2-induced score with the second E2-induced score, wherein a decrease in the second E2-induced score relative to the first E2-induced score is predictive of an individual who is likely to respond to treatment with an endocrine therapy.

Embodiment 34. The method of embodiment 33, wherein the second E2-induced score is decreased relative to the first E2-induced score, and the method further comprises administering an additional dose of the endocrine therapy to the individual.

Embodiment 35. The method of embodiment 33 or 34, wherein the decrease in the second E2-induced score relative to the first E2-induced score is a decrease of at least 0.1.

Embodiment 36. The method of any one of embodiments 33-35, wherein the first E2-induced score is: (a) an E2-induced score determined from a sample from the individual obtained prior to administration of a first dose of an endocrine therapy; (b) an E2-induced score determined from a sample from the individual at a previous time point, wherein the previous time point is following administration of a first dose of an endocrine therapy; or (c) a pre-assigned E2-induced score.

Embodiment 37. The method of any one of embodiments 1-6, 8-24, and 26-36, wherein the sample is a tissue sample.

Embodiment 38. The method of embodiment 37, wherein the tissue sample is a tumor tissue sample.

Embodiment 39. The method of embodiment 38, wherein the tumor tissue sample is a formalin-fixed and paraffin-embedded (FFPE) sample, a fresh frozen (FF) sample, an archival sample, a fresh sample, or a frozen sample.

Embodiment 40. The method of embodiment 39, wherein the tumor tissue sample is a FFPE sample.

Embodiment 41. The method of embodiment 39, wherein the tumor tissue sample is a FF sample.

Embodiment 42. The method of any one of embodiments 1-41, wherein the breast cancer is an ER+ breast cancer.

Embodiment 43. The method of embodiment 42, wherein the ER+ breast cancer is a luminal A breast cancer.

Embodiment 44. The method of embodiment 42, wherein the ER+ breast cancer is a luminal B breast cancer.

Embodiment 45. The method of any one of embodiments 1-44, wherein the breast cancer is an advanced or a metastatic breast cancer.

Embodiment 46. The method of any one of embodiments 3, 5-18, 21, and 23-45, wherein the endocrine therapy is administered orally, intravenously, intratumorally, intramuscularly, subcutaneously, topically, or intranasally.

Embodiment 47. The method of embodiment 46, wherein the endocrine therapy is administered orally.

Embodiment 48. The method of embodiment 46, wherein the endocrine therapy is administered intramuscularly.

Embodiment 49. A method of detecting estrogen receptor (ER) pathway activity in a subject that has breast cancer, the method comprising detecting an expression level of at least five genes set forth in Table 1 and at least five genes set forth in Table 4; at least five genes set forth in Table 2 and at least five genes set forth in Table 5; or at least five genes set forth in Table 3 and at least five genes set forth in Table 6.

Embodiment 50. The method of embodiment 49, wherein the expression level of said at least five genes set forth in Table 1, at least five genes set forth in Table 2 or at least five genes set forth in Table 3 are greater than a standard control.

Embodiment 51. The method of embodiment 49, wherein the expression level of said at least five genes set forth in Table 4, at least five genes set forth in Table 5 or at least five genes set forth in Table 6 are less than a standard control.

Embodiment 52. The method of one of embodiments 49 to 51, wherein the subject has been treated with an endocrine therapy prior to said detecting.

Embodiment 53. The method of one of embodiments 49 to 52, wherein the subject is treated with an endocrine therapy subsequent to said detecting.

Embodiment 54. The method of one of embodiments 49 to 53 comprising detecting an expression level of all genes set forth in Table 1 and all genes set forth in Table 4.

Embodiment 55. The method of one of embodiments 49 to 53 comprising detecting an expression level of all genes set forth in Table 2 and all genes set forth in Table 5.

Embodiment 56. The method of one of embodiments 49 to 53 comprising detecting an expression level of all genes set forth in Table 3 and all genes set forth in Table 6.

Embodiment 57. The method of one of embodiments 49 to 53 comprising detecting an expression level of all genes set forth in Table 1 and all genes set forth in Table 4 and not detecting an expression level of any other genes in said subject.

Embodiment 58. The method of one of embodiments 49 to 53 comprising detecting an expression level of all genes set forth in Table 2 and all genes set forth in Table 5 and not detecting an expression level of any other genes in said subject.

Embodiment 59. The method of one of embodiments 49 to 53 comprising detecting an expression level of all genes set forth in Table 3 and all genes set forth in Table 6 and not detecting an expression level of any other genes in said subject.

Embodiment 60. The method of one of embodiments 49 to 59, wherein the subject is treated with an endocrine therapy comprising a selective estrogen receptor degrader.

Embodiment 61. The method of one of embodiments 49 to 60, further comprising determining an estrogen receptor (ER) pathway activity score from a sample from the subject.

Embodiment 62. The method of embodiment 61, wherein an ER pathway activity score from the sample that is at or above a reference ER pathway activity score identifies the individual as one who may benefit from a treatment comprising an endocrine therapy.

Embodiment 63. The method of embodiment 61, further comprising comparing an ER pathway activity score from the sample that is at or above a reference ER pathway activity score identifies the individual as one who may benefit from a treatment comprising an endocrine therapy.

Embodiment 64. A method, comprising: detecting, by one or more processors, a first expression level of at least five genes set forth in Table 1, at least five genes set forth in Table 2, or at least five genes set forth in Table 3; detecting, by the one or more processors, a second expression level of at least five genes set forth in Table 4, at least five genes set forth in Table 5 or at least five genes set forth in Table 6; and detecting, based at least on the first expression level and/or the second expression level, estrogen receptor (ER) pathway activity in a subject that has cancer.

Embodiment 65. The method of embodiment 64, wherein the expression level of said at least five genes set forth in Table 1, at least five genes set forth in Table 2 or at least five genes set forth in Table 3 are greater than a standard control.

Embodiment 66. The method of embodiment 64, wherein the expression level of said at least five genes set forth in Table 4, at least five genes set forth in Table 5 or at least five genes set forth in Table 6 are less than a standard control.

Embodiment 67. The method of one of embodiments 64 to 66, further comprising: treating the subject with an endocrine therapy prior to said detecting.

Embodiment 68. The method of one of embodiments 64 to 67, further comprising treating, based at least on the estrogen receptor (ER) pathway activity detected in the subject, the subject with an endocrine therapy.

Embodiment 69. The method of any one of embodiments 1-68, wherein the endocrine therapy comprises a selective estrogen receptor degrader (SERD), a selective estrogen receptor modulator (SERM), a selective estrogen receptor covalent antagonist (SERCA), a selective human estrogen receptor agonist (ShERPA), an aromatase inhibitor (AI), or a combination thereof.

Embodiment 70. The method of embodiment 69, wherein the SERD comprises brilanestrant (GDC-0810) having the structure:

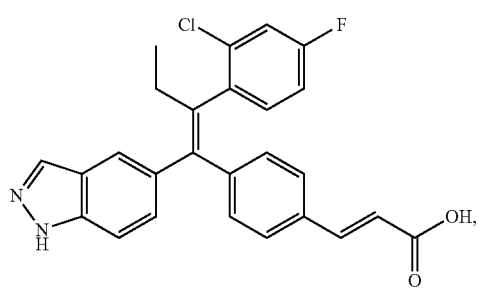 [SMILES: CC/C(=C(/c1ccc(/C=C/C(=O)O)cc1)c1ccc2[nH]ncc2c1)c1ccc(F)cc1Cl]
or a pharmaceutically acceptable salt thereof.
Embodiment 71. The method of embodiment 69, wherein the SERD comprises GDC-0927 (SRN-0927) having the structure:
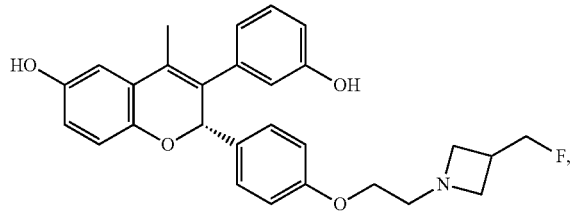 [SMILES: CC1=C(c2cccc(O)c2)[C@H](c2ccc(OCCN3CC(CF)C3)cc2)Oc2ccc(O)cc21]
or a pharmaceutically acceptable salt thereof.
Embodiment 72. The method of any one of embodiments 1-68, wherein the endocrine therapy comprises a compound having formula:
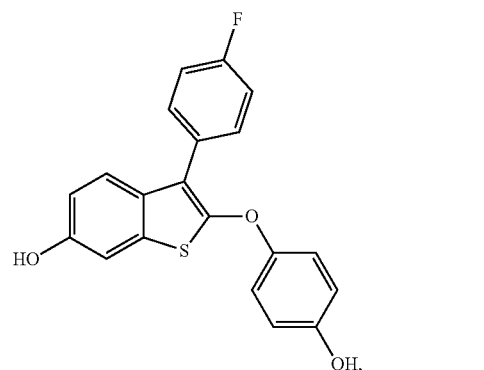
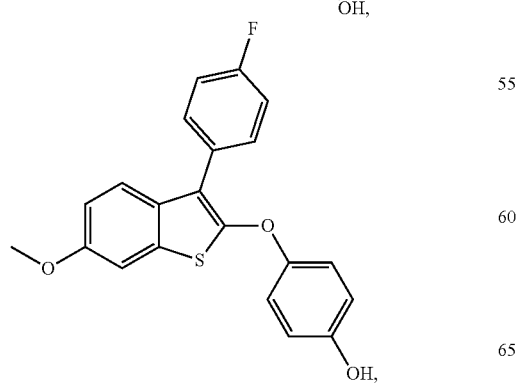
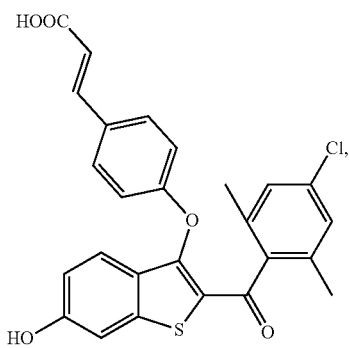
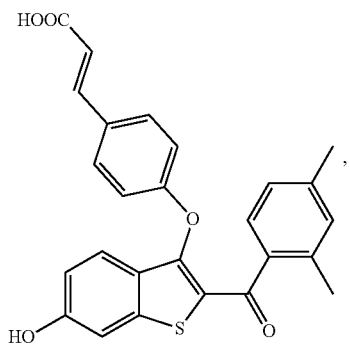
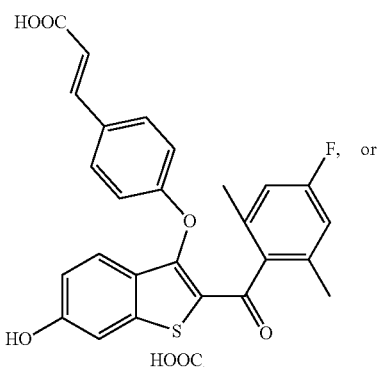
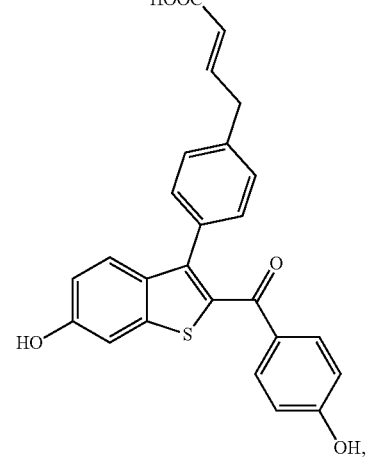
or a pharmaceutically acceptable salt thereof.

Embodiment 73. The method of any one of embodiments 1-68, wherein the endocrine therapy comprises a compound having formula:

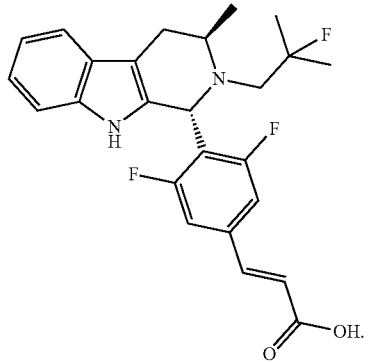 [SMILES: C[C@@H]1Cc2c([nH]c3ccccc23)[C@@H](c2c(F)cc(/C=C/C(=O)O)cc2F)N1CC(C)(C)F]

Embodiment 74. The method of any one of embodiments 1-68, wherein the endocrine therapy comprises a compound having formula:

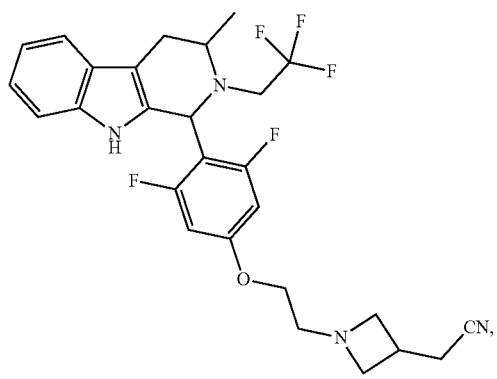 [SMILES: CC1Cc2c([nH]c3ccccc23)C(c2c(F)cc(OCCN3CC(CC#N)C3)cc2F)N1CC(F)(F)F]

or a pharmaceutically acceptable salt thereof.

Embodiment 75. The method of any one of embodiments 1-68, wherein the endocrine therapy comprises a compound having formula:

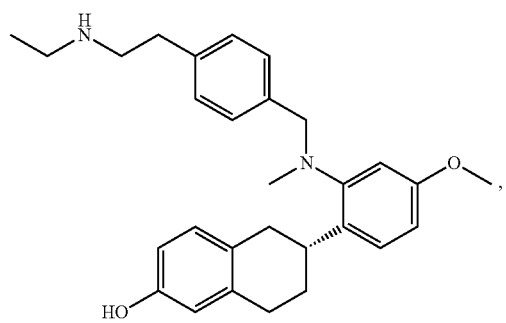 [SMILES: CCNCCc1ccc(CN(C)c2cc(OC)ccc2[C@@H]2CCc3cc(O)ccc3C2)cc1]

or a pharmaceutically acceptable salt thereof.

Embodiment 76. The method of any one of embodiments 1-68, wherein the endocrine therapy comprises a compound having formula:

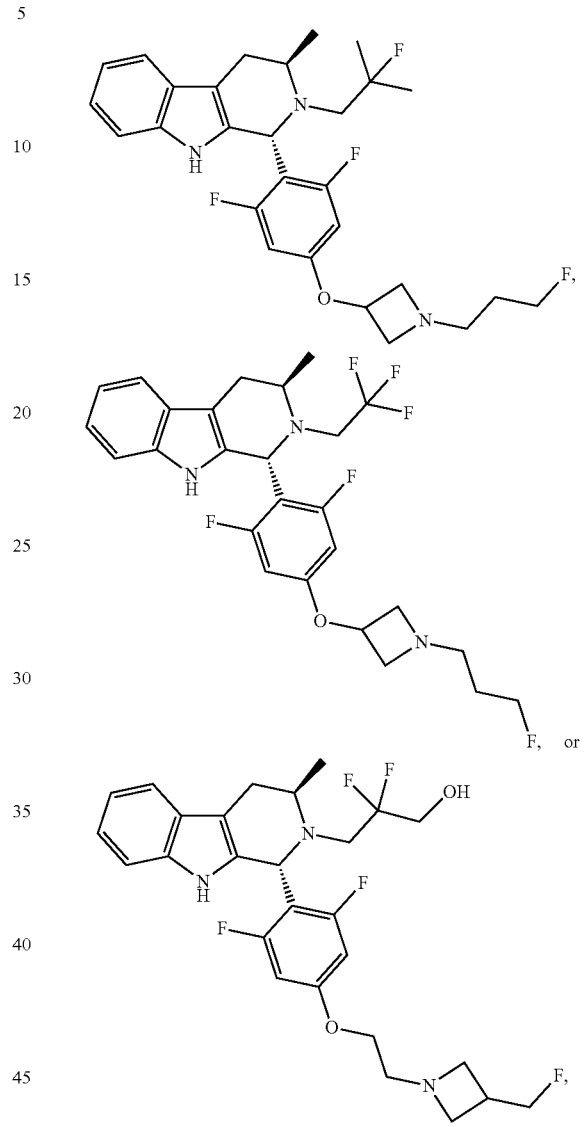

or a pharmaceutically acceptable salt thereof.

Embodiment 77. The method of any one of embodiments 1-68, wherein the endocrine therapy comprises a compound having formula:

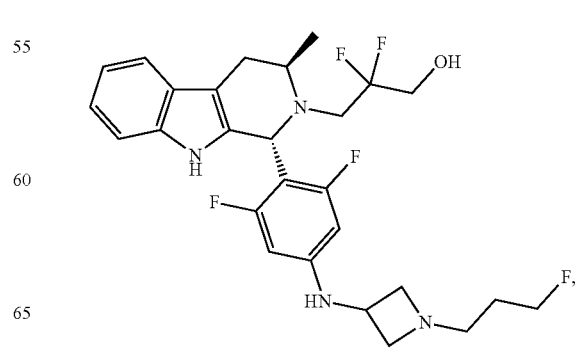

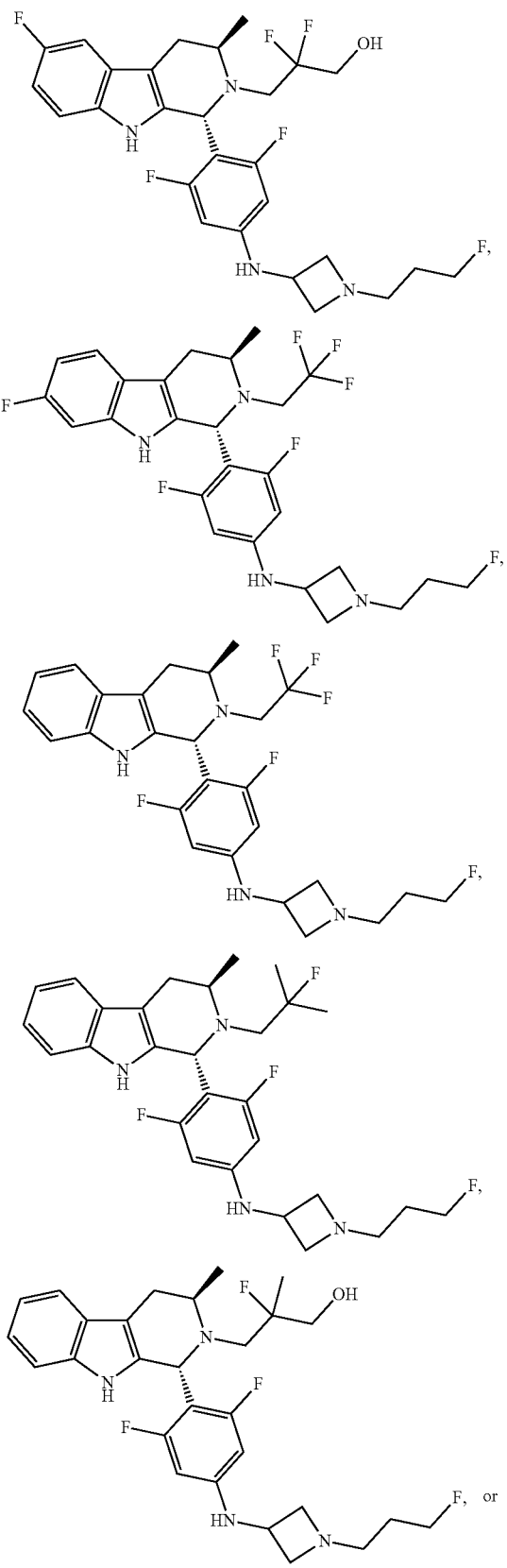

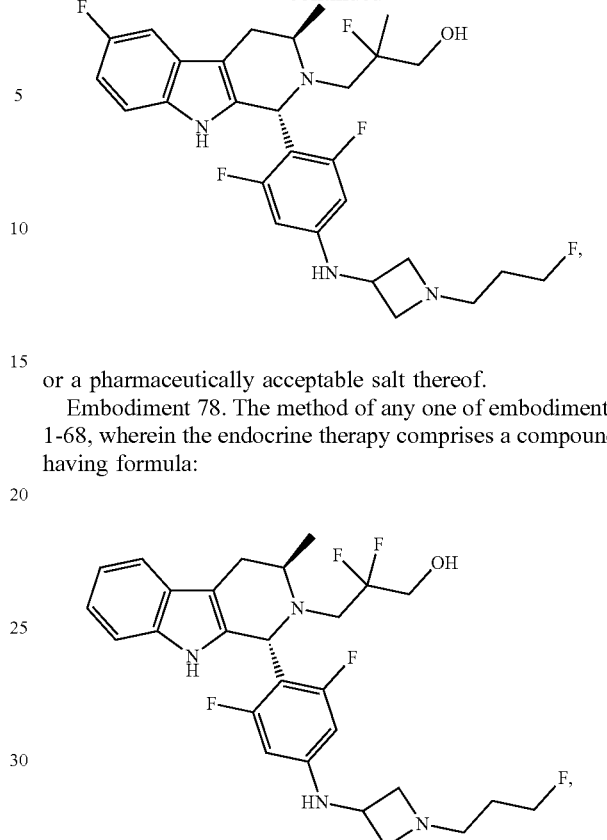

or a pharmaceutically acceptable salt thereof.

Embodiment 78. The method of any one of embodiments 1-68, wherein the endocrine therapy comprises a compound having formula:

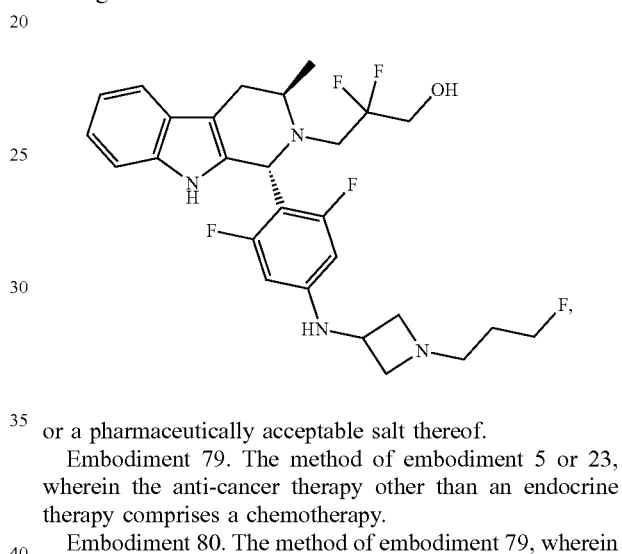

or a pharmaceutically acceptable salt thereof.

Embodiment 79. The method of embodiment 5 or 23, wherein the anti-cancer therapy other than an endocrine therapy comprises a chemotherapy.

Embodiment 80. The method of embodiment 79, wherein the chemotherapy comprises an anthracycline, a taxane, 5-flurouracil, cyclophosphamide, a platinum agent, vinorelbine, capecitabine, gemcitabine, ixabepilone, eribulin, or a combination thereof.

Embodiment 81. The method of embodiment 79, wherein the anti-cancer therapy other than an endocrine therapy comprises a PI3K inhibitor, an mTOR inhibitor, a CDK4/6 inhibitor, or a combination thereof.

Embodiment 82. The method of any one of embodiments 1-81, wherein the individual is a human.

Embodiment 83. A kit comprising a plurality of nucleic acids, wherein said plurality of nucleic acids are at least 5 nucleotides in length and are at least 95% identical to a 5 nucleotide continuous sequence within at least five genes set forth in Table 1 and at least five genes set forth in Table 4; at least five genes set forth in Table 2 and at least five genes set forth in Table 4; or at least five genes set forth in Table 3 and at least five genes set forth in Table 6, or 95% identical to a sequence complementary to said 5 nucleotide continuous sequence.

Embodiment 84. The kit of embodiment 83, wherein said plurality of nucleic acids are attached to a solid support.

Embodiment 85. The kit of embodiment 84, wherein said plurality of nucleic acids comprise a detectable label.

Embodiment 86. The kit of embodiment 83, wherein said plurality of nucleic acids are at least 95% identical to a 5 nucleotide continuous sequence within at least five genes set forth in Table 1, at least five genes set forth in Table 2 or at least five genes set forth in Table 3 are greater than a standard control.

Embodiment 87. The kit of embodiment 83, wherein said plurality of nucleic acids are at least 95% identical to a 5 nucleotide continuous sequence within at least five genes set forth in Table 4, at least five genes set forth in Table 5 or at least five genes set forth in Table 6 are less than a standard control.

Embodiment 88. The kit of one of embodiments 83-87, wherein said plurality of nucleic acids are at least 95% identical to a 5 nucleotide continuous sequence within all genes set forth in Table 1 and all genes set forth in Table 4.

Embodiment 89. The kit of one of embodiments 83-87, wherein said plurality of nucleic acids are at least 95% identical to a 5 nucleotide continuous sequence within all genes set forth in Table 2 and all genes set forth in Table 5.

Embodiment 90. The kit of one of embodiments 83-87, wherein said plurality of nucleic acids are at least 95% identical to a 5 nucleotide continuous sequence within all genes set forth in Table 3 and all genes set forth in Table 6.

Embodiment 91. The kit of one of embodiments 83-87, wherein said plurality of nucleic acids are at least 95% identical to a 5 nucleotide continuous sequence within all genes set forth in Table 1 and all genes set forth in Table 4 and no other genes.

Embodiment 92. The kit of one of embodiments 83-87, wherein said plurality of nucleic acids are at least 95% identical to a 5 nucleotide continuous sequence within all genes set forth in Table 2 and all genes set forth in Table 5 and no other genes.

Embodiment 93. The kit of one of embodiments 83-87, wherein said plurality of nucleic acids are at least 95% identical to a 5 nucleotide continuous sequence within all genes set forth in Table 3 and all genes set forth in Table 6 and no other genes in said subject.

Embodiment 94. The kit of one of embodiments 83-93, wherein the plurality of nucleic acids are identical to a 5 nucleotide continuous sequence within said genes.

Embodiment 95. The kit of one of embodiments 83-94, wherein the plurality of nucleic acids are identical to a continuous nucleotide sequence comprising at least 10, 20, 25, 50, 75, 100, 150, or 200 nucleotides.

What is claimed is:

1. A method of treating breast cancer in an individual in need thereof, the method comprising:
   (i) determining an estrogen receptor (ER) pathway activity score from a sample from the individual, wherein the ER pathway activity score from the sample is at or above a reference ER pathway activity score;
   wherein the ER pathway activity score is calculated by subtracting an E2-repressed score, determined from the average z-scored expression of at least 4 of the E2-repressed genes selected from the group consisting of BAMBI, BCAS1, CCNG2, DDIT4, EGLN3, FAM171B, GRM4, IL1R1, LIPH, NBEA, PNPLA7, PSCA, SEMA3E, SSPO, STON1, TGFB3, TP53INP1, and TP53INP2, from an E2-induced score, determined from the average z-scored expression of 23 of the E2-induced genes selected from the group consisting of AGR3, AMZ1, AREG, C5AR2, CELSR2, CT62, FKBP4, FMN1, GREB1, IGFBP4, NOS1AP, NXPH3, OLFM1, PGR, PPM1J, RAPGEFL1, RBM24, RERG, RET, SGK3, SLC9A3R1, TFF1, and ZNF703; and
   (ii) administering to the individual an effective amount of an endocrine therapy selected from the group consisting of:
      (a) a selective estrogen receptor degrader, a selective estrogen receptor modulator, a selective estrogen receptor covalent antagonist, a selective human estrogen receptor agonist, an aromatase inhibitor, or a combination of two or more thereof;
      (b) letrozole, anastrozole, exemestane, testolactone, hydroxytamoxifen, clomifene, toremifene, raloxifene, anordrin, bazedoxifene, broparestrol, cyclofenil, lasofoxifene, ormeloxifene, acolbifene, elacestrant, brilanestrant, clomifenoxide, droloxifene, etacstil, ospemifene, G1T48, AZ9496, GDC-0927, LX-039, fulvestrant, or GDC-9545, a pharmaceutically acceptable salt of one of the foregoing, or a combination of two or more of the foregoing; and
      (c) a compound having formula:

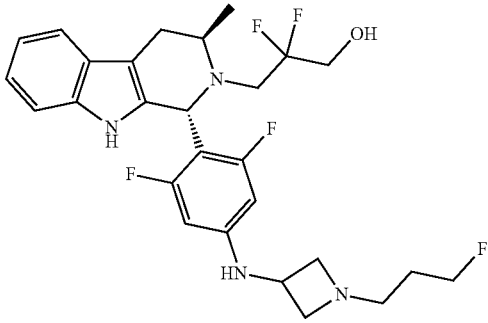 [SMILES: C[C@@H]1Cc2c([nH]c3ccccc23)[C@@H](c2c(F)cc(NC3CN(CCCF)C3)cc2F)N1CC(F)(F)CO]

or a pharmaceutically acceptable salt thereof.

2. The method of claim 1, wherein the ER pathway activity score is calculated by subtracting an E2-repressed score, determined from the average z-scored expression of all of the E2-repressed genes set selected from the group consisting of BAMBI, BCAS1, CCNG2, DDIT4, EGLN3, FAM171B, GRM4, IL1R1, LIPH, NBEA, PNPLA7, PSCA, SEMA3E, SSPO, STON1, TGFB3, TP53INP1, and TP53INP2, from an E2-induced score, determined from the average z-scored expression of all of the E2-induced genes selected from the group consisting of AGR3, AMZ1, AREG, C5AR2, CELSR2, CT62, FKBP4, FMN1, GREB1, IGFBP4, NOS1AP, NXPH3, OLFM1, PGR, PPM1J, RAPGEFL1, RBM24, RERG, RET, SGK3, SLC9A3R1, TFF1, and ZNF703.

3. The method of claim 1, wherein the endocrine therapy comprises a selective estrogen receptor degrader, a selective estrogen receptor modulator, a selective estrogen receptor covalent antagonist, a selective human estrogen receptor agonist, an aromatase inhibitor, or a combination of two or more thereof.

4. The method of claim 1, wherein the endocrine therapy comprises letrozole, anastrozole, exemestane, testolactone, hydroxytamoxifen, clomifene, toremifene, raloxifene, anordrin, bazedoxifene, broparestrol, cyclofenil, lasofoxifene, ormeloxifene, acolbifene, elacestrant, brilanestrant, clomifenoxide, droloxifene, etacstil, ospemifene, G1T48, AZ9496, GDC-0927, LX-039, fulvestrant, or GDC-9545, a pharmaceutically acceptable salt of one of the foregoing, or a combination of two or more of the foregoing.

5. The method of claim 1, wherein the endocrine therapy comprises a compound having formula:

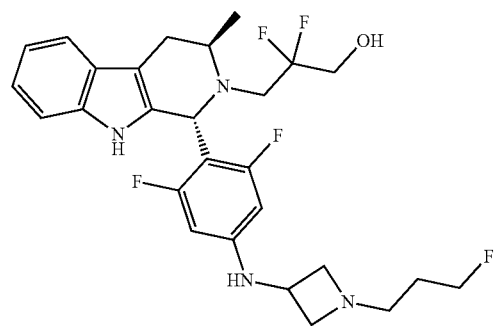 [SMILES: C[C@@H]1Cc2c([nH]c3ccccc23)[C@@H](c2c(F)cc(NC3CN(CCCF)C3)cc2F)N1CC(F)(F)CO]

or a pharmaceutically acceptable salt thereof.

6. A method for treating breast cancer in an individual in need thereof, the method comprising:
   (a) determining a first ER pathway activity score from a sample from the individual at a first time point, wherein the first ER pathway activity score is calculated by subtracting an E2-repressed score, determined from the average z-scored expression of at least 4 of the E2-repressed genes selected from the group consisting of BAMBI, BCAS1, CCNG2, DDIT4, EGLN3, FAM171B, GRM4, IL1R1, LIPH, NBEA, PNPLA7, PSCA, SEMA3E, SSPO, STON1, TGFB3, TP53INP1, and TP53INP2, from an E2-induced score, determined from the average z-scored expression of 23 of the E2-induced genes selected from the group consisting of AGR3, AMZ1, AREG, C5AR2, CELSR2, CT62, FKBP4, FMN1, GREB1, IGFBP4, NOS1AP, NXPH3, OLFM1, PGR, PPM1J, RAPGEFL1, RBM24, RERG, RET, SGK3, SLC9A3R1, TFF1, and ZNF703;

(b) following step (a), administering to the individual an effective amount of an endocrine therapy selected from the group consisting of:
  (i) a selective estrogen receptor degrader, a selective estrogen receptor modulator, a selective estrogen receptor covalent antagonist, a selective human estrogen receptor agonist, an aromatase inhibitor, or a combination of two or more thereof;
  (ii) letrozole, anastrozole, exemestane, testolactone, hydroxytamoxifen, clomifene, toremifene, raloxifene, anordrin, bazedoxifene, broparestrol, cyclofenil, lasofoxifene, ormeloxifene, acolbifene, elacestrant, brilanestrant, clomifenoxide, droloxifene, etacstil, ospemifene, G1T48, AZ9496, GDC-0927, LX-039, fulvestrant, or GDC-9545, a pharmaceutically acceptable salt of one of the foregoing, or a combination of two or more of the foregoing; and
  (iii) a compound having formula:

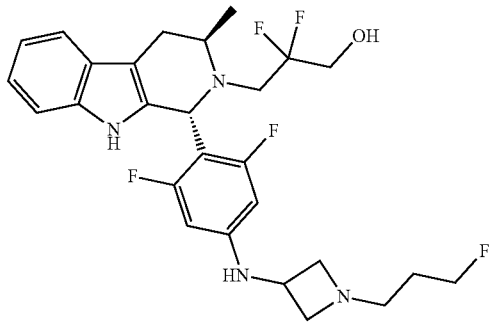 [SMILES: C[C@@H]1Cc2c([nH]c3ccccc23)[C@@H](c2c(F)cc(NC3CN(CCCF)C3)cc2F)N1CC(F)(F)CO]

or a pharmaceutically acceptable salt thereof; and
(c) determining a second ER pathway activity score, wherein the second ER pathway activity score is calculated by subtracting an E2-repressed score, determined from the average z-scored expression of at least 4 of the E2-repressed genes selected from the group consisting of BAMBI, BCAS1, CCNG2, DDIT4, EGLN3, FAM171B, GRM4, IL1R1, LIPH, NBEA, PNPLA7, PSCA, SEMA3E, SSPO, STON1, TGFB3, TP53INP1, and TP53INP2, from an E2-induced score, determined from the average z-scored expression of 23 of the E2-induced genes selected from the group consisting of AGR3, AMZ1, AREG, C5AR2, CELSR2, CT62, FKBP4, FMN1, GREB1, IGFBP4, NOS1AP, NXPH3, OLFM1, PGR, PPM1J, RAPGEFL1, RBM24, RERG, RET, SGK3, SLC9A3R1, TFF1, and ZNF703 from a sample from the individual at a second time point following step (b), wherein the second ER pathway activity score is decreased relative to the first ER pathway activity score.

7. The method of claim 6, further comprising administering an additional dose of the endocrine therapy to the individual following step (c).

8. The method of claim 6, wherein each ER pathway activity score is calculated by subtracting an E2-repressed score, determined from the average z-scored expression of all of the E2-repressed genes selected from the group consisting of BAMBI, BCAS1, CCNG2, DDIT4, EGLN3, FAM171B, GRM4, IL1R1, LIPH, NBEA, PNPLA7, PSCA, SEMA3E, SSPO, STON1, TGFB3, TP53INP1, and TP53INP2, from an E2-induced score, determined from the average z-scored expression of all of the E2-induced genes selected from the group consisting of AGR3, AMZ1, AREG, C5AR2, CELSR2, CT62, FKBP4, FMN1, GREB1, IGFBP4, NOS1AP, NXPH3, OLFM1, PGR, PPM1J, RAPGEFL1, RBM24, RERG, RET, SGK3, SLC9A3R1, TFF1, and ZNF703.

9. The method of claim 6, wherein the first ER pathway activity score is:
  (a) an ER pathway activity score determined from a sample from the individual obtained prior to administration of a first dose of an endocrine therapy;
  (b) an ER pathway activity score determined from a sample from the individual at a previous time point, wherein the previous time point is following administration of a first dose of an endocrine therapy; or
  (c) a pre-assigned ER pathway activity score.

10. The method of claim 6, wherein the endocrine therapy comprises a selective estrogen receptor degrader, a selective estrogen receptor modulator, a selective estrogen receptor covalent antagonist, a selective human estrogen receptor agonist, an aromatase inhibitor, or a combination of two or more thereof.

11. The method of claim 6, wherein the endocrine therapy comprises letrozole, anastrozole, exemestane, testolactone, hydroxytamoxifen, clomifene, toremifene, raloxifene, anordrin, bazedoxifene, broparestrol, cyclofenil, lasofoxifene, ormeloxifene, acolbifene, elacestrant, brilanestrant, clomifenoxide, droloxifene, etacstil, ospemifene, G1T48, AZ9496, GDC-0927, LX-039, fulvestrant, or GDC-9545, a pharmaceutically acceptable salt of one of the foregoing, or a combination of two or more of the foregoing.

12. The method of claim 6, wherein the endocrine therapy comprises a compound having formula:

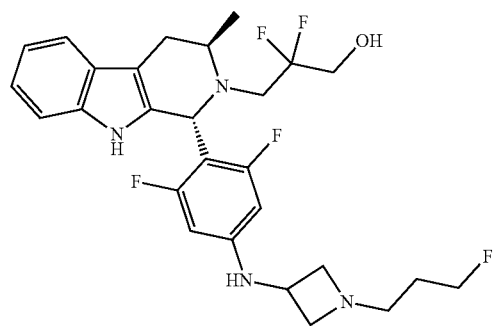 [SMILES: C[C@@H]1Cc2c([nH]c3ccccc23)[C@@H](c2c(F)cc(NC3CN(CCCF)C3)cc2F)N1CC(F)(F)CO]

or a pharmaceutically acceptable salt thereof.

13. A method of treating breast cancer in an individual in need thereof, the method comprising:
  (i) determining an estradiol (E2)-induced score from a sample from the individual as determined from the average z-scored expression of all of the E2-induced genes selected from the group consisting of AGR3, AMZ1, AREG, C5AR2, CELSR2, CT62, FKBP4, FMN1, GREB1, IGFBP4, NOS1AP, NXPH3, OLFM1, PGR, PPM1J, RAPGEFL1, RBM24, RERG, RET, SGK3, SLC9A3R1, TFF1, and ZNF703, wherein the E2-induced score from the sample is at or above a reference E2-induced score; and (i) administering to the individual an effective amount of an endocrine therapy selected from the group consisting of:
  (a) a selective estrogen receptor degrader, a selective estrogen receptor modulator, a selective estrogen receptor covalent antagonist, a selective human estrogen receptor agonist, an aromatase inhibitor, or a combination of two or more thereof a selective estrogen receptor degrader, a selective estrogen receptor modulator, a selective estrogen receptor covalent antagonist, a selective human estrogen receptor agonist, an aromatase inhibitor, or a combination of two or more thereof a selective estrogen receptor degrader, a selective estrogen receptor modulator, a selective estrogen receptor covalent antagonist, a selective human estrogen receptor agonist, an aromatase inhibitor, or a combination of two or more thereof;
  (b) letrozole, anastrozole, exemestane, testolactone, hydroxytamoxifen, clomifene, toremifene, raloxifene, anordrin, bazedoxifene, broparestrol, cyclofenil, lasofoxifene, ormeloxifene, acolbifene, elacestrant, brilanestrant, clomifenoxide, droloxifene, etacstil, ospemifene, G1T48, AZ9496, GDC-0927, LX-039, fulvestrant, or GDC-9545, a pharmaceutically acceptable salt of one of the foregoing, or a combination of two or more of the foregoing; and
  (c) a compound having formula:

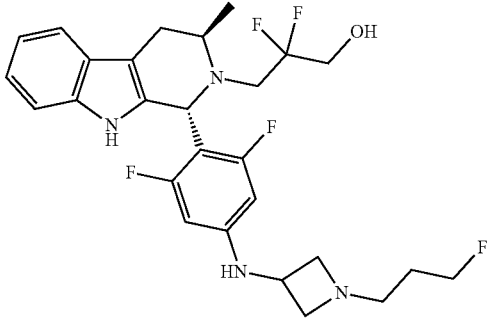 [SMILES: C[C@@H]1Cc2c([nH]c3ccccc23)[C@@H](c2c(F)cc(NC3CN(CCCF)C3)cc2F)N1CC(F)(F)CO]

or a pharmaceutically acceptable salt thereof.

14. The method of claim 13, wherein the endocrine therapy comprises a selective estrogen receptor degrader, a selective estrogen receptor modulator, a selective estrogen receptor covalent antagonist, a selective human estrogen receptor agonist, an aromatase inhibitor, or a combination of two or more thereof.

15. The method of claim 13, wherein the endocrine therapy comprises letrozole, anastrozole, exemestane, testolactone, hydroxytamoxifen, clomifene, toremifene, raloxifene, anordrin, bazedoxifene, broparestrol, cyclofenil, lasofoxifene, ormeloxifene, acolbifene, elacestrant, brilanestrant, clomifenoxide, droloxifene, etacstil, ospemifene, G1T48, AZ9496, GDC-0927, LX-039, fulvestrant, or GDC-9545, a pharmaceutically acceptable salt of one of the foregoing, or a combination of two or more of the foregoing.

16. The method of claim 13, wherein the endocrine therapy comprises a compound having formula:

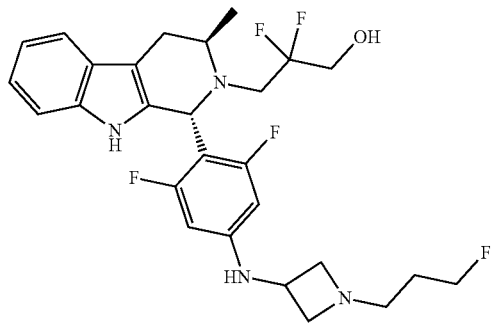 [SMILES: C[C@@H]1Cc2c([nH]c3ccccc23)[C@@H](c2c(F)cc(NC3CN(CCCF)C3)cc2F)N1CC(F)(F)CO]

or a pharmaceutically acceptable salt thereof.

17. A method for treating breast cancer in individual in need thereof, the method comprising:
  (a) determining a first E2-induced score from a sample from the individual at a first time point wherein the first E2-induced score is determined from the average z-scored expression of all of the E2-induced genes selected from the group consisting of AGR3, AMZ1, AREG, C5AR2, CELSR2, CT62, FKBP4, FMN1, GREB1, IGFBP4, NOS1AP, NXPH3, OLFM1, PGR, PPM1J, RAPGEFL1, RBM24, RERG, RET, SGK3, SLC9A3R1, TFF1, and ZNF703;
  (b) following step (a), administering to the individual an effective amount of an endocrine therapy selected from the group consisting of:
    (i) a selective estrogen receptor degrader, a selective estrogen receptor modulator, a selective estrogen receptor covalent antagonist, a selective human estrogen receptor agonist, an aromatase inhibitor, or a combination of two or more thereof;
    (ii) letrozole, anastrozole, exemestane, testolactone, hydroxytamoxifen, clomifene, toremifene, raloxifene, anordrin, bazedoxifene, broparestrol, cyclofenil, lasofoxifene, ormeloxifene, acolbifene, elacestrant, brilanestrant, clomifenoxide, droloxifene, etacstil, ospemifene, G1T48, AZ9496, GDC-0927, LX-039, fulvestrant, or GDC-9545, a pharmaceutically acceptable salt of one of the foregoing, or a combination of two or more of the foregoing; and
    (iii) a compound having formula:

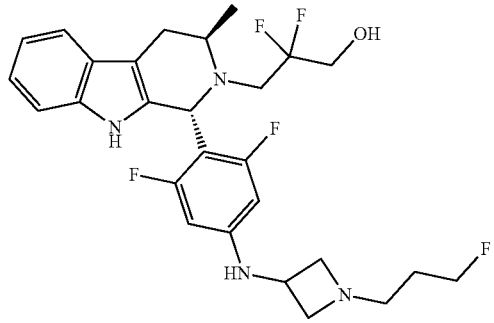 [SMILES: C[C@@H]1Cc2c([nH]c3ccccc23)[C@@H](c2c(F)cc(NC3CN(CCCF)C3)cc2F)N1CC(F)(F)CO]

or a pharmaceutically acceptable salt thereof; and
  (c) determining a second E2-induced score from a sample from the individual at a second time point following step (b), wherein the second E2-induced score is determined from the average z-scored expression of all of the E2-induced genes selected from the group consisting of AGR3, AMZ1, AREG, C5AR2, CELSR2, CT62, FKBP4, FMN1, GREB1, IGFBP4, NOS1AP, NXPH3, OLFM1, PGR, PPM1J, RAPGEFL1, RBM24, RERG, RET, SGK3, SLC9A3R1, TFF1, and ZNF703, and wherein the second E2-induced score is decreased relative to the first E2-induced score.

18. The method of claim 17, further comprising administering an additional dose of the endocrine therapy to the individual.

19. The method of claim 17, wherein the first E2-induced score is:
(a) an E2-induced score determined from a sample from the individual obtained prior to administration of a first dose of an endocrine therapy;
(b) an E2-induced score determined from a sample from the individual at a previous time point, wherein the previous time point is following administration of a first dose of an endocrine therapy; or
(c) a pre-assigned E2-induced score.

20. The method of claim 17, wherein the endocrine therapy comprises a selective estrogen receptor degrader, a selective estrogen receptor modulator, a selective estrogen receptor covalent antagonist, a selective human estrogen receptor agonist, an aromatase inhibitor, or a combination of two or more thereof.

21. The method of claim 17, wherein the endocrine therapy comprises letrozole, anastrozole, exemestane, testolactone, hydroxytamoxifen, clomifene, toremifene, raloxifene, anordrin, bazedoxifene, broparestrol, cyclofenil, lasofoxifene, ormeloxifene, acolbifene, elacestrant, brilanestrant, clomifenoxide, droloxifene, etacstil, ospemifene, G1T48, AZ9496, GDC-0927, LX-039, fulvestrant, or GDC-9545, a pharmaceutically acceptable salt of one of the foregoing, or a combination of two or more of the foregoing.

22. The method of claim 17, wherein the endocrine therapy comprises a compound having formula:

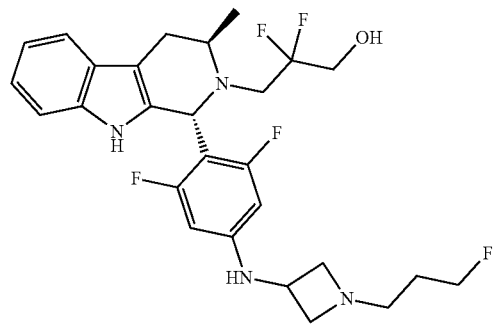 [SMILES: C[C@@H]1Cc2c([nH]c3ccccc23)[C@@H](c2c(F)cc(NC3CN(CCCF)C3)cc2F)N1CC(F)(F)CO]

or a pharmaceutically acceptable salt thereof.

* * * * *